(12) United States Patent
Bruce et al.

(10) Patent No.: US 7,629,141 B2
(45) Date of Patent: Dec. 8, 2009

(54) **ESSENTIAL AND IMPORTANT GENES OF *PSEUDOMONAS AERUGINOSA* AND THE USE THEREOF TO DESIGN OR IDENTIFY ANTIBACTERIAL AGENTS**

(75) Inventors: Kim Folger Bruce, Seattle, WA (US); Paul Warrener, Seattle, WA (US); Kevin Hou, Issaquah, WA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 463 days.

(21) Appl. No.: 11/246,458

(22) Filed: Oct. 11, 2005
(Under 37 CFR 1.47)

(65) Prior Publication Data

US 2007/0196829 A1 Aug. 23, 2007

Related U.S. Application Data

(63) Continuation-in-part of application No. 11/176,497, filed on Jul. 8, 2005, now abandoned, which is a continuation of application No. 11/014,899, filed on Dec. 20, 2004, now abandoned, which is a continuation of application No. 10/480,838, filed as application No. PCT/US02/19153 on Jun. 17, 2002, now abandoned, application No. 11/246,458, which is a continuation-in-part of application No. 10/511,151, filed as application No. PCT/US02/35518 on Nov. 5, 2002, now abandoned.

(60) Provisional application No. 60/372,095, filed on Apr. 15, 2002, provisional application No. 60/298,109, filed on Jun. 15, 2001.

(51) Int. Cl.
*C12Q 1/18* (2006.01)

(52) U.S. Cl. .......................................... 435/32; 435/7.1
(58) Field of Classification Search ....................... None
See application file for complete search history.

(56) References Cited

U.S. PATENT DOCUMENTS

| 5,706,498 A | 1/1998 | Fujiyama et al. | 435/6 |
| 5,876,931 A | 3/1999 | Holden | 435/6 |
| 6,037,137 A | 3/2000 | Komoriya et al. | 435/23 |

OTHER PUBLICATIONS

Onishi et al, Science 274: 980 (1996).*
Costerton et al., "Bacterial Biofilms: A common cause of persistant infections," *Science* 284, 1318-22, May 21, 1999.
Hyland et al., "Cloning, expression, and purification of UDP-3-O-acyl-GlcNAc deacetylase from *Pseudomonas aeruginosa*: a metalloamidase of the lipid A biosynthesis pathway," *J. Bacteriol.* 179, 2029-37, 1997.
Stover et al., "Complete genome sequence of *Pseudomonas aeruginosa* PA01, an opportunistic pathogen," *Nature* 406, 959-64, Aug. 31, 2000.

* cited by examiner

*Primary Examiner*—James Martinell
(74) *Attorney, Agent, or Firm*—Helen Lee; Lisa M. Hemmendinger; Robert J. Gorman

(57) ABSTRACT

The invention includes a database of candidate essential genes in *Pseudomonas aeruginosa*, as well as other important genes that, when mutated, lead to a growth attenuated phenotype. Such genes and mutants of such genes are important for identifying antibacterial agents suitable for treating and preventing *Pseudomonas aeruginosa* infections. The invention includes methods for confirming the essentiality or importance of candidate genes, as well as methods for utilizing those genes to screen for new antibacterial drugs. The invention also includes the antibacterial agents identified using the disclosed methods, as well as methods of using the same for treating and preventing *Pseudomonas* infection.

4 Claims, 18 Drawing Sheets

Figure 1. Single-crossover recombination.
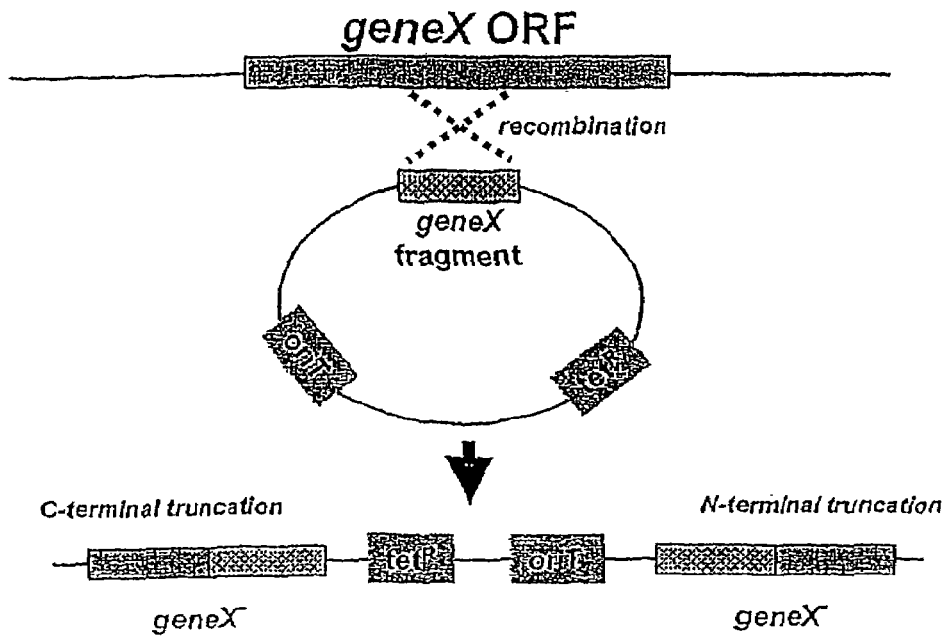
Figure 2. Promoter Swap.
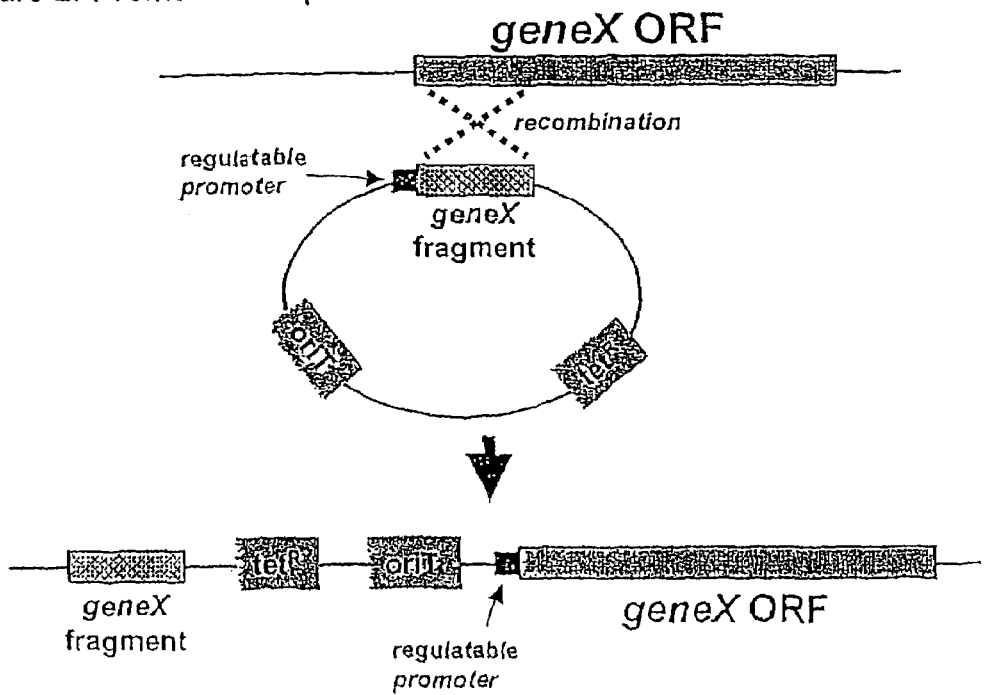

Distinct ORFs disrupted by Tn5 as a function of increasing transposon insertion sites mapped in ORFs of the PAO1 genome

SEQUENCE LISTING

<160> NUMBER OF SEQ ID NOS: 12

<210> SEQ ID NO 1
<211> LENGTH: 38
<212> TYPE: DNA
<213> ORGANISM: Artificial Sequence
<220> FEATURE:
<223> OTHER INFORMATION: primer

<400> SEQUENCE: 1
gggaattcca tatgatcaaa caaaggacac ttaaacgt                          38

<210> SEQ ID NO 2
<211> LENGTH: 34
<212> TYPE: DNA
<213> ORGANISM: Artificial Sequence
<220> FEATURE:
<223> OTHER INFORMATION: primer

<400> SEQUENCE: 2
ccggaattct tatgccagta cagctgaagg cgct                              34

<210> SEQ ID NO 3
<211> LENGTH: 43
<212> TYPE: DNA
<213> ORGANISM: Artificial Sequence
<220> FEATURE:
<223> OTHER INFORMATION: primer

<400> SEQUENCE: 3
gggaattcca tatgatgatc aaacaacgca ccttgaagaa cat                    43

<210> SEQ ID NO 4
<211> LENGTH: 37
<212> TYPE: DNA
<213> ORGANISM: Artificial Sequence
<220> FEATURE:
<223> OTHER INFORMATION: primer

<400> SEQUENCE: 4
ccggaattcc tacactgccg ccgccgggcg catatag                           37

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
agatctcaag ggttggtttg cgca                                         24

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
gaattctaat tctcatgttt gaca                                         24

<210> SEQ ID NO 7
<211> LENGTH: 25

```
<212> TYPE: DNA
<213> ORGANISM: Artificial Sequence
<220> FEATURE:
<223> OTHER INFORMATION: primer

<400> SEQUENCE: 7
ctcaggcatg cataatgtgc ctgtc                                          25

<210> SEQ ID NO 8
<211> LENGTH: 28
<212> TYPE: DNA
<213> ORGANISM: Artificial Sequence
<220> FEATURE:
<223> OTHER INFORMATION: primer

<400> SEQUENCE: 8
aagcttctcc tgttagccca aaaaaacg                                       28

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
gcgcgcggac gaaagtaaac ccactgg                                        27

<210> SEQ ID NO 10
<211> LENGTH: 34
<212> TYPE: DNA
<213> ORGANISM: Artificial Sequence
<220> FEATURE:
<223> OTHER INFORMATION: primer

<400> SEQUENCE: 10
aagcttattc agaaggttag cccaaaaaaa cggg                                34

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
aagcttatga tcaaacaacg cacctt                                         26

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
tctagaagcg ctgccatcca tgatcgg                                        27
```

ESSENTIAL AND IMPORTANT GENES OF *PSEUDOMONAS AERUGINOSA* AND THE USE THEREOF TO DESIGN OR IDENTIFY ANTIBACTERIAL AGENTS

CROSS REFERENCE RELATED TO RELATED APPLICATIONS

This application is a continuation-in-part of co-pending application Ser. No. 11/176,497 filed Jul. 8, 2005, which is a continuation of co-pending application Ser. No. 11/014,899 filed Dec. 20, 2004, which is a continuation of application Ser. No. 10/480,838, filed Dec. 15, 2003 which is a National Stage application of PCT/US02/19153 filed Jun. 17, 2002, which was published in English under PCT Article 21(2) on Dec. 27, 2002. PCT/US02/19153 claims the benefit of U.S. Provisional Ser. No. 60/298,109, filed on Jun. 15, 2001 and U.S. Provisional Ser. No. 60/372,095, filed on Apr. 15, 2002. This application also is a continuation-in-part of co-pending application Ser. No. 10/511,151 filed Oct. 14, 2004, which is a National Stage application of PCT/US02/35518 filed Nov. 5, 2002. PCT/US02/35518 claims the benefit of U.S. Provisional application Ser. No. 60/327,095 filed Apr. 15, 2002. Each of these applications is incorporated in its entirety by reference herein.

FIELD OF INVENTION

The present invention relates to the identification of essential and important genes in *Pseudomonas aeruginosa*, and the use thereof in screening assays and diagnostic methods to identify, evaluate or design antibacterial agents useful for the treatment of *Pseudomonas* infections. Such agents are particularly useful in preventing and treating opportunistic infections in immunocompromised individuals and for treating and preventing pulmonary infections in patients having cystic fibrosis disease. Also disclosed is a Bayessian statistical model that may be utilized to increase the statistical confidence that any given gene identified using the disclosed methodology is essential.

BACKGROUND OF INVENTION

*Pseudomonas aeruginosa* is a versatile Gram-negative bacterium that is able to adapt to and thrive in many ecological niches, from water and soil to plant and animal tissues. The bacterium is capable of utilizing a wide range of organic compounds as food sources, thus giving it an exceptional ability to colonize ecological niches where nutrients are limited, such as soil, marshes and coastal marine habitats. Hardalo, C. & Edberg, S. C. *Pseudomonas aeruginosa*: assessment of risk from drinking water. *Crit. Rev. Microbiol.* 23,47-75 (1997). It also forms biofilms on wet surfaces such as those of rocks and soil. Costerton, J. W., Stewart, P. S. & Greenberg, E. P. Bacterial biofilms: a common cause of persistent infections. *Science* 284,13181322 (1999).Aheam, D. G., Borazjani, R. N., Simmons, R. B. & Gabriel, M. M. Primary adhesion of *Pseudomonas aeruginosa* to inanimate surfaces including biomaterials. *Methods Enzymol.* 310, 551-557 (1999). Analysis of the *P. aeruginosa* genome has identified genes involved in locomotion, attachment, transport and utilization of nutrients, antibiotic efflux, and two component and other regulatory systems involved in sensing and responding to environmental changes. Because its natural habitat is the soil, where it exposed to bacilli, actinomycetes and molds, it has developed resistance to a variety of their naturally-occurring antibiotics.

The emergence of *P. aeruginosa* as a major opportunistic human pathogen during the past century may be a consequence of its resistance to the antibiotics and disinfectants that eliminate other environmental bacteria. *P. aeruginosa* is now a significant source of bacteraemia in burn victims, urinary-tract infections in catheterized patients, and hospital-acquired pneumonia in patients on respirators. Bodey, G. P., Bolivar, R., Fainstein, V. & Jadeja, L. Infections caused by *Pseudomonas aeruginosa*. *Rev. Infect. Dis.* 5, 279-313 (1983). It is also the predominant cause of morbidity and mortality in cystic fibrosis patients, whose abnormal airway epithelia allow long-term colonization of the lungs by *P. aeruginosa*. Thus, people with cystic fibrosis, burn victims, individuals with cancer and AIDS, and patients requiring extensive stays in intensive care units are particularly at risk of disease resulting from *P. aeruginosa* infection. *P. aeruginosa* is also a cause of a variety of different disorders including septicemia, urinary tract infections, pneumonia and chronic lung infections, endocarditis, dermatitis, osteochondritis, ear and eye infections, bone and joint infections, gastrointestinal infections and skin and soft tissue infections, including wound infections, pyoderma and dermatitis.

Cystic fibrosis is one of the most common fatal genetic disorders in the United States, affecting about 30,000 individuals. A comparable number of people in Europe also have CF. It is most prevalent in the Caucasian population, occurring in one of every 3,300 live births. The gene involved in cystic fibrosis was identified in 1989 and codes for a protein called the cystic fibrosis transmembrane conductance regulator (CFTR). This protein, normally produced in a number of tissues throughout the body, regulates the movement of salt and water in and out of these cells. One hallmark of CF is the presence of a thick mucus secretion that clogs the bronchial tubes in the lungs and plugs the exit passages from pancreas and intestines, leading to loss of function of these organs and resulting in a predisposition toward chronic bacterial infections. *Pseudomonas aeruginosa*, having a propensity to live in warm, wet environments, is a particular problem for CF patients, whose lungs typically become colonized (inhabited long-term) by *P. aeruginosa* before their 10th birthday. Although antibiotics can decrease the frequency and duration of these attacks, resistant bacteria are quick to develop and the bacteria are never completely eradicated from the lung. More effective antibiotics are necessary for improving lung function and quality of life for CF patients for extended time periods.

*Pseudomonas aeruginosa* is notorious for its resistance to antibiotics and is, therefore, a particularly dangerous and dreaded pathogen. Todor, K. 2000 *Pseudomonas aeruginosa*, University of Wisconsin-Madison, available on Apr. 25, 2001 at the URL address: http file type, www host server, domain name bact.wisc.edu, microtextbook/disease directory. The permeability barrier afforded by its outer membrane LPS also contributes to its natural antibiotic resistance, as do the presence of two antibiotic resistance plasmids, both R-factors and RTFs, which are commonly transferred between cells by the bacterial processes of transduction and conjugation. Only a few antibiotics are effective against *Pseudomonas*, including tobramyocin (TOBI; Chiron), fluoroquinolone, gentamicin and imipenem, and even these antibiotics are not effective against all strains.

*Pseudomonas aeruginosa* disease generally begins with some alteration or circumvention of normal host defenses and may involve several different virulence determinants. Todor, 2000, supra. The ultimate *Pseudomonas* infection may be seen as composed of three distinct stages: (1) bacterial attachment and colonization; (2) local invasion; (3) disseminated systemic disease. Particular bacterial determinants of virulence mediate each of these stages and are ultimately responsible for the characteristic syndromes that accompany the disease. For instance, *Pseudomonas* utilize fimbriae or pili to adhere to the epithelial cells, apparently via binding to specific galactose or mannose or sialic acid receptors on epithelial cells. Fimbrial adherence may be an important step in *Pseudomonas* keratitis and urinary tract infections, as well as infections of the respiratory tract. Mucoid strains, which produce an a exopolysaccharide (alginate) have an additional or alternative adhesin which attaches to the tracheobronchial mucin (N-acetylglucosamine). Therefore, mucoid strains of *P. aeruginosa* are commonly seen in lung infections.

The ability of *P. aeruginosa* to invade tissues depends upon its resistance to phagocytosis and the host immune defenses, and the extracellular enzymes-and toxins that break down physical barriers and otherwise contribute to bacterial invasion. Todor, 2000, supra. For instance, *Pseudomonas* elastase cleaves collagen, IgG, IgA, and complement, and also lyses fibronectin to expose receptors for bacterial attachment on the mucosa of the lung. Alkaline protease interferes with fibrin formation and lyses fibrin. Together, elastase and alkaline protease destroy the ground substance of the cornea and other supporting structures composed of fibrin and elastin. Elastase and alkaline protease together are also reported to cause the inactivation of ganmna Interferon (IFN) and Tumior Necrosis Factor (TNF).

*P. aeruginosa* produces three other soluble proteins involved in invasion, including a cytotoxin (MW 25,000) and two hemolysins. Todor, 2000, supra. The cytotoxin is a pore-forming protein originally named leukocidin because of its effect on neutrophils, but it appears to be cytotoxic for most eukaryotic cells. Of the two hemolysins, one is a phospholipase and the other is a lecithinase. They appear to act synergistically to break down lipids and lecithin. The cytotoxin and hemolysins contribute to invasion through their cytotoxic effects on eukaryotic cells.

*Pseudornonas aeruginosa* also produces two extracellular protein toxins, Exoenzyme S and Exotoxin A. Exoenzyme S may act to impair the function of phagocytic cells in the bloodstream and internal organs to prepare for invasion by *P. aeruginosa*, and is typically produced by bacteria growing in burned tissue. Exotoxin A is partially identical to diphtheria toxin, and exhibits a necrotizing activity at the site of bacterial colonization and is thereby thought to contribute to the colonization process. Indirect evidence involving the role of exotoxin A in disease is seen in the increased chance of survival in patients with *Pseudomonas* septicemia that is correlated with the titer of anti-exotoxin A antibodies in the serum.

While therapeutic measures aimed at any of the above virulence factors may help to slow the progression of an infection and may be useful in combined therapeutic regimens, given the variety of virulence factors of *P. aeruginosa*, antibacterial agents that inhibit growing bacteria by interacting with essential genes and essential gene products are necessary. Although, this is not to say that genes encoding virulence factors would not be essential to survival in particular niches or environments, emphasizing the importance of screening for gene essentiality in various pathogenic environments. See, e.g., Coulter et al., 1998, *Staphylococcus aureus* genetic loci impacting growth and survival in multiple infection environments, Mol. Microbiol. 30(2): 393-404. However, as *P. aeruginosa* becomes more and more resistant to existing antibacterial agents, new compounds are required.

Indeed, reports of bacterial strains resistant to the most powerful known antibiotics are becoming more common, signaling that new antibiotics are needed for all bacteria, not only *P. aeruginosa*. For instance, the United States Center for Disease Control recently announced that one of the most powerful known antibiotics, vancomycin, was unable to treat an infection of *Staphylococcus aureus* (staph), an organism commonly found in the environment and responsible for many nosocomial infections. If this trend continues, some have warned that we could return to a time when a common bacterial infection is a life threatening matter. See Zyskind et al., WO 00/44906, published Aug. 3, 2000.

Historically, however, the identification of new antibacterial drugs has been painstaking and laborious with no guarantee of success. Traditional methods involve blindly and randomly testing potential drug candidate molecules, with the hopes that one might be effective. Today, the average cost to discover and develop a new drug is nearly $500 million, and the average time is 15 years from laboratory to patient. New identification and screening methods that shorten and improve this process are much needed.

A newly emerging technique for identifying new antibacterial agents is to first identify gene sequences and proteins required for the proliferation of bacteria, or "essential" genes and proteins, and then conduct a biochemical and structural analysis of that target gene or protein in order to derive compounds that interact with the target. Such methodology employs molecular modeling techniques, combinatorial chemistry and other means to design candidate drugs, and offers a more directed alternative to merely screening random compounds with the hope that one might be suitable for a particular bacterium.

Nevertheless, even this preferred approach presents obstacles including the identification of essential genes and proteins, and the design of new assays for the genes thus identified in order to efficiently screen candidate compounds. Several groups have proposed systems for the identification of essential genes. For instance, Zyskind and colleagues propose a method of identifying essential genes in *Escherichia coli* by subcloning a library of *E. coli* nucleic acid sequences into an inducible expression vector, introducing the vectors into a population of *E. coli* cells, isolating those vectors that, upon activation and expression, negatively impact the growth of the *E. coil* cell, and characterizing the nucleic acid sequences and open reading frames contained on the subclones identified. See WO 00/44906, herein incorporated by reference. The disadvantage of this method is that the overexpression of nonessential genes can also negatively impact the cell, particularly the overexpression of membrane proteins and sugar transport proteins that are not necessary for growth where alternative carbon sources exist. Such proteins typically become trapped in membrane export systems when the cell is overloaded, and would be identified by this methodology. See Muller, FEMS Microbiol. Lett. 1999 Jul. 1;176 (1):219-27.

Another group proposes the identification of growth conditional mutants, and more specifically temperature sensitive (ts) mutants, as a means to identify essential genes in *Staphylococcus aureus*. See Benton et al., U.S. Pat. No. 6,037,123, issued Mar. 14, 2000, herein incorporated by reference. Each gene is identified by isolating recombinant bacteria derived from growth conditional mutant strains, i.e., following introduction of a vector containing a library of nucleic acid sequences, which would grow under non-permissive conditions but which were not revertants. These recombinant bacteria were found to contain DNA inserts that encoded wild type gene products that replaced the function of the mutated gene under non-permissive growth conditions. By this method, Benton and colleagues were able to identify 38 loci on the *S. aureus* chromosome, each consisting of at least one essential gene.

The disadvantages of this method are first, the chemical employed to induce mutagenesis (diethyl sulfate, DES) is capable of causing several mutations in the same cell, thereby complicating interpretation of the results. Second, the method is particularly labor intensive in that one must painstakingly analyze replica plates of individual colonies grown at permissive and non-permissive temperatures, where replica plates include both mutant and non-mutant cells. Thus, employing the appropriate level of mutagen to achieve a balance between minimizing the number of non-mutant colonies one must screen in order to identify one mutant, while at the same time avoiding multiple mutations in the same cell, may be an arduous task.

Another group has proposed a transposon mutagenesis system for identifying essential genes called "GAMBIT" ("genomic analysis and mapping by in vitro transposition"), and has used the system to identify essential genes first in the gram positive bacteria *Haemophilus influenzae* and *Streptococcus pneumoniae*, and more recently in *Pseudomonas aeruginosa*. See Akerley et al., Systematic identification of essential genes by In vitro mariner mutagenesis, Proc. Natl. Acad. Sci USA 95(15): 8927-32; Wong and Mekalanos, 2000, Proc. Natl. Acad. Sci. USA 97(18): 10191-96; and Mekalanos et al., U.S. Pat. No. 6,207,384, issued Mar. 27, 2001, herein incorporated by reference. GAMBIT involves first isolating and purifying specific genomic segments of approximately 10 kilobases using extended-length PCR, and creating a high density transposon insertion map of the isolated region using Himar1 transposon mutagenesis. The transposon insertions are then transferred to the chromosome following transformation of the bacteria with the transposon containing vectors, and selection for the antibiotic resistance marker on the transposon. The position of each transposon insertion with respect to a given PCR primer is then determined by genetic footprinting, i.e., by amplifying sub-PCR products using one of the original PCR primers and a primer that recognizes an internal site in the Himer1 transposon. By analyzing the length of PCR fragments thus identified, it is possible to identify regions that are devoid of transposon insertions, thereby signaling regions that might contain essential genes.

While the GAMBIT method is a good technique for looking at a small region of the genome for essential genes, it would be extremely labor intensive to use this method for analyzing the entire genome. This is particularly true for *P. aeruginosa*, whose genome (~6 megabases) is about 70% greater in size than the *H. influenzae* genome (~1.8 megabases). Furthermore, GAMBIT would not be readily applicable to use in organisms that are less recombinogenic than *H. influenzae*. Indeed, while the *H. influenzae* genome contains about 1700 protein coding genes, *P. aeruginosa* contains about 5570. According to U.S. Pat. No. 6,207,384, one would need to clone and mutagenize the 6 million base pair genome of *P. aeruginosa* in 10,000 base pair fragments, isolating and characterizing 400-800 mutants per 10,000 base pair fragment. Generating $6 \times 10^5$ mutants and characterizing them via PCR on gels would require a significant investment of labor, materials and time.

Another group at Abbott Laboratories has proposed a genome scanning method for identification of putative essential genes in *H. influeinzae*, whereby random transposon insertions are mapped and analyzed to identify open reading frames containing no insertion in order to identify putative essential genes. Reich et al., 1999, Genome Scanning in *Haemophilus influenzae* for Identification of Essential Genes, J. Bacteriol. 181(16): 4961-68. However, even though transposon insertions were isolated that spanned the whole genome, the authors employed a genomic footprinting technique similar to that used in GAMBIT to map insertions in a short contiguous region of the chromosome. The method further employs the methods of mutation exclusion and zero time analysis in order to monitor the fate of individual insertions after transformation in growing culture, which looks at individual insertions on a case-by-case basis. Again, such techniques would be extremely labor-intensive for the *P. aeruginosa* genome, which is 70% larger than the genome of *H. influenzae*.

Wong and Mekalanos also proposed identifying essential genes in *P. aeruginosa* by starting with the knowledge of three essential genes in *H. influenzae* and using genetic footprint analysis to determine if the homologues of these genes are essential in *P. aeruginosa*. Of three homologues tested, only one was unable to accommodate a transposon insertion. See Wong and Mekalanos, supra. Such results underscore the fact that a gene that is shown to be essential in one species will not necessarily be essential in another, given that some gene products may fulfill different functional roles in different species. Furthermore, given the larger coding capacity of the *P. aeruginosa* genome relative to that of other bacteria, it would not be surprising for *P. aeruginosa* to possess an increase in redundant gene functions, thereby decreasing the actual number of essential genes, and making them more difficult to identify.

Another method is entitled Transposon Mediated Differential Hybridisation (TMDH), which is disclosed in WO 01/07651, herein incorporated by reference. This method entails (i) providing a library of transposon mutants of the target organism; (ii) isolating polynucleotide sequences from the library which flank inserted transposons; (iii) hybridising said polynucleotide sequences with a polynucleotide library from said organism; and (iv) identifying a polynucleotide in the polynucleotide library to which said polynucleotide sequences do not hybridise in order to identify an essential gene of the organism. However, the problem with this methodology is that it has a high propensity to lead to false positives, and many essential genes will be missed. Furthermore, the method does not yield any detailed information regarding the loci disrupted by transposons, or whether they were hit more than once.

Thus, there is a great need for more efficient methods to identify essential genes, particularly in *P. aeruginosa*, so that new antibacterial agents may be designed therefrom for use in treatment of *P. aeruginosa* infections.

SUMMARY OF INVENTION

The present inventors have devised a database of potential essential or otherwise important genes in *P. aeruginosa*, which may be used to verify essentiality and design antibacterial agents active against the targets thus identified In particular, the inventors have isolated and mapped a library of at least about 5,000 to at least about 14,000 transposon insertions in the genome of *P. aeruginosa*, and more preferably a library of at least about 8000 to at least about 14,000 transposon insertions, and even more preferably a library of at least about 10,000 to at least about 14,000 transposon insertions, using the recently published *P. aeruginosa* gene sequence. The map thus generated was used to form a database of approximately 1500 to 3000 open reading frames, or more preferably about 1500 to 2000 open reading frames, for which no transposon insertions could be obtained, each of which possibly represents an essential gene required for growth and proliferation of *P. aeruginosa* on rich media, or an important gene, the mutation of which results in an attenuated growth mutant. Also disclosed is a Bayessian statistical model that may be utilized to increase the statistical confidence that any given gene identified using the disclosed methodology is essential.

Thus, one aspect of the invention is a database of putative essential or otherwise important genes, defined by the absence of transposon insertions in those genes in a High Throughput Transposon Insertion Map (HTTIM) database comprising about 10,000 to about 14,000 transposon insertions in the genome of *Pseudomnonas aeruginosa*. Minimally, such a database comprises approximately 1800 open reading frames (ORFs), each of which may be further tested for essentiality using a variety of tests disclosed herein. However, predictions of essentiality or importance may be bolstered based on length of the ORF and predicted function and other statistical factors, thereby providing for more narrow databases of putative essential genes. Thus, the invention also includes databases that are more narrow and comprise only those genes for which essentiality or importance may be predicted with at least an 80% confidence level, and include at least about 850 to about 875 genes. The invention also includes databases assigned a confidence level of about 85% and including at least about 675 to about 700 genes. The invention further includes databases assigned a confidence level of about 90% including at least about 475 to about 500 genes. Further, the invention includes databases assigned a confidence level of about 95% and including at least about 200 to 250 genes.

The transposon insertion map and database of putative essential or otherwise important open reading frames (ORFs) obtained may be used to confirm the essentiality or importance of genes, for example by integration knock outs in the presence of chromosomal complementation or by integration and activation of a regulatable promoter. An "essential" gene is one that cannot be "knocked out," i.e. for which null mutants having complete absence of the gene product are not viable. This does not mean, however, that such genes could not tolerate point mutations or truncations that preserve sufficient gene product function so as to enable cell growth and survival. Essential genes are to be distinguished from "important" genes, which are also included in the present invention, in that a "knock out" of an important gene does not lead to cell death but rather results in an attenuated growth mutant. Such genes may be included in the database of open reading frames not hit by random transposon mutagenesis as described herein, because attenuated growth colonies may be significantly smaller than the average *P. aeruginosa* colony and may have been overlooked when transposon insertion mutants were picked to generate the high throughput transposon insertion database (HTTIM).

Nevertheless, important gene products may interact with or regulate other genes, gene products or cellular processes that are essential, thereby making such gene products appropriate targets for drug design. Moreover, most drugs don't effectively kill all the pathogenic bacteria in the body, rather, they kill or growth attenuate a portion of the bacteria, empowering the immune system to target the remainder. Hence, important genes that, when targeted with an antibacterial agent, result in attenuated growth, are also targets for the antibacterial drugs of the present invention.

The invention also includes a database of attenuated growth mutants identified from the HTTIM transposon database. The genes marked by such mutations are of the same class of importance as the "important" genes identified in the no-hit database of genes, except that the growth attenuated nature of such transposon mutants was discovered at the transposon mutagenesis stage, rather than at the stage where essentiality is tested via targeted knock out. Thus, genes that when mutated confer attenuated growth may be identified from two sources: (1) from the library of open reading frames that did not receive a transposon insertion during HTTIM but were subsequently identified as an important gene when essentiality was tested via knock out and/or promoter swap strategies, and (2) from the HTTIM database itself when in the process of accumulating transposon insertion mutants it was observed that a particular insertion conferred an attenuated growth phenotype.

Such attenuated mutants grow more slowly than wild type, and may grow more slowly due to reduced expression of an essential gene, i.e., transposon is in gene that regulates expression of an essential gene, or due to expression of a truncated form of an essential gene, i.e., transposon is in the essential gene itself and leads to expression of a truncated mRNA. For example, mutants that show a higher drug susceptibility could be the result of insertions in a gene that potentiates resistance, such an efflux pump, or due to reduced expression of essential genes involved in the mechanism of action of the drug. Expression of mutated forms of essential and important genes may make the cell more susceptible to compounds that inhibit that particular gene or gene product, and may allow the identification of antibacterial agents with greater sensitivity. Furthermore, screening in whole cells overcomes the potential problems of uptake and efflux that are sometimes an issue for compounds identified via enzyme-based assays.

The essential and important genes of the invention may be used to design, screen for and evaluate potential antibacterial agents for the purpose of developing new treatments for *P. aeruginosa* infection. Antibacterial agents identified according to the invention may have activity against the gene or against the corresponding gene product or metabolic pathways requiring the gene product. For instance, antibacterial agents according to the invention may include antisense nucleic acids or regulatory proteins that bind to open reading frames, to upstream polar sequences or to promoters that drive expression of the genes encoded by such open reading frames. Active agents according to the invention may also include antibodies or proteins that bind to proteins encoded by open reading frames, or to transcriptional or translational regulators of such genes or proteins, or to binding partners of such proteins. Agents may also be chemical compounds designed following molecular modeling of essential gene products according to the invention, or mutant proteins designed therefrom that compete with the essential wild type protein for reactive cell components or for interacting nutrients, as well as agents from random chemical.

The present invention therefore includes methods and assays for identifying antibacterial agents having specificity for the essential or important open reading frames identified, or to genes and proteins that interact with such open reading frames or the products encoded thereby. Once essential and important open reading frames are identified, antibacterial agents may be identified using the assays and methods described herein, or by any suitable assay. Such assays may vary depending on the function delineated for each essential locus, as would be apparent to those of skill in the art. For instance, enzyme assays may be designed based on the predicted function of essential and important genes in order to define classes of inhibitors to be tested. Also, random chemical libraries may be screened for activity against the isolated genes or gene products. Cell lines may be designed or isolated that demonstrate reduced expression of essential genes, thereby providing a sensitive screening tool for inhibitors that effect the activity of that gene or gene product as it functions in the cell. Such cell lines may be devised from cells having transposon insertions that lead to attenuated growth, or may be constructed by the promoter swap techniques described herein, by using a regulatable promoter that can be used to increase gene expression, allowing for confirmation of target specificity. Here, the minimal inhibitory concentration of the inhibitor is directly related to the expression level of the target gene, such that under low expression, an attenuated growth cell is more susceptible to an inhibitor than the wild type strain, and as you raise the expression level, the minimum inhibitory concentration (MIC) increases. The MIC shift will be consistent when the inhibitor acts on the regulated target.

Active agents and compounds can be formulated into pharmaceutical compounds and compositions, effective for treating and preventing *Pseudomonas* infections in accordance with the methods of the invention. Such therapy will be particularly useful in the hospital setting for preventing and treating nosocomial infections, and for administering to cystic fibrosis patients to improve lung function and quality of life. Depending on the activity of the essential or important gene targeted, such agents could also be useful in treating all types of *Pseudomonas* infections ranging from bacteraemia and septicemia, urinary-tract infections, pneumonia and chronic lung infections, burn infections, cancer, AIDS, endocarditis, dermatitis, osteochondritis, ear and eye infections, bone and joint infections, gastrointestinal infections and skin and soft tissue infections, including wound infections, pyoderma and dermatitis. Further, the invention provides pharmaceutical compositions appropriate for use in methods of treating bacterial infections described above.

BRIEF DESCRIPTION OF THE DRAWINGS

FIG. 1. Depiction of a single crossover recombination event resulting in integration of a plasmid into the bacterial chromosome. Isolation of such recombinants indicates that the targeted gene is not essential.

FIG. 2. Single crossover and integration of a plasmid resulting in the replacement of a wild type promoter with a regulatable promoter.

FIG. 10. Histogram depicting the number of ORFs in the *P. aeruginosa* genome.

FIG. 16.

Figure 3:
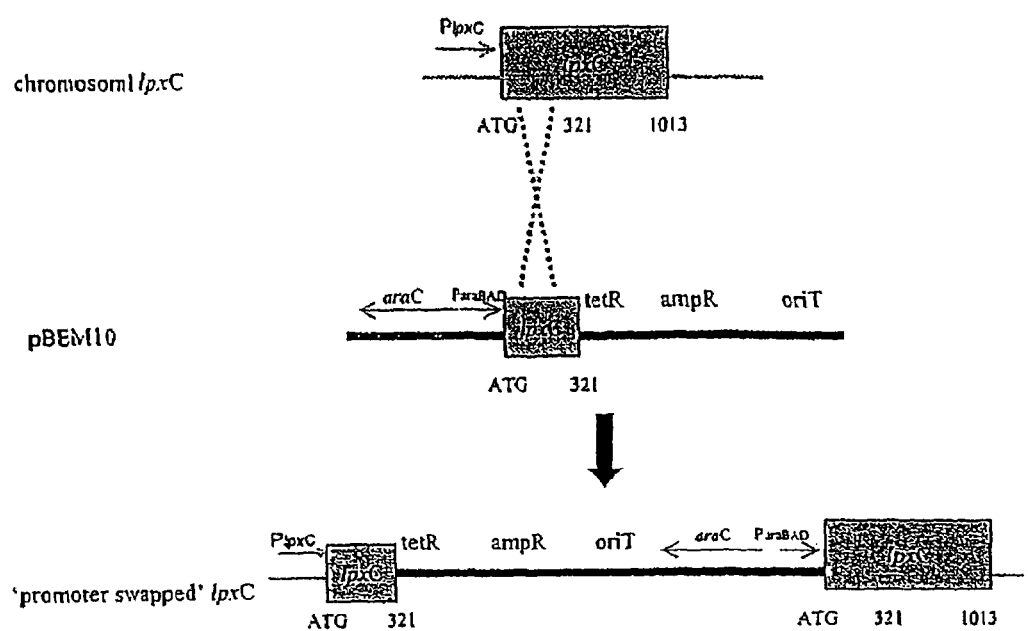
FIG. 3. Depiction of the 'promoter swap' strategy, using transformation of pBEM10 into *P. aeruginosa* in order to replace the lpxC promoter with the arabinose araBAD promoter, thereby allowing modulation of its lpxC expression by the use of a simple sugar, arabinose.

The essential and important open reading frames identified in the present invention were originally part of a library of putative nucleic acid sequences generated from *P. aeruginosa* strains PA01 and PAK. See Table 1. Nevertheless, it is expected that the genes identified will also be essential or important in related *P. aeruginosa* strains as well as other *Pseudomonas* species, given the low sequence diversity that exists between *P. aeruginosa* strains of widely diverse environments and the pronounced structural and functional homology of gene products. See, e.g., Spangenberg et al., 1998, Structural and functional implications of sequence diversity of *Pseudomonas aeruginosa* genes oriT, ampC and fliC, Electrophoresis 19(4): 545-50; Ruimy et al., 2001, Genetic diversity of *Pseudomnonas aeruginosa* strains isolated from ventilated patients with nosocomial pneumonia, cancer patients, bacteremia, and environmental water, Infect. Immun. 69(1): 584-8. For instance, comparative sequencing of several *P. aeruginosa* genes from several environmental and clinical isolates revealed the sequence diversity to be about one order of magnitude lower than in comparable housekeeping genes from *Salmonella*. See Kiewitz and Tummler, 2000, Sequence diversity of *Pseudomonas aeruginosa*: impact on population structure and genome evolution, J. Bacteriol. 182(11): 3125-35. Thus, it is expected that agents identified as antibacterial based on their interaction with genes or gene products of *P. aeruginosa* PA01 or PAK will be broadly applicable as antibacterial agents against a variety of *Pseudomonas* species as well as other bacteria including but not limited to *Escherichia, Hemophilts, Vibrio, Borrelia, Enterococcus, Heliobacter, Legionella, Mycobacterium, Mycoplasma, Neisseria, Staphylococcus, Streptococcus*, etc.

Thus, the present invention encompasses an isolated nucleic acid molecule comprising a nucleic acid sequence encoding a polypeptide having at least 80% sequence identity to a polypeptide encoded by a nucleic acid sequence selected from the group consisting of the *Pseudomonas aeruginosa* open reading frames (ORFs) listed in Table 1. More preferably, the present invention encompasses an isolated nucleic acid molecule comprising a nucleic acid sequence encoding a polypeptide having at least about 85 to 90% sequence identity to a polypeptide encoded by a nucleic acid sequence selected from the group consisting of the *Pseudomonas aeruginosa* open reading frames (ORFs) listed in Table 1. Even more preferably, the present invention encompasses an isolated nucleic acid molecule comprising a nucleic acid sequence encoding a polypeptide having at least about 90 to about 95% sequence identity to a polypeptide encoded by a nucleic acid sequence selected from the group consisting of the *Pseudomonas aeruginosa* open reading frames (ORFs) listed in Table 1.

In particular, the invention encompasses isolated nucleic acid molecules comprising nucleic acid sequences encoding polypeptides having at least 80% sequence identity, or more preferably at least about 85 to 90 to 95% identity, to a polypeptide encoded by an essential or important nucleic acid sequence selected from the group consisting of the *Pseudomonas aeruginosa* open reading frames (ORFs) listed in Table 1, wherein essentiality or importance of said nucleic acid sequence is determined by integration knock-out coupled with extra-chromosomal complementation. Likewise, the invention encompasses isolated nucleic acid molecules comprising nucleic acid sequences encoding polypeptides having at least 80% sequence identity, or more preferably at least about 85 to 90 to 95% identity, to a polypeptide encoded by an essential nucleic acid sequence selected from the group consisting of the *Pseudonmonas aeruginosa* open reading frames (ORFs) listed in Table 1, wherein essentiality or importance of said nucleic acid sequence is determined by integration of a regulatable promoter into the gene, or via any other suitable method.

In one embodiment, the polynucleotides of the invention are recombinant. Recombinant polynucleotides of the invention include proteins of genomic, cDNA, semisynthetic, or synthetic origin, which, by virtue of its origin or manipulation (1) is not associated with all or a portion of a polynucleotide with which it is associated in nature; (2) is linked to a polynucleotide other than that to which it is lined in nature; or (3) does not occur in nature.

Given that the library of nucleic acid sequences encompassed in Table 1 provides an unprecedented tool useful for the identification of essential and otherwise important genes in *Pseudomonas* and the construction and isolation of attenuated mutants, the present invention includes a library of nucleic acid sequences consisting essentially of nucleic acid sequences having at least 70% sequence identity, or more preferably at least about 80 to 90 to 95% identity, to a nucleic acid sequence selected from the group consisting of the *Pseudomonas aeruginosa* open reading frames (ORFs) listed in Table 1, wherein said library of nucleic acid sequences is employed to identify essential or otherwise important genes or to construct or isolate attenuated mutants in *Pseudomonas*.

Figure 9:
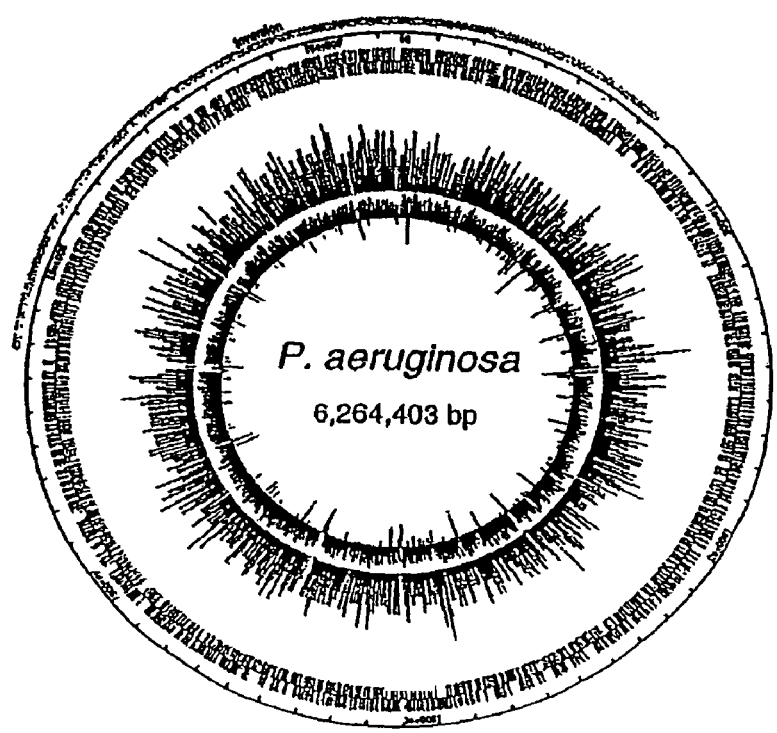
FIG. 9. A circular map of the *P. aeruginosa* genome showing distribution of transposon insertion sites constituting a HTTIM of the invention, and demonstrating the random nature of the transposon employed. The length of the bars radiating outward from the center of the circular map reflect the number of transposon insertions per non-overlapping kilobase.

Also encompassed in the invention is a map of at least about 10,000 to about 14,000 transposon insertions in the genome of *Pseudomonas aeruginosa* (High-Throughput Transposon Insertion Database or HTTIM), wherein said map is useful for identifying genes that are essential or important for survival of said *Pseudomonas aeruginosa*, i.e., by permitting the generation of a database of open reading frames that do not contain a transposon insertion. FIG. 9 contains a circular map of the *P. aeruginosa* genome depicting 12,000 to 13,000 transposon insertion sites constituting a HTTIM of the invention, and demonstrates the random nature of the transposon employed. The length of the bars radiating outward from the center of the circular map reflect the number of transposon insertions per non-overlapping kilobase. Table 3 contains a list of 13,515 specific Tn5 transposon insertion sites generated in either PAK or PA01, with the 473 mutants 12516-13043 being identified as attenuated for growth.

Thus, the databases and libraries disclosed herein may be used to formulate useful subsets of these libraries and databases. Accordingly, the invention includes subsets of the databases and libraries disclosed. For instance, mutants 12516-13043 are identified as attenuated for growth and as such, the genes in this subset could be useful drug targets. Accordingly, this group of 473 mutants from the HTTIM database of 13,515 transposon hits provides a useful subset database for comparing homologies with essential genes of other organisms, for computer modeling of potential antibacterial agents, etc. A particularly useful database subset is one containing essential genes from *P. aeruginosa* that are also identified as essential in other Gram negative or Gram positive bacteria. Indeed, genes that have essential homologs in other bugs are likely to provide useful targets for broad spectrum antibacterial agents, i.e., agents that have broad spectrum activity as an antibacterial agent. Genes in the putative essential or important gene database have already been identified via BLAST or other database analyses, and constitute an exemplary subset database of the present invention. See Table 4.

Further, the databases and subset databases of the present invention may also be used as comparative tools with other like databases or database subsets to identify broad spectrum. For instance, particularly envisioned is an embodiment wherein the database of putative essential and important genes identified in *P. aeruginosa* is cross-referenced with a similar database formed from *S. aureus*, wherein homologues present in both databases signal a potential target for a broad spectrum antibacterial agent. Cross-referencing between *P. aeruginosa* and *S. aureus* in particular will identify antibacterial targets for identifying broad spectrum antibiotics active against both Gram negative and Gram positive bacteria. However, databases derived from any bacteria could be employed in such comparisons, as well as databases formed from yeast, fungi, mycoplasma, and other potential pathogens.

Also encompassed in the invention is the use of essential and important genes and the corresponding proteins expressed thereto in the design of vaccines for eliciting prophylactic or therapeutic immune responses against *Pseudomnonas aeruginosa*.

Such vaccines will typically comprise a *Pseudomonas aeruginosa* protein antigen or fragment or variant thereof encoded by an essential gene. Additionally, such antigens will preferably be a protein expressed on the surface of the bacteria.

Such vaccines will typically comprise a *Pseudomonas aeruginosa* protein antigen or fragment or derivative thereof encoded by an essential or important gene. Preferably, the protein antigen expressed from a recombinant polynucleotide.

Where the invention is directed to a fragment of a protein encoded by an essential or important gene, said fragment is preferably at least 8 to 12 amino acids long, and even more preferably at least about 20 to 30 amino acids long. Preferably, the fragment comprises either a B cell or a T cell epitope.

Where the invention is directed to a derivative of a protein encoded by an essential or important gene, said derivative contains one or more amino acid substitutions, additions or deletions. Preferably, the amino acid substitutions are conservative amino acid replacements. Conservative amino acid replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonably predictable that an isolated replacement of a leucine with an isoleucine or valine, an asparate with glutamate, a threonine with a serine, or a similar conservative replacement of an amino acid with a structurally related amino acid will not have a major effect on the biological activity. Polypeptide molecules having substantially the same amino acid sequence as the protein by possessing minor amino acid substitutions that do not substantially affect the functional aspects are encompassed with the scope of derivatives of the proteins of the invention.

The polypeptide fragment or derivative is preferably immunologically identifiable with the polypeptide encoded by the essential or important gene. The polypeptide fragment or derivative is preferably immunogenic and is able to cause a humoral and/or cellular immune response, either alone or when linked to a carrier, in the presence or absence of an adjuvant. The polypeptide fragment or derivative may be fused to or incorporated into another polypeptide sequence. This other polypeptide sequence may include one or more other proteins, fragments or derivatives thereof encoded by an essential or important gene. The other polypeptide sequence may also include a polypeptide sequence which allows for presentation of the polypeptide fragment or derivative.

Accordingly, the present invention encompasses an isolated polypeptide and fragments and derivatives thereof, wherein said polypeptide has at least 80% sequence identity to a polypeptide encoded by a nucleic acid sequence selected from the group consisting of the *Pseudomonas aeruginosa* open reading frames (ORFs) listed in Table 1. More preferably, the present invention encompasses an isolated polypeptide and fragments and derivatives thereof, wherein said polypeptide has at least about 85 to 90% sequence identity to a polypeptide encoded by a nucleic acid sequence selected from the group consisting of the *Pseudomonas aeruginosa* open reading frames (ORFs) listed in Table 1. Even more preferably, the present invention encompasses an isolated polypeptide and fragments and derivatives thereof, wherein said polypeptide has at least about 90% to about 95% sequence identity to a polypeptide encoded by a nucleic acid sequence selected from the group consisting of the *Pseudomonas aeruginosa* open reading frames (ORFs) listed in Table 1.

In particular, the invention encompasses isolated polypeptides and fragments and derivatives thereof, wherein said polypeptides have at least about 80% sequence identity, or more preferably at least about 85 to 90 to 95% identity, to a polypeptide encoded by an essential or important nucleic acid sequence selected from the group consisting of the *Pseudomonas aeruginosa* open reading frames (ORFs) listed in Table 1, wherein the essentiality or importance of said nucleic acid sequence is determined by integration knock-out couple with extra-chromosomal complementation. Likewise, the invention encompasses isolated polypeptides and fragments and derivatives thereof, wherein said polypeptides have at least 80% sequence identify, or more preferably at least about 85 to 90 to 95% identity, to a polypeptide encoded by an essential nucleic acid sequence selected from the group consisting of the *Pseudomonas aeruginosa* open reading frames (ORFs) listed in Table 1, wherein essentiality or importance of said nucleic acid sequence is determined by integration of a regulatable promoter into the gene, or via any other suitable method.

Also encompassed in the invention are therapeutic and prophylactic vaccines that comprise ligands that specifically bind antigens encoded by essential or important genes identified according to the invention, for use in, for instance, passive immunization. Preferred ligands are antibodies and antibody fragments that specifically bind the antigen encoded by the essential gene. Such antibodies may be polyclonal or monoclonal. Types of antibodies and antibody fragments include by way of examples murine antibodies, chimeric, antibodies, humanized antibodies, Fab fragments, $Fab_2$ fragments and human antibodies and scFv's. Methods for producing antibodies and antibody fragments by recombinant and non-recombinant methods are well known to those skilled in the art. In some embodiments the antigen used in such passive immunization may be attached to a cytotoxic moiety, e.g., a radionuclide or other agent that is cytotoxic against the bacteria.

Further encompassed within the scope of the invention are cells or viral vectors that express on their surface a *Pseudomonas aeruginosa* essential gene, fragment or variant identified according to the invention.

In the case of prophylactic vaccines, the vaccine will comprise an immunogenic composition comprising a prophylactically effective amount of an antigen, antibody, cells or vector expressing an antigen encoded by an essential or important gene and will be formulated such that upon administration it elicits a protective immune response. In the case of therapeutic vaccines, the vaccine will comprise an immunogenic composition comprising a therapeutically effective amount of an antigen, antibody, cells or vectors expressing an antigen encoded by an essential or important gene and will be formulated such that upon administration it elicits a therapeutic immune response. Dosage effective amounts of prophylactic and therapeutic vaccines will be determined by known methods and will typically vary from about 0.00001 g/kg body weight to about 5-10 g/kg body weight.

The immunogenic compositions of the invention can be administered by known methods, i.e., mucosally or parenterally.

Suitable routes of mucosal administration include oral, intranasal (IN), intragastric, pulmonary, intestinal, rectal, ocular, and vaginal routes. Preferably, mucosal administration is oral or intranasal.

Where mucosal administration is used, the immunogenic composition is preferably adapted for mucosal administration. For instance, where the composition is administered orally, it may be in the form of tablets or capsules (optionally enteric-coated), liquid, transgenic plants, etc. Where the composition is administered intranasally, it may be in the form of a nasal spray, nasal drops, gel or powder. Where the antigen composition is adapted for mucosal administration, it may further be formulated such that the antigen remains stable, for instance by the use of carriers and excipients.

The immunogenic compositions of the invention can further comprise a mucosal adjuvant. Mucosal adjuvants suitable for use in the invention include (a) *E.coli* heat-labile enterotoxin ("LT"), or detoxified mutants thereof, such as the K63 or R72 mutants; (B) cholera toxin ("CT"), or detoxified mutants thereof; or (C) microparticles (i.e., a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone etc.); (D) a polyoxyethylene ether or a polyoxyethylene ester (see International patent application WO 99/52549); (E) a polyoxyethylene sorbitan ester surfactant in combination with an octoxynol (see International patent application WO 01/21207) or a polyoxyethylene alkyl ether or ester surfactant in combination with at least-one additional non-ionic surfactant such as an octoxynol (see International patent application WO 01/21152); (F) chitosan (e.g. International patent application WO 99/27960) and (G) an immunostimulatory oligonucleotide (e.g. a CpG oligonucleotide) and a saponin (see International patent application WO 00/62800). Other mucosal adjuvants are also available (e.g. see chapter 7 of *Vaccine design: the subunit and adjuvant aproach*, eds. Powell & Newman, Plenum Press 1995 (ISBN 0-306-44867-X).

Mutants of LT are preferred mucosal adjuvants, in particular the "K63" and "R72" mutants (e.g. see International patent application WO 98/18928), as these result in an enhanced immune response.

Microparticles are also preferred mucosal adjuvants. These are preferably derived from a poly(α-hydroxy acid), in particular, from a poly(lactide) ("PLA"), a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered antigen.

Antigen may be entrapped within the microparticles, or may be adsorbed to them.

Entrapment within PLG microparticles is preferred. PLG microparticles are discussed in further detail in Morris et al., (1994), Vaccine, 12:5-11, in chapter 13 of Mucosal Vaccines, eds. Kiyono et al., Academic Press 1996 (ISBN 012410587), and in chapters 16 & 18 of *Vaccine design: the subunit and adjuvant aproach*, eds. Powell & Newman, Plenum Press 1995 (ISBN 0-306-44867-X).

LT mutants may advantageously be used in combination with microparticle-entrapped antigen, resulting in significantly enhanced immune responses.

Suitable routes of parenteral administration include intramuscular (IM), subcutaneous, intravenous, intraperitoneal, intradermal, transcutaneous, and transdermal (see e.g., International patent application WO 98/20734) routes, as well as delivery to the interstitial space of a tissue.

The immunogenic compositions of the invention may be adapted for parenteral administration (e.g., in the form of an injectable, which will typically be sterile and pyrogen-free).

The immunogenic composition may further comprise a parenteral adjuvant. Parenteral adjuvants suitable for use in the invention include: (A) aluminum compounds (e.g. aluminum hydroxide, aluminum phosphate, aluminum hydroxyphosphate, oxyhydroxide, orthophosphate, sulfate etc. (e.g. see chapters 8 & 9 of *Vaccine design: the subunit and adjuvant aproach*, eds. Powell & Newman, Plenum Press 1995 (ISBN 0-306-44867-X) (hereinafter "Vaccine design"), or mixtures of different aluminum compounds, with the compounds taking any suitable form (e.g. gel, crystalling, amorphous etc.), and with adsorption being preferred; (B) MF59 (5% Squalene, 0.5% Tween 80, and 0.5% Span 85, formulated into submicron particles using a microfluidizer) (see Chapter 10 of *Vaccine design*; see also International patent application WO 90/14837); (C) liposomes (see Chapters 13 and 14 of *Vaccine design*); (D) ISCOMs (see Chapter 23 of *Vaccine design*); (E) SAF, containing 10% Squalane, 0.4% Tween 80, 5% pluronic-block polymer L121, and thr-MDP, either microfluidized into a submicron emulsion or vortexed to generate a larger particle size emulsion (see Chapter 12 of *Vaccine design*); (F) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21 (see Chapter 22 of *Vaccine design*), also known as Stimulon™; (H) ISCOMs, which may be devoid of additional detergent (International patent application WO 00/07621); (I) complete Freund's adjuvant (CFA) and incomplete Freund's adjuvant (IFA); (J) cytokines, such as interleukis (e.g. IL-1, IL-2, IL-4, IL-5, IL-6, IL-7, IL-12, etc.), interferons (e.g interferon-γ), macrophage colony stimulating factor, tumor necrosis factor, etc. (see Chapters 27 & 28 of *Vaccine design*); (K) microparticles (see above); (L) monophosphoryl lipid A (MPL) or 3-O-deacylated MPL (3dMPL) (e.g. chapter 21 of *Vaccine design*); (M) combinations of 3dWPL with, for example, QS21 and/or oil-in-water emulsions (European patent applications 0835318, 0735898 and 0761231); (N) oligonucleotides comprising CpG motifs (see Krieg (2000) Vaccine, 19:618-622; Krieg (2001) *Curr. Opin. Mol. Ther.*, 2001, 3:15-24; WO 96/02555, WO 98/16247, WO 98/18810, WO 98/40100, WO 98/55495, WO 98/37919 and WO 98/52581, etc.) I.e. containing at least one CG dinucleotide, with 5-methylcytosine optionally being used in place of cytosine; (O) a polyoxyethylene ether or a polyoxyethylene ester (International patent application WO 99/52549); (P) a polyoxyethylene sorbitan ester surfactant in combination with an octoxynol (International patent application WO 01/21207) or a polyoxyethylene alkyl ether or ester surfactant in combination with at least one additional non-ionic surfactant such as an octoxynol (International patent application WO 01/21152); (Q) an immunostimulatory oligonucleotide (e.g. a CpG oligonucleotide) and a saponin (International patent application WO 00/62800); R) an immunostimulant and a particle of metal salt (International patent application WO 00/23105); (S) a saponin and an oil-in-water emulsion (International patent application WO 99/11241); (T) a saponin (e.g. QS21)+3dMPL+IL-12 (optionally+a sterol) (International patent application WO 98/57659); and (U) other substances that act as immunostimulating agents to enhance the effectiveness of the composition (e.g. see Chapter 7 of *Vaccine design*).

Aluminium compounds and MF59 are preferred adjuvants for parenteral use.

The immunognic compositions of the invention may be administered in a single dose, or as part of an administration regime. The regime may include priming and boosting doses, which may be administered mucosally, parenterally, or various combinations thereof.

In some instances the vaccines of the invention may comprise several antigens, fragments or variants encoded by essential genes identified according to the invention. Alternatively, the vaccine may further comprise antigens identified by other methods, or specific to other bacteria, e.g., in order to provide multivalent vaccines.

With respect to libraries according to the invention, a library of polynucleotides or a library of transposon insertion sites is a collection of sequence information, which information is provided in either biochemical form (e.g., as a collection of polynucleotide molecules), or in electronic form (e.g., as a collection of polynucleotide sequences stored in a computer-readable form, as in a computer system and/or as part of a computer program). The sequence information of the polynucleotides can be used in a variety of ways, for instance as a resource for gene discovery, i.e., for identifying and verifying essential and important genes in *P. aeruginosa*, or for identifying essential or important homologues in other genera or species. A polynucleotide sequence in a library can be a polynucleotide that represents an mRNA, polypeptide, or other gene product encoded by the polynucleotide, and accordingly such a polynucleotide library could be used to formulate corresponding RNA or amino acid libraries according to the sequences of the library members.

The nucleotide sequence information of the library can be embodied in any suitable form, e.g., electronic or biochemical forms. For example, a library of sequence information embodied in electronic form comprises an accessible computer data file (or, in biochemical form, a collection of nucleic acid molecules) that contains the representative nucleotide sequences of essential and important genes and/or insertion mutants that are differentially expressed (e.g., attenuated growth mutants). Other combinations and comparisons of cells affected by various diseases or stages of disease will be readily apparent to the ordinarily skilled artisan. Biochemical embodiments of the library include a collection of nucleic acids that have the sequences of the genes or transposon insertion sites in the library, where the nucleic acids can correspond to the entire gene in the library or to a fragment thereof, as described in greater detail below.

The polynucleotide libraries of the subject invention generally comprise sequence information of a plurality of polynucleotide sequences, where at least one of the polynucleotides has a sequence of any of the sequences in Tables 1-3. By plurality is meant at least 2, usually at least 3 and can include up to all of the sequences included in these tables. The length and number of polynucleotides in the library will vary with the nature of the library, e.g., if the library is an oligonucleotide array, a cDNA array, a, computer database of the sequence information, etc.

Where the library is an electronic library, the nucleic acid sequence information can be present in a variety of media. "Media" refers to a manufacture, other than an isolated nucleic acid molecule, that contains the sequence information of the present invention. Such a manufacture provides the genome sequence or a subset thereof in a form that can be examined by means not directly applicable to the sequence as it exists in a nucleic acid. For example, the nucleotide sequence of the present invention, e.g. the nucleic acid sequences of any of the polynucleotides of Tables 1-3, can be recorded on computer readable media, e.g. any medium that can be read and accessed directly by a computer. Such media include, but are not limited to: magnetic storage media, such as a floppy disc, a hard disc storage medium, and a magnetic tape; optical storage media such as CD-ROM; electrical storage media such as RAM and ROM; and hybrids of these categories such as magnetic/optical storage media One of skill in the art can readily appreciate how any of the presently known computer readable mediums can be used to create a manufacture comprising a recording of the present sequence information "Recorded" refers to a process for storing information on computer readable medium, using any such methods as known in the art. Any convenient data storage structure can be chosen, based on the means used for stored information. A variety of data processor programs and formats can be used for storage, e.g. word processing text file, database format, etc. In addition to the sequence information, electronic versions of the libraries of the invention can be provided in conjunction or connection with other computer-readable information and/or other types of computer-readable files (e.g., searchable files, executable files, etc, including, but not87 limited to, for example, search program software, etc.).

By providing the nucleotide sequence in computer readable form, the information can be accessed for a variety of purposes. Computer software to access sequence information is publicly available. For example, the gapped BLAST (Altschul et al. *Nucleic Acids Res.* (1997) 25:3389-3402) and BLAZE (Brutlag et al. *Comp. Chem.* (1993) 17:203) search algorithms on a Sybase system can be used to identify open reading frames (ORFs) within the genome that contain homology to ORFs from other organisms.

As used herein, "a computer-based system" refers to the hardware means, software means, and data storage means used to analyze the nucleotide sequence information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means can comprise any manufacture comprising a recording of the present sequence information as described above, or a memory access means that can access such a manufacture.

"Search means" refers to one or more programs implemented on the computer-based system, to compare a target sequence or target structural motif, or expression levels of a polynucleotide in a sample, with the stored sequence information. Search means can be used to identify fragments or regions of the genome that match a particular target sequence or target motif A variety of known algorithms are publicly known and commercially available, e.g. MacPattern (EMBL), BLASTN and BLASTX (NCBI). A "target sequence" can be any polynucleotide or amino acid sequence of six or more contiguous nucleotides or two or more amino acids, preferably from about 10 to 100 amino acids or from about 30 to 300 nucleotides. A variety of comparing means can be used to accomplish comparison of sequence information from a sample (e.g., to analyze target sequences, target motifs, or relative expression levels) with the data storage means. A skilled artisan can readily recognize that any one of the publicly available homology search programs can be used as the search means for the computer based systems of the present invention to accomplish comparison of target sequences and motifs. Computer programs to analyze expression levels in a sample and in controls are also known in the art.

A "target structural motif," or "target motif," refers to any rationally selected sequence or combination of sequences in which the sequence(s) are chosen based on a three-dimensional configuration that is formed upon the folding of the target motif, or on consensus sequences of regulatory or active sites. There are a variety of target motifs known in the art. Protein target motifs include, but are not limited to, enzyme active sites and signal sequences. Nucleic acid target motifs include, but are not limited to, hairpin structures, promoter sequences and other expression elements such as binding sites for transcription factors.

The present invention encompasses the use of the library of essential and important genes to search for polynucleotide and amino acid sequences in common among the essential and important genes. Such identified sequences can be used to design and develop antibacterial agents and vaccines against *Pseudomonas aeruginosa*.

A variety of structural formats for the input and output means can be used to input and output the information in the computer-based systems of the present invention. One format for an output means ranks the relative expression levels of different polynucleotides. Such presentation provides a skilled artisan with a ranking of relative expression levels to determine a gene expression profile.

As discussed above, the "library" as used herein also encompasses biochemical libraries of the polynucleotides of Tables 1-3, e.g., collections of nucleic acids representing the provided polynucleotides. The biochemical libraries can take a variety of forms, e.g., a solution of cDNAs, a pattern of probe nucleic acids stably associated with a surface of a solid support (i.e., an array) and the like. Of particular interest are nucleic acid arrays in which one or more of the sequences of Tables 1-3 is represented on the array. By "array" is meant a an article of manufacture that has at least a substrate with at least two distinct nucleic acid targets on one of its surfaces, where the number of distinct nucleic acids can be considerably higher, typically being at least 10 nt, usually at least 20 nt and often at least 25 nt. A variety of different array formats have been developed and are known to those of skill in the art. The arrays of the subject invention find use in a variety of applications, including gene expression analysis, drug screening, mutation analysis and the like, as disclosed in the above-listed exemplary patent documents.

In addition to the above nucleic acid libraries, analogous libraries of polypeptides are also provided, where the polypeptides of the library will represent at least a portion of the polypeptides encoded by a gene corresponding to one or more of the sequences in Tables 1-3.

"Identity" as it is used in the present invention should be distinguished from "homology" or "homologous." In the context of the coding sequences and genes of this invention, "homologous" refers to genes whose expression results in expression products which have a combination of amino acid sequence similarity (or base sequence similarity for transcript products) and functional equivalence, and are therefore homologous genes. In general such genes also have a high level of DNA sequence similarity (i.e., greater than 80% identity when such sequences are identified among members of the same genus, but lower when these similarities are noted across bacterial genera), but are not identical. Relationships across bacterial genera between homologous genes are more easily identified at the polypeptide (i.e., the gene product) rather than the DNA level. The combination of functional equivalence and sequence similarity means that if one gene is useful, e.g., as a target for an antibacterial agent, or for screening for such agents, then the homologous gene is probably also useful, but may not react in the same manner or to the same degree to the activity of a specific antibacterial agent.

Nevertheless, the identifcation of one such gene serves to identify a homologous gene through the same relationships as indicated above, and can serve as a starting point to determine whether the homologous gene is also essential, whether it responds to the same antibacterial agents, etc. Typically, such homologous genes are found in other bacterial species, especially, but not restricted to, closely related species. Due to the DNA sequence similarity, homologous genes are often identified by hybridizing with probes from the initially identified gene under hybridizing conditions that allow stable binding under appropriately stringent conditions. For instance, nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided polynucleotide sequences, e.g. allelic variants, genetically altered versions of the gene, etc., bind to the provided polynucleotide sequences under stringent hybridization conditions. By using probes, particularly labeled probes of DNA sequences, one can isolate homologous or related or substantially identical genes. The equivalent function of the product is then verified using appropriate biological and/or biochemical assays.

Using such hybridization technique for the identification of homologous genes, it will be possible to screen other species of bacteria, particularly other genera of gram negative pathogenic bacteria although gram positive bacteria may also be screened, to determine if any essential or important gene identified herein has a homologue in that particular genus of bacteria. If so, such gene could be cloned and isolated for essentiality in the particular genus, and further tested for sensitivity or susceptibility to the antibacterial agents and inhibitors identified herein. Specific genera of bacteria particularly appropriate for hybridization screening for the presence of homologues of essential and important genes include *Escherichia, Hemophilus, Vibrio, Borrelia, Enterococcus, Heliobacter, Legionella, Mycobacterium, Mycoplasma, Neisseria, Staphylococcus, Streptococcus*, etc.

"Identity," on the other hand, is gauged from the starting point of complete homology. Thereafter, identity may be described in terms of percentages according to the number of base changes in the DNA sequence taking into account any gaps. For purposes of the present invention, variants of the invention have a sequence identity greater than at least about 65%, preferably at least about 75%, more preferably at least about 85%, and can be greater than at least about 90% or more as determined by the Smith-Waterman homology search algorithm as implemented in MPSRCH program (Oxford Molecular). A preferred method of calculating percent identity is the Smith-Waterman algorithm, using the following. Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

Amino acid sequence variants are also included in the invention. Preferably, naturally or non-naturally occurring protein variants have amino acid sequences which are at least 85%, 90%, or 95% identical to the amino acid sequences identified herein, or to a shorter portion of these sequences. More preferably, the molecules are 98% or 99% identical. Percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman, *Adv. Appl. Math.* (1981) 2:482-489.

Also included in the invention are fragments of the nucleic acid sequences and amino acid sequences identified herein, as well as RNAs and RNA fragments corresponding to the DNA sequences disclosed. Such nucleic acid fragments are at least about 10 nucleotides, more preferably at least about 20 to 25 nucleotides, and more preferably at least about 50 to 100 nucleotides, and can include any fragment or variant of a fragment. Such nucleic acid fragments may be used as probes for identifying similar or substantially identical or identical nucleic acid sequences in other genera, or as tools in constructing nucleic acid vectors for knock out and promoter swap experiments. Such amino acid fragments are at least about four amino acids in length, more preferably at least about 8 to 12 amino acids in length, and more preferably at least about 20 to 30 amino acids in length, and more antagonists to test binding interactions of the proteins disclosed herein, or alternatively as immunogens to isolate antibodies that recognize and bind to specific epitopes of a target protein.

Once a gene is identified as being essential or important for Pseudomonas growth on rich media or in any specific environment, the invention also encompasses the identification of antibacterial agents that have specific activity against the essential or important genes or their gene products or the biochemical pathways in which they are involved. In this context, the term "biochemical pathway" refers to a connected series of biochemical reactions normally occurring in a cell, or more broadly a cellular event such as cellular division or DNA replication. Typically, the steps in such a biochemical pathway act in a coordinated fashion to produce a specific product or products or to produce some other particular biochemical action. Such a biochemical pathway requires the expression product of a gene if the absence of that expression product either directly or indirectly prevents the completion of one or more steps in that pathway, thereby preventing or significantly reducing the production of one or more normal products or effects of that pathway.

Thus, an agent specifically inhibits such a biochemical pathway requiring the expression product of a particular gene if the presence of the agent stops or substantially reduces the completion of the series of steps in that pathway. Such an agent, may, but does not necessarily, act directly on the expression product of that particular gene. An "expression product" of a gene means that, in a bacterial cell of interest, the gene is transcribed to form RNA molecules. For those genes that are transcribed into mRNAs, the mRNA is translated to form polypeptides. More generally, in this context, "expressed" means that a gene product is formed at the biological level that would normally have the relevant biological activity (i.e., RNA or polypeptide level).

Thus, the invention includes a method of screening for an antibacterial agent, comprising determining whether a test compound is active against an essential or important bacterial gene identified by the methods herein. The invention also includes a method of screening for an antibacterial agent, comprising determining whether a test compound is active against a protein encoded by an essential bacterial gene identified herein, or active to inhibit the biochemical pathway that involves said protein. The term "antibacterial agent" refers to both naturally occurring antibiotics produced by microorganisms to suppress the growth of other microorganisms, and agents synthesized or modified in the laboratory which have either bactericidal or bacteriostatic activity. An "active" agent in this context will inhibit the growth of P. aeruginosa and possibly related species. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half life, etc. to compounds in order to correlate enzyme inhibition with growth inhibition.

Assays may include any suitable method and may be expected to vary on the type of essential gene or protein involved. For instance, one embodiment is a method comprising the steps of:
 a) contacting said protein or a biologically active fragment thereof with a test compound; and
 b) determining whether said test compound binds to said essential gene product or protein or fragment of said protein;
 wherein binding of said test compound to said polypeptide or said fragment is indicative that said test compound is an antibacterial agent. It is quite common in identifying antibacterial agents, to assay for binding of a compound to a particular polypeptide where binding is an indication of a compound which is active to modulate the activity of the polypeptide. Binding may be determined by any means according to the agent tested and techniques known in the art.

Also, agents that inhibit binding of two proteins or polypeptides may also be identified, for instance using a yeast two-hybrid system. Such a system will entail cloning the genes encoding each protein and expressing each in a reporter cell system such that interaction between the two proteins is monitored by observing the expression of a reporter gene. For instance, cDNAs cloned in a yeast two-hybrid expression system (Chien et al. (1991) Proc. Natl. Acad. Sci. (U.S.A) 88: 9578; Zervos et al. (1993) Cell 72: 233) can be used to identify other cDNAs encoding proteins that interact with the protein encoded by the first, thereby produce expression of the GAL4-dependent reporter gene. Thereafter, cells expressing both proteins leading to expression of the reporter gene are used to screen for agents that interact with either protein, or the gene encoding either protein. Such systems are well known in the art and are well within the realm of ordinary skill.

Another embodiment is a method for evaluating a test agent for inhibition of expression of an essential gene identified according to the methods herein, comprising:
 a) contacting a cell expressing said essential gene with said agent; and
 b) determining the amount or level of expression of said essential gene in said sample.

The exact determination method will be expected to vary depending on the characteristics of the expression product as would be readily apparent to one of ordinary skill in the art. Such methods can include, for example, antibody binding methods, enzymatic activity determinations, and substrate analog binding assays. Such level of expression could be monitored by monitoring the level of the product of the essential gene in the cell, i.e., by SDS-PAGE, or by calorimetric assays using, for example, a lacZ gene or protein fusion and detection on media using X-Gal or spectrophotometric detection.

When such fusions are employed, fusions may be designed using the chromosomal gene so long as the fusion does not disrupt the function of the essential gene, i.e., as with a gene fusion where lacZ is inserted just downstream of the essential gene and is expressed from the same promoter as the essential gene. Alternatively, one could employ an extrachromosomal fusion construct whereby the wild type chromosomal copy of the gene is not disrupted. In this case, one could employ a protein fusion, i.e., where a portion of lacZ sufficient to be detected with a colorimetric test is fused in frame with the coding region of the essential gene such that a fusion protein is obtained. Other detectable or measurable proteins commonly used in the art may be used as an alternative to lacZ, for instance, phoA, Lux/luciferase, etc.

Another method of the invention for evaluating an potential antibacterial agent, comprises the steps of:
a) providing a bacterial strain comprising a mutant or normal form of the essential or important gene, wherein said mutant form of the gene confers a growth conditional phenotype;
b) contacting bacteria of said bacterial strain with a test compound in semi-permissive or permissive growth conditions; and
c) determining whether the growth of said bacterial strain comprising said mutant form of a gene is reduced in the presence of said test compound to a greater extent than a comparison bacteria comprising a normal form of said gene.

In this context, a "mutant form" of a gene is a gene which has been altered, either naturally or artificially, changing the base sequence of the gene, which results in a change in the amino acid sequence of an encoded polypeptide. The change in the base sequence may be of several different types, including changes of one or more bases for different bases, small deletions, and small insertions. Mutations may also include transposon insertions that lead to attenuated activity, i.e., by resulting in expression of a truncated protein. By contrast, a normal form of a gene is a form commonly found in a natural population of a bacterial strain. Commonly a single form of a gene will predominate in natural populations. In general, such a gene is suitable as a normal form of a gene, however, other forms which provide similar functional characteristics may also be used as a normal gene. In particular, a normal form of a gene does not confer a growth conditional phenotype on the bacterial strain having that gene, while a mutant form of a gene suitable for use in these methods does provide such a growth conditional phenotype.

As used in the present disclosure, the term "growth conditional phenotype" indicates that a bacterial strain having such a phenotype exhibits a significantly greater difference in growth rates in response to a change in one or more of the culture parameters than an otherwise similar strain not having a growth conditional phenotype. Typically, a growth conditional phenotype is described with respect to a single growth culture parameter, such as temperature. Thus, a temperature (or heat-sensitive) mutant (i.e., a bacterial strain having a heat-sensitive phenotype) exhibits significantly reduced growth, and preferably no growth, under non-permissive temperature conditions as compared to growth under permissive conditions. In addition, such mutants preferably also show intermediate growth rates at intermediate, or semi-permissive, temperatures. Similar responses also result from the appropriate growth changes for other types of growth conditional phenotypes. A growth conditional phenotype can also be conferred by cloning an essential or important gene behind a regulatable promoter, for instance, a promoter that is only active, or only leads to transcription, under particular environmental conditions or in response to a specific environmental stimulus. Such growth conditional promoter mutants may be isolated according to the promoter swap strategies described herein.

"Semi-permissive conditions" are conditions in which the relevant culture parameter for a particular growth conditional phenotype is intermediate between permissive conditions and non-permissive conditions. Consequently, in semi-permissive conditions the bacteria having a growth conditional phenotype will exhibit growth rates intermediate between those shown in permissive conditions and non-permissive conditions. In general, such intermediate growth rate is due to a mutant cellular component which is partially functional under semi-permissive conditions, essentially fully functional under permissive conditions, and is non-functional or has very low function under non-permissive conditions, where the level of function of that component is related to the growth rate of the bacteria.

The term "method of screening" means that the method is suitable, and is typically used, for testing for a particular property or effect in a large number of compounds. Therefore, the method requires only a small amount of time for each compound tested; typically more than one compound may be tested simultaneously (as in a 96-well microtiter plate, or in a series of replica plates), and preferably significant portions of the procedure can be automated. "Method of screening" also refers to determining a set of different properties or effects of one compound simultaneously.

Because the essential and important genes identified herein can be readily isolated and the genes cloned into a variety of vectors known in the art, the invention also encompasses vectors comprising the nucleic acid sequences, open reading frames and genes of the invention, as well as host cells containing such vectors. Because the essential genes identified herein can be readily isolated and the encoded gene products expressed by routine methods, the invention also provides the polypeptides encoded by those genes, as well as genes having at least about 50%, or more preferably about 60%, or more preferably about 70%, or more preferably about 80%, or more preferably about 90%, or most preferably about 95% protein sequence identity.

Thus, by identifying certain essential and/or important genes, this invention provides a method of screening for an antibacterial agent by contacting a polypeptide encoded by one of the identified essential or important genes, or a biologically active fragment of such a polypeptide, with a test compound, and determining whether the test compound binds to the polypeptide or polypeptide fragment. In addition, to simple binding determinations, the invention provides a method for identifying or evaluating an agent active on one of the identified essential genes. The method involves contacting a sample containing an expression product of one of the identified genes with the known or potential agent, and determining the amount or level of activity of the expression product in the sample.

In particular, antibodies to essential and important gene products are anticipated to be suitable diagnostic binding and antibacterial agents. Thus, antibodies to the proteins encoded by the essential and important genes identified by the methods described herein are also included in the invention. Such antibodies may be isolated according to well known techniques in the art, i.e., Kohler and Milstein for monoclonal antibodies. Also included are polyclonal antibodies and antibody fragments such as Fv, Fab and Fab$_2$ fragments, as well as chimeric and humanized antibodies, and human antibodies, i.e., made using a Xeno mouse.

In a further aspect, this invention provides a method of diagnosing the presence of a bacterial strain having one of the genes identified above, by probing with an oligonucleotide at least 15 nucleotides in length, which specifically hybridizes to a nucleotide sequence which is the same as or complementary to the sequence of one of the bacterial genes identified above. In some cases, it is practical to detect the presence of a particular bacterial strain by direct hybridization of a labeled oligonucleotide to the particular gene. In other cases, it is preferable to first amplify the gene or a portion of the gene before hybridizing labeled oligonucleotides to those amplified copies.

In a related aspect, this invention provides a method of diagnosing the presence of a bacterial strain by specifically detecting the presence of the transcriptional or translational product of the gene. Typically, a transcriptional (RNA) product is detected by hybridizing a labeled RNA or DNA probe to the transcript. Detection of a specific translational (protein) product can be performed by a variety of different tests depending on the specific protein product. Examples would be binding of the product by specific labeled antibodies and, in some cases, detection of a specific reaction involving the protein product. Diagnostic assays find particular use in assaying tissue and fluid samples of patients suspect of having a *Pseudomnonas* infection.

Antibacterial agents identified according to the methods of the invention may be employed in pharmaceutical compositions. Such compositions may be administered to patients in order to treat an infection by or involving *P. aeruginosa*, either alone or in combination with secondary agents targeted at, for instance virulence factors of *P. aeruginosa*, or other bacteria that may be present in addition to *P. aeruginosa*. In this context, the term "administration" or "administering" refers to a method of giving a dosage of an antibacterial pharmaceutical composition to a mammal, where the method is, e.g., topical, oral, intranasal, inhaled, intravenous, transdermal, intraperitoneal, or intramuscular. The preferred method of administration can vary depending on various factors, e.g., the components of the pharmaceutical composition, the site of the potential or actual bacterial infection, the bacterium involved, and the severity of an actual bacterial infection.

As used above and throughout this application, "hybridize" has its usual meaning from molecular biology. It refers to the formation of a base-paired interaction between nucleotide polymers. The presence of base pairing implies that at least an appreciable fraction of the nucleotides in each of two nucleotide sequences are complementary to the other according to the usual base pairing rules. The exact fraction of the nucleotides which must be complementary in order to obtain stable hybridization will vary with a number of factors, including nucleotide sequence, salt concentration of the solution, temperature, and pH.

The term, "DNA molecule", should be understood to refer to a linear polymer of deoxyribonucleotides, as well as to the linear polymer, base-paired with its complementary strand, forming double-strand DNA (dsDNA). The term is used as equivalent to "DNA chain" or "a DNA" or "DNA polymer" or "DNA sequence", so this description of the term meaning applies to those terms also. The term does not necessarily imply that the specified "DNA molecule" is a discrete entity with no bonding with other entities. The specified DNA molecule may have H-bonding interactions with other DNA molecules, as well as a variety of interactions with other molecules, including RNA molecules. In addition, the specified DNA molecule may be covalently linked in a longer DNA chain at one, or both ends. Any such DNA molecule can be identified in a variety of ways, including, by its particular nucleotide sequence, by its ability to base pair under stringent conditions with another DNA or RNA molecule having a specified sequence, or by a method of isolation which includes hybridization under stringent conditions with another DNA or RNA molecule having a specified sequence.

References to a "portion" of a DNA or RNA chain mean a linear chain which has a nucleotide sequence which is the same as a sequential subset of the sequence of the chain to which the portion refers. Such a subset may contain all of the sequence of the primary chain or may contain only a shorter sequence. The subset will contain at least 15 bases in a single strand. However, by "same" is meant "substantially the same"; deletions, additions, or substitutions of specific nucleotides of the sequence, or a combination of these changes, which affect a small percentage of the full sequence will still leave the sequences substantially the same. Preferably this percentage of change will be less than 20%, more preferably less than 10%, and even more preferably less than 3%. "Same" is therefore distinguished from "identical"; for identical sequences there cannot be any difference in nucleotide sequences.

As used in reference to nucleotide sequences, "complementary" has its usual meaning from molecular biology. Two nucleotide sequences or strands are complementary if they have sequences that would allow base pairing between the strands according to the usual pairing rules. This does not require that the strands would necessarily base pair at every nucleotide; two sequences can still be complementary with a low level of base mismatch such as that created by deletion, addition, or substitution of one or a few (up to 5 in a linear chain of 25 bases) nucleotides, or a combination of such changes.

Other embodiments of the invention will be immediately envisaged by those of skill in the art upon reading the methods and examples to follow. Such examples are merely illustrative of the invention, and should not be construed as limiting the scope of the invention in any way.

Methodology

Generation of Transposon Library

Transposon insertions were generated using an improved transposon system for *P. aeruginosa* that utilizes a mini-Tn5-type transposon on a delivery vector that does not replicate in *Pseudomonas*. The delivery vector contains a modified transposase gene with three amino acid substitutions that have been shown to increase the frequency of Tn5 insertions. Weinreich et al., 1994, Evidence that cis preference of the Tn5 transposase is caused by nonproductive multimerizatior, Genes Dev. 8(19): 2363-74. The Tn5 transposase was placed under control of a lac promoter and the complete transposable element was minimized to 1.7 kilobases in length, including a tetracycline resistance marker and transcription terminator to prevent read-through into the genome. The transposon vector is delivered to *P. aeruginosa* via conjugation from a suitable *E. coli* host (e.g. SM10λpir). Following conjugation, transposon mutant are selected by resistance to tetracycline conferred by the trasnposable element.

Libraries were created in both *P. aeruginosa* PAK and PA01. The average diversity of the libraries created using this strategy is estimated to be ~40,000 to ~50,000 independent mutants per conjugation. Care is taken to minimize passage of each transposon conjugation before plating for mutant selection in an effort to minimize the potential for siblings, i.e., by stopping the conjugation after sufficient time for a single round of conjugation events.

High-Throughput Transposon Insertion Mapping (HTTIM)

Precise transposon insertion sites were determined by an anchored, semi-random PCR method for amplification of the transposase/genome junction region. O'Toole and Kolter, 1998, Initiation of biofilm formation in *Pseudomonas fluorescens* WCS365 proceeds via multiple, convergent signaling pathways: a genetic analysis, Mol. Microbiol. 28(3): 449-61. The technique, HTTIM, uses both Tn5 specific and semi-random primers with conserved primer tails. A small aliquot of transposon mutant liquid culture is used as a template and amplification of a fragment containing an insertion site is achieved in a two-step process. The PCR product is then sequenced and the insertion site is entered into an Oracle database for analysis. To date, more than 10,000 to 14,000 insertions have been mapped, each insertion representing the disruption of a gene or intergenic region that is not essential for survival on rich media.

With every insertion added to the map, the regions of the genome containing essential genes, and particularly those containing operons containing essential genes (because of potential polar effects of insertions in upstream genes), begin to become apparent because these regions will not be able to accommodate transposon insertions. Table 1 shows a listing of the open reading frames identified as existing between transposon insertions, as well as an indication of whether the gene has homologues that have been identified in other bacteria pursuant to BLAST sequence database analysis. Open reading frames were tentatively assigned names prior to being identified pursuant to HTTIM analysis, as disclosed in the *Pseudomonas* genome project, and reported in Stover et al., Complete genome sequence of *Pseudomonas aeruginosa* PAO1, an opportunistic pathogen, Aug. 21, 2000, Nature 406: 959-964, herein incorporated by reference in its entirety. For instance, the predicted ORFs were examined individually for (1) identity with known genes of *P. aeruginosa* with sequences deposited in GenBank, (2) similarity with well-characterized genes from other bacteria, or (3) presence of known functional motifs. In each case the literature was searched to ensure that the proteins encoded by the homologous genes were functionally characterized to avoid the perpetuation of poorly supported functional assignments. In addition, 61 researchers who were members of the *P. aeruginosa* research community or had experience in particular aspects of bacterial physiology were enlisted for the *Pseudomonas* Community Annotation Project (PseudoCAP) to provide expert assistance and confirmatory information in the genome project for the analysis of identified ORFs and assigned functions.

The genome project was able to assign a functional class to 54.2% of ORFs. As in other bacterial genomes, a large proportion of the genome (45.8% of ORFs) consists of genes for which no function could be determined or proposed (confidence level 4). Of these, nearly a third (769 ORFs) possess homology to genes of unknown function predicted in other bacterial genomes, and the remainder (32% of ORFs) do not have strong homology with any reported sequence. The 372 ORFs from the entire genome analysis that are known *P. aeruginosa* genes with demonstrated functions (confidence level 1) are primarily genes encoding lipopolysaccharide biosynthetic enzymes, virulence factors, such as exoenzymes and the systems that secrete them, and proteins involved in motility and adhesion. ORFs with strong homology to genes in other organisms with demonstrated functions (confidence level 2; 1,059 ORFs) include those required for DNA replication, protein synthesis, cell-wall biosynthesis and intermediary metabolism.

The ORFs that provided the most new information about *P. aeruginosa* biology via the genome annotation were those that could be assigned a probable function on the basis of similarity to established sequence motifs, but could not be assigned a definite name (confidence level 3; 1,590 ORFs). Most of these genes encode products that are in one of three functional classes: putative enzymes (405 genes), transcriptional regulators (341 genes) or transporters of small molecules (408 genes). In some cases genomic context provided additional information, allowing us to identify loci that appear to encode systems such as metabolic pathways and secretion systems, although the substrates for such systems could not be identified. The system for assigning name and putative function to each essential or important gene was gleaned from the *Pseudomonas* genome project data already available.

Statistical Analysis of Putative Essential and Important Genes

The open reading frames listed in Table 1 are also presented in Table 2, wherein the ORFs are listed in order of length of base pairs from longest to shortest. Also listed in Table 2 is the probability of essentiality assigned to each of the open reading frames. Probability correlates with length of the ORF, such that the longer the ORF, the higher the probability of hitting the ORF in a random transposon mutagenesis experiment, and the higher the confidence level that the ORF represents an essential or an important gene given that no transposon insertions therein were isolated. Statistical confidence levels in essentiality or importance can help narrow the focus in the screening of specific genes, thereby shortening the verification process and the, subsequent identification of antibacterial agents specific for that gene or gene product. Thus, one of the benefits of the HTTIM approach is that it is a quantitative approach that lends itself well to statistical analysis.

The High-Throughput Transposon Insertion Mapping (HTTIM) strategy utilizes a transposon, which is a small, mobile DNA element that randomly inserts into the chromosome. Although HTTIM was performed using a Tn5 transposon, any transposon may be employed so long as its insertion into the chromosome is random, i.e., devoid of hot spots. Reznikoff, W. S., 1993, The Tn5 transposon, Annu. Rev. Microbiol. 47: 945-63. Although the Tn5 derivative employed here contained a modified transposase gene with three amino acid substitutions that have been shown to increase the frequency of Tn5 insertions (see supra), the frequency of insertion is generally quite low. For instance, mutants with even one insertion occur at a rate of only 1 in $10^5$ or $10^6$ bacteria, and must be specifically selected from a background of cells with no insertions. Because the frequency of a single insertion is so low, the frequency of a double insertion is so low as to be insignificant.

Figure 7:
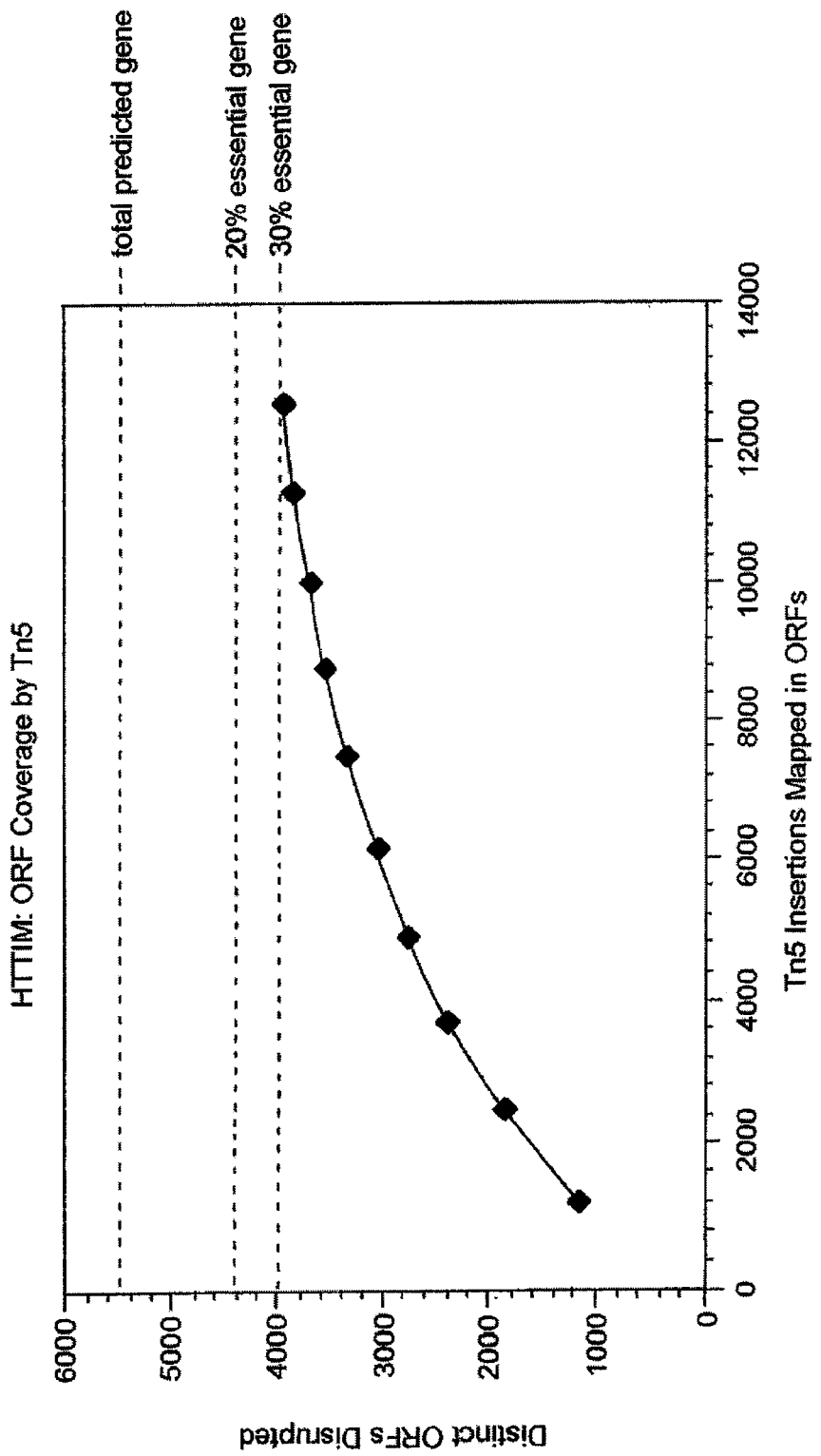
FIG. 7. Graph illustrating ORF coverage by Tn5 achieved in High-Throughput Transposon Insertion Mapping (HT-TIM, wherein 30% of the genes in the genome are candidate essential genes where ORF size is not taken into account in predicting essentiality.

When the transposon insertion disrupts one of the 5570 genes in the *Pseudomonas* genome, the function of that gene is lost. If the disrupted gene is essential for growth, the transposon insertion mutant dies and cannot be characterized. If the transposon disrupts a gene that is non-essential, the mutant survives, grows and the transposon insertion site is mapped. By examining the insertion sites of a large number of transposon mutants, all, of the non-essential *P. aeruginosa* genes can be identified, and by implication, all of the essential genes maybe identified as well. Characterization of over 13,000 transposon insertions revealed insertions in 3890 genes and resulted in an even distribution of insertions across the entire length of the genome. The remaining 1658 genes, in which a transposon insertion has never been observed, are candidates of essential genes (30%). See FIG. 7, showing a graph illustrating ORF coverage by Tn5 achieved in High-Throughput Transposon Insertion Mapping (HTTIM), wherein 30% of the genes in the genome are candidate essential genes where ORF size is not taken into account in predicting essentiality.

Figure 8:
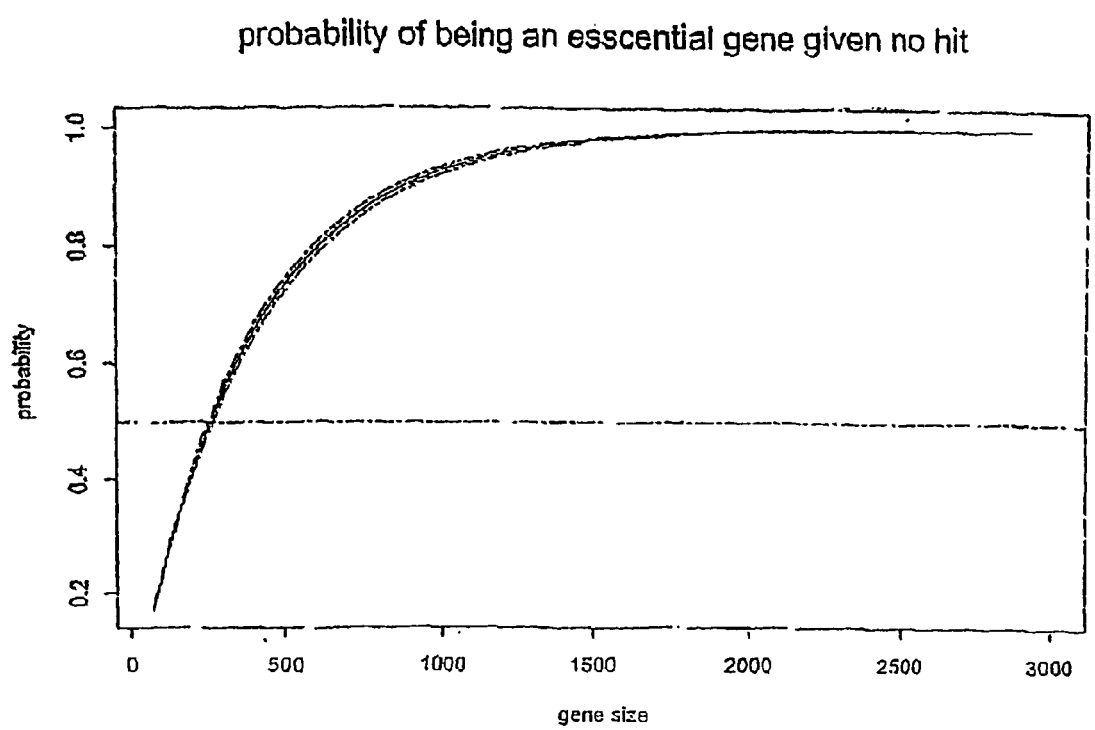
FIG. 8. Graph depicting the probability of identifying an essential gene given no transposon insertion, as a function of gene size.

Because insertion of the transposon used here into the chromosome was. proposed to be random, it was possible that some of the 1658 genes that did not receive a transposon insertion were simply not hit by random chance. One cannot truly know that a transposon has no hot spots and is entirely random until the data is analyzed, and the data here confirmed that the Tn5 derivative employed underwent random insertion in *P. aeruginosa*. Thus, the chance that a gene will not be hit by the transposon as a matter of random chance increases as the length of the gene decreases, particularly for very small genes (<600 base pairs). See FIG. 8, Probability of Being an Essential Gene Given No Hit. Thus, by deleting smaller ORFs (<600 base pairs) in which there is a lower confidence in essentiality, the probability of essentiality goes up while the number of predicted essential genes decreases. Further, the curve in the graph depicted in FIG. 8 should level off faster. Thus, in predicting the essentiality of genes from the HTTIM candidate set, the closer one can come to a probability of 1.0 as depicted in FIG. 8, the higher the confidence level of essentiality that can be assigned to each gene in the candidate subset. For a representation of the number of ORFs of various lengths in *P. aeruginosa*, see the histogram in FIG. 9.

A Bayessian statistical model for truncated counting data was applied to the candidate essential gene set, and permitted a determination that 16 to 17 percent of *P. aeruginosa* genes are essential. Such a model may therefore be utilized to increase the statistical confidence that a given gene in the candidate subset is essential. An exemplary statistical model is provided in Example 1.

Physical Methods for Target Gene Validation

While the above methodology and the database of putative essential and important gene candidates established thereby is believed to be superior to existing methods with regard to the quantity of experimentation required to identify essential and important genes in *Pseudomonas aeruginosa* and the degree of confidence conferred, it should be understood that the methodology described herein can be incorporated into combined protocols with technology known in the art. For instance, the methods for verifying essentiality disclose in WO 01/07651, herein incorporated by reference in its entirety, would be useful as a secondary method to be utilized in combination with the methods described in this disclosure. Alternatively or additionally, one of several approaches may be used to determine whether a particular gene is essential (absolutely required for survival on rich medium) or important (the absence of which results in attenuated growth) to *P. aeruginosa*.

Integration Knockouts

This is the simplest and most rapid strategy. PCR is used to amplify a small (200-500 base pairs) portion of the coding sequence, or open reading frame (ORF) of the gene of interest. This gene fragment must be centrally located within the ORF—it cannot include either termini of the gene's coding region. This fragment is cloned into a plasmid vector that can replicate in *E. coli*, but not in *Pseudomonas*. The vector used should have a drug resistance marker that is suitable for selection in *Pseudomonas*, and an origin for conjugal transfer. This feature allows the plasmid to be transferred by conjugation from a suitable *E. coli* donor strain to a *Pseudomonas* strain when the two are co-cultured under the appropriate conditions.

Following conjugation the co-cultured mixture is harvested and plated on media which selects against the *E. coli* donor and for *Pseudomonas* which contain the plasmid. Since the plasmid is incapable of extra-chromosomal replication in *Pseudomonas*, colonies that arise are the result of homologous recombination between the *Pseudomonas* chromosome and the cloned gene fragment on the plasmid. This is referred to as single-crossover recombination; a single recombination event takes place between the plasmid and the chromosome. The result is integration of the plasmid into the bacterial chromosome and disruption of the gene from which the fragment was amplified (FIG. 1).

Variations of this approach are possible. For instance, one could clone out the entire locus and isolate transposon insertion mutants in *E.coli* using known techniques, i.e., by transposition from the *E. coli* genome, selecting plasmid insertions by mobilizing the vector into a recipient cell that does not contain the transposon or the antibiotic resistance marker encoded by the transposon, and screening the plasmid for insertions in the cloned gene. Thereafter, a similar assay could be performed by screening for double crossover events in *P. aeruginosa* that result in recombination of the transposon into the chromosomal locus from a suicide vector.

Integration of the plasmid or other insertion at the locus can be confirmed by a relatively rapid PCR-based screen of recombinant colonies. The advantage of this strategy, particularly the plasmid single crossover strategy, is that it requires only amplification of a short stretch of DNA followed by a single cloning step before recombination experiments can be performed. The disadvantage is that if the target gene is essential, no recombinants can be obtained. Failure to obtain recombinants as proof of essentiality is pretty thin evidence. However, if a gene is in fact non-essential, this method will demonstrate that quickly.

Integration Knockouts with Extra-chromosomal Complementation

This variation of the above method provides more convincing data when the target gene is essential. It employs the same type of non-replicating integration plasmid described above, but recombinations are performed in strains already carrying a second copy of the target gene on an extra-chromosomal plasmid. This second copy can then supply the essential function when the chromosomal copy is disrupted. If disruptions can only be obtained when a complementing plasmid is present and not when a control plasmid is present, this is rather strong evidence that the target gene is essential. The advantage of this method is that you obtain colonies even when your gene is essential. The disadvantage is that construction and sequencing of the complementation plasmid takes additional time.

Integration with a Regulatable Promoter (Promoter Swap)

This approach also involves selecting for chromosomal integration of non-replicating plasmids via homologous recombination. However, the design of the integrating plasmid is different In this case, the N-terminal coding sequence (300-500 base pairs) of the target gene is PCR amplified and cloned into a vector downstream of a regulatable promoter, i.e., a lac promoter, which is inducible in the presence of IPTG, or an arabinose promoter (pABD), inducible in the presence of arabinose. The activity of the promoter can be modulated by the presence of a specific inducer molecule.

The plasmid is conjugated into *Pseudomonas* and integration selected for under conditions where the regulatable promoter is active. The resulting chromosomal integration replaces the target gene's natural promoter with the regulatable promoter from the plasmid (FIG. 2). If the target gene is essential, recombinants can only survive when the inducer molecule is present in their growth media to stimulate gene expression. If the gene is non-essential, the recombinant's growth is independent of the addition of the inducer. The advantage of this strategy is that it requires only amplification of a short stretch of DNA followed by a single cloning step before recombination experiments can be performed.

EXAMPLES

Essential Genes Identified

Example 1

A Bayessian Statistical Model for Increasing Statistical Confidence of Essentiality When the Tn5 transposon inserts into the *Pseudomonas* DNA, one of three things happen: 1) The insertion disrupts a nonessential gene. The cell survives to be characterized and the location of the insertion is determined. 2) The insertion disrupts an essential gene. The cell does not survive and the insertion site is not determined. 3) The insertion is in an intergenic region (between genes) and no information is gained. Genes with identified insertions are nonessential genes. However, genes without identified insertions could be essential genes or nonessential genes with zero transposon insertion. To determine the number of essential genes, we have developed a multivariate Bayession model for truncated Poisson data and applied it to the *Pseudomonas* genome data set. A likelihood gain based searching algorithm was developed to obtain maximum likelihood estimates. The property of the algorithm was studied Different approaches were compared for both multivariate and univariate approaches.

A. Structure of the Data and Preliminary Considerations

Figure 10A:
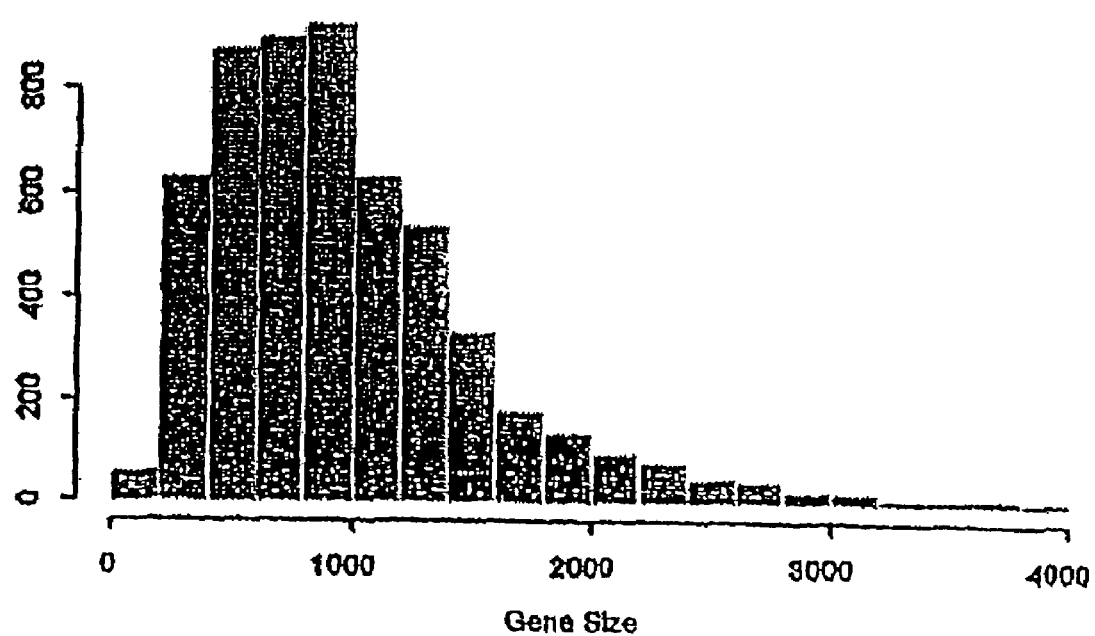
FIG. 10A, up to 4000 base pairs.
Figure 10B:
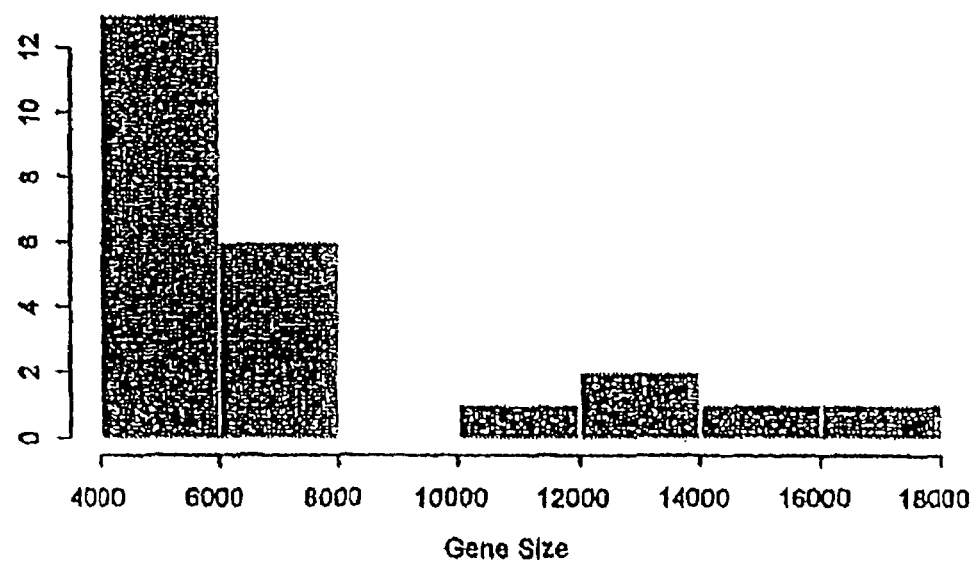
FIG. 10B, from 4000 up to 16884 base pairs.

A transposon Tn5 insertion mutagenesis library was constructed in *Pseudomonas aeruginosa* strains PAK and PAO1. Mutants were randomly picked and their genomic insertion site sequence determined through polymerase chain reaction (PCR) and automated DNA sequencing. BLASTN analysis of transposon/genome junction sequences was used to map the location of the insertions relative to the completed strain PAO1 genome sequence. More than 20,000 mutants were analyzed which resulted in 12,219 independent insertions being mapped. In order to identify essential genes, transposon insertion sites were analyzed with respect to the protein-encoding genes in this organism A data set consists of the ID of genes, their length in DNA base-pairs, and the number of transposon insertions were obtained from experiments. The data set consists of 5570 genes with 881 different sizes ranging from 72 to 16884 DNA base-pairs. The distribution of the gene sizes are extremely skewed to the right with majority of the genes being smaller than 2000 DNA base-pairs as shown in FIG. 10.

A randomly selected subset of the data is shown in Table 4, where $\delta$ is gene size, x is the observed number of transposon insertions. Insertions to essential genes are not observable since the insertion mutants can not survive for characterization when the transposon is inserted into an essential gene. Therefore, a gene with zero observed transposon insertions can either be an essential gene or a nonessential gene with zero transposon insertion. Consequently, the count of transposon insertions x is truncated with the truncation region being a single element $\{0\}$.

TABLE 4

A sample of the gene data set

| Gene id | $\delta$ | x |
|---------|------|---|
| 298 | 1359 | 3 |
| 4047 | 618 | 0 |
| 1170 | 735 | 1 |
| 4953 | 1044 | 1 |
| 5526 | 213 | 0 |
| 4624 | 1707 | 4 |
| 5069 | 426 | 3 |

Since the insertion into the chromosome of *Pseudomonas aeruginosa* is random (Reznikoff W S. 1993), and the probability of receiving an insertion for a given gene is proportional to its size measured in DNA base-pairs, the number of transposon insertions into a gene is distributed as truncated Poisson with parameter $\lambda\delta$, where $\delta$ is the size of the gene and $\lambda$ is an unknown parameter, which is independent of gene size.

B. A Bayesian Model

Let R be a measurable subset of the probability space $\Omega$ such that a random variable X is observable only if $X \in \Omega \backslash R$. In this example, no observations can be obtained from essential genes, whereas only nonzero observations can be obtained from nonessential genes, the set R consists of a single element $\{0\}$.

1.

a. One Gene Size

Assume all genes in a genome have same size, $\delta$, and let N be the number of nonessential genes in this genome. Then the observations $X_1, X_2, \ldots, X_N$ from the N nonessential genes are i.i.d. Poisson($\lambda \cdot \delta$), of which, all observations of value zero are truncated. The product $\lambda \cdot \delta$ indicates that the probability of a gene receiving an insertion is proportional to its size.

Let $\{X_1^*, X_2^*, \ldots, X_n^*\} \subseteq \{X_1, X_2, \ldots, X_N\}$ denote the subset of all nonzero observations. Then this subset composes a random sample of size n from a truncated Poisson distribution whose distribution function can be written as $$f(x, \lambda \cdot \delta) = e^{-\lambda \cdot \delta} \frac{(\lambda \cdot \delta)^x}{x!} / (1 - e^{-\lambda \cdot \delta}), \quad x = 1, 2, \ldots \quad (3.1)$$

Let $q = 1 - e^{-\lambda \cdot \delta}$ denote the probability that an observation from Poisson($\lambda \cdot \delta$) is not truncated, and let $p = 1 - q \approx e^{-\lambda \cdot \delta}$. Then, conditional on the parameters n and N, the likelihood function of the joint distribution of $\{X_1^*, X_2^*, \ldots, X_n^*\}$ can be written as $$L(\lambda | n, N) = (\lambda \cdot \delta)^{\sum_{i=1}^n X_i^*} \left(\frac{p}{q}\right)^n \left(\prod_{i=1}^n X_i^*!\right)^{-1}. \quad (3.2)$$

Let $S = X_1^* + X_2^* + \ldots + X_n^* \quad (3.3)$ denote the sum of all nonzero observations and notice that n follows a binomial distribution B(N, q). The likelihood function of the joint distribution of $\{n, X_1^*, X_2^*, \ldots, X_n^*\}$, conditional on the parameter N, can be obtained as $$L(\lambda \mid N) = \binom{N}{n} q^n p^{N-n} (\lambda \cdot \delta)^S \left(\frac{p}{q}\right)^n \left(\prod_{i=1}^{n} X_i^*!\right)^{-1} \quad (3.4)$$

$$\propto \binom{N}{n} \lambda^S e^{-(\lambda \cdot \delta)N}.$$

The Bayesian model consists of the conditional model (2.4) and a prior distribution of the parameter N. Assuming N, the number of nonessential genes, is binomial B(M, γ), where M is the total number of genes of size δ, which is known, and γ is the portion of nonessential genes which is unknown and is independent of gene size, we can write the likelihood function of the joint distribution of $\{n, N, X_1^*, X_2^*, \ldots, X_n^*\}$ as $$L(\gamma, \lambda, N) \propto \binom{M}{N}\binom{N}{n} \gamma^N (1-\gamma)^{M-N} \lambda^S e^{-(\lambda \cdot \delta)N}. \quad (3.5)$$

This is the likelihood function of n nonzero observations from M genes of the same size δ, of which N genes are nonessential. It is easy to see that (3.5) is proportional to the likelihood function of the posterior distribution of N given observations n and S.

2.

b. Multiple Gene Sizes

For a given genome consists of genes of different sizes, let $\vec{\delta} = (\delta_1, \delta_2, \ldots, \delta_g)^T$ denote the vector of g different gene sizes, and let $\vec{M} = (M_1, M_2, \ldots, M_g)^t$ the vector of known numbers of total genes, $\vec{N} = (N_1, N_2, \ldots, N_g)^T$ the unknown numbers of nonessential genes, $\vec{n} = (n_1, n_2, \ldots, n_g)^T$ the numbers of nonzero observations from the nonessential genes, and $\vec{S} = (S_1, S_2, \ldots, S_g)^T$ the sums of nonzero observations, as defined in (3.3).

The likelihood function of the joint distribution of $\{\vec{n}, \vec{N}, \vec{S}\}$ can be written as $$L(\gamma, \lambda, \vec{N}) \propto \quad (3.6)$$

$$\gamma^{\|\vec{N}\|} (1-\gamma)^{\|\vec{M}\| - \|\vec{N}\|} \lambda^{\|\vec{S}\|} e^{-\lambda \cdot (\vec{\delta}^T \cdot \vec{N})} \prod_{i=1}^{g} \binom{M_i}{N_i}\binom{N_i}{n_i}$$

where ||*|| is the $L_1$ norm of a vector, and $$\vec{\delta}^T \cdot \vec{N} = \sum_{i=1}^{g} \delta_i \cdot N_i.$$

Let $\Im = \ln(L)$. Then up to an additive constant, the log likelihood function of the joint distribution of $\{\vec{n}, \vec{N}, \vec{S}\}$ can be written as $$\Im(\gamma, \lambda, \vec{N}) = \|\vec{N}\| \cdot \ln(\gamma) + (\|\vec{M}\| - \|\vec{N}\|) \cdot \ln(1-\gamma) + \|\vec{S}\| \cdot \ln(\lambda) - \quad (3.7)$$

$$\lambda \cdot (\vec{\delta}^T \cdot \vec{N}) - \sum_{i=1}^{g} \ln((M_i - N_i)!) - \sum_{i=1}^{g} ((N_i - n_i)!),$$

where $(\gamma, \lambda, \vec{N})$ are the parameters of interests. The vector $\vec{N}$ is defined on $\{n_i \leq N_i \leq M_i: i=1, 2, \ldots, g\}$ and $\Im(\gamma, \lambda, \vec{N})$ is proportional to the likelihood function of the posterior distribution of $\vec{N}$ given $\vec{n}$ and $\vec{S}$.

When g is large, say, in the order of hundreds as in the situation we are dealing with in this paper, obtaining the maximum likelihood (ML) estimate of $\vec{N} = (N_1, N_2, \ldots, N_g)^T$ from (3.7) in such a high dimensional parameter space is a very difficult task both theoretically and computationally. In the next section, we will present a stepwise, maximum likelihood gain based method to obtain the ML estimation.

C. ML Estimation of Parameters

For any $\vec{N} = (N_1, N_2, \ldots, N_g)^T$, it is easy to verify using (3.7) that the ML estimations of the parameters γ and λ are $$\hat{\gamma} = \|\vec{N}\| / \|\vec{M}\| \quad (4.1)$$

and $$\hat{\lambda} = \|\vec{S}\| / (\vec{\delta}^T \cdot \vec{N}) \quad (4.2)$$

respectively. Substituting (4.1) and (4.2) for γ and λ in (3.7), we have $$\Im^*(\vec{N}) \propto \|\vec{N}\| \cdot \ln(\|\vec{N}\|) + (\|\vec{M}\| - \|\vec{N}\|) \cdot \ln(\|\vec{M}\| - \|\vec{N}\|) - \quad (4.3)$$

$$\|\vec{S}\| \cdot \ln(\vec{\delta}^T \cdot \vec{N}) - \sum_{i=1}^{g} (\ln((M_i - N_i)!) + \ln((N_i - n_i)!)).$$

For $1 \leq i \leq g$, define $$\Delta_i \Im^*(\vec{N}) = \Im^*(\vec{N} + \vec{1}_i) - \Im^*(\vec{N}) \quad (4.4)$$

for any $\vec{N} \in \{n_i \leq N_i < M_i, n_j \leq N_j \leq M_j: i \neq j\}$. In equation (4.4), $\vec{1}_i = (0, \ldots, 0, 1, 0, \ldots, 0)^T$ with 1 at the $i^{th}$ position. For notational purpose, let $$\eta(k) = k \cdot \ln(k) + (\|\vec{M}\| - k) \cdot \ln(\|\vec{M}\| - k) \quad (4.5)$$

for $\|\vec{n}\| \leq k < \|\vec{M}\|$. Then, (3.4) can be written as $$\Delta_i \Im^*(\vec{N}) = \quad (4.6)$$

$$\eta(\|\vec{N}\| + 1) - \eta(\|\vec{N}\|) - \|\vec{S}\| \cdot \ln\left(1 + \delta_i / \vec{\delta}^T \cdot \vec{N}\right) + \ln\left(\frac{M_i - N_i}{N_i - n_i + 1}\right).$$

To obtain ML estimation of $\vec{N}$, we define an operator, ⊕, between the observed vector $\vec{n}$ and any integer k with $0 \leq k \leq \|\vec{M}\| - \|\vec{n}\|$ as follows:

$$\vec{n} \oplus 0 = \vec{n},$$

$$\vec{n} \oplus 1 = \{\vec{n} + \vec{1}_i : \Delta_i \Im^*(\vec{n}) \geq \Delta_j \Im^*(\vec{n}) \text{ for all } j \neq i\}, \text{ and}$$

$$\vec{n} \oplus k = (\vec{n} \oplus (k-1)) \oplus 1 \text{ for } k \geq 2. \quad (4.7)$$

We also define a likelihood-gain function G with G(0)=0 and $$G(k) = \Im^*(\vec{n} \oplus k) - \Im^*(\vec{n} \oplus (k-1)) \quad (4.8)$$

for $1 \leq k \leq \|\vec{M}\| - \|\vec{n}\|$.

Using this likelihood-gain function, we can search the ML estimation for $\vec{N}$ as follows:

1. Start with the observation $\vec{n}$ as the initial estimate of $\vec{N}$, and denote it as $\vec{N}^0$.
2. For each gene size $\delta_i$ with $n_i<M_i$, i=1, 2, . . . , g, calculate a likelihood difference $\Delta_i\Im^*(\vec{N}^0)=\Im^*(\vec{N}^0+\vec{1}_i)-\Im^*(\vec{N}^0)$ by set $N_i^0=n_i+1$ and $N_j^0=n_j$ for all $j\neq i$.
3. Update the initial values $\vec{N}^0$ by setting $N_i^0=N_i^0+1$ such that $\Delta_i\Im^*(\vec{N}^0)=\max\{\Delta_j\Im^*(\vec{N}^0), j=1,2,\ldots,g\}$. This maximum likelihood difference is the likelihood gain defined in (4.8).
4. Repeat the process until it converges. By convergence we mean that either the estimated number of nonessential genes equals to the number of genes in each size group or when increasing the number of nonessential genes in any size groups will result in a loss of likelihood.

Figure 11:
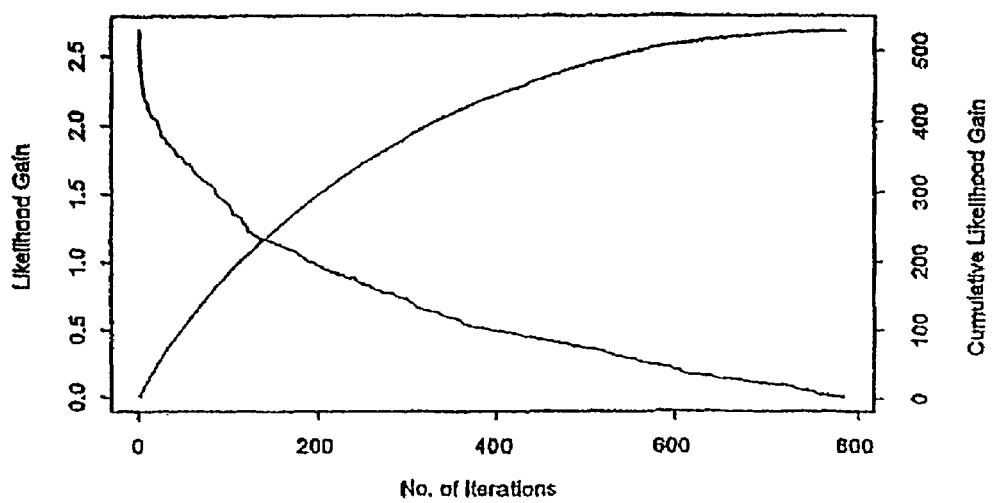
FIG. 11. Graph showing likelihood and accumulative likelihood gains.
Figure 12:
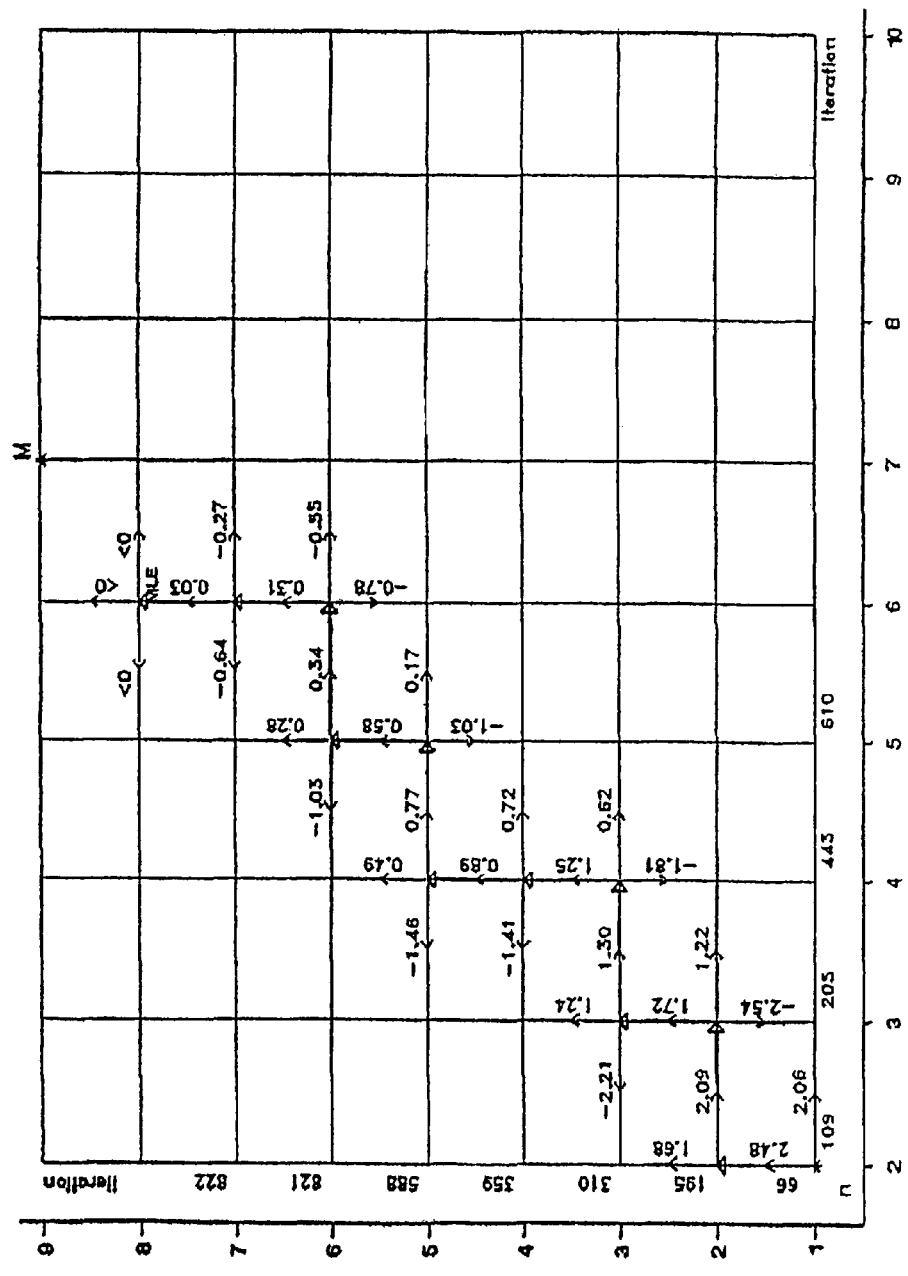
FIG. 12. Trajectory of the algorithm projected in a subspace spanned by two gene sizes. The x-axis represents genes of sizes 151-160 DNA base-pairs and y-axis represents genes of sizes 171-180 DNA basepairs. Here n=(2,1) and M=(7,9). The median gene size of each group is used as the gene size. At iteration number 66, the likelihood gain is maximum in the direction of increasing the number of nonessential genes by one for genes with size 171-180 DNA base-pairs. At iteration number 443, the largest likelihood gain is obtained in the direction of increasing one nonessential genes for genes of sizes 151-160 DNA base pair. At any point, moving backwards has a negative likelihood gain.

This algorithm searches the ML estimator in a high dimensional space (881 in our study) along a path such that at each iteration, it moves in a direction (that is, increases the number of nonessential genes in this size group by one) along which the likelihood gain is maximum among all possible directions. Because the searching algorithm prohibits reversal of previous moves at any later iteration, it moves towards the ML estimator along the shortest path with the deepest ascending (maximum likelihood gain) at each step. Table 5 and FIGS. 11 and 12 show the values of likelihood gains in each iteration. With very few exceptions where the monotonous is violated only at the fourth or fifth decimal places that probably can be attributed to rounding errors, the likelihood gain is a monotonously decreasing function.

TABLE 5

A Sample of Likelihood Gains at Each Iteration

| Iteration | id | δ | M | n | $\hat{N}(i)$ | G(i) |
|---|---|---|---|---|---|---|
| 1 | 28 | 210 | 13 | 2 | 3 | 2.67559 |
| 2 | 60 | 306 | 14 | 3 | 4 | 2.41082 |
| 3 | 44 | 258 | 14 | 5 | 6 | 2.34388 |
| 4 | 63 | 315 | 15 | 5 | 6 | 2.29243 |
| ... | ... | ... | ... | ... | ... | ... |
| 18 | 32 | 222 | 7 | 1 | 2 | 2.05160 |
| 19 | 81 | 369 | 11 | 2 | 3 | 2.05166 |
| ... | ... | ... | ... | ... | ... | ... |
| 774 | 122 | 492 | 12 | 8 | 11 | 0.00692 |
| 775 | 266 | 924 | 16 | 14 | 15 | 0.00544 |
| 776 | 85 | 381 | 14 | 3 | 11 | 0.00531 |

The following three theorems show that the estimates obtained through the above algorithm are indeed the maximum likelihood estimates.

Theorem 1: if $$\sum_{i=1}^{g}\left(n_i-\exp\left(\frac{\delta_i\cdot\|\vec{S}\|}{\vec{\delta}^T\cdot\vec{n}}\right)\right)>0, \quad (4.9)$$

then G(1)>0.

Proof: If $G(1)\leq 0$, then by (4.5), $\Delta_i\Im^*(\vec{n})\leq 0$ for all $1\leq i\leq g$, which leads to $$\eta(\|\vec{n}\|+1)-\eta(\|\vec{n}\|)-\|\vec{S}\|\cdot in(1+\delta_i/(\vec{\delta}^T\cdot\vec{n}))+\ln(M_i-n_i)\leq 0$$

$$\Rightarrow \|\vec{S}\|\cdot in\left(1+\delta_i\Big/\left(\vec{\delta}^T\cdot\vec{n}\right)\right)-\ln(M_i-n_i)\geq \eta(\|\vec{n}\|+1)-\eta(\|\vec{n}\|)$$

$$\Rightarrow \frac{\left(1+\delta_i\Big/\left(\vec{\delta}^T\cdot\vec{n}\right)\right)^{\|\vec{S}\|}}{M_i-n_i}\geq \frac{(\|\vec{n}\|+1)^{\|\vec{n}\|+1}\cdot(\|\vec{M}\|-\|\vec{n}\|-1)^{\|\vec{M}\|-\|\vec{n}\|-1}}{(\|\vec{n}\|)^{\|\vec{n}\|+1}\cdot(\|\vec{M}\|-\|\vec{n}\|)^{\|\vec{M}\|-\|\vec{n}\|}}$$

$$\Rightarrow \sum_{i=1}^{g}\left(1+\delta_i\Big/\left(\vec{\delta}^T\cdot\vec{n}\right)\right)^{\|\vec{S}\|}\geq \|\vec{n}\|\cdot(1+1/\|\vec{n}\|)^{\|\vec{n}\|+1}\cdot$$

$$(1+1/(\|\vec{M}\|-\|\vec{n}\|))^{\|\vec{M}\|-\|\vec{n}\|-1}$$

Using the facts that $(1+1/x)^x<e$, $(1+1/x)^{x+1}>e$, and $(1-1/x)^{x-1}>e^{-1}$ for any $x>0$, we obtain $$\sum_{i=1}^{g}\exp\left(\frac{\delta_i\cdot\|\vec{S}\|}{\vec{\delta}^T\cdot\vec{n}}\right)\geq \|\vec{n}\|\cdot e\cdot e^{-1}=\|\vec{n}\|$$

$$\Rightarrow \sum_{i=1}^{g}\left(n_i-\exp\left(\frac{\delta_i\cdot\|\vec{S}\|}{\vec{\delta}^T\cdot\vec{n}}\right)\right)<0$$

This is contradictory to condition (4.9).

For g=1, (4.9) becomes $\ln(n)>(X_1+X_2+\ldots+X_n)/n$. Hence, when the mean of the observed transposon insertions is less than the log of the number of nonzero observations, the vector $\vec{n}$ can not be the ML estimator of $\vec{N}$ and there must be truncated observations from nonessential genes.

Theorem 2:

$$\Delta_i\Im^*(\vec{N})>\Delta_i\Im^*(\vec{N}-\vec{1}_j) \text{ for all } i\neq j \quad (4.10)$$

Proof: By definition in (4.5), $$\frac{d[\eta(x+1)-\eta(x)]}{dx}=\ln\left(\frac{x+1}{x}\cdot\frac{\|\vec{M}\|-x}{\|\vec{M}\|-x-1}\right)>0$$

for any $0<x<\|\vec{M}\|$. Hence $\eta(\|\vec{N}\|+1)-\eta(\|\vec{N}\|)$ is an increase function of $\|\vec{N}\|$. Using this result, we have $$\Delta_i\Im^*(\vec{N})-\Delta_i\mathcal{T}^*(\vec{N}-\vec{1}_j)=(\eta(\|\vec{N}\|+1)-\eta(\|\vec{N}\|)-\eta(\|\vec{N}\|-1))-$$

$$\|\vec{S}\|\cdot\ln\left(1+\delta_i\Big/\left(\vec{\delta}^T\cdot\vec{N}\right)\right)+\|\vec{S}\|\cdot\ln\left(1+\delta_i\Big/\left(\vec{\delta}^T\cdot\vec{N}-\delta_j\right)\right)>$$

$$\|\vec{S}\|\cdot\left[\ln\left(1+\delta_i\Big/\left(\vec{\delta}_i\cdot\vec{N}-\sigma_j\right)\right)-\ln\left(1+\delta_i\Big/\left(\vec{\delta}^T\cdot\vec{N}\right)\right)\right]>0$$

Theorem 3:
Under (4.9), for any $1\leq j\leq g$ and $1\leq k\leq K^*$, with $K^*=\max\{k^*\geq 0: G(k)\geq 0 \text{ for all } 0\leq k\leq k^*\}$, if $\vec{N}=\vec{n}\oplus k-\vec{1}_j\in\{n_j\leq N_j\leq M_j\}$, then $$\Im^*(\vec{n}\oplus k)>\Im^*(\vec{n}\oplus k-\vec{1}_j) \quad (4.11)$$

Proof: This is obviously true when k=1. Assume (3.11) is true for integers 1,2, ..., k. For integer k+1, we have $$\Im^*(\vec{n} \oplus (k+1) - \vec{1}_j) - \Im^*(\vec{n} \oplus k) =$$
$$[\Im^*(\vec{n} \oplus (k+1) - \vec{1}_j) - \Im^*(\vec{n} \oplus k - \vec{1}_j)] +$$
$$[\Im^*(\vec{n} \oplus k - \vec{1}_j) - \Im^*(\vec{n} \oplus k)] <$$
$$[\Im^*(\vec{n} \oplus (k+1) - \vec{1}_j) - \Im^*(\vec{n} \oplus k - \vec{1}_j)]$$

By theorem 2, $$\Im^*(\vec{n} \oplus (k+1) - \vec{1}_j) - \Im^*(\vec{n} \oplus k - \vec{1}_j) < \Im^*(\vec{n} \oplus (k+1)) - \Im^*(\vec{n} \oplus k)$$

Therefore $$\Im^*(\vec{n} \oplus (k+1)) > \Im^*(\vec{n} \oplus (k+1) - \vec{1}_j)$$

Combining theorems 1-3, we obtain

Theorem 4: If the likelihood function defined in (3.7) has an unique solution, the ML estimator of $\vec{N}$ is:

$$\vec{N} = \vec{n} \oplus K^* \quad (4.12)$$

Figure 4:
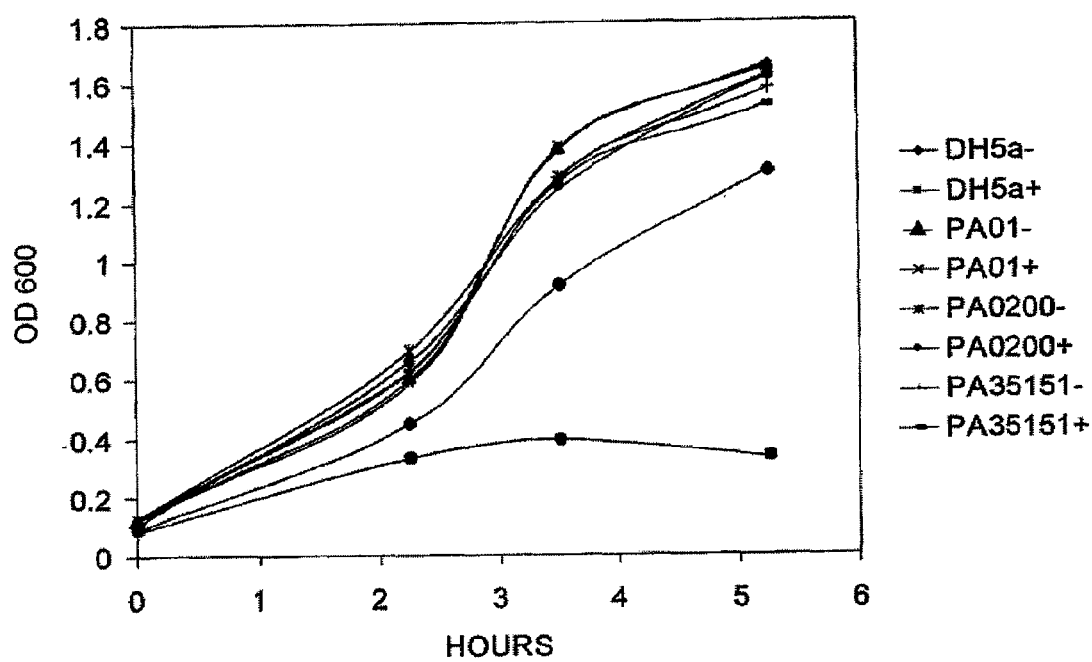
FIG. 4. Graph showing the susceptibility or non-susceptibility of various *E. coli* and *P. aeruginosa* strains to the inhibitor L161,240.
Figure 13:
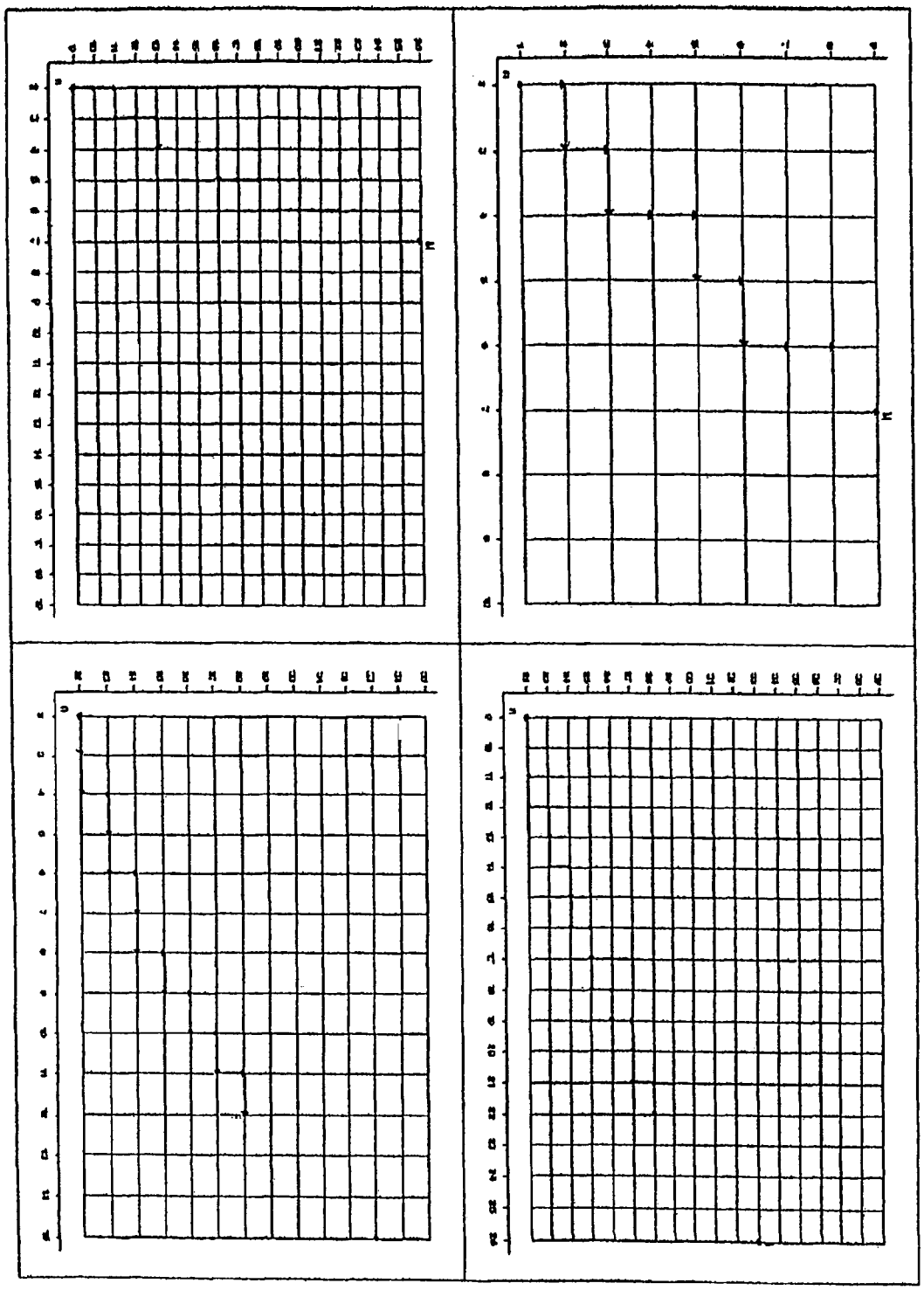
FIG. 13. More trajectories of the searching algorithm projected in different subspaces.

Theorem 3 guarantees that the trajectory of the searching algorithm follows the shortest path in the sense that a reversal of a previous move (that is, removal of a previously added nonessential gene of any gene size) at any later state will result in a loss of likelihood. This property is illustrated in FIG. 4 which shows the trajectory of the searching algorithm projected in a subspace spanned by two different gene sizes. For illustration purpose, genes are grouped into 143 groups by grouping genes with similar sizes together to increase the length of the trajectory. As indicated in the plot at any state, moving backwards in any direction results in a loss of likelihood. FIG. 13 shows more trajectories projected in different subspaces.

Now we need to demonstrate that the likelihood function (3.7), which is defined in a high dimensional discrete space, has an unique solution. This can be established if the same estimations are obtained from different initial values. Since the initial values can be any value between the observation $\vec{n}$ and the total number of genes $\vec{M}$, we need to extend the searching algorithm (4.7) as follows:

For any initial value $\{\vec{N}^0: n_i \leq N_i^0 < M_i \text{ for } i=1,2, \ldots, g\}$ and any integer k with $$0 \leq k \leq \|\vec{M}\| - \|\vec{N}^0\| \text{ such that} \quad (4.13)$$

$$\vec{N}^0 \oplus 0 = \vec{N}^0,$$

$$\vec{N}^0 \oplus 1 = \{\vec{N}^0 \pm 1_i: \Delta_i \Im^*(\vec{N}^0) \geq \Delta_j \Im^*(\vec{N}^0) \text{ for all } j \neq i\}, \text{ and}$$

$$\vec{N}^0 \oplus k = (\vec{N}^0 \oplus (k-1)) \oplus 1 \text{ for } k \geq 2.$$

The likelihood gain function is extended similarly as G(0)=0 and $$G(k) = \Im^*(\vec{N}^0 \oplus k) - \Im^*(\vec{N}^0 \oplus (k-1)) \quad (4.14)$$

for $1 \leq k \leq \|\vec{M}\| - \|\vec{N}^0\|$.

Algorithm (4.13) preserves all the properties of algorithm (4.7) and it searches the ML estimator the same way as that of algorithm (4.7) with two exceptions. Unlike algorithm (4.7), which uses $\vec{n}$ as initial values of $\vec{N}$ and at each iteration, the number of nonessential genes is increased by one in gene groups of size $\delta_i$ to find the maximum likelihood gain, this algorithm uses $\vec{N}^0$ as initial values of $\vec{N}$ which can be greater than the ML estimator. Therefore, at each iteration, the number of nonessential genes in a group with size $\delta_i$ can be either increased or decreased by one such that the likelihood gain is maximum.

Figure 14:
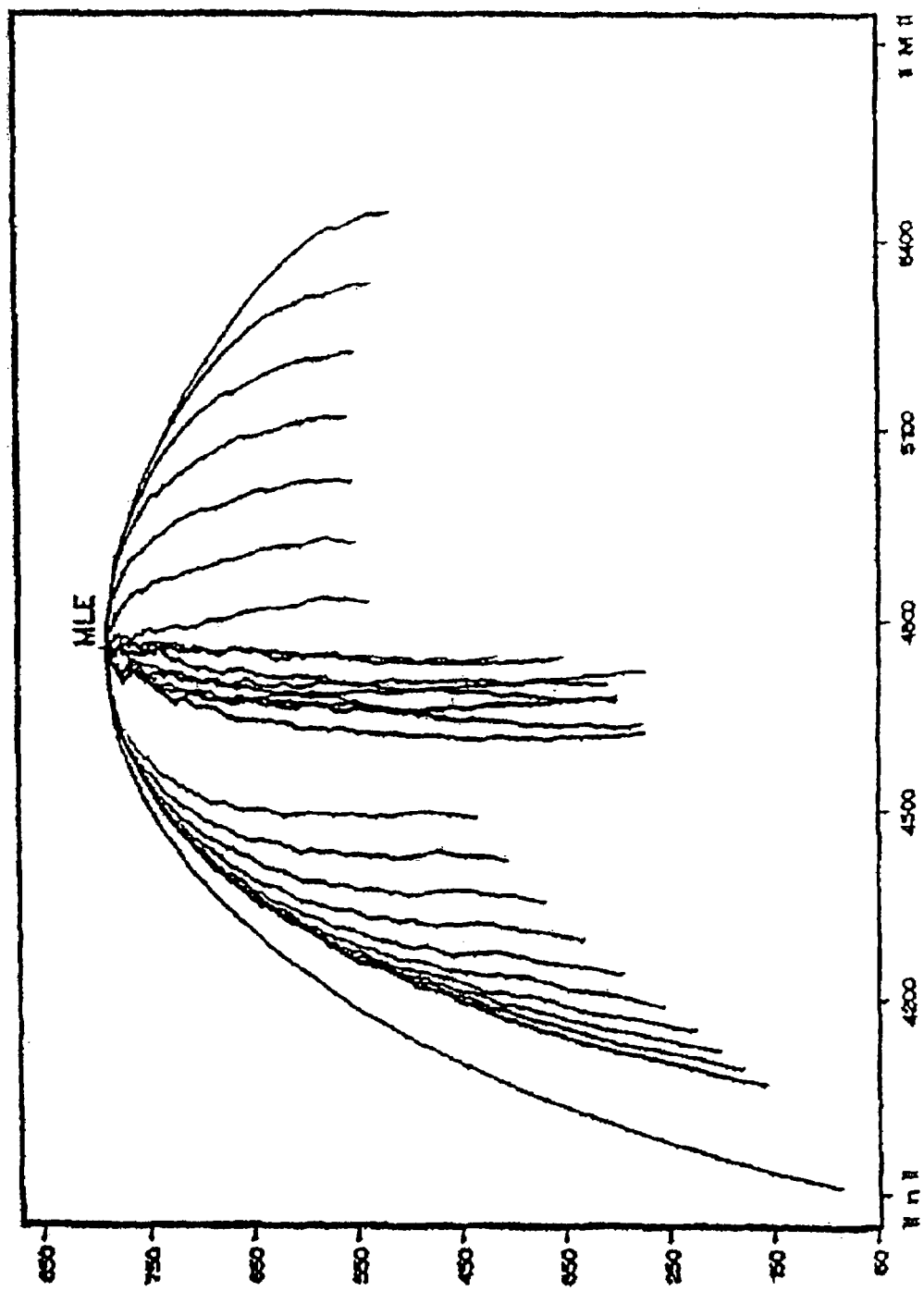
FIG. 14. Plot of likelihood for different initial values.
Figure 15:
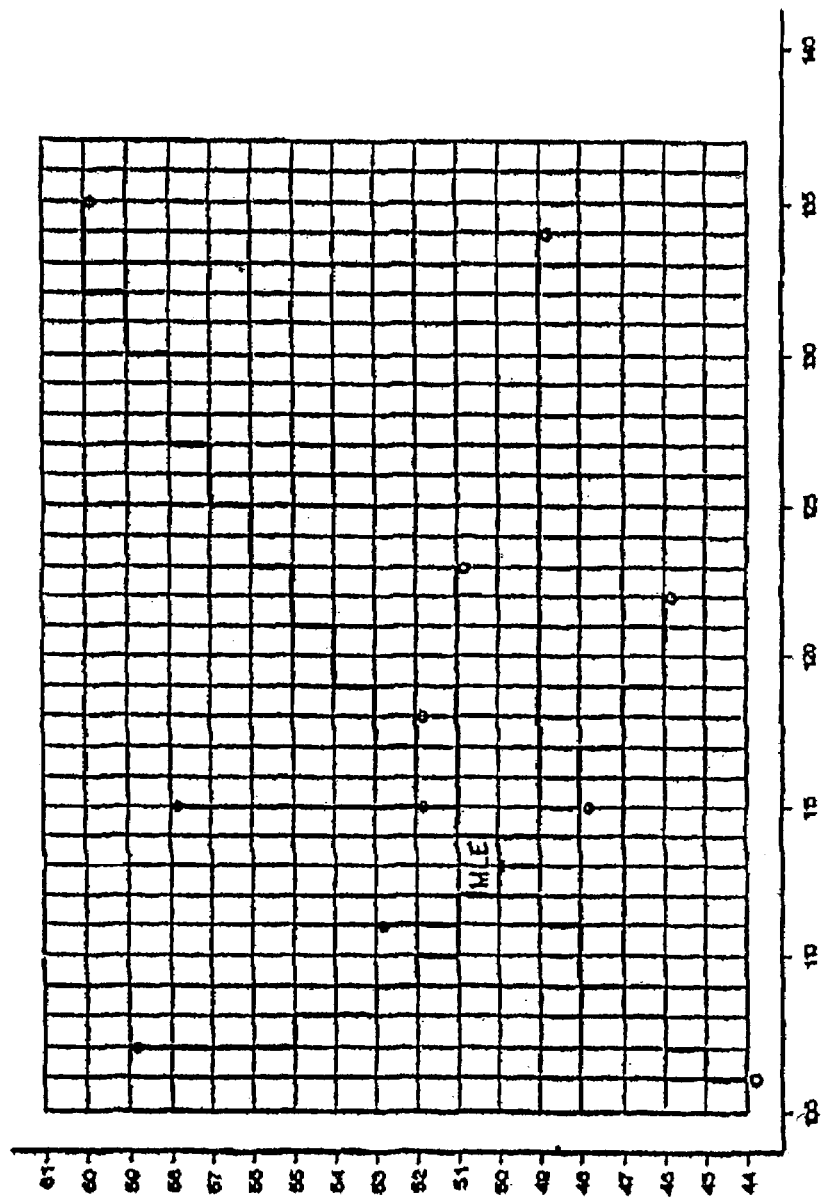
FIG. 15. Trajectories of the algorithm with different starting values projected in the subspace spanned by two gene sizes: 1101-1150 DNA base-pairs for X-axis and 921-930 DNA basepairs for y-axis.

Randomly selected initial values $\vec{N}^0$ were used for data with grouped gene sizes and data with exact gene sizes. The estimations of all parameters are exactly the same and the final likelihood for all initial values $\vec{N}^0$ are exactly the same as indicated in FIG. 14, which plots twenty seven different initial values of $\vec{N}^0$. The line in the far left represents the likelihood when $\vec{N}^0 = \vec{n}$, and the lines in the middle are randomly selected. FIG. 15 is the trajectory projected into a subspace spanned by two gene sizes. Each circle represents the projection of a different initial value $\vec{N}^0$. Regardless of the initial values, the trajectories all converge to the ML estimator.

D. Analysis of *Pseudomonas Aeruginosa* Data

1. Multivariate Model with Exact Gene Sizes

Figure 16A:
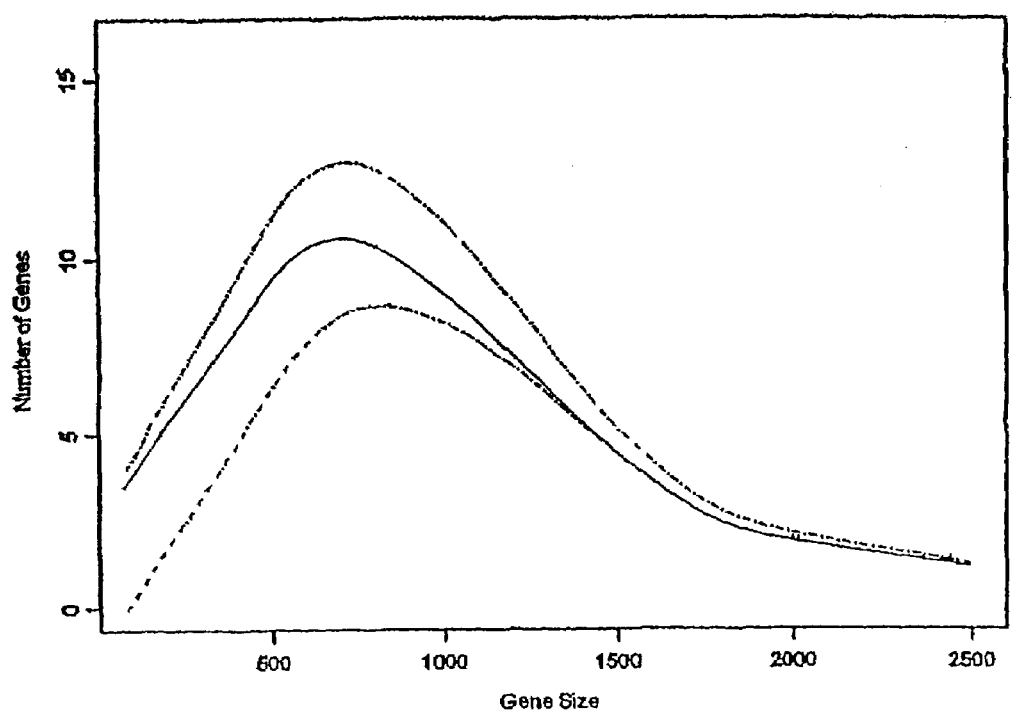
FIG. 16A The top line is M, number of genes, the bottom line is n, the number of genes with at least one observed insertion; the line in the middle is N, the number of estimated nonessential genes. For demonstration purpose, a cubic spline smooth is applied to the data.
Figure 16B:
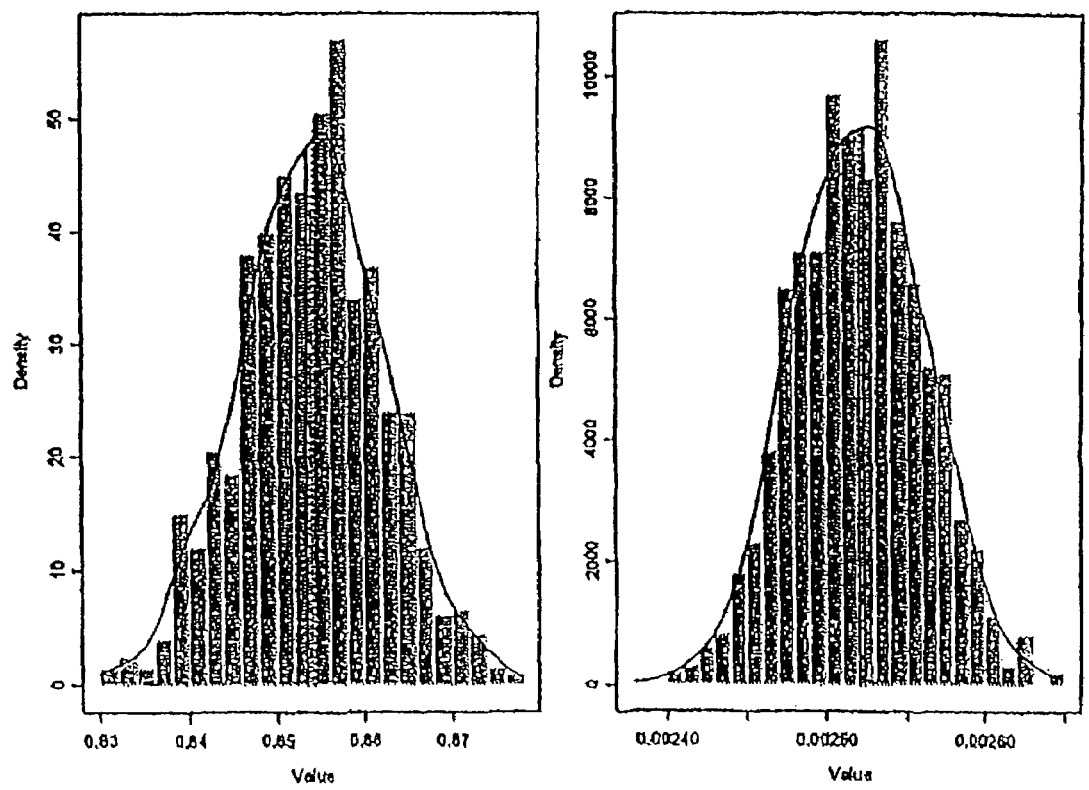
FIG. 16B, histogram of resamples of $\hat{\gamma}$ (left) and $\hat{\lambda}$ (right).

The data considered here consist of observations from 5570 genes in 881 different sizes, ranging from 72 to 16884 DNA base-pairs. Distribution of gene size is severely skewed to the right as indicated in FIG. 10. For many sizes, especially for sizes smaller than 200 or greater than 2000 DNA base-pairs, there is only one gene in a given size and the observation of transposon insertions for small genes are usually truncated. Since all genes are modeled simultaneously in a single model with a prior $\gamma$ enforcing the essentialness of a gene being independent of its size, the sparseness of the data does not impose limitations on the computation. However, as discussed in the next section, the prior may play a dominating role for small genes where data are sparse. The estimations of $\gamma$ and $\lambda$, together with the 95 percent BCa confidence intervals are presented in Table 6 and the estimation of $\vec{N}$ is presented in FIG. 16.

TABLE 6

Parameter Estimation of $\gamma$ and $\lambda$

| | Estimate | Bias | SE | BCa Confidence Intervals |
|---|---|---|---|---|
| $\gamma$ | 0.8434 | $3.942 \times 10^{-3}$ | $9.893 \times 10^{-3}$ | (0.818, 0.859) |
| $\lambda$ | $2.547 \times 10^{-3}$ | $-1.027 \times 10^{-5}$ | $4.392 \times 10^{-5}$ | (0.00247, 0.00264) |

Here the bias and standard error are estimated with bootstrap

2. Multivariate Model with Grouped Gene Sizes

The prior $\gamma$ plays an important role in enforcing the fact that the essentialness of a gene is independent of its size. It also made possible to estimate the number of essential genes where data are very sparse. However, for small genes where data are extremely sparse, the prior $\gamma$ becomes the dominating source of information. In order to moderate the dominance of the prior on small genes with sparse observations, we grouped the genes into 143 groups according to their sizes, using the median size of each group as the gene size. Table 7 is a sample of estimated $\vec{N}$ based on grouped and exact gene sizes. In the table, m is the number of unique sizes in each group; $N_1$ is estimated using grouped data and $N_2$ is estimated using ungrouped data.

TABLE 7

Estimated N with Grouped and Exact Gene Sizes

| Gene size | m | M | x | N | $N_1$ | $N_2$ |
|---|---|---|---|---|---|---|
| [72, 120] | 6 | 7 | 3 | 2 | 6 | 7 |
| (120, 150] | 4 | 7 | 3 | 2 | 6 | 7 |
| (150, 160] | 3 | 7 | 2 | 2 | 6 | 7 |
| (160, 170] | 2 | 8 | 0 | 0 | 7 | 7 |
| (170, 180] | 3 | 9 | 1 | 1 | 8 | 8 |
| (180, 190] | 3 | 9 | 1 | 1 | 8 | 8 |
| (190, 200] | 3 | 12 | 4 | 4 | 11 | 11 |
| (200, 210] | 4 | 27 | 7 | 7 | 23 | 24 |
| (210, 220] | 3 | 19 | 7 | 5 | 16 | 17 |
| ... | ... | ... | ... | ... | ... | ... |

We see that here $N_2 \geq N_1$. However, this is true only for data in the above table where the ungrouped data are extremely sparse and most of the data are truncated. The estimated proportion of non-essential genes, $\gamma$, is actually larger for grouped data which is presented in Table 8. Grouping genes with similar sizes reduces the sparseness of the data and consequently, the dominance of the prior. Another obvious advantage of grouping is dimension reduction of the parameter space, and therefore, drastic reduction of computation time. Of cause, such grouping introduces another source of variation, and the algorithm could be unrobust against different grouping. In our study, however, different grouping resulted only in slight difference in estimates.

3. Conditional Maximum Likelihood Estimates

For a given gene size $\delta_j$, the likelihood function (3.4) can be written differently as $$L_j(\gamma, \lambda | N_j) = \binom{N_j}{n_j} q_j^{n_j} p_j^{N_j - n_j} \prod_{i=1}^{n_j} f(x_{j,i}^*, \delta_j \lambda) \qquad (5.1)$$

Here $f(.,.)$ is defined in (3.1), and $x_{j,1}^*, x_{j,2}^*, \ldots, x_{j,n_j}^*$ are the $n_j$ nonzero observations from $N_j$ genes of size $\delta_j$. Assume there are g different gene sizes, the likelihood function can be written as $$L = \left( \prod_{j=1}^{g} \binom{N_j}{n_j} q_j^{n_j} p_j^{N_j - n_j} \right) \cdot \left( \prod_{j=1}^{g} \prod_{i=1}^{n_j} f(x_{j,i}^*, \delta_j \lambda) \right) = L_1 \cdot L_2 \qquad (5.2)$$

with $$\sum_{j=1}^{g} n_j = n.$$

Assuming the number of observations $n_j$ for each gene size $\delta_j$ being fixed, we can obtain the conditional maximum likelihood estimate of $\lambda$ by maximize $L_2$ as $$\hat{\lambda} = \|S\| / \sum_{j=1}^{g} n_j \frac{\delta_j}{1 - e^{-\hat{\lambda}\delta_j}}, \qquad (5.3)$$

where $$\|S\| = \sum_{j=1}^{g} \sum_{i=1}^{n_j} x_{j,i}^* = \sum_{i=1}^{n} x_i^*.$$

Equation (5.3) reduces to equation (4.2) if we estimate $N_j$ by $$N_j = \frac{n_j}{1 - e^{-\hat{\lambda}\delta_j}}.$$

The proportion of truncated nonessential genes can be calculated as $$\hat{p} = P(x = 0 | \text{non essential}) = \int_{\Omega} e^{-\hat{\lambda}\delta} dF(\delta). \qquad (5.4)$$

Here $\Omega$ is the set of nonessential genes, which can be approximated by the set of all untruncated genes. Therefore, $$\hat{\gamma} = \frac{n}{M} + \hat{p} \qquad (5.5)$$

Figure 17:
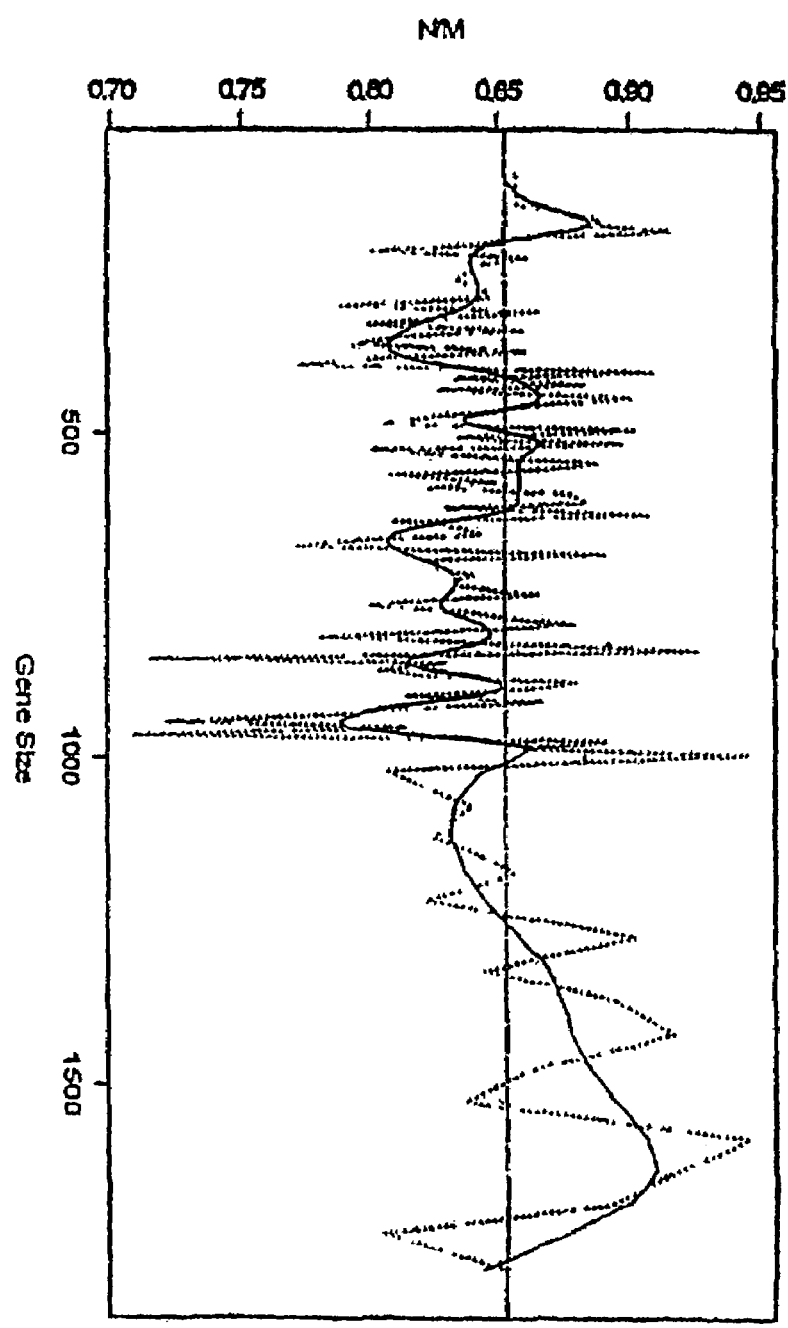
FIG. 17. Plot of $\hat{N}_1/M_1$. The doted line is the value of $\hat{N}_1/M_1$ and the solid line is a moving average smooth.

Estimations from the three approaches are very similar as shown in Table 8. If the primary interest is to estimate $\lambda$ and $\gamma$, the conditional MLE approach has the advantage of simplicity. However, in estimating $\lambda$, this approach omitted information of $\vec{M}$, and $\gamma$ is estimated separately after $\lambda$ is estimated. Another obvious limitation of this approach is that it can only estimate $\|\vec{N}\|$, the total number of nonessential genes by $\|\vec{n}\|/\hat{\gamma}$. The estimation of $\vec{N}$ by $\vec{n}/\hat{\gamma}$ is not reasonable because even though $\gamma$ is independent of gene size, we can not assume the proportion of non-essential genes in different sizes being the same as shown in FIG. 17.

TABLE 8

Estimates of $\gamma$ and $\lambda$, with the Three Approaches

| | | Estimates | Bias | SE | 95% BCa Confidence intervals |
|---|---|---|---|---|---|
| Multivariate Model with Exact Gene Sizes | $\gamma$ | 0.843 | $3.942 \times 10^{-3}$ | $9.893 \times 10^{-3}$ | (0.818, 0.859) |
| | $\lambda$ | $2.547 \times 10^{-3}$ | $-1.024 \times 10^{-5}$ | $4.320 \times 10^{-5}$ | $(2.473, 2.642) \times 10^{-3}$ |

TABLE 8-continued

Estimates of γ and λ, with the Three Approaches

|  |  | Estimates | Bias | SE | 95% BCa Confidence intervals |
|---|---|---|---|---|---|
| Multivariate Model with | γ | 0.853 | $7.221 \times 10^{-4}$ | $8.051 \times 10^{-3}$ | (0.835, 0.867) |
| Grouped Gene Sizes | λ | $2.524 \times 10^{-3}$ | $2.803 \times 10^{-6}$ | $4.063 \times 10^{-5}$ | $(2.451, 2.610) \times 10^{-3}$ |
| Conditional Maximum | γ | 0.828 | $-7.621 \times 10^{-5}$ | $7.273 \times 10^{-3}$ | (0.815, 0.843) |
| Likelihood Estimates | λ | $2.539 \times 10^{-3}$ | $9.713 \times 10^{-7}$ | $4.058 \times 10^{-5}$ | $(2.455, 2.618) \times 10^{-3}$ |

E. Discussion of One Dimentsional Case

When the model does not depend on gene size, which can happen for example, when we study a subset of genes with a fixed size, or in other settings where the distribution is identical, model (2.6) reduces to (2.5). Blumenthal, Dayhiya, and Gross (1978) studies estimations of complete sample size from an incomplete Poisson sample using conditional, unconditional, and modified maximum likelihood functions. The modified likelihood estimation weights the likelihood function and maximizes it. This approach is similar to providing priors to λ and N. Table 9 presents four types of estimations of N using data randomly selected from the 143 grouped genes. Here M and n are number of genes and number of genes with at least one observed transposon insertions. $N_{m-b}$ is a subset of $N_1$ in Table 7, which is estimated using model (2.6) with grouped data; $N_b$ is estimated with model (2.5); $N_c$ and $N_u$ are conditional and unconditional estimates of N as described in Blumenthal., Dayhiya, and Gross (1978).

TABLE 9

Comparison of Estimations with Different Methods

| Gene size | M | n | $N_{m-b}$ | $N_b$ | $N_u$ | $N_c$ |
|---|---|---|---|---|---|---|
| [72, 120] | 7 | 2 | 6 | 2 | 3 | 2 |
| (400–410] | 44 | 31 | 40 | 37 | 36 | 36 |
| (430–440] | 46 | 22 | 38 | 25 | 25 | 26 |
| (470–480] | 80 | 42 | 66 | 57 | 56 | 57 |
| (500–510] | 54 | 30 | 45 | 39 | 39 | 39 |
| (610–620] | 47 | 29 | 39 | 33 | 33 | 34 |
| (640–650] | 54 | 35 | 45 | 44 | 43 | 43 |
| (710–720] | 50 | 35 | 42 | 41 | 41 | 41 |
| (750–760] | 56 | 37 | 46 | 39 | 46 | 40 |
| (770–780] | 61 | 43 | 51 | 53 | 52 | 52 |
| (910–920] | 60 | 47 | 52 | 53 | 53 | 52 |
| (980–990] | 57 | 45 | 49 | 52 | 51 | 51 |
| (1050–1100] | 137 | 107 | 115 | 117 | 115 | 117 |
| (1200–1250] | 129 | 100 | 106 | 106 | 106 | 106 |
| (1400–1450] | 121 | 110 | 111 | 112 | 112 | 112 |
| (2100–2150] | 23 | 20 | 20 | 20 | 20 | 20 |

We see that the estimations from the three univariate models are very similar. For fairly large genes, estimations from the multivariate model are similar to those of the univariate models. However, for small genes with high truncation rate, estimations from the multivariate model are larger than estimations from the univariate models. In the univariate models, only the information related to a particular gene size is used and the estimations are obtained separately for each gene size. This approach tends to underestimate N for small genes with sparse observations. The multivariate model uses a prior to enforce the fact that the essentialness of a gene is independent of its size and maximizes the likelihood jointly for all genes. Therefore, it alleviates the underestimation of N for small genes with high truncation rate.

Example 2 lpxC

Lipid A constitutes the outer layer of the outer membranes of gram-negative bacteria and is essential for bacterial growth. This makes all the enzymes involved in the biosynthesis of this molecule essential for bacterial growth, and therefore ideal targets for drug design. A series of synthetic molecules was previously identified that inhibited the first committed step in lipid A biosynthesis. Onishi H. R., B. A. Pelak, L. S. Gerckens, L. L. Silver, F. M Kahan, M-H Chen, A. A. Patchett, S. M. Galloway, S. A. Hyland, M. S. Anderson, and C. R. H. Raetz. 1996. Science. 274: 980-982. This step is catalyzed by a unique deacetylase (UDP-3-O-[R-3-hydroxymyristoyl]-GlcNAc deacetylase), LpxC.

UDP-3-O-[R-3-hydroxymyristoyl]-GlcNAc deacetylase (LpxC) is a deacetylase that catalyzes the first committed step of lipopolysaccharide (LPS) biosynthesis in gram negative bacteria. This is the second step following the first acylation of N-Acetylglucosamine (GlcNAc). This enzyme functions to deacetylate the UDP-3-O-[R-3-hydroxymyristoyl]-GlcNAc. This step was shown to be essential for growth in E. coli wherein a point mutant (EnvA1) expresses an LpxC protein that has reduced activity. Beall B. and J. Lutkenhaus, 1987. Sequence analysis, transcriptional organization, and insertional mutagenesis of the envA gene of Escherichia coli. J. Bacteriol. 169: 5408-5415. A 30% reduction in the amount of LPS on the cell wall of such mutants results in hypersensitivity to antibiotics. Attempts to create null mutants in lpxC were unsuccessful in a number of pathogenic bacteria, indicating that inhibitors of LpxC would be effective antibiotics for a number of gram negative organisms.

Previously identified inhibitors are chiral hydroxamic acids that had unique hydrophobic aromatic moieties, and were suspected to bind a metal in the active site of the deacetylase. The most potent inhibitor, L-161,240, displayed a minimal inhibitory concentration of about 1 microgram per milliliter against E. coli, caused three logs of bacterial killing in 4 hours, and cured mice infected with a lethal intraperitoneal dose of E. coli. Considering the very high degree of homology between the E. coli and P. aeruginosa enzymes, it was initially presumed that an inhibitor of the E. coli enzyme might also inhibit the P. aeruginosa enzyme. However, this molecule inhibited LpxC from P. aeruginosa only at very high concentrations, and even then it did so poorly. It had no effect on bacterial growth in this organism. Thus, there was some question as to whether the lpxC homologue had the same function in P. aeruginosa, and whether it was essential to P. aeruginosa given its decreased sensitivity to the L,161,240 inhibitor.

Nevertheless, *P. aeruginosa* lpxC was one nucleic acid identified as being unable to accommodate a transposon insertion in the library depicted in Table 1 (PA4406). To test the essentiality of *P. aeruginosa* lpxC, we first tested the sensitivity of *P. aeruginosa* transformants expressing *E. coli* LpxC following a "promoter swap" integration. Using this technique, we completely shut off expression of the native *P. aeruginosa* lpxC, while expressing only the *E. coli* enzyme encoded on a plasmid. This strategy resulted in a *P. aeruginosa* mutant that was more sensitive to L-161,240. This suggested that the *E coli* lpxC gene was substituting for the function of the *P. aeruginosa* gene, and moreover, that there were no duplicate functional homologues in *P. aeruginosa* that were active in the absence of lpxC.

Materials. *Pseudomonas aeruginosa* PAO1 was grown at 37° C. in Luria-Bertani (LB) broth (Difco) or plated on sheep blood agar (Remel). Tetracycline at 100 μg/ml in LB media was used to maintain the selection of the integrated plasmid pBEM10 in PAO1. LB broth or agarwith 10 μg/ml of tetracycline was used for growing *E. coli* DH5α (Gibco BRL) and *E. coli* S-17 transformants. Plasmids pPS72 and pBADHisB were from Promega and Invitrogen, respectively. EDTA, bistri buffer, sucrose, arabinose, and DMSO were purchased from Sigma as Ultrapure agents. Yeast extract and Tryptone were obtained from Difco. Restriction enzymes, and T4 DNA Ligase, and their reaction buffers were from New England Biolabs. Polymixin B nonapeptide was from Sigma. The antibiotics, tetracycline, ampicillin, carbenicillin, gentamicin, and kanamycin were all purchased from Sigma. DNA and deduced amino acid information were analyzed using a family of programs included in the Dnastar package. BLASTP was used to search for amino acid similarities among a host of protein databases available on-line through the National Library of Medicine (USA). Altschul, T. F., W. Gish, W. Miller, E. W. Myers, and D. J. Lipman. 1990. Basic local alignment tool. J. Mol. Biol. 215: 403-410.

DNA manipulations. Standard recombinant DNA procedures were used. Sambrook J., E. F. Fritsch, and T. Maniatis. 1989. *Molecular cloning: a Laboratory Manual*, $2^{nd}$ Edition. Cold Spring Harbor, N.Y.: Cold Spring Harbor Laboratory. Primers were designed to the N- and C-terminal regions of the *E. coli* or *P. aeruginosa* lpxC gene that encompassed only the coding region and included NdeI and EcoRI restriction sites for subsequent cloning. For the *E. coli* gene the primers were (5'-GGGAATTCCATATGATCAAACAAAGGA-CACTTAAACGT-3' and 5'-CCGGAATTCTTATGCCAG-TACAGCTGAAGGCGCT-3') (SEQ ID NOS:1 and 2) and for the *P. aeruginosa* gene they were (5'-GGGAATTC-CATATGATGATCAAACAACGCACCTTGAAGAACAT-3' and 5'-CCGGAATTCCTACACTGCCGCCGC-CGGGCGCATATAG-3') (SEQ ID NOS:3 and 4). These primers were used in a polymerase chain reaction (PCR) containing either *P. aeruginosa* genomic DNA (10-50 μg) or plasmid pKD6 containing the *E. coli* lpxC gene (1.0 μg) as template (Sorensen, P. G., J. Lutkenhaus, K. Young, S. S. Eveland, M. S. Anderson, and c.R.H. Raetz. 1996. Regulation of UDP-3-O-[R-hydroxymyristoyl]-N-acetylglucosamine deacetylase in *Escherichia coli*. The second enzymatic step of lipid A bioynthesis. J. Biol. Chem. 271 (42): 25898-25905). The lpxC genes were amplified using Pwo DNA polymerase (Roche) in a 100 μl reaction mixture containing 200 μM concentration of each dNTP and 0.5 μM concentration of each primer for 30 cycles (94° C. denaturation, 55° C. annealing, and 72° C. polymerization (according to the manufacturer's instructions). The PCR products were purified with the Qiaquick PCR Purification Kit from Qiagen (according to the manufacturer's instructions) and digested with NdeI and EcoRI restriction enzymes at sites introduced by the primer sequences. Bands of the correct sizes predicted for the lpxC genes were separated by gel electrophoresis, and the excised DNA purified using the Qiaquick Gel Extraction Kit from Qiagen (according to the manufacturer's instructions). The purified DNA was ligated into the T7 expression vector (Studier, F. W., A. H. Rosenberg, J. J. Dunn, and J. W. Dubendorff. 1990. Use of T7 RNA polymerase to direct expression of cloned genes. Methods Enzymol. 185: 60-89). Plasmid pET21b (Novagen), that had been cut in the multiple cloning site with the same enzymes, was transformed into DH5α and plated on LB agar containing ampicillin (250 μg/ml). The resulting clones had their DNA sequenced to confirm the fidelity of the PCR reactions before it could be transferred into the expression strain. Subcloning of these fragments into other vectors was carried out as needed for expression in various backgrounds. These included pEX18T (cbR) for allelic exchange mutagenesis in *P. aeruginosa* (Schweizer, H. P. and T. T. Hoang. 1995. An improved system for gene replacement and xylE fusion analysis in *Pseudomonas aeruginosa*. Gene 158(1): 15-22), pDN19 (tetR) for low copy number complementation of *E. coli* JBK-1 (Nunn, D., S. Bergman, and S. Lory. 1990. Products of three accessory genes, pilB, pilC, and pilD, are required for biogenesis of *Pseudomonas aeruginosa* pili. J. Bacteriol. 172(6): 2911-2919), and pUCP30T (gmR) for *P. aeruginosa* 'promoter swap' mutant complementation (Schweizer, H. P., T. R. Classen, and T. Hoang. 1996. Improved methods for gene analysis and expression in *Pseudomonas*. In: Nakazawa, T., K. Furukawa, D. Haas, S. Silver. (Eds.) Molecular Biology of *Pseudomonas*. American Society for Microbiology, Washington, D.C. pp. 229-237).

Construction of pBEM10 and 'promoter swap' mutagenesis. Plasmid pPW101 was made by ligating oriT, the region that encodes conjugative plasmid transfer, into pSP72 (Promega). oriT had been amplified from plasmid pEX100T (Schweizer and Hoang, 1995, supra) with an introduction of an NdeI and AatII restriction sites. To create the lpxC 'promoter swap' vector, pBEM10, the following different DNA pieces were amplified and sequentially ligated into pPW101. These included the tetracycline resistance marker (tetR) from plasmid pUCP26 (Olsen, R. H., G. DeBusscher and R. R. McCombie. 1982. Development of broad-host-range vectors and gene banks: self-cloning of the *Pseudomonas aeruginosa* PAO chromosome. J. Bacteriol. 150: 60-69), the araBAD promoter from the plasmid pBAD HisB (Invitrogen) with an altered ribosome binding site (rbs) (Guzman, L. M., D. Belin, M. J. Carson, and J. Beckwith. 1995. Tight regulation, modulation, and high-level expression by vectors containing the arabinose pBAD promoter. J. Bacteriol. 177(14):4121-4130), the araC gene, also from pBAD HisB (Lee, N. 1980. Molecular aspects of ara regulation. In *The Operon*. J. H. Miller and W. S. Reznikoff, eds. Cold Spring Harbor, N.Y. Cold Spring Harbor Laboratory, pp. 389-410; and Schleif, R. S. 1992. DNA looping. Ann. Rev. Biochem. 61: 199-223), and the first 340 base pairs of the *P. aeruginosa* lpxC gene. The tetR marker was amplified using a forward primer that introduced a BglII site (5'-AGATCTCAAGGGTTGGTTTGCGCA-3', SEQ ID NO:5) and a reverse primer that introduced an EcoRI site (5'-GAATTCTAATTCTCATGTTTGACA-3', SEQ ID NO:6). The araBAD promoter and araC gene were amplified as one piece from the pBAD HisB vector. The forward primer introduced an XhoI site (5'-CTCGAGGCATGCATAATGT-GCCTGTC-3', SEQ ID NO:7) and the reverse primer introduced a HindIII site (5'-AAGCTTCTCCTGTTAGC-CCAAAAAAACG-3', SEQ ID NO:8). The rbs was altered from its original AGGAG to CTTCT. The following primer set was used to make these changes and introduced an upstream BssHII site (5'-GCGCGCGGACGAAAGTAAAC-CCACTGG-3', SEQ ID NO:9) and a downstream HindIII site (5'-AAGCTTATTCAGAAGGTTAGC-CCAAAAAAACGGG-3', SEQ ID NO:10). The first 340 bases of PAO1 lpxC were amplified from PAO1 genomic DNA. The forward primer introduced a HindIII site (5'AAGCTTATGATCAAACAACGCACCTT-3', SEQ ID NO:11) and the reverse primer introduced an XbaI site (5'-TCTAGAAGCGCTGCCATCCATGATCGG-3', SEQ ID NO:12). These pieces were then ligated into pPW101 to form the final product, pBEM10, which was used for the 'promoter swap' mutagenesis of lpxC. The 'promoter swap' scheme is a homologous recombination strategy, whereby transformation of pBEM10 into P. aeruginosa removed the native lpxC promoter and placed the tightly regulated araBAD promoter upstream of the chromosomal copy of lpxC, allowing modulation of its expression by the use of a simple sugar, arabinose (FIG. 3). In the absence of arabinose the lpxC was effectively shut off, and expression was inducible by addition of arabinose. Such mutants were selected in the presence of arabinose, and if lpxC is essential, these mutants would not be viable in media that is not supplemented with arabinose, but fully capable of growth in the presence of arabinose.

Growth curves. Bacterial cultures were prepared by diluting stationary phase overnight cultures to an $OD_{600}$ of 0.1 in 5 ml of LB. The inhibitor, L-161,240, was resuspended in DMSO to a final concentration of 10 mg/ml and added to the bacterial cultures to a final concentration of 50 μg/ml or 10 μg/ml. In the samples without inhibitor, DMSO was added to keep the final concentration of DMSO equivalent between samples. The cultures were incubated with shaking and 0.8 ml was taken for $OD_{600}$ readings over the course of the experiment. DH5α, PA01, and PA0200 (Schweizer, H. P. 1998. Intrinsic resistance to inhibitors of fatty acid biosynthesis in Pseudomonas aeruginosa is due to efflux: application of a novel technique for generation of unmarked chromosomal mutations for the study of efflux systems. Antimicrob. Agents Chemother. 42: 394-398) were all grown at 37° C. In the cases where temperature sensitive JBK strains were being assayed, the cultures were grown at 42° C. for both the overnight and the time course cultures.

Outer membrane permeabilization. Polymixin B nonapeptide (Sigma) was prepared as a suspension in DMSO at 3 mg/ml final concentration. Erythromycin and Tetracycline were resuspended in DMSO to a final concentration of 250 mg/ml and 125 mg/ml, respectively. L-161,240 was prepared as above in DMSO to a final concentration of 10 mg/ml. These DMSO antibiotic solutions were individually added to LB to the appropriate final concentration and mixed. Polymixin B nonapeptide was then added to the appropriate samples and mixed. DMSO was added to each sample to keep the final concentration of DMSO equivalent between samples. A stationary phase overnight culture of PA01 was added to each sample to bring the final concentration to 0.1 $OD_{600}$. Samples were removed for $OD_{600}$ determinations every 1-2 hours for 6.5 hours and the data from these time points were plotted.

MIC determinations for 'promoter swapped' mutants. Single colonies of DH5α, PA01 and each promoter swap strain were picked and grown in LB at 37° C. with shaking for approximately 4 hours. Assuming that an $OD_{600}$ reading of 1.0 is equivalent to $10^9$ cells/ml, dilutions were made of all cultures to $5 \times 10^5$ cells/ml. 200 μl of each diluted culture was added to each well where a two-fold serial dilution of inhibitor had been placed. The 96-well plates were incubated at 37° C. overnight and their $OD_{600}$ determined using the Spectramax Plus (Molecular Devices) plate reader.

To confirm the effect of the arabinose-sensitive promoter in regulating the lpxC expression in the swapped mutants, MIC determinations were performed as above, except that arabinose was added to induce expression of the chromosomal locus and override the effects of the plasmid borne lpxC. In this case the stationary-phase overnight bacterial culture was diluted to $5 \times 10^5$ cells/ml in LB containing Arabinose to a final concentration of 0.2% (a 20% stock made up in water).

RESULTS AND DISCUSSION

Homology between the E. coli and the P. aeruginosa LpxC enzymes. Using protein analysis software, this study and others have compared the deduced amino acid sequence of LpxC from both E. coli and P. aeruginosa (Hyland, S. A., S. S. Eveland, and M. S. Anderson. 1997. Cloning, expression, and Purification of UDP-3-O-Acyl-GlcNAc Deacetylase from Pseudomonas aeruginosa: a metalloamidase of the lipid A biosynthesis pathway. J. Bacteriol. 179 (6): 2029-2037). This comparison revealed 82% similarity and 57% identity shared between the two sequences. This homology was found over the entire length of the protein sequence (data not shown). Significant homology with other known acetyl- or acyltransferases was not found, suggesting that LpxC is unique among acetyltranferases. The two proteins also share a total of five fully conserved Histidine residues that are presumed to be responsible for the zinc metal cofactor coordination. It was therefore expected that an inhibitor that functions by chelating the metal cofactor away would affect both enzymes similarly.

LpxC is essential for growth in P. aeruginosa. Since the hydroxamate inhibitor was effective in preventing growth of E. coli, but completely ineffective against P. aeruginosa, there was a possibility that LpxC was not essential in P. aeruginosa. This could be as a result of the presence of another enzyme that catalyzed a similar function. If that were the case, elimination of the LpxC function should be possible without inhibiting bacterial growth. A thorough analysis of the P. aeruginosa genome sequence revealed only one LpxC homologue. An attempt to disrupt the function of this LpxC homologue was made by conjugating wild type PAO1 with a suicide vector (pEX18T) carrying lpxC whose BamHI-SalI fragment had been replaced with a gentamicin cassette. However, P. aeruginosa null mutants could not be established by this method. In several attempts a few gentamicin resistant trans-conjugants were obtained, but in all these cases allelic replacement of the chromosomal lpxC by the defective copy had not occurred. Instead, a gene duplication had occurred, placing the suicide vector and the disrupted copy next to the wild type allele (data not shown). This could be demonstrated by the carbenicillin resistance and sucrose sensitivity acquired by these trans-conjugants, both of which are encoded on the suicide vector. These data indicated a strong negative selection for the sought after disruption of lpxC suggesting that lpxC is essential for growth. To confirm this, an experiment was carried out whereby the trans-conjugants were transformed with either lpxC on a low copy, replicating vector, or vector alone. In 100% of lpxC transformants, resolution of the gene duplication as demonstrated by the loss of carbenicillin resistance and sucrose sensitivity was observed, as opposed to no such resolution among those transformed with vector alone. These results suggested that the wild type genomic allele could be disrupted if a functional copy was present on the transforming plasmid.

In another attempt at demonstrating essentiality of LpxC in *P. aeruginosa*, the 'promoter swap' strategy as described in materials and methods was carried out. 'Promoter swapped' *pseudomonas* mutants were fully capable of growth in the presence of arabinose when the arabinose sensitive lpxC promoter was turned on, but completely incapable of growth in the absence of this inducer. This further confirmed that in *P. aeruginosa*, just as in *E. coli*, LpxC is essential for growth.

*E. coil* expressing LpxC from *P. aeruginosa* is more resistant to L-161, 240. The *E. coli* strain JBK-1/pKD6 contains the chromosomal lpxC gene disrupted with a kan element and a wild type copy of *E. coli* lpxC on the temperature-sensitive replicon pKD6. The strain was constructed as described by Sorensen et al., 1996. Since lpxC is essential for growth, this strain is not viable at 42° C. because the functional copy is on the temperature sensitive replicon. Transforming JBK-1/pKD6 with lpxC from either *E. coli* or *P. aeruginosa* on a non-temperature-sensitive replicon (pKD19, TetR) and selecting at 42° C., produced transformants that were viable at 42° C., tetracycline resistant, and kanamycin sensitive. This result indicated that lpxC from *P. aeruginosa* could be expressed in the *E. coli* background, and was capable of substituting for the missing chromosomal copy. An unexpected result was that whereas the JBK-1 carrying the lpxC copy from *E. coli* was still sensitive to killing by a slightly higher concentration of L-161,240, the JBK-1 carrying the lpxC copy from *P. aeruginosa* was resistant to up to 50 µg/ml, about 50 times above the MIC of the wild type organisms (data not shown). This suggested that the *P. aeruginosa* enzyme was uniquely resistant to this inhibitor. It also meant that this resistance was the reason for the failure to inhibit growth of *P. aeruginosa*, and not reduced permeability, or efflux or modification of drug by the pseudomonal enzymes. This, in turn, suggests that a program designed to search for inhibitors for the pseudomonal enzyme should be based on screening directly on that enzyme, and not the surrogate enzyme from *E. coli*.

L-161, 240 is a substrate for the major drug efflux pump of *P. aeruginosa*. The completed *P. aeruginosa* genome reveals genes for at least nine homologous, multicomponent, multidrug efflux systems (Stover et al., 2000, Complete genome sequence of *Pseudomonas aeruginosa* PA01, an opportunistic pathogen, Nature 406: 959-64). However the only one that is constitutively expressed to a high degree in the wild type strains is MexAB-OprM (Kohler, T., M. Michea-Hamzehpour, and U. Henze. 1997. Characterization of MexE-MexF-OprN, a positively regulated multidrug efflux system of *Pseudomonas aeruginosa*. Mol. Microbiol. 23: 345-354). Therefore, mutants of this efflux system can be used to evaluate the consequences of diminished efflux pump activity. These mutants would be expected to be highly sensitive to a number of antibiotics. Such a mutant, PAO 200, has been isolated (Schweizer, 1998, supra), and whereas it shows a higher level of sensitivity to a number of antibiotics (Westbrock-Wadman, S. D. R. Sherman, M. J. Hickey, S. N. Coulter, Y. Q. Zhu, P. Warrener, L. Y. Nguyen, R. M. Shawar, K. R. Folger, and C. K Stover. 1999. Characterization of a *Pseudomonas aeruginosa* Efflux Pump Contributing to Aminoglycoside Impermeability. Antimicrobial Agents and Chemotherapy. 43 (12): 2975-2983), it was not more sensitive to L-161,240 (FIG. 4). This suggests that this drug compound is not a substrate for this efflux system in *P. aeruginosa*.

Figure 5:
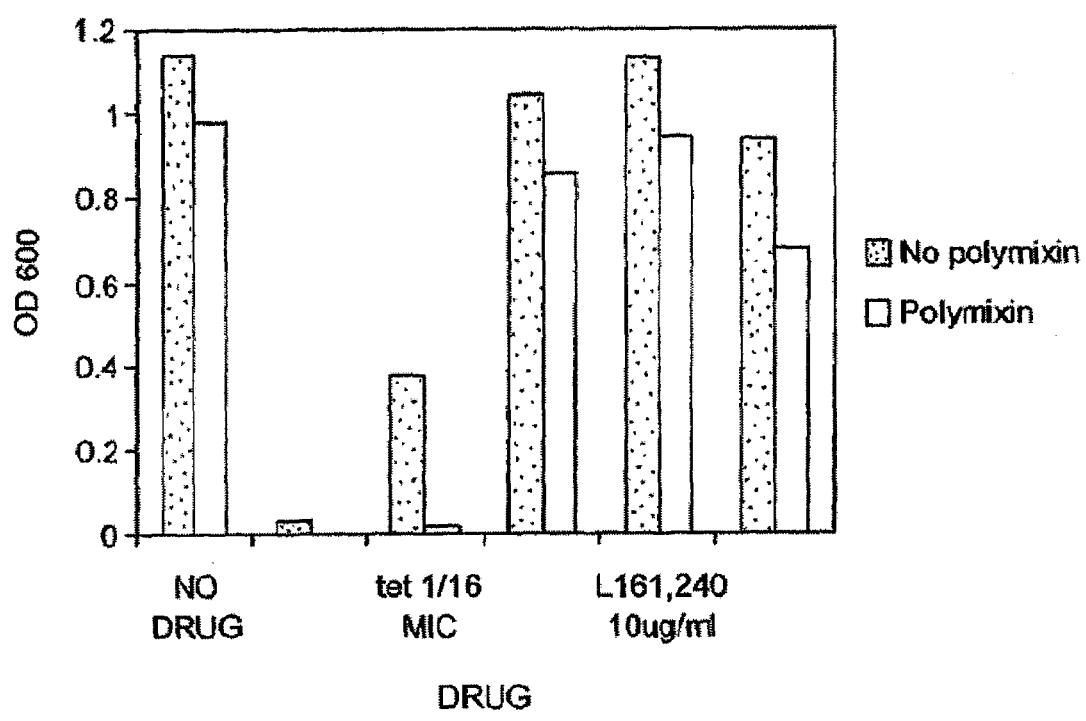
FIG. 5. Graph depicting the effect of tetracycline and L161, 240 on the growth of *P. aeruginosa* strain PA01 with and without polymixin permeabilization.

*P. aeruginosa* is not less permeable to L-161,240. Low permeability of the outer membrane is a major contributing factor to the observed high levels of intrinsic drug resistance in *P. aeruginosa* (Nikaido, H. 1998. The role of outer membrane and efflux pumps in the resistance of gram-negative bacteria. Can we improve access? Drug Resistance Updates. 1: 93-98). This low permeability is due to the fact that *P. aeruginosa* lacks the homolog of the relatively efficient, trimeric porins like OmpF. *P. aeruginosa* has, instead, OprF, the OmpA homolog, which produces channels only when it is folded into a rare conformation, and only a small fraction of these channels occurs in the open conformation. As is usually the case with *P. aeruginosa* it was assumed that the reason L-161,240 was ineffective against *P. aeruginosa* was the lack of permeability of the outer membrane to this inhibitor. Polymixin B nonapeptide (PMBN), a derivative of Polymixin B that lacks the fatty acid tail, is capable of binding to the polyanionic LPS molecules and disrupting the bilayer structure, thus increasing the permeability of the outer membrane. PMBN has been used this way to permeabilize the outer membrane of many gram-negative bacteria (Vaara, M. and T. Vaara. 1983. Sensitization of gram-negative bacteria to antibiotics and complement by a nontoxic oligopeptide. Nature 303: 526-528), including *P. aeruginosa* (Vilianen, P. and M. Vaara, 1984. Susceptibility of gram-negative bacteria to polymixin B nonapeptide. Antimicro Agents Chemother. 25: 701-705) and effectively sensitize them to lipophilic antibiotics. Unlike the acylated polymixin B, PMBN is not cidal. In order to determine the effect of outer membrane exclusion of L-161,240, we exposed *P. aeruginosa* to PMBN in combination with L-161,240, and with other lipophilic antibiotics as positive controls. Whereas PMBN lowered the MIC of tetracycline for *P. aeruginosa* more than 16 fold, the sensitivity towards L-161,240 remained unchanged (FIG. 5). This, together with the *E. coli* expression data indicated that permeability was not a major factor causing the inability of L-161,240 to inhibit pseudomonal growth.

Figure 6:
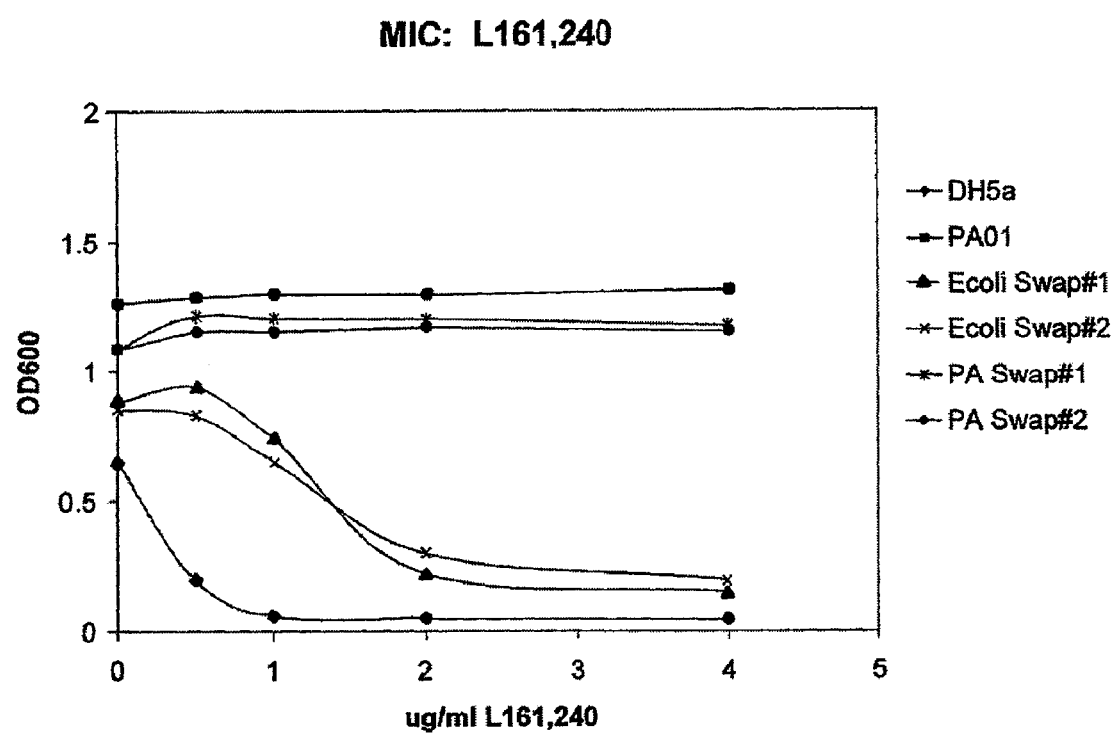
FIG. 6. Sensitivity of various *E. coli* and *P. aeruginosa* strains to inhibitor L161,240 following promoter swap and transformation with vector expressing *E. coli* lpxC or *P. aeruginosa* lpxC. *E. coli* "swaps" refer to *P. aeruginosa* containing a vector comprising *E. coli* lpxC, and "PA swaps" refer to *P. aeruginosa* containing a vector comprising *P. aeruginosa* lpxC.

*P. aeruginosa* expressing only *E. coli* LpxC is more sensitive to L161-240 than wild type. Using the 'promoter swap' technique as described in the methods, it was possible to replace expression from the wild type chromosomal copy of *P. aeruginosa* lpxC, with expression solely from a plasmid borne copy. For this experiment, 'promoter swapped' *P. aeruginosa* was transformed with either vector containing *P. aeruginosa* lpxC ("PA Swap #1"), or vector containing *E. coli* lpxC ("PA Swap #2'). The transformants were then exposed to various concentrations of L-161,240 for MIC determination. Transformants expressing the *E. coli* enzyme only were much more sensitive to the inhibitor compared to organisms expressing the *P. aeruginosa* enzyme (FIG. 6). These transformants were sensitive enough to b comparable with the sensitivity seen in *E. coli*. Since the validity of this observation relied on the un-induced arabinose-sensitive promoter to shut down expression from the chromosomal copy of lpxC, it was necessary to demonstrate how effectively this happens. To do that, MIC determinations were performed as above, except that arabinose was added to induce expression of the chromosomal locus. For this experiment stationary-phase overnight bacterial cultures were diluted to $5 \times 10^5$ cells/ml in LB containing 0.2% arabinose. In this case all the transformants, regardless of what gene the vector contained, were resistant to killing due to the expression of the chromosomal copy of *P. aeruginosa* lpxC. This confirmed that certain intrinsic properties of the *P. aeruginosa* enzyme are resistant to inhibition by this hydroxamate inhibitor. It also confirmed that neither reduced uptake, efflux, nor modification of the inhibitor play a significant role in this observed resistance. Considering the very high similarity between the two enzymes, this finding was not expected.

But on further examination and analysis of existing data, it was possible to recognize some inherent differences that might explain this finding. Whereas both these enzymes share five conserved Histidine residues, the *E. coli* enzyme has two more Histidines that have no counterparts in the *P. aeruginosa* enzyme. This is an important difference because these residues are probably involved in the metal cofactor coordination. It was also observed earlier that whereas the *E. coli* enzyme is not sensitive to EDTA, the *P. aeruginosa* enzyme was significantly inhibited by as little as 2 µM EDTA. Evidence that the *E. coli* enzyme is also a metalloenzyme is that the envA1 mutation, which has one of the conserved Histidines (His 19) replaced by a Serine, is sensitive to EDTA. It was because of these observations that these investigators suggested that the *E. coli* enzyme has a more stably bound metal than that of the EnvA1 mutant protein, and thus it is less accessible to EDTA than the wild type *P. aeruginosa* enzyme. These observations suggest that the Histidine 'patch' that is involved in the metal coordination is not similar between the two enzymes. It is conceivable therefore that since the inhibitor works by chelating the metal cofactor away from the enzyme, each 'patch' has unique features that result in disparate reactivities towards the inhibitor. It is also important to consider the findings of Wyckoff et al., 1998. Hydrocarbon rulers in UDP-N-acetylglucosamine acyltransferases. J. Biol. Chem. 273 (49): 32369-32372. These investigators found that LpxA, the first enzyme of lipid A biosynthesis, is very selective for the length of its acyl donor substrates. Whereas *E. coli* LpxA prefers R-3-hydroxymyristoyl-ACP to R-3-hydroxydecanoyl-ACP, *P. aeruginosa* LpxA prefers the opposite. The products of the LpxA reaction therefore differ in the carbon chain length of their lipid moieties between the two bacteria. Since the product of the LpxA reaction is the substrate of the LpxC reaction, this observation suggests that the two LpxCs would have substrate binding pockets of different sizes to accommodate the different size substrate. That would, in turn, suggest that inhibitors that have to occupy that active site would be unique for each enzyme.

Examples 3-7 ispA, ispB, uppS, aroC, aroK and metK

Several more candidate genes from the HTTIM gene database were tested for essentiality using a single crossover knock-out strategy. The *Pseudomonas* genes targeted for knocking out were ispA, ispB, uppS, metK, aroC, and aroK. To attempt knock-outs, regions of about 300 bp were cloned into the vector pPW120. These regions were selected so that known active site residues (or highly conserved residues likely to be essential for enzyme function) would be separated after generation of a single-crossover knock-out. The regions were (numbering from the start codon): ispA, 283-594; ispB, 319-610; uppS, 103-402; metK, 415-732; aroC, 385-684; aroK, 175-375.

The pPW120 vector carries an *E. coli* origin of replication, but not a *Pseudomonas* origin of replication, making it a suicide vector. It also carries an origin of conjugal transfer and antibiotic resistance genes for tetracycline and ampicillin. An *E. coli* donor strain (SM10) carrying the pPW120 knockout constructs was incubated with *Pseudomonas* strain PAO1 to allow conjugal transfer, and recombinants were selected by plating onto media containing tetracycline at 100 µg/mL and chloramphenicol at 10 µg/mL. *Pseudomonas* recombinants will be resistant to this antibiotic mixture while wild-type PAO1 and the *E. coli* donor strain will be sensitive. Aromatic amino acid recombinants (aroC and aroK) were then tested for auxotrophy by plating onto minimal media with and without phenylalanine, tryptophan, tyrosine, and folic acid at 100 µg/mL while maintaining tetracycline selection. The genes ispB, uppS and metK did not yield recombinants, demonstrating that they are essential genes in all media conditions, while ispA yielded slow-growing recombinants (suggesting that this gene may nevertheless be an "importane" gene according to the invention).

For ispA, ispB, uppsS and metK, the conjugation procedure was also done in the presence of the complementing plasmid pBAD/HisP. This plasmid has both *E. coli* and *Pseudomonas* origins of replication, an antibiotic resistance gene for carbenicillin, and an arabinose-inducible copy of the full-length wild-type gene. In this way, recombinants with the chromosomal copies of ispA, ispB, uppS, and metK knocked out could be isolated since the vector copy would provide complementation.

The genes ispB, uppS, and metK are novel with regard to *P. aeruginosa*. The gene ispB (PA4569, ranging from 5116864 to 5117832 in the genome), has 67% similarity/52% identity to IspB in *E. coli*, and was assigned to the function class concerned with biosynthesis of cofactors, protein groups and carriers, and energy metabolism, with a confidence level of 2. It is thought to be involved in the pathway of ubiquinone biosynthesis.

The gene uppS (PA3652, ranging from 4091654 to 4090899), coding for undecaprenyl pyrophosphate synthetase, has 69% similarity/57% identity to the uppS gene in *E. coli*, and was assigned to the function class involved in biosynthesis of cofactors, protein groups and carriers, cell wall and capsule, with a confidence level of 2. It is separated by one gene (cdsA) from dxr, which is involved in the synthesis of isopentenyl diphosphate, a precursor of undecaprenol phosphate.

The gene metK (PA0546, ranging from 604896 to 603706) had never been characterized in *P. aeruginosa*, although it is 82% similar/72% identical to MetK in *E. coli*. The gene encodes methionine adenosyltransferase (adomet synthetase) which is involved specifically in methionine metabolism, and was originally assigned to a function class of amino acid biosynthesis and metabolism and central intermediate metabolism with a confidence level of 2.

Example 8 rrF

The essentiality of the *P. aeruginosa* rrF (PA3653, ranging from 4092227 to 4091670) gene was tested using the promoter swap methodology disclosed herein. The N-terminus region (position 1-327) of the gene encoding the ribosome recycling factor (frr) was cloned into the plasmid vector pBEM10. A single crossover was constructed as described above for lpxC. Recombinants were unable to grow in the absence of arabinose, confiring the essentiality of this gene. The rrf gene encodes ribosome recycling factor, alternatively known as ribosome releasing factor, assigned to the functional class pertaining to translation, post-tanslational modification and degradation with a confidence level of 1. Although this gene was previously known in *Pseudomonas aeruginosa*, confirming the essentiality of known genes using the methods disclosed herein will reveal new utilities for such genes as targets for the identification and design of new antibacterial drugs.

REFERENCES

Hardalo, C., Edberg, S. (1991), "*Pseudomonas aeruginosa*: assessment of risk from drinking water", Critical Reviews in Microbiology; 23(1), 47-75.

Stover, K., Pham, X., Erwin, L., Mizoguchi, D., Warrener, P., Hickey, J., Brinkman, S., Hufnagle, W., Kowalik, J., Lagrou, M., Garber, L., Goltry, L., Tolentino, E., Westbrock-Wadman, S., Yuan, Y., Brody, L., Coulter, N., Folger, K, Kas, A., Larbig, K., Lim, R., Smith, K., Spencer, D., Wong, G, Wu, Z., Paulsen, I. (2000), "Complete genome sequence of *Pseudomonas aeruginosa* PA01, an opportunistic pathogen," Nature. 406 (6799), 959-964.

Bodey, G., Bolivar, R., Fainstein, V., Jadeja, L. (1983), "Infections caused by *Pseudomonas Aeruginosa*," Reviews of Infectious Diseases, 5(2), 279-313.

Tummler, B., Bosshammer, J., Breitenstein, S., Brockhausen, I., Gudowius, P., Herrmann, C., Herrmann, S., Heuer, T., Kubesch, P. Mekus, F, Romling, U., Schmidt, K, Spangenberg, C., Walter, S. (1997), "Infections with *Pseudomonas aeruginosa* in patients with cystic fibrosis," Behring Institute Mitteilungen, 98 249-55.

Reznikoff, W. (1993), "The Tn5 Transposon," Annual Review of Microbiology; 47, 945-63.

Blumenthal, S., Dayhiya, R. C., and Gross, A. j. (1978), "Estimating the Complete Sample Size from an Incomplete Possion Sample," Journal of American Statistical Association, 73, 182-187.

TABLE 1

| PANumber | GenBank ID | Protein_Name | Gene_Name | Alt_Gene_Name |
|---|---|---|---|---|
| PA0001 | 9945819 | chromosomal replication initiator protein DnaA | dnaA | |
| PA0004 | 9945822 | DNA gyrase subunit B | gyrB | |
| PA0006 | 9945824 | conserved hypothetical protein | | yaeD |
| PA0008 | 9945826 | glycyl-tRNA synthetase beta chain | glyS | |
| PA0009 | 9945827 | glycyl-tRNA synthetase alpha chain | glyQ | |
| PA0011 | 9945830 | probable 2-OH-lauroyltransferase | | |
| PA0015 | 9945834 | hypothetical protein | | |
| PA0022 | 9945841 | conserved hypothetical protein | | yrdC |
| PA0026 | 9945846 | hypothetical protein | | |
| PA0033 | 9945854 | hypothetical protein | | |
| PA0035 | 9945856 | tryptophan synthase alpha chain | trpA | |
| PA0038 | 9945859 | hypothetical protein | | |
| PA0039 | 9945860 | hypothetical protein | | |
| PA0042 | 9945864 | hypothetical protein | | |
| PA0047 | 9945869 | hypothetical protein | | |
| PA0052 | 9945875 | hypothetical protein | | |
| PA0053 | 9945876 | hypothetical protein | | |
| PA0054 | 9945877 | conserved hypothetical protein | | yjiI |
| PA0055 | 9945878 | hypothetical protein | | |
| PA0058 | 9945881 | hypothetical protein | | |
| PA0059 | 9945882 | osmotically inducible protein OsmC | osmC | |
| PA0060 | 9945883 | conserved hypothetical protein | | |
| PA0061 | 9945884 | hypothetical protein | | |
| PA0065 | 9945889 | hypothetical protein | | |
| PA0068 | 9945892 | hypothetical protein | | |
| PA0069 | 9945893 | conserved hypothetical protein | | |
| PA0070 | 9945894 | hypothetical protein | | |
| PA0080 | 9945905 | hypothetical protein | | |
| PA0082 | 9945907 | hypothetical protein | | |
| PA0094 | 9945920 | hypothetical protein | | |
| PA0098 | 9945924 | hypothetical protein | | |
| PA0100 | 9945926 | hypothetical protein | | |
| PA0105 | 9945932 | cytochrome c oxidase, subunit II | coxB | coII |
| PA0109 | 9945936 | hypothetical protein | | |
| PA0111 | 9945938 | hypothetical protein | | |
| PA0113 | 9945940 | probable cytochrome c oxidase assembly factor | | |
| PA0114 | 9945941 | conserved hypothetical protein | | |
| PA0115 | 9945942 | conserved hypothetical protein | | elaA |
| PA0116 | 9945944 | hypothetical protein | | |
| PA0119 | 9945947 | probable dicarboxylate transporter | | |
| PA0120 | 9945948 | probable transcriptional regulator | | |
| PA0124 | 9945952 | hypothetical protein | | |
| PA0125 | 9945953 | hypothetical protein | | |
| PA0128 | 9945956 | conserved hypothetical protein | | phnA |
| PA0131 | 9945960 | hypothetical protein | | |
| PA0133 | 9945962 | probable transcriptional regulator | | |
| PA0135 | 9945964 | hypothetical protein | | |
| PA0139 | 9945969 | alkyl hydroperoxide reductase subunit C | ahpC | |
| PA0143 | 9945973 | probable nucleoside hydrolase | | |
| PA0145 | 9945975 | hypothetical protein | | |
| PA0149 | 9945980 | probable sigma-70 factor, ECF subfamily | | |
| PA0154 | 9945985 | protocatechuate 3,4-dioxygenase alpha subun | pcaG | |
| PA0159 | 9945991 | probable transcriptional regulator | | |
| PA0161 | 9945993 | hypothetical protein | | |
| PA0167 | 9945999 | probable transcriptional regulator | | |
| PA0170 | 9946003 | hypothetical protein | | |
| PA0171 | 9946004 | hypothetical protein | | |
| PA0182 | 9946016 | probable short-chain dehydrogenase | | yjgI |
| PA0183 | 9946017 | arylsulfatase | atsA | |
| PA0184 | 9946018 | probable ATP-binding component of ABC trans | | atsC |
| PA0187 | 9946021 | hypothetical protein | | |

TABLE 1-continued

| | | | | |
|---|---|---|---|---|
| PA0188 | 9946022 | hypothetical protein | | |
| PA0200 | 9946035 | hypothetical protein | | |
| PA0202 | 9946037 | probable amidase | | |
| PA0203 | 9946038 | probable binding protein component of ABC tra | | |
| PA0204 | 9946039 | probable permease of ABC transporter | | |
| PA0205 | 9946040 | probable permease of ABC transporter | | |
| PA0207 | 9946042 | probable transcriptional regulator | | |
| PA0209 | 9946045 | conserved hypothetical protein | | mdcB |
| PA0211 | 9946047 | malonate decarboxylase beta subunit | mdcD | |
| PA0213 | 9946049 | hypothetical protein | | mdcG |
| PA0216 | 9946052 | probable transporter | | madM |
| PA0233 | 9946071 | probable transcriptional regulator | | |
| PA0236 | 9946074 | probable transcriptional regulator | | |
| PA0238 | 9946076 | hypothetical protein | | |
| PA0243 | 9946082 | probable transcriptional regulator | | |
| PA0244 | 9946083 | hypothetical protein | | |
| PA0245 | 9946084 | 3-dehydroquinate dehydratase | aroQ2 | aroD2 |
| PA0250 | 9946090 | conserved hypothetical protein | | |
| PA0251 | 9946091 | hypothetical protein | | |
| PA0258 | 9946098 | hypothetical protein | | |
| PA0260 | 9946101 | hypothetical protein | | |
| PA0261 | 9946102 | hypothetical protein | | |
| PA0264 | 9946105 | hypothetical protein | | |
| PA0273 | 9946115 | probable MFS transporter | | |
| PA0279 | 9946122 | probable transcriptional regulator | | ydfF |
| PA0280 | 9946123 | sulfate transport protein CysA | cysA | |
| PA0284 | 9946127 | hypothetical protein | | |
| PA0309 | 9946155 | hypothetical protein | | |
| PA0311 | 9946157 | hypothetical protein | | |
| PA0320 | 9946167 | conserved hypothetical protein | | |
| PA0330 | 9946178 | ribose 5-phosphate isomerase | rpiA | |
| PA0332 | 9946180 | hypothetical protein | | |
| PA0336 | 9946184 | conserved hypothetical protein | | ygdP |
| PA0339 | 9946187 | hypothetical protein | | |
| PA0341 | 9946190 | prolipoprotein diacyglycetyl transferase | lgt | umpA |
| PA0342 | 9946191 | thymidylate synthase | thyA | |
| PA0350 | 9946200 | dihydrofolate reductase | folA | tmrA |
| PA0358 | 9946208 | hypothetical protein | | |
| PA0362 | 9946213 | ferredoxin [4Fe-4S] | fdx1 | |
| PA0363 | 9946214 | phosphopantetheine adenylyltransferase | coaD | kdtB |
| PA0369 | 9946220 | hypothetical protein | | |
| PA0370 | 9946222 | conserved hypothetical protein | | yhhF |
| PA0373 | 9946225 | signal recognition particle receptor FtsY | ftsY | |
| PA0376 | 9946228 | sigma factor RpoH | rpoH | |
| PA0377 | 9946229 | hypothetical protein | | |
| PA0380 | 9946232 | conserved hypothetical protein | | |
| PA0384 | 9946237 | hypothetical protein | | |
| PA0398 | 9946252 | hypothetical protein | | |
| PA0402 | 9946256 | aspartate carbamoyltransferase | pyrB | |
| PA0403 | 9946257 | transcriptional regulator PyrR | pyrB | |
| PA0404 | 9946258 | conserved hypothetical protein | | yqgF |
| PA0405 | 9946259 | conserved hypothetical protein | | yqgE |
| PA0407 | 9946262 | glutathione synthetase | gshB | |
| PA0412 | 9946267 | methyltransferase PilK | pilK | |
| PA0416 | 9946271 | probable transcriptional regulator | | chpD |
| PA0422 | 9946278 | conserved hypothetical protein | | |
| PA0427 | 9946283 | outer membrane protein OprM precursor | oprM | |
| PA0433 | 9946290 | hypothetical protein | | |
| PA0442 | 9946300 | hypothetical protein | | |
| PA0443 | 9946301 | probable transporter | | |
| PA0445 | 9946304 | probable transposase | | |
| PA0446 | 9946305 | conserved hypothetical protein | | |
| PA0448 | 9946307 | probable transcriptional regulator | | |
| PA0453 | 9946312 | hypothetical protein | | |
| PA0456 | 9946316 | probable cold-shock protein | | |
| PA0466 | 9946327 | hypothetical protein | | |
| PA0474 | 9946336 | hypothetical protein | | |
| PA0475 | 9946337 | probable transcriptional regulator | | |
| PA0477 | 9946339 | probable transcriptional regulator | | |
| PA0479 | 9946341 | probable transcriptional regulator | | |
| PA0488 | 9946351 | conserved hypothetical protein | | yfiM |
| PA0489 | 9946352 | probable phosphoribosyl transferase | | |
| PA0490 | 9946353 | hypothetical protein | | |
| PA0493 | 9946356 | probable biotin-requiring enzyme | | |
| PA0498 | 9946362 | hypothetical protein | | |
| PA0501 | 9946365 | 8-amino-7-oxononanoate synthase | bioF | |
| PA0502 | 9946366 | probable biotin biosynthesis protein bioH | | bioH |
| PA0503 | 9946367 | probable biotin synthesis protein BioC | | bioC |
| PA0504 | 9946368 | dethiobiotin synthase | bioD | |

TABLE 1-continued

| | | | | |
|---|---|---|---|---|
| PA0505 | 9946369 | hypothetical protein | | |
| PA0514 | 9946379 | heme d1 biosynthesis protein NirL | nirL | |
| PA0527 | 9946393 | transcriptional regulator Dnr | dnr | |
| PA0531 | 9946397 | probable glutamine amidotransferase | | |
| PA0535 | 9946402 | probable transcriptional regulator | | |
| PA0540 | 9946407 | hypothetical protein | | |
| PA0542 | 9946409 | conserved hypothetical protein | | yqjC |
| PA0543 | 9946410 | hypothetical protein | | |
| PA0544 | 9946411 | hypothetical protein | | |
| PA0546 | 9946414 | methionine adenosyltransferase | metk | |
| PA0550 | 9946418 | conserved hypothetical protein | | ygbM |
| PA0552 | 9946420 | phosphoglycerate kinase | pgk | |
| PA0553 | 9946422 | hypothetical protein | | |
| PA0555 | 9946424 | fructose-1,6-bisphosphate aldolase | fda | fbaA, cbbA, cfxB |
| PA0559 | 9946428 | conserved hypothetical protein | | yhiN |
| PA0563 | 9946432 | conserved hypothetical protein | | |
| PA0565 | 9946434 | conserved hypothetical protein | | |
| PA0567 | 9946437 | conserved hypothetical protein | | yqaE |
| PA0570 | 9946440 | hypothetical protein | | |
| PA0571 | 9946441 | hypothetical protein | | |
| PA0574 | 9946444 | hypothetical protein | | |
| PA0578 | 9946449 | conserved hypothetical protein | | |
| PA0579 | 9946450 | 30S ribosomal protein S21 | rpsU | |
| PA0580 | 9946451 | O-sialoglycoprotein endopeptidase | gcp | ygjD |
| PA0582 | 9946453 | dihydroneopterin aldolase | folB | |
| PA0585 | 9946456 | hypothetical protein | | |
| PA0589 | 9946461 | conserved hypothetical protein | | glpE |
| PA0591 | 9946463 | conserved hypothetical protein | | apaG |
| PA0593 | 9946465 | pyridoxal phosphate biosynthetic protein PdxA | pdxA | |
| PA0594 | 9946466 | peptidyl-prolyl cis-trans isomerase SurA | surA | |
| PA0595 | 9946467 | organic solvent tolerance protein OstA precurs | ostA | imp |
| PA0607 | 9946481 | ribulose-phosphate 3-epimerase | rpe | dod |
| PA0610 | 9946484 | transcriptional regulator PrtN | prtN | |
| PA0611 | 9946485 | transcriptional regulator PrtR | prtR | |
| PA0613 | 9946487 | hypothetical protein | | |
| PA0614 | 9946488 | hypothetical protein | | |
| PA0617 | 9946492 | probable bacteriophage protein | | |
| PA0626 | 9946501 | hypothetical protein | | |
| PA0627 | 9946502 | conserved hypothetical protein | | |
| PA0630 | 9946505 | hypothetical protein | | |
| PA0632 | 9946507 | hypothetical protein | | |
| PA0635 | 9946511 | hypothetical protein | | |
| PA0639 | 9946515 | conserved hypothetical protein | | |
| PA0642 | 9946518 | hypothetical protein | | |
| PA0643 | 9946519 | hypothetical protein | | |
| PA0644 | 9946520 | hypothetical protein | | |
| PA0646 | 9946523 | hypothetical protein | | |
| PA0647 | 9946524 | hypothetical protein | | |
| PA0648 | 9946525 | hypothetical protein | | |
| PA0652 | 9946529 | transcriptional regulator Vfr | vfr | |
| PA0653 | 9946530 | conserved hypothetical protein | | yhfA |
| PA0655 | 9946532 | hypothetical protein | | |
| PA0660 | 9946538 | hypothetical protein | | |
| PA0661 | 9946539 | conserved hypothetical protein | | |
| PA0665 | 9946543 | conserved hypothetical protein | | yadR |
| PA0678 | 9946558 | probable type II secretion system protein | | hxcU |
| PA0679 | 9948559 | hypothetical protein | | hxcP |
| PA0680 | 9946560 | probable type II secretion system protein | | hxcV |
| PA0684 | 9946564 | probable type II secretion system protein | | hxcZ |
| PA0686 | 9946566 | probable type II secretion system protein | | hxcR |
| PA0687 | 9946567 | probable type II secretion system protein | | hxcS |
| PA0689 | 9946570 | hypothetical protein | | |
| PA0697 | 9946579 | hypothetical protein | | |
| PA0698 | 9946580 | hypothetical protein | | |
| PA0700 | 9946582 | hypothetical protein | | |
| PA0702 | 9946585 | hypothetical protein | | |
| PA0704 | 9946587 | probably amidase | | |
| PA0705 | 9946588 | probable glycosyl transferase | | migA |
| PA0708 | 9946591 | probable transcriptional regulator | | |
| PA0709 | 9946592 | hypothetical protein | | |
| PA0710 | 9946593 | lactoylglutathione lyase | gloA2 | |
| PA0712 | 9946595 | hypothetical protein | | |
| PA0714 | 9946598 | hypothetical protein | | |
| PA0715 | 9946599 | hypothetical protein | | |
| PA0716 | 9946600 | hypothetical protein | | |
| PA0717 | 9946601 | hypothetical protein of bacteriophage Pf1 | | |
| PA0720 | 9946604 | helix destabilizing protein of bacteriophage Pf1 | | |
| PA0728 | 9946613 | probable bacteriophage integrase | | |
| PA0729 | 9946614 | hypothetical protein | | |

TABLE 1-continued

| | | | | |
|---|---|---|---|---|
| PA0730 | 9946615 | probable transferase | | |
| PA0733 | 9946618 | probable pseudouridylate synthase | | rsuA |
| PA0734 | 9946619 | hypothetical protein | | |
| PA0738 | 9946624 | conserved hypothetical protein | | |
| PA0742 | 9946628 | hypothetical protein | | |
| PA0759 | 9946647 | conserved hypothetical protein | | |
| PA0763 | 9946651 | anti-sigma factor MucA | mucA | |
| PA0767 | 9946655 | GTP-binding protein LepA | lepA | |
| PA0768 | 9946656 | signal peptidase I | lepB | lep; SPASE I |
| PA0771 | 9946660 | GTP-binding protein Era | era | |
| PA0776 | 9946665 | hypothetical protein | | |
| PA0778 | 9946667 | hypothetical protein | | |
| PA0786 | 9946676 | probable transporter | | |
| PA0787 | 9946677 | hypothetical protein | | |
| PA0790 | 9946681 | hypothetical protein | | |
| PA0802 | 9946694 | hypothetical protein | | |
| PA0805 | 9946697 | hypothetical protein | | |
| PA0808 | 9946701 | hypothetical protein | | |
| PA0815 | 9946708 | probable transcriptional regulator | | |
| PA0818 | 9946712 | hypothetical protein | | |
| PA0820 | 9946714 | hypothetical protein | | |
| PA0822 | 9946716 | hypothetical protein | | |
| PA0825 | 9946719 | hypothetical protein | | |
| PA0826 | 9946720 | hypothetical protein | | |
| PA0829 | 9946723 | probable hydrolase | | |
| PA0837 | 9946732 | peptidyl-prolyl cis-trans isomerase SlyD | slyD | |
| PA0850 | 9946747 | hypothetical protein | | |
| PA0851 | 9946748 | hypothetical protein | | |
| PA0853 | 9946750 | probable oxidoreductase | | |
| PA0857 | 9946754 | morphogore protein BolA | bolA | |
| PA0862 | 9946760 | hypothetical protein | | |
| PA0867 | 9946765 | hypothetical protein | | |
| PA0868 | 9946766 | conserved hypothetical protein | | yaeJ |
| PA0869 | 9946767 | D-alanyl-D-alanine-endopeptidase | pbpG | |
| PA0871 | 9946770 | pterin-4-alpha-carbinolamine dehydratase | phhB | |
| PA0874 | 9946773 | hypothetical protein | | |
| PA0880 | 9946779 | probable ring-cleaving dioxygenase | | |
| PA0894 | 9946794 | hypothetical protein | | |
| PA0900 | 9946801 | hypothetical protein | | |
| PA0903 | 9946804 | alanyl-tRNA synthetase | alaS | sya |
| PA0904 | 9946806 | aspartate kinase alpha and beta chain | lysC | ask; akaB |
| PA0905 | 9946807 | carbon storage regulator | csrA | |
| PA0906 | 9946808 | probable transcriptional regulator | | |
| PA0908 | 9946810 | hypothetical protein | | |
| PA0909 | 9946811 | hypothetical protein | | |
| PA0913 | 9946815 | probable Mg transporter MgtE | mgtE | |
| PA0922 | 9946825 | hypothetical protein | | |
| PA0927 | 9946831 | D-lactate dehydrogenas(fermentative) | ldhA | ldhD |
| PA0932 | 9946836 | cysteine synthase B | cysM | |
| PA0937 | 9946842 | conserved hypothetical protein | | yaiL |
| PA0939 | 9946844 | hypothetical protein | | |
| PA0944 | 9945849 | phosphoribosylaminoimidazole synthetase | purN | |
| PA0945 | 9946850 | phosphoribosylaminoimidazole synthetase | PurM | |
| PA0947 | 9946853 | conserved hypothetical protein | | |
| PA0953 | 9946859 | probable thioredoxin | | helX |
| PA0954 | 9946860 | probable acylphosphatase | | |
| PA0956 | 9946862 | prolyl-tRNA synthetase | proS | |
| PA0960 | 9946867 | hypothetical protein | | |
| PA0962 | 9946869 | probable dna-binding stress protein | | |
| PA0969 | 9946876 | TolQ protein | tolQ | |
| PA0970 | 9946877 | TolR protein | tolR | |
| PA0971 | 9946878 | TolA protein | tolA | |
| PA0972 | 9946879 | TolB protein | tolB | |
| PA0973 | 9946880 | outer membrane protein OprL precursor | oprL | pal excC |
| PA0976 | 9946884 | conserved hypothetical protein | | |
| PA0978 | 9946886 | conserved hypothetical protein | | |
| PA0979 | 9946887 | conserved hypothetical protein | | |
| PA0980 | 9946888 | hypothetical protein | | |
| PA0981 | 9946889 | hypothetical protein | | |
| PA0983 | 9946891 | conserved hypothetical protein | | |
| PA0985 | 9946893 | probable colicin-like toxin | | |
| PA0986 | 9946894 | conserved hypothetical protein | | |
| PA0990 | 9946899 | conserved hypothetical protein | | |
| PA0991 | 9946900 | hypothetical protein | | |
| PA0993 | 9946902 | probable pili assembly chaperone | | |
| PA1000 | 9946909 | hypothetical protein | | |
| PA1006 | 9946916 | conserved hypothetical protein | | yrkl |
| PA1008 | 9946918 | bacterioferritin comigratory protein | bcp | |
| PA1010 | 9946920 | dihydrodipicolinate synthase | dapA | |

TABLE 1-continued

| | | | | |
|---|---|---|---|---|
| PA1012 | 9946922 | conserved hypothetical protein | | yycJ |
| PA1013 | 9946923 | phosphoribosylaminoimidazole-succinocarbox | purC | |
| PA1021 | 9946932 | probable ehoyl-CoA hydratase/isomerase | | |
| PA1026 | 9946938 | hypothetical protein | | |
| PA1035 | 9946948 | hypothetical protein | | |
| PA1038 | 9946951 | hypothetical protein | | |
| PA1039 | 9946952 | conserved hypothetical protein | | ychJ |
| PA1049 | 9946963 | pyridoxine 5'-phosphate oxidase | pdxH | |
| PA1055 | 9946969 | conserved hypothetical protein | | phaC |
| PA1063 | 9946978 | hypothetical protein | | |
| PA1068 | 9946983 | probable heat shock protein (hsp90 family) | | |
| PA1076 | 9946992 | hypothetical protein | | |
| PA1088 | 9947004 | hypothetical protein | | |
| PA1089 | 9947005 | conserved hypothetical protein | | |
| PA1090 | 9947006 | hypothetical protein | | |
| PA1095 | 9947012 | hypothetical protein | | fliS |
| PA1098 | 9947015 | two-component sensor | fleS | |
| PA1102 | 9947019 | flagellar motor switch protein FliG | fliG | |
| PA1105 | 9947022 | flagellar protein FliJ | fliJ | |
| PA1106 | 9947023 | hypothetical protein | | |
| PA1107 | 9947025 | conserved hypothetical protein | | |
| PA1114 | 9947032 | hypothetical protein | | |
| PA1118 | 9947037 | hypothetical protein | | |
| PA1120 | 9947039 | conserved hypothetical protein | | yfiN |
| PA1122 | 9947041 | probable peptide deformylase | | def, pdf, fms |
| PA1125 | 9947044 | probable cobalamin biosynthetic protein | | cobB |
| PA1129 | 9947049 | probable fosfomycin resistance protein | | |
| PA1134 | 9947054 | hypothetical protein | | |
| PA1135 | 9947055 | conserved hypothetical protein | | yedU |
| PA1138 | 9947058 | probable transcriptional regulator | | |
| PA1145 | 9947066 | probable transcriptional regulator | | |
| PA1149 | 9947071 | hypothetical protein | | |
| PA1151 | 9947073 | pyocin S2 immunity protein | imm2 | |
| PA1154 | 9947076 | conserved hypothetical protein | | |
| PA1155 | 9947077 | ribonucleoside reductase, small chain | nrdB | |
| PA1156 | 9947078 | ribonucleoside reductase, large chain | nrdA | |
| PA1157 | 9947080 | probable two-component response regulator | | |
| PA1159 | 9947082 | probable cold-shock protein | | |
| PA1160 | 9947083 | hypothetical protein | | |
| PA1162 | 9947085 | succinyl-diaminopimelate desuccinylase | dapE | |
| PA1164 | 9947087 | conserved hypothetical protein | | |
| PA1165 | 9947088 | hypothetical protein | | |
| PA1167 | 9947091 | hypothetical protein | | |
| PA1168 | 9947092 | hypothetical protein | | |
| PA1172 | 9947096 | cytochrome c-type protein NapC | napC | |
| PA1173 | 9947097 | cytochrome c-type protein NapB precursor | napB | |
| PA1176 | 9947100 | ferredoxin protein NapF | napF | |
| PA1177 | 9947101 | periplasmic nitrate reductase protein NapE | napE | |
| PA1183 | 9947108 | C4-dicarboxylate transport protein | dctA | |
| PA1193 | 9947119 | hypothetical protein | | |
| PA1203 | 9947130 | hypothetical protein | | |
| PA1204 | 9947131 | conserved hypothetical protein | | yieF |
| PA1206 | 9947133 | hypothetical protein | | |
| PA1213 | 9947141 | hypothetical protein | | |
| PA1215 | 9947143 | hypothetical protein | | |
| PA1216 | 9947144 | hypothetical protein | | |
| PA1217 | 9947145 | probable 2-isopropylmalate synthase | | |
| PA1219 | 9947147 | hypothetical protein | | |
| PA1223 | 9947152 | probable transcriptional regulator | | |
| PA1224 | 9947153 | probable NAD(P)H dehydrogenase | | |
| PA1228 | 9947157 | hypothetical protein | | |
| PA1230 | 9947159 | hypothetical protein | | |
| PA1233 | 9947162 | hypothetical protein | | |
| PA1237 | 9947167 | probable multidrug resistance efflux pump | | |
| PA1250 | 9947181 | alkaline proteinase inhibitor AprI | aprI | |
| PA1261 | 9947193 | probable transcriptional regulator | | |
| PA1269 | 9947202 | probable transcriptional regulator | | |
| PA1280 | 9947214 | hypothetical protein | | cobC |
| PA1285 | 9947220 | probable transcriptional regulator | | |
| PA1295 | 9947231 | conserved hypothetical protein | | ycgL |
| PA1298 | 9947234 | conserved hypothetical protein | | yohL |
| PA1300 | 9947236 | probable sigma-70 factor, ECF subfamily | | |
| PA1306 | 9947243 | probable HIT family protein | | |
| PA1307 | 9947244 | conserved hypothetical protein | | yafJ |
| PA1315 | 9947252 | probable transcriptional regulator | | |
| PA1321 | 9947259 | cytochrome o ubiquinol oxidase protein CyoE | cyoE | |
| PA1323 | 9947261 | hypothetical protein | | |
| PA1328 | 9947267 | probable transcriptional regulator | | |
| PA1331 | 9947270 | conserved hypothetical protein | | yegH |

TABLE 1-continued

| | | | | |
|---|---|---|---|---|
| PA1342 | 9947282 | probable binding protein component of ABC tra | | |
| PA1348 | 9947289 | hypothetical protein | | |
| PA1349 | 9947290 | conserved hypothetical protein | | |
| PA1350 | 9947291 | hypothetical protein | | |
| PA1352 | 9947293 | conserved hypothetical protein | | |
| PA1353 | 9947295 | hypothetical protein | | |
| PA1355 | 9947297 | hypothetical protein | | |
| PA1358 | 9947300 | hypothetical protein | | |
| PA1362 | 9947304 | hypothetical protein | | |
| PA1364 | 9947306 | probable transmembrane sensor | | |
| PA1366 | 9947309 | hypothetical protein | | |
| PA1369 | 9947312 | hypothetical protein | | |
| PA1370 | 9947313 | hypothetical protein | | |
| PA1371 | 9947314 | hypothetical protein | | |
| PA1372 | 9947315 | hypothetical protein | | |
| PA1375 | 9947319 | erythronate-4-phosphate dehydrogenase | pdxB | |
| PA1377 | 9947321 | conserved hypothetical protein | | yhhY |
| PA1378 | 9947322 | hypothetical protein | | |
| PA1379 | 9947323 | probable short-chain dehydroenase | | |
| PA1394 | 9947340 | hypothetical protein | | |
| PA1397 | 9947343 | probable two-component response regulator | | |
| PA1398 | 9947344 | hypothetical protein | | |
| PA1404 | 9947351 | hypothetical protein | | |
| PA1409 | 9947356 | acetylpolyamine aminohydrolase | aphA | |
| PA1426 | 9947375 | hypothetical protein | | |
| PA1427 | 9947376 | hypothetical protein | | |
| PA1431 | 9947380 | regulatory protein RsaL | rsaL | |
| PA1432 | 9947381 | autoinducer synthesis protein LasI | lasI | |
| PA1442 | 9947393 | conserved hypothetical protein | | fliL |
| PA1447 | 9947398 | flagellar biosynthetic protein FliQ | fliQ | |
| PA1454 | 9947406 | flagellar synthesis regulator FleN | | |
| PA1456 | 9947408 | two-component response regulator CheY | cheY | |
| PA1461 | 9947413 | probable chemotaxis protein | | motB |
| PA1462 | 9947414 | probable plasmid partitioning protein | | |
| PA1464 | 9947417 | Probable purine-binding chemotaxis protein | | cheW |
| PA1465 | 9947418 | hypothetical protein | | |
| PA1468 | 9947421 | hypothetical protein | | |
| PA1472 | 9947425 | conserved hypothetical protein | | |
| PA1475 | 9947428 | heme exporter protein CcmA | ccmA | #NAME? |
| PA1476 | 9947429 | heme exporter protein CcmB | ccmB | cyt10; cycW; helB |
| PA1477 | 9947431 | heme exporter protein CcmC | ccmC | pfcyt1 cycZ helC |
| PA1478 | 9947432 | hypothetical protein | | pfcyt2 ccmD cycX helD |
| PA1480 | 9947434 | cytochrome C-type biogenesis protein CcmF | ccmF | cyck; ccl1 |
| PA1481 | 9947435 | cytochrome C biogenesis protein CcmG | ccmG | dsbE |
| PA1482 | 9947436 | cytochrome C-type biogenesis protein CcmH | ccmH | ccl2 cycL |
| PA1488 | 9947442 | hypothetical protein | | |
| PA1489 | 9947443 | hypothetical protein | | |
| PA1492 | 9947447 | hypothetical protein | | |
| PA1496 | 9947451 | probable potassium channel | | |
| PA1504 | 9947460 | probable transcriptional regulator | | |
| PA1508 | 9947464 | hypothetical protein | | |
| PA1509 | 9947465 | hypothetical protein | | |
| PA1514 | 9947471 | conserved hypothetical protein | | ybbT |
| PA1517 | 9947474 | conserved hypothetical protein | | |
| PA1518 | 9947475 | conserved hypothetical protein | | |
| PA1526 | 9947484 | probable transcriptional regulator | | |
| PA1528 | 9947486 | cell division protein ZipA | zipA | |
| PA1529 | 9947487 | DNA ligase | lig | dnaL ligA |
| PA1532 | 9947490 | DNA polymerase subunits gamma and tau | dnaX | |
| PA1533 | 9947491 | conserved hypothetical protein | | |
| PA1535 | 9947494 | probable acyl-CoA dehydrogenase | | |
| PA1533 | 9947498 | hypothetical protein | | |
| PA1540 | 9947499 | conserved hypothetical protein | | |
| PA1541 | 9947500 | probable drug efflux transporter | | |
| PA1548 | 9947508 | conserved hypothetical protein | | fixS |
| PA1551 | 9947511 | probable ferredoxin | | fixG |
| PA1555 | 9947515 | probable cytochrome c | | fixP ccoP |
| PA1558 | 9947519 | hypothetical protein | | |
| PA1559 | 9947520 | hypothetical protein | | |
| PA1560 | 9947521 | hypothetical protein | | |
| PA1564 | 9947526 | conserved hypothetical protein | | |
| PA1568 | 9947530 | conserved hypothetical protein | | |
| PA1571 | 9947533 | hypothetical protein | | |
| PA1581 | 9947544 | succinate dehydrogenase (C subunit) | sdhC | cybA |
| PA1582 | 9947545 | succinate dehydrogenase (D subunit) | sdhD | |
| PA1583 | 9947546 | succinate dehydrogenase (A subunit) | sdhA | |
| PA1584 | 9947547 | succinate dehydrogenase (B subunit) | sdhB | |
| PA1587 | 9947550 | lipoamide dehydrogenase-glc | lpdG | lpdA |
| PA1588 | 9947552 | succinyl-CoA synthetase beta chain | sucC | |

TABLE 1-continued

| | | | | | |
|---|---|---|---|---|---|
| PA1589 | 9947553 | succinyl-CoA synthetase alpha chain | sucD | | |
| PA1591 | 9947555 | hypothetical protein | | | |
| PA1592 | 9947556 | hypothetical protein | | | |
| PA1593 | 9947557 | hypothetical protein | | | |
| PA1594 | 9947558 | hypothetical protein | | | |
| PA1595 | 9947559 | hypothetical protein | | | |
| PA1610 | 9947576 | beta-hydroxydecanoyl-ACP dehydrase | fabA | | |
| PA1618 | 9947584 | conserved hypothetical protein | | ybdB | |
| PA1619 | 9947585 | probable transcriptional regulator | | | |
| PA1622 | 9947589 | probable hydrolase | | | |
| PA1623 | 9947590 | conserved hypothetical protein | | | |
| PA1624 | 9947591 | hypothetical protein | | | |
| PA1630 | 9947597 | probable transcriptional regulator | | | |
| PA1632 | 9947600 | KdpF protein | kdpF | | |
| PA1635 | 9947603 | potassium-transporing ATPase, C chain | kdpC | atkC | |
| PA1638 | 9947606 | conserved hypothetical protein | | yneH | |
| PA1641 | 9947610 | hypothetical protein | | | |
| PA1645 | 9947614 | hypothetical protein | | | |
| PA1657 | 9947627 | conserved hypothetical protein | | | |
| PA1664 | 9947635 | hypothetical protein | | | |
| PA1666 | 9947637 | hypothetical protein | | | |
| PA1673 | 9947645 | hypothetical protein | | | |
| PA1674 | 9947646 | GTP cyclohydrolase I precursor | folE2 | | |
| PA1675 | 9947647 | conserved hypothetical protein | | | |
| PA1676 | 9947648 | hypothetioal protein | | | |
| PA1687 | 9947660 | spermidine synthase | speE | | |
| PA6909 | 9947663 | translocation protein in type III secretion | pscU | | |
| PA1691 | 9947664 | translocation protein in type III secretion | pscT | | |
| PA1696 | 9947669 | translocation protein in type III secretion | pscO | | |
| PA1698 | 9947672 | outer membrane protein PopN | popN | | |
| PA1701 | 9947675 | conserved hypothetical protein in type III secretion | | pcr3 | |
| PA1702 | 9947676 | conserved hypothetical protein in type III secretion | | pcr4 | |
| PA1705 | 9947679 | regulator in type III secretion | pcrG | | |
| PA1710 | 9947684 | exoenzyme S synthesis protein C precursor | exsC | | |
| PA1711 | 9947685 | hypothetical protein | | | |
| PA1718 | 9947693 | type III export protein PscE | pscE | | |
| PA1719 | 9947694 | type III export protein PscF | pscF | | |
| PA1720 | 9947695 | type III export protein PscG | pscG | | |
| PA1722 | 9947697 | type III export protein PscI | pscI | | |
| PA1732 | 9947708 | conserved hypothetical protein | | | |
| PA1733 | 9947709 | conserved hypothetical protein | | | |
| PA1743 | 9947720 | hypothetical protein | | | |
| PA1745 | 9947722 | hypothetical protein | | | |
| PA1747 | 9947725 | hypothetical protein | | | |
| PA1750 | 9947728 | phospho-2-dehydro-3-deoxyheptonate aldolase | | | |
| PA1757 | 9947735 | homoserine kinase | thrH | | |
| PA1768 | 9947747 | hypothetical protein | | | |
| PA1772 | 9947752 | probable methyltransferase | | menG | |
| PA1777 | 9947757 | outer membrane protein OprF precursor | oprF | | |
| PA1780 | 9947760 | assimilatory nitrite reductase small subunit | nirD | nasE | |
| PA1783 | 9947764 | nitrate transporter | nasA | nasT | |
| PA1785 | 9947766 | conserved hypothetical protein | | nasT | |
| PA1787 | 9947768 | aconitate hydratase 2 | acnB | | |
| PA1790 | 9947772 | hypothetical protein | | | |
| PA1792 | 9947774 | conserved hypothetical protein | | ybbF | |
| PA1794 | 9947776 | glutaminyl-tRNA synthetase | glnS | | |
| PA1795 | 9947777 | cysteinyl-tRNA synthetase | cysS | | |
| PA1796 | 9947778 | 5,10-methylene-tetrahydrofolate dehydrogena | folD | | |
| PA1803 | 9947786 | Lon protease | lon | capR deg muc lopA | |
| PA1815 | 9947800 | ribonuclease H | rnhA | | |
| PA1816 | 9947801 | DNA polymerase III, epsilon chain | dnaQ | mutD | |
| PA1817 | 9947802 | hypothetical protein | | | |
| PA1820 | 9947805 | sodium/proton antiporter NhaB | | nhaB | |
| PA1825 | 9947811 | hypothetical protein | | | |
| PA1830 | 9947816 | hypothetical protein | | | |
| PA1835 | 9947821 | hypothetical protein | | | |
| PA1837 | 9947823 | hypothetical protein | | | |
| PA1840 | 9947827 | hypothetical protein | | | |
| PA1842 | 9947829 | hypothetical protein | | | |
| PA1845 | 9947832 | hypothetical protein | | | |
| PA1847 | 9947835 | conserved hypothetical protein | | yhgI | |
| PA1852 | 9947840 | hypothetical protein | | | |
| PA1855 | 9947843 | hypothetical protein | | | |
| PA1859 | 9947848 | probable transcriptional regulator | | | |
| PA1862 | 9947851 | molybdenum transport protein ModB | modB | | |
| PA1867 | 9947857 | hypothetical protein | | xphA | |
| PA1869 | 9947859 | probable acyl carrier protein | | | |
| PA1872 | 9947862 | hypothetical protein | | | |
| PA1882 | 9947873 | probable transporter | | | |

TABLE 1-continued

| | | | | |
|---|---|---|---|---|
| PA1883 | 9947874 | probable NADH-ubiquinone/plastoquinone oxid | | |
| PA1884 | 9947875 | probable transcriptional regulator | | |
| PA1885 | 9947876 | conserved hypothetical protein | | |
| PA1892 | 9947884 | hypothetical protein | | |
| PA1894 | 9947886 | hypothetical protein | | |
| PA1895 | 9947887 | hypothetical protein | | |
| PA1896 | 9947788 | hypothetical protein | | |
| PA1897 | 9947789 | hypothetical protein | | |
| PA1899 | 9947892 | probable phenazine biosynthesis protein | | phzA2 |
| PA1900 | 9947893 | probable phenazine biosynthesis protein | | phzB2 |
| PA1905 | 9950429 | probable pyridoxamine 5'-phosphate oxidase | | phzG2 |
| PA1911 | 9947904 | probable transmembrane sensor | | |
| PA1912 | 9947905 | probable sigma-70 factor, ECF subfamily | | |
| PA1914 | 9947907 | conserved hypothetical protein | | hvn |
| PA1917 | 9947910 | hypothetical protein | | |
| PA1924 | 9947918 | hypothetical protein | | |
| PA1925 | 9947919 | hypothetical protein | | |
| PA1928 | 9947923 | ribosomal protein alanine acetyltransferase | rimJ | |
| PA1929 | 9947924 | hypothetical protein | | |
| PA1936 | 9947932 | hypothetical protein | | |
| PA1937 | 9947933 | conserved hypothetical protein | | |
| PA1938 | 9947934 | conserved hypothetical protein | | |
| PA1939 | 9947935 | hypothetical protein | | |
| PA1951 | 9947949 | hypothetical protein | | |
| PA1952 | 9947950 | hypothetical protein | | |
| PA1955 | 9947953 | hypothetical protein | | |
| PA1956 | 9947954 | hypothetical protein | | |
| PA1962 | 9947960 | conserved hypothetical protein | | |
| PA1963 | 9947962 | hypothetical protein | | |
| PA1965 | 9947964 | hypothetical protein | | |
| PA1967 | 9947966 | hypothetical protein | | |
| PA1968 | 9947967 | hypothetical protein | | |
| PA1974 | 9947974 | hypothetical protein | | |
| PA1978 | 9947978 | probable transcriptional regulator | | agmR |
| PA1980 | 9947980 | probable two-component response regulator | | |
| PA1985 | 9947986 | pyrroloquinoline quinone biosynthesis protein A | pqqA | |
| PA1986 | 9947987 | pyrroloquinoline quinone biosynthesis protein B | pqqB | |
| PA1988 | 9947989 | pyrroloquinoline quinone biosynthesis protein D | pqqD | |
| PA1994 | 9947996 | hypothetical protein | | |
| PA1995 | 9947997 | hypothetical protein | | |
| PA1996 | 9947998 | peptidyl-prolyl cis-trans isomerase C1 | ppiC1 | |
| PA2001 | 9948003 | acetyl-CoA acetyltransferase | atoB | |
| PA2002 | 9948004 | conserved hypothetical protein | | atoE |
| PA2007 | 9948010 | maleylacetoacetate isomerase | maiA | |
| PA2010 | 9948013 | probable transcriptional regulator | | |
| PA2013 | 9948016 | probable enoyl-CoA hydratase/isomerase | | menB |
| PA2015 | 9948019 | probable acyl-CoA dehydrogenase | | |
| PA2016 | 9948020 | probable transcriptional regulator | | |
| PA2017 | 9948021 | hypothetical protein | | |
| PA2021 | 9948025 | hypothetical protein | | |
| PA2026 | 9948031 | conserved hypothetical protein | | yfeH |
| PA2029 | 9948034 | hypothetical protein | | |
| PA2031 | 9948036 | hypothetical protein | | |
| PA2034 | 9948039 | hypothetical protein | | |
| PA2037 | 9948043 | hypothetical protein | | |
| PA2042 | 9948048 | probably transporter (membrane subunit) | | ygjU |
| PA2051 | 9948058 | probable transmembrane sensor | | |
| PA2052 | 9948059 | cyanate lyase | cynS | |
| PA2060 | 9948068 | probable permease of ABC transporter | | |
| PA2062 | 9948071 | probable pyridoxal-phosphate dependent enzy | | |
| PA2066 | 9948075 | hypothetical protein | | |
| PA2071 | 9948081 | elongation factor G | fusA2 | |
| PA2073 | 9948083 | probable transporter (membrane subunit) | | |
| PA2074 | 9948084 | hypothetical protein | | |
| PA2075 | 9948086 | hypothetical protein | | |
| PA2080 | 9948091 | hypothetical protein | | |
| PA2088 | 9948100 | hypothetical protein | | |
| PA2090 | 9948102 | hypothetical protein | | |
| PA2092 | 9948104 | probable MFS transporter | | |
| PA2095 | 9948108 | hypothetical protein | | |
| PA2097 | 9948110 | probable flavin-binding monooxygenase | | |
| PA2101 | 9948114 | conserved hypothetical protein | | |
| PA2103 | 9948117 | probable molybdopterin biosynthesis protein MoeB | | moeB |
| PA2105 | 9948119 | probable acetyltransferase | | |
| PA2107 | 9948121 | hypothetical protein | | |
| PA2110 | 9948124 | hypothetical protein | | |
| PA2118 | 9948133 | O6-methylguanine-DNA methyltransferase | ada | |
| PA2119 | 9948134 | alcohol dehydrogenase (Zn-dependent) | | adh |
| PA2120 | 9948135 | hypothetical protein | | |

TABLE 1-continued

| | | | | |
|---|---|---|---|---|
| PA2123 | 9948138 | probable transcriptional regulator | | |
| PA2126 | 9948142 | conserved hypothetical protein | | |
| PA2131 | 9948147 | hypothetical protein | | |
| PA2136 | 9948153 | hypothetical protein | | |
| PA2142 | 9948159 | probable short-chain dehydrogenase | | yhxC |
| PA2143 | 9948160 | hypothetical protein | | |
| PA2146 | 9948164 | conserved hypothetical protein | | yciG |
| PA2149 | 9948167 | hypothetical protein | | |
| PA2157 | 9948175 | hypothetical protein | | |
| PA2161 | 9948180 | hypothetical protein | | |
| PA2166 | 9948186 | hypothetical protein | | |
| PA2167 | 9948187 | hypothetical protein | | |
| PA2170 | 9948190 | hypothetical protein | | |
| PA2171 | 9948191 | hypothetical protein | | |
| PA2174 | 9948194 | hypothetical protein | | |
| PA2175 | 9948195 | hypothetical protein | | |
| PA2182 | 9948203 | hypothetical protein | | |
| PA2183 | 9948204 | hypothetical protein | | |
| PA2184 | 9948205 | conserved hypothetical protein | | yciE |
| PA2185 | 9948206 | hypothetical protein | | |
| PA2186 | 9948207 | hypothetical protein | | |
| PA2187 | 9948208 | hypothetical protein | | |
| PA2190 | 9948211 | conserved hypothetical protein | | |
| PA2192 | 9948214 | conserved hypothetical protein | | |
| PA2196 | 9948218 | probable transcriptional regulator | | |
| PA2197 | 9948219 | conserved hypothetical protein | | ycnB |
| PA2205 | 9948228 | hypothetical protein | | |
| PA2207 | 9948230 | hypothetical protein | | |
| PA2211 | 9948234 | conserved hypothetical protein | | |
| PA2214 | 9948238 | probable MFS transporter | | |
| PA2219 | 9948243 | membrane protein OpdE | opdE | |
| PA2220 | 9948244 | probable transcriptional regulator | | opdR |
| PA2221 | 9948245 | conserved hypothetical protein | | |
| PA2222 | 9948247 | hypothetical protein | | |
| PA2223 | 9948248 | hypothetical protein | | |
| PA9948 | 9948249 | hypothetical protein | | |
| PA2225 | 9948250 | hypothetical protein | | |
| PA2226 | 9948251 | hypothetical protein | | |
| PA2227 | 9948252 | probable transcriptional regulator | | |
| PA2228 | 9948253 | hypothetical protein | | |
| PA2229 | 9948254 | conserved hypothetical protein | | yiiM |
| PA2234 | 9948259 | probable exopolysaccharide transporter | | |
| PA2242 | 9948268 | hypothetical protein | | |
| PA2245 | 9948271 | hypothetical protein | | |
| PA2251 | 9948278 | hypothetical protein | | |
| PA2253 | 9948280 | L asparaginase I | ansA | |
| PA2257 | 9948284 | pyoverdine biosynthesis protein PvcD | pvcD | |
| PA2258 | 9948285 | transcriptronai regulator PtXR | ptxR | |
| PA2260 | 9948288 | hypothetical protein | | |
| PA2280 | 9948309 | conserved hypothetical protein | | arsH |
| PA2282 | 9948312 | hypothetical protein | | |
| PA2284 | 9948314 | hypothetical protein | | |
| PA2292 | 9948323 | hypothetical protein | | |
| PA2293 | 9948324 | hypothetical protein | | |
| PA2294 | 9948325 | probable ATP-binding component of ABC trans | | |
| PA2295 | 9948326 | probable permease of ABC transporter | | |
| PA2297 | 9948328 | probable ferredoxin | | |
| PA2298 | 9948329 | probable oxidoreductase | | |
| PA2303 | 9948335 | hypothetical protein | | |
| PA2311 | 9948344 | hypothetical protein | | |
| PA2316 | 9948349 | probable transcriptional regulator | | |
| PA2329 | 9948364 | probable ATP-binding component of ABC trans | | |
| PA2331 | 9948366 | hypothetical protein | | |
| PA2336 | 9948371 | hypothetical protein | | |
| PA2338 | 9948374 | probable binding protein component of ABC m | | mtlE |
| PA2343 | 9948379 | xylulose kinase | mtlY | |
| PA2347 | 9948384 | hypothetical protein | | |
| PA2349 | 9948386 | conserved hypothetical protein | | |
| PA2351 | 9948388 | probable permease of ABC transporter | | |
| PA2365 | 9948403 | conserved hypothetical protein | | |
| PA2367 | 9948406 | hypothetical protein | | |
| PA2368 | 9948407 | hypothetical protein | | |
| PA2370 | 9948409 | hypothetical protein | | |
| PA2372 | 9948411 | hypothetical protein | | |
| PA2375 | 9948414 | hypothetical protein | | |
| PA2383 | 9948423 | probable transcriptional regulator | | |
| PA2391 | 9948432 | probable outer membrane protein | | |
| PA2405 | 9948449 | hypothetical protein | | |
| PA2406 | 9948450 | hypothetical protein | | |

TABLE 1-continued

| | | | | |
|---|---|---|---|---|
| PA2411 | 9948455 | probable thioesterase | | |
| PA2412 | 9948456 | conserved hypothetical protein | | |
| PA2418 | 9948463 | hypothetical protein | | |
| PA2422 | 9948467 | hypothetical protein | | |
| PA2427 | 9948473 | hypothetical protein | | |
| PA2428 | 9948474 | hypothetical protein | | |
| PA2429 | 9948475 | hypothetical protein | | |
| PA2434 | 9948480 | hypothetical protein | | |
| PA2436 | 9948482 | hypothetical protein | | |
| PA2441 | 9948488 | hypothetical protein | | |
| PA2442 | 9948489 | glycine cleavage system protein T2 | gcvT2 | |
| PA2446 | 9948494 | glycine cleavage system protein H2 | gcvH2 | |
| PA2451 | 9948499 | hypothetical protein | | |
| PA2453 | 9948502 | hypothetical protein | | |
| PA2455 | 9948504 | hypothetical protein | | |
| PA2456 | 9948505 | hypothetical protein | | |
| PA2459 | 9948508 | hypothetical protein | | |
| PA2460 | 9948509 | hypothetical protein | | |
| PA2461 | 9948510 | hypothetical protein | | |
| PA2464 | 9948514 | hypothetical protein | | |
| PA2467 | 9948517 | probable transmembrane sensor | | |
| PA2469 | 9948519 | probable transcriptional regulator | | |
| PA2473 | 9948524 | probable glutathione S-transferase | | |
| PA2474 | 9948525 | hypothetical protein | | |
| PA2475 | 9948526 | probable cytochrome P450 | | |
| PA2485 | 9948537 | hypothetical protein | | |
| PA2487 | 9948539 | hypothetical protein | | |
| PA2490 | 9948542 | conserved hypothetical protein | | ydbB |
| PA2491 | 9948543 | probable oxidoreductase | | |
| PA2492 | 9948544 | transcriptional regulator MexT | mexT | |
| PA2496 | 9948549 | hypothetical protein | | |
| PA2500 | 9948553 | probable MFS transporter | | cynX |
| PA2501 | 9948554 | hypothetical protein | | |
| PA2504 | 9948557 | hypothetical protein | | |
| PA2507 | 9948561 | catechol 1,2-dioxygenase | catA | |
| PA2515 | 9948569 | cis-1,2-dihydroxycyclohexa-3,4-diene carboxyl | axylL | |
| PA2517 | 9948571 | toluate 1,2-dioxygenase beta subunit | xylY | |
| PA2521 | 9948576 | RND divalent metal cation efflux membrane fu | czcB | |
| PA2536 | 9948593 | probable phosphatidate cytidylyltransferase | | ynbB |
| PA2538 | 9948595 | hypothetical protein | | |
| PA2539 | 9948596 | conserved hypothetical protein | | ynbD |
| PA2544 | 9948602 | hypothetical protein | | |
| PA2549 | 9948608 | conserved hypothetical protein | | ygjT |
| PA2561 | 9948610 | probable transcriptional regulator | | |
| PA2552 | 9948611 | probable acyl-CoA dehydrogenase | | acdB |
| PA2553 | 9948612 | probable acyl-CoA thiolase | | |
| PA2554 | 9948613 | probable short-chaindehydrogenase | | |
| PA2577 | 9948639 | probable transcriptional regulator | | |
| PA2584 | 9948647 | CDP-diacylglycerol-glycerol-3-phosphate-3-ph | pgsA | |
| PA2591 | 9948655 | probable transcriptional regulator | | |
| PA2602 | 9948667 | hypothetical protein | | |
| PA2605 | 9948670 | conserved hypothetical protein | | yheN |
| PA2606 | 9948671 | conserved hypothetical protein | | yheM |
| PA2607 | 9948672 | consented hypothetical protein | | |
| PA2608 | 9948673 | conserved hypothetical protein | | yccK |
| PA2612 | 9948677 | seryl tRNA synthetase | serS | |
| PA2614 | 9948680 | periplasmic chaperone LolA | lolA | |
| PA2615 | 9948681 | cell division protein FtsK | ftsK | |
| PA2617 | 9948683 | leucyl/phenylalanyl-tRNA-protein transferase | aat | |
| PA2619 | 9948685 | initiation factor | infA | |
| PA2621 | 9948687 | conserved hypothetical protein | | |
| PA2626 | 9948693 | tRNA methyltransferase | trmU | asuE |
| PA2629 | 9948696 | adenylosuccinate lyase | purB | |
| PA2638 | 9948706 | NADH dehydrogenase I chain B | nuoB | |
| PA2641 | 9948709 | NADH dehydrogenase I chain F | nuoF | |
| PA2645 | 9948714 | NADH dehydrogenase I chain J | nuoJ | |
| PA2646 | 9948715 | NADH dehydrogenase I chain K | nuoK | |
| PA2658 | 9948728 | hypothetical protein | | |
| PA2663 | 9948734 | hypothetical protein | | |
| PA2666 | 9948737 | probable 6-pyruvoyl tetrahydrobiopterin syntha | | ptpS |
| PA2667 | 9948738 | conserved hypothetical protein | | |
| PA2668 | 9948739 | hypothetical protein | | |
| PA2673 | 9948744 | probable type II secretion system protein | | hplV |
| PA2674 | 9948745 | probable type II secretion system protein | | hplU |
| PA2675 | 9948746 | probable type II secretion system protein | | hplT |
| PA2678 | 9948749 | probable permease of ABC-2 transporter | | |
| PA2681 | 9948753 | probable transcriptional regulator | | |
| PA2683 | 9948755 | probable serine/threonine dehydratase, degrad | | tdcB |
| PA2689 | 9948762 | hypothetical protein | | |

TABLE 1-continued

| | | | |
|---|---|---|---|
| PA2690 | 9948763 | probable transposase | |
| PA2694 | 9948767 | probable thioredoxin | |
| PA2697 | 9948771 | hypothetical protein | |
| PA2703 | 9948777 | hypothetical protein | |
| PA2706 | 9948780 | hypothetical protein | |
| PA2715 | 9948790 | probable ferredoxin | |
| PA2719 | 9948795 | hypothetical protein | |
| PA2720 | 9948796 | hypothetical protein | |
| PA2721 | 9948797 | hypothetical protein | |
| PA2722 | 9948798 | hypothetical protein | |
| PA2723 | 9948799 | hypothetical protein | |
| PA2726 | 9948802 | probable radical activating enzyme | |
| PA2730 | 9948807 | hypothetical protein | |
| PA2731 | 9948808 | hypothetical protein | |
| PA2733 | 9948810 | conserved hypothetical protein | |
| PA2734 | 9948811 | hypothetical protein | |
| PA2736 | 9948814 | hypothetical protein | |
| PA2737 | 9948815 | conserved hypothetical protein | |
| PA2738 | 9948816 | integration host factor, alpha subunit | himA |
| PA2739 | 9948817 | phenylalanyl-tRNA synthetase, beta subunit | pheT |
| PA2740 | 9948818 | phenylalanyl-tRNA synthetase, alpha-subunit | pheS |
| PA2741 | 9948819 | 50S ribosomal protein L20 | rplT |
| PA2742 | 9948820 | 50S ribosomal protein L35 | rpmI |
| PA2743 | 9948821 | translation initiation factor IF-3 | infC |
| PA2744 | 9948822 | threonyl tRNA synthetase | thrS |
| PA2749 | 9948828 | DNA-specific endonuclease I | endA |
| PA2753 | 9948832 | hypothetical protein | |
| PA2758 | 9948835 | hypothetical protein | |
| PA2759 | 9948839 | hypothetical protein | |
| PA2762 | 9948842 | hypothetical protein | |
| PA2763 | 9948843 | hypothetical protein | |
| PA2767 | 9948847 | probable enoyl-CoA hydratase/isomerase | |
| PA2768 | 9948848 | hypothetical protein | |
| PA2769 | 9948849 | hypothetical protein | |
| PA2774 | 9948855 | hypothetical protein | |
| PA2775 | 9948856 | hypothetical protein | |
| PA2780 | 9948861 | hypothetical protein | |
| PA2781 | 9948862 | hypothetical protein | |
| PA2782 | 9948863 | hypothetical protein | |
| PA2784 | 9948866 | hypothetical protein | |
| PA2785 | 9948867 | conserved hypothetical protein | |
| PA2786 | 9948868 | hypothetical protein | |
| PA2792 | 9948874 | hypothetical protein | |
| PA2794 | 9948877 | hypothetical protein | |
| PA2797 | 9948880 | hypothetical protein | |
| PA2799 | 9948882 | hypothetical protein | |
| PA2800 | 9948883 | conserved hypothetical protein | vacJ |
| PA2803 | 9948886 | hypothetical protein | |
| PA2805 | 9948888 | hypothetical protein | |
| PA2807 | 9948891 | hypothetical protein | |
| PA2808 | 9948892 | hypothetical protein | |
| PA2811 | 9948895 | probable permease of ABC-2 transporter | yadH |
| PA2818 | 9948902 | hypothetical protein | |
| PA2819 | 9948903 | hypothetical protein | |
| PA2827 | 9948912 | conserved hypothetical protein | yeaA |
| PA2829 | 9948914 | hypothetical protein | |
| PA2831 | 9948917 | conserved hypothetical protein | |
| PA2832 | 9948918 | thiopurine methyltransferase | tpm |
| PA2839 | 9948925 | conserved hypothetical protein | ygiD |
| PA2843 | 9948930 | probable aldolase | |
| PA2845 | 9948932 | hypothetical protein | |
| PA2851 | 9948938 | translation elongation factor P | efp |
| PA2852 | 9948939 | hypothetical protein | |
| PA2853 | 9948941 | outer membrane lipoprotein OprI precursor | oprI |
| PA2854 | 9948942 | conserved hypothetical protein | erfK |
| PA2859 | 9948947 | transcription elongation factor GreB | greB |
| PA2863 | 9948951 | lipase modulator protein | lipH |
| PA2868 | 9948957 | hypothetical protein | |
| PA2874 | 9948963 | hypothetical protein | |
| PA2876 | 9948966 | orotidine 5'-phosphate decarboxylase | pyrF |
| PA2877 | 9948967 | probable transcriptional regulator | |
| PA2879 | 9948969 | probable transcriptional regulator | hpkR |
| PA2883 | 9948973 | hypothetical protein | |
| PA2894 | 9948985 | hypothetical protein | |
| PA2898 | 9948990 | hypothetical protein | |
| PA2901 | 9948993 | hypothetical protein | |
| PA2910 | 9949003 | conserved hypothetical protein | yebN |
| PA2915 | 9949008 | hypothetical protein | |
| PA2916 | 9949010 | hypothetical protein | |

TABLE 1-continued

| | | | | |
|---|---|---|---|---|
| PA2922 | 9949016 | probable hydrolas | | |
| PA2928 | 9949023 | hypothetical protein | | |
| PA2935 | 9949030 | hypothetical protein | | |
| PA2936 | 9949031 | hypothetical protein | | |
| PA2936 | 9949033 | hypothetical protein | | |
| PA2940 | 9949036 | probable acyl-CoA thiolase | | |
| PA2949 | 9949046 | probable lipase | | |
| PA2951 | 9949048 | electron transfer flavoprotein alpha-subunit | etfA | |
| PA2952 | 9949049 | electron transfer flavoprotein beta-subunit | etfB | |
| PA2953 | 9949050 | electron transfer flavoprotein-ubiquinone oxido | | |
| PA2960 | 9949058 | type 4 fimbrial biogenesis protein PilZ | pilZ | |
| PA2961 | 9949059 | DNA polymerase III, delta prime subunit | holB | |
| PA2962 | 9949060 | thymidylate kinase | tmk | |
| PA2963 | 9949061 | conserved hypothetical protein | | yceG |
| PA2966 | 9949064 | acyl carrier protein | acpP | |
| PA2967 | 9949065 | 3 oxoacyl-[acyl-carrier-protein] reductase | fabG | |
| PA2968 | 9949066 | malonyl-CoA-[acyl-carrier-protein] transacylase | fabD | |
| PA2970 | 9949069 | 50S ribosomal protein L32 | rpmF | |
| PA2971 | 9949070 | conserved hypothetical protein | | yceD |
| PA2975 | 9949074 | ribosomal large subunit pseudouridine synthas | rluC | yceC |
| PA2977 | 9949076 | UDP-N-acetylpyruvoylglucosamine reductase | murB | |
| PA2978 | 9949077 | phosphotyrosine protein phosphatase | ptpA | |
| PA2979 | 9949078 | 3-deoxy-manno-octulosonate cytidylyltransfer | kdsB | |
| PA2980 | 9949079 | conserved hypothetical protein | | ycaR |
| PA2981 | 9949080 | tetraacyldisaccharide 4*-kinase | lpxK | |
| PA2982 | 9949081 | conserved hypothetical protein | | |
| PA2983 | 9949082 | probable tolQ-type transport protein | | |
| PA2985 | 9949085 | hypothetical protein | | |
| PA2988 | 9949086 | conserved hypothetical protein | | |
| PA2987 | 9949087 | probable ATP-binding component of ABC trans | | ycfV |
| PA2988 | 9949088 | conserved hypothetical protein | | |
| PA2989 | 9949089 | hypothetical protein | | |
| PA2991 | 9949091 | soluble pyridine nucleotide transhydrogenase | sth | |
| PA2992 | 9949092 | hypothetical protein | | |
| PA2996 | 9949096 | Na+-translocating NADH: uniquinone oxioredu | nqrD | |
| PA3001 | 9949102 | probable glyceraldehyde-3-phosphate dehydro | | |
| PA3004 | 9949105 | probable nucleoside phosphorylase | | |
| PA3009 | 9949111 | hypothetical protein | | |
| PA3011 | 9949113 | DNA topoisomerase I | topA | |
| PA3012 | 9949114 | hypothetical protein | | |
| PA3017 | 9949120 | conserved hypothetical protein | | |
| PA3021 | 9949124 | hypothetical protein | | |
| PA3022 | 9949125 | hypothetical protein | | |
| PA3024 | 9949127 | probable carbohydrate kinase | | |
| PA3030 | 9949134 | probable molybdopterin-guanine dinucleotide b | | mobA |
| PA3033 | 9949137 | hypothetical protein | | |
| PA3036 | 9949140 | hypothetical protein | | |
| PA3040 | 9949145 | conserved hypothetical protein | | yqjD |
| PA3041 | 9949146 | hypothetical protein | | yqjE |
| PA3042 | 9949147 | hypothetical protein | | |
| PA3046 | 9949151 | conserved hypothetical protein | | yggL |
| PA3049 | 9949155 | ribosome modulation factor | rmf | |
| PA3051 | 9949157 | hypothetical protein | | |
| PA3067 | 9949174 | probable transcriptional regulator | | |
| PA3081 | 9949189 | conserved hypothetical protein | | |
| PA3086 | 9949193 | hypothetical protein | | |
| PA3088 | 9949197 | conserved hypothetical protein | | vfjB |
| PA3089 | 9949198 | hypothetical protein | | |
| PA3093 | 9949202 | hypothetical protein | | |
| PA3095 | 9949205 | general secretion pathway protein M | xcpZ | |
| PA3096 | 9949206 | general secretion pathway protein L | xcpY | |
| PA3100 | 9949210 | general secretion pathway protein H | xcpU | pddB |
| PA3103 | 9949213 | general secretion pathway protein E | xcpR | |
| PA3110 | 9949221 | hypothetical protein | | |
| PA3112 | 9949223 | acetyl CoA carboxylase beta subunit | accD | dedB |
| PA3117 | 9949229 | aspartate semialdehyde dehydrogenase | asd | |
| PA3123 | 9949235 | conserved hypothetical protein | | |
| PA4314 | 9949254 | hypothetical protein | | |
| PA3142 | 9949256 | hypothetical protein | | |
| PA3144 | 9949256 | hypothetical protein | | |
| PA3145 | 9949259 | glycosyltransferase WbpL | wbpL | |
| PA3146 | 9949260 | probable NAD-dependent epimerase/dehydrate | wbpK | |
| PA3147 | 9949261 | probable glycosyl transferase WbpJ | wbpJ | |
| PA3148 | 9949262 | probable UDP-N-acetylglucosamine 2-epimera | wbpI | |
| PA3149 | 9949263 | probable glycosyltransferase WbpH | wbpH | |
| PA3150 | 9949264 | LPS biosynthesis protein WbpG | wbpG | |
| PA3151 | 9949266 | imidazoleglycerol-phosphate synthase, cyclase | hisF2 | |
| PA3152 | 9949267 | glutamine amidotransferase | hisH2 | |
| PA3153 | 9949268 | O-antigen translocase | wzx | wbpF, rfbX |

TABLE 1-continued

| | | | | |
|---|---|---|---|---|
| PA3154 | 9949269 | B-band O-antigen polymerase | wzy | rfc |
| PA3165 | 9949270 | probable aminotransferase WbpE | wbpE | |
| PA3156 | 9949271 | probable acetyltransferase WbpD | wbpD | |
| PA3157 | 9949272 | probable acetyltransferase | | wbpC |
| PA3158 | 9949273 | probable oxidoreductase WpbB | wbpB | |
| PA3159 | 9949274 | probable UDP-glucose/GDP-mannose dehydro | wbpA | |
| PA3160 | 9949276 | O-antigen chain length regulator | wzz | cld, rol |
| PA3161 | 9949277 | integration host factor beta subunit | himD | |
| PA3162 | 9949278 | 30S ribosoml protein S1 | rpsA | |
| PA3163 | 9949279 | cytidylate kinase | cmk | |
| PA3167 | 9949283 | 3-phosphoserine aminotransferase | serC | |
| PA3168 | 9949285 | DNA gyrase subunit A | gyrA | |
| PA317T | 9949288 | 3-demethylubiquinone-9 3-methyltransferase | ubiG | |
| PA3178 | 9949296 | hypothetical protein | | |
| PA3181 | 9949299 | 2-keto-3-deoxy-6-phosphogluconate aldolase | | edaA |
| PA3185 | 9949303 | hypothetical protein | | |
| PA3195 | 9949314 | glyceraldehyde 3-phosphate dehydrogenase | gapA | |
| PA3202 | 9949322 | conserved hypothetical protein | | ycil |
| PA3203 | 9949323 | hypothetical protein | | |
| PA3207 | 9949327 | hypothetical protein | | |
| PA3211 | 9949331 | probable permease of ABC transporter | | |
| PA3220 | 9949341 | probable transcriptional regulator | | |
| PA3227 | 9949348 | peptidyl-prolyl cis-trans isomerase A | ppiA | cypH |
| PA3230 | 9949352 | conserved hypothetical protein | | |
| PA3232 | 9949354 | probable nuclease | | |
| PA3237 | 9949359 | hypothetical protein | | |
| PA3242 | 9949365 | probable lauroyl acyltransferase | | htrB |
| PA3245 | 9949368 | cell division topological specificity factor MinE | minE | |
| PA3246 | 9949369 | pseudouridine synthase RluA | rluA | yabO |
| PA3249 | 9949372 | probable transcriptional regulator | | |
| PA3255 | 9949379 | hypothetical protein | | |
| PA3260 | 9949384 | probable transcriptional regulator | | |
| PA3266 | 9949391 | cold acclimation protein B | capB | cspA |
| PA3273 | 9949398 | hypothetical protein | | |
| PA3274 | 9949399 | hypothetical protein | | |
| PA3275 | 9949401 | conserved hypothetical protein | | ynfA |
| PA3278 | 9949404 | hypothetical protein | | |
| PA3280 | 9949406 | outer membrane porin OprO precursor | oprO | |
| PA3281 | 9949407 | hypothetical protein | | |
| PA3287 | 9949414 | conserved hypothetical protein | | |
| PA3288 | 9949415 | hypothetical protein | | |
| PA3289 | 9949416 | hypothetical protein | | |
| PA3291 | 9949416 | hypothetical protein | | |
| PA3292 | 9949419 | hypothetical protein | | |
| PA3298 | 9949426 | hypothetical protein | | |
| PA3302 | 9949430 | conserved hypothetical protein | | |
| PA3309 | 9949438 | conserved hypothetical protein | | |
| PA3312 | 9949441 | probable 3-hydroxyisobutyrate dehydrogenase | | |
| PA3314 | 9949443 | probable ATP-binding component of ABC trans | | |
| PA3315 | 9949444 | probable permease of ABC transporter | | |
| PA3317 | 9949447 | hypothetical protein | | |
| PA3316 | 9949448 | hypothetical protein | | |
| PA3320 | 9949450 | hypothetical protein | | |
| PA3326 | 9949457 | probable Clp-family ATP-dependent protease | | |
| PA3330 | 9949461 | probable short chain dehydrogenase | | |
| PA3332 | 9949463 | conserved hypothetical protein | | |
| PA3334 | 9949465 | probable acyl carrier protein | | |
| PA3338 | 9949470 | hypothetical protein | | |
| PA3341 | 9949473 | probable transcription regulator | | |
| PA3347 | 9949480 | hypothetical protein | | |
| PA3348 | 9949481 | probable chemotaxis protein methyltransferase | | cheR1 |
| PA3351 | 9949484 | hypothetical protein | | flgM |
| PA3353 | 9949486 | hypothetical protein | | |
| PA3354 | 9949487 | hypothetical protein | | |
| PA3360 | 9949494 | probable secretion protein | | |
| PA3367 | 9949502 | hypothetical protein | | ydcA |
| PA3368 | 9949503 | probable acetyltransferase | | |
| PA3370 | 9949505 | hypothetical protein | | |
| PA3371 | 9949506 | hypothetical protein | | |
| PA3380 | 9949515 | conserved hypothetical protein | | phnG |
| PA3384 | 9949519 | ATP binding component of ABC phosphonate | phnC | |
| PA3390 | 9949525 | hypothetical protein | | |
| PA3395 | 9949531 | NosY protein | nosY | |
| PA3396 | 9949532 | NosL protein | nosL | |
| PA3397 | 9949534 | ferredoxin—NADP + reductase | fpr | |
| PA3403 | 9949540 | hypothetical protein | | |
| PA3407 | 9949545 | heme acquisition protein HasAp | hasAp | |
| PA3413 | 9949551 | conserved hypothetical protein | | yebG |
| PA3414 | 9949552 | hypothetical protein | | |

TABLE 1-continued

| | | | | |
|---|---|---|---|---|
| PA3416 | 9949554 | probable pyruvate dehydrogenase E1 compon | | |
| PA3432 | 9949572 | hypothetical protein | | |
| PA3433 | 9949573 | probable transcriptional regulator | | ywbI |
| PA3434 | 9949574 | probable transposase | | |
| PA3435 | 9949575 | conserved hypothetical protein | | mioC |
| PA3438 | 9949578 | GTP cyclohydrolase I precursor | folE1 | |
| PA3459 | 9949579 | d-erythro-7,8-dihydroneopteiln triphosphate | folX | |
| PA3443 | 9949584 | probable permease of ABC transporter | | ssuC ycbM |
| PA3444 | 9949585 | conserved hypothetical protein | | ssuD |
| PA3445 | 9949586 | conserved hypothetical protein | | |
| PA3446 | 9949587 | conserved hypothetical protein | | ssuE |
| PA3450 | 9949591 | probable antioxidant protein | | lsfA |
| PA3451 | 9949592 | hypothetical protein | | |
| PA3460 | 9949602 | probable acetyltransferase | | |
| PA3470 | 9949614 | hypothetical protein | | |
| PA3472 | 9949616 | hypothetical protein | | |
| PA3477 | 9949621 | transcriptional regulator RhlR | rhlR | |
| PA3482 | 9949627 | methlonyl-tRNA synthetase | metG | |
| PA3488 | 9949634 | hypothetical protein | | |
| PA3489 | 9949635 | conserved hypothetical protein | | rnfA |
| PA3492 | 9949638 | conserved hypothetical protein | | rnfD |
| PA3494 | 9949640 | conserved hypothetical protein | | rnfE |
| PA3495 | 9949641 | endonuclease III | nth | |
| PA3496 | 9949642 | hypothetical protein | | |
| PA3501 | 9949647 | hypothetical protein | | |
| PA3502 | 9949648 | hypothetical protein | | |
| PA3505 | 9949652 | hypothetical protein | | |
| PA3512 | 9949659 | probable permease of ABC transporter | | |
| PA3519 | 9949667 | hypothetical protein | | |
| PA3520 | 9949668 | hypothetical protein | | |
| PA3523 | 9949671 | probable RND efflux membrane fusion protein | | |
| PA3528 | 9949677 | ribonuclease T | rnt | |
| PA3530 | 9949679 | conserved hypothetical protein | | bfd |
| PA3533 | 9949682 | conserved hypothetical protein | | ydhD |
| PA3542 | 9949693 | alginate biosynthesis protein Alg44 | | alg44 |
| PA3550 | 9949702 | alginate O-acetyltransferase AlgF | algF | |
| PA3558 | 9949710 | hypothetical protein | | |
| PA3566 | 9949719 | conserved hypothetical protein | | ycnE |
| PA3570 | 9949724 | methylmalonate-semialdehyde dehydragenase | mmsA | |
| PA3572 | 9949726 | hypothetical protein | | |
| PA3575 | 9949729 | hypothetical protein | | |
| PA3578 | 9949732 | conserved hypothetical protein | | |
| PA3589 | 9949744 | probable acyl-CoA thiolase | | |
| PA3600 | 9949756 | conserved hypothetical protein | | rpl36 |
| PA3601 | 9949757 | conserved hypothetical protein | | ykgM |
| PA3605 | 9949762 | hypothetical protein | | |
| PA3606 | 9949763 | conserved hypothetical protein | yfiP | |
| PA3609 | 9949766 | polyamine transport protein PotC | potC | |
| PA3611 | 9949768 | hypothetical protein | | |
| PA3612 | 9949769 | conserved hypothetical protein | | ypeB |
| PA3616 | 9949774 | conserved hypothetical protein | | recX |
| PA3617 | 9949775 | RecA protein | recA | |
| PA3627 | 9949785 | conserved hypothetical protein | | ygbB |
| PA3632 | 9949791 | conserved hypothetical protein | | yedF |
| PA3633 | 9949792 | conserved hypothetical protein | | ygbP |
| PA3634 | 9949793 | conserved hypothetical protein | | ybgQ |
| PA3635 | 9949794 | enolase | eno | |
| PA3636 | 9949795 | 2-dehydro-3-deoxyphosphooctonate aldolase | kdsA | |
| PA3637 | 9949796 | CTP synthase | pyrG | |
| PA3638 | 9949797 | conserved hypothetical protein | | mesJ |
| PA3639 | 9949798 | acetyl-coenzyme A carboxylase carboxyl tran | accA | |
| PA3640 | 9949800 | DNA polymerase III, alpha chain | dnaE | polC |
| PA3643 | 9949803 | lipid A-disaccharide synthase | lpxB | pgsB |
| PA3644 | 9949804 | UDP-N-acetylglucosamine acyltransferase | lpxA | |
| PA3645 | 9949805 | (3R)-hydroxymyristoyl-[acyl carrier protein] deh | fabZ | sefA |
| PA3646 | 9949806 | UDP-3-O-[3-hydroxylauroyl] glucosamine N-ac | lpxD | firA omsA |
| PA3647 | 9949807 | probable outer membrane protein precursor | | |
| PA3648 | 9949808 | probable outer membrane protein | | |
| PA3650 | 9949811 | 1-deoxy-d-xylulose 5-phosphate reductoisome | dxr | yaeM |
| PA3651 | 9949812 | phosphatidate cytidylyltransferase | cdsA | |
| PA3652 | 9949813 | undecaprenyl pyrophosphate synthetase | uppS | yaeS |
| PA3653 | 9949814 | ribosome recycling factor | frr | rrf |
| PA3654 | 9949815 | uridylate kinase | pyrH | smbA |
| PA3655 | 9949816 | elongation factor Ts | tsf | |
| PA3656 | 9949817 | 30S ribosomal protein S2 | rpsB | |
| PA3657 | 9949818 | methionine aminopeptidase | map | |
| PA3662 | 9949824 | hypothetical protein | | |
| PA3664 | 9949826 | conserved hypothetical protein | | yffB |
| PA3666 | 9949828 | tetrahydrodipicolinate succinylase | dapD | |

TABLE 1-continued

| | | | | |
|---|---|---|---|---|
| PA3671 | 9949833 | probable permease of ABC transporter | | |
| PA3674 | 9949837 | hypothetical protein | | |
| PA3678 | 9949841 | probable transcriptional regulator | | |
| PA3681 | 9949844 | hypothetical protein | | |
| PA3684 | 9949848 | hypothetical protein | | |
| PA3685 | 9949849 | conserved hypothetical protein | | |
| PA3688 | 9949852 | hypothetical protein | | |
| PA3893 | 9949858 | conserved hypothetical protein | | |
| PA3701 | | peptide chain release factor 2 | prfB | |
| PA3704 | 9949868 | probable chemotaxis sensor/effector fusion pro | | |
| PA3719 | 9949885 | hypothetical protein | | |
| PA3725 | 9949891 | single-stranded-DNA-specific exonuclease Re | recJ | |
| PA3726 | 9949892 | conserved hypothetical protein | | yaeQ |
| PA3730 | 9949897 | hypothetical protein | | |
| PA3731 | 9949898 | conserved hypothetical protein | | yjfJ |
| PA3733 | 9949900 | hypothetical protein | | |
| PA3742 | 9949910 | 50S ribosomal protein L19 | rplS | |
| PA3743 | 9949911 | tRNA (guanine-N1)-methyltransferase | trmD | |
| PA3744 | 9949912 | 16S rRNA processing protein | rimM | |
| PA3745 | 9949913 | 30S ribosomal protein S16 | rpsP | |
| PA3746 | 9949914 | signal recognition particle protein Ffh | ffh | |
| PA3752 | 9949921 | hypothetical protein | | |
| PA3754 | 9949923 | hypothetical protein | | yeaB |
| PA3756 | 9949925 | hypothetical protein | | yafK |
| PA3759 | 9949928 | probable aminotransferase | | |
| PA3765 | 9949935 | hypothetical protein | | |
| PA3767 | 9949937 | conserved hypothetical protein | | yfhC |
| PA3769 | 9949940 | GMP synthase | guaA | |
| PA3773 | 9949944 | hypothetical protein | | |
| PA3776 | 9949947 | probable transcriptional regulator | | |
| PA3777 | 9949948 | exodeoxyribonuclease VII large subunit | xseA | |
| PA3782 | 9949954 | probable transcriptional regulator | | |
| PA3784 | 9949956 | hypothetical protein | | |
| PA3785 | 9949957 | conserved hypothetical protein | | |
| PA3787 | 9949959 | conserved hypothetical protein | | |
| PA3788 | 9949960 | hypothetical protein | | |
| PA3796 | 9949969 | hypothetical protein | | |
| PA3800 | 9949973 | conserved hypothetical protein | | |
| PA3803 | 9949976 | conserved hypothetical protein | | gcpE |
| PA3805 | 9949978 | type 4 fimbrial biogenesis protein PilF | pilF | |
| PA3806 | 9949979 | conserved hypothetical protein | | yfgB |
| PA3807 | 9949980 | nucleoside diphosphate kinase | ndk | |
| PA3808 | 9949982 | conserved hypothetical protein | | yfhJ |
| PA3809 | 9949983 | ferredoxin [2Fe-2S] | fdx2 | |
| PA3810 | 9949984 | heat shock protein HscA | hscA | |
| PA3811 | 9949985 | heat shock protein HscB | hscB | |
| PA3812 | 9949986 | probable iron-binding protein IscA | iscA | |
| PA3813 | 9949987 | probable iron-binding protein IscU | iscU | |
| PA3815 | 9949989 | conserved hypothetical protein | | |
| PA3821 | 9949995 | secretion protein SecD | secD | |
| PA3822 | 9949996 | conserved hypothetical protein | | yajC |
| PA3827 | 9950002 | conserved hypothetical protein | | yjgQ |
| PA3828 | 9950003 | conserved hypothetical protein | | yjgP |
| PA3829 | 9950004 | hypothetical protein | | |
| PA3833 | 9950008 | hypothetical protein | | |
| PA3834 | 9950009 | valyl-tRNA synthetase | valS | |
| PA3835 | 9950010 | hypothetical protein | | |
| PA3840 | 9950016 | conserved hypothetical protein | | ybiN |
| PA3843 | 9950019 | hypothetical protein | | |
| PA3850 | 9950027 | hypothetical protein | | |
| PA3851 | 9950028 | hypothetical protein | | |
| PA3854 | 9950031 | hypothetical protein | | |
| PA3856 | 9950033 | hypothetical protein | | |
| PA3867 | 9960034 | conserved hypothetical protein | | |
| PA3859 | 9950037 | probable carboxylesterase | | |
| PA3867 | 9950046 | probable DNA invertase | | |
| PA3868 | 9950047 | hypothetical protein | | |
| PA3869 | 9950048 | hypothetical protein | | |
| PA3876 | 9950056 | nitrite extrusion protein 2 | narK2 | |
| PA3884 | 9950064 | hypothetical protein | | |
| PA3886 | 9950066 | hypothetical protein | | |
| PA3888 | 9950069 | probable permease of ABC transporter | | |
| PA3890 | 9950071 | probable permease of ABC transporter | | |
| PA3891 | 9950072 | probable ATP-binding component of ABC tran | | |
| PA3892 | 9950073 | conserved hypothetical protein | | |
| PA3904 | 9950087 | hypothetical protein | | |
| PA3905 | 9950088 | hypothetical protein | | |
| PA3906 | 9950089 | hypothetical protein | | |
| PA3911 | 9950094 | conserved hypothetical protein | | yhbT |

TABLE 1-continued

| | | | | |
|---|---|---|---|---|
| PA3916 | 9950100 | molybdopterin converting factor, large subunit | moaE | |
| PA3917 | 9950101 | molybdopterin converting factor, small subunit | moaD | |
| PA3918 | 9950102 | molybdopterin biosynthetic protein C | moaC | |
| PA3936 | 9950122 | probable permease of ABC taurine transported | | tauC |
| PA3940 | 9950127 | probable DNA binding protein | | |
| PA3960 | 9950149 | hypothetical protein | | |
| PA3962 | 9950151 | hypothetical protein | | |
| PA3965 | 9950154 | probable transcriptional regulator | | |
| PA3967 | 9950156 | hypothetical protein | | |
| PA3969 | 9950158 | conserved hypothetical protein | | |
| PA3973 | 9950163 | probable transcriptional regulator | | |
| PA3977 | 9950167 | glutamate-1-semialdehyde 2,1-aminomutase | hemL | |
| PA3979 | 9950170 | hypothetical protein | | |
| PA3981 | 9950172 | conserved hypothetical protein | | ybeZ |
| PA3982 | 9950173 | conserved hypothetical protein | | |
| PA3984 | 9950175 | apolipoprotein N-acyltransferase | lnt | cutE |
| PA3986 | 9950177 | hypothetical protein | | |
| PA3987 | 9950178 | leucyl-tRNA synthetase | leuS | |
| PA3988 | 9950179 | hypothetical protein | | |
| PA3989 | 9950180 | DNA polymerase III, delta subunit | holA | |
| PA3990 | 9950182 | conserved hypothetical protein | | |
| PA3993 | 9950185 | probable transposase | | |
| PA3996 | 9950188 | lipoate synthase | lipA | lip |
| PA3998 | 9950190 | conserved hypothetical protein | | ybeD |
| PA4002 | 9950194 | rod shape-determining protein | rodA | mrdB |
| PA4005 | 9950197 | conserved hypothetical protein | | ybeB |
| PA4005 | 9950198 | hypothetical protein | | ybeN |
| PA4008 | 9950201 | probable hydrolase | | |
| PA4012 | 9950205 | hypothetical protein | | |
| PA4018 | 9950211 | hypothetical protein | | |
| PA4019 | 9950212 | probable aromatic acid decarboxylase | | |
| PA4028 | 9950222 | hypothetical protein | | |
| PA4029 | 9950224 | conserved hypothetical protein | | dedA |
| PA4031 | 9950226 | inorganic pyrophosphatase | ppa | ipyR |
| PA4033 | 9950228 | hypothetical protein | | |
| PA4037 | 9950232 | probable ATP-binding component of ABC trans | | |
| PA4043 | 9950239 | geranyltranstransferase | ispA | |
| PA4044 | 9950240 | 1-deoxyxylulose-5-phosphate synthase | dxs | |
| PA4047 | 9950243 | GTP cyclohydrolase II | ribA | |
| PA4049 | 9950245 | hypothetical protein | | |
| PA4050 | 9950246 | phosphatidylycerophosphatase A | pgpA | |
| PA4051 | 9950247 | thiamine monophosphate kinase | thiL | |
| PA4052 | 9950248 | NusB protein | nusB | ssyB |
| PA4053 | 9950249 | 6,7-dimethyl-8-ribityllumazine synthase | ribE | ribH |
| PA4055 | 9950252 | riboflavin synthase alpha chain | ribC | ribB |
| PA4056 | 9950253 | riboflavin-specific deaminase/reductase | ribC | ribG |
| PA4057 | 9950254 | conserved hypothetical protein | | ybaD |
| PA4059 | 9950256 | hypothetical protein | | |
| PA4060 | 9950257 | hypothetical protein | | |
| PA4063 | 9950260 | hypothetical protein | | |
| PA4064 | 9950261 | probable ATP-binding component of ABC trans | | |
| PA4068 | 9950266 | probable epimerase | | |
| PA4076 | 9950274 | hypothetical protein | | |
| PA4077 | 9950275 | probable transcriptional regulator | | |
| PA4083 | 9950282 | probable pili assembly chaperone | | |
| PA4097 | 9950298 | probable alcohol dehydrogenase (Zn-dependent) | | ydjL |
| PA4099 | 9950300 | hypothetical protein | | |
| PA4104 | 9950305 | conserved hypothetical protein | | |
| PA4107 | 9950309 | hypothetical protein | | |
| PA4114 | 9950317 | spermidine acetyltransferase | | bltD |
| PA4121 | 9950324 | conserved hypothetical protein | | |
| PA4122 | 9950325 | conserved hypothetical protein | | |
| PA4125 | 9950329 | 5-carboxymethyl-2-hydroxymuconate isomera | | hpcD |
| PA4134 | 9950339 | hypothetical protein | | |
| PA4141 | 9950346 | hypothetical protein | | |
| PA4149 | 9950351 | conserved hypothetical protein | | acoX |
| PA4151 | 9950357 | acetoin catabolism protein AcoB | acoB | |
| PA4157 | 9950364 | probable transcriptional regulator | | |
| PA4164 | 9950372 | hypothetical protein | | |
| PA4167 | 9950375 | probable oxidoreductase | | yafB |
| PA4169 | 9950377 | conserved hypothetical protein | | |
| PA4170 | 9950378 | hypothetical protein | | |
| PA4171 | 9950379 | probable protease | | |
| PA4174 | 9950383 | probable transcriptional regulator | | |
| PA4176 | 9950385 | peptidyl-prolyl cis-trans isomerase C2 | ppiC2 | |
| PA4181 | 9950390 | hypothetical protein | | |
| PA4182 | 9950391 | hypothetical protein | | |
| PA4183 | 9950392 | hypothetical protein | | |
| PA4190 | 9950400 | probable FAD-dependent monooxygenase | | |

TABLE 1-continued

| | | | | |
|---|---|---|---|---|
| PA4209 | 9950421 | probable O-methyltransferase | | |
| PA4210 | 9950423 | probable phenazine biosynthesis protein | | phzA1 |
| PA4211 | 9950424 | probable phenazine biosynthesis protein | | phzB1 |
| PA4212 | 9950425 | phenazine biosynthesis protein PhzC | | phzC1 |
| PA4215 | 9950428 | probable phenazine biosynthesis protein | | phzF1 |
| PA4216 | 9950430 | probable pyridoxamine 5'-phosphate oxidase | | phzG1 |
| PA4219 | 9950433 | hypothetical protein | | yfpB |
| PA4230 | 9950446 | salicylate biosynthesis protein PchB | pchB | |
| PA4232 | 9950448 | single-stranded DNA-binding protein | ssb | |
| PA4237 | 9950454 | 50S ribosomal protein L17 | rplQ | |
| PA4238 | 9950455 | DNA-directed RNA polymerase alpha chain | rpoA | |
| PA4239 | 9950456 | 30S ribosomal protein S4 | rpsD | |
| PA4240 | 9950457 | 30S ribosomal protein S11 | rpsK | |
| PA4241 | 9950458 | 30S ribosomal protein S13 | rpsM | |
| PA4242 | 9950459 | 50S ribosomal protein L36 | rpmJ | |
| PA4243 | 9950460 | secretion protein SecY | secY | prlA |
| PA4244 | 9950461 | 50S ribosomal protein L15 | rplO | |
| PA4245 | 9950462 | 50S ribosomal protein L30 | rpmD | |
| PA4246 | 9950463 | 30S ribosomal protein S5 | rpsE | |
| PA4247 | 9950454 | 50S ribosomal protein L18 | rplR | |
| PA4248 | 9950465 | 50S ribosomal protein L6 | rplF | |
| PA4249 | 9950466 | 30S ribosomal protein S8 | rpsH | |
| PA4250 | 9950467 | 30S ribosomal protein S14 | rpsN | |
| PA4251 | 9950468 | 50S ribosomal protein L5 | rplE | |
| PA4252 | 9950469 | 50S ribosomal protein L24 | rplX | |
| PA4253 | 9950470 | 50S ribosomal protein L14 | rplN | |
| PA4254 | 9950471 | 30S ribosomal protein S17 | rpsQ | |
| PA4255 | 9950472 | 50S ribosomal protein L29 | rpmC | |
| PA4256 | 9950473 | 50S ribosomal protein L16 | rplP | |
| PA4257 | 9950474 | 30S ribosomal protein S3 | rpsC | |
| PA4258 | 9950475 | 50S ribosomal protein L22 | rplV | |
| PA4259 | 9950476 | 30S ribosomal protein S19 | rpsS | |
| PA4260 | 9950477 | 50S ribosomal protein L2 | rplB | |
| PA4261 | 9950478 | 50S ribosomal protein L23 | rplW | |
| PA4262 | 9950479 | 50S ribosomal protein L4 | rplD | |
| PA4263 | 9950480 | 50S ribosomal protein L3 | rplC | |
| PA4264 | 9950482 | 30S ribosomal protein S10 | rpsJ | |
| PA4267 | 9950485 | 30S ribosomal protein S7 | rpsG | |
| PA4268 | 9950486 | 30S ribosomal protein S12 | rpsL | str |
| PA4269 | 9950487 | DNA-directed RNA polymerase beta* chain | rpoC | |
| PA4270 | 9950488 | DNA-directed RNA polymerase beta chain | rpoB | |
| PA4271 | 9950490 | 50S ribosomal protein L7 / L12 | rplL | |
| PA4272 | 9950491 | 50S ribosomal protein L10 | rplJ | |
| PA4273 | 9950492 | 50S ribosomal protein L1 | rplA | |
| PA4274 | 9950493 | 50S ribosomal protein L11 | rplK | |
| PA4275 | 9950494 | transcription antitermination protein NusG | nusG | |
| PA4276 | 9950495 | secretion protein SecE | secE | prlG |
| PA4279 | 9950498 | hypothetical protein | | |
| PA4295 | 9950516 | hypothetical protein | | |
| PA4296 | 9950518 | probable two-component response regulator | | |
| PA4298 | 9950520 | hypothetical protein | | |
| PA4299 | 9950521 | hypothetical protein | | |
| PA4305 | 9950527 | hypothetical protein | | |
| PA4306 | 9950529 | hypothetical protein | | |
| PA4314 | 9950538 | formyltetrahydrofolate deformylase | purU1 | |
| PA4322 | 9950546 | conserved hypothetical protein | | |
| PA4324 | 9950548 | hypothetical protein | | |
| PA4329 | 9950554 | pyruvate kinase II | pykA | pyk-II |
| PA4330 | 9950555 | probable enoyl-CoA hydratase/isomerase | | |
| PA4341 | 9950567 | probable transcriptional regulator | | |
| PA4345 | 9950572 | hypothetical protein | | |
| PA4348 | 9950575 | conserved hypothetical protein | | |
| PA4349 | 9950576 | hypothetical protein | | |
| PA4350 | 9950577 | conserved hypothetical protein | | |
| PA4354 | 9950581 | conserved hypothetical protein | | |
| PA4357 | 9950584 | conserved hypothetical protein | | yhgG |
| PA4359 | 9950585 | conserved hypothetical protein | | feoA |
| PA4366 | 9950594 | superoxide dismutase | sodB | |
| PA4373 | 9960602 | hypothetical protein | | |
| PA4377 | 9960607 | hypothetical protein | | |
| PA4383 | 9950613 | conserved hypothetical protein | | crcB |
| PA4385 | 9950615 | GroEL protein | groEL | mopA |
| PA4386 | 9950616 | GroES protein | groES | mopB |
| PA4388 | 9950618 | hypothetical protein | | |
| PA4389 | 9950619 | probable short-chain dehydrogenase | | |
| PA4392 | 9950623 | conserved hypothetical protein | | ybaZ |
| PA4395 | 9950626 | conserved hypothetical protein | | yajQ |
| PA4403 | 9950635 | secretion protein SecA | secA | |
| PA4405 | 9950637 | hypothetical protein | | |

TABLE 1-continued

| | | | | |
|---|---|---|---|---|
| PA4406 | 9950638 | UDP-3-O-acyl-N-acetylglucosamine deacetyla | lpxC | envA asmB |
| PA4407 | 9950639 | cell division protein FtsZ | ftsZ | |
| PA4408 | 9950640 | cell division protein FtsA | ftsA | |
| PA4409 | 9950641 | cell division protein FtsQ | ftsQ | |
| PA4411 | 9950643 | UDP-N-acetylmuramate--alanine ligase | murC | |
| PA4412 | 9950644 | UDP N acetylglucosarnine--N-acetylmuramyl | murG | |
| PA4413 | 9950645 | cell division protein FtsW | ftsW | |
| PA4414 | 9950646 | UDP-N-acetylnluramoylalanine--D-glutamate | murD | |
| PA4415 | 9950647 | phospho-N-acetylmuramoyl-pentapeptide-tran | mraY | ORF Y |
| PA4416 | 9950648 | UDP-N-acetylmuramoylalanyl-D-glutamyl-2, 6- | murF | |
| PA4417 | 9950649 | UDP-N-acetylmuramoylalanyl-D-glutamate-2, 6 | murE | |
| PA4418 | 9950650 | penicillin-binding protein 3 | ftsI | pbpB |
| PA4419 | 9950651 | cell division protein FtsL | ftsL | |
| PA4420 | 9950652 | conserved hypothetical protein | | mraW yabC ylxA |
| PA4421 | 9950653 | conserved hypothetical protein | | yabB |
| PA4424 | 9950657 | conserved hypothetical protein | | yraN |
| PA4425 | 9950658 | probable phosphoheptose isomerase | | yraO |
| PA4427 | 9950660 | stringent starvation protein B | sspB | |
| PA4428 | 9950661 | stringent starvation protein A | sspA | ssp pog |
| PA4430 | 9950663 | probable cytochrome b | | |
| PA4432 | 9950665 | 30S ribosomal protein S9 | rpsI | |
| PA4433 | 9950666 | 50S ribosomal protein L13 | rplM | |
| PA4436 | 9950670 | probable transcriptional regulator | | |
| PA4438 | 9950672 | conserved hypothetical protein | | yhcM |
| PA4439 | 9950673 | tryptophanyl-tRNA synthetase | trpS | |
| PA4440 | 9950674 | hypothetical protein | | |
| PA4450 | 9950685 | UDP-N-acetylglucosamine 1-carboxyvinyltrans | murA | |
| PA4452 | 9950687 | conserved hypothetical protein | | |
| PA4453 | 9950688 | conserved hypothetical protein | | |
| PA4454 | 9950689 | conserved hypothetical protein | | yrbD |
| PA4455 | 9950690 | probable permease of ABC transporter | | yrbE |
| PA4457 | 9950693 | conserved hypothetical protein | | yrbH kpsF |
| PA4459 | 9950695 | conserved hypothetical protein | | yrbK |
| PA4460 | 9950696 | conserved hypothetical protein | | yhbN |
| PA4461 | 9950697 | probable ATP-binding component of ABC trans | | yhbG |
| PA4462 | 9950698 | RNA polymerase sigrna-54 factor | rpoN | ntrA |
| PA4463 | 9950699 | conserved hypothetical protein | | yhbH |
| PA4464 | 9950700 | nitrogen regulatory IIA protein | ptsN | |
| PA4466 | 9950702 | probable phosphoryl carrier protein | | |
| PA4471 | 9950707 | hypothetical protein | | fagA |
| PA4480 | 9950718 | rod shape-determining protein MreC | mreC | |
| PA4481 | 9950719 | rod shape-determining protein MreB | mreB | envB rodY |
| PA4482 | 9950720 | Glu-tRNA(Gln) amidotransferase subunit C | gatC | |
| PA4483 | 9950721 | Glu-tRNA(Gln) amidotransferase subunit A | gatA | |
| PA4484 | 9950722 | Glu-tRNA(Gln) amidotransferase subunit B | gatB | |
| PA4485 | 9950723 | conserved hypothetical protein | | |
| PA4492 | 9950730 | conserved hypothetical protein | | |
| PA4499 | 9950738 | probable transcriptional regulator | | |
| PA4507 | 9950747 | hypothetical protein | | |
| PA4524 | 9950766 | nicotinate-nucleotide pyrophosphorylase | nadC | |
| PA4525 | 9950767 | type 4 fimbrial precursor PilA | pilA | |
| PA4526 | 9950768 | type 4 fimbrial biogenesis protein PilB | pilB | |
| PA4527 | 9950770 | still frameshift type 4 fimbrial biogenesis prote | pilC | |
| PA4529 | 9950772 | conserved hypothetical protein | | |
| PA4530 | 9950773 | conserved hypothetical protein | | |
| PA4537 | 9950780 | hypothetical protein | | |
| PA4544 | 9950788 | pseudouridine synthase | rluD | yfiI |
| PA4547 | 9950791 | two-component response regulator PilR | pilR | |
| PA4552 | 9950797 | type 4 fimbrial biogenesis protein PilW | pilW | |
| PA4553 | 9950798 | type 4 fimbrial biogenesis protein PilX | pilX | |
| PA4557 | 9950802 | LytB protein | lytB | |
| PA4559 | 9950804 | prolipoprotein signal peptidase | lspA | |
| PA4560 | 9950805 | isoleucyl-tRNA synthetase | ileS | |
| PA4561 | 9950806 | riboflavin kinase/FAD synthase | ribF | |
| PA4563 | 9950809 | 30S ribosomal protein S20 | rpsT | |
| PA4564 | 9950810 | conserved hypothetical protein | | creA |
| PA4565 | 9950811 | glutamate 5-kinase | proB | |
| PA4566 | 9950812 | GTP-binding protein Obg | obg | |
| PA4567 | 9950813 | 50S ribosomal protein L27 | rpmA | |
| PA4558 | 9950814 | 50S ribosomal protein L21 | rplU | |
| PA4569 | 9950815 | octaprenyl-diphosphate synthase | ispB | cel |
| PA4674 | 9950821 | conserved hypothetical protein | | yqhA |
| PA4575 | 9950822 | hypothetical protein | | |
| PA4577 | 9950824 | hypothetical protein | | |
| PA4586 | 9950834 | hypothetical protein | | |
| PA4600 | 9950850 | transcriptional regulator NfxB | nfxB | |
| PA4603 | 9950853 | hypothetical protein | | |
| PA4610 | 9950861 | hypothetical protein | | |
| PA4611 | 9950862 | hypothetical protein | | |

TABLE 1-continued

| | | | | |
|---|---|---|---|---|
| PA4617 | 9950868 | conserved hypothetical protein | | yqjO |
| PA4630 | 9950883 | hypothetical protein | | |
| PA4636 | 9950890 | hypothetical protein | | |
| PA4637 | 9950891 | hypothetical protein | | |
| PA4638 | 9950892 | hypothetical protein | | |
| PA4642 | 9950895 | hypothetical protein | | |
| PA4644 | 9950897 | hypothetical protein | | |
| PA4646 | 9950899 | uracil phosphoribosyltransferase | upp | |
| PA4649 | 9950903 | hypothetical protein | | |
| PA4651 | 9950905 | probable pili assembly chaperone | | |
| PA4655 | 9950909 | ferrochelatase | hemH | visA |
| PA4662 | 9950917 | glutamate racemase | murI | |
| PA4663 | 9950918 | molybdopterin biosynthesis MoeB protein | moeB | chlN |
| PA4665 | 9950920 | peptide chain release factor 1 | prfA | rf1 |
| PA4666 | 9950921 | glutamyl-tRNA reductase | hemA | hem1; glutR |
| PA4668 | 9950923 | probable lipoprotein localization protein LolB | | lolB |
| PA4669 | 9950924 | isopentenyl monophosphate kinase | ipk | ychB |
| PA4670 | 9950925 | ribose-phosphate pyrophosphokinase | prs | prsA |
| PA4671 | 9950927 | probable ribosomal protein L25 | | rplY |
| PA4672 | 9950928 | peptidyl-tRNA hydrolase | | pth |
| PA4674 | 9950930 | conserved hypothetical protein | | vapl |
| PA4676 | 9950932 | probable carbonic anhydrase | | yadF |
| PA4679 | 9950935 | hypothetical protein | | |
| PA4681 | 9950937 | hypothetical protein | | |
| PA4693 | 9950950 | phosphatidylserine synthase | pssA | |
| PA4696 | 9950953 | acetolactate synthase large subunit | ilvI | |
| PA4697 | 9950955 | hypothetical protein | | |
| PA4698 | 9950956 | hypothetical protein | | yqcC |
| PA4699 | 9950957 | hypothetical protein | | |
| PA4702 | 9950960 | hypothetical protein | | |
| PA4706 | 9950964 | probable ATP-binding component of ABC trans | | phuV |
| PA4711 | 9950970 | hypothetical protein | | |
| PA4718 | 9950977 | hypothetical protein | | |
| PA4728 | 9950988 | 2-amino-4-hydroxy-6-hydroxymethyldihydropte | folK | |
| PA4729 | 9950989 | 3-methyl-2-oxobutanoate hydroxymethyltransfe | panB | |
| PA4731 | 9950992 | aspartate 1-decarboxylase precursor | panD | |
| PA4732 | 9950993 | glucose-6-phosphate isomerase | pgi | |
| PA4737 | 9950998 | hypothetical protein | | |
| PA4738 | 9950999 | conserved hypothetical protein | | yjbJ |
| PA4739 | 9951000 | conserved hypothetical protein | | |
| PA4740 | 9951002 | polyribonucleotide nucleotidyltransferase | pnp | |
| PA4741 | 9951003 | 30S ribosomal protein S15 | rpsO | |
| PA4744 | 9951006 | translation initiation factor IF-2 | infB | |
| PA4745 | 9951007 | N utilization substance protein A | nusA | |
| PA4746 | 9951008 | conserved hypothetical protein | | yhbC |
| PA4747 | 9951009 | secretion protein SecG | secG | |
| PA4748 | 9951010 | triosephosphate isomerase | tpiA | tpi |
| PA4749 | 9951011 | phosphoglucosaminemutase | glmM | yhbF, mrsA |
| PA4750 | 9951012 | dihydropteroate synthase | folP | dhpS |
| PA4752 | 9951015 | cell division protein FtsJ | ftsJ | |
| PA4753 | 9951016 | conserved hypothetical protein | | yhbY |
| PA4757 | 9951020 | conserved hypothetical protein | | yeaS |
| PA4759 | 9951022 | dihydrodipicolinate reductase | dapB | |
| PA4762 | 9951028 | heat shock protein GrpE | gpE | |
| PA4764 | 9951028 | ferric uptake regulation protein | fur | |
| PA4765 | 9951029 | outer membrane lipoprotein OmlA | omlA | oprX |
| PA4767 | 9951031 | conserved hypothetical protein | | yfjG |
| PA4773 | 9951038 | hypothetical protein | | |
| PA4776 | 9951041 | probable two-component response regulator | | |
| PA4778 | 9951043 | probable transcriptional regulator | | ybbl |
| PA4782 | 9951047 | hypothetical protein | | |
| PA4788 | 9951054 | hypothetical protein | | |
| PA4789 | 9951055 | conserved hypothetical protein | | |
| PA4790 | 9951056 | conserved hypothetical protein | | smtA |
| PA4792 | 9951058 | conserved hypothetical protein | | |
| PA4797 | 9951064 | probable transposase | | |
| PA4802 | 9951069 | hypothetical protein | | |
| PA4809 | 9951077 | FdhE protein | fdhE | |
| PA4813 | 9951080 | lipase LipC | lipC | |
| PA4823 | 9951091 | hypothetical protein | | |
| PA4826 | 9951095 | hypothetical protein | | |
| PA4828 | 9951097 | conserved hypothtial protein | | |
| PA4831 | 9951100 | probable transcriptional regulator | | |
| PA4841 | 9951111 | conserved hypothetical protein | | |
| PA4484 | 9951118 | biotin carboxyl carrier protein (BCCP) | accB | fabE |
| PA4848 | 9951119 | biotin carboxylase | accC | |
| PA4850 | 9951121 | ribosomal protein L11 methyltransferase | prmA | |
| PA4853 | 9951124 | DNA-binding protein Fis | fis | |
| PA4861 | 9951133 | probable ATP-binding component of ABC trans | | |

TABLE 1-continued

| | | | | | |
|---|---|---|---|---|---|
| PA4864 | 9951137 | urease accessory protein | ureD | | |
| PA4866 | 9951139 | conserved hypothetical protein | | | |
| PA4868 | 9951141 | urease alpha subunit | ureC | | |
| PA4870 | 9951143 | conserved hypothetical protein | | ybil | |
| PA4871 | 9951144 | hypothetical protein | | | |
| PA4874 | 9951148 | conserved hypothetical protein | | psiF | |
| PA4875 | 9951149 | hypothetical protein | | | |
| PA4878 | 9951152 | probable transcriptional regulator | | | |
| PA4885 | 9951159 | two-component response regulator | irlR | | |
| PA4887 | 9951161 | probable MFS transporter | | | |
| PA4890 | 9951165 | conserved hypothetical protein | | yijC | |
| PA4892 | 9951167 | urease accessory protein UreF | ureF | | |
| PA4894 | 9951169 | hypothetical protein | | | |
| PA4895 | 9951170 | probable transmembrane sensor | | | |
| PA4906 | 9951182 | probable transcriptional regulator | | | |
| PA4908 | 9951185 | hypothetical protein | | | |
| PA4916 | 9951193 | hypothetical protein | | | |
| PA4920 | 9951198 | NH3-dependent NAD synthetase | nadE | | |
| PA4923 | 9951201 | conserved hypothetical protein | | | |
| PA4925 | 9951203 | conserved hypothetical protein | | | |
| PA4926 | 9951204 | conserved hypothetical protein | | | |
| PA4931 | 9951210 | replicative DNA helicase | dnaB | | |
| PA4934 | 9951213 | 30S ribosomal protein S18 | rpsR | | |
| PA4935 | 9951214 | 30S ribosomal protein S6 | rpsF | | |
| PA4938 | 9951218 | adenylosuccinate synthetase | purA | | |
| PA4940 | 9951220 | conserved hypothetical protein | | yjeT | |
| PA4944 | 9951224 | conserved hypothetical protein | | hfq | |
| PA4945 | 9951225 | delta 2-isopentenylpyrophosphate transferase | miaA | | |
| PA4948 | 9951228 | conserved hypothetical protein | | yjeE | |
| PA4952 | 9951233 | conserved hypothetical protein | | yjeQ | |
| PA4956 | 9951237 | thiosulfate sulfurtransferase | rhdA | | |
| PA4951 | 9951243 | hypothetical protein | | | |
| PA4962 | 9951244 | conserved hypothetical protein | | ybcl | |
| PA4964 | 9951246 | topoisomerase IV subunit A | parC | | |
| PA4965 | 9951247 | hypothetical protein | | | |
| PA4966 | 9951248 | hypothetical protein | | | |
| PA4967 | 9951249 | topoisomerase IV subunit B | parE | | |
| PA4969 | 9951252 | conserved hypothetical protein | | icc | |
| PA4972 | 9951255 | hypothetical protein | | | |
| PA4980 | 9951263 | probable enoyl-CoA hydratase/isomerase | | | |
| PA4988 | 9951272 | 3-deoxy-D-manno-octulosonic-acid (KDO) tran | waaA | kdtA | |
| PA4990 | 9951275 | SMR multidrug efflux transporter | | | |
| PA4991 | 9951276 | hypothetical protein | | | |
| PA4992 | 9951277 | hypothetical protein | | | |
| PA4997 | 9951282 | transport protein MsbA | msbA | | |
| PA4998 | 9951283 | conserved hypothetical protein | | | |
| PA5006 | 9951292 | hypothetical protein | | | |
| PA5007 | 9951293 | hypothetical protein | | wapQ inaA | |
| PA5008 | 9951294 | hypothetical protein | | wapP waaX | |
| PA5009 | 9951295 | lipopolysaccharide core biosynthesis protein W | waaP | rfaP | |
| PA5010 | 9951296 | UDP-glucose:(heptosyl) LPS alpha 1,3-glucosy | waaG | rfaG | |
| PA5011 | 9951297 | heptosyltransferase I | waaC | rfaC | |
| PA5012 | 9951298 | heptosyltransferase II | waaF | rfaF | |
| PA5028 | 9951317 | conserved hypothetical protein | | | |
| PA5032 | 9951321 | probable transcriptional regulator | | | |
| PA5033 | 9951322 | hypothetical protein | | | |
| PA5034 | 9951323 | uroporphyrinogen decarboxylase | hemE | | |
| PA5039 | 9951329 | shikimate kinase | aroK | | |
| PA5044 | 9951334 | type 4 fimbrial biogenesis protein PilM | pilM | | |
| PA5050 | 9951341 | primosomal protein N' | priA | | |
| PA5051 | 9951342 | arginyl-tRNA synthetase | argS | | |
| PA5052 | 9951343 | hypothetical protein | | | |
| PA5061 | 9951353 | conserved hypothetical protein | | phal | |
| PA5063 | 9951355 | ubiquinone biosynthesis methyltransferase Ub | ubiE | | |
| PA5064 | 9951356 | hypothetical protein | | | |
| PA5065 | 9951357 | conserved hypothetical protein | | aarF yigR | |
| PA5067 | 9951360 | phosphoribosyl-ATP pyrophosphohydrolase | hisE | | |
| PA5068 | 9951361 | translocation protein TatA | tatA | mttA yigT | |
| PA5071 | 9951364 | conserved hypothetical protein | | | |
| PA5072 | 9951365 | probable chemotaxis transducer | | | |
| PA5081 | 9951375 | hypothetical protein | | | |
| PA5085 | 9951379 | probable transcriptional regulator | | | |
| PA5110 | 9951406 | fructose-1,6-bisphosphatase | fbp | cbbF, cfxF | |
| PA5111 | 9951408 | lactoylglutathione lyase | gloA3 | glo1 | |
| PA5116 | 9951413 | probable transcriptional regulator | | | |
| PA5119 | 9951417 | glutamine synthetase | glnA | | |
| PA5128 | 9951427 | secretion protein SecB | secB | | |
| PA5129 | 9951428 | glutaredoxin | grx | | |
| PA5130 | 9951429 | conserved hypothetical protein | | yibN | |

TABLE 1-continued

| | | | | |
|---|---|---|---|---|
| PA5131 | 9951430 | phosphoglycerate mutase | pgm | yibO |
| PA5132 | 9951431 | hypothetical protein | | |
| PA5142 | 9951442 | glutamine amidotransferase | hisH1 | |
| PA5144 | 9951444 | hypothetical protein | | |
| PA5148 | 9951448 | conserved hypothetical protein | | yggX |
| PA5154 | 9951455 | probable permease of ABC transporter | | |
| PA5161 | 9951463 | dTDP-D-glucose 4,6-dehydratase | rmlB | rfbB |
| PA5162 | 9951464 | dTDP-4-dehydrorhamnose reductase | rmlD | rfbD |
| PA5163 | 9951465 | glucose-1-phosphate thymidylyltransferase | rmlA | rfbA |
| PA5164 | 9951466 | dTDP-4-dehydrorhamnose 3,5-epimerase | rmlC | rfbC |
| PA5173 | 9951476 | carbamate kinase | arcC | |
| PA5176 | 9951479 | conserved hypothetical protein | | yrfE |
| PA5178 | 9951481 | conserved hypothetical protein | | |
| PA5182 | 9951486 | hypothetical protein | | |
| PA5187 | 9951491 | probable acyl-CoA dehydrogenase | | |
| PA5190 | 9951495 | probable nitroreductase | | |
| PA5195 | 9951500 | probable heat shock protein | | yrfH |
| PA5221 | 9951529 | probable FAD-dependent monooxygenase | | visC |
| PA5222 | 9951530 | hypothetical protein | | |
| PA5224 | 9951532 | aminopeptidase P | pepP | |
| PA5225 | 9951533 | hypothetical protein | | |
| PA5227 | 9951535 | conserved hypothetical protein | | ygfE |
| PA5229 | 9951537 | conserved hypothetical protein | | |
| PA5237 | 9951546 | conserved hypothetical protein | | yigC |
| PA5239 | 9951548 | transcription termination factor Rho | rho | |
| PA5240 | 9951549 | thioredoxin | trxA | |
| PA5246 | 9951556 | conserved hypothetical protein | | yigI |
| PA5247 | 9951557 | conserved hypothetical protein | | yaiI |
| PA5259 | 9951570 | uroporphyrinogen-III synthetase | hemD | |
| PA5260 | 9951571 | porphobilinogen deaminase | hemC | popE |
| PA5275 | 9951588 | conserved hypothetical protein | | cyaY |
| PA5276 | 9951589 | lipopeptide LppL precursor | lppL | |
| PA5278 | 9951591 | diaminopimelate epimerase | dapF | |
| PA5281 | 9951594 | probable hydrolase | | yigB |
| PA5288 | 9951602 | nitrogen regulatory protein P-II 2 | glnK | |
| PA5296 | 9951611 | ATP-dependent DNA helicase Rep | rep | |
| PA5300 | 9951616 | cytochrome c5 | cycB | |
| PA5303 | 9951619 | conserved hypothetical protein | | |
| PA5316 | 9951633 | 50S ribosomal protein L28 | rpmB | |
| PA5319 | 9951636 | DNA repair protein RadC | radC | |
| PA5320 | 9951637 | DNA/pantothenate metabolism flavoprotein | dfp | |
| PA5321 | 9951638 | deoxyuridine 5'-triphosphate nucleotidohydrola | dut | |
| PA5325 | 9951643 | hypothetical protein | | |
| PA5327 | 9951646 | probable cytochrome c(mono-heme type) | | |
| PA5330 | 9951648 | hypothetical protein | | |
| PA5331 | 9961649 | orotate phosphoribosyltransferase | pyrE | |
| PA5333 | 9951652 | conserved hypothetical protein | | |
| PA5334 | 9951653 | ribonuclease PH | rph | |
| PA5335 | 9951654 | conserveci hypothetical protein | | yicC |
| PA5336 | 9951655 | guanylate kinase | gmk | |
| PA5339 | 9951658 | conserved hypothetical protein | | |
| PA5347 | 9951667 | hypothetical protein | | |
| PA5350 | 9951670 | rubredoxin | | |
| PA5351 | 9951671 | rubredoxin | | |
| PA5358 | 9951678 | 4-hydroxybenzoate-octaprenyl transferase | ubiA | |
| PA5364 | 9951685 | probable two-component response regulator | | |
| PA5381 | 9951704 | hypothetical protein | | |
| PA5385 | 9951709 | hypothetical protein | | |
| PA5390 | 9951714 | probable peptidic bond hydrolase | | |
| PA5396 | 9951721 | hypothetical protein | | |
| PA5403 | 9951729 | probable transcriptional regulator | | |
| PA5404 | 9951730 | hypothetical protein | | |
| PA5406 | 9951732 | hypothetical protein | | |
| PA5408 | 9951734 | hypothetical protein | | |
| PA5417 | 9951744 | sarcosine oxidase delta subunit | soxD | |
| PA5457 | 9951788 | hypothetical protein | | |
| PA5460 | 9951792 | hypothetical protein | | |
| PA5465 | 9951797 | hypothetical protein | | |
| PA5469 | 9951801 | conserved hypothetical protein | | |
| PA5470 | 9951802 | probable peptide chain release factor | | prfH |
| PA5480 | 9951813 | hypothetical protein | | |
| PA5482 | 9951816 | hypothetical protein | | |
| PA5496 | 9951831 | hypothetical protein | | |
| PA5503 | 9951839 | probable ATP-binding component of ABC trans | | |
| PA5526 | 9951864 | hypothetical protein | | |
| PA5529 | 9951867 | probable sodium/proton antiporter | | |
| PA5531 | 9951869 | TonB protein | tonB | |
| PA5533 | 9951871 | hypothetical protein | | |
| PA5534 | 9951873 | hypothetical protein | | |

TABLE 1-continued

| | | | | | |
|---|---|---|---|---|---|
| PA5543 | 9951882 | hypothetical protein | | | |
| PA5549 | 9951889 | glucosamine--fructose-6-phosphate aminotran | glmS | | |
| PA5552 | 9951692 | glucosamine-1-phosphate acetyltransferase/N | glmU | gcaD | |
| PA5553 | 9951893 | ATP synthase epsilon chain | atpC | uncC papG | |
| PA5554 | 9951894 | ATP synthase beta chain | atpD | uncD papB | |
| PA5555 | 9951895 | ATP synthase gamma chain | atpG | uncG papC | |
| PA5556 | 9951896 | ATP synthase alpha chain | atpA | uncA papA | |
| PA5557 | 9951897 | ATP synthase delta chain | atpH | uncH papE | |
| PA5558 | 9951898 | ATP synthase B chain | atpF | uncF papF | |
| PA5559 | 9951899 | atp synthase C chain | atpE | uncE papH | |
| PA5560 | 9951900 | ATP synthase A chain | atpB | unoB papD | |
| PA5561 | 9951901 | ATP synthase protein I | atpI | uncI | |
| PA5562 | 9951903 | chromosome partitioning protein SpoOJ | spoOJ | | |
| PA5566 | 9951907 | hypothetical protein | | | |
| PA5568 | 9951909 | conserved hypothetical protein | | yidC | |
| PA5569 | 9951910 | ribonuclease P protein component | rnpA | | |
| PA5570 | 9951911 | 50S ribosomal protein L34 | rpmH | | |

| Primary Function | Range From | Range To |
|---|---|---|
| DNA replication, recombination, modification | 483 | 2027 |
| DNA replication, recombination, modification | 4275 | 6695 |
| Hypothetical, unclassified, unknown | 8339 | 7803 |
| Translation, post-translational modification | 12488 | 10434 |
| Translation, post-translational modification | 13435 | 12488 |
| Cell wall / LPS / capsule | 14235 | 15122 |
| Hypothetical, unclassified, unknown | 17217 | 16900 |
| Hypothetical, unclassified, unknown | 24001 | 24558 |
| Hypothetical, unclassified, unknown | 27646 | 28632 |
| Hypothetical, unclassified, unknown | 36270 | 35905 |
| Amino acid biosynthesis and metabolism | 37893 | 37087 |
| Hypothetical, unclassified, unknown | 40190 | 40405 |
| Hypothetical, unclassified, unknown | 40589 | 40816 |
| Hypothetical, unclassified, unknown | 56546 | 56941 |
| Hypothetical, unclassified, unknown | 61879 | 62388 |
| Hypothetical, unclassified, unknown | 68618 | 68188 |
| Hypothetical, unclassified, unknown | 69272 | 69526 |
| Hypothetical, unclassified, unknown | 70091 | 69543 |
| Hypothetical, unclassified, unknown | 70636 | 70130 |
| Hypothetical, unclassified, unknown | 72680 | 73384 |
| Adaptation, protection | 73468 | 73923 |
| Hypothetical, unclassified, unknown | 74034 | 74267 |
| Hypothetical, unclassified, unknown | 74716 | 74279 |
| Hypothetical, unclassified, unknown | 78097 | 77432 |
| Hypothetical, unclassified, unknown | 80752 | 81027 |
| Hypothetical, unclassified, unknown | 81116 | 82174 |
| Hypothetical, unclassified, unknown | 83318 | 82404 |
| Hypothetical, unclassified, unknown | 98218 | 97754 |
| Hypothetical, unclassified, unknown | 100124 | 101158 |
| Hypothetical, unclassified, unknown | 115045 | 114611 |
| Hypothetical, unclassified, unknown | 119127 | 120164 |
| Hypothetical, unclassified, unknown | 121346 | 122266 |
| Energy metabolism | 127378 | 128502 |
| Hypothetical, unclassified, unknown | 131792 | 131583 |
| Hypothetical, unclassified, unknown | 132577 | 133155 |
| Energy metabolism | 134319 | 135233 |
| Hypothetical, unclassified, unknown | 135259 | 135894 |
| Hypothetical, unclassified, unknown | 136386 | 135934 |
| Hypothetical, unclassified, unknown | 136518 | 136991 |
| Transport of small molecules | 138818 | 140167 |
| Transcriptional regulators | 140216 | 140902 |
| Hypothetical, unclassified, unknown | 143848 | 143567 |
| Hypothetical, unclassified, unknown | 144072 | 143845 |
| Hypothetical, unclassified, unknown | 145542 | 145883 |
| Hypothetical, unclassified, unknown | 149425 | 149138 |
| Transcriptional regulators | 150906 | 151823 |
| Hypothetical, unclassified, unknown | 153696 | 153836 |
| Adaptation, protection | 158199 | 158762 |
| Nucleotide biosynthesis and metabolism | 163426 | 184415 |
| Hypothetical, unclassified, unknown | 165737 | 165219 |
| Transcriptional regulators | 169361 | 169906 |
| Carbon compound catabolism | 175503 | 176108 |
| Transcriptional regulators | 182768 | 183706 |
| Hypothetical, unclassified, unknown | 184287 | 184439 |
| Transcriptional regulators | 191697 | 192362 |
| Hypothetical, unclassified, unknown | 194179 | 193799 |
| Hypothetical, unclassified, unknown | 194748 | 194206 |
| Putative enzymes | 207071 | 207823 |
| Carbon compound catabolism | 209533 | 207923 |

TABLE 1-continued

| | | |
|---|---|---|
| Transport of small molecules | 210460 | 209621 |
| Hypothetical, unclassified, unknown | 213819 | 214634 |
| Hypothetical, unclassified, unknown | 214631 | 215512 |
| Hypothetical, unclassified, unknown | 229738 | 229526 |
| Putative enzymes | 232000 | 230543 |
| Transport of small molecules | 233100 | 232066 |
| Transport of small molecules | 233932 | 233123 |
| Transport of small molecules | 234849 | 233929 |
| Transcriptional regulators | 236218 | 237111 |
| Hypothetical, unclassified, unknown | 238896 | 239777 |
| Carbon compound catabolism | 240071 | 240934 |
| Hypothetical, unclassified, unknown | 241753 | 242445 |
| Transport of small molecules | 243841 | 244605 |
| Transcriptional regulators | 262557 | 263498 |
| Transcriptional regulators | 266616 | 267395 |
| Hypothetical, unclassified, unknown | 268704 | 269519 |
| Transcriptional regulators | 275772 | 276440 |
| Hypothetical, unclassified, unknown | 277334 | 276480 |
| Amino acid biosynthesis and metabolism | 277777 | 277331 |
| Hypothetical, unclassified, unknown | 282767 | 282323 |
| Hypothetical, unclassified, unknown | 283553 | 282912 |
| Hypothetical, unclassified, unknown | 289390 | 289205 |
| Hypothetical, unclassified, unknown | 293304 | 291154 |
| Hypothetical, unclassified, unknown | 293798 | 293301 |
| Hypothetical, unclassified, unknown | 299497 | 299081 |
| Transport of small molecules | 309092 | 307878 |
| Transcriptional regulators | 313227 | 313925 |
| Transport of small molecules | 314927 | 313938 |
| Hypothetical, unclassified, unknown | 318148 | 317966 |
| Hypothetical, unclassified, unknown | 350841 | 350089 |
| Hypothetical, unclassified, unknown | 352164 | 351610 |
| Hypothetical, unclassified, unknown | 359982 | 360332 |
| Energy metabolism | 371833 | 371162 |
| Hypothetical, unclassified, unknown | 373725 | 374192 |
| Hypothetical, unclassified, unknown | 378096 | 378575 |
| Hypothetical, unclassified, unknown | 382792 | 382037 |
| Fatty acid and phospholipid metabolism | 383727 | 384527 |
| Nucleotide biosynthesis and metabolism | 384733 | 385527 |
| Biosynthesis of cofactors, prosthetic group | 393308 | 393814 |
| Hypothetical, unclassified, unknown | 402020 | 402598 |
| Energy metabolism | 406498 | 406247 |
| Central intermediary metabolism | 407098 | 406619 |
| Hypothetical, unclassified, unknown | 413654 | 413364 |
| Hypothetical, unclassified, unknown | 414529 | 413933 |
| Protein secretion/export apparatus | 417527 | 418894 |
| Transcriptional regulators | 420683 | 421537 |
| Hypothetical, unclassified, unknown | 421602 | 422207 |
| Hypothetical, unclassified, unknown | 423460 | 423660 |
| Hypothetical, unclassified, unknown | 427120 | 426863 |
| Hypothetical, unclassified, unknown | 439991 | 440395 |
| Nucleotide biosynthesis and metabolism | 445691 | 444687 |
| Transcriptional regulators | 446227 | 445715 |
| Hypothetical, unclassified, unknown | 446773 | 446339 |
| Hypothetical, unclassified, unknown | 447342 | 446773 |
| Biosynthesis of cofactors, prosthetic group | 449384 | 448431 |
| Motility & Attachment | 453239 | 454114 |
| Transcriptional regulators | 463079 | 463873 |
| Hypothetical, unclassified, unknown | 470081 | 470650 |
| Transport of small molecules | 476333 | 477790 |
| Hypothetical, unclassified, unknown | 484404 | 484838 |
| Hypothetical, unclassified, unknown | 496478 | 496362 |
| Transport of small molecules | 496871 | 498361 |
| Related to phage, transposon, or plasmid | 501120 | 500104 |
| Hypothetical, unclassified, unknown | 502599 | 501376 |
| Transcriptional regulators | 504121 | 505029 |
| Hypothetical, unclassified, unknown | 510499 | 509825 |
| Adaptation, protection | 514775 | 514984 |
| Hypothetical, unclassified, unknown | 526877 | 527179 |
| Hypothetical, unclassified, unknown | 535085 | 535489 |
| Transcriptional regulators | 535539 | 536108 |
| Transcriptional regulators | 539143 | 538217 |
| Transcriptional regulators | 540735 | 539785 |
| Hypothetical, unclassified, unknown | 549614 | 549294 |
| Putative enzymes | 550381 | 549656 |
| Hypothetical, unclassified, unknown | 550813 | 550520 |
| Putative enzymes | 552746 | 552994 |
| Hypothetical, unclassified, unknown | 558361 | 557354 |
| Biosynthesis of cofactors, prosthetic group | 560808 | 562013 |
| Biosynthesis of cofactors, prosthetic group | 562006 | 562728 |

TABLE 1-continued

| | | |
|---|---|---|
| Biosynthesis of cofactors, prosthetic group | 562721 | 563545 |
| Biosynthesis of cofactors, prosthetic group | 563549 | 564235 |
| Hypothetical, unclassified, unknown | 564344 | 564574 |
| Biosynthesis of cofactors, prosthetic group | 576040 | 575516 |
| Transcriptional regulators | 586663 | 585980 |
| Putative enzymes | 590105 | 590821 |
| Transcriptional regulators | 594580 | 595134 |
| Hypothetical, unclassified, unknown | 598608 | 598994 |
| Hypothetical, unclassified, unknown | 600176 | 599757 |
| Hypothetical, unclassified, unknown | 600426 | 601394 |
| Hypothetical, unclassified, unknown | 602141 | 601398 |
| Central intermediary metabolism | 604896 | 603706 |
| Hypothetical, unclassified, unknown | 609999 | 609202 |
| Energy metabolism | 611281 | 612444 |
| Hypothetical, unclassified, unknown | 612517 | 612717 |
| Carbon compound catabolism | 613338 | 614402 |
| Hypothetical, unclassified, unknown | 617549 | 616371 |
| Hypothetical, unclassified, unknown | 620438 | 620135 |
| Hypothetical, unclassified, unknown | 621695 | 622033 |
| Hypothetical, unclassified, unknown | 622726 | 622884 |
| Hypothetical, unclassified, unknown | 624199 | 623852 |
| Hypothetical, unclassified, unknown | 624803 | 624189 |
| Hypothetical, unclassified, unknown | 629884 | 628763 |
| Hypothetical, unclassified, unknown | 638830 | 638381 |
| Translation, post-translational modification | 639115 | 638900 |
| Translation, post-translational modification | 639316 | 640341 |
| Biosynthesis of cofactors, prosthetic group | 641073 | 641426 |
| Hypothetical, unclassified, unknown | 643714 | 643208 |
| Hypothetical, unclassified, unknown | 649263 | 648931 |
| Hypothetical, unclassified, unknown | 650538 | 650158 |
| Biosynthesis of cofactors, prosthetic group | 652483 | 651497 |
| Chaperones & heat shock proteins | 653772 | 652480 |
| Adaptation, protection | 656527 | 653753 |
| Energy metabolism | 669415 | 670089 |
| Transcriptional regulators | 673091 | 672777 |
| Transcriptional regulators | 673961 | 673191 |
| Hypothetical, unclassified, unknown | 67466 | 675026 |
| Hypothetical, unclassified, unknown | 675390 | 675839 |
| Related to phage, transposon, or plasmid | 677083 | 677409 |
| Hypothetical, unclassified, unknown | 685846 | 686718 |
| Hypothetical, unclassified, unknown | 686693 | 686899 |
| Related to phage, transposon, or plasmid | 688605 | 688967 |
| Related to phage, transposon, or plasmid | 689236 | 689466 |
| Related to phage, transposon, or plasmid | 690420 | 690674 |
| Hypothetical, unclassified, unknown | 693596 | 694366 |
| Hypothetical, unclassified, unknown | 698932 | 699720 |
| Hypothetical, unclassified, unknown | 699744 | 700835 |
| Related to phage, transposon, or plasmid | 700835 | 701170 |
| Hypothetical, unclassified, unknown | 701477 | 702529 |
| Related to phage, transposon, or plasmid | 702529 | 702831 |
| Related to phage, transposon, or plasmid | 702828 | 703058 |
| Transportation regulators | 706672 | 706028 |
| Hypothetical, unclassified, unknown | 706944 | 707366 |
| Hypothetical, unclassified, unknown | 709182 | 708535 |
| Hypothetical, unclassified, unknown | 714247 | 713279 |
| Hypothetical, unclassified, unknown | 714686 | 714264 |
| Hypothetical, unclassified, unknown | 717231 | 717581 |
| Protein secretion/export apparatus | 737530 | 737081 |
| Hypothetical, unclassified, unknown | 737677 | 738108 |
| Protein secretion/export apparatus | 738485 | 738111 |
| Protein secretion/export apparatus | 741335 | 741928 |
| Protein secretion/export apparatus | 744333 | 745742 |
| Protein secretion/export apparatus | 745742 | 746956 |
| Hypothetical, unclassified, unknown | 748662 | 749774 |
| Hypothetical, unclassified, unknown | 770156 | 770818 |
| Hypothetical, unclassified, unknown | 770847 | 771326 |
| Hypothetical, unclassified, unknown | 772275 | 772700 |
| Hypothetical, unclassified, unknown | 775321 | 774416 |
| Putative enzymes | 778181 | 776787 |
| Putative enzymes | 779208 | 778309 |
| Transcriptional regulators | 782113 | 781259 |
| Hypothetical, unclassified, unknown | 782229 | 782525 |
| Central intermediary metabolism | 782570 | 782965 |
| Hypothetical, unclassified, unknown | 783833 | 783576 |
| Hypothetical, unclassified, unknown | 784698 | 785174 |
| Hypothetical, unclassified, unknown | 785698 | 786925 |
| Hypothetical, unclassified, unknown | 786928 | 788253 |
| Related to phage, transposon, or plasmid | 789144 | 789356 |
| Related to phage, transposon, or plasmid | 790166 | 790600 |

TABLE 1-continued

| | | |
|---|---|---|
| Related to phage, transposon, or plasmid | 795793 | 796776 |
| Hypothetical, unclassified, unknown | 797251 | 797598 |
| Putative enzymes | 798827 | 797925 |
| Transcription, RNA processing and degr | 801967 | 801275 |
| Hypothetical, unclassified, unknown | 802239 | 801967 |
| Hypothetical, unclassified, unknown | 805228 | 805473 |
| Hypothetical, unclassified, unknown | 809882 | 809574 |
| Hypothetical, unclassified, unknown | 828344 | 827400 |
| Secreted Factors (toxins, enzymes, algina | 831914 | 832498 |
| Protein secretion/export apparatus | 835523 | 837322 |
| Protein secretion/export apparatus | 837328 | 838182 |
| Translation, post-translational modification | 839407 | 840324 |
| Hypothetical, unclassified, unknown | 844295 | 843723 |
| Hypothetical, unclassified, unknown | 845682 | 845278 |
| Transport of small molecules | 858646 | 858951 |
| Hypothetical, unclassified, unknown | 859007 | 860170 |
| Hypothetical, unclassified, unknown | 866451 | 865636 |
| Hypothetical, unclassified, unknown | 881077 | 881400 |
| Hypothetical, unclassified, unknown | 883216 | 882989 |
| Hypothetical, unclassified, unknown | 885635 | 886108 |
| Transcriptional regulators | 893041 | 893994 |
| Hypothetical, unclassified, unknown | 895668 | 895396 |
| Hypothetical, unclassified, unknown | 896416 | 897228 |
| Hypothetical, unclassified, unknown | 898886 | 898440 |
| Hypothetical, unclassified, unknown | 900165 | 899830 |
| Hypothetical, unclassified, unknown | 901046 | 900408 |
| Putative enzymes | 903692 | 904633 |
| Chaperones & heat shock proteins | 913086 | 913571 |
| Hypothetical, unclassified, unknown | 929084 | 929503 |
| Hypothetical, unclassified, unknown | 930476 | 929514 |
| Put active enzymes | 932725 | 932102 |
| Cell division | 935989 | 936294 |
| Hypothetical, unclassified, unknown | 942648 | 943430 |
| Hypothetical, unclassified, unknown | 948776 | 949159 |
| Hypothetical, unclassified, unknown | 949280 | 949693 |
| Cell wall / LPS / capsule | 950648 | 949716 |
| Amino acid biosynthesis and metabolism | 952514 | 952158 |
| Hypothetical, unclassified, unknown | 955722 | 955456 |
| Putative enzymes | 962545 | 962925 |
| Hypothetical, unclassified, unknown | 977743 | 977420 |
| Hypothetical, unclassified, unknown | 984245 | 984535 |
| Translation, post-translational modification | 986818 | 989442 |
| Amino acid biosynthesis and metabolism | 989590 | 990828 |
| Transcriptional regulators | 991013 | 991198 |
| Transcriptional regulators | 992543 | 991830 |
| Hypothetical, unclassified unknown | 993409 | 993783 |
| Hypothetical, unclassified, unknown | 993776 | 994051 |
| Transport of small molecules | 996038 | 997486 |
| Hypothetical, unclassified, unknown | 1007548 | 1007234 |
| Carbon compound catabolism | 1012972 | 1011983 |
| Amino acid biosynthesis and metabolism | 1020708 | 1021607 |
| Hypothetical, unclassified, unknown | 1027445 | 1027934 |
| Hypothetical, unclassified, unknown | 1030151 | 1029825 |
| Nucleotide biosynthesis and metabolism | 1032763 | 1032095 |
| Nucleotide biosynthesis and metabolism | 1033824 | 1032763 |
| Hypothetical, unclassified, unknown | 1035277 | 1035981 |
| Putative enzymes | 1039968 | 1040432 |
| Putative enzymes | 1040432 | 1040707 |
| Translation, post-translational modification | 1043404 | 1041689 |
| Hypothetical, unclassified, unknown | 1046462 | 1046671 |
| Adaptation, protection | 1048019 | 1047549 |
| Transport of small molecules | 1053848 | 1054543 |
| Transport of small molecules | 1054566 | 1055006 |
| Transport of small molecules | 1055009 | 1056052 |
| Transport of small molecules | 1056049 | 1057347 |
| Transport of small molecules | 1057400 | 1057906 |
| Hypothetical, unclassified, unknown | 1059622 | 1060296 |
| Hypothetical, unclassified, unknown | 1062034 | 1061207 |
| Hypothetical, unclassified, unknown | 1062369 | 1062061 |
| Hypothetical, unclassified, unknown | 1062601 | 1062885 |
| Hypothetical, unclassified, unknown | 1062921 | 1063544 |
| Hypothetical, unclassified, unknown | 1065138 | 1065425 |
| Secreted Factors (toxins, enzymes, algin | 1067817 | 1066321 |
| Hypothetical, unclassified, unknown | 1068193 | 1068456 |
| Hypothetical, unclassified, unknown | 1071877 | 1071239 |
| Hypothetical, unclassified, unknown | 1072462 | 1072839 |
| Chaperones & heat shock proteins | 1073960 | 1074673 |
| Hypothetical, unclassified, unknown | 1082949 | 1083854 |
| Hypothetical, unclassified, unknown | 1090606 | 1090857 |

TABLE 1-continued

| | | |
|---|---|---|
| Adaptation, protection | 1092498 | 1092025 |
| Amino acid biosynthesis and metabolism | 1093251 | 1094129 |
| Hypothetical, unclassified, unknown | 1095276 | 1096034 |
| Nucleotide biosynthesis and metabolism | 1096063 | 1096773 |
| Putative enzymes | 1107000 | 1107761 |
| Hypothetical, unclassified, unknown | 1113050 | 1112574 |
| Hypothetical, unclassified, unknown | 1123850 | 1123356 |
| Hypothetical, unclassified, unknown | 1125865 | 1125548 |
| Hypothetical, unclassified, unknown | 1126338 | 1125865 |
| Biosynthesis of cofactors, prosthetic group | 1136388 | 1137035 |
| Hypothetical, unclassified, unknown | 1144862 | 1145200 |
| Hypothetical, unclassified, unknown | 1150470 | 1150721 |
| Chaperones & heat shock proteins | 1153637 | 1155547 |
| Hypothetical, unclassified, unknown | 1163660 | 1164022 |
| Hypothetical, unclassified, unknown | 1175614 | 1176375 |
| Hypothetical, unclassified, unknown | 1176380 | 1176982 |
| Hypothetical, unclassified, unknown | 1176958 | 1177620 |
| Hypothetical unclassified, unknown | 1186606 | 1186986 |
| Two-component regulatory systems | 1189172 | 1190380 |
| Motility & Attachment | 1194207 | 1195223 |
| Motility & Attachment | 1197390 | 1197833 |
| Hypothetical, unclassified, unknown | 1198551 | 1197838 |
| Hypothetical, unclassified, unknown | 1199946 | 1198750 |
| Hypothetical, unclassified, unknown | 1207875 | 1207540 |
| Hypothetical, unclassified, unknown | 1212571 | 1211888 |
| Hypothetical, unclassified, unknown | 1214502 | 1213195 |
| Translation, post-translational modification | 1215284 | 1215727 |
| Biosynthesis of cofactors, prosthetic group | 1218181 | 1218933 |
| Antibiotic resistance and susceptibility | 1221691 | 1222098 |
| Hypothetical, unclassified, unknown | 1226278 | 1225757 |
| Hypothetical, unclassified, unknown | 1227302 | 1226427 |
| Transcriptional regulators | 1229344 | 1230219 |
| Transcriptional regulators | 1236644 | 1237546 |
| Hypothetical, unclassified, unknown | 1243118 | 1242750 |
| Adaptation, protection | 1245665 | 1245928 |
| Hypothetical, unclassified, unknown | 1249552 | 1249019 |
| Nucleotide biosynthesis and metabolism | 1251154 | 1249907 |
| Nucleotide biosynthesis and metabolism | 1254309 | 1251418 |
| Two-component regulatory systems | 1255042 | 1255752 |
| Adaptation, protection | 1257772 | 1257981 |
| Hypothetical, unclassified, unknown | 1258470 | 1258087 |
| Amino acid biosynthesis and metabolism | 1260442 | 1259291 |
| Hypothetical, unclassified, unknown | 1263378 | 1264190 |
| Hypothetical, unclassified, unknown | 1264919 | 1264191 |
| Hypothetical, unclassified, unknown | 1266111 | 1266782 |
| Hypothetical, unclassified, unknown | 1267282 | 1267602 |
| Energy metabolism | 1272796 | 1272200 |
| Energy metabolism | 1273298 | 1272807 |
| Energy metabolism | 1276608 | 1276117 |
| Energy metabolism | 1276784 | 1276617 |
| Transport of small molecules | 1284513 | 1265823 |
| Hypothetical, unclassified, unknown | 1294138 | 1294809 |
| Hypothetical, unclassified, unknown | 1303457 | 1303864 |
| Hypothetical, unclassified, unknown | 1303892 | 1304449 |
| Hypothetical, unclassified, unknown | 1305583 | 1306056 |
| Hypothetical, unclassified, unknown | 1314321 | 1313362 |
| Hypothetical, unclassified, unknown | 1317202 | 1315916 |
| Hypothetical, unclassified, unknown | 1318150 | 1317404 |
| Amino acid biosynthesis and metabolism | 1319514 | 1318147 |
| Hypothetical, unclassified, unknown | 1321000 | 1320386 |
| Transcriptional regulators | 1326939 | 1326046 |
| Putative enzymes | 1327024 | 1327803 |
| Hypothetical, unclassified, unknown | 1330467 | 1330117 |
| Hypothetical, unclassified, unknown | 1331517 | 1331714 |
| Hypothetical, unclassified, unknown | 1334671 | 1334928 |
| Antibiotic resistance and susceptibility | 1339082 | 1337931 |
| Secreted Factors (toxins, enzymes, algin | 1357317 | 1357712 |
| Transcriptional regulators | 1370092 | 1369418 |
| Transcriptional regulators | 1379168 | 1378500 |
| Hypothetical, unclassified, unknown | 1391277 | 1391861 |
| Transcriptional regulators | 1396731 | 1397180 |
| Hypothetical, unclassified, unknown | 1406459 | 1406752 |
| Hypothetical, unclassified, unknown | 1408999 | 1409274 |
| Transcriptional regulators | 1409949 | 1410476 |
| Putative enzymes | 1417500 | 1417961 |
| Hypothetical, unclassified, unknown | 1417965 | 1418738 |
| Transcriptional regulators | 1425754 | 1425140 |
| Energy metabolism | 1432037 | 1432927 |
| Hypothetical, unclassified, unknown | 1435493 | 1435825 |

TABLE 1-continued

| | | |
|---|---|---|
| Transcriptional regulators | 1441547 | 1440639 |
| Hypothetical, unclassified, unknown | 1444451 | 1442904 |
| Transport of small molecules | 1456723 | 1455815 |
| Hypothetical, unclassified, unknown | 1462696 | 1463403 |
| Hypothetical, unclassified, unknown | 1463586 | 1463936 |
| Hypothetical, unclassified, unknown | 1464111 | 1464860 |
| Hypothetical, unclassified, unknown | 1467320 | 1466109 |
| Hypothetical, unclassified, unknown | 1467901 | 1467488 |
| Hypothetical, unclassified, unknown | 1468510 | 1468890 |
| Hypothetical, unclassified, unknown | 1470978 | 1470580 |
| Hypothetical, unclassified, unknown | 1474391 | 1474714 |
| Transcriptional regulators | 1475464 | 1476306 |
| Hypothetical, unclassified, unknown | 1479791 | 1479021 |
| Hypothetical, unclassified, unknown | 1483123 | 1483875 |
| Hypothetical, unclassified, unknown | 1483898 | 1485763 |
| Hypothetical, unclassified, unknown | 1486967 | 1486266 |
| Hypothetical, unclassified, unknown | 1489095 | 1486960 |
| Biosynthesis of cofactors, prosthetic group | 1491913 | 1493055 |
| Hypothetical, unclassified, unknown | 1494959 | 1495492 |
| Hypothetical, unclassified, unknown | 1495635 | 1495997 |
| Putative enzymes | 1496920 | 1496087 |
| Hypothetical, unclassified, unknown | 1516433 | 1516687 |
| Two-component regulatory systems | 1518914 | 1519546 |
| Hypothetical, unclassified, unknown | 1519627 | 1519968 |
| Hypothetical, unclassified, unknown | 1526657 | 1526430 |
| Carbon compound catabolism | 1533238 | 1534278 |
| Hypothetical, unclassified, unknown | 1552641 | 1552997 |
| Hypothetical, unclassified, unknown | 1553112 | 1553675 |
| Transcriptional regulators | 1559122 | 1558880 |
| Adaptation, protection | 1559254 | 1559859 |
| Hypothetical, unclassified, unknown | 1572023 | 1572544 |
| Motility & Attachment | 1575290 | 1575559 |
| Motility & Attachment | 1583956 | 1584798 |
| Two-component regulatory systems | 1585640 | 1586014 |
| Chemotaxis | 1591286 | 1592176 |
| Cell division | 1592271 | 1593059 |
| Chemotaxis | 1594087 | 1594566 |
| Hypothetical, unclassified, unknown | 1594597 | 1595004 |
| Hypothetical, unclassified, unknown | 1596889 | 1597305 |
| Hypothetical, unclassified, unknown | 1599982 | 1599428 |
| Transport of small molecules | 1602179 | 1602880 |
| Transport of small molecules | 1602877 | 1603548 |
| Transport of small molecules | 1603671 | 1604429 |
| Hypothetical, unclassified | 1604426 | 1604602 |
| Energy metabolism | 1605088 | 1607061 |
| Energy metabolism | 1607065 | 1607607 |
| Energy metabolism | 1607604 | 1608071 |
| Hypothetical, unclassified, unknown | 1615908 | 1614670 |
| Hypothetical, unclassified, unknown | 1617085 | 1615895 |
| Hypothetical, unclassified, unknown | 1619907 | 1620263 |
| Transport of small molecules | 1624715 | 1623864 |
| Transcriptional regulators | 1634492 | 1633842 |
| Hypothetical, unclassified, unknown | 1638639 | 1638379 |
| Hypothetical, unclassified, unknown | 1639794 | 1638652 |
| Hypothetical, unclassified, unknown | 1647046 | 1646537 |
| Hypothetical, unclassified, unknown | 1649555 | 1648629 |
| Hypothetical, unclassified, unknown | 1649928 | 1650308 |
| Transcriptional regulators | 1660727 | 1661386 |
| Cell division | 1665065 | 1665934 |
| DNA replication, recombination, modification | 1666025 | 1668409 |
| DNA replication, recombination, modification | 1669989 | 1672034 |
| Hypothetical, unclassified, unknown | 1672080 | 1672406 |
| Putative enzymes | 1673204 | 1674352 |
| Hypothetical, unclassified, unknown | 1677559 | 1678407 |
| Hypothetical, unclassified, unknown | 1678590 | 1678261 |
| Transport of small molecules | 1678952 | 1678584 |
| Hypothetical, unclassified, unknown | 1684962 | 1684753 |
| Energy metabolism | 1689339 | 1687924 |
| Energy metabolism | 1694045 | 1693119 |
| Hypothetical, unclassified, unknown | 1696467 | 1697099 |
| Hypothetical, unclassified, unknown | 1697188 | 1697919 |
| Hypothetical, unclassified, unknown | 1697916 | 1698344 |
| Hypothetical, unclassified, unknown | 1704522 | 1704761 |
| Hypothetical, unclassified, unknown | 1709765 | 1709412 |
| Hypothetical, unclassified, unknown | 1712698 | 1712519 |
| Energy metabolism | 1720744 | 1721130 |
| Energy metabolism | 1721124 | 1721492 |
| Energy metabolism | 1721496 | 1723268 |
| Energy metabolism | 1723280 | 1723987 |

TABLE 1-continued

| | | |
|---|---|---|
| Energy metabolism | 1728416 | 1729852 |
| Energy metabolism | 1730181 | 1731347 |
| Energy metabolism | 1731347 | 1732234 |
| Hypothetical, unclassified, unknown | 1734004 | 1734768 |
| Hypothetical, unclassified, unknown | 1735063 | 1734827 |
| Hypothetical, unclassified, unknown | 1735236 | 1735709 |
| Hypothetical, unclassified, unknown | 1735706 | 1736152 |
| Hypothetical, unclassified, unknown | 1736189 | 1737418 |
| Fatty acid and phospholipid metabolism | 1753418 | 1752903 |
| Hypothetical, unclassified, unknown | 1762433 | 1762870 |
| Transcriptional regulators | 1762928 | 1763752 |
| Putative enzymes | 1765345 | 1766205 |
| Hypothetical, unclassified, unknown | 1766285 | 1766941 |
| Hypothetical, unclassified, unknown | 1766956 | 1767762 |
| Transcriptional regulators | 1773682 | 1774548 |
| Transport of small molecules | 1775945 | 1776034 |
| Transport of small molecules | 1779877 | 1780428 |
| Hypothetical, unclassified, unknown | 1784108 | 1785016 |
| Hypothetical, unclassified, unknown | 1786888 | 1787166 |
| Hypothetical, unclassified, unknown | 1790879 | 1790472 |
| Hypothetical, unclassified, unknown | 1805218 | 1805724 |
| Hypothetical, unclassified, unknown | 1814995 | 1815135 |
| Hypothetical, unclassified, unknown | 1816351 | 1816858 |
| Hypothetical, unclassified, unknown | 1824969 | 1825430 |
| Biosynthesis of cofactors, prosthetic group | 1826040 | 1825495 |
| Hypothetical, unclassified, unknown | 1826675 | 1826118 |
| Hypothetical, unclassified, unknown | 1827052 | 1826732 |
| Amino acid biosynthesis and metabolism | 1836367 | 1837227 |
| Protein secretion/export apparatus | 1841517 | 1840468 |
| Protein secretion/export apparatus | 1842302 | 1841514 |
| Protein secretion/export apparatus | 1845717 | 1845241 |
| Protein secretion/export apparatus | 1847227 | 1848093 |
| Hypothetical, unclassified, unknown | 1848707 | 1849072 |
| Hypothetical, unclassified, unknown | 1849077 | 1849406 |
| Protein secretion/export apparatus | 1851982 | 1852278 |
| Protein secretion/export apparatus | 1855862 | 1856299 |
| Hypothetical, unclassified, unknown | 1856308 | 1856553 |
| Protein secretion/export apparatus | 1882558 | 1862761 |
| Protein secretion/export apparatus | 1862764 | 1863021 |
| Protein secretion/export apparatus | 1863024 | 1863371 |
| Protein secretion/export apparatus | 1863799 | 1864137 |
| Hypothetical, unclassified, unknown | 1874967 | 1875767 |
| Hypothetical, unclassified, unknown | 1875849 | 1876580 |
| Hypothetical, unclassified, unknown | 1887297 | 1887058 |
| Hypothetical, unclassified, unknown | 1888186 | 1887698 |
| Hypothetical, unclassified, unknown | 1889173 | 1888985 |
| Amino acid biosynthesis and metabolism | 1891815 | 1890739 |
| Amino acid biosynthesis and metabolism | 1896630 | 1897247 |
| Hypothetical, unclassified, unknown | 1912756 | 1912217 |
| Biosynthesis of cofactors, prosthetic group | 1917599 | 1918087 |
| Transport of small molecules | 1921174 | 1922226 |
| Central intermediary metabolism | 1926123 | 1925797 |
| Transport of small molecules | 1931775 | 1930564 |
| Hypothetical, unclassified, unknown | 1933632 | 1933054 |
| Energy metabolism | 1937644 | 1935035 |
| Hypothetical, unclassified, unknown | 1939583 | 1940206 |
| Hypothetical, unclassified, unknown | 1942442 | 1941720 |
| Translation, post-translational modification | 1943067 | 1944737 |
| Translation, post-translational modification | 1944747 | 1946129 |
| Biosynthesis of cofactors, prosthetic group | 1947041 | 1946187 |
| Translation, post-translational modification | 1956227 | 1958623 |
| DNA replication, recombination, modification | 1972959 | 1973405 |
| Nucleotide biosynthesis and metabolism | 1973470 | 1974210 |
| Hypothetical, unclassified, unknown | 1974627 | 1974238 |
| Transport of small molecules | 1979941 | 1978439 |
| Hypothetical, unclassified, unknown | 1984389 | 1985033 |
| Hypothetical, unclassified, unknown | 1989423 | 1989109 |
| Hypothetical, unclassified, unknown | 1993898 | 1993461 |
| Hypothetical, unclassified, unknown | 1995164 | 1994667 |
| Hypothetical, unclassified, unknown | 1998587 | 1998949 |
| Hypothetical, unclassified, unknown | 1999874 | 1999512 |
| Hypothetical, unclassified, unknown | 2004892 | 2004374 |
| Hypothetical, unclassified, unknown | 2007865 | 2008249 |
| Hypothetical, unclassified, unknown | 2012530 | 2012255 |
| Hypothetical, unclassified, unknown | 2015136 | 2014915 |
| Transcriptional regulators | 2019690 | 2018803 |
| Transport of small molecules | 2022398 | 2021712 |
| Hypothetical, unclassified, unknown | 2028454 | 2028981 |
| Fatty acid and phospholipid metabolism | 2031466 | 2031705 |

TABLE 1-continued

| | | |
|---|---|---|
| Hypothetical, unclassified, unknown | 2034857 | 2034066 |
| Transport of small molecules | 2052941 | 2053264 |
| Energy metabolism | 2053277 | 2053675 |
| Transcriptional regulators | 2054223 | 2053672 |
| Hypothetical, unclassified, unknown | 2054309 | 2054842 |
| Hypothetical, unclassified, unknown | 2062401 | 2061664 |
| Hypothetical, unclassified, unknown | 2065545 | 2064853 |
| Hypothetical, unclassified, unknown | 2066767 | 2065493 |
| Hypothetical, unclassified, unknown | 2067955 | 2066786 |
| Hypothetical, unclassified, unknown | 2068728 | 2067961 |
| Secreted Factors (toxins, enzymes, algin | 2070685 | 2071173 |
| Secreted Factors (toxins, enzymes, algin | 2071209 | 2071697 |
| Secreted Factors (toxins, enzymes, algin | 2076311 | 2076958 |
| Transcriptional regulators | 2085426 | 2084476 |
| Transcriptional regulators | 2085929 | 2085423 |
| Hypothetical, unclassified, unknown | 2088034 | 2086808 |
| Hypothetical, unclassified, unknown | 2091837 | 2091490 |
| Hypothetical, unclassified, unknown | 2103294 | 2103770 |
| Hypothetical unclassified, unknown | 2103770 | 2104096 |
| Translation, post-translational modification | 2109511 | 2108942 |
| Hypothetical, unclassified, unknown | 2109854 | 2109558 |
| Hypothetical, unclassified, unknown | 2117897 | 2118097 |
| Hypothetical, unclassified, unknown | 2118585 | 2118893 |
| Hypothetical, unclassified, unknown | 2118926 | 2119747 |
| Hypothetical, unclassified, unknown | 2122222 | 2120225 |
| Hypothetical, unclassified, unknown | 2137785 | 2136520 |
| Hypothetical, unclassified, unknown | 2138598 | 2137846 |
| Hypothetical, unclassified, unknown | 2141002 | 2140433 |
| Hypothetical, unclassified, unknown | 2141487 | 2140999 |
| Hypothetical, unclassified, unknown | 2145894 | 2146502 |
| Hypothetical, unclassified, unknown | 2146609 | 2146875 |
| Hypothetical, unclassified, unknown | 2148855 | 2149189 |
| Hypothetical, unclassified, unknown | 2150364 | 2149864 |
| Hypothetical, unclassified, unknown | 2150524 | 2150781 |
| Hypothetical, unclassified, unknown | 2157968 | 2159167 |
| Transcriptional regulators | 2164548 | 2163883 |
| Two-component regulatory systems | 2165876 | 2166553 |
| Biosynthesis of cofactors, prosthetic group | 2171865 | 2171936 |
| Prosthetic group | 2171989 | 2172903 |
| Biosynthesis of cofactors, prosthetic group | 2173662 | 2173940 |
| Hypothetical, unclassified, unknown | 2181744 | 2181181 |
| Hypothetical, unclassified, unknown | 2182097 | 2181741 |
| Chaperones & heat shock proteins | 2182394 | 2182116 |
| Fatty acid and phospholipid metabolism | 2187065 | 2188246 |
| Hypothetical, unclassified, unknown | 2188459 | 2189883 |
| Carbon compound catabolism | 2196132 | 2195494 |
| Transcriptional regulators | 2198891 | 2199694 |
| Putative enzymes | 2203446 | 2202649 |
| Fatty acid and phospholipid metabolism | 2206353 | 2205190 |
| Transcriptional regulators | 2206806 | 2206402 |
| Hypothetical, unclassified, unknown | 2206999 | 2207928 |
| Hypothetical, unclassified, unknown | 2213539 | 2213315 |
| Hypothetical, unclassified, unknown | 2219099 | 2218098 |
| Hypothetical, unclassified, unknown | 2220275 | 2220574 |
| Hypothetical, unclassified, unknown | 2221157 | 2220903 |
| Hypothetical, unclassified, unknown | 2223804 | 2224478 |
| Hypothetical, unclassified, unknown | 2227541 | 2229001 |
| Transport of small molecules | 2234080 | 2235309 |
| Transcriptional regulators | 2244995 | 2245948 |
| Central intermediary metabolism | 2246456 | 2245986 |
| Transport of small molecules | 2256704 | 2257720 |
| Putative enzymes | 2259478 | 2260659 |
| Hypothetical, unclassified, unknown | 2265764 | 2265126 |
| Translation, post-translational modification | 2272460 | 2274568 |
| Transport of small molecules | 2277552 | 2278982 |
| Hypothetical, unclassified, unknown | 2278982 | 2279794 |
| Hypothetical, unclassified, unknown | 2281578 | 2279917 |
| Hypothetical, unclassified, unknown | 2290335 | 2289085 |
| Hypothetical, unclassified, unknown | 2297072 | 2297920 |
| Hypothetical, unclassified, unknown | 2300676 | 2301755 |
| Transport of small molecules | 2303022 | 2304215 |
| Hypothetical, unclassified, unknown | 2306627 | 2305782 |
| Carbon compound catabolism | 2307957 | 2309432 |
| Hypothetical, unclassified, unknown | 2312899 | 2313789 |
| Biosynthesis of cofactors, prosthetic group | 2314512 | 2315690 |
| Putative enzymes | 2316708 | 2317403 |
| Hypothetical, unclassified, unknown | 2318624 | 2318226 |
| Hypothetical, unclassified, unknown | 2322071 | 2321130 |
| DNA replication, recombination, modification | 2329348 | 2330424 |

TABLE 1-continued

| | | |
|---|---|---|
| Putative enzymes | 2332059 | 2330959 |
| Hypothetical, unclassified, unknown | 2332820 | 2332392 |
| Transcriptional regulators | 2335172 | 2336104 |
| Hypothetical, unclassified, unknown | 2339987 | 2339352 |
| Hypothetical, unclassified, unknown | 2346477 | 2347838 |
| Hypothetical, unclassified, unknown | 2352430 | 2351906 |
| Putative enzymes | 2356713 | 2357573 |
| Hypothetical, unclassified, unknown | 2358024 | 2358311 |
| Hypothetical, unclassified, unknown | 2361706 | 2361873 |
| Hypothetical, unclassified, unknown | 2364816 | 2365058 |
| Hypothetical, unclassified, unknown | 2377476 | 2376538 |
| Hypothetical, unclassified, unknown | 2381778 | 2381473 |
| Hypothetical, unclassified, unknown | 2390255 | 2390620 |
| Hypothetical, unclassified, unknown | 2390949 | 2392046 |
| Hypothetical, unclassified, unknown | 2393424 | 2393633 |
| Hypothetical, unclassified, unknown | 2393708 | 2394178 |
| Hypothetical, unclassified, unknown | 2396252 | 2395944 |
| Hypothetical, unclassified, unknown | 2396883 | 2396536 |
| Hypothetical, unclassified, unknown | 2404655 | 2404386 |
| Hypothetical, unclassified, unknown | 2405233 | 2404949 |
| Hypothetical, unclassified, unknown | 2405739 | 2405230 |
| Hypothetical, unclassified, unknown | 2405993 | 2406877 |
| Hypothetical, unclassified, unknown | 2406961 | 2407131 |
| Hypothetical, unclassified, unknown | 2407236 | 2407661 |
| Hypothetical, unclassified, unknown | 2409837 | 2410181 |
| Hypothetical, unclassified, unknown | 2411709 | 2412122 |
| Transcriptional regulators | 2415661 | 2416245 |
| Hypothetical, unclassified, unknown | 2416376 | 2417413 |
| Hypothetical, unclassified, unknown | 2424400 | 2423924 |
| Hypothetical, unclassified, unknown | 2427017 | 2425497 |
| Hypothetical, unclassified, unknown | 2430170 | 2431129 |
| Transport of small molecules | 2433748 | 2435070 |
| Transport of small molecules | 2441555 | 2440347 |
| Transcriptional regulators | 2441771 | 2442691 |
| Hypothetical, unclassified, unknown | 2443161 | 2444366 |
| Hypothetical, unclassified, unknown | 2445533 | 2444886 |
| Hypothetical, unclassified, unknown | 2446564 | 2445545 |
| Hypothetical, unclassified, unknown | 2447325 | 2446597 |
| Hypothetical, unclassified, unknown | 2447989 | 2447573 |
| Hypothetical, unclassified, unknown | 2448533 | 2448033 |
| Transcriptional regulators | 2449545 | 2448568 |
| Hypothetical, unclassified, unknown | 2450765 | 2449554 |
| Hypothetical, unclassified, unknown | 2451707 | 2452426 |
| Transport of small molecules | 2457510 | 2458280 |
| Hypothetical, unclassified, unknown | 2468032 | 2469099 |
| Hypothetical, unclassified, unknown | 2472104 | 2472409 |
| Hypothetical, unclassified, unknown | 2479130 | 2478312 |
| Amino acid biosynthesis and metabolism | 2480844 | 2481830 |
| Secreted Factors (toxins, enzymes, algina | 2485471 | 2486118 |
| Transcriptional regulators | 2487293 | 2486355 |
| Hypothetical, unclassified, unknown | 2488950 | 2489732 |
| Hypothetical, unclassified, unknown | 2508775 | 2509467 |
| Hypothetical, unclassified, unknown | 2510622 | 2511050 |
| Hypothetical, unclassified, unknown | 2512511 | 2513182 |
| Hypothetical, unclassified, unknown | 2523239 | 2522958 |
| Hypothetical, unclassified, unknown | 2524201 | 2523236 |
| Transport of small molecules | 2525052 | 2524198 |
| Transport of small molecules | 2525846 | 2525049 |
| Energy metabolism | 2527657 | 2527412 |
| Putative enzymes | 2529467 | 2527743 |
| Hypothetical, unclassified, unknown | 2540082 | 2539063 |
| Hypothetical, unclassified unknown | 2549748 | 2549906 |
| Transcriptional regulators | 2553965 | 2554858 |
| Transport of small molecules | 2571691 | 2570855 |
| Hypothetical, unclassified, unknown | 2573365 | 2572805 |
| Hypothetical, unclassified, unknown | 2579542 | 2580882 |
| Transport of small molecules | 2582097 | 2583407 |
| Carbon compound catabolism | 2587906 | 2589414 |
| Hypothetical, unclassified, unknown | 2593330 | 2594547 |
| Hypothetical, unclassified, unknown | 2595985 | 2596779 |
| Transport of small molecules | 2597869 | 2598522 |
| Hypothetical, unclassified, unknown | 2614893 | 2615438 |
| Hypothetical, unclassified, unknown | 2617019 | 2617516 |
| Hypothetical, unclassified, unknown | 2617529 | 2617954 |
| Hypothetical, unclassified, unknown | 2619695 | 2620711 |
| Hypothetical, unclassified, unknown | 2623284 | 2623856 |
| Hypothetical, unclassified, unknown | 2627175 | 2626780 |
| Transcriptional regulators | 2635971 | 2636051 |
| Transport of small molecules | 2645303 | 2646727 |

TABLE 1-continued

| | | |
|---|---|---|
| Hypothetical, unclassified, unknown | 2689240 | 2689569 |
| Hypothetical, unclassified, unknown | 2689566 | 2690126 |
| Putative enzymes | 2694544 | 2693780 |
| Hypothetical, unclassified, unknown | 2694763 | 2694545 |
| Hypothetical, unclassified, unknown | 2701205 | 2702065 |
| Hypothetical, unclassified, unknown | 2705772 | 2706086 |
| Hypothetical, unclassified, unknown | 2723221 | 2722754 |
| Hypothetical, unclassified, unknown | 2724222 | 2723308 |
| Hypothetical, unclassified, unknown | 2724484 | 2724729 |
| Hypothetical, unclassified, unknown | 2730520 | 2729975 |
| Hypothetical, unclassified, unknown | 2732965 | 2732531 |
| Hypothetical, unclassified, unknown | 2738840 | 2739715 |
| Amino acid biosynthesis and metabolism | 2740882 | 2739761 |
| Amino acid biosynthesis and metabolism | 2747072 | 2746689 |
| Hypothetical, unclassified, unknown | 2753464 | 2752865 |
| Hypothetical, unclassified, unknown | 2754601 | 2754822 |
| Hypothetical, unclassified, unknown | 2755724 | 2754851 |
| Hypothetical, unclassified, unknown | 2756308 | 2756649 |
| Hypothetical, unclassified, unknown | 2760086 | 2759481 |
| Hypothetical, unclassified, unknown | 2760618 | 2760322 |
| Hypothetical, unclassified, unknown | 2761350 | 2760871 |
| Hypothetical, unclassified, unknown | 2781450 | 2780926 |
| Transcriptional regulators | 2786355 | 2785369 |
| Transcriptional regulators | 2787885 | 2786971 |
| Central intermediary metabolism | 2791219 | 2791863 |
| Hypothetical, unclassified, unknown | 2791905 | 2792816 |
| Putative enzymes | 2794132 | 2792798 |
| Hypothetical, unclassified, unknown | 2803344 | 2803622 |
| Hypothetical, unclassified, unknown | 2804131 | 2803859 |
| Hypothetical, unclassified, unknown | 2805916 | 2806290 |
| Putative enzymes | 2807368 | 2806349 |
| Transcriptional regulators | 2807468 | 2808511 |
| Hypothetical, unclassified, unknown | 2815281 | 2814766 |
| Transport of small molecules | 2817448 | 2818674 |
| Hypothetical, unclassified, unknown | 2818885 | 2818718 |
| Hypothetical, unclassified, unknown | 2822321 | 2821704 |
| Carbon compound catabolism | 2825590 | 2824658 |
| Carbon compound catabolism | 2833129 | 2832368 |
| Carbon compound catabolism | 2834689 | 2834201 |
| Transport of small molecules | 2841965 | 2840511 |
| Fatty acid and phospholipid metabolism | 2865104 | 2864169 |
| Hypothetical, unclassified, unknown | 2866199 | 2865747 |
| Hypothetical, unclassified, unknown | 2867505 | 2866192 |
| Hypothetical, unclassified, unknown | 2876409 | 2875696 |
| Hypothetical, unclassified, unknown | 2880519 | 2881562 |
| Transcriptional regulators | 2883156 | 2884088 |
| Putative enzymes | 2885332 | 2884205 |
| Putative enzymes | 2886551 | 2885361 |
| Putative enzymes | 2887336 | 2886569 |
| Transcriptional regulators | 2913921 | 2914358 |
| Fatty acid and phospholipid metabolism | 2923926 | 2923366 |
| Transcriptional regulators | 2934387 | 2933581 |
| Hypothetical, unclassified, unknown | 2945263 | 2945868 |
| Hypothetical, unclassified, unknown | 2948581 | 2948976 |
| Hypothetical, unclassified, unknown | 2948973 | 2949332 |
| Hypothetical, unclassified, unknown | 2949332 | 2949637 |
| Hypothetical, unclassified, unknown | 2949634 | 2949969 |
| Translation, post-translational modification | 2954695 | 2953415 |
| Chaperones & heat shock proteins | 2956778 | 2956152 |
| Cell division | 2959239 | 2956804 |
| Translation, post-translational modification | 2960455 | 2961135 |
| Translation, post-translational modification | 2962002 | 2962220 |
| Hypothetical, unclassified, unknown | 2964842 | 2964606 |
| transcription, RNA processing and degr | 2969986 | 2971113 |
| Nucleotide biosynthesis and metabolism | 2972698 | 2974068 |
| Energy metabolism | 2983204 | 2983881 |
| Energy metabolism | 2986242 | 2987588 |
| Energy metabolism | 2992001 | 2992501 |
| Energy metabolism | 2992547 | 2992855 |
| Hypothetical, unclassified, unknown | 3008323 | 3008009 |
| Hypothetical, unclassified, unknown | 3012536 | 3012279 |
| Biosynthesis of cofactors, prosthetic grout | 3015581 | 3015937 |
| Hypothetical, unclassified, unknown | 3016245 | 3016598 |
| Hypothetical, unclassified, unknown | 3016883 | 3016674 |
| Protein secretion/export apparatus | 3020928 | 3020503 |
| Protein secretion/export apparatus | 3021338 | 3020928 |
| Protein secretion/export apparatus | 3021741 | 3021307 |
| Transport of small molecules | 3025507 | 3024704 |
| Transcriptional regulators | 3028074 | 3029003 |

TABLE 1-continued

| | | |
|---|---|---|
| Amino acid biosynthesis and metabolism | 3031397 | 3030435 |
| Hypothetical, unclassified, unknown | 3042501 | 3043415 |
| Related to phage, transposon, or plasmid | 3044765 | 3043749 |
| Energy metabolism | 3047969 | 3047643 |
| Hypothetical, unclassified, unknown | 3050611 | 3050330 |
| Hypothetical, unclassified, unknown | 3057375 | 3057608 |
| Hypothetical, unclassified, unknown | 3060659 | 3060264 |
| Energy metabolism | 3070365 | 3070703 |
| Hypothetical, unclassified, unknown | 3073731 | 3074417 |
| Hypothetical, unclassified, unknown | 3075217 | 3074579 |
| Hypothetical, unclassified, unknown | 3075410 | 3075889 |
| Hypothetical, unclassified, unknown | 3075921 | 3076313 |
| Hypothetical, unclassified, unknown | 3076343 | 3076621 |
| Central intermediary metabolism | 3079196 | 3079834 |
| Hypothetical, unclassified, unknown | 3089612 | 3088659 |
| Hypothetical, unclassified, unknown | 3090107 | 3089643 |
| Hypothetical, unclassified, unknown | 3094184 | 3093657 |
| Hypothetical, unclassified, unknown | 3096051 | 3094756 |
| Hypothetical, unclassified, unknown | 3098978 | 3098625 |
| Hypothetical, unclassified, unknown | 3099729 | 3099472 |
| DNA replication, recombination, modification | 3100111 | 3099809 |
| Translation, post-translational modification | 3102493 | 3100115 |
| Translation, post-translational modification | 3103544 | 3102528 |
| Translation, post-translational modification | 3103998 | 3103642 |
| Translation, post-translational modification | 3104216 | 3104022 |
| Translation, post-translational modification | 3104829 | 3104278 |
| Translation, post-translational modification | 3106751 | 3104829 |
| DNA replication, recombination, modification | 3110900 | 3111613 |
| Hypothetical, unclassified, unknown | 3114818 | 3115192 |
| Hypothetical, unclassified, unknown | 3117610 | 3117176 |
| Hypothetical, unclassified, unknown | 3119707 | 3119393 |
| Hypothetical, unclassified, unknown | 3122264 | 3121920 |
| Hypothetical, unclassified, unknown | 3122585 | 3122376 |
| Putative enzymes | 3126251 | 3127219 |
| Hypothetical, unclassified, unknown | 3127225 | 3127707 |
| Hypothetical, unclassified, unknown | 3128269 | 3127859 |
| Hypothetical, unclassified, unknown | 3132815 | 3132228 |
| Hypothetical, unclassified, unknown | 3133257 | 3132820 |
| Hypothetical, unclassified, unknown | 3137849 | 3138193 |
| Hypothetical, unclassified, unknown | 3138190 | 3138531 |
| Hypothetical, unclassified, unknown | 3139010 | 3139669 |
| Hypothetical, unclassified, unknown | 3141718 | 3142275 |
| Hypothetical, unclassified, unknown | 3142284 | 3142502 |
| Hypothetical, unclassified, unknown | 3142617 | 3143084 |
| Hypothetical, unclassified, unknown | 3149318 | 3148722 |
| Hypothetical, unclassified, unknown | 3152201 | 3150885 |
| Hypothetical, unclassified, unknown | 3155074 | 3154592 |
| Hypothetical, unclassified, unknown | 3156502 | 3156801 |
| Hypothetical, unclassified, unknown | 3157563 | 3156859 |
| Hypothetical, unclassified, unknown | 3158925 | 3159668 |
| Hypothetical, unclassified, unknown | 3160320 | 3160583 |
| Hypothetical, unclassified, unknown | 3162215 | 3161598 |
| Hypothetical, unclassified, unknown | 3162578 | 3162387 |
| Transport of small molecules | 3165541 | 3164762 |
| Hypothetical, unclassified, unknown | 3173174 | 3171597 |
| Hypothetical, unclassified, unknown | 3173243 | 3173722 |
| Hypothetical, unclassified, unknown | 3180951 | 3180553 |
| Hypothetical, unclassified, unknown | 3182399 | 3182851 |
| Hypothetical, unclassified, unknown | 3184001 | 3185128 |
| Adaptation, protection | 3185816 | 3185160 |
| Hypothetical, unclassified, unknown | 3192748 | 3193518 |
| Putative enzymes | 3197641 | 3198987 |
| Hypothetical, unclassified, unknown | 3200552 | 3200319 |
| Translation, post-translational modification | 3205079 | 3204513 |
| Hypothetical, unclassified, unknown | 3206252 | 3205122 |
| Membrane proteins | 3206914 | 3207165 |
| Hypothetical, unclassified, unknown | 3208260 | 3207289 |
| Transcription, RNA processing and degr | 3212524 | 3213030 |
| Secreted Factors (toxins, enzymes, algina | 3215422 | 3216288 |
| Hypothetical, unclassified, unknown | 3221205 | 3221564 |
| Hypothetical, unclassified, unknown | 3228336 | 3227383 |
| Nucleotide biosynthesis and metabolism | 3230181 | 3229483 |
| Transcriptional regulators | 3231171 | 3230278 |
| Transcriptional regulators | 3232771 | 3231881 |
| Hypothetical, unclassified, unknown | 3235793 | 3235960 |
| Hypothetical, unclassified, unknown | 3249630 | 3249208 |
| Hypothetical, unclassified, unknown | 3253679 | 3253311 |
| Hypothetical, unclassified, unknown | 3255765 | 3255406 |
| Hypothetical, unclassified, unknown | 3265210 | 3264641 |

TABLE 1-continued

| | | |
|---|---|---|
| Hypothetical, unclassified, unknown | 3271692 | 3270826 |
| Hypothetical, unclassified, unknown | 3272405 | 3271812 |
| Putative enzymes | 3277408 | 3278577 |
| Hypothetical, unclassified, unknown | 3284597 | 3283374 |
| Hypothetical, unclassified, unknown | 3291172 | 3290693 |
| Hypothetical, unclassified, unknown | 3291282 | 3291863 |
| Hypothetical, unclassified, unknown | 3291959 | 3292267 |
| Putative enzymes | 3297117 | 3295978 |
| Putative enzymes | 3308390 | 3309337 |
| Energy metabolism | 3311720 | 3310791 |
| Energy metabolism | 3312469 | 3311720 |
| Energy metabolism | 3312790 | 3314445 |
| Motility & Attachment | 3320029 | 3319673 |
| DNA replication, recombination, modification | 3321049 | 3320063 |
| Nucleotide biosynthesis and metabolism | 3321674 | 3321042 |
| Hypothetical, unclassified, unknown | 3322752 | 3321703 |
| Fatty acid and phospholipid metabolism | 3325182 | 3324946 |
| Fatty acid and phospholipid metabolism | 3326121 | 3325378 |
| Fatty acid and phospholipid metabolism | 3327082 | 3326144 |
| Translation, post-translational modification | 3328384 | 3328202 |
| Hypothetical, unclassified, unknown | 3328934 | 3328398 |
| Transcription, RNA processing and degr | 3332303 | 3331347 |
| Cell wall / LPS / capsule | 3337230 | 3336211 |
| Translation, post-translational modification | 3337691 | 3337227 |
| Cell wall / LPS / capsule | 3338455 | 3337691 |
| Hypothetical, unclassified, unknown | 3338640 | 3338455 |
| Cell wall / LPS / capsule | 3339676 | 3338678 |
| Hypothetical, unclassified, unknown | 3340116 | 3339676 |
| Transport of small molecules | 3340748 | 3340113 |
| Hypothetical, unclassified, unknown | 3343177 | 3343710 |
| Hypothetical, unclassified, unknown | 3345099 | 3343798 |
| Transport of small molecules | 3345795 | 3345112 |
| Hypothetical, unclassified, unknown | 3347038 | 3345788 |
| Hypothetical, unclassified, unknown | 3346976 | 3347740 |
| Nucleotide biosynthesis and metabolism | 3350231 | 3348837 |
| Hypothetical, unclassified, unknown | 3350637 | 3350410 |
| Energy metabolism | 3354171 | 3353497 |
| Putative enzymes | 3360653 | 3359268 |
| Nucleotide biosynthesis and metabolism | 3365743 | 3365006 |
| Hypothetical, unclassified, unknown | 3369268 | 3369035 |
| DNA replication, recombination, modification | 3372705 | 3370099 |
| Hypothetical, unclassified, unknown | 3373170 | 3372796 |
| Hypothetical, unclassified, unknown | 3378511 | 3378948 |
| Hypothetical, unclassified, unknown j | 3383947 | 3384333 |
| Hypothetical, unclassified, unknown | 3385183 | 3384377 |
| Putative enzymes | 3387828 | 3386269 |
| Biosynthesis of cofactors, prosthetic group | 3394087 | 3394683 |
| Hypothetical, unclassified, unknown | 3397373 | 3397095 |
| Hypothetical, unclassified, unknown | 3398716 | 3399648 |
| Hypothetical, unclassified, unknown | 3403811 | 3404140 |
| Hypothetical, unclassified, unknown | 3404144 | 3404524 |
| Hypothetical, unclassified, unknown | 3404538 | 3404861 |
| Hypothetical, unclassified, unknown | 3409952 | 3409608 |
| Translation, post-translational modification | 3414400 | 3414612 |
| Hypothetical, unclassified, unknown | 3416066 | 3415785 |
| Transcriptional regulators | 3436429 | 3435986 |
| Hypothetical, unclassified, unknown | 3457909 | 3456542 |
| Hypothetical, unclassified, unknown | 3464151 | 3463888 |
| Hypothetical unclassified, unknown | 3466959 | 3466072 |
| Hypothetical, unclassified, unknown | 3467084 | 3468049 |
| Hypothetical, unclassified, unknown | 3473017 | 3474135 |
| Protein secretion/export apparatus | 3476479 | 3475955 |
| Protein secretion/export apparatus | 3477629 | 3476481 |
| Protein secretion/export apparatus | 3480238 | 3479720 |
| Protein secretion/export apparatus | 3483421 | 3481913 |
| Hypothetical, unclassified, unknown | 3491410 | 3490751 |
| Fatty acid and phospholipid metabolism | 3493572 | 3492700 |
| Amino acid biosynthesis and metabolism | 3500597 | 3499485 |
| Hypothetical, unclassified, unknown | 3506241 | 3505864 |
| Hypothetical, unclassified, unknown | 3524489 | 3524160 |
| Hypothetical, unclassified, unknown | 3527733 | 3527428 |
| Hypothetical, unclassified, unknown | 3528349 | 3528230 |
| Cell wall / LPS / capsule | 3529446 | 3528427 |
| Cell wall / LPS / capsule | 3530457 | 3529507 |
| Cell wall / LPS / capsule | 3531707 | 3530466 |
| Cell wall / LPS / capsule | 3532814 | 3531750 |
| Cell wall / LPS / capsule | 3533932 | 3532811 |
| Cell wall / LPS / capsule | 3535080 | 3533947 |
| Amino acid biosynthesis and metabolism | 3535970 | 3535215 |

TABLE 1-continued

| | | |
|---|---|---|
| Amino acid biosynthesis and metabolism | 3536578 | 3535970 |
| Cell wall / LPS / capsule | 3537810 | 3536575 |
| Cell wall / LPS / capsule | 3539123 | 3537807 |
| Cell wall / LPS / capsule | 3540206 | 3539127 |
| Cell wall / LPS / capsule | 3540784 | 3540209 |
| Cell wall / LPS / capsule | 3542670 | 3540781 |
| Cell wall / LPS / capsule | 3543689 | 3542739 |
| Cell wall / LPS / capsule | 3545073 | 3543763 |
| Cell wall / LPS / capsule | 3546926 | 3545880 |
| DNA replication, recombination, modification | 3547972 | 3547688 |
| Translation, post-translational modification | 3549788 | 3548109 |
| Nucleotide biosynthesis and metabolism | 3550745 | 3550056 |
| Biosynthesis of cofactors, prosthetic group | 3556338 | 3555253 |
| DNA replication, recombination, modification | 3559197 | 3556426 |
| Biosynthesis of cofactors, prosthetic group | 3562105 | 3562803 |
| Hypothetical, unclassified, unknown | 3569012 | 3568635 |
| Carbon compound catabolism | 3571602 | 3570940 |
| Hypothetical, unclassified, unknown | 3575696 | 3574845 |
| Carbon compound catabolism | 3587432 | 3588436 |
| Hypothetical, unclassified, unknown | 3593732 | 3594031 |
| Hypothetical, unclassified, unknown | 3594207 | 3594569 |
| Hypothetical, unclassified, unknown | 3597318 | 3597797 |
| Transport of small molecules | 3600453 | 3601598 |
| Transcriptional regulators | 3609075 | 3609839 |
| Chaperones & heat shock proteins | 3614303 | 3614866 |
| Hypothetical, unclassified, unknown | 3618466 | 3617342 |
| Putative enzymes | 3619618 | 3618992 |
| Hypothetical, unclassified, unknown | 3624836 | 3625057 |
| Cell wall / LPS / capsule | 3630604 | 3629666 |
| Cell division | 3632429 | 3632683 |
| Transcription, RNA processing and degr | 3632787 | 3633422 |
| Transcriptional regulators | 3636256 | 3635540 |
| Hypothetical, unclassified, unknown | 3641232 | 3641810 |
| Transcriptional regulators | 3648065 | 3647754 |
| Adaptation, protection | 3653666 | 3653875 |
| Hypothetical, unclassified, unknown | 3668522 | 3667923 |
| Hypothetical, unclassified, unknown | 3668473 | 3668760 |
| Hypothetical, unclassified, unknown | 3669168 | 3668839 |
| Hypothetical, unclassified, unknown | 3671057 | 3670758 |
| Transport of small molecules | 3674323 | 3673007 |
| Hypothetical, unclassified, unknown | 3675159 | 3674569 |
| Hypothetical, unclassified, unknown | 3679945 | 3680460 |
| Hypothetical, unclassified, unknown | 3680967 | 3680464 |
| Hypothetical, unclassified, unknown | 3681047 | 3681460 |
| Hypothetical, unclassified, unknown | 3684716 | 3684162 |
| Hypothetical, unclassified, unknown | 3685761 | 3684904 |
| Hypothetical, unclassified, unknown | 3695480 | 3695178 |
| Hypothetical, unclassified, unknown | 3700315 | 3700785 |
| Hypothetical, unclassified, unknown | 3710224 | 3710679 |
| Putative enzymes | 3715804 | 3714914 |
| Transport of small molecules | 3716807 | 3717610 |
| Transport of small molecules | 3717604 | 3718437 |
| Hypothetical, unclassified, unknown | 3719328 | 3720056 |
| Hypothetical, unclassified, unknown | 3720122 | 3720622 |
| Hypothetical, unclassified, unknown | 3723444 | 3722989 |
| Translation, post-translational modification | 3730075 | 3729470 |
| Putative enzymes | 3740104 | 3741018 |
| Hypothetical, unclassified, unknown | 3742264 | 3742689 |
| Fatty acid and phospholipid metabolism | 3743699 | 3743938 |
| Hypothetical, unclassified, unknown | 3747455 | 3747165 |
| Transcriptional regulators | 3752477 | 3752043 |
| Hypothetical, unclassified, unknown | 3759680 | 3759375 |
| Chemotaxis | 3760819 | 3759995 |
| Hypothetical, unclassified, unknown | 3762803 | 3763126 |
| Hypothetical, unclassified, unknown | 3763680 | 3764471 |
| Hypothetical, unclassified, unknown | 3765086 | 3764475 |
| Secreted Factors (toxins, enzymes, algina | 3772560 | 3771502 |
| Hypothetical, unclassified, unknown | 3778265 | 3778603 |
| Putative enzymes | 3778703 | 3779368 |
| Hypothetical, unclassified, unknown | 3779929 | 3780075 |
| Hypothetical, unclassified, unknown | 3780127 | 3780312 |
| Hypothetical, unclassified, unknown | 3787478 | 3787020 |
| Transport of small molecules | 3790985 | 3790149 |
| Hypothetical unclassified, unknown | 3794116 | 3793814 |
| Energy metabolism | 3801103 | 3801930 |
| Energy metabolism | 3801947 | 3802483 |
| Energy metabolism | 3803342 | 3802566 |
| Hypothetical, unclassified, unknown | 3808802 | 3808317 |
| Transport of small molecules | 3814574 | 3813957 |

TABLE 1-continued

| | | |
|---|---|---|
| Hypothetical, unclassified, unknown | 3820005 | 3820271 |
| Hypothetical, unclassified, unknown | 3820307 | 3820891 |
| Energy metabolism | 3823515 | 3822514 |
| Hypothetical, unclassified, unknown | 3840747 | 3840358 |
| Transcriptional regulators | 3840843 | 3841736 |
| Related to phage, transposon, or plasmid | 3843289 | 3842273 |
| Hypothetical, unclassified, unknown | 3844104 | 3843652 |
| Biosynthesis of cofactors, prosthetic group | 3845774 | 3846334 |
| Biosynthesis of cofactors, prosthetic group | 3846336 | 3846707 |
| Transport of small molecules | 3849582 | 3848794 |
| Hypothetical, unclassified, unknown | 3850751 | 3849603 |
| Hypothetical, unclassified, unknown | 3851800 | 3850829 |
| Hypothetical, unclassified, unknown | 3852512 | 3851919 |
| Adaptation, protection | 3856130 | 3855492 |
| Hypothetical, unclassified, unknown | 3856336 | 3856545 |
| Putative enzymes | 3867706 | 3869463 |
| Hypothetical, unclassified, unknown | 3882979 | 3883437 |
| Hypothetical, unclassified, unknown | 3885710 | 3886306 |
| Transcriptional regulators | 3890649 | 3889924 |
| Translation, post-translational modification | 3895323 | 3897356 |
| Hypothetical, unclassified, unknown | 3906390 | 3907088 |
| Hypothetical, unclassified, unknown | 3907267 | 3907851 |
| Hypothetical, unclassified, unknown | 3910738 | 3911772 |
| Hypothetical, unclassified, unknown | 3912409 | 3913131 |
| DNA replication, recombination, modification | 3913128 | 3913766 |
| Hypothetical, unclassified, unknown | 3913875 | 3914054 |
| Hypothetical, unclassified, unknown | 3918468 | 3918250 |
| Hypothetical, unclassified, unknown | 3918787 | 3918470 |
| Hypothetical, unclassified, unknown | 3922072 | 3921269 |
| Transport of small molecules | 3928333 | 3927557 |
| Hypothetical, unclassified, unknown | 3936836 | 3935799 |
| Hypothetical, unclassified, unknown | 3937431 | 3937237 |
| Transport of small molecus | 3943806 | 3942649 |
| Transcription, RNA processing and degra | 3948137 | 3948811 |
| Hypothetical unclassified, unknown | 3949852 | 3950073 |
| Hypothetical, unclassified, unknown | 3952386 | 3952060 |
| Secreted Factors (toxins, enzymes, algina | 3965841 | 3967010 |
| Secreted Factors (toxins, enzymes, algina | 3977183 | 3977833 |
| Hypothetical, unclassified, unknown | 3986879 | 3937292 |
| Hypothetical, unclassified, unknown | 3997821 | 3998114 |
| Carbon compound catabolism | 4003600 | 4002107 |
| Hypothetical, unclassified, unknown | 4004782 | 4004958 |
| Hypothetical, unclassified, unknown | 4007506 | 4008036 |
| Hypothetical, unclassified, unknown | 4010326 | 4009541 |
| Carbon compound catabolism | 4023176 | 4021971 |
| Hypothetical, unclassified, unknown | 4035757 | 4035605 |
| Hypothetical, unclassified, unknown | 4036020 | 4035757 |
| Hypothetical, unclassified, unknown | 4039173 | 4040099 |
| Hypothetical, unclassified, unknown | 4040819 | 4040103 |
| Transport of small molecules | 4043060 | 4043830 |
| Hypothetical, unclassified, unknown | 4045159 | 4045569 |
| Hypothetical, unclassified, unknown | 4045588 | 4045809 |
| Hypothetical, unclassified, unknown | 4051557 | 4051096 |
| DNA replication, recombination, modification | 4052603 | 4051563 |
| Hypothetical, unclassified, unknown | 4062898 | 4062425 |
| Hypothetical, unclassified, unknown | 4067294 | 4067542 |
| Hypothetical, unclassified, unknown | 4068307 | 4067603 |
| Hypothetical, unclassified, unknown | 4068611 | 4068327 |
| Carbon compound catabolism | 4069961 | 4068676 |
| Cell wall / LPS / capsule | 4070856 | 4070011 |
| Nucleotide biosynthesis and metabolism | 4072487 | 4070859 |
| Hypothetical, unclassified, unknown | 4073986 | 4072658 |
| Fatty acid and phospholipid metabolism | 4075006 | 4074056 |
| DNA replication, recombination, modification | 4078677 | 4075156 |
| Cell wall / LPS / capsule | 4082180 | 4081044 |
| Cell wall / LPS / capsule | 4082960 | 4082184 |
| Fatty acid and phospholipid metabolism | 4083397 | 4082957 |
| Cell wall / LPS / capsule | 4084504 | 4083443 |
| Transport of small molecules | 4085010 | 4084504 |
| Transport of small molecules | 4087454 | 4085061 |
| Biosynthesis of cofactors, prosthetic group | 4090093 | 4088903 |
| Fatty acid and phospholipid metabolism | 4090905 | 4090090 |
| Cell wall / LPS / capsule | 4091654 | 4090899 |
| Translation, post-translational modification | 4092227 | 4091670 |
| Nucleotide biosynthesis and metabolism | 4092967 | 4092230 |
| Translation, post-translational modification | 4094035 | 4093166 |
| Translation, post-translational modification | 4094906 | 4094166 |
| Translation, post-translational modification | 4095171 | 4095956 |
| Hypothetical, unclassified, unknown | 4102767 | 4103060 |

TABLE 1-continued

| | | |
|---|---|---|
| Hypothetical, unclassified, unknown | 4103731 | 4104078 |
| Cell wall / LPS / capsule | 4104744 | 4105778 |
| Transport of small molecules | 4111080 | 4110346 |
| Hypothetical, unclassified, unknown | 4114932 | 4115330 |
| Transcriptional regulators | 4120468 | 4121106 |
| Hypothetical, unclassified, unknown | 4123955 | 4123260 |
| Hypothetical, unclassified, unknown | 4126089 | 4125742 |
| Hypothetical, unclassified, unknown | 4126843 | 4126163 |
| Hypothetical, unclassified, unknown | 4130598 | 4130942 |
| Hypothetical, unclassified, unknown | 4135972 | 4135451 |
| Translation, post-translational modification | 4143664 | 4142569 |
| Chemotaxis | 4148251 | 4145942 |
| Hypothetical, unclassified, unknown | 4165879 | 4165718 |
| DNA replication, recombination, modification | 4172484 | 4170769 |
| Hypothetical, unclassified, unknown | 4173067 | 4172528 |
| Hypothetical, unclassified, unknown | 4182018 | 4181377 |
| Hypothetical, unclassified, unknown | 4182769 | 4182074 |
| Hypothetical, unclassified, unknown | 4183709 | 4184938 |
| Translation, post-translational modification | 4195357 | 4195007 |
| Transcription, RNA processing and degra | 4196157 | 4195399 |
| Transcription, RNA processing and degra | 4196691 | 4196164 |
| Translation, post-translational modification | 4196958 | 4196707 |
| Protein secretion/export apparatus | 4198541 | 4197168 |
| Hypothetical, unclassified, unknown | 4204736 | 4204542 |
| Hypothetical, unclassified, unknown | 4205906 | 4205295 |
| Hypothetical, unclassified, unknown | 4206664 | 4207164 |
| Putative enzymes | 4209255 | 4210277 |
| Hypothetical, unclassified, unknown | 4221796 | 4221212 |
| Hypothetical, unclassified, unknown | 4224115 | 4223567 |
| Nucleotide biosynthesis and metabolism | 4227236 | 4225659 |
| Hypothetical, unclassified, unknown | 4231070 | 4232227 |
| Transcriptional regulators | 4234274 | 4235182 |
| DNA replication, recombination, modification | 4235219 | 4236598 |
| Transcriptional regulators | 4242294 | 4241341 |
| Hypothetical, unclassified, unknown | 4243651 | 4243079 |
| Hypothetical, unclassified, unknown | 4244184 | 4243708 |
| Hypothetical, unclassified, unknown | 4244875 | 4245723 |
| Hypothetical, unclassified, unknown | 4245809 | 4246204 |
| Hypothetical, unclassified, unknown | 4255323 | 4254736 |
| Hypothetical, unclassified, unknown | 4260396 | 4259254 |
| Hypothetical, unclassified, unknown | 4263492 | 4262377 |
| Motility & Attachment | 4265287 | 4264629 |
| Hypothetical, unclassified, unknown | 4256444 | 4265305 |
| Nucleotide biosynthesis and metabolism | 4266900 | 4266469 |
| Hypothetical, unclassified, unknown | 4267344 | 4267144 |
| Energy metabolism | 4267709 | 4267371 |
| Chaperones & heat shock proteins | 4269575 | 4267716 |
| Chaperones & heat shock proteins | 4270139 | 4269618 |
| Biosynthesis of cofactors, prosthetic group | 4270470 | 4270147 |
| Biosynthesis of cofactors, prosthetic group | 4270884 | 4270498 |
| Hypothetical, unclassified, unknown | 4272655 | 4272164 |
| Protein secretion/export apparatus | 4278945 | 4277084 |
| Hypothetical, unclassified, unknown | 4279344 | 4279006 |
| Hypothetical, unclassified, unknown | 4285483 | 4284416 |
| Hypothetical, unclassified, unknown | 4286594 | 4285476 |
| Hypothetical, unclassified, unknown | 4287709 | 4286786 |
| Hypothetical, unclassified, unknown | 4290866 | 4291234 |
| Translation, post-translational modification | 4291355 | 4294207 |
| Hypothetical, unclassified, unknown | 4294604 | 4294254 |
| Hypothetical, unclassified, unknown | 4302040 | 4303050 |
| Hypothetical, unclassified, unknown | 4305063 | 4305425 |
| Hypothetical, unclassified, unknown | 4311861 | 4310950 |
| Hypothetical, unclassified, unknown | 4312702 | 4311950 |
| Hypothetical, unclassified, unknown | 4314794 | 4314480 |
| Hypothetical, unclassified, unknown | 4316037 | 4315555 |
| Hypothetical, unclassified, unknown | 4316824 | 4316108 |
| Putative enzymes | 4318258 | 4318905 |
| DNA replication, recombination, modficat | 4330320 | 4330895 |
| Hypothetical, unclassified, unknown | 4331451 | 4332461 |
| Hypothetical, unclassified, unknown | 4332652 | 4333035 |
| Transport of small molecules | 4343527 | 4342121 |
| Hypothetical, unclassified, unknown | 4350352 | 4350738 |
| Hypothetical, unclassified, unknown | 4351594 | 4352493 |
| Transport of small molecules | 4354543 | 4355265 |
| Transport of small molecules | 4356200 | 4356862 |
| Transport of small molecules | 4356875 | 4358038 |
| Hypothetical, unclassified, unknown | 4359074 | 4358166 |
| Hypothetical, unclassified, unknown | 4373937 | 4374332 |
| Hypothetical, unclassified, unknown | 4374329 | 4374856 |

TABLE 1-continued

| | | |
|---|---|---|
| Hypothetical, unclassified, unknown | 4374849 | 4375232 |
| Hypothetical, unclassified, unknown | 4382015 | 4381500 |
| Biosynthesis of cofactors, prosthetic group | 4386351 | 4385899 |
| Biosynthesis of cofactors, prosthetic group | 4386607 | 4386356 |
| Biosynthesis of cofactors, prosthetic group | 4387086 | 4386604 |
| Transport of small molecules | 4414949 | 4414131 |
| NA replication, recombination, modification | 4418302 | 4418583 |
| Hypothetical, unclassified, unknown | 4439376 | 4439783 |
| Hypothetical, unclassified, unknown | 4442452 | 4442868 |
| Transcriptional regulators | 4444977 | 4445486 |
| Hypothetical, unclassified, unknown | 4445998 | 4446390 |
| Hypothetical, unclassified, unknown | 4447132 | 4448217 |
| Transcriptional regulators | 4453182 | 4452535 |
| Biosynthesis of cofactors, prosthetic group | 4457361 | 4458644 |
| Hypothetical, unclassified, unknown | 4459749 | 4459417 |
| Hypothetical, unclassified, unknown | 4461387 | 4462409 |
| Hypothetical, unclassified, unknown | 4462399 | 4462881 |
| Translation, post-translational modification | 4463903 | 4465438 |
| Hypothetical, unclassified, unknown | 4466753 | 4466322 |
| Translation, post-translational modification | 4466924 | 4469545 |
| Hypothetical, unclassified, unknown | 4469612 | 4470235 |
| DNA replication, recombination, modification | 4470273 | 4471310 |
| Hypothetical, unclassified, unknown | 4471402 | 4471554 |
| Related to phage, transposon, or plasmid | 4473622 | 4474638 |
| Biosynthesis of cofactors, prosthetic group | 4477976 | 4476993 |
| Hypothetical, unclassified, unknown | 4478907 | 4478626 |
| Cell wall / LPS / capsule | 4483363 | 4482260 |
| Hypothetical, unclassified, unknown | 4486179 | 4485823 |
| Hypothetical, unclassified, unknown | 4486846 | 4486202 |
| Putative enzymes | 4488409 | 4489632 |
| Secreted Factors (toxins, enzymes, algina | 4713795 | 4714283 |
| Secreted Factors (toxins, enzymes, algina | 4714313 | 4714801 |
| Secreted Factors (toxins, enzymes, algin | 4714825 | 4716042 |
| Secreted Factors (toxins, enzymes, algin | 4718556 | 4719392 |
| Secreted Factors (toxins, enzymes, algina | 4719418 | 4720062 |
| Hypothetical, unclassified, unknown | 4724034 | 4722850 |
| Transport of small molecules | 4744818 | 4745123 |
| DNA replication, recombination, modification | 4747136 | 4746639 |
| Translation, post-translational modification | 4754378 | 4753989 |
| Transcription, RNA processing and degra | 4755423 | 4754422 |
| Translation, post-translational modification | 4756066 | 4755446 |
| Translation, post-translational modification | 4756472 | 4756083 |
| Translation, post-translational modification | 4756847 | 4756491 |
| Translation, post-translational modification | 4757094 | 4756978 |
| Protein secretion/export apparatus | 4758451 | 4757123 |
| Translation, post-translational modification | 4758886 | 4758452 |
| Translation, post-translational modification | 4759066 | 4758890 |
| Translation, post-translational modification | 4759569 | 4759069 |
| Translation, post-translational modification | 4759923 | 4759573 |
| Translation, post-translational modification | 4760467 | 4759934 |
| Translation, post-translational modification | 4760871 | 4760479 |
| Translation, post-translational modification | 4761366 | 4761061 |
| Translation, post-translational modification | 4761919 | 4761380 |
| Translation, post-translational modification | 4762253 | 4761939 |
| Translation, post-translational modification | 4762634 | 4762266 |
| Translation, post-translational modification | 4762924 | 4762658 |
| Translation, post-translational modification | 4763118 | 4762927 |
| Translation, post-translational modification | 4763531 | 4763118 |
| Translation, post-translational modification | 4764229 | 4763543 |
| Translation, post-translational modification | 4764574 | 4764242 |
| Translation, post-translational modification | 4764862 | 4764587 |
| Translation, post-translational modification | 4765700 | 4764879 |
| Translation, post-translational modification | 4766011 | 4765712 |
| Translation, post-translational modification | 4766610 | 4766008 |
| Translation, post-translational modification | 4767259 | 4766624 |
| Translation, post-translational modification | 4767653 | 4767342 |
| Translation, post-translational modification | 4771655 | 4771185 |
| Translation, post-translational modification | 4772126 | 4771755 |
| Transcription, RNA processing and degr | 4776477 | 4772278 |
| Transcription, RNA processing and degr | 4780616 | 4776543 |
| Translation, post-translational modification | 4781206 | 4780838 |
| Translation, post-translational modification | 4781785 | 4781285 |
| Translation, post-translational modification | 4782679 | 4781984 |
| Translation, post-translational modification | 4783110 | 4782679 |
| Transcription, RNA processing and dea | 4783760 | 4783227 |
| Protein secretion/export apparatus | 4784138 | 4783770 |
| Hypothetical, unclassified, unknown | 4787479 | 4786733 |
| Hypothetical, unclassified, unknown | 4819927 | 4820409 |
| Two-component regulatory systems | 4820531 | 4821358 |

TABLE 1-continued

| | | |
|---|---|---|
| Hypothetical, unclassified, unknown | 4823363 | 4823079 |
| Hypothetical, unclassified, unknown | 4824123 | 4823386 |
| Hypothetical, unclassified, unknown | 4830553 | 4829642 |
| Hypothetical, unclassified, unknown | 4830963 | 4831181 |
| Nucleotide biosynthesis and metabolism | 4843551 | 4842700 |
| Hypothetical, unclassified, unknown | 4851309 | 4852316 |
| Hypothetical, unclassified, unknown | 4854008 | 4853649 |
| Carbon compound catabolism | 4856959 | 4858410 |
| Putative enzymes | 4859262 | 4858489 |
| Transcriptional regulators | 4870327 | 4869557 |
| Hypothetical, unclassified, unknown | 4875244 | 4874654 |
| Hypothetical, unclassified, unknown | 4877605 | 4876820 |
| Hypothetical, unclassified, unknown | 4878586 | 4877690 |
| Hypothetical, unclassified, unknown | 4878789 | 4879544 |
| Hypothetical, unclassified, unknown | 4882052 | 4882354 |
| Hypothetical, unclassified, unknown | 4884960 | 4884718 |
| Hypothetical, unclassified, unknown | 4887505 | 4887278 |
| Adaptation, protection | 4893696 | 4894277 |
| Hypothetical, unclassified, unknown | 4902201 | 4903295 |
| Hypothetical, unclassified, unknown | 4909403 | 4909161 |
| Hypothetical, unclassified, unknown | 4914509 | 4914126 |
| Chaperones & heat shock proteins | 4917123 | 4915480 |
| Chaperones & heat shock proteins | 4917467 | 4917174 |
| Hypothetical, unclassified, unknown | 4918932 | 4918198 |
| Putative enzymes | 4919041 | 4919799 |
| Hypothetical, unclassified, unknown | 4921980 | 4922363 |
| Hypothetical, unclassified, unknown | 4925794 | 4925315 |
| protein secretion/export apparatus | 4936615 | 4933865 |
| Hypothetical, unclassified, unknown | 4937819 | 4938214 |
| Cell wall / LPS / capsule | 4939186 | 4938275 |
| Cell division | 4940483 | 4939299 |
| Cell division | 4941787 | 4940534 |
| Cell division | 4942672 | 4941809 |
| Cell wall LPS / capsule | 4945074 | 4943632 |
| Cell wall LPS / capsule | 4946140 | 4945067 |
| Cell division | 4947329 | 4946130 |
| Cell wall / LPS / capsule | 4948675 | 4947329 |
| Cell wall / LPS / capsule | 4949771 | 4948689 |
| Cell wall / LPS / capsule | 4951147 | 4949771 |
| Cell wall / LPS / capsule | 4952603 | 4951140 |
| Cell wall / LPS / capsule | 4954342 | 4952603 |
| Cell division | 4954632 | 4954339 |
| Hypothetical, unclassified, unknown | 4955570 | 4954629 |
| Hypothetical, unclassified, unknown | 4956028 | 4955573 |
| Hypothetical, unclassified, unknown | 4959519 | 4959896 |
| Putative enzymes | 4959925 | 4960518 |
| Adaptation, protection | 4961557 | 4961150 |
| Adaptation, protection | 4962186 | 4961569 |
| Energy metabolism | 4964265 | 4963054 |
| Translation, post-translational modification | 4965500 | 4965108 |
| Translation, post-translational modification | 4965943 | 4965515 |
| Transcriptional regulators | 4968711 | 4969610 |
| Hypothetical, unclassified, unknown | 4971890 | 4970796 |
| Translation, post-translational modification | 4973331 | 4971985 |
| Hypothetical, unclassified, unknown | 4974028 | 4973399 |
| Cell wall / LPS / capsule | 4985469 | 4984204 |
| Hypothetical, unclassified, unknown | 4986154 | 4985846 |
| Hypothetical, unclassified, unknown | 4986798 | 4986151 |
| Hypothetical, unclassified, unknown | 4987283 | 4986810 |
| Transport of small molecules | 4988081 | 4987284 |
| Hypothetical, unclassified, unknown | 4989304 | 4990284 |
| Hypothetical, unclassified, unknown | 4990832 | 4991404 |
| Hypothetical, unclassified, unknown | 4991391 | 4991918 |
| Transport of small molecules | 4991918 | 4992643 |
| Transcriptional regulators | 4992869 | 4994362 |
| Hypothetical, unclassified, unknown | 4994440 | 4994748 |
| Transport of small molecules | 4994762 | 4995226 |
| Transport of small molecules | 4996118 | 4996390 |
| Hypothetical, unclassified, unknown | 5000303 | 4999908 |
| Cell division | 5012313 | 5011321 |
| Cell division | 5013430 | 5012393 |
| Translation, post-translational modification | 5013670 | 5013960 |
| Translation, post-translational modification | 5013973 | 5015427 |
| Translation, post-translational modification | 5015534 | 5016979 |
| Hypothetical, unclassified, unknown | 5017039 | 5017416 |
| Hypothetical, unclassified, unknown | 5028230 | 5027421 |
| Transcriptional regulators | 5036244 | 5036807 |
| Hypothetical, unclassified, unknown | 5046663 | 5046031 |
| Biosynthesis of cofactors, prosthetic group | 5068031 | 5068879 |

TABLE 1-continued

| | | |
|---|---|---|
| Motility & Attachment | 5069530 | 5069081 |
| Motility & Attachment | 5069762 | 5071462 |
| Motility & Attachment | 5071566 | 5072690 |
| Hypothetical, unclassified, unknown | 5073563 | 5074174 |
| Hypothetical, unclassified, unknown | 5074171 | 5074371 |
| Hypothetical, unclassified, unknown | 5077535 | 5077705 |
| Transcription, RNA processing and degr | 5091814 | 5090852 |
| Two-component regulatory systems | 5094984 | 5096321 |
| Motility & Attachment | 5099262 | 5100086 |
| Motility & Attachment | 5100083 | 5100670 |
| Adaptation, protection | 5105929 | 5104985 |
| Translation, post-translational modification | 5106957 | 5106448 |
| Translation, post-translational modification | 5109781 | 5106950 |
| Biosynthesis of cofactors, prosthetic group | 5110743 | 5109805 |
| Translation, post-translational modification | 5112662 | 5112937 |
| Hypothetical, unclassified, unknown | 5113468 | 5113004 |
| Amino acid biosynthesis and metabolism | 5114598 | 5113480 |
| Adaptation, protection | 5115889 | 5114669 |
| Translation, post-translational modification | 5116288 | 5116031 |
| Translation, post-translational modification | 5116623 | 5116312 |
| Biosynthesis of cofactors, prosthetic group | 5116854 | 5117832 |
| Hypothetical, unclassified, unknown | 5122386 | 5121898 |
| Hypothetical, unclassified, unknown | 5122901 | 5122560 |
| Hypothetical, unclassified, unknown | 5125930 | 5125604 |
| Hypothetical, unclassified, unknown | 5135815 | 5136192 |
| Transcriptional regulators | 5155560 | 5156123 |
| Hypothetical, unclassified, unknown | 5162448 | 5162068 |
| Hypothetical, unclassified, unknown | 5168754 | 5169188 |
| Hypothetical, unclassified, unknown | 5169504 | 5169250 |
| Hypothetical, unclassified, unknown | 5174979 | 5176103 |
| Hypothetical, unclassified, unknown | 5197880 | 5198323 |
| Hypothetical, unclassified, unknown | 5204927 | 5206087 |
| Hypothetical, unclassified, unknown | 5206486 | 5206208 |
| Hypothetical, unclassified, unknown | 5207006 | 5206719 |
| Hypothetical, unclassified, unknown | 5210995 | 5210705 |
| Hypothetical, unclassified, unknown | 5212104 | 5211631 |
| Nucleotide biosynthesis and metabolism | 5212832 | 5213470 |
| Hypothetical, unclassified, unknown | 5215669 | 5216202 |
| Chaperones & heat shock proteins | 5216763 | 5217551 |
| Biosynthesis of cofactors, prosthetic group | 5223561 | 5222539 |
| Cell wall / LPS / capsule | 5230910 | 5230113 |
| Biosynthesis of cofactors, prosthetic group | 5231658 | 5230900 |
| Translation, post-translational modification | 5233566 | 5232484 |
| Translation, post-translational modification | 5234852 | 5233584 |
| Cell wall / LPS / capsule | 5236773 | 5237390 |
| Biosynthesis of cofactors, prosthetic group | 5237392 | 5238240 |
| Nucleotide biosynthesis and metabolism | 5238407 | 5239348 |
| Translation, post-translational modification | 5239465 | 5240079 |
| Translation, post-translational modification | 5240121 | 5240705 |
| Hypothetical, unclassified, unknown | 5242558 | 5242253 |
| Putative enzymes | 5246122 | 5245475 |
| Hypothetical, unclassified, unknown | 5248771 | 5248070 |
| Hypothetical, unclassified, unknown | 5250617 | 5249598 |
| Fatty acid and phospholipid metabolism | 5272299 | 5271484 |
| Amino acid biosynthesis and metabolism | 5275731 | 5274007 |
| Hypothetical, unclassified, unknown | 5276282 | 5276734 |
| Hypothetical, unclassified, unknown | 5277171 | 5276842 |
| Hypothetical, unclassified, unknown | 5277950 | 5277171 |
| Hypothetical, unclassified, unknown | 5282158 | 5282505 |
| Transport of small molecules | 5286034 | 5285267 |
| Hypothetical, unclassified, unknown | 5291613 | 5291960 |
| Hypothetical, unclassified, unknown | 5297482 | 5297006 |
| Biosynthesis of cofactors, prosthetic group | 5310725 | 5311213 |
| Biosynthesis of cofactors, prosthetic group | 5311463 | 5312263 |
| Biosynthesis of cofactors, prosthetic group | 5313205 | 5313585 |
| Energy metabolism | 5313675 | 5315339 |
| Hypothetical, unclassified, unknown | 5322234 | 5322449 |
| Hypothetical, unclassified, unknown | 5322706 | 5322509 |
| Hypothetical, unclassified, unknown | 5323100 | 5322756 |
| Transcription, RNA processing and degr | 5325478 | 5323373 |
| Translation, post-translational modification | 5325921 | 5325652 |
| Translation, post-translational modification | 5329948 | 5327426 |
| Transcription, RNA processing and degra | 5331457 | 5329976 |
| Hypothetical, unclassified, unknown | 5331960 | 5331502 |
| Protein secretion/export apparatus | 5332742 | 5332353 |
| Energy metabolism | 5333500 | 5332745 |
| Cell wall / LPS / capsule | 5334903 | 5333566 |
| Biosynthesis of cofactors, prosthetic rots | 5335771 | 5334920 |
| Cell division | 5338522 | 5337899 |

TABLE 1-continued

| | | |
|---|---|---|
| Hypothetical, unclassified, unknown | 5338617 | 5338931 |
| Hypothetical, unclassified, unknown | 5343754 | 5343104 |
| Amino acid biosynthesis and metabolism | 5345891 | 5345085 |
| Chaperones & heat shock proteins | 5349760 | 5349200 |
| Transcriptional regulators | 5352078 | 5351674 |
| Transport of small molecules | 5352176 | 5352706 |
| Hypothetical, unclassified, unknown | 5353506 | 5353072 |
| Hypothetical, unclassified, unknown | 5361585 | 5362067 |
| Two-component regulatory systems | 5364070 | 5364735 |
| Transcriptional regulators | 5366256 | 5366654 |
| Hypothetical, unclassified, unknown | 5370720 | 5370475 |
| Hypothetical, unclassified, unknown | 5376851 | 5377708 |
| Hypothetical, unclassified, unknown | 5377790 | 5378095 |
| Hypothetical, unclassified, unknown | 5378092 | 5378841 |
| Hypothetical, unclassified, unknown | 5380447 | 5379512 |
| Related to phage, transposon, or plasmid | 5383811 | 5382795 |
| Hypothetical, unclassified, unknown | 5386999 | 5387721 |
| Energy metabolism | 5396858 | 5395929 |
| Fatty acid and phospholipid metabolism | 5402944 | 5402015 |
| Hypothetical, unclassified, unknown | 5414487 | 5414278 |
| Hypothetical, unclassified, unknown | 5418563 | 5418350 |
| Hypothetical, unclassified, unknown | 5419862 | 5420317 |
| Transcriptional regulators | 5422505 | 5423065 |
| Hypothetical, unclassified, unknown | 5434651 | 5434115 |
| Fatty acid and phospholipid metabolism | 5442303 | 5442773 |
| Fatty acid and phospholipid metabolism | 5442791 | 5444140 |
| Translation, post-translational modification | 5445198 | 5446082 |
| Transcription, RNA processing and degr | 5448642 | 5448965 |
| Transport of small molecules | 5460525 | 5461382 |
| Central intermediary metabolism | 5462762 | 5463604 |
| Hypothetical, unclassified, unknown | 5463917 | 5464435 |
| Central intermediary metabolism | 5464820 | 5466520 |
| Hypothetical, unclassified, unknown | 5468282 | 5468016 |
| Hypothetical, unclassified, unknown | 5468408 | 5469022 |
| Hypothetical, unclassified, unknown | 5472041 | 5471625 |
| Hypothetical, unclassified, unknown | 5472438 | 5472734 |
| Transcriptional regulators | 5473765 | 5474577 |
| Two-component regulatory systems | 5480401 | 5481090 |
| Transport of small molecules | 5483767 | 5482451 |
| Hypothetical, unclassified, unknown | 5486355 | 5486984 |
| Biosynthesis of cofactors, prosthetic group | 5487714 | 5488385 |
| Hypothetical, unclassified, unknown | 5489040 | 5489612 |
| Transcriptional reulators | 5490651 | 5489629 |
| Transcriptional regulators | 5505783 | 5505070 |
| Hypothetical, unclassified, unknown | 5507897 | 5506965 |
| Hypothetical, unclassified, unknown | 5517093 | 5516398 |
| Biosynthesis of cofactors, prosthetic group | 5519710 | 5520537 |
| Hypothetical, unclassified, unknown | 5522385 | 5522972 |
| Hypothetical, unclassified, unknown | 5524718 | 5523867 |
| Hypothetical, unclassified, unknown | 5525904 | 5524969 |
| DNA replication, recombination, modification | 5535555 | 5534161 |
| Translation, post-translational modification | 5537288 | 5537058 |
| Translation, post-translational modification | 5537737 | 5537318 |
| Nucleotide biosynthesis and metabolism | 5543364 | 5542072 |
| Hypothetical, unclassified, unknown | 5544820 | 5544635 |
| Hypothetical, unclassified, unknown | 5548644 | 5548396 |
| Translation, post-translational modification | 5549721 | 5548750 |
| Hypothetical, unclassified, unknown | 5553583 | 5553116 |
| Hypothetical, unclassified, unknown | 5556934 | 5557953 |
| Central intermediary metabolism | 5561598 | 5562413 |
| Hypothetical, unclassified, unknown | 5569089 | 5570627 |
| Hypothetical, unclassified, unknown | 5570624 | 5571160 |
| DNA replication, recombination, modification | 5574485 | 5572221 |
| Hypothetical, unclassified, unknown | 5575017 | 5574493 |
| Hypothetical, unclassified, unknown | 5576027 | 5575014 |
| DNA replication, recombination, modification | 5577916 | 5576027 |
| Hypothetical, unclassified, unknown | 5579498 | 5578680 |
| Hypothetical, unclassified, unknown | 5580961 | 5581707 |
| Putative enzymes | 5593423 | 5592632 |
| Cell wall / LPS / capsule | 5605097 | 5603820 |
| Antibiotic resistance and susceptibility | 5606102 | 5606434 |
| Hypothetical, unclassified, unknown | 5606495 | 5607670 |
| Hypothetical, unclassified, unknown | 5607667 | 5608479 |
| Transport of small molecules | 5615543 | 5613732 |
| Hypothetical, unclassified, unknown | 5615651 | 5616301 |
| Hypothetical, unclassified, unknown | 5626378 | 5624900 |
| Hypothetical, unclassified, unknown | 5627133 | 5626375 |
| Hypothetical, unclassified, unknown | 5627864 | 5627130 |
| Cell wall / LPS / capsule | 5628670 | 5627864 |

TABLE 1-continued

| | | |
|---|---|---|
| Cell wall / LPS / capsule | 5629788 | 5628667 |
| Cell wall / LPS / capsule | 5630852 | 5629785 |
| Cell wall / LPS / capsule | 5631886 | 5630849 |
| Hypothetical, unclassified, unknown | 5659184 | 5658417 |
| Transcriptional regulators | 5662741 | 5663814 |
| Hypothetical, unclassified, unknown | 5663888 | 5664868 |
| Biosynthesis of cofactors, prosthetic group | 5666056 | 5664989 |
| Amino acid biosynthesis and metabolism | 5675701 | 5675183 |
| Biotility & Attachment | 5680712 | 5679648 |
| DNA replication, recombination, modification | 5687495 | 5689714 |
| Translation, post-translational modification | 5689963 | 5691726 |
| Hypothetical, unclassified, unknown | 5691761 | 5692456 |
| Hypothetical, unclassified, unknown | 5702113 | 5701697 |
| Biosynthesis of cofactors, prosthetic group | 5702668 | 5703438 |
| Hypothetical, unclassified, unknown | 5703453 | 5704079 |
| Hypothetical, unclassified, unknown | 5704076 | 5705677 |
| Amino acid biosynthesis and metabolism | 5706190 | 5706525 |
| Protein secretion/export apparatus | 5706551 | 5706799 |
| Hypothetical, unclassified, unknown | 5708035 | 5708742 |
| Chemotaxis | 5708954 | 5710897 |
| Hypothetical, unclassified, unknown | 5720468 | 5720944 |
| Transcriptional regulators | 5723581 | 5724537 |
| Carbon compound catabolism | 5753473 | 5752463 |
| Central intermediary metabolism | 5754143 | 5753613 |
| Transcriptional regulators | 5762149 | 5762574 |
| Amino acid biosynthesis and metabolism | 5766483 | 5767892 |
| Protein secretion/export apparatus | 5777096 | 5776605 |
| Nucleotide biosynthesis and metabolism | 5777387 | 5777133 |
| Hypothetical, unclassified, unknown | 5777808 | 5777389 |
| Carbon compound catabolism | 5778133 | 5779680 |
| Hypothetical, unclassified, unknown | 5779994 | 5780812 |
| Amino acid biosynthesis and metabolism | 5791085 | 5790444 |
| Hypothetical, unclassified, unknown | 5791836 | 5792234 |
| Hypothetical, unclassified, unknown | 5797064 | 5797336 |
| Transport of small molecules | 5802128 | 5802823 |
| Cell wall / LPS / capsule | 5810280 | 5811338 |
| Cell wall / LPS / capsule | 5811335 | 5812243 |
| Cell wall / LPS / capsule | 5812240 | 5813121 |
| Cell wall LPS / capsule | 5813121 | 5813666 |
| Amino acid biosynthesis and metabolism | 5824786 | 5825718 |
| Hypothetical, unclassified, unknown | 5829469 | 5828903 |
| Hypothetical, unclassified, unknown | 5830749 | 5830312 |
| Hypothetical, unclassified, unknown | 5835481 | 5835894 |
| Putative enzymes | 5840894 | 5839104 |
| Putative enzymes | 5843799 | 5843197 |
| Chaperones & heat shock proteins | 5848366 | 5847971 |
| Putative enzymes | 5879970 | 5878753 |
| Hypothetical, unclassified, unknown | 5880481 | 5879999 |
| Translation, post-translational modification | 5883012 | 5881678 |
| Hypothetical, unclassified, unknown | 5883576 | 5883022 |
| Hypothetical, unclassified, unknown | 5883971 | 5884285 |
| Hypothetical, unclassified, unknown | 5885485 | 5885943 |
| Hypothetical, unclassified, unknown | 5896726 | 5895260 |
| Transcription, RNA processing and degr | 5900123 | 5898864 |
| Energy metabolism | 5900694 | 5900368 |
| Hypothetical, unclassified, unknown | 5907389 | 5907862 |
| Hypothetical, unclassified, unknown | 5908329 | 5907847 |
| Biosynthesis of cofactors, prosthetic group | 5921496 | 5920741 |
| Biosynthesis of cofactors, prosthetic group | 5922434 | 5921493 |
| Hypothetical, unclassified, unknown | 5941081 | 5940746 |
| Cell wall / LPS / capsule | 5941335 | 5941475 |
| Amino acid biosynthesis and metabolism | 5942744 | 5943574 |
| Putative enzymes | 5945234 | 5945932 |
| Central intermediary metabolism | 5952820 | 5952482 |
| DNA replication, recombination, modaficat | 5962715 | 5964724 |
| Energy metabolism | 5969764 | 5969354 |
| Hypothetical, unclassified, unknown | 5972202 | 5971849 |
| Translation, post-translational modificatio | 5986118 | 5985882 |
| DNA replication, recombination, modification | 5989319 | 5988645 |
| DNA replication, recombination, modification | 5989459 | 5990667 |
| Nucleotide biosynthesis and metabolism | 5990675 | 5991130 |
| Hypothetical, unclassified, unknown | 5996035 | 5996985 |
| Energy metabolism | 6000142 | 5999753 |
| Hypothetical, unclassified, unknown | 6001377 | 6000760 |
| Nucleotide biosynthesis and metabolism | 6002039 | 6001398 |
| Hypothetical, unclassified, unknown | 6003329 | 6002958 |
| Transcription, RNA processing and deg | 6004095 | 6003376 |
| Hypothetical, unclassified, unknown | 6004276 | 6005139 |
| Nucleotide biosynthesis and metabolism | 6005198 | 6005809 |

TABLE 1-continued

| | | |
|---|---|---|
| Hypothetical, unclassified, unknown | 6008397 | 6008777 |
| Hypothetical, unclassified, unknown | 6017013 | 6016621 |
| Carbon compound catabolism | 6018996 | 6018829 |
| Carbon compound catabolism | 6019347 | 6019180 |
| Biosynthesis of cofactors, prosthetic group | 6025304 | 6026194 |
| Two-component regulatory systems | 6032267 | 6031365 |
| Hypothetical, unclassified, unknown | 6060199 | 6059822 |
| Hypothetical, unclassified, unknown | 6063831 | 6063352 |
| Putative enzymes | 6069098 | 6067944 |
| Hypothetical, unclassified, unknown | 6074229 | 6075206 |
| Transcriptional regulators | 6082866 | 6083072 |
| Hypothetical, unclassified, unknown | 6083104 | 6083508 |
| Hypothetical, unclassified, unknown | 6083752 | 6084084 |
| Hypothetical, unclassified, unknown | 6084544 | 6084368 |
| Carbon compound catabolism | 6096706 | 6097026 |
| Hypothetical, unclassified, unknown | 6148318 | 6149181 |
| Hypothetical, unclassified, unknown | 6151313 | 6151525 |
| Hypothetical, unclassified, unknown | 6155202 | 6154783 |
| Hypothetical, unclassified, unknown | 6158178 | 6158942 |
| Translation, post-translational modification | 6159562 | 6158948 |
| Hypothetical, unclassified, unknown | 6171732 | 6171926 |
| Hypothetical, unclassified, unknown | 6172872 | 6172711 |
| Hypothetical, unclassified, unknown | 6188854 | 6188165 |
| Transport of small molecules | 6195308 | 6196315 |
| Hypothetical, unclassified, unknown | 6219068 | 6218856 |
| Transport of small molecules | 6221100 | 6222857 |
| Transport of small molecules | 6225924 | 6224896 |
| Hypothetical, unclassified, unknown | 6227081 | 6227449 |
| Hypothetical, unclassified, unknown | 6228243 | 6227602 |
| Hypothetical, unclassified, unknown | 6236228 | 6235830 |
| Central intermediary metabolism | 6244945 | 6243110 |
| Cell wall / LPS / capsule | 6247689 | 6246325 |
| Energy metabolism | 6248235 | 6247810 |
| Energy metabolism | 6249653 | 6248277 |
| Energy metabolism | 6250544 | 6249684 |
| Energy metabolism | 6252139 | 6250595 |
| Energy metabolism | 6252694 | 6252158 |
| Energy metabolism | 6253176 | 6252706 |
| Energy metabolism | 6253491 | 6253234 |
| Energy metabolism | 6254410 | 6253541 |
| Energy metabolism | 6254807 | 6254427 |
| Cell division | 6255843 | 6254971 |
| Hypothetical, unclassified, unknown | 6260053 | 6259670 |
| Hypothetical, unclassified, unknown | 6263563 | 6261827 |
| Translation, post-translational modification | 6264211 | 6263804 |
| Translation, post-translational modification | 6264360 | 6264226 |

TABLE 2

| Pa_ID | nt length | prob | Gene Name |
|---|---|---|---|
| 4269 | 4200 | 0.9999719 | rpoC |
| 4270 | 4074 | 0.9999719 | rpoB |
| 3640 | 3522 | 0.9999058 | dnaE |
| 1156 | 2892 | 0.9995054 | nrdA |
| 3834 | 2853 | 0.9994519 | valS |
| 4560 | 2832 | 0.9994208 | ileS |
| 595 | 2775 | 0.999327 | ostA |
| 3168 | 2772 | 0.9993217 | gyrA |
| 4403 | 2751 | 0.9992831 | secA |
| 903 | 2625 | 0.9990012 | alaS |
| 3987 | 2622 | 0.9989933 | leuS |
| 1787 | 2610 | 0.998961 | acnB |
| 3011 | 2607 | 0.9989528 | topA |
| 4744 | 2523 | 0.9986937 | infB |
| 2615 | 2436 | 0.9983575 | ftsK |
| 4 | 2421 | 0.9982914 | gyrB |
| 1803 | 2397 | 0.99818 | lon |
| 3648 | 2394 | 0.9981655 | |
| 1529 | 2385 | 0.9981216 | lig |
| 2739 | 2379 | 0.9980917 | pheT |
| 3704 | 2310 | 0.9977116 | |
| 4964 | 2265 | 0.9974239 | parC |
| 5050 | 2220 | 0.9971 | priA |
| 260 | 2151 | 0.9965225 | |
| 1372 | 2136 | 0.9963824 | |
| 2071 | 2109 | 0.996116 | fusA2 |
| 4740 | 2106 | 0.9960852 | pnp |
| 8 | 2055 | 0.9955228 | glyS |
| 1532 | 2046 | 0.9954155 | dnaX |
| 3482 | 2034 | 0.9952684 | metG |
| 5296 | 2010 | 0.9949599 | rep |
| 1939 | 1998 | 0.9947981 | |
| 1480 | 1974 | 0.9944589 | ccmF |
| 5072 | 1944 | 0.9940037 | |
| 2744 | 1923 | 0.9936629 | thrS |
| 1068 | 1911 | 0.9934596 | |
| 1596 | 1905 | 0.9933555 | htpG |
| 3157 | 1890 | 0.9930879 | |
| 4967 | 1890 | 0.9930879 | parE |
| 4044 | 1884 | 0.9929779 | dxs |
| 1370 | 1866 | 0.9926372 | |
| 3821 | 1863 | 0.9925788 | secD |
| 3810 | 1860 | 0.99252 | hscA |
| 1810 | 1848 | 0.99228 | |
| 5549 | 1836 | 0.9920322 | glmS |
| 4997 | 1812 | 0.9915127 | msbA |
| 767 | 1800 | 0.9912404 | lepA |
| 5187 | 1791 | 0.9910304 | |
| 1583 | 1773 | 0.9905952 | sdhA |
| 5051 | 1764 | 0.9903698 | argS |

TABLE 2-continued

| | | | |
|---|---|---|---|
| 5529 | 1758 | 0.9902165 | |
| 3460 | 1758 | 0.9902165 | |
| 4418 | 1740 | 0.9897418 | ftsI |
| 5568 | 1737 | 0.9896605 | |
| 2298 | 1725 | 0.9893287 | |
| 4696 | 1725 | 0.9893287 | ilvI |
| 3725 | 1716 | 0.9890729 | recJ |
| 956 | 1716 | 0.9890729 | proS |
| 4868 | 1701 | 0.9886329 | ureC |
| 4526 | 1701 | 0.9886329 | pilB |
| 3162 | 1680 | 0.9879869 | rpsA |
| 1794 | 1671 | 0.987699 | glnS |
| 4732 | 1665 | 0.9875032 | pgi |
| 2075 | 1662 | 0.9874041 | |
| 2953 | 1656 | 0.9872036 | |
| 4385 | 1644 | 0.986793 | groEL |
| 3637 | 1629 | 0.9862612 | pyrG |
| 1251 | 1626 | 0.9861522 | |
| 183 | 1611 | 0.9855946 | atsA |
| 5065 | 1602 | 0.9852493 | |
| 3769 | 1578 | 0.9842875 | guaA |
| 2818 | 1578 | 0.9842875 | |
| 3024 | 1560 | 0.9835251 | |
| 5131 | 1548 | 0.9829965 | pgm |
| 1331 | 1548 | 0.9829965 | |
| 1 | 1545 | 0.9828617 | dnaA |
| 5556 | 1545 | 0.9828617 | atpA |
| 4961 | 1539 | 0.9825889 | |
| 3984 | 1536 | 0.9824509 | lnt |
| 2207 | 1521 | 0.9817442 | |
| 2343 | 1509 | 0.9811584 | mtlY |
| 3103 | 1509 | 0.9811584 | xcpR. |
| 1820 | 1503 | 0.9808585 | nhaB |
| 985 | 1497 | 0.9805538 | |
| 3570 | 1494 | 0.9803997 | mmsA |
| 4462 | 1494 | 0.9803997 | rpoN |
| 443 | 1491 | 0.9802443 | |
| 4745 | 1482 | 0.9797707 | nusA |
| 5006 | 1479 | 0.9796104 | |
| 2097 | 1476 | 0.9794487 | |
| 5237 | 1467 | 0.9789561 | |
| 4417 | 1464 | 0.9787893 | murE |
| 2037 | 1461 | 0.9786211 | |
| 202 | 1458 | 0.9784516 | |
| 427 | 1458 | 0.9784516 | oprM |
| 2521 | 1455 | 0.9782808 | czcB |
| 4483 | 1455 | 0.9782808 | gatA |
| 4329 | 1452 | 0.9781087 | pykA |
| 913 | 1449 | 0.9779351 | mgtE |
| 4484 | 1446 | 0.9777602 | gatB |
| 4411 | 1443 | 0.9775839 | murC |
| 1587 | 1437 | 0.9772271 | lpdG |
| 2073 | 1431 | 0.9768646 | |
| 2002 | 1425 | 0.9764964 | |
| 2391 | 1425 | 0.9764964 | |
| 1551 | 1416 | 0.975933 | |
| 5119 | 1410 | 0.9755499 | glnA |
| 686 | 1410 | 0.9755499 | |
| 3876 | 1407 | 0.9753561 | narK2 |
| 704 | 1395 | 0.9745653 | |
| 2991 | 1395 | 0.9745653 | sth |
| 4931 | 1395 | 0.9745653 | dnaB |
| 3001 | 1386 | 0.9739556 | |
| 1795 | 1383 | 0.9737491 | cysS |
| 3777 | 1380 | 0.973541 | xseA |
| 4416 | 1377 | 0.9733313 | murF |
| 5554 | 1377 | 0.9733313 | atpD |
| 3746 | 1374 | 0.9731199 | ffh |
| 2629 | 1371 | 0.9729068 | purB |
| 373 | 1368 | 0.972692 | ftsY |
| 1217 | 1368 | 0.972692 | |
| 3081 | 1368 | 0.972692 | |
| 2131 | 1362 | 0.9722573 | |
| 2729 | 1350 | 0.9713671 | |
| 119 | 1350 | 0.9713671 | |
| 4848 | 1350 | 0.9713671 | accC |
| 4439 | 1347 | 0.9711402 | trpS |
| 4414 | 1347 | 0.9711402 | murD |
| 2641 | 1347 | 0.9711402 | nuoF |
| 2843 | 1347 | 0.9711402 | |
| 2336 | 1341 | 0.9706808 | |
| 4547 | 1338 | 0.9704484 | pilR |
| 4749 | 1338 | 0.9704484 | glmM |
| 5224 | 1335 | 0.9702141 | pepP |
| 2475 | 1335 | 0.9702141 | |
| 3638 | 1329 | 0.96974 | |
| 4243 | 1329 | 0.96974 | secY |
| 716 | 1326 | 0.9695001 | |
| 2214 | 1323 | 0.9692583 | |
| 2794 | 1317 | 0.968769 | |
| 4887 | 1317 | 0.968769 | |
| 3280 | 1317 | 0.968769 | oprO |
| 3154 | 1317 | 0.968769 | wzy |
| 2539 | 1314 | 0.9685214 | |
| 3159 | 1311 | 0.9682719 | wbpA |
| 2338 | 1311 | 0.9682719 | |
| 1183 | 1311 | 0.9682719 | dctA |
| 1120 | 1308 | 0.9680204 | |
| 4099 | 1305 | 0.9677669 | |
| 2986 | 1302 | 0.9675113 | |
| 972 | 1299 | 0.9672538 | tolB |
| 2734 | 1296 | 0.9669942 | |
| 4938 | 1293 | 0.9667326 | purA |
| 594 | 1293 | 0.9667326 | surA |
| 3635 | 1290 | 0.9664688 | eno |
| 1215 | 1287 | 0.966203 | |
| 3977 | 1284 | 0.9659351 | hemL |
| 2612 | 1281 | 0.9656651 | serS |
| 4988 | 1278 | 0.9653929 | waaA |
| 1895 | 1275 | 0.9651185 | |
| 1373 | 1269 | 0.9645633 | fabF2 |
| 4666 | 1269 | 0.9645633 | hemA |
| 4450 | 1266 | 0.9642824 | murA |
| 1951 | 1266 | 0.9642824 | |
| 5239 | 1260 | 0.9637139 | rho |
| 4408 | 1254 | 0.9631363 | ftsA |
| 2080 | 1251 | 0.9628441 | |
| 2988 | 1251 | 0.9628441 | |
| 1155 | 1248 | 0.9625495 | nrdB |
| 3147 | 1242 | 0.9619534 | wbpJ |
| 1488 | 1239 | 0.9616518 | |
| 904 | 1239 | 0.9616518 | lysC |
| 3153 | 1236 | 0.9613478 | wzx |
| 3733 | 1230 | 0.9607326 | |
| 1595 | 1230 | 0.9607326 | |
| 2042 | 1230 | 0.9607326 | |
| 1914 | 1227 | 0.9604213 | |
| 2500 | 1227 | 0.9604213 | |
| 446 | 1224 | 0.9601075 | |
| 4008 | 1224 | 0.9601075 | |
| 2928 | 1224 | 0.9601075 | |
| 4566 | 1221 | 0.9597913 | obg |
| 5221 | 1218 | 0.9594726 | |
| 2347 | 1218 | 0.9594726 | |
| 4212 | 1218 | 0.9594726 | |
| 687 | 1215 | 0.9591513 | |
| 273 | 1215 | 0.9591513 | |
| 1352 | 1212 | 0.9588275 | |
| 1783 | 1212 | 0.9588275 | nasA |
| 4430 | 1212 | 0.9588275 | |
| 2228 | 1212 | 0.9588275 | |
| 5320 | 1209 | 0.9585011 | dfp |
| 2219 | 1209 | 0.9585011 | opdE |
| 1098 | 1209 | 0.9585011 | fleS |
| 3589 | 1206 | 0.9581721 | |
| 501 | 1206 | 0.9581721 | bioF |
| 2221 | 1206 | 0.9581721 | |
| 4413 | 1200 | 0.9575063 | ftsW |
| 1974 | 1200 | 0.9575063 | |
| 4190 | 1197 | 0.9571695 | |
| 1107 | 1197 | 0.9571695 | |
| 2092 | 1194 | 0.9568299 | |
| 2553 | 1191 | 0.9564877 | |
| 1489 | 1191 | 0.9564877 | |
| 3650 | 1191 | 0.9564877 | dxr |
| 546 | 1191 | 0.9564877 | metK |
| 4407 | 1185 | 0.9557951 | ftsZ |
| 4219 | 1185 | 0.9557951 | |

TABLE 2-continued

| | | | |
|---|---|---|---|
| 2062 | 1182 | 0.9554447 | |
| 2001 | 1182 | 0.9554447 | atoB |
| 2103 | 1179 | 0.9550915 | |
| 559 | 1179 | 0.9550915 | |
| 4991 | 1176 | 0.9547355 | |
| 3542 | 1170 | 0.954015 | |
| 1896 | 1170 | 0.954015 | |
| 2922 | 1170 | 0.954015 | |
| 1588 | 1167 | 0.9536505 | sucC |
| 787 | 1164 | 0.953283 | |
| 3891 | 1164 | 0.953283 | |
| 2015 | 1164 | 0.953283 | |
| 552 | 1164 | 0.953283 | pgk |
| 4636 | 1161 | 0.9529127 | |
| 3773 | 1158 | 0.9525394 | |
| 3523 | 1158 | 0.9525394 | |
| 5390 | 1155 | 0.9521632 | |
| 1237 | 1152 | 0.951784 | |
| 1162 | 1152 | 0.951784 | dapE |
| 3444 | 1149 | 0.9514018 | |
| 1535 | 1149 | 0.9514018 | |
| 3096 | 1149 | 0.9514018 | xcpY |
| 3211 | 1146 | 0.9510165 | |
| 1375 | 1143 | 0.9506282 | pdxB |
| 3800 | 1143 | 0.9506282 | |
| 1509 | 1143 | 0.9506282 | |
| 2940 | 1140 | 0.9502368 | |
| 3806 | 1140 | 0.9502368 | |
| 3643 | 1137 | 0.9498423 | lpxB |
| 3150 | 1134 | 0.9494447 | wbpG |
| 2852 | 1131 | 0.949044 | |
| 2626 | 1128 | 0.94864 | trmU |
| 2552 | 1128 | 0.94864 | |
| 2831 | 1128 | 0.94664 | |
| 4617 | 1125 | 0.9482329 | |
| 4527 | 1125 | 0.9482329 | pilC |
| 105 | 1125 | 0.9482329 | coxB |
| 3230 | 1125 | 0.9482329 | |
| 4056 | 1122 | 0.9478225 | ribD |
| 3149 | 1122 | 0.9478225 | wbpH |
| 2442 | 1122 | 0.9478225 | gcvT2 |
| 2509 | 1122 | 0.9478225 | catB |
| 5010 | 1122 | 0.9478225 | waaG |
| 574 | 1122 | 0.9478225 | |
| 4565 | 1119 | 0.9474089 | proB |
| 3828 | 1119 | 0.9474089 | |
| 3093 | 1119 | 0.9474089 | |
| 3803 | 1116 | 0.946992 | |
| 689 | 1113 | 0.9465718 | |
| 3117 | 1113 | 0.9465718 | asd |
| 4002 | 1104 | 0.9452911 | rodA |
| 2119 | 1101 | 0.9448574 | |
| 146 | 1098 | 0.9444202 | |
| 2167 | 1098 | 0.9444202 | |
| 3701 | 1096 | 0.9441269 | prfB |
| 4373 | 1095 | 0.9439796 | |
| 4438 | 1095 | 0.9439796 | |
| 643 | 1092 | 0.9435355 | |
| 3969 | 1086 | 0.9426368 | |
| 3167 | 1086 | 0.9426368 | serC |
| 4665 | 1083 | 0.9421821 | prfA |
| 4415 | 1083 | 0.9421821 | mraY |
| 2090 | 1080 | 0.9417237 | |
| 3155 | 1080 | 0.9417237 | wbpE |
| 1750 | 1077 | 0.9412617 | |
| 2118 | 1077 | 0.9412617 | ada |
| 5032 | 1074 | 0.9407961 | |
| 4412 | 1074 | 0.9407961 | murG |
| 5034 | 1068 | 0.9398537 | hemE |
| 2242 | 1068 | 0.9398537 | |
| 5011 | 1068 | 0.9398537 | waaC |
| 3827 | 1068 | 0.9398537 | |
| 555 | 1065 | 0.9393769 | fda |
| 5044 | 1065 | 0.9393769 | pilM |
| 3148 | 1065 | 0.9393769 | wbpI |
| 945 | 1062 | 0.9388964 | purM |
| 3646 | 1062 | 0.9388964 | lpxD |
| 1004 | 1059 | 0.938412 | nadA |
| 3360 | 1059 | 0.938412 | |
| 4097 | 1059 | 0.938412 | |
| 69 | 1059 | 0.938412 | |
| 5161 | 1059 | 0.938412 | rmlB |
| 1777 | 1053 | 0.9374317 | oprF |
| 646 | 1053 | 0.9374317 | |
| 2963 | 1050 | 0.9369357 | |
| 1690 | 1050 | 0.9369357 | pscU |
| 3160 | 1047 | 0.9364357 | wzz |
| 971 | 1044 | 0.9359319 | tolA |
| 2492 | 1044 | 0.9359319 | mexT |
| 2549 | 1044 | 0.9359319 | |
| 1409 | 1041 | 0.935424 | aphA |
| 4149 | 1041 | 0.935424 | |
| 3617 | 1041 | 0.935424 | recA |
| 5012 | 1038 | 0.9349121 | waaF |
| 3519 | 1038 | 0.9349121 | |
| 2197 | 1038 | 0.9349121 | |
| 4481 | 1038 | 0.9349121 | mreB |
| 98 | 1038 | 0.9349121 | |
| 3989 | 1038 | 0.9349121 | holA |
| 3666 | 1035 | 0.9343961 | dapD |
| 203 | 1035 | 0.9343961 | |
| 82 | 1035 | 0.9343961 | |
| 3492 | 1035 | 0.9343961 | |
| 5531 | 1029 | 0.933519 | tonB |
| 580 | 1026 | 0.9328235 | gcp |
| 4655 | 1023 | 0.932291 | hemH |
| 3981 | 1023 | 0.932291 | |
| 3759 | 1023 | 0.932291 | |
| 4895 | 1023 | 0.932291 | |
| 2977 | 1020 | 0.9317542 | murB |
| 4681 | 1020 | 0.9317542 | |
| 4151 | 1020 | 0.9317542 | acoB |
| 4952 | 1020 | 0.9317542 | |
| 2491 | 1020 | 0.9317542 | |
| 2303 | 1020 | 0.9317542 | |
| 3145 | 1020 | 0.9317542 | wbpL |
| 2223 | 1020 | 0.9317542 | |
| 3434 | 1017 | 0.9312132 | |
| 1102 | 1017 | 0.9312132 | fliG |
| 2370 | 1017 | 0.9312132 | |
| 4797 | 1017 | 0.9312132 | |
| 2690 | 1017 | 0.9312132 | |
| 3993 | 1017 | 0.9312132 | |
| 445 | 1017 | 0.9312132 | |
| 2740 | 1017 | 0.9312132 | pheS |
| 2060 | 1017 | 0.9312132 | |
| 4966 | 1014 | 0.930668 | |
| 3868 | 1011 | 0.9301183 | |
| 5110 | 1011 | 0.9301183 | fbp |
| 3840 | 1011 | 0.9301183 | |
| 5503 | 1008 | 0.9295644 | |
| 4322 | 1008 | 0.9295644 | |
| 498 | 1008 | 0.9295644 | |
| 4209 | 1005 | 0.929006 | |
| 402 | 1005 | 0.929006 | pyrB |
| 3195 | 1005 | 0.929006 | gapA |
| 2026 | 1002 | 0.9284432 | |
| 4238 | 1002 | 0.9284432 | rpoA |
| 3416 | 1002 | 0.9284432 | |
| 2981 | 999 | 0.927876 | lpxK |
| 4480 | 993 | 0.9267279 | mreC |
| 927 | 990 | 0.9261471 | ldhA |
| 280 | 990 | 0.9261471 | cysA |
| 143 | 990 | 0.9261471 | |
| 593 | 987 | 0.9255616 | pdxA |
| 2467 | 987 | 0.9255616 | |
| 2961 | 987 | 0.9255616 | holB |
| 2253 | 987 | 0.9255616 | ansA |
| 26 | 987 | 0.9255616 | |
| 728 | 984 | 0.9249716 | |
| 3996 | 984 | 0.9249716 | lipA |
| 5033 | 981 | 0.9243768 | |
| 4457 | 981 | 0.9243768 | |
| 5396 | 978 | 0.9237773 | |
| 2227 | 978 | 0.9237773 | |
| 3445 | 972 | 0.922564 | |
| 2854 | 972 | 0.922564 | |
| 4945 | 972 | 0.922564 | miaA |

TABLE 2-continued

| | | | |
|---|---|---|---|
| 4569 | 969 | 0.9219502 | ispB |
| 660 | 969 | 0.9219502 | |
| 543 | 969 | 0.9219502 | |
| 2767 | 969 | 0.9219502 | |
| 4051 | 969 | 0.9219502 | thiL |
| 3089 | 966 | 0.9213315 | |
| 2293 | 966 | 0.9213315 | |
| 851 | 963 | 0.9207078 | |
| 2683 | 963 | 0.9207078 | |
| 4544 | 963 | 0.9207078 | rluD |
| 2211 | 960 | 0.9200793 | |
| 1213 | 960 | 0.9200793 | |
| 2975 | 957 | 0.9194457 | rluC |
| 5085 | 957 | 0.9194457 | |
| 715 | 957 | 0.9194457 | |
| 2051 | 954 | 0.9188071 | |
| 2874 | 954 | 0.9188071 | |
| 815 | 954 | 0.9188071 | |
| 3782 | 954 | 0.9188071 | |
| 407 | 954 | 0.9188071 | gshB |
| 2730 | 954 | 0.9188071 | |
| 2407 | 954 | 0.9188071 | |
| 3639 | 951 | 0.9181635 | accA |
| 479 | 951 | 0.9181635 | |
| 3146 | 951 | 0.9181635 | wbpK |
| 3158 | 951 | 0.9181635 | wbpB |
| 1911 | 951 | 0.9181635 | |
| 5325 | 951 | 0.9181635 | |
| 9 | 948 | 0.9175148 | glyQ |
| 2949 | 948 | 0.9175148 | |
| 4557 | 945 | 0.9168609 | lytB |
| 759 | 945 | 0.9168609 | |
| 829 | 942 | 0.9162018 | |
| 4670 | 942 | 0.9162018 | prs |
| 2110 | 942 | 0.9162018 | |
| 4420 | 942 | 0.9162018 | |
| 5260 | 942 | 0.9162018 | hemC |
| 233 | 942 | 0.9162018 | |
| 3242 | 939 | 0.9155375 | |
| 2258 | 939 | 0.9155375 | ptxR |
| 159 | 939 | 0.9155375 | |
| 2157 | 939 | 0.9155375 | |
| 2968 | 939 | 0.9155375 | fabD |
| 4561 | 939 | 0.9155375 | ribF |
| 4926 | 936 | 0.914868 | |
| 4792 | 936 | 0.914868 | |
| 2536 | 936 | 0.914868 | |
| 3036 | 933 | 0.9141931 | |
| 5173 | 933 | 0.9141931 | |
| 4170 | 933 | 0.9141931 | arcC |
| 2551 | 933 | 0.9141931 | |
| 2507 | 933 | 0.9141931 | catA |
| 869 | 933 | 0.9141931 | pbpG |
| 2123 | 933 | 0.9141931 | |
| 4908 | 933 | 0.9141931 | |
| 4068 | 930 | 0.9135129 | |
| 4813 | 930 | 0.9135129 | lipC |
| 2681 | 930 | 0.9135129 | |
| 2951 | 930 | 0.9135129 | etfA |
| 4809 | 930 | 0.9135129 | fdhE |
| 2017 | 930 | 0.9135129 | |
| 3605 | 927 | 0.9128273 | |
| 1517 | 927 | 0.9128273 | |
| 4037 | 927 | 0.9128273 | |
| 1555 | 927 | 0.9128273 | |
| 477 | 927 | 0.9128273 | |
| 3829 | 924 | 0.9121363 | |
| 4174 | 924 | 0.9121363 | |
| 205 | 921 | 0.9114397 | |
| 100 | 921 | 0.9114397 | |
| 2220 | 921 | 0.9114397 | |
| 2383 | 921 | 0.9114397 | |
| 133 | 918 | 0.9107377 | |
| 771 | 918 | 0.9107377 | era |
| 2469 | 915 | 0.9100301 | |
| 1986 | 915 | 0.9100301 | pqqB |
| 113 | 915 | 0.9100301 | |
| 2689 | 915 | 0.9100301 | |
| 70 | 915 | 0.9100301 | |
| 3330 | 915 | 0.9100301 | |
| 2428 | 915 | 0.9100301 | |
| 3850 | 912 | 0.9093169 | |
| 2474 | 912 | 0.9093169 | |
| 4305 | 912 | 0.9093169 | |
| 4406 | 912 | 0.9093169 | lpxC |
| 3776 | 909 | 0.908598 | |
| 448 | 909 | 0.908598 | |
| 1638 | 909 | 0.908598 | |
| 1342 | 909 | 0.908598 | |
| 5162 | 909 | 0.908598 | rmlD |
| 3892 | 909 | 0.908598 | |
| 1328 | 909 | 0.908598 | |
| 702 | 906 | 0.9078734 | |
| 1000 | 906 | 0.9078734 | |
| 1145 | 903 | 0.9071431 | |
| 730 | 903 | 0.9071431 | |
| 5364 | 903 | 0.9071431 | |
| 4436 | 900 | 0.906407 | |
| 3886 | 900 | 0.906407 | |
| 932 | 900 | 0.906407 | cysM |
| 705 | 900 | 0.906407 | |
| 4349 | 897 | 0.9056651 | |
| 1223 | 894 | 0.9049173 | |
| 2316 | 894 | 0.9049173 | |
| 2877 | 894 | 0.9049173 | |
| 207 | 894 | 0.9049173 | |
| 3433 | 894 | 0.9049173 | |
| 1321 | 891 | 0.9041635 | cyoE |
| 3312 | 891 | 0.9041635 | |
| 2879 | 891 | 0.9041635 | |
| 5358 | 891 | 0.9041635 | ubiA |
| 1461 | 891 | 0.9041635 | |
| 2101 | 891 | 0.9041635 | |
| 11 | 888 | 0.9034038 | |
| 1859 | 888 | 0.9034038 | sucD |
| 1589 | 888 | 0.9034038 | |
| 3088 | 888 | 0.9034038 | |
| 4043 | 888 | 0.9034038 | ispA |
| 2185 | 885 | 0.9026381 | |
| 4850 | 885 | 0.9026381 | prmA |
| 5163 | 882 | 0.9018663 | rmlA |
| 209 | 882 | 0.9018663 | |
| 188 | 882 | 0.9018663 | |
| 1010 | 879 | 0.9010883 | dapA |
| 2830 | 876 | 0.9003042 | htpX |
| 412 | 876 | 0.9003042 | pilK |
| 1138 | 876 | 0.9003042 | |
| 1135 | 876 | 0.9003042 | |
| 2441 | 876 | 0.9003042 | |
| 5562 | 873 | 0.8995139 | spoOJ |
| 626 | 873 | 0.8995139 | |
| 3112 | 873 | 0.8995139 | accD |
| 3655 | 870 | 0.8987173 | tsf |
| 1528 | 870 | 0.8987173 | zipA |
| 5560 | 870 | 0.8987173 | atpB |
| 1698 | 867 | 0.8979144 | popN |
| 2863 | 867 | 0.8979144 | lipH |
| 2915 | 867 | 0.8979144 | |
| 1630 | 867 | 0.8979144 | |
| 5335 | 864 | 0.8971052 | |
| 5457 | 864 | 0.8971052 | |
| 4409 | 864 | 0.8971052 | ftsQ |
| 211 | 864 | 0.8971052 | mdcD |
| 5555 | 861 | 0.8962895 | atpG |
| 1622 | 861 | 0.8962895 | |
| 2418 | 861 | 0.8962895 | |
| 2142 | 861 | 0.8962895 | |
| 1687 | 861 | 0.8962895 | speE |
| 4861 | 858 | 0.8954674 | |
| 4788 | 858 | 0.8954674 | |
| 3292 | 858 | 0.8954674 | |
| 2294 | 855 | 0.8946387 | |
| 244 | 855 | 0.8946387 | |
| 708 | 855 | 0.8946387 | |
| 1796 | 855 | 0.8946387 | folD |
| 376 | 855 | 0.8946387 | rpoH |
| 768 | 855 | 0.8946387 | lepB |
| 3185 | 852 | 0.8938035 | |

TABLE 2-continued

| | | | |
|---|---|---|---|
| 4314 | 852 | 0.8938035 | purU1 |
| 4750 | 852 | 0.8938035 | folP |
| 4925 | 852 | 0.8938035 | |
| 1496 | 852 | 0.8938035 | |
| 4669 | 849 | 0.8929616 | ipk |
| 1539 | 849 | 0.8929616 | |
| 2088 | 849 | 0.8929616 | |
| 4524 | 849 | 0.8929616 | nadC |
| 3787 | 849 | 0.8929616 | |
| 2095 | 846 | 0.8921131 | |
| 3836 | 846 | 0.8921131 | kdsA |
| 1364 | 843 | 0.8912579 | |
| 4864 | 843 | 0.8912579 | ureD |
| 1454 | 843 | 0.8912579 | |
| 184 | 840 | 0.8903958 | |
| 4215 | 837 | 0.889527 | |
| 3384 | 837 | 0.889527 | phnC |
| 2329 | 837 | 0.889527 | |
| 3315 | 834 | 0.8886512 | |
| 1379 | 834 | 0.8886512 | |
| 5278 | 831 | 0.8877685 | dapF |
| 4296 | 828 | 0.8868789 | |
| 978 | 828 | 0.8868789 | |
| 4920 | 828 | 0.8868789 | nadE |
| 3395 | 828 | 0.8868789 | nosY |
| 503 | 825 | 0.8859821 | |
| 1619 | 825 | 0.8859821 | |
| 4552 | 825 | 0.8859821 | pilW |
| 3348 | 825 | 0.8859821 | |
| 1938 | 822 | 0.8850783 | |
| 4260 | 822 | 0.8850783 | rplB |
| 2251 | 819 | 0.8841673 | |
| 4167 | 819 | 0.8841673 | |
| 3936 | 819 | 0.8841673 | |
| 4969 | 819 | 0.8841673 | |
| 5132 | 819 | 0.8841673 | |
| 238 | 816 | 0.883249 | |
| 3651 | 816 | 0.883249 | cdsA |
| 4693 | 816 | 0.883249 | pssA |
| 187 | 816 | 0.883249 | |
| 4956 | 816 | 0.883249 | rhdA |
| 790 | 816 | 0.883249 | |
| 1164 | 813 | 0.8823235 | |
| 820 | 813 | 0.8823235 | |
| 2074 | 813 | 0.8823235 | |
| 4992 | 813 | 0.8823235 | |
| 4878 | 813 | 0.8823235 | |
| 204 | 810 | 0.8813907 | |
| 4492 | 810 | 0.8813907 | |
| 2591 | 607 | 0.8804504 | |
| 1624 | 807 | 0.8804504 | |
| 4759 | 807 | 0.8804504 | dapB |
| 3022 | 807 | 0.8804504 | |
| 5009 | 807 | 0.8804504 | waaP |
| 35 | 807 | 0.8804504 | trpA |
| 3314 | 804 | 0.8795027 | |
| 3505 | 804 | 0.8795027 | |
| 2678 | 804 | 0.8795027 | |
| 2010 | 804 | 0.8795027 | |
| 1732 | 801 | 0.8785475 | |
| 341 | 801 | 0.8785475 | lgt |
| 4729 | 801 | 0.8785475 | panB |
| 4662 | 798 | 0.8775847 | murI |
| 550 | 798 | 0.8775847 | |
| 4455 | 798 | 0.8775847 | |
| 2295 | 798 | 0.8775847 | |
| 2013 | 798 | 0.8775847 | |
| 416 | 795 | 0.8766143 | |
| 2349 | 795 | 0.8766143 | |
| 342 | 795 | 0.8766143 | |
| 1872 | 792 | 0.8756362 | thyA |
| 3353 | 792 | 0.8756362 | |
| 4980 | 792 | 0.8756362 | |
| 1691 | 789 | 0.8746503 | pscT |
| 642 | 789 | 0.8746503 | |
| 4651 | 789 | 0.8746503 | |
| 4157 | 789 | 0.8746503 | |
| 1462 | 789 | 0.8746503 | |
| 3443 | 789 | 0.8746503 | |
| 3578 | 786 | 0.8736566 | |
| 3657 | 786 | 0.8736566 | map |
| 4348 | 786 | 0.8736566 | |
| 2260 | 783 | 0.8726551 | |
| 862 | 783 | 0.8726551 | |
| 236 | 780 | 0.8716456 | |
| 2811 | 780 | 0.8716456 | |
| 1224 | 780 | 0.8716456 | |
| 4122 | 780 | 0.8716456 | |
| 4699 | 780 | 0.8716456 | |
| 3644 | 777 | 0.8706281 | lpxA |
| 3397 | 777 | 0.8706281 | fpr |
| 3512 | 777 | 0.8706281 | |
| 1307 | 774 | 0.8696025 | |
| 4330 | 774 | 0.8696025 | |
| 3609 | 771 | 0.8685688 | potC |
| 5063 | 771 | 0.8685688 | ubiE |
| 1366 | 771 | 0.8685688 | |
| 611 | 771 | 0.8685688 | prtR |
| 639 | 771 | 0.8685688 | |
| 4341 | 771 | 0.8685688 | |
| 2839 | 771 | 0.8685688 | |
| 2234 | 771 | 0.8685688 | |
| 4706 | 768 | 0.8675269 | |
| 1897 | 768 | 0.8675269 | |
| 2554 | 768 | 0.8675269 | |
| 5028 | 768 | 0.8675269 | |
| 2979 | 765 | 0.8664768 | kdsB |
| 216 | 765 | 0.8664768 | |
| 5469 | 765 | 0.8664768 | |
| 3220 | 765 | 0.8664768 | |
| 2411 | 765 | 0.8664768 | |
| 1591 | 765 | 0.8664768 | |
| 2989 | 765 | 0.8664768 | |
| 1088 | 762 | 0.8654183 | |
| 2515 | 762 | 0.8654183 | xylL |
| 1021 | 762 | 0.8654183 | |
| 4663 | 759 | 0.8643515 | moeB |
| 4389 | 759 | 0.8643515 | |
| 1012 | 759 | 0.8643515 | |
| 1477 | 759 | 0.8643515 | ccmC |
| 5007 | 759 | 0.8643515 | |
| 3743 | 759 | 0.8643515 | trmD |
| 3805 | 759 | 0.8643515 | pilF |
| 3151 | 756 | 0.8632761 | hisF2 |
| 4350 | 756 | 0.8632761 | |
| 4748 | 756 | 0.8632761 | tpiA |
| 5259 | 756 | 0.8632761 | hemD |
| 3652 | 756 | 0.8632761 | uppS |
| 339 | 756 | 0.8632761 | |
| 1125 | 753 | 0.8621923 | |
| 3851 | 753 | 0.8621923 | |
| 1369 | 753 | 0.8621923 | |
| 1952 | 753 | 0.8621923 | |
| 182 | 753 | 0.8621923 | |
| 309 | 753 | 0.8621923 | |
| 2952 | 750 | 0.8610999 | etfB |
| 4790 | 750 | 0.8610999 | |
| 1350 | 750 | 0.8610999 | |
| 4049 | 747 | 0.8599988 | |
| 1216 | 747 | 0.8599988 | |
| 4972 | 747 | 0.8599988 | |
| 4279 | 747 | 0.8599988 | |
| 2967 | 744 | 0.8588889 | fabG |
| 2803 | 744 | 0.8588889 | |
| 544 | 744 | 0.8588889 | |
| 4083 | 741 | 0.8577703 | |
| 1816 | 741 | 0.8577703 | dnaQ |
| 3656 | 741 | 0.8577703 | rpsB |
| 4299 | 738 | 0.8566428 | |
| 1892 | 738 | 0.8566428 | |
| 3004 | 738 | 0.8566428 | |
| 3654 | 738 | 0.8566428 | pyrH |
| 4388 | 735 | 0.8555064 | |
| 3671 | 735 | 0.8555064 | |
| 5008 | 735 | 0.8555064 | |
| 1559 | 732 | 0.854361 | |
| 1733 | 732 | 0.854361 | |
| 1165 | 729 | 0.8632064 | |

TABLE 2-continued

| | | | |
|---|---|---|---|
| 2224 | 729 | 0.8532064 | |
| 3317 | 729 | 0.8532064 | |
| 3477 | 726 | 0.8520428 | rhlR |
| 489 | 726 | 0.8520428 | |
| 4461 | 726 | 0.8520428 | |
| 1792 | 723 | 0.8508699 | |
| 3494 | 723 | 0.8508699 | |
| 4802 | 723 | 0.8508699 | |
| 502 | 723 | 0.8508699 | |
| 3888 | 723 | 0.8508699 | |
| 4181 | 720 | 0.8496877 | |
| 2229 | 720 | 0.8496877 | |
| 5334 | 720 | 0.8496877 | rph |
| 531 | 717 | 0.8484961 | |
| 3857 | 717 | 0.8484961 | |
| 3249 | 717 | 0.8484961 | |
| 3606 | 717 | 0.8484961 | |
| 906 | 714 | 0.8472951 | |
| 2749 | 714 | 0.8472951 | endA |
| 4906 | 714 | 0.8472951 | |
| 2544 | 714 | 0.8472951 | |
| 1106 | 714 | 0.8472951 | |
| 993 | 714 | 0.8472951 | |
| 1157 | 711 | 0.8460846 | |
| 1013 | 711 | 0.8460846 | purC |
| 1584 | 708 | 0.8448844 | sdhB |
| 1348 | 708 | 0.8448644 | |
| 5071 | 708 | 0.8448644 | |
| 58 | 705 | 0.8436346 | |
| 947 | 705 | 0.8436346 | |
| 3633 | 705 | 0.8436346 | |
| 2800 | 705 | 0.8436346 | |
| 4064 | 705 | 0.8436346 | |
| 1475 | 702 | 0.8423951 | ccmA |
| 1371 | 702 | 0.8423951 | |
| 4679 | 702 | 0.8423951 | |
| 279 | 699 | 0.8411457 | |
| 3171 | 699 | 0.8411457 | ubiG |
| 5281 | 699 | 0.8411457 | |
| 2876 | 699 | 0.8411457 | pyrF |
| 3488 | 699 | 0.8411457 | |
| 3681 | 696 | 0.8398864 | |
| 4273 | 696 | 0.8398864 | rplA |
| 3731 | 696 | 0.8398864 | |
| 5154 | 696 | 0.8398864 | |
| 4916 | 696 | 0.8398864 | |
| 2105 | 696 | 0.8398864 | |
| 5052 | 696 | 0.8398864 | |
| 969 | 696 | 0.8398864 | tolQ |
| 1894 | 693 | 0.8386172 | |
| 2280 | 693 | 0.8386172 | |
| 213 | 693 | 0.8386172 | |
| 733 | 693 | 0.8386172 | |
| 3163 | 690 | 0.8373379 | cmk |
| 5496 | 690 | 0.8373379 | |
| 4885 | 690 | 0.8373379 | irlR |
| 4257 | 687 | 0.8360484 | rpsC |
| 2719 | 687 | 0.8360484 | |
| 120 | 687 | 0.8360484 | |
| 504 | 687 | 0.8360484 | bioD |
| 1862 | 687 | 0.8360484 | modB |
| 527 | 684 | 0.8347487 | dnr |
| 1118 | 684 | 0.8347487 | |
| 2987 | 684 | 0.8347487 | |
| 2617 | 681 | 0.8334387 | aat |
| 3685 | 681 | 0.8334387 | |
| 2638 | 678 | 0.8321183 | nuoB |
| 1980 | 678 | 0.8321183 | |
| 2034 | 675 | 0.8307875 | |
| 1261 | 675 | 0.8307875 | |
| 2996 | 675 | 0.8307875 | nqrD |
| 3528 | 675 | 0.8307875 | rnt |
| 453 | 675 | 0.8307875 | |
| 976 | 675 | 0.8307875 | |
| 5319 | 675 | 0.8307875 | radC |
| 607 | 675 | 0.8307875 | rpe |
| 2284 | 672 | 0.8294461 | |
| 1167 | 672 | 0.8294461 | |
| 1476 | 672 | 0.8294461 | ccmB |
| 1193 | 672 | 0.8294461 | |
| 4892 | 672 | 0.8294461 | ureF |
| 330 | 672 | 0.8294461 | rpiA |
| 944 | 669 | 0.8280941 | purN |
| 1269 | 669 | 0.8280941 | |
| 243 | 669 | 0.8280941 | |
| 167 | 666 | 0.8287314 | |
| 65 | 666 | 0.8267314 | |
| 4029 | 666 | 0.8267314 | |
| 3368 | 666 | 0.8267314 | |
| 1978 | 666 | 0.8267314 | |
| 4776 | 666 | 0.8267314 | |
| 1623 | 663 | 0.8253578 | |
| 3181 | 663 | 0.8253578 | |
| 3890 | 663 | 0.8253578 | |
| 1090 | 663 | 0.8253578 | |
| 697 | 663 | 0.8253578 | |
| 1526 | 660 | 0.8239734 | |
| 2782 | 660 | 0.8239734 | |
| 3110 | 660 | 0.8239734 | |
| 4055 | 660 | 0.8239734 | ribC |
| 4121 | 660 | 0.8239734 | |
| 2832 | 657 | 0.822578 | tpm |
| 2351 | 654 | 0.8211715 | |
| 3550 | 651 | 0.8197539 | algF |
| 4998 | 651 | 0.8197539 | |
| 4757 | 651 | 0.8197539 | |
| 1504 | 651 | 0.8197539 | |
| 1049 | 648 | 0.818325 | pdxH |
| 655 | 648 | 0.818325 | |
| 2222 | 648 | 0.818325 | |
| 3859 | 648 | 0.818325 | |
| 2257 | 648 | 0.818325 | pvcD |
| 3973 | 648 | 0.818325 | |
| 4676 | 648 | 0.818325 | |
| 4453 | 648 | 0.818325 | |
| 1905 | 648 | 0.818325 | |
| 4216 | 645 | 0.8168848 | |
| 4006 | 645 | 0.8168848 | |
| 2473 | 645 | 0.8168848 | |
| 1825 | 645 | 0.8168848 | |
| 652 | 645 | 0.8168848 | vfr |
| 251 | 642 | 0.8154332 | |
| 5331 | 642 | 0.8154332 | pyrE |
| 5142 | 642 | 0.8154332 | hisH1 |
| 5534 | 642 | 0.8154332 | |
| 3730 | 642 | 0.8154332 | |
| 2007 | 639 | 0.8139701 | maiA |
| 2726 | 639 | 0.8139701 | |
| 2720 | 639 | 0.8139701 | |
| 4646 | 639 | 0.8139701 | upp |
| 826 | 639 | 0.8139701 | |
| 3495 | 639 | 0.8139701 | nth |
| 3678 | 639 | 0.8139701 | |
| 3450 | 639 | 0.8139701 | |
| 2066 | 639 | 0.8139701 | |
| 990 | 639 | 0.8139701 | |
| 4182 | 639 | 0.8139701 | |
| 2983 | 636 | 0.8124954 | |
| 3246 | 636 | 0.8124954 | rluA |
| 114 | 636 | 0.8124954 | |
| 4263 | 636 | 0.8124954 | rplC |
| 2126 | 636 | 0.8124954 | |
| 4507 | 633 | 0.811009 | |
| 1558 | 633 | 0.811009 | |
| 1397 | 633 | 0.811009 | |
| 2962 | 633 | 0.811009 | tmk |
| 4890 | 630 | 0.8095108 | |
| 629 | 630 | 0.8095108 | |
| 4019 | 630 | 0.8095108 | |
| 4440 | 630 | 0.8095108 | |
| 3232 | 627 | 0.8080008 | |
| 2614 | 627 | 0.8080008 | lolA |
| 5064 | 627 | 0.8080008 | |
| 853 | 624 | 0.8064788 | |
| 3665 | 624 | 0.8064788 | |
| 1790 | 624 | 0.8064788 | |
| 4752 | 624 | 0.8064788 | ftsJ |
| 981 | 624 | 0.8064788 | |

TABLE 2-continued

| | | | |
|---|---|---|---|
| 3988 | 624 | 0.8064788 | |
| 5341 | 621 | 0.8049447 | |
| 4239 | 621 | 0.8049447 | rpsD |
| 1757 | 618 | 0.8033984 | thrH |
| 2504 | 618 | 0.8033984 | |
| 4668 | 618 | 0.8033984 | |
| 4428 | 618 | 0.8033984 | sspA |
| 5330 | 618 | 0.8033984 | |
| 4047 | 618 | 0.8033984 | ribA |
| 2807 | 618 | 0.8033984 | |
| 3407 | 618 | 0.8033984 | hasAp |
| 1315 | 615 | 0.8018399 | |
| 5470 | 615 | 0.8018399 | |
| 4671 | 615 | 0.8018399 | |
| 1219 | 615 | 0.8018399 | |
| 571 | 615 | 0.8018399 | |
| 4871 | 615 | 0.8018399 | |
| 3754 | 612 | 0.800269 | |
| 3354 | 612 | 0.800269 | |
| 4529 | 612 | 0.800269 | |
| 5336 | 612 | 0.800269 | gmk |
| 3152 | 609 | 0.7986857 | hisH2 |
| 1962 | 609 | 0.7986857 | |
| 2459 | 606 | 0.7970898 | |
| 154 | 606 | 0.7970898 | pcaG |
| 2602 | 606 | 0.7970898 | |
| 1432 | 606 | 0.7970898 | lasI |
| 3326 | 606 | 0.7970898 | |
| 377 | 606 | 0.7970898 | |
| 4262 | 603 | 0.7954813 | rplD |
| 1089 | 603 | 0.7954813 | |
| 5190 | 603 | 0.7954813 | |
| 3273 | 600 | 0.7938601 | |
| 2451 | 600 | 0.7938601 | |
| 3472 | 597 | 0.7922259 | |
| 370 | 597 | 0.7922259 | |
| 3030 | 597 | 0.7922259 | |
| 2792 | 597 | 0.7922259 | |
| 1172 | 597 | 0.7922259 | napC |
| 3446 | 594 | 0.7905789 | |
| 4012 | 594 | 0.7905789 | |
| 2916 | 594 | 0.7905789 | |
| 4425 | 594 | 0.7905789 | |
| 684 | 594 | 0.7905789 | |
| 4345 | 591 | 0.7889187 | |
| 4063 | 591 | 0.7889187 | |
| 3281 | 591 | 0.7889187 | |
| 3796 | 588 | 0.7872454 | |
| 2774 | 588 | 0.7872454 | |
| 4553 | 588 | 0.7872454 | pilX |
| 4923 | 588 | 0.7872454 | |
| 763 | 585 | 0.7855589 | mucA |
| 2196 | 585 | 0.7855589 | |
| 3765 | 585 | 0.7855589 | |
| 1847 | 585 | 0.7855589 | |
| 3489 | 585 | 0.7855589 | |
| 3414 | 585 | 0.7855589 | |
| 4672 | 585 | 0.7855589 | |
| 1280 | 585 | 0.7855589 | |
| 4366 | 582 | 0.7838589 | sodB |
| 2936 | 582 | 0.7838589 | |
| 3255 | 579 | 0.7821455 | |
| 1785 | 579 | 0.7821455 | |
| 111 | 579 | 0.7821455 | |
| 358 | 579 | 0.7821455 | |
| 3867 | 576 | 0.7804185 | |
| 3156 | 576 | 0.7804185 | wbpD |
| 776 | 573 | 0.7786779 | |
| 3784 | 573 | 0.7786779 | |
| 4894 | 573 | 0.7786779 | |
| 4459 | 573 | 0.7786779 | |
| 2372 | 573 | 0.7786779 | |
| 2910 | 570 | 0.7769234 | |
| 1928 | 570 | 0.7769234 | rimJ |
| 475 | 570 | 0.7769234 | |
| 1955 | 570 | 0.7769234 | |
| 422 | 570 | 0.7769234 | |
| 405 | 570 | 0.7769234 | efp |
| 2851 | 567 | 0.775155 | |
| 5176 | 567 | 0.775155 | |
| 1994 | 564 | 0.7733726 | |
| 4600 | 564 | 0.7733726 | nfxB |
| 4499 | 564 | 0.7733726 | |
| 4171 | 564 | 0.7733726 | |
| 139 | 564 | 0.7733726 | ahpC |
| 3227 | 564 | 0.7733726 | ppiA |
| 1427 | 564 | 0.7733726 | |
| 2331 | 561 | 0.7715761 | |
| 2406 | 561 | 0.7715761 | |
| 3438 | 561 | 0.7715761 | folE1 |
| 4831 | 561 | 0.7715761 | |
| 4762 | 561 | 0.7715761 | grpE |
| 2584 | 561 | 0.7715761 | pgsA |
| 1204 | 558 | 0.7697653 | |
| 1675 | 558 | 0.7697653 | |
| 3653 | 558 | 0.7697653 | frr |
| 22 | 558 | 0.7697653 | |
| 2784 | 558 | 0.7697653 | |
| 3291 | 555 | 0.7679402 | |
| 5225 | 555 | 0.7679402 | |
| 535 | 555 | 0.7679402 | |
| 1472 | 555 | 0.7679402 | |
| 311 | 555 | 0.7679402 | |
| 2743 | 552 | 0.7661006 | infC |
| 1635 | 552 | 0.7661006 | kdpC |
| 1884 | 552 | 0.7661006 | |
| 54 | 549 | 0.7642464 | |
| 3767 | 549 | 0.7642464 | |
| 1543 | 549 | 0.7642464 | apt |
| 2365 | 546 | 0.7623775 | |
| 5164 | 546 | 0.7623775 | rmlC |
| 2434 | 546 | 0.7623775 | |
| 149 | 546 | 0.7623775 | |
| 1674 | 546 | 0.7623775 | folE2 |
| 171 | 543 | 0.7604938 | |
| 1481 | 543 | 0.7604938 | ccmG |
| 3726 | 540 | 0.7585952 | |
| 4251 | 540 | 0.7585952 | rplE |
| 1768 | 540 | 0.7585952 | |
| 937 | 540 | 0.7585952 | |
| 6 | 537 | 0.7566615 | |
| 5557 | 537 | 0.7566815 | atpH |
| 3396 | 537 | 0.7566815 | nosL |
| 4841 | 537 | 0.7566815 | |
| 2971 | 537 | 0.7566815 | |
| 4962 | 537 | 0.7566815 | |
| 4248 | 534 | 0.7547527 | rplF |
| 1377 | 534 | 0.7547527 | |
| 1885 | 534 | 0.7547527 | |
| 4275 | 534 | 0.7547527 | nusG |
| 4649 | 534 | 0.7547527 | |
| 2985 | 534 | 0.7547527 | |
| 1154 | 534 | 0.7547527 | |
| 5111 | 531 | 0.7528085 | gloA3 |
| 4765 | 531 | 0.7528085 | omlA |
| 3575 | 531 | 0.7528085 | |
| 4031 | 528 | 0.750849 | ppa |
| 1300 | 528 | 0.750849 | |
| 2733 | 528 | 0.750849 | |
| 4460 | 528 | 0.750849 | |
| 3905 | 528 | 0.750849 | |
| 3744 | 528 | 0.750849 | rimM |
| 1867 | 528 | 0.750849 | |
| 2455 | 528 | 0.750849 | |
| 514 | 525 | 0.7488739 | nirL |
| 4965 | 525 | 0.7488739 | |
| 2464 | 525 | 0.7488739 | |
| 3095 | 525 | 0.7488739 | xcpZ |
| 2136 | 525 | 0.7488739 | |
| 1134 | 522 | 0.7468831 | |
| 1062 | 522 | 0.7468831 | |
| 1442 | 522 | 0.7468831 | |
| 3693 | 522 | 0.7468831 | |
| 3811 | 522 | 0.7468831 | hscB |
| 145 | 519 | 0.7448766 | |
| 1845 | 519 | 0.7448766 | |
| 3100 | 519 | 0.7448766 | xcpU |
| 4866 | 519 | 0.7448766 | |

TABLE 2-continued

| | | | |
|---|---|---|---|
| 5039 | 519 | 0.7448766 | arok |
| 2496 | 516 | 0.7428542 | |
| 3911 | 516 | 0.7428542 | |
| 4050 | 516 | 0.7428542 | pgpA |
| 1610 | 516 | 0.7428542 | fabA |
| 3287 | 516 | 0.7428542 | |
| 403 | 513 | 0.7408157 | pyrR |
| 1514 | 510 | 0.7387611 | |
| 4114 | 510 | 0.7387611 | |
| 4559 | 510 | 0.7387611 | lspA |
| 47 | 510 | 0.7387611 | |
| 4104 | 510 | 0.7387611 | |
| 3965 | 510 | 0.7387611 | |
| 2184 | 510 | 0.7387611 | |
| 1912 | 507 | 0.7366902 | |
| 1657 | 507 | 0.7366902 | |
| 1666 | 507 | 0.7366902 | |
| 55 | 507 | 0.7366902 | |
| 3647 | 507 | 0.7366902 | |
| 973 | 507 | 0.7366902 | |
| 585 | 507 | 0.7366902 | |
| 2859 | 507 | 0.7366902 | greB |
| 350 | 507 | 0.7366902 | folA |
| 3288 | 504 | 0.7346029 | |
| 1967 | 501 | 0.732499 | |
| 4272 | 501 | 0.732499 | rplJ |
| 4246 | 501 | 0.732499 | rpsE |
| 3318 | 501 | 0.732499 | |
| 3756 | 501 | 0.732499 | |
| 2226 | 501 | 0.732499 | |
| 2645 | 501 | 0.7324991 | nuoJ |
| 2367 | 498 | 0.7303785 | |
| 1837 | 498 | 0.7303785 | |
| 261 | 498 | 0.7303785 | |
| 4232 | 498 | 0.7303785 | ssb |
| 1035 | 495 | 0.7282411 | |
| 5128 | 492 | 0.7260868 | secB |
| 1173 | 492 | 0.7260868 | napB |
| 1176 | 492 | 0.7260868 | napF |
| 1772 | 489 | 0.7239154 | |
| 4211 | 489 | 0.7239154 | |
| 1900 | 489 | 0.7239154 | |
| 1899 | 489 | 0.7239154 | |
| 1745 | 489 | 0.7239154 | |
| 1956 | 489 | 0.7239154 | |
| 4210 | 489 | 0.7239154 | |
| 4574 | 489 | 0.7239154 | |
| 2517 | 489 | 0.7239154 | xylY |
| 4728 | 489 | 0.7239154 | folK |
| 3403 | 486 | 0.7217268 | |
| 837 | 486 | 0.7217268 | slyD |
| 2768 | 483 | 0.7195209 | |
| 3856 | 483 | 0.7195209 | |
| 4295 | 483 | 0.7195209 | |
| 2797 | 483 | 0.7195209 | |
| 3918 | 483 | 0.7195209 | moaC |
| 3982 | 483 | 0.7195209 | |
| 4773 | 483 | 0.7195209 | |
| 5247 | 483 | 0.7195209 | |
| 5222 | 483 | 0.7195209 | |
| 5385 | 480 | 0.7172975 | |
| 4052 | 480 | 0.7172975 | nusB |
| 363 | 480 | 0.7172975 | coaD |
| 2935 | 480 | 0.7172975 | |
| 2461 | 480 | 0.7172975 | |
| 2819 | 480 | 0.7172975 | |
| 2721 | 480 | 0.7172975 | |
| 698 | 480 | 0.7172975 | |
| 336 | 480 | 0.7172975 | |
| 4395 | 480 | 0.7172975 | |
| 3207 | 480 | 0.7172975 | |
| 1464 | 480 | 0.7172975 | |
| 1026 | 477 | 0.7150564 | |
| 714 | 477 | 0.7150564 | |
| 2205 | 477 | 0.7150564 | |
| 4053 | 477 | 0.7150564 | ribE |
| 5081 | 477 | 0.7150564 | |
| 3785 | 477 | 0.7150564 | |
| 1696 | 477 | 0.7150564 | pscO |
| 1924 | 477 | 0.7150564 | |
| 4718 | 477 | 0.7150564 | |
| 808 | 474 | 0.7127976 | |
| 4644 | 474 | 0.7127976 | |
| 1593 | 474 | 0.7127976 | |
| 5246 | 474 | 0.7127976 | |
| 4454 | 474 | 0.7127976 | |
| 1008 | 474 | 0.7127976 | bcp |
| 1039 | 474 | 0.7127976 | |
| 116 | 474 | 0.7127976 | |
| 1206 | 474 | 0.7127976 | |
| 3627 | 474 | 0.7127976 | |
| 3302 | 471 | 0.7105208 | |
| 5558 | 471 | 0.7105208 | atpF |
| 4267 | 471 | 0.7105208 | rpsG |
| 2052 | 471 | 0.7105208 | cynS |
| 4847 | 471 | 0.7105208 | accB |
| 962 | 471 | 0.7105208 | |
| 2171 | 471 | 0.7105208 | |
| 4948 | 468 | 0.7082261 | |
| 332 | 468 | 0.7082261 | |
| 4107 | 468 | 0.7082261 | |
| 1482 | 468 | 0.7082261 | ccmH |
| 4183 | 468 | 0.7082261 | |
| 2427 | 468 | 0.7082261 | |
| 2786 | 468 | 0.7082261 | |
| 953 | 465 | 0.7059131 | |
| 4564 | 465 | 0.7059131 | |
| 2731 | 465 | 0.7059131 | |
| 4464 | 465 | 0.7059131 | ptsN |
| 80 | 465 | 0.7059131 | |
| 4057 | 465 | 0.7059131 | |
| 2978 | 465 | 0.7059131 | ptpA |
| 1306 | 462 | 0.7035818 | |
| 3616 | 462 | 0.7035818 | |
| 1673 | 462 | 0.7035818 | |
| 3470 | 459 | 0.701232 | |
| 3380 | 459 | 0.701232 | |
| 4746 | 459 | 0.701232 | |
| 5229 | 459 | 0.701232 | |
| 3320 | 456 | 0.6988636 | |
| 2499 | 456 | 0.6988636 | |
| 3309 | 456 | 0.6988636 | |
| 4828 | 456 | 0.6988636 | |
| 59 | 456 | 0.6988636 | osmC |
| 5321 | 456 | 0.6988636 | dut |
| 4421 | 456 | 0.6988636 | |
| 4697 | 453 | 0.6964764 | |
| 2538 | 453 | 0.6964764 | |
| 2829 | 453 | 0.6964764 | |
| 3916 | 453 | 0.6964764 | moaE |
| 3435 | 453 | 0.6964764 | |
| 115 | 453 | 0.6964764 | |
| 578 | 450 | 0.6940703 | |
| 678 | 450 | 0.6940703 | |
| 4525 | 450 | 0.6940703 | pilA |
| 1285 | 450 | 0.6940703 | |
| 614 | 450 | 0.6940703 | |
| 822 | 447 | 0.6916451 | |
| 245 | 447 | 0.6916451 | aroQ2 |
| 1815 | 447 | 0.6916451 | rnhA |
| 1594 | 447 | 0.6916451 | |
| 4630 | 444 | 0.6892007 | |
| 1122 | 444 | 0.6892007 | |
| 3067 | 444 | 0.6892007 | |
| 1105 | 444 | 0.6892007 | fliJ |
| 970 | 441 | 0.6867369 | tolR |
| 2982 | 441 | 0.6867369 | |
| 3645 | 441 | 0.6867369 | fabZ |
| 61 | 438 | 0.6842536 | |
| 1835 | 438 | 0.6842536 | |
| 5178 | 438 | 0.6842536 | |
| 1618 | 438 | 0.6842536 | |
| 2577 | 438 | 0.6842536 | |
| 3017 | 438 | 0.6842536 | |
| 2775 | 438 | 0.6842538 | |
| 1710 | 438 | 0.6842536 | exsC |
| 3341 | 435 | 0.6817506 | |
| 94 | 435 | 0.6817506 | |

TABLE 2-continued

| | | | |
|---|---|---|---|
| 2436 | 435 | 0.6817506 | |
| 4244 | 435 | 0.6817506 | rplO |
| 2756 | 435 | 0.6817506 | |
| 404 | 435 | 0.6817506 | |
| 4610 | 435 | 0.6817506 | |
| 250 | 435 | 0.6817506 | |
| 4767 | 435 | 0.6817506 | |
| 433 | 435 | 0.6817506 | |
| 2675 | 435 | 0.6817506 | |
| 720 | 435 | 0.6817506 | |
| 679 | 432 | 0.6792278 | |
| 3807 | 432 | 0.6792278 | ndk |
| 4274 | 432 | 0.6792278 | rplK |
| 3986 | 432 | 0.6792278 | |
| 52 | 429 | 0.6766849 | |
| 4433 | 429 | 0.6766849 | rplM |
| 1560 | 429 | 0.6766849 | |
| 2282 | 429 | 0.6766849 | |
| 2120 | 429 | 0.6766849 | |
| 4169 | 429 | 0.6766849 | |
| 5116 | 426 | 0.6741219 | |
| 2368 | 426 | 0.6741219 | |
| 2673 | 426 | 0.6741219 | |
| 700 | 426 | 0.6741219 | |
| 5553 | 426 | 0.6741219 | atpC |
| 2187 | 426 | 0.6741219 | |
| 3332 | 426 | 0.6741219 | |
| 45181 | 426 | 0.6741219 | |
| 2894 | 423 | 0.6715386 | |
| 653 | 423 | 0.6715386 | |
| 661 | 423 | 0.6715386 | |
| 542 | 420 | 0.6689348 | |
| 5130 | 420 | 0.6689348 | |
| 5465 | 420 | 0.6689348 | |
| 4935 | 420 | 0.6689348 | rpsF |
| 850 | 420 | 0.6689348 | |
| 2225 | 417 | 0.6663104 | |
| 4874 | 417 | 0.6663104 | |
| 5061 | 417 | 0.6663104 | |
| 1468 | 417 | 0.6663104 | |
| 264 | 417 | 0.6663104 | |
| 3962 | 417 | 0.6663104 | |
| 868 | 414 | 0.6636651 | |
| 5182 | 414 | 0.6636651 | |
| 1353 | 414 | 0.6636651 | |
| 2192 | 414 | 0.6636651 | |
| 3289 | 414 | 0.6636651 | |
| 4256 | 414 | 0.6636651 | rplP |
| 3558 | 414 | 0.6636651 | |
| 2674 | 411 | 0.6609989 | |
| 3611 | 411 | 0.6609989 | |
| 5300 | 411 | 0.6609989 | cycB |
| 2769 | 411 | 0.6609989 | |
| 3960 | 408 | 0.6583116 | |
| 1203 | 408 | 0.6583116 | |
| 5569 | 408 | 0.6583116 | rnpA |
| 4427 | 408 | 0.6583116 | sspB |
| 1129 | 408 | 0.6583116 | |
| 1465 | 408 | 0.6583116 | |
| 1645 | 408 | 0.6583116 | |
| 1659 | 408 | 0.6583116 | |
| 4764 | 405 | 0.6556029 | fur |
| 778 | 405 | 0.6556029 | |
| 474 | 405 | 0.6556029 | |
| 5404 | 405 | 0.6558029 | |
| 398 | 405 | 0.6556029 | |
| 2016 | 405 | 0.6556029 | |
| 1883 | 399 | 0.650121 | |
| 5144 | 399 | 0.650121 | |
| 2827 | 399 | 0.650121 | |
| 2107 | 399 | 0.650121 | |
| 5543 | 399 | 0.650121 | |
| 3674 | 399 | 0.650121 | |
| 4778 | 399 | 0.650121 | |
| 1358 | 399 | 0.650121 | |
| 2706 | 396 | 0.6473475 | |
| 1250 | 396 | 0.6473475 | aprI |
| 710 | 396 | 0.6473475 | gloA2 |
| 3788 | 396 | 0.6473475 | |
| 42 | 396 | 0.6473475 | |
| 2375 | 396 | 0.6473475 | |
| 5195 | 396 | 0.6473475 | |
| 4405 | 396 | 0.6473475 | |
| 2605 | 396 | 0.6473475 | |
| 3904 | 396 | 0.6473475 | |
| 4471 | 396 | 0.6473475 | |
| 4249 | 393 | 0.6445519 | rpsH |
| 5347 | 393 | 0.6445519 | |
| 4125 | 393 | 0.6445519 | hpcD |
| 4432 | 393 | 0.6445519 | rpsI |
| 3967 | 393 | 0.6445519 | |
| 2722 | 393 | 0.6445519 | |
| 5328 | 390 | 0.6417342 | |
| 4240 | 390 | 0.6417342 | rpsK |
| 4237 | 390 | 0.6417342 | rplQ |
| 4747 | 390 | 0.6417342 | secG |
| 1817 | 390 | 0.6417342 | |
| 3432 | 390 | 0.6417342 | |
| 3884 | 387 | 0.6388941 | |
| 3813 | 387 | 0.6388941 | iscU |
| 1581 | 387 | 0.6388941 | sdhC |
| 540 | 387 | 0.8388941 | |
| 3021 | 387 | 0.6388941 | |
| 4383 | 384 | 0.6360315 | |
| 4392 | 384 | 0.6360315 | |
| 2446 | 384 | 0.6360315 | gcvH2 |
| 5566 | 384 | 0.6360315 | |
| 3869 | 384 | 0.6360315 | |
| 1160 | 384 | 0.6360315 | |
| 3906 | 384 | 0.6360315 | |
| 867 | 384 | 0.6360315 | |
| 4731 | 381 | 0.6331462 | panD |
| 1355 | 381 | 0.6331462 | |
| 3041 | 381 | 0.6331462 | |
| 5339 | 381 | 0.6331462 | |
| 880 | 381 | 0.6331462 | |
| 1095 | 381 | 0.6331462 | |
| 561 | 381 | 0.6331462 | atpI |
| 591 | 381 | 0.6331462 | |
| 1518 | 381 | 0.6331462 | |
| 170 | 381 | 0.6331462 | |
| 4603 | 381 | 0.6331462 | |
| 3123 | 378 | 0.6302381 | |
| 4424 | 378 | 0.6302381 | |
| 4586 | 378 | 0.6302381 | |
| 3178 | 378 | 0.6302381 | |
| 991 | 378 | 0.6302381 | |
| 4059 | 378 | 0.6302381 | |
| 4485 | 378 | 0.6302381 | |
| 5381 | 378 | 0.6302381 | |
| 908 | 375 | 0.6273069 | |
| 2490 | 375 | 0.6273069 | |
| 680 | 375 | 0.6273069 | |
| 2753 | 375 | 0.6273069 | |
| 1456 | 375 | 0.6273069 | cheY |
| 3012 | 375 | 0.6273069 | |
| 4076 | 375 | 0.6273069 | |
| 4315 | 375 | 0.6273069 | mvaT |
| 3439 | 372 | 0.6243525 | folX |
| 4268 | 372 | 0.6243525 | rpsL |
| 5333 | 372 | 0.6243525 | |
| 2898 | 369 | 0.6213746 | |
| 5533 | 369 | 0.6213746 | |
| 1541 | 369 | 0.6213746 | |
| 4253 | 369 | 0.6213746 | rplN |
| 3833 | 369 | 0.6213746 | |
| 1149 | 369 | 0.6213746 | |
| 4271 | 369 | 0.6213746 | rplL |
| 4276 | 369 | 0.6213746 | secE |
| 1582 | 369 | 0.6213746 | sdhD |
| 2166 | 366 | 0.6183732 | |
| 33 | 366 | 0.6183732 | |
| 1701 | 366 | 0.6183732 | |
| 1842 | 363 | 0.6153479 | |
| 1378 | 363 | 0.6153479 | |
| 3203 | 363 | 0.6153479 | |
| 1840 | 363 | 0.6153479 | |
| 3843 | 363 | 0.6153479 | |

TABLE 2-continued

| | | | |
|---|---|---|---|
| 1076 | 363 | 0.6153479 | |
| 630 | 363 | 0.6153479 | |
| 613 | 360 | 0.6122987 | |
| 2901 | 360 | 0.6122987 | |
| 2606 | 360 | 0.6122987 | |
| 4324 | 360 | 0.6122987 | |
| 2868 | 360 | 0.6122987 | |
| 1492 | 357 | 0.6092253 | |
| 4005 | 357 | 0.6092253 | |
| 2741 | 357 | 0.6092253 | rplT |
| 2666 | 357 | 0.6092253 | |
| 1426 | 357 | 0.6092253 | |
| 4241 | 357 | 0.6092253 | rpsM |
| 2960 | 357 | 0.6092253 | pilZ |
| 871 | 357 | 0.6092253 | phhB |
| 1995 | 357 | 0.6092253 | |
| 2667 | 354 | 0.6061275 | |
| 5303 | 354 | 0.6061275 | |
| 582 | 354 | 0.6061275 | folB |
| 1568 | 354 | 0.6061275 | |
| 2736 | 354 | 0.6061275 | |
| 563 | 354 | 0.6061275 | |
| 1349 | 351 | 0.6030052 | |
| 665 | 351 | 0.6030052 | |
| 4247 | 351 | 0.6030052 | rplR |
| 320 | 351 | 0.6030052 | |
| 3742 | 351 | 0.6030052 | rplS |
| 3835 | 351 | 0.6030052 | |
| 1228 | 351 | 0.6030052 | |
| 2175 | 348 | 0.5998581 | |
| 729 | 348 | 0.5998581 | |
| 570 | 348 | 0.5998581 | |
| 1720 | 348 | 0.5998581 | pscG |
| 4711 | 348 | 0.5998581 | |
| 3684 | 348 | 0.5998581 | |
| 4702 | 348 | 0.5998581 | |
| 3664 | 348 | 0.5998581 | |
| 1917 | 348 | 0.5998581 | |
| 2190 | 345 | 0.5966861 | |
| 2762 | 345 | 0.5966861 | |
| 3688 | 345 | 0.5966861 | |
| 2780 | 345 | 0.5966861 | |
| 3046 | 345 | 0.5966861 | |
| 4739 | 345 | 0.5966861 | |
| 1398 | 342 | 0.5934889 | |
| 128 | 342 | 0.5934889 | |
| 4575 | 342 | 0.5934889 | |
| 2456 | 342 | 0.5934889 | |
| 2781 | 342 | 0.5934889 | |
| 2715 | 339 | 0.5902664 | |
| 5288 | 339 | 0.5902664 | glnK |
| 3809 | 339 | 0.5902664 | fdx2 |
| 3822 | 339 | 0.5902664 | |
| 1055 | 339 | 0.5902664 | |
| 1722 | 339 | 0.5902664 | pscI |
| 3367 | 339 | 0.5902664 | |
| 565 | 339 | 0.5902664 | |
| 2608 | 336 | 0.5870183 | |
| 1965 | 336 | 0.5870183 | |
| 644 | 336 | 0.5870183 | |
| 825 | 336 | 0.5870183 | |
| 1114 | 336 | 0.5870183 | |
| 5275 | 336 | 0.5870183 | |
| 5067 | 336 | 0.5870183 | hisE |
| 589 | 333 | 0.5837445 | |
| 4258 | 333 | 0.5837445 | rplV |
| 4990 | 333 | 0.5837445 | |
| 1323 | 333 | 0.5837445 | |
| 5406 | 333 | 0.5837445 | |
| 3979 | 333 | 0.5837445 | |
| 3140 | 330 | 0.5804447 | |
| 2405 | 330 | 0.5804447 | |
| 1540 | 330 | 0.5804447 | |
| 3275 | 330 | 0.5804447 | |
| 4698 | 330 | 0.5804447 | |
| 1702 | 330 | 0.5804447 | |
| 3040 | 330 | 0.5804447 | |
| 939 | 327 | 0.5771188 | |
| 1925 | 327 | 0.5771188 | |
| 1780 | 327 | 0.5771188 | nirD |
| 4577 | 327 | 0.5771188 | |
| 3533 | 327 | 0.5771188 | |
| 2694 | 327 | 0.5771188 | |
| 5240 | 327 | 0.5771188 | trxA |
| 617 | 327 | 0.5771188 | |
| 1533 | 327 | 0.5771188 | |
| 4164 | 327 | 0.5771188 | |
| 1882 | 324 | 0.5737665 | |
| 3351 | 324 | 0.5737665 | |
| 894 | 324 | 0.5737665 | |
| 3042 | 324 | 0.5737665 | |
| 1362 | 324 | 0.5737665 | |
| 3812 | 324 | 0.5737665 | iscA |
| 802 | 324 | 0.5737665 | |
| 4853 | 324 | 0.5737665 | fis |
| 2384 | 324 | 0.5737665 | |
| 488 | 321 | 0.5703877 | |
| 1123 | 321 | 0.5703877 | |
| 1676 | 321 | 0.5703877 | |
| 1168 | 321 | 0.5703877 | |
| 5417 | 321 | 0.5703877 | soxD |
| 3502 | 318 | 0.566982 | |
| 1038 | 318 | 0.566982 | |
| 15 | 318 | 0.566982 | |
| 2422 | 315 | 0.5635494 | |
| 3854 | 315 | 0.5635494 | |
| 610 | 315 | 0.5635494 | prtN |
| 4252 | 315 | 0.5635494 | rplX |
| 2658 | 315 | 0.5635494 | |
| 1830 | 315 | 0.5635494 | |
| 4753 | 315 | 0.5635494 | |
| 922 | 315 | 0.5635494 | |
| 2759 | 315 | 0.5635494 | |
| 5227 | 315 | 0.5635494 | |
| 4264 | 312 | 0.5600895 | rpsJ |
| 3260 | 312 | 0.5600895 | |
| 4568 | 312 | 0.5600895 | rplU |
| 742 | 309 | 0.5566022 | |
| 2937 | 309 | 0.5566022 | |
| 2646 | 309 | 0.5566022 | nuoK |
| 979 | 309 | 0.5566022 | |
| 4463 | 309 | 0.5566022 | |
| 4452 | 309 | 0.5566022 | |
| 2174 | 309 | 0.5566022 | |
| 1937 | 309 | 0.5566022 | |
| 786 | 306 | 0.5530873 | |
| 3142 | 306 | 0.5530873 | |
| 4674 | 306 | 0.5530873 | |
| 3347 | 306 | 0.5530873 | |
| 2161 | 306 | 0.5530873 | |
| 4230 | 306 | 0.5530873 | pchB |
| 2245 | 306 | 0.5530873 | |
| 4789 | 306 | 0.5530873 | |
| 4250 | 306 | 0.5530873 | rpsN |
| 2607 | 306 | 0.5530873 | |
| 857 | 306 | 0.5530873 | bolA |
| 466 | 303 | 0.5495445 | |
| 3390 | 303 | 0.5495445 | |
| 647 | 303 | 0.5495445 | |
| 3298 | 303 | 0.5495445 | |
| 2738 | 303 | 0.5495445 | |
| 4354 | 303 | 0.5495445 | himA |
| 3278 | 300 | 0.5459736 | |
| 4261 | 300 | 0.5459736 | rplW |
| 2029 | 300 | 0.5459736 | |
| 4141 | 300 | 0.5459736 | |
| 3202 | 300 | 0.5459736 | |
| 2799 | 300 | 0.5459736 | |
| 2460 | 297 | 0.5423744 | |
| 1929 | 297 | 0.5423744 | |
| 709 | 297 | 0.5423744 | |
| 4875 | 297 | 0.5423744 | |
| 1705 | 297 | 0.5423744 | pcrG |
| 3662 | 294 | 0.5387467 | |
| 4419 | 294 | 0.5387467 | ftsL |
| 4386 | 294 | 0.5387467 | groES |
| 3566 | 294 | 0.5387467 | |
| 1295 | 294 | 0.5387467 | |

TABLE 2-continued

| | | | |
|---|---|---|---|
| 490 | 294 | 0.5387467 | |
| 900 | 291 | 0.5350903 | |
| 4482 | 291 | 0.5350903 | gatC |
| 369 | 291 | 0.5350903 | |
| 4642 | 291 | 0.5350903 | |
| 3338 | 291 | 0.5350903 | |
| 4638 | 288 | 0.5314048 | |
| 2143 | 288 | 0.5314048 | |
| 983 | 288 | 0.5314048 | |
| 131 | 288 | 0.5314048 | |
| 3274 | 288 | 0.5314048 | |
| 980 | 285 | 0.5276901 | |
| 3634 | 285 | 0.5276901 | |
| 3161 | 285 | 0.5276901 | himD |
| 4298 | 285 | 0.5276901 | |
| 2183 | 285 | 0.5276901 | |
| 3998 | 282 | 0.523946 | |
| 3051 | 282 | 0.523946 | |
| 124 | 282 | 0.523946 | |
| 2292 | 282 | 0.523946 | |
| 3940 | 282 | 0.523946 | |
| 4176 | 282 | 0.523946 | ppiC2 |
| 2697 | 282 | 0.523946 | |
| 1641 | 279 | 0.5201722 | |
| 3033 | 279 | 0.5201722 | |
| 1988 | 279 | 0.5201722 | pqqD |
| 1996 | 279 | 0.5201722 | ppiC1 |
| 2485 | 279 | 0.5201722 | |
| 4060 | 279 | 0.5201722 | |
| 2723 | 279 | 0.5201722 | |
| 4637 | 279 | 0.5201722 | |
| 4018 | 276 | 0.5163685 | |
| 4563 | 276 | 0.5163685 | rpsT |
| 909 | 276 | 0.5163685 | |
| 4259 | 276 | 0.5163685 | rpsS |
| 68 | 276 | 0.5163685 | |
| 954 | 276 | 0.5163685 | |
| 1852 | 276 | 0.5163685 | |
| 1298 | 276 | 0.5163685 | |
| 5148 | 273 | 0.5125346 | |
| 734 | 273 | 0.5125346 | |
| 4466 | 273 | 0.5125346 | |
| 2487 | 273 | 0.5125346 | |
| 818 | 273 | 0.5125346 | |
| 2182 | 270 | 0.5086704 | |
| 1447 | 270 | 0.5086704 | fliQ |
| 4033 | 270 | 0.5086704 | |
| 4741 | 270 | 0.5086704 | rpsO |
| 4870 | 267 | 0.5047755 | |
| 3413 | 267 | 0.5047755 | |
| 4254 | 267 | 0.5047755 | rpsQ |
| 874 | 267 | 0.5047755 | |
| 1963 | 267 | 0.5047755 | |
| 2805 | 264 | 0.5008497 | |
| 3601 | 264 | 0.5008497 | |
| 3085 | 264 | 0.5008497 | |
| 986 | 264 | 0.5008497 | |
| 1151 | 264 | 0.5008497 | imm2 |
| 1508 | 261 | 0.4968928 | |
| 712 | 258 | 0.4929045 | |
| 1968 | 258 | 0.4929045 | |
| 2663 | 258 | 0.4929045 | |
| 1719 | 258 | 0.4929045 | pscF |
| 5559 | 258 | 0.4929045 | atpE |
| 1233 | 258 | 0.4929045 | |
| 384 | 258 | 0.4929045 | |
| 4567 | 258 | 0.4929045 | rpmA |
| 2737 | 258 | 0.4929045 | |
| 635 | 255 | 0.4888847 | |
| 5129 | 255 | 0.4888847 | grx |
| 1394 | 255 | 0.4888847 | |
| 4611 | 255 | 0.4888847 | |
| 53 | 255 | 0.4888847 | |
| 2031 | 255 | 0.4888847 | |
| 3245 | 255 | 0.4888847 | minE |
| 3917 | 252 | 0.4848329 | moaD |
| 2853 | 252 | 0.4848329 | oprI |
| 1063 | 252 | 0.4848329 | |
| 3745 | 252 | 0.4848329 | rpsP |

| | | | |
|---|---|---|---|
| 362 | 252 | 0.4848329 | fdx1 |
| 1006 | 252 | 0.4848329 | |
| 4944 | 249 | 0.4807491 | |
| 493 | 249 | 0.4807491 | |
| 5068 | 249 | 0.4807491 | tatA |
| 3632 | 249 | 0.4807491 | |
| 4782 | 246 | 0.4766328 | |
| 2429 | 246 | 0.4766328 | |
| 1711 | 246 | 0.4766328 | |
| 2297 | 246 | 0.4766328 | |
| 738 | 246 | 0.4766328 | |
| 4134 | 243 | 0.472484 | |
| 4377 | 243 | 0.472484 | |
| 1431 | 243 | 0.472484 | rsaL |
| 4357 | 243 | 0.472484 | |
| 2149 | 243 | 0.472484 | |
| 1849 | 243 | 0.472484 | |
| 1869 | 240 | 0.4683022 | |
| 1564 | 240 | 0.4683022 | |
| 3334 | 240 | 0.4683022 | |
| 1743 | 240 | 0.4683022 | |
| 2621 | 237 | 0.4640873 | |
| 1592 | 237 | 0.4640873 | |
| 5316 | 237 | 0.4640873 | rpmB |
| 2966 | 237 | 0.4640873 | acpP |
| 2845 | 234 | 0.4598397 | |
| 3009 | 234 | 0.459839 | |
| 60 | 234 | 0.459839 | |
| 2703 | 234 | 0.459839 | |
| 505 | 231 | 0.455557 | |
| 4934 | 231 | 0.455557 | rpsR |
| 648 | 231 | 0.455557 | |
| 632 | 231 | 0.455557 | |
| 1404 | 228 | 0.451241 | |
| 805 | 228 | 0.451241 | |
| 125 | 228 | 0.451241 | |
| 39 | 228 | 0.451241 | |
| 2992 | 226 | 0.451241 | |
| 4359 | 228 | 0.451241 | |
| 2021 | 225 | 0.4468909 | |
| 3530 | 222 | 0.4425063 | |
| 2453 | 222 | 0.4425063 | |
| 1855 | 222 | 0.4425063 | |
| 3612 | 222 | 0.4425063 | |
| 3031 | 222 | 0.4425063 | |
| 4028 | 222 | 0.4425063 | |
| 3237 | 222 | 0.4425063 | |
| 2785 | 219 | 0.4380869 | |
| 3501 | 219 | 0.4380869 | |
| 2412 | 219 | 0.4380869 | |
| 2619 | 219 | 0.4380869 | infA |
| 4306 | 219 | 0.4380869 | |
| 4826 | 219 | 0.4380869 | |
| 38 | 216 | 0.4336324 | |
| 4737 | 216 | 0.4336324 | |
| 579 | 216 | 0.4336324 | rpsU |
| 717 | 213 | 0.4291427 | rmf |
| 3049 | 213 | 0.4291427 | |
| 5526 | 213 | 0.4291427 | |
| 5460 | 213 | 0.4291427 | |
| 200 | 213 | 0.4291427 | |
| 2763 | 210 | 0.4246174 | |
| 2170 | 210 | 0.4246174 | |
| 456 | 210 | 0.4246174 | |
| 4823 | 210 | 0.4246174 | |
| 109 | 210 | 0.4246174 | |
| 960 | 210 | 0.4246174 | |
| 2668 | 210 | 0.4246174 | |
| 1159 | 210 | 0.4246174 | |
| 3266 | 210 | 0.4246174 | capB |
| 3451 | 210 | 0.4246174 | |
| 627 | 207 | 0.4200562 | |
| 5403 | 207 | 0.4200562 | |
| 4077 | 207 | 0.4200562 | |
| 1718 | 204 | 0.4154588 | pscE |
| 4530 | 201 | 0.410825 | |
| 380 | 201 | 0.410825 | |
| 553 | 201 | 0.410825 | |
| 3808 | 201 | 0.410825 | |

TABLE 2-continued

| | | | |
|---|---|---|---|
| 4738 | 198 | 0.4061544 | |
| 1230 | 198 | 0.4061544 | |
| 3520 | 195 | 0.4014469 | |
| 3752 | 195 | 0.4014469 | |
| 5480 | 195 | 0.4014469 | |
| 2742 | 195 | 0.4014469 | rpmI |
| 2808 | 192 | 0.396702 | |
| 4255 | 192 | 0.396702 | rpmC |
| 1747 | 189 | 0.3919195 | |
| 905 | 186 | 0.3870991 | csrA |
| 3371 | 186 | 0.3870991 | |
| 258 | 186 | 0.3870991 | |
| 2980 | 186 | 0.3870991 | |
| 4940 | 186 | 0.3870991 | |
| 284 | 183 | 0.3822405 | |
| 2970 | 183 | 0.3822405 | rpmF |
| 1571 | 180 | 0.3773433 | |
| 3496 | 180 | 0.3773433 | |
| 1478 | 177 | 0.3724074 | |
| 5408 | 177 | 0.3724074 | |
| 3572 | 177 | 0.3724074 | |
| 4245 | 177 | 0.3724074 | rpmD |
| 2186 | 171 | 0.3624178 | |
| 4537 | 171 | 0.3624178 | |
| 2501 | 168 | 0.3573635 | |
| 2883 | 168 | 0.3573635 | |
| 1177 | 168 | 0.3573635 | napE |
| 5351 | 168 | 0.3573635 | |
| 5350 | 168 | 0.3573635 | |
| 2146 | 168 | 0.3573635 | |
| 3719 | 162 | 0.3471344 | |
| 5482 | 162 | 0.3471344 | |
| 2311 | 159 | 0.341959 | |
| 587 | 159 | 0.341959 | |
| 161 | 153 | 0.3314847 | |
| 3600 | 153 | 0.3314847 | |
| 3990 | 153 | 0.3314847 | |
| 3370 | 147 | 0.3208437 | |
| 135 | 141 | 0.3100333 | |
| 5276 | 141 | 0.3100333 | lppL |
| 1664 | 141 | 0.3100333 | |
| 5570 | 135 | 0.2990509 | rpmH |
| 3144 | 120 | 0.2708239 | |
| 442 | 117 | 0.2650435 | |
| 4242 | 117 | 0.2650435 | rpmJ |
| 1632 | 90 | 0.210914 | kdpF |
| 1985 | 72 | 0.1726306 | pqqA |

Protein Name

DNA-directed RNA polymerase beta* chain
DNA-directed RNA polymerase beta chain
DNA polymerase III, alpha chain
ribonucleoside reductase, large chain
valyl-tRNA synthetase
isoleucyl-tRNA synthetase
organic solvent tolerance protein OstA precursor
DNA gyrase subunit A
secretion protein SecA
alanyl-tRNA synthetase
leucyl-tRNA synthetase
aconitate hydratase 2
DNA topoisomerase I
translation initiation factor IF-2
cell division protein FtsK
DNA gyrase subunit B
Lon protease
probable outer membrane protein
DNA ligase
phenylalanyl-tRNA synthetase, beta subunit
probable chemotaxis sensor/effector fusion protein
topoisomerase IV subunit A
primosomal protein N'
hypothetical protein
hypothetical protein
elogation factor G
polyribonucleotide nucleotidyltransferase
glycyl-tRNA synetase beta chain
DNA polymerase subunits gamma and tau
methionyl-tRNA synthetase
ATP-dependent DNA helicase Rep
hypothetical protein
cytochrome C-type biogenesis protein CcmF
probable chemotaxis transducer
threonyl-tRNA synthetase
probable heat shock protein (hsp90 family)
heat shock protein HtpG
probable acetyltransferase
topoisomerase IV subunit B
1-deoxyxylulose-5-phosphate synthase
hypothetical protein
secretion protein SecD
heat shock protein HscA
probable binding protein component of ABC transporter
glucosamine-fructose-6-phosphate aminotransferase
transport protein MsbA
GTP-binding protein LepA
probable acyl-CoA dehydrogenase
succinate dehydrogenase (A subunit)
arginyl-tRNA synthetase
probable sodium/proton antiporter
probable acetyltransferase
penicillin-binding protein 3
conserved hypothetical protein
probable oxidoreductase
acetolactate synthase large subunit
single-stranded-DNA-specific exonuclease RecJ
prolyl-tRNA synthetase
urease alpha subunit
type 4 fimbrial biogenesis protein PilB
30S ribosomal protein S1
glutaminyl-tRNA synthetase
glucose-6-phosphate isomerase
hypothetical protein
electron transfer flavoprotein-ubiquinone oxidoreductase
GroEL protein
CTP synthase
probable chemotaxis transducer
arylsulfatase
conserved hypothetical protein
GMP synthase
hypothetical protein
probable carbohydrate kinase
phosphoglycerate mutase
conserved hypothetical protein
chromosomal replication initiator protein DnaA
ATP synthase alpha chain
hypothetical protein
apolipoprotein N-acyltransferase
hypothetical protein
xylulose kinase
general secretion pathway protein E
sodium/proton antiporter NhaB
probable colicin-like toxin
methylmalonate-semialdehyde dehydrogenase
RNA polymerase sigma-54 factor
probable transporter
N utilization substance protein A
hypothetical protein
probable flavin-binding monooxygenase
conserved hypothetical protein
UDP-N-acetylmuramoylalanyl-D-glutamate-2, 6-diaminopimelate ligase
hypothetical protein
probable amidase
outer membrane protein OprM precursor
RND divalent metal cation efflux membrane fusion protein CzcB precursor
Glu-tRNA(Gln) amidotransferase subunit A
pyruvate kinase I
probable Mg transporter MgtE
Glu-tRNA(Gln) amidotransferase subunit B
UDP-N-acetylmuramate--alanine ligase
lipoamide dehydrogenase-glc
probable transporter (membrane subunit)
conserved hypothetical protein
probable outer membrane protein
probable ferredoxin
glutamine synthetase TABLE 2-continued probable type II secretion system protein
nitrite extrusion protein 2
probable amidase
soluble pyridine nucleotide transhydrogenase
replicative DNA helicase
probable glyceraldehyde-3-phosphate dehydrogenase
cysteinyl-tRNA synthetase
exodeoxyribonuclease VII large subunit
UDP-N-acetylmuramoylalanyl-D-glutamyl-2, 6-diaminopimelate--D-alanyl-D-alanyl ligase
ATP synthase beta chain
signal recognition particle protein Ffh
adenylosucinate lyase
signal recognition particle receptor FtsY
probable 2-isopropylmalate synthase
conserved hypothetical protein
hypothetical protein
hypothetical protein
probable dicarboxylate transporter
biotin carboxylase
trytophanyl-tRNA synthetase
UDP-N-acetylmuramoylalanine-D-glutamate ligase
NADH dehydrogenase I chain F
probable aldolase
hypothetical protein
two-component response regulator PilR
phosphoglucosamine mutase
aminopeptidase P
probable cytochrome P450
conserved hypothetical protein
secretion protein SecY
hypothetical protein
probable MFS transporter
hypothetical protein
probable MFS transporter
porin O precursor
B-band O-antigen polymerase
conserved hypothetical protein
probable UDP-glucose/GDP-mannose dehydrogenase WbpA
probable binding protein component of ABC maltose/mannitol transporter
C4-dicarboxylate transport protein
conserved hypothetical protein
hypothetical protein
conserved hypothetical protein
TolB protein
hypothetical protein
adenylosuccinate synthetase
peptidyl-prolyl cis-trnas isomerase SurA
enolase
hypothetical protein
glutamate-1-semialdehyde 2,1 aminomutase
seryl-tRNA synthetase
3-deoxy-D-manno-octulosonic-acid (KDO) transferase
hypothetical protein
3-oxoacyl-acyl carrier protein synthase II
glutamyl-tRNA reductase
UDP-N-acetylglucosamine 1-carboxyvinyltransferase
hypothetical protein
transcription termination factor Rho
cell division protein FtsA
hypothetical protein
conserved hypothetical protein
ribonucleoside reductase, small chain
probable glycosyl transferase WbpJ
hypothetical protein
aspartate kinase alpha and beta chain
O-antigen translocase
hypothetical protein
hypothetical protein
probable transporter (membrane subunit)
conserved hypothetical protein
probable MFS transporter
conserved hypothetical protein
probable hydrolase
hypothetical protein
GTP-binding protein Obg
probable FAD-dependent monooxygenase
hypothetical protein
phenazine biosynthesis protein PhzC TABLE 2-continued probable type II secretion system protein
probable MFS transporter
conserved hypothetical protein
nitrate transporter
probable cytochrome b
hypothetical protein
DNA/pantothenate metabolism flavoprotein
membrane protein OpdE
two-component sensor
probable acyl-CoA thiolase
8-amino-7-oxononanoate synthase
conserved hypothetical protein
cell division protein FtsW
hypothetical protein
probable FAD-dependent monooxygenase
conserved hypothetical protein
probable MFS transporter
probable acyl-CoA thiolase
hypothetical protein
1-deoxy-d-xylulose 5-phosphate reductoisomerase
methionine adenosyltransferase
cell division protein FtsZ
hypothetical protein
probable pyridoxal-phosphate dependent enzyme
acetyl-CoA acetyltransferase
probable molybdopterin biosynthesis protein MoeB
conserved hypothetical protein
hypothetical protein
alginate biosynthesis protein Alg44
hypothetical protein
probable hydrolase
succinyl-CoA synthetase beta chain
hypothetical protein
probable ATP-binding component of ABC transporter
probable acyl-CoA dehydrogenase
phosphoglycerate kinase
hypothetical protein
hypothetical protein
probable RND efflux membrane fusion protein precursor
probable peptidic bond hydrolase
probable multidrug resistance efflux pump
succinyl-diaminopimelate desuccinylase
conserved hypothetical protein
probable acyl-CoA dehydrogenase
general secretion pathway protein L
proable permease of ABC transporter
erythronate-4-phosphate dehydrogenase
conserved hypothetical protein
hypothetical protein
probable acyl-CoA thiolase
conserved hypothetical protein
lipid A-disaccharide synthase
LPS biosynthesis protein WbpG
hypothetical protein
tRNA methyltransferase
probable acyl-CoA dehydrogenase
conserved hypothetical protein
conserved hypothetical protein
still frameshift type 4 fimbrial biogenesis protein PilC
cytochrome c oxidase, subunit II
conserved hypothetical protein
riboflavin-specific deaminase/reductase
probable glycosyltransferase WbpH
glycine cleavage system protein T2
muconate cycloisomerase I
UDP-glucose:(heptosyl) LPS alpha 1,3-glucosyltransferase WaaG
hypothetical protein
glutamate 5-kinase
conserved hypothetical protein
hypothetical protein
conserved hypothetical protein
hypothetical protein
aspartate semialdehyde dehydrogenase
rod shape-determining protein
alcohol dehydrogenase (Zn-dependent)
conserved hypothetical protein
hypothetical protein
peptide chain release factor 2
hypothetical protein

TABLE 2-continued conserved hypothetical protein
hypothetical protein
conserved hypothetical protein
3-phosphoserine aminotransferase
peptide chain release factor 1
phospho-N-acetylmuramoyl-pentapeptide-transferase
hypothetical protein
probable aminotransferase WbpE
phospho-2-dehydro-3-doxyheptonate aldolase
O6-methylguanine-DNA methyltransferase
probable transcriptional regulator
UDP-N-acetylglucosamine-N-acetylmuramyl(pentapeptide) pyrophosphoryl-undecaprenol N-acetlyglucosasmine tr
uroporphyrinogen decarboxylase
hypothetical protein
heptosyltransferase I
conserved hypothetical protein
fructose-1,6-bisphosphate aldolase
type 4 fimbrial biogenesis protein PilM
probable UDP-N-acetylglucosamine 2-epimerase WbpI
phosphoribosylaminoimidazole synthetase
UDP-3-O-[3-hydroxylauroyl] glucosamine N-acyltransferase
quinolinate synthetase A
probable secretion protein
probable alcohol dehydrogenase (Zn-dependent)
conserved hypothetical protein
dTDP-D-glucose 4,6-dehydratase
outer membrane protein OprF precursor
hypothetical protein
conserved hypothetical protein
translocation protein in type III secretion
O-antigen chain length regulator
TolA protein
transcriptional regulator MexT
conserved hypothetical protein
acetylpolyamine aminohydrolase
conserved hypothetical protein
RecA protein
heptosyltransferase II
hypothetical protein
conserved hypothetical protein
rod shape-determining protein MreB
hypothetical protein
DNA polymerase III, delta subunit
tetrahydrodipicolinate succinylase
probable binding protein component of ABC transporter
hypothetical protein
conserved hypothetical protein
conserved hypothetical protein
conserved hypothetical protein
delta 2-isopentenylpyrophosphate transferase
octaprenyl-diphosphate synthase
hypothetical protein
hypothetical protein
probable enoyl-CoA hydratase/isomerase
thiamine monophosphate kinase
hypothetical protein
hypothetical protein
hypothetical protein
probable serine/threonine dehydratase, degradative
pseudouridine synthase
conserved hypothetical protein
hypothetical protein
ribosomal large subunit pseudouridine synthase C
probable transcriptional regulator
hypothetical protein
probable transmembrane sensor
hypothetical protein
probable transcriptional regulator
probable transcriptional regulator
glutathione synthetase
hypothetical protein
probable adhesion protein
acetyl-coenzyme A carboxylase carboxyl transferase (alpha subunit)
probable transcriptional regulator
probable NAD-dependent epimerase/dehydratase WbpK
probable oxidoreductase WpbB
probable transmembrane sensor
hypothetical protein

TABLE 2-continued glycyl-tRNA synthetase alpha chain
probable lipase
LytB protein
conserved hypothetical protein
probable hydrolase
ribose-phosphate pyrophosphokinase
hypothetical protein
conserved hypothetical protein
porphobilinogen deaminase
probable transcriptional regulator
probable lauroyl acyltransferase
transcriptional regulator PtxR
probable transcriptional regulator
hypothetical protein
malonyl-CoA-[acyl-carrier-protein] transacylase
riboflavin kinase/FAD synthase
conserved hypothetical protein
conserved hypothetical protein
probable phosphatidate cytidylyltransferase
hypothetical protein
carbamate kinase
hypothetical protein
probable transcriptional regulator
catechol 1,2 dioxygenase
D-alanyl-D-alanine-endopeptidase
probable transcriptional regulator
hypothetical protein
probable epimerase
lipase LipC
probable transcriptional regulator
electron transfer flavoprotein alpha-subunit
FdhE protein
hypothetical protein
hypothetical protein
conserved hypothetical protein
probable ATP-binding component of ABC transporter
probable cytochrome c
probable transcriptional regulator
hypothetical protein
probable transcriptional regulator
probable permease of ABC transporter
hypothetical protein
probable transcriptional regulator
probable transcriptional regulator
probable transcriptional regulator
GTP-binding protein Era
probable transcriptional regulator
pyrroloquinoline quinone biosynthesis protein B
probable cytochrome c oxidase assembly factor
hypothetical protein
hypothetical protein
probable short chain dehydrogenase
hypothetical protein
hypothetical protein
hypothetical protein
hypothetical protein
UDP-3-O-acyl-N-acetylglucosamine deacetylase
probable transcriptional regulator
probable transcriptional regulator
conserved hypothetical protein
probable binding protein component of ABC transporter
dTDP-4-dehydrorhamnose reductase
conserved hypothetical protein
probable transcriptional regulator
hypothetical protein
hypothetical protein
probable transcriptional regulator
probable transferase
probable two-component response regulator
probable transcriptional regulator
hypothetical protein
cysteine synthase B
probable glycosyl transferase
TonB protein
O-sialoglycoprotein endopeptidase
ferrochelatase
conserved hypothetical protein
probable aminotransferase
probable transmembrane sensor TABLE 2-continued UDP-N-acetylpyruvoylglucosamine reductase
hypothetical protein
acetoin catabolism protein AcoB
conserved hypothetical protein
probable oxidoreductase
hypothetical protein
glycosyltransferase WbpL
hypothetical protein
probable transposase
flagellar motor switch protein FliG
hypothetical protein
probable transposase
probable transposase
probable transposase
probable transposase
phenylalanyl-tRNA synthetase, alpha-subunit
probable permease of ABC transporter
hypothetical protein
hypothetical protein
fructose-1,6-bisphosphatase
conserved hypothetical protein
probable ATP-binding component of ABC transporter
conserved hypothetical protein
hypothetical protein
probable O-methyltransferase
aspartate carbamoyltransferase
glyceraldehyde 3-phosphate dehydrogenase
conserved hypothetical protein
DNA-directed RNA polymerase alpha chain
probable pyruvate dehydrogenase E1 component, beta chain
tetraacyldisaccharide 4*-kinase
rod shape-determining protein MreC
D-lactate dehydrogenase (fermentative)
sulfate transport protein CysA
probable nucleoside hydrolase
pyridoxal phosphate biosynthetic protein PdxA
probable transmembrane sensor
DNA polymerase III, delta prime subunit
L-asparaginase I
hypothetical protein
probable bacteriophage integrase
lipoate synthase
hypothetical protein
conserved hypothetical protein
hypothetical protein
probable transcriptional regulator
hypothetical protein
probable transcriptional regulator
catechol 1,2-dioxygenase
D-alanyl-D-alanine-endopeptidase
probable transcriptional regulator
hypothetical protein
probable epimerase
lipase LipC
probable transcriptional regulator
electron transfer flavoprotein alpha-subunit
FdhE protein
hypothetical protein
hypothetical protein
conserved hypothetical protein
probable ATP-binding component of ABC transporter
probable cytochrome c
probable transcriptional regulator
hypothetical protein
probable transcriptional regulator
probable permease of ABC transporter
hypothetical protein
probable transcriptional regulator
probable transcriptional regulator
probable transcriptional regulator
GTP-binding protein Era
probable transcriptional regulator
pyrroloquinoline quinone biosynthesis protein B
probable cytochrome c oxidase assembly factor
hypothetical protein
hypothetical protein
probable short chain dehydrogenase
hypothetical protein
hypothetical protein TABLE 2-continued hypothetical protein
hypothetical protein
UDP-3-O-acyl-N-acetylglucosamine deacetylase
probable transcriptional regulator
probable transcriptional regulator
conserved hypothetical protein
probable binding protein component of ABC transporter
dTDP-4-dehydrorhamnose reductase
conserved hypothetical protein
probable transcriptional regulator
hypothetical protein
hypothetical protein
probable transcriptional regulator
probable transferase
probable two-component response regulator
probable transcriptional regulator
hypothetical protein
cysteine synthase B
probable glycosyl transferase
hypothetical protein
probable transcriptional regulator
probable transcriptional regulator
probable transcriptional regulator
probable transcriptional regulator
probable transcriptional regulator
cytochrome o ubiquinol oxidase protein CyoE
probable-3-hydroxyisobutyrate dehydrogenase
probable transcriptional regulator
4-hydroxybenzoate-octaprenyl transferase
probable chemotaxis protein
conserved hypothetical protein
probable 2-OH-lauroyltransferase
probable transcriptional regulator
succinyl-CoA-synthetase alpha chain
conserved hypothetical protein
geranyltranstransferase
hypothetical protein
ribosomal protein L11 methyltransferase
glucose-1-phosphate thymidylyltransferase
conserved hypothetical protein
hypothetical protein
dihydrodipicolinate synthase
heat shock protein HtpX
methyltransferase PilK
probable transcriptional regulator
conserved hypothetical protein
hypothetical protein
chromosome partitioning protein SpoOJ
hypothetical protein
aetyl-CoA carboxylase beta subunit
elongation factor Ts
cell division protein ZipA
ATP synthase A chain
outer membrane protein PopN
lipase modulator protein
hypothetical protein
probable transcriptional regulator
conserved hypothetical protein
hypothetical protein
cell division protein FtsQ
malonate decarboxylase beta subunit
ATP synthase gamma chain
probable hydrolase
hypothetical protein
probable short-chain dehydrogenase
spermidine synthase
probable ATP-binding component of ABC transporter
hypothetical protein
hypothetical protein
probable ATP-binding component of ABC transporter
hypothetical protein
probable transcriptional regulator
5,10-methylene-tetrahydrofolate dehydrogenase/cyclohydrase
sigma factor RpoH
signal peptidase I
hypothetical protein
formyltrahydrofolate deformylase
dihydropteroate synthase
conserved hypothetical protein TABLE 2-continued probable potassium channel
isopentenyl monophosphate kinase
hypothetical protein
hypothetical protein
nicotinate-nucleotide pyrophosphorylase
conserved hypothetical protein
hypothetical protein
2-dehydro-3-deoxyphosphooctonate aldolase
probable transmembrane sensor
urease accessory protein
flagellar synthesis regulator FleN
probable ATP-binding component of ABC transporter
probable phenazine biosynthesis protein
ATP-binding component of ABC phosphonate transporter
probable ATP-binding component of ABC transporter
probable permease of ABC transporter
probable short-chain dehydrogenase
diaminopimelate epimerase
probable two-component response regulator
conserved hypothetical protein
NH3-dependent NAD snthetase
NosY protein
probable biotin synthesis protein BioC
probable transcriptional regulator
type 4 fimbrial biogenesis protein PilW
probable chemotaxis protein methyltransferase
conserved hypothetical protein
50S ribosomal protein L2
hypothetical protein
probable oxidoreductase
probable permease of ABC taurine transporter
conserved hypothetical protein
hypothetical protein
hypothetical protein
phosphatidate cytidylyltransferase
phosphatidylserine synthase
hypothetical protein
thiosulfate sulfurtransferase
hypothetical protein
conserved hypothetical protein
hypothetical protein
hypothetical protein
hypothetical protein
probable transcriptional regulator
probable permease of ABC transporter
conserved hypothetical protein
probable transcriptional regulator
hypothetical protein
dihydrodipicolinate reductase
hypothetical protein
lipopolysaccharide core biosynthesis protein WaaP
tryptophan synthase alpha chain
probable ATP-binding component of ABC transporter
hypothetical protein
probable permease of ABC-2 transporter
probable transcriptional regulator
conserved hypothetical protein
prolipoprotein diacylglyceryl transferase
3-methyl-2-oxobutanoate hydroxymethyltransferase
glutamate racemase
conserved hypothetical protein
probable permease of ABC transporter
probable permease of ABC transporter
probable enoyl-CoA hydratase/isomerase
probable transcriptional regulator
conserved hypothetical protein
thymidylate synthase
hypothetical protein
hypothetical protein
probable enoyl-CoA hydratase/isomerase
translocation protein in type III secretion
hypothetical protein
probable pili assembly chaperone
probable transcriptional regulator
probable plasmid partitioning protein
probable permease of ABC transporter
conserved hypothetical protein
methionine aminopeptidase
conserved hypothetical protein TABLE 2-continued hypothetical protein
hypothetical protein
probable transcriptional regulator
probable permease of ABC-2 transporter
probable NAD(P)H dehydrogenase
conserved hypothetical protein
hypothetical protein
UDP-N-acetylglucosamine acyltransferase
ferredoxin—NADP + reductase
probable permease of ABC transporter
conserved hypothetical protein
probable enoyl-CoA hydratase/isomerase
polyamine transport protein PotC
ubiquinone biosynthesis methyltransferase UbiE
hypothetical protein
trnscriptional regulator PrtR
conserved hypothetical protein
probable transcriptional regulator
conserved hypothetical protein
probable exopolysaccharide transporter
probable ATP-binding component of ABC transporter
hypothetical protein
probable short-chain dehydrogenase
conserved hypothetical protein
3-deoxy-manno-octulosonate cytidylyltransferase
probable transporter
conserved hypothetical protein
probable transcriptional regulator
probable thioesterase
hypothetical protein
hypothetical protein
hypothetical protein
cis-1,2-dihydroxycyclohexa-3,4-diene carboxylate dehydrogenase
probable enoyl-CoA hydratase/isomerase
molybdopterin biosynthesis MoeB protein
probable short-chain dehydrogenase
conserved hypothetical protein
heme exporter protein CcmC
hypothetical protein
tRNA (guanine-N1)-methyltransferase
type 4 fimbrial biogenesis protein PilF
imidazoleglycerol-phosphate synthase, cyclase subunit
conserved hypothetical protein
triosephosphate isomerase
uroporphyrinoen-III synthetase
undecaprenyl pyrophosphate synthetase
hypothetical protein
probable cobalamin biosynthetic protein
hypothetical protein
hypothetical protein
hypothetical protein
probable short-chain dehydrogenase
hypothetical protein
electron transfer flavoprotein beta-subunit
conserved hypothetical protein
hypothetical protein
hypothetical protein
hypothetical protein
hypothetical protein
hypothetical protein
3-oxoacyl-[acyl-carrier-protein] reductase
hypothetical protein
hypothetical protein
probable pili assembly chaperone
DNA polymerase III, epsilon chain
30S ribosomal protein S2
hypothetical protein
hypothetical protein
probable nucleoside phosphorylase
uridylate kinase
hypothetical protein
probable permease of ABC transporter
hypothetical protein
hypothetical protein
conserved hypothetical protein
hypothetical protein
hypothetical protein
hypothetical protein
transcriptional regulator RhlR TABLE 2-continued probable phosphoribosyl transferase
probable ATP-binding component of ABC transporter
conserved hypothetical protein
conserved hypothetical protein
hypothetical protein
probable biotin biosynthesis protein bioH
probable permease of ABC transporter
hypothetical protein
conserved hypothetical protein
ribonuclease PH
probable glutamine amidotransferase
conserved hypothetical protein
probable transcriptional regulator
conserved hypothetical protein
probable transcriptional regulator
DNA-specific endonuclease I
probable transcriptional regulator
hypothetical protein
hypothetical protein
probable pili assembly chaperone
probable two-component response regulator
phosphoribosylaminoimidazole-succinocarboxamide synthase
succinate dehydrogenase (B subunit)
hypothetical protein
conserved hypothetical protein
hypothetical protein
conserved hypothetical protein
conserved hypothetical protein
conserved hypothetical protein
probable ATP-binding component of ABC transporter
heme exporter protein CcmA
hypothetical protein
hypothetical protein
probable transcriptional regulator
3-demethylubiquinone-9 3-methyltransferase
probable hydrolase
orotidine 5'-phosphate decarboxylase
hypothetical protein
hypothetical protein
50S ribosomal protein L1
conserved hypothetical protein
probable permease of ABC transporter
hypothetical protein
probable acetyltransferase
hypothetical protein
TolQ protein
hypothetical protein
conserved hypothetical protein
hypothetical protein
probable pseudouridylate synthase
cytidylate kinase
hypothetical protein
two-component response regulator
30S ribosomal protein S3
hypothetical protein
probable transcriptional regulator
dethiobiotin synthase
molybdenum transport protein ModB
transcriptional regulator Dnr
hypothetical protein
probable ATP-binding component of ABC transporter
leucyl/phenylalanyl-tRNA-protein transferase
conserved hypothetical protein
NADH dehydrogenase I chain B
probable two-component response regulator
hypothetical protein
probable transcriptional regulator
Na+-translocating NADH:uniquinone oxidoreductase subunit Nqr4
ribonuclease T
hypothetical protein
conserved hypothetical protein
DNA repair protein RadC
ribulose-phosphate 3-epimerase
hypothetical protein
hypothetical protein
heme exporter protein CcmB
hypothetical protein
urease accessory protein UreF
ribose 5-phosphate isomerase TABLE 2-continued phosphoribosylaminoimidazole synthetase
probable transcriptional regulator
probable transcriptional regulator
probable transcriptional regulator
hypothetical protein
conserved hypothetical protein
probable acetyltransferase
probable transcriptional regulator
probable two-component response regulator
conserved hypothetical protein
2-keto-3-deoxy-6-phosphogluconate aldolase
probable permease of ABC transporter
hypothetical protein
hypothetical protein
probable transcriptional regulator
hypothetical protein
hypothetical protein
riboflavin synthase alpha chain
conserved hypothetical protein
thiopurine methyltransferase
probable permease of ABC transporter
alginate o-acetyltransferase AlgF
conserved hypothetical protein
conserved hypothetical protein
probable transcriptional regulator
pyridoxine 5'-phosphate oxidase
hypothetical protein
hypothetical protein
probable carboxylesterase
pyoverdine biosynthesis protein PvcD
probable transcriptional regulator
probable carbonic anhydrase
conserved hypothetical protein
probable pyridoxamine 5'-phosphate oxidase
probable pyridoxamine 5'-phosphate oxidase
hypothetical protein
probable glutathione S-transferase
hypothetical protein
transcriptional regulator Vfr
hypothetical protein
orotate phoshoribosyltransferase
glutamine amidotransferase
hypothetical protein
hypothetical protein
maleylacetoacetate isomerase
probable radical activating enzyme
hypothetical protein
uracil phosphoribosyltransferase
hypothetical protein
endonuclease III
probable transcrptional regulator
probable antioxidant protein
hypothetical protein
conserved hypothetical protein
hypothetical protein
probable tolQ-type transport protein
pseudouridine synthase RluA
conserved hypothetical protein
50S ribosomal protein L3
conserved hypothetical protein
hypothetical protein
hypothetical protein
probable two-component response regulator
thymidylate kinase
conserved hypothetical protein
conserved hypothetical protein
probable aromatic acid decarboxdase
hypothetical protein
probable nuclease
periplasmic chaperone LolA
hypothetical protein
probable oxidoreductase
hypothetical protein
hypothetical protein
cell division protein FtsJ
hypothetical protein
hypothetical protein
hypothetical protein
30S ribosomal protein S4

TABLE 2-continued homoserine kinase
hypothetical protein
probable lipoprotein localization protein LolB
stringent starvation protein A
hypothetical protein
GTP cyclohydrolase II
hypothetical protein
heme acquisition protein HasAp
probable transcriptional regulator
probable peptide chain release factor
probable ribosomal protein L25
hypothetical protein
hypothetical protein
hypothetical protein
hypothetical protein
conserved hypothetical protein
guanylate kinase
glutamine amidotransferase
conserved hypothetical protein
hypothetical protein
protocatechuate 3,4-dioxygenase, alpha subunit
hypothetical protein
autoinducer synthesis protein LasI
probable Clp-family ATP-dependent protease
hypothetical protein
50S ribosomal protein L4
conserved hypothetical protein
probable nitroreductase
hypothetical protein
hypothetical protein
hypothetical protein
conserved hypothetical protein
probable molybdopterin-guanine dinucleotide biosynthesis protein MobA
hypothetical protein
cytochrome c-type protein NapC
conserved hypothetical protein
hypothetical protein
hypothetical protein
probable phosphoheptose isomerase
ribosome recycling factor
conserved hypothetical protein
hypothetical protein
hypothetical protein
hypothetical protein
probable transcriptional regulator
conserved hypothetical protein
hypothetical protein
translation initiation factor IF-3
potassium-transporting ATPase, C chain
probable transcriptional regulator
conserved hypothetical protein
conserved hypothetical protein
adenine phosphoribosyltransferase
conserved hypothetical protein
dTDP-4-dehydrorhamnose 3,5-epimerase
hypothetical protein
probable sigma-70 factor, ECF subfamily
GTP cyclohydrolase I precursor
hypothetical protein
cytochrome C biogenesis protein CcmG
conserved hypothetical protein
50S ribosomal protein L5
hypothetical protein
conserved hypothetical protein
conserved hypothetical protein
ATP synthase delta chain
NosL protein
conserved hypothetical protein
conserved hypothetical protein
conserved hypothetical protein
50S ribosomal protein L6
conserved hypothetical protein
conserved hypothetical protein
transcription antitermination protein NusG
hypothetical protein
hypothetical protein
conserved hypothetical protein
lactoylglutathione lyase TABLE 2-continued outer membrane lipoprotein OmlA
hypothetical protein
inoranic pyrophosphatase
probable sigma-70 factor, ECF subfamily
conserved hypothetical protein
conserved hypothetical protein
hypothetical protein
16S rRNA processing protein
hypothetical protein
hypothetical protein
heme d1 biosynthesis protein NirL
hypothetical protein
hypothetical protein
general secretion pathway protein M
hypothetical protein
hypothetical protein
hypothetical protein
conserved hypothetical protein
conserved hypothetical protein
heat shock protein HscB
hypothetical protein
hypothetical protein
general secretion pathway protein H
conserved hypothetical protein
shikimate kinase
hypothetical protein
conserved hypothetical protein
phosphatidylglycerophosphatase A
beta-hydroxydecanoyl-ACP dehydrase
conserved hypothetical protein
transcriptional regulator PyrR
conserved hypothetical protein
spermidine acetyltransferase
prolipoprotein signal peptidase
hypothetical protein
conserved hypothetical protein
probable transcriptional regulator
conserved hypothetical protein
probable sigma-70 factor, ECF subfamily
conserved hypothetical protein
hypothetical protein
hypothetical protein
probable outer membrane protein precursor
probable outer membrane protein
hypothetical protein
transcription elongation factor GreB
dihydrofolate reductase
hypothetical protein
hypothetical protein
50S ribosomal protein L10
30S ribosomal protein S5
hypothetical protein
hypothetical protein
hypothetical protein
NADH dehydrogenase I chain J
hypothetical protein
hypothetical protein
hypothetical protein
single-stranded DNA-binding protein
hypothetical protein
secretion protein SecB
conserved hypothetical protein
cytochrome c-type protein NapB precursor
ferredoxin protein NapF
probable methyltransferase
probable phenazine biosynthesis protein
probable phenazine biosynthesis protein
probable phenazine biosynthesis protein
hypothetical protein
hypothetical protein
probable phenazine biosynthesis protein
conserved hypothetical protein
toluate 1,2-dioxygenase beta subunit
2-amino-4-hydroxy-6-hydroxymethyldihydropterdine pyrophosphoknase
hypothetical protein
peptidyl-prolyl cis-trans isomerase SlyD
hypothetical protein
hypothetical protein
hypothetical protein TABLE 2-continued hypothetical protein
molybdopterin biosynthetic protein C
conserved hypothetical protein
hypothetical protein
conserved hypothetical protein
hypothetical protein
hypothetical protein
NusB protein
phosphopantetheine adenylyltransferase
hypothetical protein
hypothetical protein
hypothetical protein
hypothetical protein
hypothetical protein
conserved hypothetical protein
conserved hypothetical protein
hypothetical protein
probable purine-binding chemotaxis protein
hypothetical protein
hypothetical protein
hypothetical protein
6,7-dimethyl-8-ribityllumazine synthase
hypothetical protein
conserved hypothetical protein
translocation protein in type III secretion
hypothetical protein
hypothetical protein
hypothetical protein
hypothetical protein
hypothetical protein
conserved hypothetical protein
conserved hypothetical protein
bacterioferritin comigratory protein
conserved hypothetical protein
hypothetical protein
hypothetical protein
conserved hypothetical protein
conserved hypothetical protein
ATP synthase B chain
30S ribosomal protein S7
cyanate lyase
biotin carboxyl carrier protein (BCCP)
probable dna-binding stress protein
hypothetical protein
conserved hypothetical protein
hypothetical protein
hypothetical protein
cytochrome C-type biogenesis protein CcmH
hypothetical protein
hypothetical protein
hypothetical protein
probable thioredoxin
conserved hypothetical protein
hypothetical protein
nitrogen regulatory IIA protein
hypothetical protein
conserved hypothetical protein
phosphotyrosine protein phosphatase
probable HIT family protein
conserved hypothetical protein
hypothetical protein
hypothetical protein
conserved hypothetical protein
conserved hypothetical protein
conserved hypothetical protein
hypothetical protein
probable deaminase
conserved hypothetical protein
conserved hypothetical protein
osmotically inducible protein OsmC
deoxyuridine 5'-triphosphate nucleotidohydrolase
conserved hypothetical protein
hypothetical protein
hypothetical protein
hypothetical protein
molybdopterin converting factor, large subunit
conserved hypothetical protein
conserved hypothetical protein
conserved hypothetical protein TABLE 2-continued probable type II secretion system protein
type 4 fimbrial precursor PilA
probable transcriptional regulator
hypothetical protein
hypothetical protein
3-dehydroquinate dehydratase
ribonuclease H
hypothetical protein
hypothetical protein
probable peptide deformylase
probable transcriptional regulator
flagellar protein FliJ
TolR protein
conserved hypothetical protein
(3R)-hydroxymyristoyl-[acyl carrier protein] dehydratase
hypothetical protein
hypothetical protein
conserved hypothetical protein
conserved hypothetical protein
probable transcriptional regulator
conserved hypothetical protein
hypothetical protein
exoenzyme S synthesis protein C precursor
probable transcriptional regulator
hypothetical protein
hypothetical protein
50S ribosomal protein L15
hypothetical protein
conservedl hypothetical protein
hypothetical protein
conserved hypothetical protein
conserved hypothetical protein
hypothetical protein
probable type II secretion system protein
helix destabilizing protein of bacteriophage Pf1
hypothetical protein
nucleoside diphosphate kinase
50S ribosomal protein L11
hypothetical protein
hypothetical protein
50S ribosomal protein L13
hypothetical protein
hypothetical protein
hypothetical protein
conserved hypothetical protein
probable transcriptional regulator
hypothetical protein
probable type II secretion system protein
hypothetical protein
ATP synthase epsilon chain
hypothetical protein
conserved hypothetical protein
hypothetical protein
hypothetical protein
conserved hypothetical protein
conserved hypothetical protein
conserved hypothetical protein
conserved hypothetical protein
hypothetical protein
30S ribosomal protein S6
hypothetical protein
hypothetical protein
conserved hypothetical protein
conserved hypothetical protein
hypothetical protein
hypothetical protein
hypothetical protein
conserved hypothetical protein
hypothetical protein
hypothetical protein
conserved hypothetical protein
hypothetical protein
50S ribosomal protein L16
hypothetical protein
probable type II secretion system protein
hypothetical protein
cytochrome c5
hypothetical protein
hypothetical protein TABLE 2-continued hypothetical protein
ribonuclease P protein component
stringent starvation protein B
probable fosfomycin resistance protein
hypothetical protein
hypothetical protein
hypothetical protein
ferric uptake regulation protein
hypothetical protein
hypothetical protein
hypothetical protein
hypothetical protein
probable transcriptional regulator
probable NADH-ubiquinone/plastoquinone oxidoreductase
hypothetical protein
conserved hypothetical protein
hypothetical protein
hypothetical protein
hypothetical protein
probable transcriptional regulator
hypothetical protein
hypothetical protein
alkaline proteinase inhibitor AprI
lactoylglutathione lyase
hypothetical protein
hypothetical protein
hypothetical protein
probable heat shock protein
hypothetical protein
conserved hypothetical protein
hypothetical protein
hypothetical protein
30S ribosomal protein S8
hypothetical protein
5-carboxymethyl-2-hydroxymuconate isomerase
30S ribosomal pretein S9
hypothetical protein
hypothetical protein
probable cytochrome c(monoheme type)
30S ribosomal protein S11
50S ribosomal protein L17
secretion protein SecG
hypothetical protein
hypothetical protein
hypothetical protein
probable iron-binding protein lscU
succinate dehydrogenase (C subunit)
hypothetical protein
hypothetical protein
conserved hypothetical protein
conserved hypothetical protein
glycine cleavage system protein H2
hypothetical protein
hypothetical protein
hypothetical protein
hypothetical protein
hypothetical protein
aspartate 1-decarboxylase precursor
hypothetical protein
hypothetical protein
conserved hypothetical protein
probable ring-cleaving dioxygenase
hypothetical protein
ATP synthase protein I
conserved hypothetical protein
conserved hypothetical protein
hypothetical protein
hypothetical protein
conserved hypothetical protein
conserved hypothetical protein
hypothetical protein
hypothetical protein
hypothetical protein
hypothetical protein
conserved hypothetical protein
hypothetical protein
hypothetical protein
conserved hypothetical protein
probable type II secretion system protein TABLE 2-continued hypothetical protein
two-component response regulator CheY
hypothetical protein
hypothetical protein
transcriptional regulator MvaT, P16 subunit
d-erythro-7,8-dihydroneopterin triphosphate epimerase
30S ribosomal protein S12
conserved hypothetical protein
hypothetical protein
hypothetical protein
probable drug efflux transporter
50S ribosomal protein L14
hypothetical protein
hypothetical protein
50S ribosomal protein L7/L12
secretion protein SecE
succinate dehydrogeriase (D subunit)
hypothetical protein
hypothetical protein
conserved hypothetical protein in type III secretion
hypothetical protein
hypothetical protein
hypothetical protein
hypothetical protein
hypothetical protein
hypothetical protein
hypothetical protein
hypothetical protein
conserved hypothetical protein
hypothetical protein
hypothetical protein
hypothetical protein
conserved hypothetical protein
50S ribosomal protein L20
probable 6-pyruvoyl tetrahydrobiopterin synthase
hypothetical protein
30S ribosomal protein S13
type 4 fimbrial biogenesis protein PilZ
pterin-4-alpha-carbinolamine dehydratase
hypothetical protein
conserved hypothetical protein
conserved hypothetical protein
dihydroneopterin aldolase
conserved hypothetical protein
hypothetical protein
conserved hypothetical protein
conserved hypothetical protein
conserved hypothetical protein
50S ribosomal protein L18
conserved hypothetical protein
50S ribosomal protein L19
hypothetical protein
hypothetical protein
hypothetical protein
hypothetical protein
type III export protein PscG
hypothetical protein
hypothetical protein
hypothetical protein
conserved hypothetical protein
hypothetical protein
conserved hypothetical protein
hypothetical protein
hypothetical protein
hypothetical protein
conserved hypothetical protein
conserved hypothetical protein
hypothetical protein
conserved hypothetical protein
hypothetical protein
hypothetical protein
hypothetical protein
probable ferredoxin
nitrogen regulatory protein P-II 2
ferredoxin [2Fe-2S]
conserved hypothetical protein
conserved hypothetical protein

TABLE 2-continued type III export protein PscI
hypothetical protein
conserved hypothetical protein
conserved hypothetical protein
hypothetical protein
hypothetical protein
hypothetical protein
hypothetical protein
conserved hypothetical protein
phosphoribosyl-ATP pyrophosphohydrolase
conserved hypothetical protein
50S ribosomal protein L22
SMR multidrug efflux transporter
hypothetical protein
hypothetical protein
hypothetical protein
hypothetical protein
hypothetical protein
conserved hypothetical protein
conserved hypothetical protein
hypothetical protein
conserved hypothetical protein in type III secretion
conserved hypothetical protein
hypothetical protein
hypothetical protein
assimilatory nitrite reductase small subunit
hypothetical protein
conserved hypothetical protein
probable thioredoxin
thioredoxin
probable bacteriophage protein
conserved hypothetical protein
hypothetical protein
probable transporter

TABLE 3

| Mutant Name | Insertion Point | host strain |
|---|---|---|
| 001A01 | 3254036 | PAK |
| 001A03 | 4214526 | PAK |
| 001A04 | 800208 | PAK |
| 001A05 | 3627210 | PAK |
| 001A06 | 4931913 | PAK |
| 001A07 | 1034469 | PAK |
| 001A08 | 6144940 | PAK |
| 001A09 | 4102307 | PAK |
| 001A11 | 1515737 | PAK |
| 001A12 | 1244688 | PAK |
| 001B02 | 5924618 | PAK |
| 001B03 | 3267350 | PAK |
| 001B04 | 3302119 | PAK |
| 001B05 | 3108121 | PAK |
| 001B06 | 3987545 | PAK |
| 001B07 | 5585518 | PAK |
| 001B09 | 4682141 | PAK |
| 001B10 | 5041902 | PAK |
| 001B11 | 3187871 | PAK |
| 001C01 | 5924618 | PAK |
| 001C02 | 2871514 | PAK |
| 001C03 | 474619 | PAK |
| 001C04 | 5156931 | PAK |
| 001C05 | 6155744 | PAK |
| 001C06 | 5741543 | PAK |
| 001C08 | 594556 | PAK |
| 001C09 | 2370763 | PAK |
| 001C10 | 4186878 | PAK |
| 001C11 | 2016482 | PAK |
| 001C12 | 5610441 | PAK |
| 001D01 | 6193619 | PAK |
| 001D03 | 6078034 | PAK |
| 001D04 | 6139878 | PAK |
| 001D05 | 522531 | PAK |
| 001D06 | 3567982 | PAK |
| 001D08 | 3998726 | PAK |
| 001D09 | 2140251 | PAK |

TABLE 3-continued

| Mutant Name | Insertion Point | host strain |
|---|---|---|
| 001D10 | 1301169 | PAK |
| 001D11 | 3423519 | PAK |
| 001D12 | 3472670 | PAK |
| 001E02 | 800936 | PAK |
| 001E03 | 4246525 | PAK |
| 001E04 | 477959 | PAK |
| 001E05 | 477959 | PAK |
| 001E06 | 5939777 | PAK |
| 001E07 | 5471284 | PAK |
| 001E08 | 5582311 | PAK |
| 001E09 | 442285 | PAK |
| 001E10 | 4514879 | PAK |
| 001E11 | 4514879 | PAK |
| 001E12 | 5064081 | PAK |
| 001F01 | 903376 | PAK |
| 001F02 | 1889581 | PAK |
| 001F03 | 1230813 | PAK |
| 001F04 | 5755640 | PAK |
| 001F05 | 5355403 | PAK |
| 001F06 | 4493238 | PAK |
| 001F07 | 850016 | PAK |
| 001F08 | 5286479 | PAK |
| 001F09 | 3035834 | PAK |
| 001F10 | 270414 | PAK |
| 001F11 | 4300290 | PAK |
| 001F12 | 34717403 | PAK |
| 001G01 | 5431778 | PAK |
| 001G06 | 5064081 | PAK |
| 001G07 | 353196 | PAK |
| 001G08 | 4881356 | PAK |
| 001G09 | 4684466 | PAK |
| 001G10 | 1340542 | PAK |
| 001G11 | 2659761 | PAK |
| 001G12 | 4553600 | PAK |
| 001G01 | 5431778 | PAK |
| 001G02 | 627197 | PAK |
| 001G03 | 3005616 | PAK |
| 001G05 | 2300131 | PAK |
| 001G06 | 5064081 | PAK |
| 001G07 | 3531951 | PAK |
| 001G08 | 4881356 | PAK |
| 001G09 | 4684465 | PAK |
| 001H01 | 4600925 | PAK |
| 001H02 | 4465691 | PAK |
| 001H03 | 435295 | PAK |
| 001H04 | 5583961 | PAK |
| 001H06 | 5823734 | PAK |
| 001H08 | 3880466 | PAK |
| 001H09 | 271720 | PAK |
| 001H10 | 433381 | PAK |
| 001H11 | 395319 | PAK |
| 002A01 | 3652524 | PAK |
| 002A02 | 3987593 | PAK |
| 002A03 | 530429 | PAK |
| 002A04 | 6232877 | PAK |
| 002A05 | 1543845 | PAK |
| 002A06 | 619210 | PAK |
| 002A07 | 4795351 | PAK |
| 002A09 | 1152202 | PAK |
| 002A10 | 1205010 | PAK |
| 002A11 | 449470 | PAK |
| 002B01 | 5643797 | PAK |
| 002B02 | 3423910 | PAK |
| 002B03 | 3616916 | PAK |
| 002B04 | 1511758 | PAK |
| 002B05 | 3809953 | PAK |
| 002B06 | 127793 | PAK |
| 002B07 | 1277942 | PAK |
| 002B08 | 5436760 | PAK |
| 002B09 | 1030808 | PAK |
| 002B10 | 1030806 | PAK |
| 002B11 | 3355560 | PAK |
| 002B12 | 3935624 | PAK |
| 003A01 | 2016406 | PAK |
| 003A02 | 4987284 | PAK |
| 003A03 | 1713832 | PAK |
| 003A04 | 1859681 | PAK |

TABLE 3-continued

| Mutant Name | Insertion Point | host strain |
|---|---|---|
| 003A05 | 433381 | PAK |
| 003A06 | 6241260 | PAK |
| 003A08 | 1026213 | PAK |
| 003A09 | 4822426 | PAK |
| 003A10 | 513656 | PAK |
| 003A11 | 5050248 | PAK |
| 003B04 | 3377875 | PAK |
| 003B06 | 1969305 | PAK |
| 003B07 | 433381 | PAK |
| 003B08 | 1034469 | PAK |
| 003B09 | 5907415 | PAK |
| 003B10 | 4192241 | PAK |
| 003B11 | 4192241 | PAK |
| 003C01 | 5713913 | PAK |
| 003C02 | 2609592 | PAK |
| 003C03 | 2095164 | PAK |
| 003C04 | 5369447 | PAK |
| 003C05 | 799610 | PAK |
| 003C07 | 2410828 | PAK |
| 003C08 | 1576887 | PAK |
| 003C09 | 3998623 | PAK |
| 003C10 | 3771149 | PAK |
| 003C11 | 1408282 | PAK |
| 003C12 | 814349 | PAK |
| 003D01 | 433382 | PAK |
| 003D02 | 259586 | PAK |
| 003D03 | 1700770 | PAK |
| 003D04 | 433381 | PAK |
| 003D05 | 4893664 | PAK |
| 003D07 | 810409 | PAK |
| 003D08 | 433381 | PAK |
| 003D09 | 5970386 | PAK |
| 003D12 | 2049456 | PAK |
| 003E01 | 1819428 | PAK |
| 003E03 | 2555440 | PAK |
| 003E06 | 5415888 | PAK |
| 003E07 | 5929820 | PAK |
| 003E08 | 5414529 | PAK |
| 003E09 | 835119 | PAK |
| 003E10 | 4855368 | PAK |
| 003E12 | 5159655 | PAK |
| 003F01 | 683274 | PAK |
| 003F02 | 1428758 | PAK |
| 003F04 | 4638260 | PAK |
| 003F05 | 2695523 | PAK |
| 003F07 | 3607969 | PAK |
| 003F08 | 1082510 | PAK |
| 003F09 | 1031737 | PAK |
| 003F10 | 433381 | PAK |
| 003F11 | 3422289 | PAK |
| 003F12 | 2922974 | PAK |
| 003G01 | 4707158 | PAK |
| 003G02 | 5428282 | PAK |
| 003G04 | 5649040 | PAK |
| 003G05 | 433381 | PAK |
| 003G06 | 2581798 | PAK |
| 003G07 | 648767 | PAK |
| 003G10 | 5758975 | PAK |
| 003G11 | 6015681 | PAK |
| 003G12 | 6139731 | PAK |
| 003H01 | 3445197 | PAK |
| 003H02 | 1525921 | PAK |
| 003H03 | 5315736 | PAK |
| 003H04 | 1291849 | PAK |
| 003H05 | 30684 | PAK |
| 003H06 | 3266054 | PAK |
| 003H07 | 2049456 | PAK |
| 003H08 | 433381 | PAK |
| 003H09 | 879532 | PAK |
| 004A01 | 1566541 | PAK |
| 004A03 | 1503899 | PAK |
| 004A04 | 45765 | PAK |
| 004A05 | 5735233 | PAK |
| 004A06 | 5075716 | PAK |
| 004A07 | 2157575 | PAK |
| 004A08 | 3471740 | PAK |
| 004A09 | 2271949 | PAK |
| 004A10 | 2796245 | PAK |
| 004A11 | 4454450 | PAK |
| 004B01 | 5951238 | PAK |
| 004B02 | 1351731 | PAK |
| 004B04 | 433381 | PAK |
| 004B05 | 2848857 | PAK |
| 004B06 | 732379 | PAK |
| 004B07 | 4316856 | PAK |
| 004B08 | 4550848 | PAK |
| 004B09 | 5223972 | PAK |
| 004B12 | 454432 | PAK |
| 004C01 | 3293171 | PAK |
| 004C03 | 1835520 | PAK |
| 004C04 | 2188343 | PAK |
| 004C05 | 3047374 | PAK |
| 004C06 | 5315858 | PAK |
| 004C09 | 1460144 | PAK |
| 004C10 | 2049699 | PAK |
| 004C11 | 5988345 | PAK |
| 004C12 | 1104579 | PAK |
| 004D01 | 751552 | PAK |
| 004D02 | 3944498 | PAK |
| 004D03 | 1883754 | PAK |
| 004D04 | 910624 | PAK |
| 004D05 | 5437535 | PAK |
| 004D06 | 5097189 | PAK |
| 004D07 | 5397511 | PAK |
| 004D08 | 4193733 | PAK |
| 004D09 | 3400490 | PAK |
| 004D10 | 5308284 | PAK |
| 004D11 | 5859357 | PAK |
| 004D12 | 4364415 | PAK |
| 004E01 | 3312704 | PAK |
| 004E04 | 1566516 | PAK |
| 004E05 | 5799481 | PAK |
| 004E06 | 1897781 | PAK |
| 004E08 | 1166054 | PAK |
| 004E09 | 5865140 | PAK |
| 004E10 | 2471733 | PAK |
| 004E11 | 5956163 | PAK |
| 004E12 | 1653588 | PAK |
| 004F01 | 5865145 | PAK |
| 004F06 | 1122958 | PAK |
| 004F07 | 1884758 | PAK |
| 004F08 | 156187 | PAK |
| 004F09 | 3723875 | PAK |
| 004F11 | 1034468 | PAK |
| 004F12 | 3047374 | PAK |
| 004G02 | 6100910 | PAK |
| 004G03 | 3885608 | PAK |
| 004G06 | 5004165 | PAK |
| 004G07 | 629956 | PAK |
| 004G09 | 2231219 | PAK |
| 004G11 | 5772930 | PAK |
| 004G12 | 392997 | PAK |
| 004H02 | 1595508 | PAK |
| 004H03 | 1595508 | PAK |
| 004H04 | 3635403 | PAK |
| 004H05 | 5988173 | PAK |
| 004H06 | 1821975 | PAK |
| 004H08 | 5150834 | PAK |
| 004H09 | 422703 | PAK |
| 004H10 | 5511104 | PAK |
| 004H11 | 395319 | PAK |
| 005A01 | 6121145 | PAK |
| 005A02 | 4637976 | PAK |
| 005A03 | 5251656 | PAK |
| 005A04 | 1358579 | PAK |
| 005A05 | 2826665 | PAK |
| 005A06 | 351028 | PAK |
| 005A08 | 2009564 | PAK |
| 005A09 | 1779817 | PAK |
| 005A11 | 2636229 | PAK |
| 005A12 | 3726006 | PAK |
| 005B03 | 4797603 | PAK |
| 005B05 | 1423578 | PAK |
| 005B06 | 1086897 | PAK |

TABLE 3-continued

| Mutant Name | Insertion Point | host strain |
|---|---|---|
| 005B07 | 3463110 | PAK |
| 005B08 | 1490094 | PAK |
| 005B09 | 1583954 | PAK |
| 005B10 | 681527 | PAK |
| 005B11 | 2537467 | PAK |
| 005B12 | 6223150 | PAK |
| 005C02 | 1445969 | PAK |
| 005C03 | 6112259 | PAK |
| 005C04 | 4104568 | PAK |
| 005C07 | 260868 | PAK |
| 005C08 | 1659915 | PAK |
| 005C09 | 6978331 | PAK |
| 005C10 | 3642669 | PAK |
| 005C11 | 543492 | PAK |
| 005C12 | 543492 | PAK |
| 005D01 | 1739361 | PAK |
| 005D02 | 4375879 | PAK |
| 005D03 | 2854969 | PAK |
| 005D04 | 3183786 | PAK |
| 005D05 | 3715903 | PAK |
| 005D06 | 45493251 | PAK |
| 005D08 | 806743 | PAK |
| 005D10 | 5054137 | PAK |
| 005D11 | 5218315 | PAK |
| 005D12 | 4981489 | PAK |
| 005E03 | 7475951 | PAK |
| 005E04 | 19912441 | PAK |
| 005E05 | 7475951 | PAK |
| 005E06 | 5945978 | PAK |
| 005E07 | 3075241 | PAK |
| 005E09 | 1868247 | PAK |
| 005E11 | 3306428 | PAK |
| 005E12 | 947510 | PAK |
| 005F01 | 3225856 | PAK |
| 005F03 | 1309650 | PAK |
| 005F04 | 3709087 | PAK |
| 005F05 | 5077881 | PAK |
| 005F08 | 1680865 | PAK |
| 005F10 | 2185333 | PAK |
| 005F11 | 4299947 | PAK |
| 005F12 | 1130487 | PAK |
| 005G02 | 5018107 | PAK |
| 005G03 | 4422899 | PAK |
| 005G06 | 4517577 | PAK |
| 005G07 | 5059743 | PAK |
| 005G08 | 1843340 | PAK |
| 005G09 | 6107697 | PAK |
| 005G10 | 4364428 | PAK |
| 005G11 | 4026064 | PAK |
| 005G12 | 1099396 | PAK |
| 005H03 | 6214274 | PAK |
| 005H04 | 2144520 | PAK |
| 005H05 | 1807286 | PAK |
| 005H06 | 1807286 | PAK |
| 005H08 | 3699645 | PAK |
| 005H10 | 1515737 | PAK |
| 005H11 | 395319 | PAK |
| 006A01 | 6231371 | PAK |
| 006A02 | 3402303 | PAK |
| 006A04 | 2079699 | PAK |
| 006A05 | 2008375 | PAK |
| 006A06 | 433381 | PAK |
| 006A08 | 3592139 | PAK |
| 006A09 | 3453875 | PAK |
| 006A10 | 794950 | PAK |
| 006A11 | 5819801 | PAK |
| 006A12 | 3468427 | PAK |
| 006B01 | 1966899 | PAK |
| 006B02 | 3160110 | PAK |
| 006B03 | 2955666 | PAK |
| 006B04 | 3511738 | PAK |
| 006B05 | 4241233 | PAK |
| 006B06 | 2471515 | PAK |
| 006B07 | 2048265 | PAK |
| 006B08 | 2469575 | PAK |
| 006B09 | 696492 | PAK |
| 006B10 | 846315 | PAK |
| 006B11 | 166648 | PAK |
| 006B12 | 4741112 | PAK |
| 006C01 | 433381 | PAK |
| 006C02 | 4064994 | PAK |
| 006C03 | 1280374 | PAK |
| 006C04 | 3596440 | PAK |
| 006C05 | 1442814 | PAK |
| 006C07 | 577497 | PAK |
| 006C09 | 1784068 | PAK |
| 006C10 | 2240534 | PAK |
| 006C12 | 4047002 | PAK |
| 006D01 | 4070007 | PAK |
| 006D02 | 6085314 | PAK |
| 006D03 | 1150463 | PAK |
| 006D05 | 3610871 | PAK |
| 006D06 | 5310625 | PAK |
| 006D07 | 517361 | PAK |
| 006D08 | 2892863 | PAK |
| 006D09 | 3327334 | PAK |
| 006D10 | 2229992 | PAK |
| 006D11 | 1878712 | PAK |
| 006D12 | 3916203 | PAK |
| 006E01 | 147621 | PAK |
| 006E02 | 147622 | PAK |
| 006E03 | 688108 | PAK |
| 006E04 | 688115 | PAK |
| 006E06 | 5023473 | PAK |
| 006E11 | 4844174 | PAK |
| 006F03 | 6230087 | PAK |
| 006F06 | 6257292 | PAK |
| 006F07 | 3086149 | PAK |
| 006F10 | 3020409 | PAK |
| 006F11 | 5211588 | PAK |
| 006F12 | 5211588 | PAK |
| 006H03 | 2264576 | PAK |
| 006H05 | 5597985 | PAK |
| 006H06 | 1824523 | PAK |
| 006H10 | 43336 | PAK |
| 007A01 | 5912381 | PAK |
| 007A02 | 4996527 | PAK |
| 007A03 | 2506689 | PAK |
| 007A04 | 5047557 | PAK |
| 007A05 | 1356486 | PAK |
| 007A08 | 5119129 | PAK |
| 007A09 | 1241181 | PAK |
| 007A10 | 1116321 | PAK |
| 007A11 | 5531202 | PAK |
| 007B03 | 381725 | PAK |
| 007B04 | 5202438 | PAK |
| 007B07 | 1088380 | PAK |
| 007B08 | 761021 | PAK |
| 007B12 | 319136 | PAK |
| 007C01 | 4999394 | PAK |
| 007C03 | 6925605 | PAK |
| 007C04 | 3147742 | PAK |
| 007C05 | 1298405 | PAK |
| 007C06 | 6009818 | PAK |
| 007C07 | 4964806 | PAK |
| 007C08 | 1820366 | PAN |
| 007C12 | 5906710 | PAN |
| 007D01 | 981051 | PAN |
| 007D02 | 2653952 | PAN |
| 007D03 | 5864257 | PAK |
| 007D05 | 2610279 | PAK |
| 007D06 | 518876 | PAK |
| 007D09 | 6104097 | PAK |
| 007D10 | 623589 | PAK |
| 007D11 | 5998366 | PAK |
| 007D12 | 5906710 | PAK |
| 007E01 | 5906711 | PAK |
| 007E03 | 3039779 | PAK |
| 007E04 | 2817098 | PAK |
| 007E05 | 433381 | PAK |
| 007E06 | 3364220 | PAK |
| 007E07 | 2073712 | PAK |
| 007E08 | 5437249 | PAK |
| 007E09 | 4006770 | PAK |

TABLE 3-continued

| Mutant Name | Insertion Point | host strain |
|---|---|---|
| 007E12 | 2007273 | PAK |
| 007F01 | 5932975 | PAK |
| 007F02 | 2569309 | PAK |
| 007F03 | 2690178 | PAK |
| 007F06 | 281863 | PAK |
| 007F07 | 2145275 | PAK |
| 007F09 | 5736865 | PAK |
| 007F10 | 1216239 | PAK |
| 007F11 | 2268589 | PAK |
| 007G01 | 2597565 | PAK |
| 007G02 | 429397 | PAK |
| 007G03 | 433381 | PAK |
| 007G05 | 5802881 | PAK |
| 007G08 | 4976058 | PAK |
| 007G09 | 5862511 | PAK |
| 007G12 | 5053880 | PAK |
| 007H01 | 1138541 | PAK |
| 007H06 | 3395040 | PAK |
| 007H07 | 6160185 | PAK |
| 007H09 | 1472036 | PAK |
| 007H10 | 5903098 | PAK |
| 007H11 | 395319 | PAK |
| 008A02 | 1401775 | PAK |
| 008A03 | 5533650 | PAK |
| 008A06 | 1220616 | PAK |
| 008A09 | 5177910 | PAK |
| 008A10 | 1427316 | PAK |
| 008A11 | 5391551 | PAK |
| 008A12 | 3266259 | PAK |
| 008B02 | 3196439 | PAK |
| 008B03 | 5908754 | PAK |
| 008B04 | 1306276 | PAK |
| 008B05 | 2293871 | PAK |
| 008B07 | 302152 | PAK |
| 008B08 | 2126711 | PAK |
| 008B09 | 1506280 | PAK |
| 008B10 | 4317738 | PAK |
| 008B11 | 2365611 | PAK |
| 008B12 | 5052784 | PAK |
| 008C01 | 1445520 | PAK |
| 008C02 | 1530109 | PAK |
| 008C04 | 5760742 | PAK |
| 008C05 | 4119860 | PAK |
| 008C06 | 5984580 | PAK |
| 008C07 | 3521902 | PAK |
| 008C08 | 3316846 | PAK |
| 008C09 | 5414529 | PAK |
| 008C10 | 3163477 | PAK |
| 008C11 | 3196682 | PAK |
| 008C12 | 1340468 | PAK |
| 008D02 | 4004133 | PAK |
| 008D03 | 1950036 | PAK |
| 008D04 | 1585228 | PAK |
| 008D05 | 2700127 | PAK |
| 008D06 | 5783753 | PAK |
| 008D07 | 3758033 | PAK |
| 008D09 | 2094095 | PAK |
| 008D10 | 1540459 | PAK |
| 008D12 | 3899774 | PAK |
| 008E01 | 1262833 | PAK |
| 008E02 | 2020234 | PAK |
| 008E03 | 3157955 | PAK |
| 008E05 | 6141393 | PAK |
| 008E06 | 1904921 | PAK |
| 008E08 | 5262133 | PAK |
| 008E10 | 2843945 | PAK |
| 008E11 | 6067378 | PAK |
| 008E12 | 5838321 | PAK |
| 008F01 | 2509916 | PAK |
| 008F02 | 2951706 | PAK |
| 008F03 | 5966138 | PAK |
| 008F04 | 5667462 | PAK |
| 008F06 | 1010280 | PAK |
| 008F07 | 4170604 | PAK |
| 008F08 | 878841 | PAK |
| 008F10 | 5170483 | PAK |
| 008F11 | 1925218 | PAK |
| 008G01 | 4364130 | PAK |
| 008G02 | 1233542 | PAK |
| 008G03 | 3831294 | PAK |
| 008G06 | 2375310 | PAK |
| 008G07 | 5236287 | PAK |
| 008G08 | 703219 | PAK |
| 008G09 | 3427382 | PAK |
| 008G11 | 3471740 | PAK |
| 008G12 | 5928996 | PAK |
| 008H01 | 5158949 | PAK |
| 008H02 | 4505522 | PAK |
| 008H03 | 320285 | PAK |
| 008H04 | 6026655 | PAK |
| 008H05 | 5044220 | PAK |
| 008H06 | 5426161 | PAK |
| 008H07 | 1513042 | PAK |
| 008H08 | 3194944 | PAK |
| 008H09 | 6228340 | PAK |
| 008H10 | 2423594 | PAK |
| 008H11 | 395319 | PAK |
| 009A01 | 4618214 | PAK |
| 009A02 | 5247824 | PAK |
| 009A03 | 4273793 | PAK |
| 009A04 | 1114992 | PAK |
| 009A05 | 5793024 | PAK |
| 009A06 | 1235603 | PAK |
| 009A07 | 5683951 | PAK |
| 009A08 | 179152 | PAK |
| 009A09 | 5944765 | PAK |
| 009A10 | 179152 | PAK |
| 009A12 | 755224 | PAK |
| 009B01 | 3727745 | PAK |
| 009B02 | 1705085 | PAK |
| 009B03 | 212212 | PAK |
| 009B04 | 1100801 | PAK |
| 009B05 | 495336 | PAK |
| 009B06 | 931243 | PAK |
| 009B07 | 2902526 | PAK |
| 009B10 | 2903004 | PAK |
| 009B11 | 6036075 | PAK |
| 009B12 | 4839325 | PAK |
| 009C02 | 4849653 | PAK |
| 009C04 | 6192850 | PAK |
| 009C05 | 4865184 | PAK |
| 009C06 | 5188867 | PAK |
| 009C07 | 5950052 | PAK |
| 009C10 | 861532 | PAK |
| 009C11 | 1002811 | PAK |
| 009C12 | 4839325 | PAK |
| 009D02 | 1896144 | PAK |
| 009D04 | 1001159 | PAK |
| 009D05 | 5398428 | PAK |
| 009D06 | 5831979 | PAK |
| 009D07 | 5359312 | PAK |
| 009D08 | 3014940 | PAK |
| 009D09 | 2839554 | PAK |
| 009D10 | 3462293 | PAK |
| 009D11 | 4907028 | PAK |
| 009E01 | 2492946 | PAK |
| 009E08 | 1647568 | PAK |
| 009E11 | 3248346 | PAK |
| 009E12 | 5712210 | PAK |
| 009F02 | 109260 | PAK |
| 009F03 | 5700966 | PAK |
| 009F06 | 5370056 | PAK |
| 009F07 | 3885693 | PAK |
| 009F08 | 1034469 | PAK |
| 009F10 | 2728956 | PAK |
| 009F12 | 5938984 | PAK |
| 009G02 | 5289936 | PAK |
| 009G03 | 113028 | PAK |
| 009G04 | 3797650 | PAK |
| 009G06 | 1934170 | PAK |
| 009G07 | 6002903 | PAK |
| 009G08 | 2397433 | PAK |
| 009G10 | 3722009 | PAK |
| 009G11 | 5120195 | PAK |

TABLE 3-continued

| Mutant Name | Insertion Point | host strain |
|---|---|---|
| 009H01 | 4079716 | PAK |
| 009H02 | 4079717 | PAK |
| 009H04 | 2696078 | PAK |
| 009H05 | 807759 | PAK |
| 009H06 | 902991 | PAK |
| 009H08 | 3835217 | PAK |
| 009H09 | 3019813 | PAK |
| 009H10 | 4591512 | PAK |
| 010A01 | 5515754 | PAK |
| 010A02 | 1123336 | PAK |
| 010A03 | 113028 | PAK |
| 010A04 | 5391549 | PAK |
| 010A05 | 3671325 | PAK |
| 010A07 | 113028 | PAK |
| 010A08 | 343533 | PAK |
| 010A09 | 353366 | PAK |
| 010A10 | 113028 | PAK |
| 010A11 | 4004274 | PAK |
| 010B02 | 113028 | PAK |
| 010B03 | 679285 | PAK |
| 010B04 | 3109769 | PAK |
| 010B05 | 2132942 | PAK |
| 010B07 | 5743385 | PAK |
| 010B09 | 5391551 | PAK |
| 010B10 | 1612404 | PAK |
| 010B11 | 5391551 | PAK |
| 010B12 | 2801075 | PAK |
| 010C01 | 1034469 | PAK |
| 010C03 | 4229262 | PAK |
| 010C04 | 5670267 | PAK |
| 010C05 | 5003539 | PAK |
| 010C07 | 914343 | PAK |
| 010C08 | 3485914 | PAK |
| 010C09 | 1365470 | PAK |
| 010C12 | 3969922 | PAK |
| 010D02 | 3567982 | PAK |
| 010D03 | 1097715 | PAK |
| 010D04 | 5821692 | PAK |
| 010D05 | 2058204 | PAK |
| 010D06 | 1853936 | PAK |
| 010D07 | 1853936 | PAK |
| 010D09 | 1395857 | PAK |
| 010D10 | 3776755 | PAK |
| 010D12 | 2913045 | PAK |
| 01DE01 | 2913045 | PAK |
| 010E02 | 5391551 | PAK |
| 010E03 | 113028 | PAK |
| 010E04 | 5391551 | PAK |
| 010E09 | 5391551 | PAK |
| 010E10 | 4689213 | PAK |
| 010E12 | 612782 | PAK |
| 010F02 | 3840785 | PAK |
| 010F03 | 6086307 | PAK |
| 010F04 | 5855599 | PAK |
| 010F05 | 2340281 | PAK |
| 010F07 | 4873594 | PAK |
| 010F09 | 1170198 | PAK |
| 010F11 | 113028 | PAK |
| 010F12 | 5391551 | PAK |
| 010G02 | 113028 | PAK |
| 010G03 | 3603752 | PAK |
| 010G04 | 2326169 | PAK |
| 010G05 | 5391551 | PAK |
| 010G06 | 5544373 | PAK |
| 010G07 | 5097690 | PAK |
| 010G08 | 2880371 | PAK |
| 010G10 | 409856 | PAK |
| 010G11 | 5391551 | PAK |
| 010G12 | 4415590 | PAK |
| 010H01 | 6180761 | PAK |
| 010H02 | 113028 | PAK |
| 010H03 | 2324609 | PAK |
| 010H04 | 5391551 | PAK |
| 010H05 | 5391551 | PAK |
| 010H06 | 4111582 | PAK |
| 010H08 | 3569426 | PAK |
| 010H10 | 4158204 | PAK |
| 011A01 | 5391551 | PAK |
| 011A02 | 2898386 | PAK |
| 011A03 | 5391551 | PAK |
| 011A05 | 1431229 | PAK |
| 011A06 | 1587581 | PAK |
| 011A07 | 3974570 | PAK |
| 011A08 | 2319023 | PAK |
| 011A09 | 4706922 | PAK |
| 011A10 | 5391551 | PAK |
| 011B02 | 807830 | PAK |
| 011B03 | 5803345 | PAK |
| 011B04 | 5391551 | PAK |
| 011B05 | 5823675 | PAK |
| 011B06 | 5391551 | PAK |
| 011B07 | 5391551 | PAK |
| 011B08 | 1404440 | PAK |
| 011B11 | 113028 | PAK |
| 011B12 | 5391551 | PAK |
| 011C02 | 5391551 | PAK |
| 011C03 | 113028 | PAK |
| 011C04 | 4884564 | PAK |
| 011C05 | 5197600 | PAK |
| 011C06 | 5391551 | PAK |
| 011C07 | 5391551 | PAK |
| 011C09 | 5391551 | PAK |
| 011C10 | 5391551 | PAK |
| 011C11 | 113028 | PAK |
| 011D01 | 1188885 | PAK |
| 011D02 | 1629363 | PAK |
| 011D05 | 5391551 | PAK |
| 011D06 | 5391551 | PAK |
| 011D09 | 4898840 | PAK |
| 011D11 | 113028 | PAK |
| 011E01 | 647899 | PAK |
| 011E02 | 961215 | PAK |
| 011E03 | 5391551 | PAK |
| 011E05 | 5391551 | PAK |
| 011E07 | 5391551 | PAK |
| 011E08 | 1397790 | PAK |
| 011E09 | 5391551 | PAK |
| 011E10 | 3484613 | PAK |
| 011E11 | 1703765 | PAK |
| 011E12 | 5391550 | PAK |
| C11F01 | 5391551 | PAK |
| 011F02 | 5391550 | PAK |
| 011F03 | 720447 | PAK |
| 011F04 | 5391551 | PAK |
| 011F05 | 1095136 | PAK |
| 011F06 | 660912 | PAK |
| 011F07 | 5391551 | PAK |
| 011F08 | 2696404 | PAK |
| 011F09 | 709465 | PAK |
| 011F11 | 5391551 | PAK |
| 011F12 | 5391551 | PAK |
| 011G03 | 469970 | PAK |
| 011G05 | 21978 | PAK |
| 011G07 | 113028 | PAK |
| 011G08 | 5391550 | PAK |
| 011G09 | 721418 | PAK |
| 011G11 | 5391551 | PAK |
| 011G12 | 5391551 | PAK |
| 011H01 | 5391551 | PAK |
| 011H03 | 5391551 | PAK |
| 011H04 | 5391551 | PAK |
| 011H05 | 5391551 | PAK |
| 011H06 | 113028 | PAK |
| 011H07 | 4585053 | PAK |
| 011H09 | 5391551 | PAK |
| 011H10 | 5391551 | PAK |
| 012A04 | 5318503 | PAK |
| 012A05 | 731213 | PAK |
| 012A06 | 821134 | PAK |
| 012A07 | 4394536 | PAK |
| 012A12 | 2012884 | PAK |
| 012B01 | 3690219 | PAK |
| 012B05 | 3885693 | PAK |
| 012B06 | 4978974 | PAK |

TABLE 3-continued

| Mutant Name | Insertion Point | host strain |
|---|---|---|
| 012B07 | 3693435 | PAK |
| 012B08 | 915061 | PAK |
| 012B09 | 2488381 | PAK |
| 012B10 | 4444032 | PAK |
| 012B11 | 5969350 | PAK |
| 012B12 | 4444032 | PAK |
| 012C05 | 3676968 | PAK |
| 012C06 | 5076344 | PAK |
| 012C07 | 5275801 | PAK |
| 012C08 | 716532 | PAK |
| 012C10 | 5532453 | PAK |
| 012C12 | 5856125 | PAK |
| 012D02 | 2605217 | PAK |
| 012D03 | 6219887 | PAK |
| 012D05 | 3676968 | PAK |
| 012D06 | 5076344 | PAK |
| 012D07 | 5275801 | PAK |
| 012D08 | 716532 | PAK |
| 012D10 | 5532453 | PAK |
| 012D11 | 5280104 | PAK |
| 012E04 | 5290122 | PAK |
| 012E08 | 5204468 | PAK |
| 012E10 | 526706 | PAK |
| 012E11 | 5868065 | PAK |
| 012E12 | 167550 | PAK |
| 012F07 | 1597750 | PAK |
| 012F08 | 5139506 | PAK |
| 012F10 | 618745 | PAK |
| 012F11 | 542500 | PAK |
| 012F12 | 5796929 | PAK |
| 012G02 | 1621935 | PAK |
| 012G03 | 3218742 | PAK |
| 012G08 | 5371277 | PAK |
| 012G09 | 362164 | PAK |
| 012G10 | 602919 | PAK |
| 012G11 | 1078985 | PAK |
| 012G12 | 533509 | PAK |
| 012H01 | 4542767 | PAK |
| 012H02 | 1110594 | PAK |
| 012H03 | 1878963 | PAK |
| 012H06 | 5978919 | PAK |
| 012H07 | 5369447 | PAK |
| 012H08 | 6098130 | PAK |
| 012H09 | 747582 | PAK |
| 012H10 | 954479 | PAK |
| 012H11 | 5902508 | PAK |
| 013A01 | 800844 | PAK |
| 013A02 | 5908961 | PAK |
| 013A03 | 8205517 | PAK |
| 013A04 | 4419033 | PAK |
| 013A05 | 6084970 | PAK |
| 013A06 | 852272 | PAK |
| 013A07 | 5162666 | PAK |
| 013A08 | 2870523 | PAK |
| 013A09 | 3187469 | PAK |
| 013A10 | 6024027 | PAK |
| 013A11 | 3879965 | PAK |
| 013A12 | 4447098 | PAK |
| 013B01 | 5369448 | PAK |
| 013B02 | 614648 | PAK |
| 013B04 | 1893982 | PAK |
| 013B05 | 5471374 | PAK |
| 013B06 | 40365342 | PAK |
| 013B07 | 5242983 | PAK |
| 013B10 | 5609996 | PAK |
| 013B11 | 5523251 | PAK |
| 013C01 | 5436102 | PAK |
| 013C02 | 5932975 | PAK |
| 013C04 | 2559803 | PAK |
| 013C05 | 1163038 | PAK |
| 013C06 | 273331 | PAK |
| 013C07 | 4876644 | PAK |
| 013C08 | 3994085 | PAK |
| 013C09 | 6081571 | PAK |
| 013C10 | 5948078 | PAK |
| 013C11 | 250578 | PAK |
| 013C12 | 3219235 | PAK |
| 013D01 | 158183 | PAK |
| 013D02 | 4571208 | PAK |
| 013D03 | 4163619 | PAK |
| 013D04 | 519535 | PAK |
| 013D05 | 5804720 | PAK |
| 013D06 | 4545468 | PAK |
| 013D07 | 479428 | PAK |
| 013D08 | 5748672 | PAK |
| 013D09 | 1459780 | PAK |
| 013D10 | 6090276 | PAK |
| 013D11 | 1555086 | PAK |
| 013D12 | 6210466 | PAK |
| 013E01 | 2216724 | PAK |
| 013E02 | 5997074 | PAK |
| 013E04 | 5005930 | PAK |
| 013E07 | 2519548 | PAK |
| 013E08 | 2365956 | PAK |
| 013E09 | 1136241 | PAK |
| 013E10 | 645265 | PAK |
| 013E11 | 3672743 | PAK |
| 013F02 | 6092147 | PAK |
| 013F04 | 916670 | PAK |
| 013F05 | 4276230 | PAK |
| 013F06 | 974863 | PAK |
| 013F08 | 2900554 | PAK |
| 013F09 | 2016407 | PAK |
| 013F10 | 3423519 | PAK |
| 013G03 | 661997 | PAK |
| 013G04 | 3231365 | PAK |
| 013G05 | 4869306 | PAK |
| 013G06 | 2105867 | PAK |
| 013G07 | 3617181 | PAK |
| 013G08 | 3186074 | PAK |
| 013G10 | 76731 | PAK |
| 013G11 | 5858905 | PAK |
| 013G12 | 3735863 | PAK |
| 013H02 | 478997 | PAK |
| 013H03 | 3216741 | PAK |
| 013H05 | 419757 | PAK |
| 013H07 | 4078724 | PAK |
| 013H09 | 381467 | PAK |
| 013H11 | 2051342 | PAK |
| 013H12 | 395319 | PAK |
| 014A02 | 4854459 | PAK |
| 014A05 | 3715912 | PAK |
| 014A06 | 5045094 | PAK |
| 014A08 | 1674912 | PAK |
| 014A10 | 1311742 | PAK |
| 014A12 | 4208244 | PAK |
| 014B01 | 5968741 | PAK |
| 014B02 | 181429 | PAK |
| 014B03 | 75214 | PAK |
| 014B05 | 1086960 | PAK |
| 014B06 | 4444809 | PAK |
| 014B07 | 1235195 | PAK |
| 014B08 | 4174090 | PAK |
| 014B09 | 2492651 | PAK |
| 014B10 | 2290579 | PAK |
| 014B11 | 4540140 | PAK |
| 014B12 | 2877350 | PAK |
| 014C02 | 3014982 | PAK |
| 014C04 | 5999079 | PAK |
| 014C05 | 285020 | PAK |
| 014C06 | 1136274 | PAK |
| 014C08 | 4208719 | PAK |
| 014C09 | 6137118 | PAK |
| 014C11 | 1383921 | PAK |
| 014C12 | 734720 | PAK |
| 014D02 | 2542978 | PAK |
| 014D03 | 3147545 | PAK |
| 014D05 | 5785606 | PAK |
| 014D06 | 603462 | PAK |
| 014D07 | 3606734 | PAK |
| 014D08 | 1877722 | PAK |
| 014D09 | 1395225 | PAK |
| 014D10 | 3465130 | PAK |
| 014D11 | 1761895 | PAK |

TABLE 3-continued

| Mutant Name | Insertion Point | host strain |
|---|---|---|
| 014D12 | 2924666 | PAK |
| 014E01 | 3498508 | PAK |
| 014E02 | 5818308 | PAK |
| 014E04 | 4711093 | PAK |
| 014E09 | 644912 | PAK |
| 014E10 | 5977819 | PAK |
| 014E11 | 812886 | PAK |
| 014E12 | 178912 | PAK |
| 014F01 | 4396106 | PAK |
| 014F02 | 4044701 | PAK |
| 014F03 | 4369528 | PAK |
| 014F04 | 1100801 | PAK |
| 014F05 | 3040618 | PAK |
| 014F06 | 1116356 | PAK |
| 014F09 | 5319457 | PAK |
| 014F11 | 986202 | PAK |
| 014F12 | 1167213 | PAK |
| 014G01 | 4979503 | PAK |
| 014G02 | 1916999 | PAK |
| 014G04 | 56099 | PAK |
| 014G06 | 5961260 | PAK |
| 014G07 | 19616 | PAK |
| 014G09 | 1272235 | PAK |
| 014G10 | 3323089 | PAK |
| 014G11 | 5979829 | PAK |
| 014G12 | 1224072 | PAK |
| 014H03 | 4623706 | PAK |
| 014H04 | 2317527 | PAK |
| 014H05 | 3407432 | PAK |
| 014H06 | 2417526 | PAK |
| 014H07 | 4408092 | PAK |
| 014H10 | 4623706 | PAK |
| 014H11 | 4596084 | PAK |
| 015A01 | 5522165 | PAK |
| 015A05 | 5918131 | PAK |
| 015A06 | 5004735 | PAK |
| 015A07 | 2327789 | PAK |
| 015A08 | 647763 | PAK |
| 015A10 | 6170456 | PAK |
| 015A11 | 1460144 | PAK |
| 015B01 | 5938984 | PAK |
| 015B02 | 2996734 | PAK |
| 015B04 | 711795 | PAK |
| 015B05 | 5178911 | PAK |
| 015B09 | 5292137 | PAK |
| 015B10 | 2795731 | PAK |
| 015B11 | 4115981 | PAK |
| 015B12 | 1010781 | PAK |
| 015C01 | 5835465 | PAK |
| 015C02 | 1789102 | PAK |
| 015C03 | 4875596 | PAK |
| 015C04 | 5171411 | PAK |
| 015C05 | 2271694 | PAK |
| 015C07 | 1497968 | PAK |
| 015C08 | 2429830 | PAK |
| 015C09 | 1460144 | PAK |
| 015C10 | 6212320 | PAK |
| 015C12 | 5657549 | PAK |
| 015D01 | 5835465 | PAK |
| 015D02 | 6213520 | PAK |
| 015D03 | 5906155 | PAK |
| 015D04 | 4180794 | PAK |
| 015D05 | 2271694 | PAK |
| 015D06 | 5031841 | PAK |
| 015D07 | 1497968 | PAK |
| 015D08 | 2429830 | PAK |
| 015D10 | 6212320 | PAK |
| 015D11 | 320315 | PAK |
| 015D12 | 2007273 | PAK |
| 015E01 | 2200575 | PAK |
| 015E02 | 514461 | PAK |
| 015E03 | 4898840 | PAK |
| 015E04 | 6023617 | PAK |
| 015E07 | 1132845 | PAK |
| 015E10 | 592214 | PAK |
| 015E12 | 3508921 | PAK |
| 015F01 | 5304135 | PAK |
| 015F03 | 3573515 | PAK |
| 015F06 | 2435651 | PAK |
| 015F07 | 2656739 | PAK |
| 015F10 | 2180374 | PAK |
| 015F11 | 6168996 | PAK |
| 015F12 | 1010607 | PAK |
| 015G01 | 648754 | PAK |
| 015G03 | 5146352 | PAK |
| 015G04 | 5789435 | PAK |
| 015G06 | 5683172 | PAK |
| 015G07 | 542954 | PAK |
| 015G10 | 5005509 | PAK |
| 015G12 | 5005509 | PAK |
| 015H04 | 469200 | PAK |
| 015H07 | 1623332 | PAK |
| 015H09 | 935687 | PAK |
| 015H10 | 5886551 | PAK |
| 016A02 | 794261 | PAK |
| 016A03 | 1173402 | PAK |
| 016A04 | 1034469 | PAK |
| 016A05 | 2325018 | PAK |
| 016A06 | 1460144 | PAK |
| 016A07 | 5064891 | PAK |
| 016A08 | 5362271 | PAK |
| 016B01 | 1460143 | PAK |
| 016B02 | 635345 | PAK |
| 017B01 | 4136702 | PAK |
| 017B02 | 5066149 | PAK |
| 017B03 | 4624612 | PAK |
| 017B08 | 565077 | PAK |
| 017B09 | 5379478 | PAK |
| 017B10 | 5537955 | PAK |
| 017B12 | 5586757 | PAK |
| 017C01 | 1034473 | PAK |
| 017C02 | 4519101 | PAK |
| 017C03 | 6021646 | PAK |
| 017C04 | 111664 | PAK |
| 017C05 | 1750668 | PAK |
| 017C08 | 3274923 | PAK |
| 017C10 | 2891653 | PAK |
| 017C11 | 564914 | PAK |
| 017C12 | 3139771 | PAK |
| 017D01 | 4106825 | PAK |
| 017D02 | 835114 | PAK |
| 017D03 | 3124696 | PAK |
| 017D04 | 4244318 | PAK |
| 017D05 | 5958291 | PAK |
| 017D06 | 1156076 | PAK |
| 017D07 | 5369448 | PAK |
| 017D08 | 571222 | PAK |
| 017D10 | 2483755 | PAK |
| 017D11 | 1964084 | PAK |
| 017D12 | 2568161 | PAK |
| 017E02 | 4655650 | PAK |
| 017E04 | 6161205 | PAK |
| 017E05 | 5735984 | PAK |
| 017E06 | 3596336 | PAK |
| 017E07 | 58971 | PAK |
| 017E09 | 970805 | PAK |
| 017E10 | 3626396 | PAK |
| 017E11 | 3874111 | PAK |
| 017E12 | 5884512 | PAK |
| 017F01 | 1991658 | PAK |
| 017F02 | 1328770 | PAK |
| 017F03 | 3440887 | PAK |
| 017F04 | 5315430 | PAK |
| 017F05 | 40533 | PAK |
| 017F06 | 4348188 | PAK |
| 017F07 | 4495283 | PAK |
| 017G02 | 5313098 | PAK |
| 017G04 | 5347122 | PAK |
| 017G06 | 3578962 | PAK |
| 017G07 | 3578962 | PAK |
| 017G08 | 3240059 | PAK |
| 017G09 | 535442 | PAK |
| 017G12 | 852272 | PAK |
| 017H03 | 2997910 | PAK |

TABLE 3-continued

| Mutant Name | Insertion Point | host strain |
|---|---|---|
| 017H04 | 5188419 | PAK |
| 017H06 | 2940676 | PAK |
| 017H08 | 2548132 | PAK |
| 017H09 | 1796309 | PAK |
| 017H11 | 4160045 | PAK |
| 018C01 | 5969351 | PAK |
| 018C03 | 1991658 | PAK |
| 018C04 | 3689170 | PAK |
| 018C05 | 2010263 | PAK |
| 018C07 | 1202189 | PAK |
| 018C10 | 6070774 | PAK |
| 018C11 | 5878669 | PAK |
| 019A04 | 5290540 | PAK |
| 019A05 | 368352 | PAK |
| 019A08 | 659142 | PAK |
| 019A09 | 4014611 | PAK |
| 019A10 | 2016407 | PAK |
| 019A11 | 5371154 | PAK |
| 019A12 | 1477010 | PAK |
| 019B01 | 6092460 | PAK |
| 019B02 | 6092460 | PAK |
| 019B03 | 884055 | PAK |
| 019B04 | 3804124 | PAK |
| 019B05 | 3665692 | PAK |
| 019B06 | 5938984 | PAK |
| 019B07 | 1308828 | PAK |
| 019B08 | 5938984 | PAK |
| 019B09 | 5533910 | PAK |
| 019B10 | 503484 | PAK |
| 019B11 | 3940297 | PAK |
| 019C02 | 3792100 | PAK |
| 019C03 | 940225 | PAK |
| 019C04 | 5244238 | PAK |
| 019C05 | 4337422 | PAK |
| 019C06 | 3033131 | PAK |
| 019C07 | 3602210 | PAK |
| 019C09 | 5163695 | PAK |
| 019C11 | 1368996 | PAK |
| 019C12 | 5938984 | PAK |
| 019D02 | 4248315 | PAK |
| 019D03 | 5938984 | PAK |
| 019D05 | 2789814 | PAK |
| 019D06 | 3225681 | PAK |
| 019D07 | 1679524 | PAK |
| 019D10 | 896011 | PAK |
| 019D11 | 5980181 | PAK |
| 019D12 | 682403 | PAK |
| 019E01 | 4396977 | PAK |
| 019E02 | 1914294 | PAK |
| 019E03 | 464522 | PAK |
| 019E04 | 4455438 | PAK |
| 019E05 | 3379083 | PAK |
| 019E07 | 5938984 | PAK |
| 019E09 | 5392754 | PAK |
| 019E11 | 5938984 | PAK |
| 019F01 | 4396977 | PAK |
| 019F02 | 1747643 | PAK |
| 019F03 | 6029230 | PAK |
| 019F04 | 4444027 | PAK |
| 019F05 | 1041173 | PAK |
| 019F07 | 3174550 | PAK |
| 019F08 | 5418654 | PAK |
| 019F09 | 5938984 | PAK |
| 019F10 | 5938984 | PAK |
| 019F11 | 4020544 | PAK |
| 019F12 | 1307759 | PAK |
| 019G03 | 701297 | PAK |
| 019G04 | 4003779 | PAK |
| 019G05 | 4360435 | PAK |
| 019G06 | 5938983 | PAK |
| 019G07 | 5938984 | PAK |
| 019G08 | 5938984 | PAK |
| 019G09 | 5887396 | PAK |
| 019G11 | 5938984 | PAK |
| 019G12 | 1307759 | PAK |
| 019H01 | 5938983 | PAK |
| 019H02 | 1275418 | PAK |
| 019H03 | 5938983 | PAK |
| 019H04 | 5938984 | PAK |
| 019H05 | 1145752 | PAK |
| 019H06 | 5938984 | PAK |
| 019H08 | 5938983 | PAK |
| 019H10 | 4282000 | PAK |
| 021A02 | 3071600 | PAK |
| 021A03 | 295020 | PAK |
| 021A05 | 579496 | PAK |
| 021A06 | 4148925 | PAK |
| 021A07 | 1446923 | PAK |
| 021A08 | 1878971 | PAK |
| 021A09 | 1401775 | PAK |
| 021A11 | 5593801 | PAK |
| 021A12 | 6000256 | PAK |
| 021B01 | 603281 | PAK |
| 021B02 | 4927535 | PAK |
| 021B03 | 3967585 | PAK |
| 021B04 | 968147 | PAK |
| 021B05 | 5994281 | PAK |
| 021B06 | 4611237 | PAK |
| 021B09 | 5653202 | PAK |
| 021B10 | 596083 | PAK |
| 021B11 | 4306140 | PAK |
| 021B12 | 3808062 | PAK |
| 021C01 | 1760212 | PAK |
| 021C02 | 3753988 | PAK |
| 021C04 | 3598518 | PAK |
| 021C05 | 4388018 | PAK |
| 021C06 | 4800119 | PAK |
| 021C08 | 5169602 | PAK |
| 021C09 | 3390625 | PAK |
| 021C11 | 2608842 | PAK |
| 021C12 | 5545208 | PAK |
| 021D04 | 920043 | PAK |
| 021D05 | 6146637 | PAK |
| 021D06 | 248536 | PAK |
| 021D08 | 4431627 | PAK |
| 021D10 | 310215 | PAK |
| 021D11 | 2470939 | PAK |
| 021E01 | 4325951 | PAK |
| 021E02 | 4997801 | PAK |
| 021E03 | 5754729 | PAK |
| 021E05 | 1457370 | PAK |
| 021E06 | 4628283 | PAK |
| 021E07 | 1847010 | PAK |
| 021E08 | 2489769 | PAK |
| 021E10 | 392789 | PAK |
| 021F06 | 5136534 | PAK |
| 021F08 | 1771189 | PAK |
| 021F09 | 4883025 | PAK |
| 021F11 | 2522269 | PAK |
| 021F12 | 5085503 | PAK |
| 021G01 | 6104643 | PAK |
| 021G02 | 17851 | PAK |
| 021G03 | 2522269 | PAK |
| 021G05 | 1577478 | PAK |
| 021G06 | 404874 | PAK |
| 021G07 | 577497 | PAK |
| 021G09 | 4103187 | PAK |
| 021G10 | 3148097 | PAK |
| 021G11 | 186052 | PAK |
| 021G12 | 1086539 | PAK |
| 021H01 | 2501395 | PAK |
| 021H02 | 2522269 | PAK |
| 021H03 | 3753987 | PAK |
| 021H04 | 3872613 | PAK |
| 021H05 | 1001912 | PAK |
| 021H07 | 3753989 | PAK |
| 021H08 | 2522268 | PAK |
| 021H10 | 703214 | PAK |
| 023A01 | 1873208 | PAK |
| 023A02 | 1248256 | PAK |
| 023A03 | 5307512 | PAK |
| 023A05 | 513571 | PAK |
| 023A06 | 4443361 | PAK |
| 023A07 | 5741246 | PAK |

TABLE 3-continued

| Mutant Name | Insertion Point | host strain |
|---|---|---|
| 023A08 | 334359 | PAK |
| 023A09 | 5891154 | PAK |
| 023A10 | 1699457 | PAK |
| 023A11 | 2569970 | PAK |
| 023A12 | 5998196 | PAK |
| 023B02 | 1687395 | PAK |
| 023B03 | 1574073 | PAK |
| 023B04 | 5550063 | PAK |
| 023B05 | 5057305 | PAK |
| 023B06 | 1520523 | PAK |
| 023B07 | 4549995 | PAK |
| 023B09 | 5369448 | PAK |
| 023B10 | 3994085 | PAK |
| 023B11 | 3728902 | PAK |
| 023C01 | 3233482 | PAK |
| 023C02 | 4163973 | PAK |
| 023C03 | 3667874 | PAK |
| 023C05 | 2578745 | PAK |
| 023C06 | 3664490 | PAK |
| 023C07 | 1890482 | PAK |
| 023C08 | 6111439 | PAK |
| 023C09 | 5034140 | PAK |
| 023C10 | 875574 | PAK |
| 023C11 | 4691338 | PAK |
| 023C12 | 5937879 | PAK |
| 023D01 | 302987 | PAK |
| 023D02 | 5513649 | PAK |
| 023D03 | 1494250 | PAK |
| 023D05 | 3276337 | PAK |
| 023D06 | 4733116 | PAK |
| 023D07 | 5464629 | PAK |
| 023D08 | 374285 | PAK |
| 023D09 | 180610 | PAK |
| 023D10 | 3235122 | PAK |
| 023D11 | 3847723 | PAK |
| 023D12 | 850932 | PAK |
| 023E01 | 4957043 | PAK |
| 023E02 | 577282 | PAK |
| 023E03 | 3427114 | PAK |
| 023E12 | 5137507 | PAK |
| 023F02 | 2522269 | PAK |
| 023F03 | 3167836 | PAK |
| 023F08 | 3167835 | PAK |
| 023F12 | 1814047 | PAK |
| 023G07 | 1814047 | PAK |
| 023G12 | 2385112 | PAK |
| 023H02 | 1430988 | PAK |
| 023H03 | 6092304 | PAK |
| 023H04 | 2235501 | PAK |
| 023H05 | 4968309 | PAK |
| 023H06 | 3972575 | PAK |
| 023H07 | 2589897 | PAK |
| 023H08 | 2270940 | PAK |
| 023H09 | 2428623 | PAK |
| 023H10 | 6151992 | PAK |
| 023H11 | 4975797 | PAK |
| 024A01 | 2998744 | PAK |
| 024A02 | 3273707 | PAK |
| 024A03 | 3273707 | PAK |
| 024A04 | 4211295 | PAK |
| 024A05 | 5805927 | PAK |
| 024A06 | 1120674 | PAK |
| 024A07 | 3847363 | PAK |
| 024A08 | 4540975 | PAK |
| 024A09 | 1590327 | PAK |
| 024A10 | 4865593 | PAK |
| 024A11 | 582184 | PAK |
| 024A12 | 2314014 | PAK |
| 024B01 | 887612 | PAK |
| 024B02 | 812138 | PAK |
| 024B03 | 5454438 | PAK |
| 024B04 | 1422529 | PAK |
| 024B05 | 840409 | PAK |
| 024B08 | 3887120 | PAK |
| 024B09 | 553895 | PAK |
| 024B10 | 2231391 | PAK |
| 024B11 | 5986505 | PAK |
| 024B12 | 3268838 | PAK |
| 024C01 | 3454969 | PAK |
| 024C02 | 3166825 | PAK |
| 024C03 | 3045547 | PAK |
| 024C04 | 4549940 | PAK |
| 024C05 | 4024205 | PAK |
| 024C07 | 5224518 | PAK |
| 024C08 | 6187097 | PAK |
| 024C09 | 13962 | PAK |
| 024C10 | 4133782 | PAK |
| 024C11 | 5544419 | PAK |
| 024C12 | 5549737 | PAK |
| 024D01 | 224834 | PAK |
| 024D02 | 1541365 | PAK |
| 024D03 | 2600561 | PAK |
| 024D04 | 5271081 | PAK |
| 024D05 | 438718 | PAK |
| 024D06 | 2506689 | PAK |
| 024D07 | 376685 | PAK |
| 024D08 | 3753989 | PAK |
| 024D09 | 477959 | PAK |
| 024D10 | 4415413 | PAK |
| 024D11 | 1949144 | PAK |
| 024D12 | 2574093 | PAK |
| 024E02 | 397241 | PAK |
| 024E03 | 1422615 | PAK |
| 024E04 | 5558858 | PAK |
| 024E05 | 248534 | PAK |
| 024E06 | 2482205 | PAK |
| 024E07 | 6094556 | PAK |
| 024E08 | 2089704 | PAK |
| 024E09 | 57949 | PAK |
| 024E11 | 1573198 | PAK |
| 024E12 | 960638 | PAK |
| 025A01 | 1021934 | PAK |
| 025A02 | 4648327 | PAK |
| 025A03 | 2585665 | PAK |
| 025A04 | 2880224 | PAK |
| 025A05 | 1084732 | PAK |
| 025A06 | 4008735 | PAK |
| 025A07 | 3049679 | PAK |
| 025A08 | 3865426 | PAK |
| 025A09 | 3460940 | PAK |
| 025A10 | 1314551 | PAK |
| 025B01 | 6186765 | PAK |
| 025B02 | 2370762 | PAK |
| 025B03 | 4428734 | PAK |
| 025B04 | 242528 | PAK |
| 025B05 | 315160 | PAK |
| 025B06 | 5076807 | PAK |
| 025B07 | 3573568 | PAK |
| 025B08 | 2173452 | PAK |
| 025B10 | 5251498 | PAK |
| 025C01 | 3126126 | PAK |
| 025C02 | 3280479 | PAK |
| 025C03 | 5118049 | PAK |
| 025C04 | 5894522 | PAK |
| 025C06 | 2486212 | PAK |
| 025C07 | 274942 | PAK |
| 025C08 | 2830968 | PAK |
| 025C09 | 2711664 | PAK |
| 025C10 | 1755172 | PAK |
| 025C11 | 2395192 | PAK |
| 025C12 | 5582311 | PAK |
| 025D01 | 956925 | PAK |
| 025D02 | 3907963 | PAK |
| 025D03 | 1536023 | PAK |
| 025D04 | 5681475 | PAK |
| 025D06 | 5045391 | PAK |
| 025D07 | 3956187 | PAK |
| 025D08 | 6147445 | PAK |
| 025D09 | 5807032 | PAK |
| 025D10 | 6231260 | PAK |
| 025D11 | 6122296 | PAK |
| 025D12 | 6228503 | PAK |
| 026A01 | 2783421 | PAK |
| 026A02 | 4413275 | PAK |

TABLE 3-continued

| Mutant Name | Insertion Point | host strain |
|---|---|---|
| 026A03 | 4867611 | PAK |
| 026A04 | 6193243 | PAK |
| 026A05 | 2661389 | PAK |
| 026A06 | 2993040 | PAK |
| 026A07 | 5859934 | PAK |
| 026A09 | 6091935 | PAK |
| 026A10 | 6017292 | PAK |
| 026A11 | 1534280 | PAK |
| 026A12 | 5997458 | PAK |
| 026B01 | 1286664 | PAK |
| 026B03 | 3570047 | PAK |
| 026B05 | 1526371 | PAK |
| 026B06 | 3124858 | PAK |
| 026B07 | 4496523 | PAK |
| 026B08 | 243633 | PAK |
| 026B09 | 4113174 | PAK |
| 026B10 | 2471714 | PAK |
| 026B11 | 621504 | PAK |
| 026B12 | 5929327 | PAK |
| 026C02 | 4490246 | PAK |
| 026C03 | 1646169 | PAK |
| 026C04 | 1614082 | PAK |
| 026C05 | 5833075 | PAK |
| 026C06 | 1757938 | PAK |
| 026C07 | 5038965 | PAK |
| 026C08 | 5484284 | PAK |
| 026C10 | 1614082 | PAK |
| 026C11 | 142425 | PAK |
| 026D01 | 6093458 | PAK |
| 026D02 | 4872457 | PAK |
| 026D03 | 2476413 | PAK |
| 026D04 | 1916042 | PAK |
| 026D05 | 337863 | PAK |
| 026D06 | 1271024 | PAK |
| 026D08 | 5256245 | PAK |
| 026D09 | 2353267 | PAK |
| 026D10 | 1424992 | PAK |
| 026D11 | 2902738 | PAK |
| 026D12 | 4836286 | PAK |
| 026E01 | 5633101 | PAK |
| 026E02 | 5389787 | PAK |
| 026E03 | 5200833 | PAK |
| 026E04 | 3710864 | PAK |
| 026E05 | 1026191 | PAK |
| 026E06 | 731222 | PAK |
| 026E07 | 4369758 | PAK |
| 026E08 | 6206863 | PAK |
| 026E09 | 2197918 | PAK |
| 026E10 | 244907 | PAK |
| 026E11 | 59881 | PAK |
| 026E12 | 4860198 | PAK |
| 026F01 | 1003254 | PAK |
| 026F02 | 3888838 | PAK |
| 026F03 | 4979513 | PAK |
| 026F04 | 3282283 | PAK |
| 026F05 | 3859347 | PAK |
| 026F07 | 2545116 | PAK |
| 026F08 | 5733113 | PAK |
| 026F09 | 1576571 | PAK |
| 026F10 | 226395 | PAK |
| 026F11 | 3617181 | PAK |
| 026F12 | 468359 | PAK |
| 026G01 | 2516258 | PAK |
| 026G02 | 1699471 | PAK |
| 026G03 | 480072 | PAK |
| 026G04 | 2836089 | PAK |
| 026G06 | 5135144 | PAK |
| 026G07 | 2759139 | PAK |
| 026G08 | 2395451 | PAK |
| 026G09 | 5353056 | PAK |
| 026G11 | 3039452 | PAK |
| 026G12 | 2858678 | PAK |
| 026H02 | 305543 | PAK |
| 026H03 | 1823060 | PAK |
| 026H04 | 5818681 | PAK |
| 026H05 | 5752024 | PAK |
| 026H06 | 3839372 | PAK |
| 026H07 | 5595512 | PAK |
| 026H08 | 6195270 | PAK |
| 026H09 | 3769758 | PAK |
| 026H11 | 395319 | PAK |
| 027A01 | 5986381 | PAK |
| 027A02 | 5610518 | PAK |
| 027A03 | 5305691 | PAK |
| 027A04 | 5806229 | PAK |
| 027A05 | 51567 | PAK |
| 027A06 | 4661991 | PAK |
| 027A07 | 5437916 | PAK |
| 027A08 | 3240695 | PAK |
| 027A10 | 5379446 | PAK |
| 027A11 | 4704474 | PAK |
| 027B01 | 2931204 | PAK |
| 027B02 | 4221177 | PAK |
| 027B03 | 2055343 | PAK |
| 027B04 | 2605433 | PAK |
| 027B05 | 671637 | PAK |
| 027B06 | 3676181 | PAK |
| 027B07 | 2342964 | PAK |
| 027B08 | 892825 | PAK |
| 027B09 | 546703 | PAK |
| 027B10 | 4611229 | PAK |
| 027B12 | 2910956 | PAK |
| 027C03 | 567842 | PAK |
| 027C04 | 2654831 | PAK |
| 027C05 | 1169335 | PAK |
| 027C06 | 3445041 | PAK |
| 027C07 | 2498028 | PAK |
| 027C08 | 1195734 | PAK |
| 027C10 | 3377875 | PAK |
| 027C12 | 544371 | PAK |
| 027D01 | 4389578 | PAK |
| 027D02 | 4137710 | PAK |
| 027D03 | 3827459 | PAK |
| 027D04 | 784615 | PAK |
| 027D05 | 1695147 | PAK |
| 027D06 | 758536 | PAK |
| 027D07 | 1331386 | PAK |
| 027D08 | 1833778 | PAK |
| 027D09 | 4423076 | PAK |
| 027D10 | 2304898 | PAK |
| 027D11 | 4178289 | PAK |
| 027D12 | 2712791 | PAK |
| 027E01 | 4510628 | PAK |
| 027E02 | 5480157 | PAK |
| 027E03 | 5367995 | PAK |
| 027E04 | 5745018 | PAK |
| 027E05 | 2770769 | PAK |
| 027E06 | 2326713 | PAK |
| 027E07 | 2845013 | PAK |
| 027E08 | 3753559 | PAK |
| 027E09 | 685539 | PAK |
| 027E10 | 441907 | PAK |
| 027E11 | 1034469 | PAK |
| 027E12 | 4957339 | PAK |
| 027F01 | 3967875 | PAK |
| 027F02 | 667543 | PAK |
| 027F03 | 6163677 | PAK |
| 027F05 | 6230076 | PAK |
| 027F06 | 4588811 | PAK |
| 027F07 | 4889646 | PAK |
| 027F09 | 4427504 | PAK |
| 027F10 | 5389108 | PAK |
| 027F12 | 1632211 | PAK |
| 027G01 | 30684 | PAK |
| 027G02 | 803737 | PAK |
| 027G03 | 1364341 | PAK |
| 027G04 | 3307198 | PAK |
| 027G05 | 5947969 | PAK |
| 027G06 | 3273085 | PAK |
| 027G07 | 138747 | PAK |
| 027G08 | 1888744 | PAK |
| 027G09 | 731388 | PAK |
| 027G10 | 16133 | PAK |
| 027G11 | 4098927 | PAK |

TABLE 3-continued

| Mutant Name | Insertion Point | host strain |
|---|---|---|
| 027G12 | 1778562 | PAK |
| 027H01 | 1892327 | PAK |
| 027H03 | 1389378 | PAK |
| 027H04 | 3873101 | PAK |
| 027H05 | 5806340 | PAK |
| 027H06 | 1362835 | PAK |
| 027H07 | 6163720 | PAK |
| 027H08 | 1800157 | PAK |
| 027H09 | 1234041 | PAK |
| 027H10 | 1053774 | PAK |
| 027H11 | 395319 | PAK |
| 028A01 | 3765920 | PAK |
| 028A02 | 5560968 | PAK |
| 028A03 | 4221105 | PAK |
| 028A05 | 5130154 | PAK |
| 028A07 | 3650968 | PAK |
| 028A08 | 2675069 | PAK |
| 028A09 | 3645865 | PAK |
| 028A10 | 2749094 | PAK |
| 028A11 | 5601444 | PAK |
| 028A12 | 5932445 | PAK |
| 028B01 | 3423519 | PAK |
| 028B03 | 5652023 | PAK |
| 028B04 | 4219974 | PAK |
| 028B05 | 2352534 | PAK |
| 028B06 | 505075 | PAK |
| 028B07 | 78114 | PAK |
| 028B08 | 4729966 | PAK |
| 028B09 | 4247808 | PAK |
| 028B10 | 2079070 | PAK |
| 028B11 | 1044061 | PAK |
| 028B12 | 434886 | PAK |
| 028C01 | 4126950 | PAK |
| 028C02 | 5559372 | PAK |
| 028C03 | 1401152 | PAK |
| 028C04 | 850425 | PAK |
| 028C05 | 1679758 | PAK |
| 028C06 | 3143823 | PAK |
| 028C07 | 6529612 | PAK |
| 028C08 | 4709538 | PAK |
| 028C09 | 3377875 | PAK |
| 028C10 | 1526202 | PAK |
| 028C11 | 218091 | PAK |
| 028D02 | 4999647 | PAK |
| 028D03 | 4895650 | PAK |
| 028D04 | 4430143 | PAK |
| 028D05 | 4529076 | PAK |
| 028D06 | 5645307 | PAK |
| 028D07 | 4167143 | PAK |
| 028D10 | 4009007 | PAK |
| 028D11 | 1168403 | PAK |
| 028E01 | 1626809 | PAK |
| 028E02 | 1929892 | PAK |
| 028E03 | 273913 | PAK |
| 028E04 | 2976635 | PAK |
| 028E05 | 2822479 | PAK |
| 028E06 | 4047865 | PAK |
| 028E07 | 1401774 | PAK |
| 028E08 | 2813519 | PAK |
| 028E09 | 619752 | PAK |
| 028E10 | 5633478 | PAK |
| 028E11 | 6026380 | PAK |
| 028E12 | 4160672 | PAK |
| 028F01 | 2464814 | PAK |
| 028F02 | 3478959 | PAK |
| 028F03 | 4365617 | PAK |
| 028F04 | 5735289 | PAK |
| 028F05 | 5073520 | PAK |
| 028F06 | 1796610 | PAK |
| 028F07 | 155971 | PAK |
| 028F08 | 3054962 | PAK |
| 028F09 | 5051554 | PAK |
| 028F10 | 5662090 | PAK |
| 028G01 | 6097792 | PAK |
| 028G02 | 519097 | PAK |
| 028G03 | 3606864 | PAK |
| 028G04 | 1352608 | PAK |
| 028G05 | 960638 | PAK |
| 028G07 | 5129901 | PAK |
| 028G09 | 4627714 | PAK |
| 028G10 | 5602270 | PAK |
| 028G11 | 5865952 | PAK |
| 028H01 | 3403124 | PAK |
| 028H02 | 5217688 | PAK |
| 028H03 | 3471740 | PAK |
| 028H04 | 6162649 | PAK |
| 028H06 | 5141234 | PAK |
| 028H07 | 3444396 | PAK |
| 028H08 | 2374238 | PAK |
| 028H09 | 21733 | PAK |
| 029A02 | 5207659 | PAK |
| 029A03 | 5756144 | PAK |
| 029A04 | 36210921 | PAK |
| 029A05 | 3590611 | PAK |
| 029A06 | 4133511 | PAK |
| 029A07 | 47760 | PAK |
| 029A08 | 9836 | PAK |
| 029A09 | 618491 | PAK |
| 029A10 | 343413 | PAK |
| 029A11 | 1418890 | PAK |
| 029A12 | 4375891 | PAK |
| 029B02 | 2251126 | PAK |
| 029B03 | 3776080 | PAK |
| 029B04 | 16129 | PAK |
| 029B05 | 511338 | PAK |
| 029B06 | 2179204 | PAK |
| 029B07 | 3006198 | PAK |
| 029B08 | 1386206 | PAK |
| 029B09 | 1022382 | PAK |
| 029B11 | 4135379 | PAK |
| 029B12 | 5522051 | PAK |
| 029C02 | 1295737 | PAK |
| 029C03 | 2556389 | PAK |
| 029C04 | 3451262 | PAK |
| 029C05 | 407468 | PAK |
| 029C06 | 5226315 | PAK |
| 029C07 | 161414 | PAK |
| 029C08 | 4998046 | PAK |
| 029C09 | 17385 | PAK |
| 029C11 | 799336 | PAK |
| 029F01 | 4280811 | PAK |
| 029F02 | 1635965 | PAK |
| 029F03 | 5047054 | PAK |
| 029F04 | 5381530 | PAK |
| 029F05 | 4841444 | PAK |
| 029F07 | 2386598 | PAK |
| 029F08 | 2237359 | PAK |
| 029F09 | 1952429 | PAK |
| 029F10 | 625852 | PAK |
| 029F11 | 1103593 | PAK |
| 029F12 | 1034469 | PAK |
| 029G03 | 571814 | PAK |
| 029G05 | 2849443 | PAK |
| 029G07 | 4140101 | PAK |
| 029G08 | 3945145 | PAK |
| 029G09 | 299474 | PAK |
| 029G10 | 1401775 | PAK |
| 029G11 | 1161506 | PAK |
| 029H01 | 2186632 | PAK |
| 029H03 | 1863417 | PAK |
| 029H04 | 4120237 | PAK |
| 029H05 | 6226875 | PAK |
| 029H06 | 3432045 | PAK |
| 029H08 | 4998046 | PAK |
| 029H09 | 3637364 | PAK |
| 029H11 | 395318 | PAK |
| 030A01 | 4419850 | PAK |
| 030A03 | 2571933 | PAK |
| 030A04 | 1098443 | PAK |
| 030A05 | 1656285 | PAK |
| 030A06 | 3196133 | PAK |
| 030A07 | 6121145 | PAK |
| 030A08 | 6111034 | PAK |
| 030A10 | 928123 | PAK |

TABLE 3-continued

| Mutant Name | Insertion Point | host strain |
|---|---|---|
| 030A11 | 3805821 | PAK |
| 030B01 | 1675284 | PAK |
| 030B02 | 3453784 | PAK |
| 030B03 | 4395196 | PAK |
| 030B06 | 3243564 | PAK |
| 030B07 | 304864 | PAK |
| 030B08 | 178218 | PAK |
| 030B09 | 1771997 | PAK |
| 030B10 | 6217358 | PAK |
| 030B11 | 2551514 | PAK |
| 030B12 | 5744471 | PAK |
| 030C01 | 2502955 | PAK |
| 030C02 | 5114608 | PAK |
| 030C06 | 2293379 | PAK |
| 030C10 | 4325281 | PAK |
| 030C11 | 4252912 | PAK |
| 030D01 | 3690212 | PAK |
| 030D02 | 5789566 | PAK |
| 030D04 | 5906822 | PAK |
| 030D06 | 4848635 | PAK |
| 030D07 | 1700770 | PAK |
| 030D08 | 2461514 | PAK |
| 030D09 | 2033740 | PAK |
| 030D10 | 735834 | PAK |
| 030D12 | 4702674 | PAK |
| 030E01 | 1952135 | PAK |
| 030E02 | 30721701 | PAK |
| 030E04 | 3268528 | PAK |
| 030E06 | 3951672 | PAK |
| 030E07 | 4021011 | PAK |
| 030E08 | 5447473 | PAK |
| 030E09 | 1034469 | PAK |
| 030E11 | 6210374 | PAK |
| 030E12 | 2322957 | PAK |
| 030F01 | 1795161 | PAK |
| 030F02 | 372700 | PAK |
| 030F03 | 1008274 | PAK |
| 030F04 | 2960227 | PAK |
| 030F05 | 2751723 | PAK |
| 030F06 | 3368821 | PAK |
| 030F07 | 2898891 | PAK |
| 030F08 | 2452830 | PAK |
| 030F10 | 3191652 | PAK |
| 030F11 | 2469502 | PAK |
| 030G01 | 3454440 | PAK |
| 030G02 | 3627048 | PAK |
| 030G03 | 4238570 | PAK |
| 030G04 | 928134 | PAK |
| 030G05 | 3825941 | PAK |
| 030G06 | 1326016 | PAK |
| 030G07 | 4494245 | PAK |
| 030G08 | 5317395 | PAK |
| 030G09 | 5272805 | PAK |
| 030G11 | 3494433 | PAK |
| 030G12 | 3410682 | PAK |
| 030H01 | 194927 | PAK |
| 030H02 | 4592027 | PAK |
| 030H03 | 852280 | PAK |
| 030H04 | 5033043 | PAK |
| 030H05 | 1408282 | PAK |
| 030H06 | 5833452 | PAK |
| 030H07 | 3627334 | PAK |
| 030H08 | 4018383 | PAK |
| 030H10 | 879592 | PAK |
| 030H11 | 395318 | PAK |
| 031A01 | 3596892 | PAK |
| 031A02 | 2654389 | PAK |
| 031A04 | 2333549 | PAK |
| 031A05 | 3235122 | PAK |
| 031A06 | 295330 | PAK |
| 031A07 | 3420473 | PAK |
| 031A08 | 517368 | PAK |
| 031A09 | 2262972 | PAK |
| 031A10 | 6143767 | PAK |
| 031A12 | 5934945 | PAK |
| 031B01 | 1032092 | PAK |
| 031B02 | 6137622 | PAK |
| 031B04 | 4999629 | PAK |
| 031B05 | 488665 | PAK |
| 031B06 | 6082612 | PAK |
| 031B07 | 2849330 | PAK |
| 031B08 | 307553 | PAK |
| 031B09 | 5586226 | PAK |
| 031B10 | 3481766 | PAK |
| 031B11 | 320046 | PAK |
| 031B12 | 4401199 | PAK |
| 031C01 | 4578536 | PAK |
| 031C02 | 117873 | PAK |
| 031C03 | 3630643 | PAK |
| 031C04 | 6153040 | PAK |
| 031C06 | 304855 | PAK |
| 031C07 | 6153040 | PAK |
| 031C08 | 5382017 | PAK |
| 031C09 | 3363510 | PAK |
| 031C10 | 4369570 | PAK |
| 031C11 | 960638 | PAK |
| 031D01 | 4494996 | PAK |
| 031D02 | 1339378 | PAK |
| 031D04 | 379414 | PAK |
| 031D05 | 2748806 | PAK |
| 031D06 | 1431043 | PAK |
| 031D08 | 4624021 | PAK |
| 031D09 | 13352462 | PAK |
| 031D10 | 4786066 | PAK |
| 031D11 | 3432785 | PAK |
| 031D12 | 5077356 | PAK |
| 031E01 | 1273307 | PAK |
| 031E02 | 1830833 | PAK |
| 031E03 | 1229021 | PAK |
| 031E04 | 1034469 | PAK |
| 031E05 | 3157955 | PAK |
| 031E06 | 5061337 | PAK |
| 031E07 | 3769683 | PAK |
| 031E08 | 6137227 | PAK |
| 031E09 | 366354 | PAK |
| 031E10 | 160100 | PAK |
| 031E12 | 6204137 | PAK |
| 031F01 | 937667 | PAK |
| 031F02 | 6172249 | PAK |
| 031F03 | 3113651 | PAK |
| 031F04 | 5399592 | PAK |
| 031F05 | 3767441 | PAK |
| 031F06 | 5860932 | PAK |
| 031F07 | 6233021 | PAK |
| 031F08 | 3853782 | PAK |
| 031F10 | 4687080 | PAK |
| 031F11 | 4745641 | PAK |
| 031F12 | 994387 | PAK |
| 031G04 | 1941512 | PAK |
| 031G06 | 911406 | PAK |
| 031G07 | 3659778 | PAK |
| 031G08 | 4361681 | PAK |
| 031G09 | 4320676 | PAK |
| 031G11 | 3651699 | PAK |
| 031G12 | 4003606 | PAK |
| 031H02 | 783325 | PAK |
| 031H03 | 159925 | PAK |
| 031H06 | 622897 | PAK |
| 031H08 | 365504 | PAK |
| 031H09 | 927977 | PAK |
| 031H10 | 21073 | PAK |
| 031H11 | 395319 | PAK |
| 032A01 | 3743984 | PAK |
| 032A02 | 4424173 | PAK |
| 032A03 | 3469166 | PAK |
| 032A04 | 2971258 | PAK |
| 032A05 | 5714569 | PAK |
| 032A06 | 1781752 | PAK |
| 032A07 | 2677866 | PAK |
| 032A08 | 3217507 | PAK |
| 032A09 | 678032 | PAK |
| 032A10 | 5471197 | PAK |
| 032A11 | 3460940 | PAK |
| 032B01 | 1583037 | PAK |

TABLE 3-continued

| Mutant Name | Insertion Point | host strain |
|---|---|---|
| 032B02 | 666644 | PAK |
| 032B03 | 4463701 | PAK |
| 032B06 | 5026321 | PAK |
| 032B07 | 4897740 | PAK |
| 032B08 | 4119859 | PAK |
| 032B09 | 3971396 | PAK |
| 032B10 | 2101615 | PAK |
| 032B11 | 3848049 | PAK |
| 032C01 | 4419245 | PAK |
| 032C03 | 2734352 | PAK |
| 032C04 | 5192269 | PAK |
| 032C05 | 2151038 | PAK |
| 032C06 | 222082 | PAK |
| 032C07 | 5959665 | PAK |
| 032C08 | 960638 | PAK |
| 032C09 | 3788806 | PAK |
| 032C10 | 133763 | PAK |
| 032C11 | 4835620 | PAK |
| 032C12 | 6246275 | PAK |
| 032D01 | 2134383 | PAK |
| 032D02 | 824017 | PAK |
| 032D03 | 703212 | PAK |
| 032D05 | 4617899 | PAK |
| 032D06 | 3161119 | PAK |
| 032D07 | 1415520 | PAK |
| 032D08 | 5819393 | PAK |
| 032D10 | 944284 | PAK |
| 032D11 | 515164 | PAK |
| 032E01 | 2296065 | PAK |
| 032E03 | 1589174 | PAK |
| 032E04 | 3496720 | PAK |
| 032E05 | 4703559 | PAK |
| 032E06 | 3429859 | PAK |
| 032E07 | 1815893 | PAK |
| 032E08 | 4512079 | PAK |
| 032E09 | 5800124 | PAK |
| 032E10 | 1282182 | PAK |
| 032E11 | 3785902 | PAK |
| 032E12 | 5121132 | PAK |
| 032F01 | 544788 | PAK |
| 032F02 | 2333549 | PAK |
| 032F03 | 4115981 | PAK |
| 032F05 | 3818322 | PAK |
| 032F06 | 1923739 | PAK |
| 032F07 | 1595291 | PAK |
| 032F08 | 2543984 | PAK |
| 032F09 | 47414081 | PAK |
| 032F11 | 392299 | PAK |
| 032F12 | 575331 | PAK |
| 032G01 | 3884321 | PAK |
| 032G02 | 1986308 | PAK |
| 032G03 | 1431612 | PAK |
| 032G04 | 3377875 | PAK |
| 032G05 | 4096444 | PAK |
| 032G07 | 1034469 | PAK |
| 032G08 | 5523553 | PAK |
| 032G09 | 1082517 | PAK |
| 032G10 | 902337 | PAK |
| 032G11 | 2285758 | PAK |
| 032H01 | 4432184 | PAK |
| 032H02 | 312089 | PAK |
| 032H03 | 3157954 | PAK |
| 032H04 | 592072 | PAK |
| 032H05 | 3584145 | PAK |
| 032H06 | 5259025 | PAK |
| 032H07 | 5040084 | PAK |
| 032H08 | 5776175 | PAK |
| 032H09 | 1470035 | PAK |
| 032H10 | 4999577 | PAK |
| 032H11 | 395319 | PAK |
| 033A02 | 5903292 | PAK |
| 033A04 | 3068005 | PAK |
| 033A05 | 2021360 | PAK |
| 033A06 | 4343557 | PAK |
| 033A07 | 4457135 | PAK |
| 033A09 | 1703596 | PAK |
| 033A11 | 193593 | PAK |
| 033A12 | 3013648 | PAK |
| 033B01 | 5215520 | PAK |
| 033B02 | 735223 | PAK |
| 033B03 | 280214 | PAK |
| 033B06 | 5734271 | PAK |
| 033B07 | 4645611 | PAK |
| 033B08 | 4158275 | PAK |
| 033B09 | 6076677 | PAK |
| 033B10 | 5846650 | PAK |
| 033B11 | 5139025 | PAK |
| 033C01 | 4565584 | PAK |
| 033C02 | 789593 | PAK |
| 033C03 | 1570353 | PAK |
| 033C07 | 5369447 | PAK |
| 033C09 | 2223722 | PAK |
| 033C10 | 3703016 | PAK |
| 033C11 | 1166054 | PAK |
| 033C12 | 1762217 | PAK |
| 033D01 | 5808697 | PAK |
| 033D02 | 92502 | PAK |
| 033D03 | 1864941 | PAK |
| 033D04 | 582632 | PAK |
| 033D05 | 1446241 | PAK |
| 033D06 | 2677981 | PAK |
| 033D08 | 1420522 | PAK |
| 033D09 | 2915371 | PAK |
| 033D10 | 5759953 | PAK |
| 033D11 | 3294152 | PAK |
| 033D12 | 4270927 | PAK |
| 033E01 | 3692905 | PAK |
| 033E02 | 3960621 | PAK |
| 033E03 | 159925 | PAK |
| 033E04 | 1146438 | PAK |
| 033E05 | 4876344 | PAK |
| 033E06 | 1401775 | PAK |
| 033E07 | 3648190 | PAK |
| 033E08 | 5155127 | PAK |
| 033E10 | 810029 | PAK |
| 033E11 | 517132 | PAK |
| 033F01 | 5384776 | PAK |
| 033F02 | 1097480 | PAK |
| 033F03 | 488949 | PAK |
| 033F04 | 3858929 | PAK |
| 033F05 | 5047867 | PAK |
| 033F06 | 6139060 | PAK |
| 033F07 | 3278728 | PAK |
| 033F08 | 2651957 | PAK |
| 033F09 | 4214354 | PAK |
| 033F10 | 5835416 | PAK |
| 033F11 | 3040970 | PAK |
| 033F12 | 5485671 | PAK |
| 033G01 | 4021011 | PAK |
| 033G02 | 2020848 | PAK |
| 033G03 | 6035097 | PAK |
| 033G04 | 622576 | PAK |
| 033G05 | 6009158 | PAK |
| 033G06 | 4921657 | PAK |
| 033G07 | 1531219 | PAK |
| 033G08 | 422371 | PAK |
| 033G09 | 5496428 | PAK |
| 033G10 | 338336 | PAK |
| 033G11 | 4872592 | PAK |
| 033G12 | 2006340 | PAK |
| 033H01 | 4283054 | PAK |
| 033H02 | 2971468 | PAK |
| 033H03 | 5734163 | PAK |
| 033H04 | 267797 | PAK |
| 033H05 | 5611225 | PAK |
| 033H06 | 5120684 | PAK |
| 033H07 | 5734795 | PAK |
| 033H08 | 5457735 | PAK |
| 033H09 | 5222171 | PAK |
| 033H10 | 1628993 | PAK |
| 033H11 | 395319 | PAK |
| 034A02 | 4102305 | PAK |
| 034A03 | 1518453 | PAK |
| 034A04 | 5871585 | PAK |

TABLE 3-continued

| Mutant Name | Insertion Point | host strain |
|---|---|---|
| 034A07 | 3659895 | PAK |
| 034A08 | 250910 | PAK |
| 034A09 | 5917488 | PAK |
| 034A10 | 4540962 | PAK |
| 034A11 | 2979372 | PAK |
| 034A12 | 863674 | PAK |
| 034B01 | 3761773 | PAK |
| 034B02 | 4976574 | PAK |
| 034B03 | 1459332 | PAK |
| 034B04 | 3231365 | PAK |
| 034B05 | 5932726 | PAK |
| 034B06 | 2169723 | PAK |
| 034B09 | 5196472 | PAK |
| 034C01 | 5972176 | PAK |
| 034C02 | 2011374 | PAK |
| 034C03 | 1169543 | PAK |
| 034C04 | 319792 | PAK |
| 034C06 | 1691904 | PAK |
| 034C07 | 4639252 | PAK |
| 034C08 | 4445806 | PAK |
| 034C09 | 2903650 | PAK |
| 034C10 | 5595620 | PAK |
| 034C11 | 1119033 | PAK |
| 034D01 | 3689177 | PAK |
| 034D02 | 265015 | PAK |
| 034D03 | 5222071 | PAK |
| 034D04 | 4349588 | PAK |
| 034D05 | 1786346 | PAK |
| 034D06 | 6155655 | PAK |
| 034D07 | 740970 | PAK |
| 034D08 | 6202406 | PAK |
| 034D09 | 1781634 | PAK |
| 034D10 | 1655416 | PAK |
| 034D11 | 5718969 | PAK |
| 034D12 | 4544971 | PAK |
| 034E01 | 619590 | PAK |
| 034E04 | 2838744 | PAK |
| 034E05 | 177057 | PAK |
| 034E06 | 582633 | PAK |
| 034E07 | 3641141 | PAK |
| 034E08 | 3446172 | PAK |
| 034E10 | 3235122 | PAK |
| 034E11 | 219478 | PAK |
| 034E12 | 923502 | PAK |
| 034F01 | 3203535 | PAK |
| 034F02 | 6107689 | PAK |
| 034F03 | 6229813 | PAK |
| 034F04 | 3085363 | PAK |
| 034F05 | 284835 | PAK |
| 034F06 | 1275941 | PAK |
| 034F07 | 3366377 | PAK |
| 034F08 | 4877665 | PAK |
| 034F09 | 332768 | PAK |
| 034F10 | 5379007 | PAK |
| 034F11 | 1302733 | PAK |
| 034G01 | 334869 | PAK |
| 034G02 | 3761844 | PAK |
| 034G03 | 223530 | PAK |
| 034G04 | 1830367 | PAK |
| 034G05 | 3693472 | PAK |
| 034G06 | 1147273 | PAK |
| 034G07 | 3069275 | PAK |
| 034G08 | 1081866 | PAK |
| 034G09 | 187713 | PAK |
| 034G10 | 1355041 | PAK |
| 034G11 | 697418 | PAK |
| 034G12 | 4080338 | PAK |
| 034H01 | 1970850 | PAK |
| 034H02 | 5145613 | PAK |
| 034H03 | 3076623 | PAK |
| 034H04 | 3107297 | PAK |
| 034H05 | 3444611 | PAK |
| 034H06 | 281283 | PAK |
| 034H07 | 537388 | PAK |
| 034H08 | 3477891 | PAK |
| 034H09 | 3477891 | PAK |
| 034H10 | 2725178 | PAK |
| 034H11 | 395318 | PAK |
| 035A01 | 5367839 | PAK |
| 035A02 | 6202613 | PAK |
| 035A03 | 4300487 | PAK |
| 035A05 | 1412301 | PAK |
| 035A06 | 585070 | PAK |
| 035A07 | 1085596 | PAK |
| 035A08 | 3786428 | PAK |
| 035A09 | 5929909 | PAk |
| 035A11 | 3884502 | PAK |
| 035A12 | 3602559 | PAK |
| 035B01 | 2516661 | PAK |
| 035B02 | 2420924 | PAK |
| 035B03 | 717964 | PAK |
| 035B05 | 5136645 | PAK |
| 035B06 | 5819437 | PAK |
| 035B07 | 6056105 | PAK |
| 035B09 | 5394247 | PAK |
| 035B10 | 4052994 | PAK |
| 035C01 | 5044009 | PAK |
| 035C02 | 2601817 | PAK |
| 035C03 | 2062191 | PAK |
| 035C05 | 2816796 | PAK |
| 035C07 | 3900713 | PAK |
| 035C08 | 2719111 | PAK |
| 035C09 | 1855637 | PAK |
| 035C11 | 6093300 | PAK |
| 035D01 | 3951836 | PAK |
| 035D02 | 5926486 | PAK |
| 035D06 | 5513972 | PAK |
| 035D08 | 2375909 | PAK |
| 035D09 | 76054 | PAK |
| 035D11 | 1580830 | PAK |
| 035D12 | 4041791 | PAK |
| 035E03 | 5947596 | PAK |
| 035E04 | 3449143 | PAK |
| 035E05 | 2925236 | PAK |
| 035E07 | 2540767 | PAK |
| 035E09 | 3625530 | PAK |
| 035E10 | 2348490 | PAK |
| 036C04 | 1195735 | PAK |
| 036C05 | 3956359 | PAK |
| 036C06 | 6063016 | PAK |
| 036C07 | 4399820 | PAK |
| 036C08 | 322374 | PAK |
| 036C09 | 6030229 | PAK |
| 036C10 | 4529112 | PAK |
| 036C11 | 5871544 | PAK |
| 036C12 | 696300 | PAK |
| 036D02 | 5426925 | PAK |
| 036D03 | 3431378 | PAK |
| 036D04 | 3055528 | PAK |
| 036D06 | 5645722 | PAK |
| 036D07 | 2575230 | PAK |
| 036D08 | 178197 | PAK |
| 036D11 | 1374723 | PAK |
| 036D12 | 1034468 | PAK |
| 036E02 | 4835850 | PAK |
| 036E03 | 5477358 | PAK |
| 036E04 | 2930906 | PAK |
| 036E05 | 4622598 | PAK |
| 036E06 | 5458668 | PAK |
| 036E07 | 1302076 | PAK |
| 036E09 | 3423518 | PAK |
| 036E10 | 5010655 | PAK |
| 036E11 | 2638015 | PAK |
| 036E12 | 5423385 | PAK |
| 036F01 | 647873 | PAK |
| 036F03 | 1210896 | PAK |
| 036F04 | 5458650 | PAK |
| 036F05 | 1983022 | PAK |
| 036F07 | 2810951 | PAK |
| 036F08 | 3956359 | PAK |
| 036F09 | 2535550 | PAK |
| 036F10 | 975612 | PAK |
| 036F11 | 2082647 | PAK |
| 036G01 | 5373180 | PAK |

TABLE 3-continued

| Mutant Name | Insertion Point | host strain |
|---|---|---|
| 036G03 | 4650508 | PAK |
| 036G04 | 401104 | PAK |
| 036G06 | 2545183 | PAK |
| 036G07 | 4833185 | PAK |
| 036G08 | 3423519 | PAK |
| 036G09 | 2470356 | PAK |
| 036G11 | 2010587 | PAK |
| 036G12 | 3996203 | PAK |
| 036H01 | 3125215 | PAK |
| 036H04 | 3125215 | PAK |
| 036H06 | 1619804 | PAK |
| 036H07 | 5491695 | PAK |
| 036H08 | 842059 | PAK |
| 036H09 | 3980107 | PAK |
| 036H10 | 96877 | PAK |
| 036H11 | 113651 | PAK |
| 037A02 | 2231259 | PAK |
| 037A03 | 4628841 | PAK |
| 037A04 | 780472 | PAK |
| 037A05 | 5989449 | PAK |
| 037A06 | 2350667 | PAK |
| 037A07 | 8780 | PAK |
| 037A09 | 1001998 | PAK |
| 037A12 | 2716718 | PAK |
| 037B01 | 2007454 | PAK |
| 037B02 | 5167396 | PAK |
| 037B03 | 470703 | PAK |
| 037B07 | 2139415 | PAK |
| 037B08 | 345984 | PAK |
| 037B09 | 2659749 | PAK |
| 037B12 | 4798154 | PAK |
| 037C03 | 2911771 | PAK |
| 037C04 | 470704 | PAK |
| 037C06 | 2502614 | PAK |
| 037C08 | 2139415 | PAK |
| 037C09 | 345984 | PAK |
| 037C12 | 5076322 | PAK |
| 037D01 | 5363209 | PAK |
| 037D02 | 3235123 | PAK |
| 037D03 | 3721795 | PAK |
| 037D04 | 1038420 | PAK |
| 037D05 | 3856924 | PAK |
| 037D07 | 708023 | PAK |
| 037D08 | 618395 | PAK |
| 037D09 | 4966387 | PAK |
| 037E02 | 6022358 | PAK |
| 037E03 | 160705 | PAK |
| 037E04 | 5191738 | PAK |
| 037E05 | 5499935 | PAK |
| 037E08 | 2862324 | PAK |
| 037E09 | 1709356 | PAK |
| 037F03 | 2421966 | PAK |
| 037F04 | 1573016 | PAK |
| 037F10 | 2736654 | PAK |
| 037G02 | 4204883 | PAK |
| 037G04 | 6161681 | PAK |
| 037G05 | 120476 | PAK |
| 037G06 | 781042 | PAK |
| 037G07 | 3735199 | PAK |
| 037G08 | 5774224 | PAK |
| 037G09 | 1565917 | PAK |
| 037G10 | 5549729 | PAK |
| 037H02 | 413078 | PAK |
| 037H03 | 3776496 | PAK |
| 037H05 | 1452823 | PAK |
| 037H08 | 361431 | PAK |
| 037H10 | 3773413 | PAK |
| 037H11 | 9792 | PAK |
| 038A01 | 2221396 | PAK |
| 038A02 | 3199548 | PAK |
| 038A03 | 6019381 | PAK |
| 038A04 | 4050601 | PAK |
| 038A05 | 1020286 | PAK |
| 038A06 | 615432 | PAK |
| 038A07 | 3886631 | PAK |
| 038A08 | 5716882 | PAK |
| 038A09 | 5979450 | PAK |
| 038A12 | 5860564 | PAK |
| 038B01 | 2531824 | PAK |
| 038B02 | 6150981 | PAK |
| 038B03 | 2950347 | PAK |
| 038B04 | 1587631 | PAK |
| 038B05 | 3472993 | PAK |
| 038B07 | 4748755 | PAK |
| 038B08 | 2800987 | PAK |
| 038B09 | 4707866 | PAK |
| 038B10 | 645622 | PAK |
| 038B11 | 6190304 | PAK |
| 038C02 | 3254208 | PAK |
| 038C03 | 1431620 | PAK |
| 038C04 | 1924360 | PAK |
| 038C05 | 2658980 | PAK |
| 038C06 | 469623 | PAK |
| 038C07 | 2587184 | PAK |
| 038C08 | 516364 | PAK |
| 038C09 | 237725 | PAK |
| 038C10 | 2877920 | PAK |
| 038C11 | 5125422 | PAK |
| 038C12 | 3464971 | PAK |
| 038D01 | 2387338 | PAK |
| 038D02 | 113703 | PAK |
| 038D03 | 1436733 | PAK |
| 038D04 | 384589 | PAK |
| 038D05 | 2094100 | PAK |
| 038D06 | 570709 | PAK |
| 038D08 | 5807652 | PAK |
| 038D10 | 5473393 | PAK |
| 038D11 | 429568 | PAK |
| 038D12 | 5026321 | PAK |
| 038E01 | 3195864 | PAK |
| 038E02 | 3642382 | PAK |
| 038E03 | 1171544 | PAK |
| 038E04 | 4207208 | PAK |
| 038E05 | 4826038 | PAK |
| 038E06 | 5600809 | PAK |
| 038E07 | 1796309 | PAK |
| 038E08 | 3355560 | PAK |
| 038E09 | 1924386 | PAK |
| 038E10 | 6216289 | PAK |
| 038E12 | 5026320 | PAK |
| 038F01 | 5222071 | PAK |
| 038F02 | 375216 | PAK |
| 038F03 | 5768619 | PAK |
| 038F04 | 2431625 | PAK |
| 038F05 | 914957 | PAK |
| 038F06 | 5925887 | PAK |
| 038F07 | 506397 | PAK |
| 038F08 | 5148190 | PAK |
| 038F09 | 3839103 | PAK |
| 038F10 | 5585561 | PAK |
| 038F11 | 2882703 | PAK |
| 038F12 | 682861 | PAK |
| 038G01 | 2177222 | PAK |
| 038G02 | 6116317 | PAK |
| 038G03 | 2550359 | PAK |
| 038G05 | 1992425 | PAK |
| 038G06 | 1612335 | PAK |
| 038G07 | 15052 | PAK |
| 038G08 | 3803643 | PAK |
| 038G09 | 117478 | PAK |
| 038G10 | 1813557 | PAK |
| 038G11 | 5786903 | PAK |
| 038G12 | 5380605 | PAK |
| 038H01 | 5970491 | PAK |
| 038H02 | 5096813 | PAK |
| 038H04 | 1537284 | PAK |
| 038H06 | 5320147 | PAK |
| 038H08 | 817773 | PAK |
| 038H09 | 1981334 | PAK |
| 038H10 | 3983996 | PAK |
| 038H11 | 395317 | PAK |
| 039A01 | 1861173 | PAK |
| 039A04 | 1393864 | PAK |
| 039A05 | 1987963 | PAK |

TABLE 3-continued

| Mutant Name | Insertion Point | host strain |
|---|---|---|
| 039A07 | 1498811 | PAK |
| 039A08 | 379701 | PAK |
| 039A09 | 247994 | PAK |
| 039A10 | 3056328 | PAK |
| 039A11 | 76401 | PAK |
| 039B01 | 3590539 | PAK |
| 039B02 | 4407855 | PAK |
| 039B03 | 3038046 | PAK |
| 039B04 | 4028900 | PAK |
| 039B06 | 307732 | PAK |
| 039B07 | 3149436 | PAK |
| 039B08 | 4028785 | PAK |
| 039B09 | 2693577 | PAK |
| 039B10 | 5287105 | PAK |
| 039B11 | 1987962 | PAK |
| 039B12 | 968744 | PAK |
| 039C01 | 3875914 | PAK |
| 039C02 | 3805947 | PAK |
| 039C03 | 307732 | PAK |
| 039C06 | 4968436 | PAK |
| 039C09 | 342829 | PAK |
| 039C12 | 681528 | PAK |
| 039D01 | 5167206 | PAK |
| 039D02 | 1070658 | PAK |
| 039D03 | 1969412 | PAK |
| 039D04 | 2757901 | PAK |
| 039D05 | 938477 | PAK |
| 039D06 | 577497 | PAK |
| 039D07 | 2200860 | PAK |
| 039D08 | 1388479 | PAK |
| 039D09 | 319945 | PAK |
| 039D10 | 3667735 | PAK |
| 039D12 | 2016496 | PAK |
| 039E01 | 4139119 | PAK |
| 039E02 | 3968970 | PAK |
| 039E03 | 5431778 | PAK |
| 039E04 | 5547411 | PAK |
| 039E05 | 6241990 | PAK |
| 039E06 | 911407 | PAK |
| 039E07 | 345171 | PAK |
| 039E11 | 489783 | PAK |
| 039E12 | 2284400 | PAK |
| 039F02 | 906002 | PAK |
| 039F03 | 5098156 | PAK |
| 039F04 | 529320 | PAK |
| 039F05 | 845748 | PAK |
| 039F06 | 88138 | PAK |
| 039F07 | 3667045 | PAK |
| 039F10 | 79235 | PAK |
| 039F12 | 5998667 | PAK |
| 039G01 | 1821233 | PAK |
| 039G02 | 3075396 | PAK |
| 039G03 | 3897511 | PAK |
| 039G04 | 711492 | PAK |
| 039G05 | 5181188 | PAK |
| 039G06 | 5090749 | PAK |
| 039G07 | 4136155 | PAK |
| 039G09 | 4708061 | PAK |
| 039G10 | 4628661 | PAK |
| 039G12 | 5998667 | PAK |
| 039H01 | 3057283 | PAK |
| 039H03 | 5915738 | PAK |
| 039H04 | 2843991 | PAK |
| 039H05 | 5452946 | PAK |
| 039H06 | 5429333 | PAK |
| 039H07 | 543741 | PAK |
| 039H08 | 1700465 | PAK |
| 039H09 | 1698665 | PAK |
| 039H10 | 118997 | PAK |
| 039H11 | 395318 | PAK |
| 040A01 | 434887 | PAK |
| 040A02 | 342738 | PAK |
| 040A03 | 5385907 | PAK |
| 040A04 | 1389522 | PAK |
| 040A05 | 5262911 | PAK |
| 040A06 | 2673778 | PAK |
| 040A08 | 3377876 | PAK |
| 040A09 | 2499248 | PAR |
| 040A10 | 3231186 | PAK |
| 040A12 | 411128 | PAK |
| 040B02 | 6151598 | PAK |
| 040B03 | 5994534 | PAK |
| 040B05 | 5894536 | PAK |
| 040B06 | 1623870 | PAK |
| 040B07 | 361469 | PAK |
| 040B08 | 5339439 | PAK |
| 040B09 | 1934092 | PAK |
| 040B10 | 5864056 | PAK |
| 040B11 | 3892936 | PAK |
| 040B12 | 4845382 | PAK |
| 040C01 | 4438751 | PAK |
| 040C02 | 2824366 | PAK |
| 040C03 | 5651282 | PAK |
| 040C04 | 659742 | PAK |
| 040C05 | 1261892 | PAK |
| 040C06 | 5765003 | PAK |
| 040C07 | 776424 | PAK |
| 040C08 | 2133360 | PAK |
| 040C09 | 917224 | PAK |
| 040C10 | 5720295 | PAK |
| 040C12 | 6213709 | PAK |
| 040D01 | 6191429 | PAK |
| 040D02 | 5499529 | PAK |
| 040D04 | 5432307 | PAK |
| 040D05 | 4709287 | PAK |
| 040D06 | 1279250 | PAK |
| 040D07 | 1740896 | PAK |
| 040D08 | 2262209 | PAK |
| 040D09 | 5187068 | PAK |
| 040D11 | 1711687 | PAK |
| 040D12 | 3560454 | PAK |
| 040E01 | 4619114 | PAK |
| 040E03 | 1401775 | PAK |
| 040E04 | 4622307 | PAK |
| 040E05 | 103643 | PAK |
| 040E06 | 3570436 | PAK |
| 040E07 | 1569295 | PAK |
| 040E08 | 5296295 | PAK |
| 040E09 | 3055456 | PAK |
| 040E10 | 2110620 | PAK |
| 040E11 | 5226445 | PAK |
| 040E12 | 3669216 | PAK |
| 040F01 | 4682463 | PAK |
| 040F02 | 714913 | PAK |
| 040F03 | 5831895 | PAK |
| 040F04 | 306705 | PAK |
| 040F05 | 1402192 | PAK |
| 040F06 | 548691 | PAK |
| 040F07 | 3423519 | PAK |
| 040F08 | 6016051 | PAK |
| 040F09 | 1161406 | PAK |
| 040F10 | 2220648 | PAK |
| 040F11 | 3177842 | PAK |
| 040F12 | 4044626 | PAK |
| 040G01 | 5651116 | PAK |
| 040G02 | 4344544 | PAK |
| 040G03 | 3659011 | PAK |
| 040G04 | 3251825 | PAK |
| 040G07 | 64056 | PAK |
| 040G08 | 5397947 | PAK |
| 040G09 | 145393 | PAK |
| 040G10 | 660579 | PAK |
| 040G11 | 3296307 | PAK |
| 040G12 | 5925184 | PAK |
| 040H01 | 3341973 | PAK |
| 040H02 | 5818863 | PAK |
| 040H03 | 348709 | PAK |
| 040H04 | 3500824 | PAK |
| 040H05 | 3230271 | PAK |
| 040H06 | 512075 | PAK |
| 040H07 | 1988705 | PAK |
| 040H08 | 4854616 | PAK |
| 040H09 | 5501819 | PAK |
| 040H10 | 3794579 | PAK |

TABLE 3-continued

| Mutant Name | Insertion Point | host strain |
|---|---|---|
| 041A02 | 5795280 | PAK |
| 041A03 | 5089134 | PAK |
| 041A05 | 907405 | PAK |
| 041A06 | 3988913 | PAK |
| 041A07 | 2606926 | PAK |
| 041A08 | 848937 | PAK |
| 041A09 | 2703672 | PAK |
| 041A10 | 890106 | PAK |
| 041A11 | 4174020 | PAK |
| 041A12 | 6179246 | PAK |
| 041B01 | 5991897 | PAK |
| 041B02 | 5588598 | PAK |
| 041B03 | 3120577 | PAK |
| 041B04 | 5243894 | PAK |
| 041B05 | 3303605 | PAK |
| 041B06 | 3285144 | PAK |
| 041B07 | 296431 | PAK |
| 041B08 | 957984 | PAK |
| 041B09 | 4431627 | PAK |
| 041B10 | 328219 | PAK |
| 041B11 | 6103841 | PAK |
| 041B12 | 6065354 | PAK |
| 041C02 | 2903519 | PAK |
| 041C03 | 3511429 | PAK |
| 041C04 | 1873863 | PAK |
| 041C05 | 3111938 | PAK |
| 041C06 | 428397 | PAK |
| 041C07 | 4594610 | PAK |
| 041C08 | 4401199 | PAK |
| 041C09 | 3174550 | PAK |
| 041C11 | 4151288 | PAK |
| 041C12 | 1287062 | PAK |
| 041D01 | 5357973 | PAK |
| 041D02 | 3875280 | PAK |
| 041D03 | 4161168 | PAK |
| 041D04 | 93630 | PAK |
| 041D06 | 6020700 | PAK |
| 041D07 | 975945 | PAK |
| 041D08 | 3675698 | PAK |
| 041D09 | 823998 | PAK |
| 041D10 | 2622431 | PAK |
| 041E01 | 1114978 | PAK |
| 041E02 | 375183 | PAK |
| 041E04 | 4160672 | PAK |
| 041E05 | 719611 | PAK |
| 041E07 | 3654975 | PAK |
| 041E09 | 4008523 | PAK |
| 041E12 | 6090501 | PAK |
| 041F01 | 425648 | PAK |
| 041F02 | 4828897 | PAK |
| 041F03 | 615898 | PAK |
| 041F04 | 807429 | PAK |
| 041F05 | 370405 | PAK |
| 041F06 | 3179248 | PAK |
| 041F07 | 2752420 | PAK |
| 041F08 | 362255 | PAK |
| 041F09 | 5284755 | PAK |
| 041F10 | 3478603 | PAK |
| 041F12 | 4212194 | PAK |
| 041G01 | 4200709 | PAK |
| 041G02 | 1084851 | PAK |
| 041G03 | 4552624 | PAK |
| 041G04 | 5283850 | PAK |
| 041G05 | 2139207 | PAK |
| 041G06 | 3522249 | PAK |
| 041G09 | 1707246 | PAK |
| 041G10 | 3746182 | PAK |
| 041G11 | 1129197 | PAK |
| 041G12 | 4444027 | PAK |
| 041H01 | 858382 | PAK |
| 041H02 | 358826 | PAK |
| 041H03 | 4463639 | PAK |
| 041H04 | 3440777 | PAK |
| 041H06 | 5581759 | PAK |
| 041H07 | 2105927 | PAK |
| 041H08 | 3265630 | PAK |
| 041H09 | 249509 | PAK |
| 041H10 | 5655168 | PAK |
| 041H11 | 395319 | PAK |
| 042A02 | 378096 | PAK |
| 042A03 | 5160395 | PAK |
| 042A04 | 4895205 | PAK |
| 042A06 | 2564555 | PAK |
| 042A07 | 4403813 | PAK |
| 042A09 | 5009261 | PAK |
| 042A10 | 5041735 | PAK |
| 042A11 | 2643401 | PAK |
| 042A12 | 3327837 | PAK |
| 042B01 | 90522 | PAK |
| 042B02 | 1206417 | PAK |
| 042B03 | 5818149 | PAK |
| 042B05 | 1520411 | PAK |
| 042B07 | 3955351 | PAK |
| 042B08 | 4983821 | PAK |
| 042B11 | 1206904 | PAK |
| 042B12 | 567257 | PAK |
| 042C01 | 1788289 | PAK |
| 042C03 | 4911287 | PAK |
| 042C04 | 2871313 | PAK |
| 042C05 | 1526845 | PAK |
| 042C06 | 6072449 | PAK |
| 042C07 | 1197211 | PAK |
| 042C08 | 1845834 | PAK |
| 042C09 | 4746475 | PAK |
| 042C10 | 967048 | PAK |
| 042C11 | 174218 | PAK |
| 042C12 | 5457038 | PAK |
| 042D01 | 682842 | PAK |
| 042D02 | 2059541 | PAK |
| 042D03 | 1696180 | PAK |
| 042D04 | 4503148 | PAK |
| 042D05 | 5985826 | PAK |
| 042D09 | 3919472 | PAK |
| 042D11 | 1135749 | PAK |
| 042D12 | 458934 | PAK |
| 042E02 | 4521112 | PAK |
| 042E03 | 128916 | PAK |
| 042E04 | 567786 | PAK |
| 042E05 | 4698400 | PAK |
| 042E06 | 5874350 | PAK |
| 042E07 | 189660 | PAK |
| 042E08 | 1536442 | PAK |
| 042E09 | 5144611 | PAK |
| 042E10 | 1207183 | PAK |
| 042E11 | 4677790 | PAK |
| 042E12 | 5048295 | PAK |
| 042F01 | 590369 | PAK |
| 042F03 | 5225172 | PAK |
| 042F04 | 3353281 | PAK |
| 042F05 | 3027378 | PAK |
| 042F06 | 747048 | PAK |
| 042F07 | 5487622 | PAK |
| 042F08 | 5804696 | PAK |
| 042F09 | 255653 | PAK |
| 042F11 | 4647076 | PAK |
| 042F12 | 5504210 | PAK |
| 042G01 | 1971615 | PAK |
| 042G02 | 2848857 | PAK |
| 042G04 | 3628786 | PAK |
| 042G05 | 5446644 | PAK |
| 042G06 | 5339050 | PAK |
| 042G07 | 2600779 | PAK |
| 042G08 | 1000091 | PAK |
| 042G09 | 4904341 | PAK |
| 042G10 | 882130 | PAK |
| 042G11 | 1576895 | PAK |
| 042G12 | 3211687 | PAK |
| 042H02 | 6130322 | PAK |
| 042H03 | 6010809 | PAK |
| 042H04 | 3148251 | PAK |
| 042H06 | 630149 | PAK |
| 042H07 | 1240086 | PAK |
| 042H08 | 4337743 | PAK |
| 042H09 | 5937841 | PAK |

TABLE 3-continued

| Mutant Name | Insertion Point | host strain |
|---|---|---|
| 042H10 | 93560 | PAK |
| 043A01 | 1241426 | PAK |
| 043A02 | 5756505 | PAK |
| 043A04 | 5430288 | PAK |
| 043A06 | 1038438 | PAK |
| 043A07 | 1952435 | PAK |
| 043A08 | 2728707 | PAK |
| 043A09 | 3483872 | PAK |
| 043A10 | 2007454 | PAK |
| 043A11 | 586791 | PAK |
| 043A12 | 5743835 | PAK |
| 043B01 | 6197780 | PAK |
| 043B02 | 5936005 | PAK |
| 043B03 | 6177770 | PAK |
| 043B04 | 5548663 | PAK |
| 043B05 | 4346022 | PAK |
| 043B06 | 2127695 | PAK |
| 043B07 | 3013253 | PAK |
| 043B08 | 5227396 | PAK |
| 043B09 | 969336 | PAK |
| 043B10 | 1626428 | PAK |
| 043B11 | 6200037 | PAK |
| 043B12 | 1319989 | PAK |
| 043C02 | 1682113 | PAK |
| 043C03 | 3565385 | PAK |
| 043C04 | 320046 | PAK |
| 043C05 | 5874827 | PAK |
| 043C06 | 4160773 | PAK |
| 043C07 | 3070964 | PAK |
| 043C08 | 1076592 | PAK |
| 043C09 | 2499325 | PAK |
| 043C10 | 5317508 | PAK |
| 043C11 | 3998650 | PAK |
| 043C12 | 5142215 | PAK |
| 043D01 | 1401775 | PAK |
| 043D02 | 3869634 | PAK |
| 043D04 | 513025 | PAK |
| 043D05 | 3623934 | PAK |
| 043D08 | 280058 | PAK |
| 043D09 | 4253179 | PAK |
| 043D10 | 1037742 | PAK |
| 043D11 | 3423519 | PAK |
| 043E01 | 5251835 | PAK |
| 043E02 | 2824274 | PAK |
| 043E03 | 2149558 | PAK |
| 043E04 | 5794941 | PAK |
| 043E05 | 4376118 | PAK |
| 043E06 | 1104648 | PAK |
| 043E07 | 3591110 | PAK |
| 043E08 | 1880000 | PAK |
| 043E09 | 424226 | PAK |
| 043E10 | 3113416 | PAK |
| 043E11 | 182449 | PAK |
| 043E12 | 4350798 | PAK |
| 043F01 | 4607711 | PAK |
| 043F02 | 3136124 | PAK |
| 043F03 | 4884632 | PAK |
| 043F04 | 1991424 | PAK |
| 043F05 | 1247975 | PAK |
| 043F06 | 3268077 | PAK |
| 043F07 | 2548617 | PAK |
| 043F08 | 6182495 | PAK |
| 043F09 | 5084172 | PAK |
| 043F11 | 4886596 | PAK |
| 043F12 | 3701207 | PAK |
| 043G01 | 2388074 | PAK |
| 043G02 | 1282414 | PAK |
| 043G03 | 758126 | PAK |
| 043G04 | 4351288 | PAK |
| 043G05 | 3309414 | PAK |
| 043G06 | 1554849 | PAK |
| 043G07 | 1589174 | PAK |
| 043G08 | 1565526 | PAK |
| 043G09 | 5550834 | PAK |
| 043G10 | 5485943 | PAK |
| 043G11 | 6032332 | PAK |
| 043G12 | 4317166 | PAK |
| 043H01 | 6218527 | PAK |
| 043H02 | 3706161 | PAK |
| 043H03 | 499812 | PAK |
| 043H04 | 2314014 | PAK |
| 043H05 | 543532 | PAK |
| 043H06 | 1034469 | PAK |
| 043H07 | 4741047 | PAK |
| 043H08 | 2522082 | PAK |
| 043H09 | 2402285 | PAK |
| 043H10 | 5784701 | PAK |
| 043H11 | 395318 | PAK |
| 044A01 | 3746195 | PAK |
| 044A02 | 5563555 | PAK |
| 044A03 | 5936673 | FAK |
| 044A04 | 3025913 | PAK |
| 044A05 | 4897894 | PAK |
| 044A06 | 4705551 | PAK |
| 044A08 | 5261706 | PAK |
| 044A09 | 896011 | PAK |
| 044A10 | 1714299 | PAK |
| 044A12 | 5995515 | PAK |
| 044B01 | 4710516 | PAK |
| 044B02 | 3591717 | PAK |
| 044B03 | 5005657 | PAK |
| 044B04 | 4376118 | PAK |
| 044B05 | 4544529 | PAK |
| 044B07 | 6130031 | PAK |
| 044B09 | 3108246 | PAK |
| 044B10 | 3721953 | PAK |
| 044B11 | 3490497 | PAK |
| 044B12 | 4059857 | PAK |
| 044C01 | 5548174 | PAK |
| 044C02 | 577497 | PAK |
| 044C03 | 2364436 | PAK |
| 044C04 | 307553 | PAK |
| 044C05 | 3166235 | PAK |
| 044C06 | 3484519 | PAK |
| 044C07 | 3694952 | PAK |
| 044C09 | 5738810 | PAK |
| 044C10 | 317671 | PAK |
| 044C11 | 2546122 | PAK |
| 044D01 | 5518033 | PAK |
| 044D02 | 4601121 | PAK |
| 044D03 | 344216 | PAK |
| 044D04 | 3929164 | PAK |
| 044D05 | 5769908 | PAK |
| 044D06 | 272034 | PAK |
| 044D08 | 5719624 | PAK |
| 044D09 | 181018 | PAK |
| 044D10 | 5173079 | PAK |
| 044D11 | 5002559 | PAK |
| 044D12 | 4214966 | PAK |
| 044E01 | 5255502 | PAK |
| 044E02 | 441514 | PAK |
| 044E03 | 3001252 | PAK |
| 044E04 | 2755069 | PAK |
| 044E07 | 1091009 | PAK |
| 044E08 | 310523 | PAK |
| 044E09 | 4415342 | PAK |
| 044E10 | 2190791 | PAK |
| 044E12 | 3773614 | PAK |
| 044F01 | 2149558 | PAK |
| 044F02 | 1857814 | PAK |
| 044F03 | 1213176 | PAK |
| 044F04 | 5785635 | PAK |
| 044F05 | 6229380 | PAK |
| 044F06 | 711479 | PAK |
| 044F07 | 4201933 | PAK |
| 044F08 | 3009134 | PAK |
| 044F09 | 5162055 | PAK |
| 044F10 | 849959 | PAK |
| 044F11 | 1239124 | PAK |
| 044F12 | 5390226 | PAK |
| 044G01 | 5039673 | PAK |
| 044G02 | 3761438 | PAK |
| 044G03 | 5002559 | PAK |
| 044G04 | 1076592 | PAK |

TABLE 3-continued

| Mutant Name | Insertion Point | host strain |
|---|---|---|
| 044G05 | 5661274 | PAK |
| 044G06 | 1598742 | PAK |
| 044G07 | 4524349 | PAK |
| 044G08 | 3115861 | PAK |
| 044G09 | 1565779 | PAK |
| 044G10 | 2968961 | PAK |
| 044G11 | 1196389 | PAK |
| 044H01 | 6065767 | PAK |
| 044H02 | 802708 | PAK |
| 044H03 | 4384287 | PAK |
| 044H05 | 543532 | PAK |
| 044H06 | 5304973 | PAK |
| 044H07 | 718206 | PAK |
| 044H08 | 3655006 | PAK |
| 044H09 | 5374555 | PAK |
| 044H10 | 5865145 | PAK |
| 045A01 | 3724781 | PAK |
| 045A02 | 5954978 | PAK |
| 045A03 | 650632 | PAK |
| 045A04 | 5783320 | PAK |
| 045A05 | 5432149 | PAK |
| 045A06 | 3819555 | PAK |
| 045A07 | 2282107 | PAK |
| 045A08 | 582633 | PAK |
| 045A11 | 3330789 | PAK |
| 045A12 | 1138641 | PAK |
| 045B02 | 1034469 | PAK |
| 045B03 | 4115840 | PAK |
| 045B05 | 4674699 | PAK |
| 045B07 | 984633 | PAK |
| 045B08 | 4248396 | PAK |
| 045B09 | 5531123 | PAK |
| 045C01 | 912090 | PAK |
| 045C02 | 2090688 | PAK |
| 045C03 | 3724781 | PAK |
| 045C05 | 1017140 | PAK |
| 045C06 | 1034467 | PAK |
| 045C07 | 4632926 | PAK |
| 045C08 | 160820 | PAK |
| 045C09 | 3485030 | PAK |
| 045C10 | 2856410 | PAK |
| 045C11 | 470704 | PAK |
| 045C12 | 195275 | PAK |
| 045D01 | 5853880 | PAK |
| 045D02 | 2660295 | PAK |
| 045D03 | 6124651 | PAK |
| 045D05 | 478726 | PAK |
| 045D06 | 1235858 | PAK |
| 045D07 | 5403076 | PAK |
| 045D09 | 264P476 | PAK |
| 045D11 | 1397290 | PAK |
| 045D12 | 4047933 | PAK |
| 045E01 | 1307839 | PAK |
| 045E02 | 4004627 | PAK |
| 045E03 | 1407619 | PAK |
| 045E04 | 1789921 | PAK |
| 045E05 | 4692184 | PAK |
| 045E06 | 1344058 | PAK |
| 045E08 | 1819649 | PAK |
| 045E09 | 3692003 | PAK |
| 045E11 | 2044843 | PAK |
| 045E12 | 1034469 | PAK |
| 045F01 | 4289483 | PAK |
| 045F02 | 426787 | PAK |
| 045F03 | 4237791 | PAK |
| 045F06 | 1082878 | PAK |
| 045F07 | 1472506 | PAK |
| 045F08 | 3231365 | PAK |
| 045F09 | 423716 | PAK |
| 045F10 | 5958064 | PAK |
| 045F11 | 3926968 | PAK |
| 045F12 | 5890873 | PAK |
| 045G01 | 5759866 | PAK |
| 045G02 | 4961128 | PAK |
| 045G03 | 5242665 | PAK |
| 045G04 | 6230190 | PAK |
| 045G05 | 3380583 | PAK |
| 045G06 | 2584533 | PAK |
| 045G07 | 1988189 | PAK |
| 045G08 | 4158022 | PAK |
| 045G09 | 2159876 | PAK |
| 045G10 | 3293589 | PAK |
| 045H01 | 3060753 | PAK |
| 045H02 | 18800 | PAK |
| 045H03 | 1595385 | PAK |
| 045H04 | 4696559 | PAK |
| 045H05 | 1197370 | PAK |
| 045H06 | 5656945 | PAK |
| 045H07 | 372047 | PAK |
| 045H08 | 2496534 | PAK |
| 045H09 | 2922974 | PAK |
| 045H10 | 2458379 | PAK |
| 046A02 | 39799 | PAK |
| 046A03 | 3700941 | PAK |
| 046A04 | 1889947 | PAK |
| 046A05 | 3307543 | PAK |
| 046A06 | 5198450 | PAK |
| 046A07 | 835641 | PAK |
| 046A08 | 5805380 | PAK |
| 046A09 | 694982 | PAK |
| 046A10 | 4877665 | PAK |
| 046A11 | 5022885 | PAK |
| 046A12 | 264975 | PAK |
| 046B01 | 1111803 | PAK |
| 046B02 | 5600143 | PAK |
| 046B06 | 3753608 | PAK |
| 046B07 | 4338833 | PAK |
| 046B08 | 3872320 | PAK |
| 046B09 | 958891 | PAK |
| 046C01 | 545141 | PAK |
| 046C02 | 5126650 | PAK |
| 046C03 | 16484261 | PAK |
| 046C04 | 4810183 | PAK |
| 046C05 | 3999283 | PAK |
| 046C06 | 1629811 | PAK |
| 046C07 | 5355604 | PAK |
| 046C08 | 2927047 | PAK |
| 046C09 | 3696510 | PAK |
| 046C10 | 2022919 | PAK |
| 046C11 | 3033816 | PAK |
| 046C12 | 3856929 | PAK |
| 046D01 | 841026 | PAK |
| 046D02 | 4700935 | PAK |
| 046D03 | 4505583 | PAK |
| 046D05 | 3113291 | PAK |
| 046D06 | 5425140 | PAK |
| 046D07 | 605472 | PAK |
| 046D08 | 982023 | PAK |
| 046D09 | 1201752 | PAK |
| 046D10 | 3839727 | PAK |
| 046D11 | 3834783 | PAK |
| 046D12 | 1778011 | PAK |
| 046E01 | 1420111 | PAK |
| 046E02 | 2896166 | PAK |
| 046E03 | 4907824 | PAK |
| 046E05 | 791139 | PAK |
| 046E06 | 6206678 | PAK |
| 046E07 | 2275990 | PAK |
| 046E08 | 309450 | PAK |
| 046E09 | 5830862 | PAK |
| 046E11 | 2927500 | PAK |
| 046E12 | 4842452 | PAK |
| 046F01 | 2638974 | PAK |
| 046F02 | 2051474 | PAK |
| 046F05 | 3511809 | PAK |
| 046F06 | 6073758 | PAK |
| 046F11 | 2914409 | PAK |
| 046F12 | 1442679 | PAK |
| 046G01 | 4131065 | PAK |
| 046G02 | 4974335 | PAK |
| 046G04 | 3841817 | PAK |
| 046G05 | 4881424 | PAK |
| 046G06 | 5416656 | PAK |
| 046G08 | 506389 | PAK |

TABLE 3-continued

| Mutant Name | Insertion Point | host strain |
|---|---|---|
| 046G10 | 1085149 | PAK |
| 046H02 | 2714657 | PAK |
| 046H03 | 6163618 | PAK |
| 046H05 | 6083533 | PAK |
| 046H06 | 4897697 | PAK |
| 046H07 | 4106350 | PAK |
| 046H08 | 6095642 | PAK |
| 046H09 | 5891644 | PAK |
| 046H10 | 6224406 | PAK |
| 047A01 | 2032572 | PAK |
| 047A02 | 57744 | PAK |
| 047A03 | 4883121 | PAK |
| 047A06 | 2038454 | PAK |
| 047A07 | 5142593 | PAK |
| 047A08 | 5906879 | PAK |
| 047A09 | 5212322 | PAK |
| 047A10 | 6202406 | PAK |
| 047A11 | 6202406 | PAK |
| 047A12 | 961308 | PAK |
| 047B01 | 5078374 | PAK |
| 047B05 | 5121683 | PAK |
| 047B08 | 625674 | PAK |
| 047B10 | 2473563 | PAK |
| 047C01 | 868047 | PAK |
| 047C02 | 5801679 | PAK |
| 047C04 | 6052662 | PAK |
| 047C05 | 531720 | PAK |
| 047C07 | 936449 | PAK |
| 047C08 | 4411168 | PAK |
| 047C09 | 2560446 | PAK |
| 047C11 | 2458906 | PAK |
| 047C12 | 4637926 | PAK |
| 047D01 | 1131825 | PAK |
| 047D02 | 6200062 | PAK |
| 047D03 | 2870664 | PAK |
| 047D04 | 3469640 | PAK |
| 047D05 | 4307149 | PAK |
| 047D07 | 2903114 | PAK |
| 047D08 | 327317 | PAK |
| 047D09 | 5721826 | PAK |
| 047D10 | 435360 | PAK |
| 047D11 | 5651896 | PAK |
| 047D12 | 5478491 | PAK |
| 047E01 | 145292 | PAK |
| 047E02 | 567204 | PAK |
| 047E03 | 3241443 | PAK |
| 047E04 | 1520376 | PAK |
| 047E06 | 5400472 | PAK |
| 047E07 | 213302 | PAK |
| 047E09 | 622460 | PAK |
| 047E10 | 4355869 | PAK |
| 047E11 | 4622390 | PAK |
| 047F01 | 3418611 | PAK |
| 047F02 | 5467041 | PAK |
| 047F03 | 315529 | PAK |
| 047F04 | 5033157 | PAK |
| 047F05 | 3513768 | PAK |
| 047F06 | 524915 | PAK |
| 047F08 | 6139295 | PAK |
| 047F09 | 3393871 | PAK |
| 048B03 | 3156492 | PAK |
| 048B04 | 3645630 | PAK |
| 048B05 | 5006994 | PAK |
| 048B07 | 2324376 | PAK |
| 048B08 | 3976706 | PAK |
| 048B09 | 3889620 | PAK |
| 048B10 | 5602961 | PAK |
| 048C02 | 6183698 | PAK |
| 048C05 | 2166572 | PAK |
| 048C06 | 2462035 | PAK |
| 048C08 | 5729364 | PAK |
| 048D01 | 442332 | PAK |
| 048D04 | 434886 | PAK |
| 048D05 | 4422630 | PAK |
| 048D06 | 221177 | PAK |
| 048D08 | 6143326 | PAK |
| 048D09 | 2670867 | PAK |
| 048D11 | 4901353 | PAK |
| 048D12 | 2671859 | PAK |
| 048H01 | 176224 | PAK |
| 048H02 | 4324350 | PAK |
| 048H03 | 1557564 | PAK |
| 048H04 | 4996836 | PAK |
| 048H07 | 5436185 | PAK |
| 048H08 | 998174 | PAK |
| 048H10 | 2281927 | PAK |
| 049A02 | 4827235 | PAK |
| 049A03 | 1630465 | PAK |
| 049A05 | 4834673 | PAK |
| 049A06 | 5894130 | PAK |
| 049A09 | 5433863 | PAK |
| 049A10 | 2024229 | PAK |
| 049A11 | 1149465 | PAK |
| 049B01 | 5073520 | PAK |
| 049B03 | 5301406 | PAK |
| 049B04 | 2745498 | PAK |
| 049B05 | 2747673 | PAK |
| 049B08 | 572745 | PAK |
| 049B09 | 2900238 | PAK |
| 049B11 | 4961063 | PAK |
| 049B12 | 4600805 | PAK |
| 049C01 | 5454008 | PAK |
| 049C02 | 4055594 | PAK |
| 049C03 | 2889673 | PAK |
| 049C04 | 3599081 | PAK |
| 049C05 | 5583365 | PAK |
| 049C06 | 4452090 | PAK |
| 049C08 | 5912429 | PAK |
| 049C09 | 5980173 | PAK |
| 049C10 | 579217 | PAK |
| 049C11 | 4167865 | PAK |
| 049C12 | 5657177 | PAK |
| 049D01 | 5984634 | PAK |
| 049D03 | 466729 | PAK |
| 049D04 | 2463041 | PAK |
| 049D05 | 1144192 | PAK |
| 049D06 | 4664900 | PAK |
| 049D07 | 1493775 | PAK |
| 049D08 | 838566 | PAK |
| 049D09 | 4202639 | PAK |
| 049D10 | 733670 | PAK |
| 049D11 | 5642982 | PAK |
| 049D12 | 4687527 | PAK |
| 049E01 | 5436192 | PAK |
| 049E02 | 1073568 | PAK |
| 049E03 | 412264 | PAK |
| 049E04 | 401664 | PAK |
| 049E06 | 1530440 | PAK |
| 049E07 | 2529887 | PAK |
| 050B05 | 147640 | PAK |
| 050B06 | 4383890 | PAK |
| 050B07 | 2904575 | PAK |
| 050B08 | 2563342 | PAK |
| 050B09 | 3786524 | PAK |
| 050B10 | 5509982 | PAK |
| 050B11 | 662493 | PAK |
| 050C01 | 3377876 | PAK |
| 050C02 | 4876506 | PAK |
| 050C03 | 4246816 | PAK |
| 050C04 | 1130409 | PAK |
| 050C05 | 5145793 | PAK |
| 050C06 | 5681062 | PAK |
| 050C08 | 3279137 | PAK |
| 050C10 | 3865780 | PAK |
| 050C11 | 1402477 | PAK |
| 050C12 | 1573691 | PAK |
| 050D01 | 6218792 | PAK |
| 050D02 | 3879741 | PAK |
| 050D04 | 137003 | PAK |
| 050D05 | 841798 | PAK |
| 050D06 | 5970491 | PAK |
| 050D07 | 703530 | PAK |
| 050D08 | 2295238 | PAK |
| 050D09 | 4066263 | PAK |

TABLE 3-continued

| Mutant Name | Insertion Point | host strain |
|---|---|---|
| 050D10 | 1549573 | PAK |
| 050D11 | 1447778 | PAK |
| 050E01 | 5187068 | PAK |
| 050E02 | 4839441 | PAK |
| 050E03 | 4898763 | PAK |
| 050E04 | 3323S63 | PAK |
| 050E05 | 4167233 | PAK |
| 050E06 | 5715126 | PAK |
| 050E07 | 4111311 | PAK |
| 050E08 | 1715494 | PAK |
| 050E09 | 5874715 | PAK |
| 050E10 | 3848466 | PAK |
| 050E11 | 3183965 | PAK |
| 050E12 | 3449937 | PAK |
| 050F01 | 792454 | PAK |
| 050F02 | 1187266 | PAK |
| 050F03 | 4416817 | PAK |
| 050F04 | 18861 | PAK |
| 050F05 | 5717345 | PAK |
| 050F06 | 4709643 | PAK |
| 050F07 | 931425 | PAK |
| 050F08 | 3241824 | PAK |
| 050F09 | 941643 | PAK |
| 050F10 | 873080 | PAK |
| 050F11 | 2661005 | PAK |
| 050F12 | 6239159 | PAK |
| 050G01 | 2876475 | PAK |
| 050G03 | 5559927 | PAK |
| 050G04 | 1350893 | PAK |
| 050G05 | 933576 | PAK |
| 050G06 | 640905 | PAK |
| 050G07 | 2267437 | PAK |
| 050G08 | 4214521 | PAK |
| 050G09 | 3370029 | PAK |
| 050G10 | 437564 | PAK |
| 050G11 | 2333549 | PAK |
| 050G12 | 659505 | PAK |
| 050H01 | 5106434 | PAK |
| 050H02 | 4529076 | PAK |
| 050H03 | 646545 | PAK |
| 050H04 | 1386341 | PAK |
| 050H05 | 152943 | PAK |
| 050H06 | 5699434 | PAK |
| 050H09 | 1701115 | PAK |
| 050H10 | 1003254 | PAK |
| 050H11 | 395319 | PAK |
| 051A02 | 2514316 | PAK |
| 051A03 | 5492589 | PAK |
| 051A04 | 815511 | PAK |
| 051A05 | 5347600 | PAK |
| 051A06 | 4524286 | PAK |
| 051A07 | 844307 | PAK |
| 051A08 | 4300479 | PAK |
| 051A09 | 1274236 | PAK |
| 051A10 | 462941 | PAK |
| 051A11 | 360857 | PAK |
| 051A12 | 4253600 | PAK |
| 051B01 | 6156485 | PAK |
| 051B02 | 5925124 | PAK |
| 051B03 | 587339 | PAK |
| 051B05 | 5966126 | PAK |
| 051B06 | 4603302 | PAK |
| 051B07 | 3605154 | PAK |
| 051B08 | 3129079 | PAK |
| 051B09 | 5427253 | PAK |
| 051B10 | 489641 | PAK |
| 051B11 | 3029371 | PAK |
| 051B12 | 4334204 | PAK |
| 051C01 | 2660015 | PAK |
| 051C02 | 3887675 | PAK |
| 051C03 | 3638514 | PAK |
| 051C04 | 307732 | PAK |
| 051C05 | 2389705 | PAK |
| 051C06 | 3406169 | PAK |
| 051C07 | 3262068 | PAK |
| 051C08 | 2306782 | PAK |
| 051C10 | 4224160 | PAK |
| 051C11 | 4035028 | PAK |
| 051C12 | 3765513 | PAK |
| 051D01 | 6073198 | PAK |
| 051D02 | 5395375 | PAK |
| 051D03 | 587339 | PAK |
| 051D04 | 1127364 | PAK |
| 051D06 | 5512888 | PAK |
| 051D07 | 6000422 | PAK |
| 051D08 | 2567886 | PAK |
| 051D09 | 49004 | PAK |
| 051D10 | 6073489 | PAK |
| 051D11 | 4347298 | PAK |
| 051D12 | 5661257 | PAK |
| 051E01 | 6073198 | PAK |
| 051E02 | 2558964 | PAK |
| 051E03 | 2151330 | PAK |
| 051E05 | 1677011 | PAK |
| 051E06 | 3330660 | PAK |
| 051E07 | 970234 | PAK |
| 051E08 | 3247494 | PAK |
| 051E09 | 2974656 | PAK |
| 051E10 | 6082177 | PAK |
| 051E11 | 6177074 | PAK |
| 051E12 | 146554 | PAK |
| 0S1F01 | 2660015 | PAK |
| 051F02 | 3887675 | PAK |
| 051F03 | 3532331 | PAK |
| 051F04 | 2796090 | PAK |
| 051F05 | 2942788 | PAK |
| 051F07 | 3068088 | PAK |
| 051F08 | 4224160 | PAK |
| 051F09 | 2971447 | PAK |
| 051F10 | 618538 | PAK |
| 051F11 | 913729 | PAK |
| 051F12 | 9453841 | PAK |
| 051G01 | 6156485 | PAK |
| 051G02 | 2149543 | PAK |
| 051G04 | 4166227 | PAK |
| 051G05 | 2890801 | PAK |
| 051G06 | 1431643 | PAK |
| 051G07 | 3894901 | PAK |
| 051G08 | 5018724 | PAK |
| 051G09 | 4188878 | PAK |
| 051G10 | 2024237 | PAK |
| 051G11 | 5842936 | PAK |
| 051G12 | 6083524 | PAK |
| 051H01 | 5581870 | PAK |
| 051H02 | 4355869 | PAK |
| 051H03 | 1377184 | PAK |
| 051H04 | 4604465 | PAK |
| 051H05 | 3162750 | PAK |
| 051H06 | 5261373 | PAK |
| 051H07 | 3514190 | PAK |
| 051H08 | 1274236 | PAK |
| 051H11 | 395319 | PAK |
| 052A01 | 181573 | PAK |
| 052A02 | 5189293 | PAK |
| 052A03 | 8849 | PAK |
| 052A04 | 464341 | PAK |
| 052A05 | 1146972 | PAK |
| 052A06 | 5284381 | PAK |
| 052A07 | 5892199 | PAK |
| 052A08 | 462476 | PAK |
| 052A10 | 6135131 | PAK |
| 052A11 | 4382102 | PAK |
| 052A12 | 5719746 | PAK |
| 052B01 | 6226484 | PAK |
| 052B02 | 3307160 | PAK |
| 052B03 | 5769515 | PAK |
| 052B04 | 5697132 | PAK |
| 052B05 | 490905 | PAK |
| 052B07 | 2634938 | PAK |
| 052B08 | 4618287 | PAK |
| 052B10 | 4106751 | PAK |
| 052B12 | 6082612 | PAK |
| 052C02 | 4415846 | PAK |
| 052C03 | 1125243 | PAK |

TABLE 3-continued

| Mutant Name | Insertion Point | host strain |
|---|---|---|
| 052C04 | 1714442 | PAK |
| 052C05 | 82307 | PAK |
| 052C06 | 806769 | PAK |
| 052C07 | 5035783 | PAK |
| 052C08 | 1242014 | PAK |
| 052C09 | 521681 | PAK |
| 052C10 | 4907028 | PAK |
| 052C11 | 5252590 | PAK |
| 052C12 | 792562 | PAK |
| 052D01 | 2897462 | PAK |
| 052D02 | 2543984 | PAK |
| 052D03 | 1774692 | PAK |
| 052D04 | 2319223 | PAK |
| 052D05 | 3731154 | PAK |
| 052D06 | 4653700 | PAK |
| 052D08 | 5758219 | PAK |
| 052D09 | 1190880 | PAK |
| 052D11 | 3783197 | PAK |
| 052D12 | 1996741 | PAK |
| 052E01 | 5528427 | PAK |
| 052E02 | 5149710 | PAK |
| 052E03 | 1165358 | PAK |
| 052E04 | 3375872 | PAK |
| 052E05 | 5936681 | PAK |
| 052E06 | 647899 | PAK |
| 052E07 | 540833 | PAK |
| 052E08 | 5862506 | PAK |
| 052E09 | 3735015 | PAK |
| 052E10 | 2865589 | PAK |
| 052E11 | 4397213 | PAK |
| 052E12 | 5785887 | PAK |
| 052F01 | 2378818 | PAK |
| 052F02 | 1393668 | PAK |
| 052F03 | 1165359 | PAK |
| 052F04 | 888252 | PAK |
| 052F05 | 5182713 | PAK |
| 052F06 | 265478 | PAK |
| 052F08 | 2276266 | PAK |
| 052F10 | 464932 | PAK |
| 052G01 | 6193680 | PAK |
| 052G03 | 5139025 | PAK |
| 052G04 | 3358477 | PAK |
| 052G05 | 172168 | PAK |
| 052G06 | 6213709 | PAK |
| 052G07 | 645622 | PAK |
| 052G08 | 1556712 | PAK |
| 052G09 | 855434 | PAK |
| 052G10 | 1078418 | PAK |
| 052G11 | 1843187 | PAK |
| 052G12 | 627073 | PAK |
| 052H01 | 5917685 | PAK |
| 052H02 | 1623038 | PAK |
| 052H03 | 285703 | PAK |
| 052H04 | 186782 | PAK |
| 052H05 | 5097409 | PAK |
| 052H06 | 4383138 | PAK |
| 052H07 | 5870186 | PAK |
| 052H08 | 854053 | PAK |
| 052H09 | 2392123 | PAK |
| 052H10 | 701214 | PAK |
| 052H11 | 395318 | PAK |
| 053A01 | 4214115 | PAK |
| 053A02 | 6200715 | PAK |
| 053A03 | 3821418 | PAK |
| 053A04 | 4122715 | PAK |
| 053A05 | 5805677 | PAK |
| 053A06 | 948519 | PAK |
| 053A07 | 5090358 | PAK |
| 053A08 | 101826 | PAK |
| 053A10 | 4246591 | PAK |
| 053A11 | 1602036 | PAK |
| 053B01 | 5511939 | PAK |
| 053B03 | 3654665 | PAK |
| 053B04 | 985206 | PAK |
| 053B06 | 6160138 | PAK |
| 053B07 | 3244045 | PAK |
| 053B08 | 3146923 | PAK |
| 053B10 | 2854153 | PAK |
| 053B11 | 6848697 | PAK |
| 053B12 | 2291583 | PAK |
| 053C01 | 3931380 | PAK |
| 053C02 | 2867681 | PAK |
| 053C03 | 1903165 | PAK |
| 053C04 | 5565761 | PAK |
| 053C05 | 4593243 | PAK |
| 053C06 | 4880286 | PAK |
| 053C07 | 1526202 | PAK |
| 053C08 | 5865230 | PAK |
| 053C09 | 271712 | PAK |
| 053C11 | 1510728 | PAK |
| 053C12 | 1405829 | PAK |
| 053D02 | 5082816 | PAK |
| 053D03 | 3036067 | PAK |
| 053D04 | 252583 | PAK |
| 053D05 | 3174550 | PAK |
| 053D06 | 356881 | PAK |
| 053D07 | 574892 | PAK |
| 053D08 | 430496 | PAK |
| 053D09 | 5077902 | PAK |
| 053D10 | 5305628 | PAK |
| 053D11 | 253657 | PAK |
| 053D12 | 3511429 | PAK |
| 053E01 | 57221 | PAK |
| 053E02 | 4304643 | PAK |
| 053E03 | 5191991 | PAK |
| 053E04 | 5686676 | PAK |
| 053E06 | 383305 | PAK |
| 053E07 | 1950781 | PAK |
| 053E08 | 5651169 | PAK |
| 053E09 | 1202486 | PAK |
| 053E10 | 5304135 | PAK |
| 053E11 | 1577166 | PAK |
| 053E12 | 1750702 | PAK |
| 053F01 | 2654867 | PAK |
| 053F02 | 3983997 | PAK |
| 053F03 | 1360709 | PAK |
| 053F05 | 4134624 | PAK |
| 053F06 | 5981408 | PAK |
| 053F07 | 3245337 | PAK |
| 053F08 | 395876 | PAK |
| 053F10 | 2784406 | PAK |
| 053F12 | 519043 | PAK |
| 053G01 | 3567062 | PAK |
| 053G03 | 149731 | PAK |
| 053G04 | 3762265 | PAK |
| 053G05 | 296382 | PAK |
| 053G06 | 5193396 | PAK |
| 053G07 | 4552422 | PAK |
| 053G08 | 6103968 | PAK |
| 053G10 | 311061 | PAK |
| 053G11 | 1398847 | PAK |
| 053G12 | 6164856 | PAK |
| 053H01 | 5791818 | PAK |
| 053H03 | 2903322 | PAK |
| 053H04 | 4928681 | PAK |
| 053H05 | 4487249 | PAK |
| 053H06 | 5104449 | PAK |
| 053H08 | 6012213 | PAK |
| 053H09 | 3419751 | PAK |
| 053H10 | 5849526 | PAK |
| 053H11 | 395319 | PAK |
| 054A02 | 5495678 | PAK |
| 054A03 | 256014 | PAK |
| 054A04 | 3682064 | PAK |
| 054A05 | 4346395 | PAK |
| 054A06 | 1895698 | PAK |
| 054A08 | 5008086 | PAK |
| 054A10 | 556089 | PAK |
| 054A12 | 1707321 | PAK |
| 054B01 | 4594778 | PAK |
| 054B02 | 5260462 | PAK |
| 054B03 | 4861255 | PAK |
| 054B04 | 1168709 | PAK |
| 054B05 | 661081 | PAK |

TABLE 3-continued

| Mutant Name | Insertion Point | host strain |
|---|---|---|
| 054B06 | 1543671 | PAK |
| 054B07 | 1168452 | PAK |
| 054B08 | 1500117 | PAK |
| 054B09 | 3597137 | PAK |
| 054B10 | 4892530 | PAK |
| 054B11 | 1821913 | PAK |
| 054B12 | 4920970 | PAK |
| 054C01 | 6208256 | PAK |
| 054C03 | 933029 | PAK |
| 054C05 | 1618956 | PAK |
| 054C06 | 1526098 | PAK |
| 054C09 | 924575 | PAK |
| 054D02 | 3773034 | PAK |
| 054D05 | 5867602 | PAK |
| 054D06 | 1713750 | PAK |
| 054D07 | 1853899 | PAK |
| 054D08 | 4334837 | PAK |
| 054D10 | 1621974 | PAK |
| 054D11 | 1013616 | PAK |
| 054E01 | 2384674 | PAK |
| 054E02 | 4616964 | PAK |
| 054E03 | 5936588 | PAK |
| 054E04 | 1236614 | PAK |
| 054E05 | 5495054 | PAK |
| 054E06 | 5004735 | PAK |
| 054E07 | 2427336 | PAK |
| 054E08 | 3140602 | PAK |
| 054E09 | 120598 | PAK |
| 054E10 | 417444 | PAK |
| 054E11 | 5784723 | PAK |
| 054E12 | 3022373 | PAK |
| 054F01 | 5151905 | PAK |
| 054F02 | 3809885 | PAK |
| 054F03 | 4825841 | PAK |
| 054F04 | 3468637 | PAK |
| 054F05 | 4677790 | PAK |
| 054F06 | 4115659 | PAK |
| 054F07 | 5376068 | PAK |
| 054F08 | 568294 | PAK |
| 054F09 | 5310625 | PAK |
| 054F10 | 4229959 | PAK |
| 054F11 | 697418 | PAK |
| 054F12 | 5970022 | PAK |
| 054G01 | 3422289 | PAK |
| 054G02 | 4977243 | PAK |
| 054G03 | 3442304 | PAK |
| 054G04 | 186722 | PAK |
| 054G05 | 4126950 | PAK |
| 054G06 | 5093213 | PAK |
| 054G07 | 3838803 | PAK |
| 054G08 | 1928099 | PAK |
| 054G09 | 342366 | PAK |
| 054G10 | 3959870 | PAK |
| 054G11 | 1877028 | PAK |
| 054G12 | 621622 | PAK |
| 054H01 | 5829968 | PAK |
| 054H02 | 3512372 | PAK |
| 054H03 | 1569734 | PAK |
| 054H04 | 6242027 | PAK |
| 054H05 | 9198901 | PAK |
| 054H06 | 4155306 | PAK |
| 054H07 | 1733791 | PAK |
| 054H08 | 5924283 | PAK |
| 054H09 | 4066664 | PAK |
| 054H10 | 4868211 | PAK |
| 055A11 | 4161640 | PAK |
| 055A12 | 216047 | PAK |
| 055802 | 2232787 | PAK |
| 055803 | 595688 | PAK |
| 055B04 | 763009 | PAK |
| 055B06 | 2553616 | PAK |
| 055B07 | 1026784 | PAK |
| 055B08 | 3375853 | PAK |
| 055B09 | 704990 | PAK |
| 055B10 | 3777900 | PAK |
| 055B11 | 5370857 | PAK |
| 055B12 | 5645395 | PAK |
| 055C01 | 3468645 | PAK |
| 055C02 | 6133330 | PAK |
| 055C03 | 1434589 | PAK |
| 055C04 | 5400274 | PAK |
| 055C05 | 3833396 | PAK |
| 055C06 | 2023159 | PAK |
| 055C07 | 514110 | PAK |
| 055C08 | 266303 | PAK |
| 055C11 | 429505 | PAK |
| 055C12 | 4499399 | PAK |
| 055D01 | 3512189 | PAK |
| 055D02 | 117900 | PAK |
| 055D03 | 1132345 | PAK |
| 055D04 | 6181750 | PAK |
| 055D06 | 1526961 | PAK |
| 055D08 | 4399180 | PAK |
| 055D09 | 3472697 | PAK |
| 055D10 | 5382009 | PAK |
| 055D11 | 709457 | PAK |
| 055D12 | 4304891 | PAK |
| 055E01 | 2935281 | PAK |
| 055E03 | 5837644 | PAK |
| 055E04 | 1415677 | PAK |
| 055E05 | 5118044 | PAK |
| 055E06 | 3485816 | PAK |
| 055E08 | 4607864 | PAK |
| 055E09 | 2225423 | PAK |
| 055E10 | 1395240 | PAK |
| 055F01 | 2134857 | PAK |
| 055F02 | 3266907 | PAK |
| 055F03 | 1097990 | PAK |
| 055F04 | 2738002 | PAK |
| 055F05 | 3771431 | PAK |
| 055F06 | 4769852 | PAK |
| 055F08 | 4415343 | PAK |
| 055F09 | 2795438 | PAK |
| 055F10 | 3811629 | PAK |
| 055F11 | 5186251 | PAK |
| 055F12 | 5462747 | PAK |
| 055G01 | 3728298 | PAK |
| 055G04 | 6131543 | PAK |
| 055G06 | 4030558 | PAK |
| 055G10 | 5521259 | PAK |
| 055G11 | 3958267 | PAK |
| 055G12 | 664961 | PAK |
| 055H02 | 5037348 | PAK |
| 055H03 | 5412162 | PAK |
| 055H06 | 3830336 | PAK |
| 055H07 | 720397 | PAK |
| 055H08 | 565447 | PAK |
| 055H09 | 5928731 | PAK |
| 055H10 | 2006780 | PAK |
| 056A02 | 56380 | PAK |
| 056A04 | 5409799 | PAK |
| 056A05 | 367235 | PAK |
| 056A06 | 3073376 | PAK |
| 056A07 | 199120 | PAK |
| 056A08 | 4544527 | PAK |
| 056A09 | 2590485 | PAK |
| 056A10 | 5133330 | PAK |
| 056A12 | 130695 | PAK |
| 056B01 | 5020126 | PAK |
| 056B02 | 376447 | PAK |
| 056B03 | 645478 | PAK |
| 056B04 | 1299668 | PAK |
| 056B05 | 3517379 | PAK |
| 056B06 | 3388880 | PAK |
| 056B08 | 5077346 | PAK |
| 056B09 | 3366077 | PAK |
| 056B10 | 4238837 | PAK |
| 056B11 | 4607019 | PAK |
| 056B12 | 3316217 | PAK |
| 056C01 | 8842581 | PAK |
| 056C02 | 3483171 | PAK |
| 056C03 | 1381290 | PAK |
| 056C04 | 3138659 | PAK |
| 056C06 | 1256831 | PAK |

TABLE 3-continued

| Mutant Name | Insertion Point | host strain |
|---|---|---|
| 056C07 | 6190164 | PAK |
| 056C08 | 619609 | PAK |
| 056C09 | 4273914 | PAK |
| 056C10 | 2462385 | PAK |
| 056C11 | 118998 | PAK |
| 056D01 | 3178167 | PAK |
| 056D02 | 1530368 | PAK |
| 056D03 | 3709078 | PAK |
| 056D04 | 5141066 | PAK |
| 056D05 | 4185403 | PAK |
| 056D06 | 1381795 | PAK |
| 056D07 | 4218516 | PAK |
| 056D08 | 962539 | PAK |
| 056D09 | 969390 | PAK |
| 056D10 | 316565 | PAK |
| 056D11 | 3716379 | PAK |
| 056D12 | 4353897 | PAK |
| 056E01 | 1991154 | PAK |
| 056E02 | 116485 | PAK |
| 056E03 | 548682 | PAK |
| 056E04 | 4538696 | PAK |
| 056E05 | 42776 | PAK |
| 056E06 | 589908 | PAK |
| 056E08 | 4359229 | PAK |
| 056E09 | 2983152 | PAK |
| 056E10 | 6115866 | PAK |
| 056E11 | 3961019 | PAK |
| 056E12 | 245490 | PAK |
| 056F01 | 3014304 | PAK |
| 056F02 | 262235 | PAK |
| 056F03 | 6060562 | PAK |
| 056F04 | 112709 | PAK |
| 056F05 | 5494429 | PAK |
| 056F06 | 1146439 | PAK |
| 056F07 | 1124229 | PAK |
| 056F08 | 580688 | PAK |
| 056F10 | 3286894 | PAK |
| 056F11 | 1924430 | PAK |
| 056F12 | 5350474 | PAK |
| 056G01 | 339467 | PAK |
| 056G02 | 5651486 | PAK |
| 056G03 | 1595773 | PAK |
| 056G04 | 5346270 | PAK |
| 056G05 | 4529331 | PAK |
| 056G06 | 5246227 | PAK |
| 056G07 | 4219585 | PAK |
| 056G09 | 5244516 | PAK |
| 056G10 | 1276817 | PAK |
| 056G11 | 2651427 | PAK |
| 056G12 | 5841852 | PAK |
| 056H01 | 5972327 | PAK |
| 056H02 | 5196732 | PAK |
| 056H03 | 4895092 | PAK |
| 056H04 | 5823416 | PAK |
| 056H05 | 4579373 | PAK |
| 056H07 | 4930535 | PAK |
| 056H08 | 4897723 | PAK |
| 056H09 | 3821421 | PAK |
| 056H10 | 936536 | PAK |
| 057A01 | 3222686 | PAK |
| 057A02 | 5564330 | PAK |
| 057A03 | 386888 | PAK |
| 057A04 | 3147690 | PAK |
| 057A05 | 949262 | PAK |
| 057A06 | 109768 | PAK |
| 057A07 | 201510 | PAK |
| 057A08 | 4433640 | PAK |
| 057A09 | 2976163 | PAK |
| 057A10 | 5386652 | PAK |
| 057A11 | 1741309 | PAK |
| 057A12 | 4450558 | PAK |
| 057B01 | 2077254 | PAK |
| 057B02 | 105317 | PAK |
| 057B03 | 941448 | PAK |
| 057B04 | 2282302 | PAK |
| 057B05 | 3259345 | PAK |
| 057B06 | 3700271 | PAK |

TABLE 3-continued

| Mutant Name | Insertion Point | host strain |
|---|---|---|
| 057B07 | 6072365 | PAK |
| 057B08 | 3835680 | PAK |
| 057B09 | 17926 | PAK |
| 057B10 | 5289656 | PAK |
| 057B11 | 587706 | PAK |
| 057B12 | 239995 | PAK |
| 057C01 | 2770008 | PAK |
| 057C02 | 224482 | PAK |
| 057C03 | 405S905 | PAK |
| 057C04 | 4794916 | PAK |
| 057C05 | 5686485 | PAK |
| 057C06 | 4109109 | PAK |
| 057C07 | 1109858 | PAK |
| 057C08 | 5784904 | PAK |
| 057C10 | 2562533 | PAK |
| 057C11 | 5049360 | PAK |
| 057C12 | 2609503 | PAK |
| 057D02 | 4139488 | PAK |
| 057D03 | 1388783 | PAK |
| 057D04 | 4162847 | PAK |
| 057D05 | 751816 | PAK |
| 057D06 | 350315 | PAK |
| 057D07 | 4396197 | PAK |
| 057D08 | 944311 | PAK |
| 057D09 | 5910700 | PAK |
| 057D10 | 317952 | PAK |
| 057D11 | 3648808 | PAK |
| 057E01 | 3677358 | PAK |
| 057E02 | 4353101 | PAK |
| 057E03 | 6100458 | PAK |
| 057E04 | 5897925 | PAK |
| 057E05 | 4181113 | PAK |
| 057E06 | 3452629 | PAK |
| 057E07 | 6058048 | PAK |
| 057E11 | 6223829 | PAK |
| 057F01 | 567570 | PAK |
| 057F02 | 5195690 | PAK |
| 057F03 | 5545226 | PAK |
| 057F05 | 5397565 | PAK |
| 057F06 | 5970328 | PAK |
| 057F07 | 5716312 | PAK |
| 057F08 | 2932270 | PAK |
| 057F10 | 6230093 | PAK |
| 057F11 | 5251711 | PAK |
| 057F12 | 2286626 | PAK |
| 057G01 | 1201538 | PAK |
| 057G02 | 4108207 | PAK |
| 057G03 | 5728337 | PAK |
| 057G04 | 5733688 | PAK |
| 057G05 | 474241 | PAK |
| 057G06 | 4162599 | PAK |
| 057G07 | 13247159 | PAK |
| 057G08 | 5506349 | PAK |
| 057G09 | 3420712 | PAK |
| 057G10 | 883970 | PAK |
| 057G12 | 751816 | PAK |
| 057H01 | 398922 | PAK |
| 057H02 | 1690946 | PAK |
| 057H04 | 2196615 | PAK |
| 057H05 | 475058 | PAK |
| 057H06 | 313054 | PAK |
| 057H08 | 4482171 | PAK |
| 057H09 | 5067404 | PAK |
| 057H10 | 2231259 | PAK |
| 058A01 | 148027 | PAK |
| 058A02 | 3261207 | PAK |
| 058A03 | 4339735 | PAK |
| 058A04 | 1126383 | PAK |
| 058A05 | 3374355 | PAK |
| 058A07 | 3446436 | PAK |
| 058A09 | 27528 | PAK |
| 058A10 | 1459449 | PAK |
| 058A12 | 6053393 | PAK |
| 058B01 | 5936170 | PAK |
| 058B02 | 895867 | PAK |
| 058B03 | 840672 | PAK |
| 058B04 | 249132 | PAK |

TABLE 3-continued

| Mutant Name | Insertion Point | host strain |
|---|---|---|
| 058B05 | 3279749 | PAK |
| 058B06 | 2508583 | PAK |
| 058B07 | 2842273 | PAK |
| 058B08 | 3986339 | PAK |
| 058B09 | 4363628 | PAK |
| 058B10 | 519227 | PAK |
| 058B12 | 3951513 | PAK |
| 058C01 | 4578591 | PAK |
| 058C02 | 1884270 | PAK |
| 058C03 | 6153466 | PAK |
| 058C04 | 54750491 | PAK |
| 058C05 | 4219961 | PAK |
| 058C06 | 4263732 | PAK |
| 058C07 | 4364050 | PAK |
| 058C09 | 5756903 | PAK |
| 058C10 | 36601 | PAK |
| 058C11 | 6072466 | PAK |
| 058C12 | 6201972 | PAK |
| 058D01 | 1761408 | PAK |
| 058D02 | 4525463 | PAK |
| 058D03 | 401591 | PAK |
| 058D04 | 324165 | PAK |
| 058D05 | 1744166 | PAK |
| 058D08 | 1531853 | PAK |
| 058D09 | 490164 | PAK |
| 058D10 | 1295999 | PAK |
| 058D11 | 1711038 | PAK |
| 058D12 | 3651388 | PAK |
| 058E01 | 465049 | PAK |
| 058E02 | 29460 | PAK |
| 058E03 | 6172291 | PAK |
| 058E04 | 6097273 | PAK |
| 058E05 | 1702230 | PAK |
| 058E06 | 434820 | PAK |
| 058E07 | 4202129 | PAK |
| 058E08 | 5252684 | PAK |
| 058E09 | 4188857 | PAK |
| 058E11 | 4859348 | PAK |
| 058E12 | 349009 | PAK |
| 058F01 | 4036463 | PAK |
| 058F02 | 5373493 | PAK |
| 058F03 | 1070132 | PAK |
| 058F04 | 752714 | PAK |
| 058F05 | 1578230 | PAK |
| 058F06 | 691265 | PAK |
| 058F07 | 2911623 | PAK |
| 058F08 | 1676112 | PAK |
| 058F09 | 2713993 | PAK |
| 058F10 | 5527951 | PAK |
| 058F11 | 491487 | PAK |
| 058F12 | 833346 | PAK |
| 058G01 | 3389264 | PAK |
| 058G02 | 5367064 | PAK |
| 058G03 | 2241093 | PAK |
| 058G05 | 4413996 | PAK |
| 058G06 | 2700347 | PAK |
| 058G07 | 4534777 | PAK |
| 058G08 | 6189474 | PAK |
| 058G10 | 444003 | PAK |
| 058G12 | 346517 | PAK |
| 058H01 | 5700263 | PAK |
| 058H02 | 3746060 | PAK |
| 058H03 | 1517731 | PAK |
| 058H04 | 3991649 | PAK |
| 058H05 | 5520972 | PAK |
| 058H06 | 399948 | PAK |
| 058H07 | 892667 | PAK |
| 058H08 | 3931380 | PAK |
| 058H09 | 843713 | PAK |
| 058H10 | 2903923 | PAK |
| 059A01 | 810409 | PAK |
| 059A02 | 2038512 | PAK |
| 059A03 | 1126439 | PAK |
| 059A05 | 3727816 | PAK |
| 059A06 | 1617471 | PAK |
| 059A09 | 472009 | PAK |
| 059A10 | 5794399 | PAK |
| 059A11 | 202127 | PAK |
| 059B01 | 4336136 | PAK |
| 059B02 | 806574 | PAK |
| 059B03 | 978820 | PAK |
| 059B04 | 2567141 | PAK |
| 059B05 | 4920588 | PAK |
| 059B06 | 1382253 | PAK |
| 059B07 | 5152654 | PAK |
| 059B08 | 5958187 | PAK |
| 059B09 | 4163144 | PAK |
| 059B10 | 3602838 | PAK |
| 059B11 | 1877002 | PAK |
| 059B12 | 390316 | PAK |
| 059C01 | 3911859 | PAK |
| 059C02 | 3400847 | PAK |
| 059C03 | 1027358 | PAK |
| 059C04 | 5128863 | PAK |
| 059C06 | 381079 | PAK |
| 059C07 | 5976838 | PAK |
| 059C08 | 5916682 | PAK |
| 059C09 | 4630070 | PAK |
| 059C10 | 4850133 | PAK |
| 059C11 | 1027358 | PAK |
| 059C12 | 5854589 | PAK |
| 059D05 | 4549333 | PAK |
| 059D06 | 5225128 | PAK |
| 059D07 | 1166408 | PAK |
| 059D08 | 88391 | PAK |
| 059D09 | 5224478 | PAK |
| 059D10 | 4471779 | PAK |
| 059D11 | 3453635 | PAK |
| 059D12 | 3626993 | PAK |
| 059E01 | 4750873 | PAK |
| 059E02 | 2310905 | PAK |
| 059E03 | 909000 | PAK |
| 059E04 | 4927958 | PAK |
| 059E05 | 4669421 | PAK |
| 059E06 | 2833291 | PAK |
| 059E07 | 4888373 | PAK |
| 059E08 | 2317772 | PAK |
| 059E09 | 482302 | PAK |
| 059E10 | 1768028 | PAK |
| 059E12 | 5955564 | PAK |
| 059F01 | 434886 | PAK |
| 059F02 | 2488013 | PAK |
| 059F03 | 2372488 | PAK |
| 059F05 | 4812241 | PAK |
| 059F06 | 1638061 | PAK |
| 059F07 | 3934960 | PAK |
| 059F08 | 4021011 | PAK |
| 059F09 | 4892909 | PAK |
| 059F10 | 4909623 | PAK |
| 059F11 | 3149429 | PAK |
| 059F12 | 2833881 | PAK |
| 059G01 | 1538830 | PAK |
| 059G02 | 1148759 | PAK |
| 059G03 | 2338604 | PAK |
| 059G05 | 3737530 | PAK |
| 059G08 | 2991535 | PAK |
| 059G09 | 3324609 | PAK |
| 059G10 | 1789972 | PAK |
| 059G12 | 163978 | PAK |
| 059H02 | 5254773 | PAK |
| 059H03 | 1166408 | PAK |
| 059H04 | 3021862 | PAK |
| 059H05 | 6162718 | PAK |
| 059H06 | 4627364 | PAK |
| 059H07 | 3491421 | PAK |
| 059H08 | 4692312 | PAK |
| 059H09 | 2343404 | PAK |
| 059H10 | 857252 | PAK |
| 059H11 | 395319 | PAK |
| 060A01 | 1934490 | PAK |
| 060A02 | 5481085 | PAK |
| 060A03 | 2764009 | PAK |
| 060A04 | 5004550 | PAK |
| 060A05 | 4012583 | PAK |

TABLE 3-continued

| Mutant Name | Insertion Point | host strain |
|---|---|---|
| 060A06 | 814341 | PAK |
| 060A08 | 5823742 | PAK |
| 060A09 | 1182611 | PAK |
| 060A10 | 1017153 | PAK |
| 060A11 | 4334204 | PAK |
| 060A12 | 1860296 | PAK |
| 060B01 | 5504107 | PAK |
| 060B03 | 473446 | PAK |
| 060B05 | 4207414 | PAK |
| 060B06 | 909988 | PAK |
| 060B07 | 3511315 | PAK |
| 060B08 | 6060554 | PAK |
| 060B09 | 4884088 | PAK |
| 060B10 | 3119810 | PAK |
| 060B11 | 2998890 | PAK |
| 060C01 | 3763199 | PAK |
| 060C03 | 806295 | PAK |
| 060C04 | 6087136 | PAK |
| 060C05 | 881060 | PAK |
| 060C06 | 3806834 | PAK |
| 060C07 | 5120922 | PAK |
| 060C08 | 5764747 | PAK |
| 060C09 | 1016409 | PAK |
| 060C10 | 3756123 | PAK |
| 060C12 | 2128974 | PAK |
| 060D01 | 848689 | PAK |
| 060D02 | 6055693 | PAK |
| 060D03 | 709790 | PAK |
| 060D04 | 6152715 | PAK |
| 060D05 | 3263979 | PAK |
| 060D08 | 525258 | PAK |
| 060D09 | 3708939 | PAK |
| 060D10 | 216491 | PAK |
| 060D11 | 2111512 | PAK |
| 060E01 | 3081659 | PAK |
| 060E03 | 258823 | PAK |
| 060E04 | 5873250 | PAK |
| 060E05 | 4128566 | PAK |
| 060E06 | 4984079 | PAK |
| 060E07 | 5984634 | PAK |
| 060E08 | 6039158 | PAK |
| 060E09 | 6066429 | PAK |
| 060E10 | 4505357 | PAK |
| 060E11 | 5877438 | PAK |
| 060E12 | 3919380 | PAK |
| 060F01 | 1717288 | PAK |
| 060F02 | 1783494 | PAK |
| 060F03 | 4905425 | PAK |
| 060F04 | 3366078 | PAK |
| 060F05 | 5644573 | PAK |
| 060F06 | 61725 | PAK |
| 060F07 | 4876596 | PAK |
| 060F08 | 5123149 | PAK |
| 060F09 | 5546465 | PAK |
| 060F10 | 5644573 | PAK |
| 060F11 | 409143 | PAK |
| 060F12 | 3973684 | PAK |
| 060G01 | 2220236 | PAK |
| 060G03 | 1242407 | PAK |
| 060G04 | 814909 | PAK |
| 060G05 | 1480411 | PAK |
| 060G06 | 4129027 | PAK |
| 060G07 | 1395518 | PAK |
| 060G08 | 822764 | PAK |
| 060G09 | 1718256 | PAK |
| 060G10 | 2093229 | PAK |
| 060G11 | 771355 | PAK |
| 060G12 | 6048608 | PAK |
| 060H01 | 1570340 | PAK |
| 060H02 | 727984 | PAK |
| 060H04 | 1058834 | PAK |
| 060H05 | 5905664 | PAK |
| 060H06 | 2578924 | PAK |
| 060H07 | 4964458 | PAK |
| 060H08 | 4742880 | PAK |
| 060H09 | 1472884 | PAK |
| 060H10 | 404195 | PAK |
| 060H11 | 3953191 | PAK |
| 061A02 | 5758277 | PAK pili- |
| 061A03 | 2348738 | PAK pili- |
| 061A04 | 2872282 | PAK pili- |
| 061A05 | 3135775 | PAK pili- |
| 061A06 | 1413257 | PAK pili- |
| 061A07 | 354982 | PAK pili- |
| 061A08 | 3247735 | PAK pili- |
| 061A09 | 1027358 | PAK pili- |
| 061A11 | 5955752 | PAK pili- |
| 061B01 | 865098 | PAK pili- |
| 061B03 | 3027439 | PAK pili- |
| 061B04 | 3228839 | PAK pili- |
| 061B05 | 26655 | PAK pili- |
| 061B06 | 670178 | PAK pili- |
| 061B07 | 750339 | PAK pili- |
| 061B08 | 6237574 | PAK pili- |
| 061B09 | 434887 | PAK pili- |
| 061B10 | 2594806 | PAK pili- |
| 061B11 | 2602819 | PAK pili- |
| 061C02 | 3669701 | PAK pili- |
| 061C03 | 5501059 | PAK pili- |
| 061C04 | 6240453 | PAK pili- |
| 061C05 | 339409 | PAK pili- |
| 061C06 | 970713 | PAK pili- |
| 061C07 | 5991897 | PAK pili- |
| 061C08 | 3845716 | PAK pili- |
| 061C09 | 1987268 | PAK pili- |
| 061C10 | 2216666 | PAK pili- |
| 061C11 | 1674612 | PAK pili- |
| 061C12 | 4185549 | PAK pili- |
| 061D02 | 3970481 | PAK pili- |
| 061D03 | 1561309 | PAK pili- |
| 061D04 | 4524167 | PAK pili- |
| 061D06 | 4401199 | PAK pili- |
| 061D07 | 4660568 | PAK pili- |
| 061D08 | 5835996 | PAK pili- |
| 061D09 | 3441962 | PAK pili- |
| 061D10 | 4322962 | PAK pili- |
| 061D11 | 5033212 | PAK pili- |
| 061D12 | 2708820 | PAK pili- |
| 061E01 | 6162007 | PAK pili- |
| 061E02 | 2398557 | PAK pili- |
| 061E04 | 472365 | PAK pili- |
| 061E05 | 1782511 | PAK pili- |
| 061E06 | 5930919 | PAK pili- |
| 061E07 | 1146276 | PAK pili- |
| 061E08 | 4521488 | PAK pili- |
| 061E09 | 4717236 | PAK pili- |
| 061E11 | 4380032 | PAK pili- |
| 061E12 | 4044343 | PAK pili- |
| 061F01 | 3301676 | PAK pili- |
| 061F02 | 5828638 | PAK pili- |
| 061F03 | 5634333 | PAK pili- |
| 061F04 | 5318976 | PAK pili- |
| 061F05 | 3420298 | PAK pili- |
| 061F06 | 6028099 | PAK pili- |
| 061F09 | 2874916 | PAK pili- |
| 061F10 | 1702230 | PAK pili- |
| 061F11 | 164740 | PAK pili- |
| 061F12 | 4169592 | PAK pili- |
| 061G05 | 2126206 | PAK pili- |
| 061G07 | 815297 | PAK pili- |
| 061G08 | 6260187 | PAK pili- |
| 061G09 | 1347823 | PAK pili- |
| 061G10 | 3775399 | PAK pili- |
| 061G11 | 4218405 | PAK pili- |
| 061G12 | 1166408 | PAK pili- |
| 061H01 | 5609073 | PAK pili- |
| 061H02 | 4186785 | PAK pili- |
| 061H03 | 3069909 | PAK pili- |
| 061H04 | 6121348 | PAK pili- |
| 061H05 | 2909905 | PAK pili- |
| 061H06 | 790965 | PAK pili- |
| 061H07 | 2061539 | PAK pili- |
| 061H08 | 2874916 | PAK pili- |
| 061H09 | 245693 | PAK pili- |

TABLE 3-continued

| Mutant Name | Insertion Point | host strain |
|---|---|---|
| 061H10 | 5207481 | PAK pili- |
| 061H11 | 395318 | PAK pili- |
| 062A01 | 522496 | PAK pili- |
| 062A02 | 2186046 | PAK pili- |
| 062A03 | 881650 | PAK pili- |
| 062A04 | 108711 | PAK pili- |
| 062A05 | 4573163 | PAK pili- |
| 062A06 | 4592778 | PAK pili- |
| 062A07 | 2767284 | PAK pili- |
| 062A08 | 245488 | PAK pili- |
| 062A09 | 245488 | PAK pili- |
| 062A11 | 4883451 | PAK pili- |
| 062A12 | 245488 | PAK pili- |
| 062B01 | 5814642 | PAK pili- |
| 062B02 | 972216 | PAK pili- |
| 062B03 | 2482611 | PAK pili- |
| 062B04 | 3763613 | PAK pili- |
| 062B07 | 6163753 | PAK pili- |
| 062B08 | 4880267 | PAK pili- |
| 062B09 | 3363603 | PAK pili- |
| 062B10 | 202392 | PAK pili- |
| 062B11 | 245488 | PAK pili- |
| 062C01 | 2796578 | PAK pili- |
| 062C02 | 1421710 | PAK pili- |
| 062C03 | 6193624 | PAK pili- |
| 062C04 | 4335461 | PAK pili- |
| 062C05 | 5582809 | PAK pili- |
| 062C06 | 1887384 | PAK pili- |
| 062C07 | 2674834 | PAK pili- |
| 062C08 | 3594859 | PAK pili- |
| 062C10 | 6126368 | PAK pili- |
| 062C11 | 6126368 | PAK pili- |
| 062C12 | 6126368 | PAK pili- |
| 062D01 | 3063043 | PAK pili- |
| 062D02 | 150387 | PAK pili- |
| 062D03 | 4879780 | PAK pili- |
| 062D06 | 5522349 | PAK pili- |
| 062D07 | 5567212 | PAK pili- |
| 062D09 | 6126368 | PAK pili- |
| 062D10 | 6126368 | PAK pili- |
| 062D11 | 6126368 | PAK pili- |
| 062D12 | 6126368 | PAK pili- |
| 062E05 | 245488 | PAK pili- |
| 062E06 | 4351023 | PAK pili- |
| 062E07 | 2219268 | PAK pili- |
| 062E08 | 6126368 | PAK pili- |
| 062E09 | 6126368 | PAK pili- |
| 062E10 | 61263631 | PAK pili- |
| 062E11 | 6126368 | PAK pili- |
| 062E12 | 6126368 | PAK pili- |
| 062F01 | 434886 | PAK pili- |
| 062F02 | 577228 | PAK pili- |
| 062F03 | 1460121 | PAK pili- |
| 062F06 | 6126368 | PAK pili- |
| 062F07 | 6126368 | PAK pili- |
| 062F08 | 6126363 | PAK pili- |
| 062F09 | 6126368 | PAK pili- |
| 062F10 | 6126368 | PAK pili- |
| 062F11 | 6126368 | PAK pili- |
| 062F12 | 6126370 | PAK pili- |
| 062G01 | 1283697 | PAK pili- |
| 062G04 | 6126368 | PAK pili- |
| 062G05 | 6126368 | PAK pili- |
| 062G06 | 6126368 | PAK pili- |
| 062G07 | 6126368 | PAK pili- |
| 062G08 | 6126368 | PAK pili- |
| 062G09 | 6126368 | PAK pili- |
| 062G10 | 6126368 | PAK pili- |
| 062G11 | 6126368 | PAK pili- |
| 062G12 | 6126368 | PAK pili- |
| 062H01 | 1838755 | PAK pili- |
| 062H02 | 3931380 | PAK pili- |
| 062H03 | 205757 | PAK pili- |
| 062H05 | 6126368 | PAK pili- |
| 062H06 | 6126368 | PAK pili- |
| 062H07 | 6126368 | PAK pili- |
| 062H08 | 6126368 | PAK pili- |
| 062H09 | 6126368 | PAK pili- |
| 062H10 | 6126368 | PAK pili- |
| 062H11 | 6126368 | PAK pili- |
| 063A01 | 1864595 | PAK |
| 063A02 | 4577583 | PAK |
| 063A03 | 4623271 | PAK |
| 063A05 | 6187365 | PAK |
| 063A07 | 4396482 | PAK |
| 063A08 | 980960 | PAK |
| 063A09 | 5389145 | PAK |
| 063A10 | 37148051 | PAK |
| 063A11 | 4859681 | PAK |
| 063A12 | 703497 | PAK |
| 063B01 | 58161 | PAK |
| 063B02 | 2480836 | PAK |
| 063B03 | 964761 | PAK |
| 063B04 | 4323451 | PAK |
| 063B05 | 3867238 | PAK |
| 063B07 | 5201475 | PAK |
| 063B08 | 5389781 | PAK |
| 063B11 | 404986 | PAK |
| 063C01 | 3837626 | PAK |
| 063C02 | 467401 | PAK |
| 063C05 | 617809 | PAK |
| 063C08 | 5817926 | PAK |
| 063C09 | 5976549 | PAK |
| 063C10 | 4691492 | PAK |
| 063C12 | 6135396 | PAK |
| 063D02 | 890907 | PAK |
| 063D03 | 820642 | PAK |
| 063D05 | 6188347 | PAK |
| 063D06 | 3418092 | PAK |
| 063D07 | 1099496 | PAK |
| 063D08 | 4185902 | PAK |
| 063D12 | 4828824 | PAK |
| 063E02 | 380103 | PAK |
| 063E05 | 5457853 | PAK |
| 063E06 | 1292848 | PAK |
| 063E07 | 5861274 | PAK |
| 063E09 | 5485515 | PAK |
| 063E10 | 662186 | PAK |
| 063E11 | 58104 | PAK |
| 063E12 | 3831435 | PAK |
| 063F01 | 3919920 | PAK |
| 063F02 | 4301739 | PAK |
| 063F04 | 4280034 | PAK |
| 063F05 | 1158788 | PAK |
| 063F07 | 6064109 | PAK |
| 063F08 | 3414689 | PAK |
| 063F10 | 5035262 | PAK |
| 063F11 | 3813526 | PAK |
| 063F12 | 6140999 | PAK |
| 063G02 | 1857879 | PAK |
| 063G03 | 080687 | PAK |
| 063G04 | 3640119 | PAK |
| 063G05 | 1265153 | PAK |
| 063G07 | 4508353 | PAK |
| 063G09 | 1317210 | PAK |
| 063G10 | 3050895 | PAK |
| 063G11 | 4019209 | PAK |
| 063H01 | 3634874 | PAK |
| 063H02 | 152357 | PAK |
| 063H03 | 3886848 | PAK |
| 063H04 | 5124231 | PAK |
| 063H06 | 6085999 | PAK |
| 063H07 | 2789478 | PAK |
| 063H10 | 5580029 | PAK |
| 064A01 | 910928 | PAK |
| 064A02 | 855436 | PAK |
| 064A03 | 5924276 | PAK |
| 064A04 | 3633746 | PAK |
| 064A05 | 4106446 | PAK |
| 064A06 | 5179182 | PAK |
| 064A07 | 1276940 | PAK |
| 064A09 | 619609 | PAK |
| 064A10 | 1149850 | PAK |
| 064A11 | 2559980 | PAK |

TABLE 3-continued

| Mutant Name | Insertion Point | host strain |
|---|---|---|
| 064A12 | 3390116 | PAK |
| 064B01 | 6127019 | PAK |
| 064B02 | 4236620 | PAK |
| 064B03 | 5340297 | PAK |
| 064B04 | 4363981 | PAK |
| 064B06 | 5605621 | PAK |
| 064B07 | 4571866 | PAK |
| 064B09 | 3257360 | PAK |
| 064B11 | 306854 | PAK |
| 064B12 | 2375623 | PAK |
| 064C01 | 4102306 | PAK |
| 064C02 | 3048716 | PAK |
| 064C04 | 4538704 | PAK |
| 064C05 | 1780529 | PAK |
| 064C06 | 178052 | PAK |
| 064C07 | 576267 | PAK |
| 064C09 | 4687072 | PAK |
| 064C10 | 5126155 | PAK |
| 064C11 | 3679268 | PAK |
| 064D01 | 5081539 | PAK |
| 064D02 | 6104666 | PAK |
| 064D03 | 2266420 | PAK |
| 064D04 | 1770947 | PAK |
| 064D05 | 5407726 | PAK |
| 064D06 | 3215213 | PAK |
| 064D07 | 1077640 | PAK |
| 064D09 | 2904482 | PAK |
| 064D10 | 4303847 | PAK |
| 064D12 | 1713618 | PAK |
| 064E01 | 179957 | PAK |
| 064E02 | 2905531 | PAK |
| 064E03 | 5293460 | PAK |
| 064E04 | 3453385 | PAK |
| 064E05 | 1045916 | PAK |
| 064E07 | 3153585 | PAK |
| 064E08 | 6234787 | PAK |
| 064E10 | 1025545 | PAK |
| 064F02 | 1832530 | PAK |
| 064F03 | 4617041 | PAK |
| 064F04 | 2503673 | PAK |
| 064F06 | 560354 | PAK |
| 064F07 | 2020127 | PAK |
| 064F08 | 2583822 | PAK |
| 064F09 | 2532110 | PAK |
| 064F10 | 3213745 | PAK |
| 064F12 | 953205 | PAK |
| 064G01 | 3274554 | PAK |
| 064G02 | 154806 | PAK |
| 064G05 | 751816 | PAK |
| 064G06 | 2839349 | PAK |
| 064G07 | 3315574 | PAK |
| 064G08 | 5129696 | PAK |
| 064G09 | 5815721 | PAK |
| 064G10 | 1292321 | PAK |
| 064G11 | 273012 | PAK |
| 064G12 | 5258655 | PAK |
| 064H02 | 864263 | PAK |
| 064H04 | 325492 | PAK |
| 064H05 | 4881106 | PAK |
| 064H06 | 5300816 | PAK |
| 064H07 | 2322929 | PAK |
| 064H08 | 6056031 | PAK |
| 064H09 | 338714 | PAK |
| 064H10 | 4239063 | PAK |
| 065A01 | 213053 | PAK pili- |
| 065A02 | 102027 | PAK pili- |
| 065A03 | 3561848 | PAK pili- |
| 065A04 | 2827456 | PAK pili- |
| 065A05 | 3691872 | PAK pili- |
| 065A06 | 3811269 | PAK pili- |
| 065A09 | 634047 | PAK pili- |
| 065A10 | 2365466 | PAK pili- |
| 065A11 | 2856356 | PAK pili- |
| 065A12 | 1465531 | PAK pili- |
| 065B01 | 5427483 | PAK pili- |
| 065B02 | 6109641 | PAK pili- |
| 065B03 | 895717 | PAK pili- |
| 065B04 | 4661329 | PAK pili- |
| 065B05 | 3373867 | PAK pili- |
| 065B06 | 4683526 | PAK pili- |
| 065B07 | 3755105 | PAK pili- |
| 065B09 | 931497 | PAK pili- |
| 065B10 | 3147506 | PAK pili- |
| 065B12 | 4156896 | PAK pili- |
| 065C01 | 2880194 | PAK pili- |
| 065C02 | 3153395 | PAK pili- |
| 065C03 | 740899 | PAK pili- |
| 065C04 | 2374394 | PAK pili- |
| 065C05 | 5476873 | PAK pili- |
| 065C07 | 583110 | PAK pili- |
| 065C08 | 2511899 | PAK pili- |
| 065C09 | 1578675 | PAK pili- |
| 065C10 | 4248094 | PAK pili- |
| 065C11 | 867526 | PAK pili- |
| 065C12 | 1133179 | PAK pili- |
| 065D03 | 5431177 | PAK pili- |
| 065D05 | 4194736 | PAK pili- |
| 065D06 | 40556 | PAK pili- |
| 065D07 | 2531813 | PAK pili- |
| 065D08 | 1493098 | PAK pili- |
| 065D10 | 330197 | PAK pili- |
| 065D11 | 220703 | PAK pili- |
| 065D12 | 6036810 | PAK pili- |
| 065E01 | 2913469 | PAK pili- |
| 065E02 | 4821487 | PAK pili- |
| 065E03 | 5815961 | PAK pili- |
| 065E04 | 1472344 | PAK pili- |
| 065E06 | 197187 | PAK pili- |
| 065E07 | 5493474 | PAK pili- |
| 065E08 | 5127092 | PAK pili- |
| 065E10 | 1907290 | PAK pili- |
| 065E11 | 4901855 | PAK pili- |
| 065F01 | 3307955 | PAK pili- |
| 065F02 | 4065383 | PAK pili- |
| 065F03 | 146511 | PAK pili- |
| 065F04 | 5204674 | PAK pili- |
| 065F06 | 5677927 | PAK pili- |
| 065F07 | 225606 | PAK pili- |
| 065F09 | 4131954 | PAK pili- |
| 065F12 | 3047361 | PAK pili- |
| 065G02 | 3201028 | PAK pili- |
| 065G03 | 3798133 | PAK pili- |
| 065G04 | 3442846 | PAK pili- |
| 065G05 | 4543237 | PAK pili- |
| 065G06 | 320024 | PAK pili- |
| 065G08 | 5093588 | PAK pili- |
| 065G09 | 3748272 | PAK pili- |
| 065G10 | 5888031 | PAK pili- |
| 065H01 | 395060 | PAK pili- |
| 065H02 | 1234143 | PAK pili- |
| 065H03 | 4282511 | PAK pili- |
| 065H04 | 1449253 | PAK pili- |
| 065H05 | 631397 | PAK pili- |
| 065H07 | 959444 | PAK pili- |
| 065H08 | 44580 | PAK pili- |
| 065H09 | 4188992 | PAK pili- |
| 065H10 | 5252649 | PAK pili- |
| 066A01 | 639405 | PAK |
| 066A02 | 950972 | PAK |
| 066A03 | 4096910 | PAK |
| 066A04 | 792936 | PAK |
| 066A05 | 2853998 | PAK |
| 066A06 | 954708 | PAK |
| 066A07 | 5528278 | PAK |
| 066A08 | 4717155 | PAK |
| 066A09 | 870436 | PAK |
| 066A10 | 4514642 | PAK |
| 066B01 | 3373489 | PAK |
| 066B02 | 6262256 | PAK |
| 066B03 | 3855210 | PAK |
| 066B04 | 861347 | PAK |
| 066B05 | 341365 | PAK |
| 066B09 | 1971103 | PAK |
| 066B10 | 3067544 | PAK |

TABLE 3-continued

| Mutant Name | Insertion Point | host strain |
|---|---|---|
| 066B11 | 1861028 | PAK |
| 066B12 | 811628 | PAK |
| 066C01 | 5134066 | PAK |
| 066C02 | 1400578 | PAK |
| 066C04 | 3408085 | PAK |
| 066C05 | 1152994 | PAK |
| 066C06 | 2712094 | PAK |
| 066C07 | 1098422 | PAK |
| 066C08 | 5538458 | PAK |
| 066C09 | 444477 | PAK |
| 066C11 | 3148189 | PAK |
| 066D01 | 6010854 | PAK |
| 066D03 | 5758451 | PAK |
| 066D04 | 235886 | PAK |
| 066D05 | 3156353 | PAK |
| 066D06 | 1878760 | PAK |
| 066D07 | 2930757 | PAK |
| 066D08 | 2263071 | PAK |
| 066D09 | 3586340 | PAK |
| 066D10 | 907398 | PAK |
| 066E01 | 5203283 | PAK |
| 066E02 | 4739343 | PAK |
| 066E03 | 962214 | PAK |
| 066E04 | 935502 | PAK |
| 066E05 | 6132671 | PAK |
| 066E07 | 5169822 | PAK |
| 086E08 | 3569363 | PAK |
| 066E09 | 5511249 | PAK |
| 066E10 | 25126 | PAK |
| 066E11 | 542926 | PAK |
| 066E12 | 4162302 | PAK |
| 066F02 | 4551124 | PAK |
| 066F03 | 1658622 | PAK |
| 066F04 | 759967 | PAK |
| 066F05 | 3965632 | PAK |
| 066F08 | 4910253 | PAK |
| 066F09 | 4210502 | PAK |
| 066F10 | 3672579 | PAK |
| 066F11 | 808137 | PAK |
| 066F12 | 475140 | PAK |
| 066G01 | 2269385 | PAK |
| 066G03 | 1480746 | PAK |
| 066G04 | 962539 | PAK |
| 066G07 | 734085 | PAK |
| 066G08 | 3679268 | PAK |
| 066G09 | 582812 | PAK |
| 066G10 | 396335 | PAK |
| 066G11 | 3241494 | PAK |
| 066H01 | 1807080 | PAK |
| 066H02 | 3397995 | PAK |
| 066H03 | 1649594 | PAK |
| 066H04 | 1632001 | PAK |
| 066H05 | 1375100 | PAK |
| 066H06 | 3908428 | PAK |
| 066H09 | 372279 | PAK |
| 066H11 | 395319 | PAK |
| 068A02 | 2094770 | PAK pili- |
| 068A04 | 1987268 | PAK pili- |
| 068A05 | 5740235 | PAK pili- |
| 068A06 | 3932206 | PAK pili- |
| 068A07 | 1660607 | PAK pili- |
| 068A08 | 1987270 | PAK pili- |
| 068A09 | 3926324 | PAK pili- |
| 068A11 | 3590093 | PAK pili- |
| 068A12 | 6120297 | PAK pili- |
| 068B01 | 1987268 | PAK pili- |
| 068B02 | 5417934 | PAK pili- |
| 068B04 | 556328 | PAK pili- |
| 068B05 | 5381209 | PAK pili- |
| 068B06 | 644690 | PAK pili- |
| 068B07 | 2901069 | PAK pili- |
| 068B08 | 3180329 | PAK pili- |
| 068B09 | 4547441 | PAK pili- |
| 068B11 | 3560647 | PAK pili- |
| 068B12 | 1373422 | PAK pili- |
| 068C02 | 4114885 | PAK pili- |
| 068C03 | 4508483 | PAK pili- |
| 068C04 | 339410 | PAK pili- |
| 068C05 | 5998779 | PAK pili- |
| 068C06 | 1438639 | PAK pili- |
| 068C07 | 5547182 | PAK pili- |
| 068C08 | 181598 | PAK pili- |
| 068C09 | 4347499 | PAK pili- |
| 068C10 | 4643796 | PAK pili- |
| 068C11 | 3382613 | PAK pili- |
| 068C12 | 6126369 | PAK pili- |
| 068D01 | 6112363 | PAK pili- |
| 068D02 | 103219 | PAK pili- |
| 068D03 | 947985 | PAK pili- |
| 068D05 | 3835199 | PAK pili- |
| 068D06 | 5370063 | PAK pili- |
| 068D07 | 3997066 | PAK pili- |
| 068D08 | 1347931 | PAK pili- |
| 068D09 | 1609368 | PAK pili- |
| 066D10 | 1934449 | PAK pili- |
| 068D11 | 5861335 | PAK pili- |
| 068D12 | 4010436 | PAK pili- |
| 068E03 | 147253 | PAK pili- |
| 068E04 | 5320966 | PAK pili- |
| 068E05 | 1753944 | PAK pili- |
| 068E06 | 1995183 | PAK pili- |
| 068E07 | 4306674 | PAK pili- |
| 068E08 | 3511207 | PAK pili- |
| 068E10 | 1137751 | PAK pili- |
| 068E11 | 4314936 | PAK pili- |
| 066F01 | 3355326 | PAK pili- |
| 068F02 | 5770189 | PAK pili- |
| 068F03 | 1345134 | PAK pili- |
| 068F05 | 1090425 | PAK pili- |
| 068F06 | 2216541 | PAK pili- |
| 068F07 | 494263 | PAK pili- |
| 068F08 | 4937550 | PAK pili- |
| 068F09 | 2079135 | PAK pili- |
| 068F10 | 3237043 | PAK pili- |
| 068F11 | 1366071 | PAK pili- |
| 068F12 | 257671 | PAK pili- |
| 068G01 | 503796 | PAK pili- |
| 068G02 | 4024172 | PAK pili- |
| 068G03 | 720922 | PAK pili- |
| 068G04 | 3520511 | PAK pili- |
| 068G06 | 1915614 | PAK pili- |
| 068G07 | 3056501 | PAK pili- |
| 068G09 | 1422135 | PAK pili- |
| 068G10 | 679204 | PAK pili- |
| 068G12 | 1235181 | PAK pili- |
| 068H01 | 1387944 | PAK pili- |
| 068H04 | 129130 | PAK pili- |
| 068H05 | 4432765 | PAK pili- |
| 068H06 | 5980173 | PAK pili- |
| 068H07 | 4459209 | PAK pili- |
| 068H08 | 281129 | PAK pili- |
| 068H09 | 3280854 | PAK pili- |
| 068H10 | 4419706 | PAK pili- |
| 068H11 | 395318 | PAK pili- |
| 069A02 | 1733608 | PAK pili- |
| 069A04 | 968280 | PAK pili- |
| 069A05 | 2017230 | PAK pili- |
| 069A06 | 4393279 | PAK pili- |
| 069A07 | 1992916 | PAK pili- |
| 069A08 | 3398642 | PAK pili- |
| 069A09 | 5742954 | PAK pili- |
| 069A10 | 907682 | PAK pili- |
| 069B02 | 6224406 | PAK pili- |
| 069B03 | 4325192 | PAK pili- |
| 069B04 | 5677171 | PAK pili- |
| 069B05 | 375214 | PAK pili- |
| 069B06 | 4099483 | PAK pili- |
| 069B07 | 2344645 | PAK pili- |
| 069B08 | 4300487 | PAK pili- |
| 069B10 | 2505909 | PAK pili- |
| 069B11 | 795009 | PAK pili- |
| 069B12 | 256603 | PAK pili- |
| 069C01 | 142679 | PAK pili- |
| 069C02 | 60183 | PAK pili- |

TABLE 3-continued

| Mutant Name | Insertion Point | host strain |
|---|---|---|
| 069C03 | 1275267 | PAK pili- |
| 069C05 | 58744 | PAK pili- |
| 069C06 | 657822 | PAK pili- |
| 069C07 | 3211190 | PAK pili- |
| 069C08 | 6224405 | PAK pili- |
| 069C09 | 3852574 | PAK pili- |
| 069C10 | 4254482 | PAK pili- |
| 069C11 | 3306237 | PAK pili- |
| 069D01 | 5097680 | PAK pili- |
| 069D02 | 4569200 | PAK pili- |
| 069D03 | 4233539 | PAK pili- |
| 069D04 | 3726006 | PAK pili- |
| 069D05 | 6230087 | PAK pili- |
| 069D06 | 4345752 | PAK pili- |
| 069D07 | 3584153 | PAK pili- |
| 069D08 | 4621816 | PAK pili- |
| 069D09 | 5915800 | PAK pili- |
| 069D10 | 4671384 | PAK pili- |
| 069D11 | 2093840 | PAK pili- |
| 069D12 | 6036374 | PAK pili- |
| 069E01 | 5097680 | PAK pili- |
| 069E02 | 6101688 | PAK pili- |
| 069E03 | 6069934 | PAK pili- |
| 069E04 | 2340646 | PAK pili- |
| 069E05 | 2814530 | PAK pili- |
| 069E06 | 330539 | PAK pili- |
| 069E07 | 3007976 | PAK pili- |
| 069E08 | 2004148 | PAK pili- |
| 069E09 | 5915800 | PAK pili- |
| 069E10 | 42435 | PAK pili- |
| 069E11 | 3231213 | PAK pili- |
| 069E12 | 1518864 | PAK pili- |
| 069F01 | 3934097 | PAK pili- |
| 069F03 | 3379728 | PAK pili- |
| 069F04 | 5789443 | PAK pili- |
| 069F05 | 2259379 | PAK pili- |
| 069F06 | 115748 | PAK pili- |
| 069F07 | 1201720 | PAK pili- |
| 069F08 | 5796176 | PAK pili- |
| 069F09 | 625784 | PAK pili- |
| 069F10 | 4436207 | PAK pili- |
| 069F11 | 556107 | PAK pili- |
| 069G02 | 5097680 | PAK pili- |
| 069G03 | 2791022 | PAK pili- |
| 069G04 | 2715493 | PAK pili- |
| 069G05 | 1287218 | PAK pili- |
| 069G06 | 4212743 | PAK pili- |
| 069G07 | 442295 | PAK pili- |
| 069G08 | 3816790 | PAK pili- |
| 069G09 | 4573179 | PAK pili- |
| 069G10 | 5582901 | PAK pili- |
| 069G11 | 2718515 | PAK pili- |
| 069G12 | 3852573 | PAK pili- |
| 069H01 | 5784895 | PAK pili- |
| 069H02 | 2132702 | PAK pili- |
| 069H04 | 3852574 | PAK pili- |
| 069H05 | 2312020 | PAK pili- |
| 069H06 | 2763870 | PAK pili- |
| 069H07 | 649830 | PAK pili- |
| 069H08 | 659793 | PAK pili- |
| 069H09 | 1516254 | PAK pili- |
| 069H10 | 2000634 | PAK pili- |
| 069H11 | 4671383 | PAK pili- |
| 070A01 | 2999079 | PAK pili- |
| 070A02 | 2284966 | PAK pili- |
| 070A04 | 5803056 | PAK pili- |
| 070A05 | 2355279 | PAK pili- |
| 070A06 | 5641595 | PAK pili- |
| 070A07 | 933108 | PAK pili- |
| 070A08 | 2749792 | PAK pili- |
| 070A09 | 5790133 | PAK pili- |
| 070A10 | 1710416 | PAK pili- |
| 070A11 | 185607 | PAK pili- |
| 070A12 | 975187 | PAK pili- |
| 070B01 | 2134856 | PAK pili- |
| 070B03 | 5913497 | PAK pili- |
| 070B04 | 3523037 | PAK pili- |
| 070B05 | 3393305 | PAK pili- |
| 070B06 | 2422663 | PAK pili- |
| 070B07 | 1600371 | PAK pili- |
| 070B08 | 1600380 | PAK pili- |
| 070B09 | 5759009 | PAK pili- |
| 070B10 | 2353738 | PAK pili- |
| 070B11 | 1029364 | PAK pili- |
| 070B12 | 3926918 | PAK pili- |
| 070C01 | 399202 | PAK pili- |
| 070C02 | 1060792 | PAK pili- |
| 070C04 | 5891379 | PAK pili- |
| 070C05 | 605654 | PAK pili- |
| 070C06 | 1376867 | PAK pili- |
| 070C07 | 662078 | PAK pili- |
| 070C08 | 6185545 | PAK pili- |
| 070C09 | 4247552 | PAK pili- |
| 070C10 | 4208023 | PAK pili- |
| 070C11 | 5384027 | PAK pili- |
| 070C12 | 185533 | PAK pili- |
| 070D01 | 5187026 | PAK pili- |
| 070D02 | 5725997 | PAK pili- |
| 070D03 | 2857224 | PAK pili- |
| 070D04 | 5189745 | PAK pili- |
| 070D05 | 1397711 | PAK pili- |
| 070D06 | 2493646 | PAK pili- |
| 070D07 | 1248501 | PAK pili- |
| 070D09 | 6224405 | PAK pili- |
| 070D10 | 5673603 | PAK pili- |
| 070D11 | 5104515 | PAK pili- |
| 070D12 | 2614864 | PAK pili- |
| 070E01 | 5258962 | PAK pili- |
| 070E02 | 2991586 | PAK pili- |
| 070E03 | 792189 | PAK pili- |
| 070E04 | 357691 | PAK pili- |
| 070E05 | 1650792 | PAK pili- |
| 070E06 | 6191015 | PAK pili- |
| 070E07 | 3368893 | PAK pili- |
| 070E08 | 4300392 | PAK pili- |
| 070E09 | 5048118 | PAK pili- |
| 070E10 | 395092 | PAK pili- |
| 070E11 | 2063344 | PAK pili- |
| 070F01 | 1331463 | PAK pili- |
| 070F02 | 597078 | PAK pili- |
| 070F03 | 5084171 | PAK pili- |
| 070F04 | 3328183 | PAK pili- |
| 070F05 | 5386304 | PAK pili- |
| 070F06 | 4481554 | PAK pili- |
| 070F08 | 5419204 | PAK pili- |
| 070F09 | 5809254 | PAK pili- |
| 070F10 | 6224406 | PAK pili- |
| 070F11 | 895395 | PAK pili- |
| 070F12 | 3831678 | PAK pili- |
| 070G04 | 3171271 | PAK pili- |
| 070G05 | 1016012 | PAK pili- |
| 070G08 | 5189682 | PAK pili- |
| 070G09 | 2574828 | PAK pili- |
| 070G10 | 3444923 | PAK pili- |
| 070G11 | 5247990 | PAK pili- |
| 070G12 | 6065579 | PAK pili- |
| 070H01 | 3833690 | PAK pili- |
| 070H02 | 715025 | PAK pili- |
| 070H03 | 3479313 | PAK pili- |
| 070H04 | 5743850 | PAK pili- |
| 070H05 | 4931184 | PAK pili- |
| 070H06 | 3272903 | PAK pili- |
| 070H07 | 6017548 | PAK pili- |
| 070H08 | 2697485 | PAK pili- |
| 070H09 | 5766050 | PAK pili- |
| 070H10 | 534983 | PAK pili- |
| 070H11 | 39531 | PAK pili- |
| 071A01 | 131016 | PAK pili- |
| 071A02 | 6019610 | PAK pili- |
| 071A03 | 5369729 | PAK pili- |
| 071A04 | 2291134 | PAK pili- |
| 071A05 | 1217393 | PAK pili- |
| 071A07 | 3071609 | PAK pili- |
| 071A08 | 1243551 | PAK pili- |

TABLE 3-continued

| Mutant Name | Insertion Point | host strain |
|---|---|---|
| 071A09 | 599455 | PAK pili- |
| 071A10 | 465518 | PAK pili- |
| 071A11 | 3875351 | PAK pili- |
| 071B02 | 5466739 | PAK pili- |
| 071B03 | 6151696 | PAK pili- |
| 071B04 | 1058650 | PAK pili- |
| 071B09 | 4809458 | PAK pili- |
| 071B10 | 3805947 | PAK pili- |
| 071B11 | 1761897 | PAK pili- |
| 071B12 | 4720148 | PAK pili- |
| 071C001 | 5355415 | PAK pili- |
| 071C002 | 848621 | PAK pili- |
| 071C03 | 4460376 | PAK pili- |
| 071C04 | 536679 | PAK pili- |
| 071C05 | 731610 | PAK pili- |
| 071C07 | 4518581 | PAK pili- |
| 071C08 | 5849598 | PAK pili- |
| 071C09 | 841894 | PAK pili- |
| 071C10 | 1398779 | PAK pili- |
| 071C11 | 1546649 | PAK pili- |
| 071C12 | 509330 | PAK pili- |
| 071D01 | 2999710 | PAK pili- |
| 071D02 | 577274 | PAK pili- |
| 071D05 | 692461 | PAK pili- |
| 071D06 | 5292742 | PAK pili- |
| 071D08 | 189433 | PAK pili- |
| 071D09 | 5903734 | PAK pili- |
| 071D10 | 2296916 | PAK pili- |
| 071D11 | 3586198 | PAK pili- |
| 071E01 | 5548314 | PAK pili- |
| 071E04 | 400557 | PAK pili- |
| 071E05 | 1160649 | PAK pili- |
| 071E06 | 5292742 | PAK pili- |
| 071E07 | 2584910 | PAK pili- |
| 071E08 | 5598484 | PAK pili- |
| 071E10 | 1015314 | PAK pili- |
| 071E11 | 6224406 | PAK pili- |
| 071E12 | 4276116 | PAK pili- |
| 071F01 | 3852574 | PAK pili- |
| 071F02 | 5693864 | PAK pili- |
| 071F03 | 4617980 | PAK pili- |
| 071F04 | 6229444 | PAK pili- |
| 071F05 | 872801 | PAK pili- |
| 071F06 | 3513860 | PAK pili- |
| 071F10 | 804727 | PAK pili- |
| 071F12 | 668476 | PAK pili- |
| 071G01 | 4863962 | PAK pili- |
| 071G03 | 5652001 | PAK pili- |
| 071G04 | 4037390 | PAK pili- |
| 071G06 | 1297596 | PAK pili- |
| 071G07 | 2721650 | PAK pili- |
| 071G08 | 416562 | PAK pili- |
| 071G09 | 4840083 | PAK pili- |
| 071G11 | 3188162 | PAK pili- |
| 071G12 | 2165171 | PAK pili- |
| 071H01 | 222650 | PAK pili- |
| 071HQ2 | 1019604 | PAK pili- |
| 071H04 | 579369 | PAK pili- |
| 071H05 | 1288860 | PAK pili- |
| 071H06 | 1699139 | PAK pili- |
| 071H07 | 6224406 | PAK pili- |
| 071H08 | 2931989 | PAK pili- |
| 071H11 | 395318 | PAK pili- |
| 072A01 | 1601639 | PAK |
| 072A02 | 1971606 | PAK |
| 072A03 | 3793264 | PAK |
| 072A04 | 6109305 | PAK |
| 072A05 | 230083 | PAK |
| 072A07 | 5515460 | PAK |
| 072A09 | 2232470 | PAK |
| 072A10 | 3642382 | PAK |
| 072A11 | 3800440 | PAK |
| 072A12 | 3120294 | PAK |
| 072B01 | 1457732 | PAK |
| 072B02 | 343305 | PAK |
| 072B03 | 2889964 | PAK |
| 072B04 | 3976706 | PAK |
| 072B05 | 984014 | PAK |
| 072B06 | 67013 | PAK |
| 072B08 | 5796227 | PAK |
| 072B10 | 1161678 | PAK |
| 072B11 | 4248542 | PAK |
| 072B12 | 1627559 | PAK |
| 072C01 | 6202406 | PAK |
| 072C02 | 640680 | PAK |
| 072C03 | 2900702 | PAK |
| 072C04 | 5755339 | PAK |
| 072C06 | 661080 | PAK |
| 072C07 | 682578 | PAK |
| 072C08 | 581618 | PAK |
| 072C09 | 5494588 | PAK |
| 072C11 | 1757694 | PAK |
| 072C12 | 2070159 | PAK |
| 072D01 | 4658867 | PAK |
| 072D02 | 6178033 | PAK |
| 072D03 | 4247708 | PAK |
| 072004 | 3798285 | PAK |
| 072005 | 932042 | PAK |
| 072D06 | 385809 | PAK |
| 072D08 | 249501 | PAK |
| 072D09 | 3065701 | PAK |
| 072D11 | 1977727 | PAK |
| 072E01 | 5698414 | PAK |
| 072E02 | 101826 | PAK |
| 072E03 | 2600263 | PAK |
| 072E04 | 2615709 | PAK |
| 072E05 | 424365 | PAK |
| 072E06 | 317679 | PAK |
| 072E07 | 6110086 | PAK |
| 072E08 | 5501819 | PAK |
| 072E09 | 2190435 | PAK |
| 072E10 | 3048478 | PAK |
| 072E11 | 365571 | PAK |
| 072E12 | 3065702 | PAK |
| 072F01 | 2518515 | PAK |
| 072F02 | 5676942 | PAK |
| 072F03 | 1034468 | PAK |
| 072F04 | 21979 | PAK |
| 072F05 | 323751 | PAK |
| 072F06 | 2688812 | PAK |
| 072F07 | 2285131 | PAK |
| 072F08 | 2135478 | PAK |
| 072F09 | 3398345 | PAK |
| 072F10 | 1927952 | PAK |
| 072F11 | 348073 | PAK |
| 072G01 | 4204972 | PAK |
| 072G02 | 6147445 | PAK |
| 072G04 | 5662204 | PAK |
| 072G05 | 1774631 | PAK |
| 072G07 | 6091885 | PAK |
| 072G09 | 776328 | PAK |
| 072G11 | 2142597 | PAK |
| 072G12 | 2134874 | PAK |
| 072H01 | 1461770 | PAK |
| 072H02 | 6024771 | PAK |
| 072H04 | 1458425 | PAK |
| 072H05 | 1769824 | PAK |
| 072H06 | 3831679 | PAK |
| 072H07 | 2203525 | PAK |
| 072H08 | 5289656 | PAK |
| 072H09 | 3231373 | PAK |
| 072H10 | 5120195 | PAK |
| 073A01 | 4704997 | PAK |
| 073A02 | 5119654 | PAK |
| 073A03 | 3174130 | PAK |
| 073A04 | 1379831 | PAK |
| 073A05 | 3170739 | PAK |
| 073A06 | 1345754 | PAK |
| 073A07 | 4383656 | PAK |
| 073A08 | 5711339 | PAK |
| 073A10 | 3211123 | PAK |
| 073A11 | 1034469 | PAK |
| 073A12 | 2236187 | PAK |
| 073B01 | 4970189 | PAK |

TABLE 3-continued

| Mutant Name | Insertion Point | host strain |
|---|---|---|
| 073B02 | 1374715 | PAK |
| 073B03 | 1034469 | PAK |
| 073B04 | 307732 | PAK |
| 073B05 | 5192039 | PAK |
| 073B06 | 4353584 | PAK |
| 073B08 | 1493579 | PAK |
| 073B09 | 5955205 | PAK |
| 073B10 | 300234 | PAK |
| 073B12 | 2032581 | PAK |
| 073C01 | 3976656 | PAK |
| 073C03 | 2538990 | PAK |
| 073C04 | 1923243 | PAK |
| 073C05 | 3901813 | PAK |
| 073C06 | 491129 | PAK |
| 073C09 | 6092304 | PAK |
| 073C10 | 1539345 | PAK |
| 073C11 | 3716552 | PAK |
| 073C12 | 3235544 | PAK |
| 073D01 | 821711 | PAK |
| 073D02 | 3245793 | PAK |
| 073D03 | 3439089 | PAK |
| 073D04 | 3520169 | PAK |
| 073D05 | 5420985 | PAK |
| 073D06 | 1034469 | PAK |
| 073D07 | 5780923 | PAK |
| 073D08 | 4036534 | PAK |
| 073D09 | 460315 | PAK |
| 073D10 | 341485 | PAK |
| 073D11 | 39877 | PAK |
| 073D12 | 578059 | PAK |
| 073E01 | 358499 | PAK |
| 073E02 | 1814951 | PAK |
| 073E04 | 162038 | PAK |
| 073E05 | 3007720 | PAK |
| 073E07 | 2163569 | PAK |
| 073E08 | 15374 | PAK |
| 073E09 | 1532348 | PAK |
| 073E10 | 2867679 | PAK |
| 073E11 | 3573935 | PAK |
| 073E12 | 1868778 | PAK |
| 073F02 | 2467111 | PAK |
| 073F04 | 3755652 | PAK |
| 073F05 | 4297306 | PAK |
| 073F06 | 5058989 | PAK |
| 073F07 | 3625059 | PAK |
| 073F10 | 3618469 | PAK |
| 073G02 | 1369113 | PAK |
| 073G03 | 3178778 | PAK |
| 073G04 | 5618494 | PAK |
| 073G05 | 4046834 | PAK |
| 073G06 | 1313050 | PAK |
| 073G07 | 4179090 | PAK |
| 073G08 | 6114122 | PAK |
| 073G09 | 3297648 | PAK |
| 073G11 | 494507 | PAK |
| 073G12 | 4834488 | PAK |
| 073H01 | 28871 | PAK |
| 073H02 | 1423098 | PAK |
| 073H03 | 6198391 | PAK |
| 073H06 | 2111752 | PAK |
| 073H07 | 6109641 | PAK |
| 073H08 | 633110 | PAK |
| 073H10 | 2006206 | PAK |
| 073H11 | 395318 | PAK |
| 074A01 | 6055860 | PAK |
| 074A02 | 5008086 | PAK |
| 074A04 | 326278 | PAK |
| 074A05 | 5023500 | PAK |
| 074A06 | 2480392 | PAK |
| 074A08 | 1715770 | PAK |
| 074A09 | 6027327 | PAK |
| 074A10 | 3377875 | PAK |
| 074A11 | 3649822 | PAK |
| 074A12 | 4930454 | PAK |
| 074B01 | 524124 | PAK |
| 074B02 | 682645 | PAK |
| 074B04 | 1683993 | PAK |
| 074B05 | 3423519 | PAK |
| 074B06 | 4979236 | PAK |
| 074B07 | 947510 | PAK |
| 074B08 | 109943 | PAK |
| 074B09 | 6092656 | PAK |
| 074B11 | 6019055 | PAK |
| 074B12 | 3804124 | PAK |
| 074F01 | 1932008 | PAK |
| 074F02 | 3224625 | PAK |
| 074F03 | 5298794 | PAK |
| 074F05 | 3731764 | PAK |
| 074F07 | 5676942 | PAK |
| 074F08 | 3986664 | PAK |
| 074F09 | 4346467 | PAK |
| 074F10 | 3986664 | PAK |
| 074F11 | 5305210 | PAK |
| 074F12 | 1034469 | PAK |
| 074G01 | 6213914 | PAK |
| 074G02 | 2560460 | PAK |
| 074G03 | 5411418 | PAK |
| 074G04 | 1523405 | PAK |
| 074G05 | 1591268 | PAK |
| 074G06 | 978337 | PAK |
| 074G07 | 6123918 | PAK |
| 074G08 | 6144878 | PAK |
| 074G09 | 6097792 | PAK |
| 074G10 | 5935375 | PAK |
| 074G11 | 4614634 | PAK |
| 074G12 | 42340 | PAK |
| 074H02 | 395394 | PAK |
| 074H03 | 3581367 | PAK |
| 074H05 | 3726807 | PAK |
| 074H06 | 4563650 | PAK |
| 074H07 | 1536028 | PAK |
| 074H08 | 44324 | PAK |
| 074H09 | 4239771 | PAK |
| 074H10 | 395319 | PAK |
| 074H11 | 395319 | PAK |
| 075A01 | 5656638 | PAK |
| 075A03 | 822399 | PAK |
| 075A04 | 4422982 | PAK |
| 075A05 | 2750712 | PAK |
| 075A06 | 814640 | PAK |
| 075A08 | 506758 | PAK |
| 075A09 | 532562 | PAK |
| 075A10 | 5745941 | PAK |
| 075A11 | 4861227 | PAK |
| 075A12 | 1538208 | PAK |
| 075B01 | 3123858 | PAK |
| 075B02 | 5702275 | PAK |
| 075B03 | 1770709 | PAK |
| 075B05 | 6027506 | PAK |
| 075B06 | 1514248 | PAK |
| 075B07 | 5771313 | PAK |
| 075B09 | 924998 | PAK |
| 075B10 | 2943370 | PAK |
| 075B11 | 312093 | PAK |
| 075D10 | 1659739 | PAK |
| 075E01 | 581476 | PAK |
| 075E03 | 4557777 | PAK |
| 075E05 | 417328 | PAK |
| 075E06 | 122584 | PAK |
| 075E07 | 514648 | PAK |
| 075E08 | 2550366 | PAK |
| 075E09 | 4398601 | PAK |
| 075E10 | 5223759 | PAK |
| 075E11 | 941676 | PAK |
| 075E12 | 3280940 | PAK |
| 075F01 | 6048432 | PAK |
| 075F02 | 3168460 | PAK |
| 075F03 | 5339124 | PAK |
| 075F04 | 5771999 | PAK |
| 075F05 | 5771999 | PAK |
| 075F06 | 530707 | PAK |
| 075F08 | 469274 | PAK |
| 075F09 | 6179663 | PAK |
| 075F10 | 658967 | PAK |

TABLE 3-continued

| Mutant Name | Insertion Point | host strain |
|---|---|---|
| 075F11 | 384567 | PAK |
| 075F12 | 2243268 | PAK |
| 075G01 | 1927607 | PAK |
| 075G02 | 5745518 | PAK |
| 075G03 | 2470827 | PAK |
| 075G05 | 1659240 | PAK |
| 075G06 | 791999 | PAK |
| 075G07 | 521744 | PAK |
| 075G08 | 2629022 | PAK |
| 075G09 | 5168547 | PAK |
| 075G10 | 1283538 | PAK |
| 075G11 | 5538672 | PAK |
| 075G12 | 929055 | PAK |
| 075H02 | 5213892 | PAK |
| 075H03 | 5877121 | PAK |
| 075H04 | 478140 | PAK |
| 075H05 | 3953947 | PAK |
| 075H06 | 4892891 | PAK |
| 075H07 | 3864331 | PAK |
| 075H08 | 733328 | PAK |
| 075H09 | 4665718 | PAK |
| 075H10 | 3986145 | PAK |
| 075H11 | 395319 | PAK |
| 076A01 | 260880 | PAK |
| 076A02 | 5531682 | PAK |
| 076A04 | 1147282 | PAK |
| 076A05 | 16462 | PAK |
| 076A06 | 5002921 | PAK |
| 076A08 | 721498 | PAK |
| 076A10 | 1230709 | PAK |
| 076A11 | 5749716 | PAK |
| 076A12 | 3887730 | PAK |
| 076B01 | 4251952 | PAK |
| 076B02 | 5893058 | PAK |
| 076B03 | 811122 | PAK |
| 076B04 | 6095758 | PAK |
| 076B05 | 6204818 | PAK |
| 076B06 | 2784084 | PAK |
| 076B07 | 4704880 | PAK |
| 076B08 | 5400412 | PAK |
| 076B09 | 2246890 | PAK |
| 076B10 | 4853308 | PAK |
| 076B11 | 4540555 | PAK |
| 076B12 | 960638 | PAK |
| 076C01 | 1545087 | PAK |
| 076C02 | 3707642 | PAK |
| 076C03 | 1167113 | PAK |
| 076C04 | 1354061 | PAK |
| 076C05 | 5211592 | PAK |
| 076C06 | 4967044 | PAK |
| 076C07 | 3033012 | PAK |
| 076C09 | 4900553 | PAK |
| 076C10 | 3423519 | PAK |
| 076C12 | 1993045 | PAK |
| 076D02 | 4167845 | PAK |
| 076D03 | 5800529 | PAK |
| 076D04 | 351028 | PAK |
| 076D05 | 442619 | PAK |
| 076D06 | 3217470 | PAK |
| 076D07 | 1419351 | PAK |
| 076D08 | 6124971 | PAK |
| 076D09 | 555929 | PAK |
| 076D11 | 6240021 | PAK |
| 076D12 | 3377875 | PAK |
| 076E01 | 2350413 | PAK |
| 076E02 | 5738127 | PAK |
| 076E03 | 5202612 | PAK |
| 076E04 | 1142928 | PAK |
| 076E05 | 2778189 | PAK |
| 076E06 | 1988280 | PAK |
| 076E07 | 4396729 | PAK |
| 076E08 | 528431 | PAK |
| 076E09 | 5019630 | PAK |
| 076E10 | 6172249 | PAK |
| 076E11 | 5365848 | PAK |
| 076E12 | 4419850 | PAK |
| 076F01 | 1635210 | PAK |
| 076F02 | 369750 | PAK |
| 076F03 | 5246142 | PAK |
| 076F04 | 1652270 | PAK |
| 076F05 | 6238494 | PAK |
| 076F06 | 3838107 | PAK |
| 076F07 | 5847589 | PAK |
| 076F08 | 3882920 | PAK |
| 076F09 | 817776 | PAK |
| 076F10 | 5744180 | PAK |
| 076F11 | 508847 | PAK |
| 076F12 | 2352639 | PAK |
| 076G01 | 3069945 | PAK |
| 076G02 | 2585153 | PAK |
| 076G03 | 1081372 | PAK |
| 076G04 | 4675503 | PAK |
| 076G05 | 930548 | PAK |
| 076G06 | 5546850 | PAK |
| 076G07 | 1691954 | PAK |
| 076G08 | 765145 | PAK |
| 076G09 | 3836930 | PAK |
| 076G10 | 1757837 | PAK |
| 076G11 | 1662009 | PAK |
| 076H01 | 2133837 | PAK |
| 076H02 | 5743023 | PAK |
| 076H03 | 2145275 | PAK |
| 076H04 | 4379971 | PAK |
| 076H05 | 3919945 | PAK |
| 076H06 | 1428295 | PAK |
| 076H09 | 495064 | PAK |
| 076H10 | 1468214 | PAK |
| 077A01 | 223091 | PAK |
| 077A02 | 3756019 | PAK |
| 077A03 | 736069 | PAK |
| 077A04 | 1188885 | PAK |
| 077A05 | 1188885 | PAK |
| 077A06 | 3481240 | PAK |
| 077A07 | 59525 | PAK |
| 077A08 | 4578056 | PAK |
| 077A09 | 1021934 | PAK |
| 077A10 | 6053485 | PAK |
| 077A11 | 1473985 | PAK |
| 077A12 | 5654603 | PAK |
| 077B01 | 1376976 | PAK |
| 077B02 | 6200549 | PAK |
| 077B03 | 672251 | PAK |
| 077B04 | 5077212 | PAK |
| 077B05 | 3725227 | PAK |
| 077B06 | 5837678 | PAK |
| 077B07 | 1298222 | PAK |
| 077B09 | 102959 | PAK |
| 077B10 | 156187 | PAK |
| 077B11 | 2574160 | PAK |
| 077B12 | 1886313 | PAK |
| 077C01 | 5974937 | PAK |
| 077C02 | 5218416 | PAK |
| 077C03 | 1121295 | PAK |
| 077C05 | 4432420 | PAK |
| 077C07 | 3898842 | PAK |
| 077C08 | 3755425 | PAK |
| 077C09 | 1828438 | PAK |
| 077C10 | 833230 | PAK |
| 077C11 | 2252024 | PAK |
| 077C12 | 2170305 | PAK |
| 077D01 | 816371 | PAK |
| 077D02 | 324105 | PAK |
| 077D03 | 1843256 | PAK |
| 077D04 | 965597 | PAK |
| 077D05 | 5893034 | PAK |
| 077D06 | 605009 | PAK |
| 077D07 | 1845747 | PAK |
| 077D09 | 3498828 | PAK |
| 077D10 | 4896729 | PAK |
| 077D11 | 5771546 | PAK |
| 077D12 | 5545974 | PAK |
| 077E02 | 4710515 | PAK |
| 077E04 | 813660 | PAK |
| 077E05 | 2921695 | PAK |

TABLE 3-continued

| Mutant Name | Insertion Point | host strain |
|---|---|---|
| 077E06 | 1208241 | PAK |
| 077E07 | 5732702 | PAK |
| 077E08 | 2698545 | PAK |
| 077E10 | 4346467 | PAK |
| 077E11 | 6224406 | PAK |
| 077E12 | 4451378 | PAK |
| 077F04 | 5645309 | PAK |
| 077F05 | 5645309 | PAK |
| 077F06 | 1493104 | PAK |
| 077F07 | 6219324 | PAK |
| 077F08 | 4153071 | PAK |
| 077F09 | 1641223 | PAK |
| 077F10 | 4561933 | PAK |
| 077F11 | 1241181 | PAK |
| 077F12 | 1241181 | PAK |
| 077G03 | 4520846 | PAK |
| 077G05 | 106467 | PAK |
| 077G06 | 3081159 | PAK |
| 077G08 | 5385089 | PAK |
| 077G09 | 2011295 | PAK |
| 077G10 | 3297732 | PAK |
| 077G11 | 2252032 | PAK |
| 077G12 | 2252032 | PAK |
| 077H02 | 4160248 | PAK |
| 077H03 | 3391643 | PAK |
| 077H06 | 917478 | PAK |
| 077H07 | 492Q846 | PAK |
| 077H08 | 2963816 | PAK |
| 077H09 | 6203764 | PAK |
| 077H11 | 574329 | PAK |
| 078A01 | 3678902 | PAK |
| 078A02 | 5877529 | PAK |
| 078A03 | 2244685 | PAK |
| 078A04 | 3703741 | PAK |
| 078A05 | 5403796 | PAK |
| 078A06 | 3990854 | PAK |
| 078A07 | 5516048 | PAK |
| 078A08 | 1343619 | PAK |
| 078A09 | 5944735 | PAK |
| 078A10 | 1463440 | PAK |
| 078B01 | 4809759 | PAK |
| 078B03 | 4604479 | PAK |
| 078B04 | 1699194 | PAK |
| 078B05 | 5292960 | PAK |
| 078B09 | 5735051 | PAK |
| 078B10 | 2927757 | PAK |
| 078B11 | 5025265 | PAK |
| 078F01 | 5320123 | PAK |
| 078F02 | 4406921 | PAK |
| 078F03 | 6240670 | PAK |
| 078F04 | 697418 | PAK |
| 078F05 | 4191601 | PAK |
| 078F06 | 4798239 | PAK |
| 078F07 | 2597833 | PAK |
| 078F06 | 657621 | PAK |
| 078F09 | 5532975 | PAK |
| 078F10 | 2709493 | PAK |
| 078F11 | 3787890 | PAK |
| 078F12 | 2857054 | PAK |
| 078G01 | 280601 | PAK |
| 078G02 | 1420709 | PAK |
| 078G03 | 1003257 | PAK |
| 078G05 | 494108 | PAK |
| 078G06 | 6161266 | PAK |
| 078G07 | 3907119 | PAK |
| 078G08 | 3634677 | PAK |
| 078G09 | 997822 | PAK |
| 078G11 | 127010 | PAK |
| 078G12 | 4687527 | PAK |
| 078H01 | 152964 | PAK |
| 078H02 | 5356413 | PAK |
| 078H03 | 318618 | PAK |
| 078H04 | 1834268 | PAK |
| 078H05 | 3254213 | PAK |
| 078H06 | 5530288 | PAK |
| 078H07 | 2010974 | PAK |
| 078H08 | 1761171 | PAK |

TABLE 3-continued

| Mutant Name | Insertion Point | host strain |
|---|---|---|
| 078H09 | 264047 | PAK |
| 078H10 | 5088529 | PAK |
| 078H11 | 395319 | PAK |
| 079A01 | 763074 | PAK |
| 079A02 | 4627720 | PAK |
| 079A03 | 3748808 | PAK |
| 079A05 | 2301986 | PAK |
| 079A06 | 2895252 | PAK |
| 079A07 | 2035641 | PAK |
| 079A08 | 2629186 | PAK |
| 079A09 | 3212093 | PAK |
| 079A10 | 2965923 | PAK |
| 079A12 | 1536133 | PAK |
| 079B01 | 2893553 | PAK |
| 079B03 | 5309838 | PAK |
| 079B05 | 6102601 | PAK |
| 079B06 | 2821177 | PAK |
| 079B08 | 506796 | PAK |
| 079B09 | 4568729 | PAK |
| 079B10 | 5950520 | PAK |
| 079B11 | 5992225 | PAK |
| 079B12 | 1741685 | PAK |
| 079C01 | 31873292 | PAK |
| 079C02 | 5200926 | PAK |
| 079C03 | 4982667 | PAK |
| 079C04 | 3502091 | PAK |
| 079C06 | 5678631 | PAK |
| 079C07 | 2166887 | PAK |
| 079C08 | 334697 | PAK |
| 079C09 | 2618287 | PAK |
| 079C11 | 3563765 | PAK |
| 079C12 | 4194359 | PAK |
| 079D01 | 2099112 | PAK |
| 079D02 | 1139664 | PAK |
| 079D03 | 4201195 | PAK |
| 079D04 | 4915077 | PAK |
| 079D06 | 2023060 | PAK |
| 079D07 | 1133396 | PAK |
| 079G01 | 5732479 | PAK |
| 079G02 | 423295 | PAK |
| 079G03 | 4912335 | PAK |
| 079G04 | 5092982 | PAK |
| 079G05 | 9590 | PAK |
| 079G06 | 2632352 | PAK |
| 079G07 | 3718786 | PAK |
| 079G08 | 6024398 | PAK |
| 079G09 | 3348529 | PAR |
| 079G11 | 1529892 | PAK |
| 079G12 | 5427253 | PAK |
| 079H01 | 1200473 | PAK |
| 079H02 | 6200450 | PAK |
| 079H03 | 346517 | PAK |
| 079H04 | 4026893 | PAK |
| 079H05 | 3405074 | PAK |
| 079H06 | 4026893 | PAK |
| 079H08 | 4056144 | PAK |
| 079H09 | 4450298 | PAK |
| 079H11 | 395319 | PAK |
| 080A01 | 4367833 | PAK |
| 080A02 | 3653261 | PAK |
| 080A03 | 4636551 | PAK |
| 080A04 | 4163326 | PAK |
| 080A05 | 1554773 | PAK |
| 080A06 | 2877511 | PAK |
| 080A07 | 2377852 | PAK |
| 080A08 | 5300484 | PAK |
| 080A10 | 5929616 | PAK |
| 080A11 | 1753451 | PAK |
| 080A12 | 3635298 | PAK |
| 080B01 | 2048639 | PAK |
| 080B03 | 6240021 | PAK |
| 080B04 | 2855772 | PAK |
| 080B05 | 3645052 | PAK |
| 080B06 | 4443513 | PAK |
| 080B09 | 5411515 | PAK |
| 080B10 | 4106210 | PAK |
| 080B11 | 5034641 | PAK |

TABLE 3-continued

| Mutant Name | Insertion Point | host strain |
|---|---|---|
| 080B12 | 4437881 | PAK |
| 080C01 | 3484061 | PAK |
| 081F04 | 5599765 | PAK |
| 081E05 | 2174542 | PAK |
| 081E06 | 1618010 | PAK |
| 081F08 | 3611556 | PAK |
| 081F09 | 5728167 | PAK |
| 081F10 | 2769512 | PAK |
| 081F11 | 1902906 | PAK |
| 081G01 | 518359 | PAK |
| 081G02 | 1908611 | PAK |
| 081G04 | 464685 | PAK |
| 081G05 | 5300484 | PAK |
| 081G07 | 2522083 | PAK |
| 081G08 | 4390762 | PAK |
| 081G10 | 2692956 | PAK |
| 081G11 | 2212653 | PAK |
| 081H01 | 5586226 | PAK |
| 081H03 | 3038230 | PAK |
| 081H05 | 2323962 | PAK |
| 081H08 | 5007784 | PAK |
| 081H09 | 3513111 | PAK |
| 081H10 | 1034469 | PAK |
| 081H11 | 395318 | PAK |
| 082A02 | 1590327 | PAK |
| 082A03 | 3728902 | PAK |
| 082A04 | 468359 | PAK |
| 082A06 | 5365306 | PAK |
| 082A08 | 3690212 | PAK |
| 082A09 | 343413 | PAK |
| 082A10 | 1452951 | PAK |
| 082A11 | 1511935 | PAK |
| 082A12 | 4453348 | PAK |
| 082B01 | 2708441 | PAK |
| 082B02 | 4583810 | PAK |
| 082B03 | 2611976 | PAK |
| 082B04 | 424679 | PAK |
| 082B05 | 589633 | PAK |
| 082B06 | 3225490 | PAK |
| 082B07 | 4913117 | PAK |
| 082B08 | 3120336 | PAK |
| 082B09 | 4912352 | PAK |
| 082B10 | 5849730 | PAK |
| 082B11 | 1401775 | PAK |
| 082B12 | 5554549 | PAK |
| 082C01 | 333765 | PAK |
| 082C05 | 957533 | PAK |
| 082C06 | 773112 | PAK |
| 082C08 | 3899586 | PAK |
| 082C09 | 5395375 | PAK |
| 082C10 | 5177027 | PAK |
| 082C11 | 6187544 | PAK |
| 082D02 | 1453831 | PAK |
| 082D04 | 2250214 | PAK |
| 082D05 | 3721017 | PAK |
| 082D06 | 625853 | PAK |
| 082D07 | 2926709 | PAK |
| 082D08 | 945275 | PAK |
| 082D09 | 1152941 | PAK |
| 082D10 | 58971 | PAK |
| 082D11 | 5386088 | PAK |
| 082D12 | 5496869 | PAK |
| 082E01 | 1389074 | PAK |
| 082E02 | 5924626 | PAK |
| 082E03 | 3388563 | PAK |
| 082E04 | 1835945 | PAK |
| 082E05 | 3938017 | PAK |
| 082E06 | 5250961 | PAK |
| 082E07 | 5532364 | PAK |
| 082E08 | 1783745 | PAK |
| 082E09 | 3288186 | PAK |
| 082E11 | 1657385 | PAK |
| 082E12 | 3932347 | PAK |
| 082F01 | 4418797 | PAK |
| 082F02 | 4506646 | PAK |
| 082F03 | 1664581 | PAK |
| 082F04 | 5290266 | PAK |

TABLE 3-continued

| Mutant Name | Insertion Point | host strain |
|---|---|---|
| 082F06 | 1082476 | PAK |
| 082F07 | 475486 | PAK |
| 082F08 | 3645337 | PAK |
| 082F09 | 1534611 | PAK |
| 082F10 | 5862122 | PAK |
| 082F12 | 2073209 | PAK |
| 082G01 | 2710202 | PAK |
| 082G02 | 2856157 | PAK |
| 082G03 | 5938326 | PAK |
| 082G04 | 3829442 | PAK |
| 082G05 | 3204370 | PAK |
| 082G06 | 4658869 | PAK |
| 082G07 | 4475854 | PAK |
| 082G08 | 1916464 | PAK |
| 082G09 | 4932770 | PAK |
| 082G10 | 2048265 | PAK |
| 082G11 | 3521198 | PAK |
| 082H01 | 3471740 | PAK |
| 082H02 | 6085673 | PAK |
| 082H04 | 5865709 | PAK |
| 082H05 | 1168547 | PAK |
| 082H06 | 1265153 | PAK |
| 082H07 | 4386353 | PAK |
| 082H08 | 22263 | PAK |
| 082H09 | 1285824 | PAK |
| 082H10 | 86352 | PAK |
| 082H11 | 395319 | PAK |
| 083A01 | 1716697 | PAK |
| 083A02 | 5722530 | PAK |
| 083A03 | 890590 | PAK |
| 083A05 | 5633945 | PAK |
| 083A08 | 5462750 | PAK |
| 083A09 | 379701 | PAK |
| 083A10 | 1169335 | PAK |
| 083A11 | 3659011 | PAK |
| 083A12 | 1289717 | PAK |
| 033B01 | 3650694 | PAK |
| 083B02 | 3110140 | PAK |
| 083B03 | 3406321 | PAK |
| 083B04 | 3808786 | PAK |
| 083B05 | 5411333 | PAK |
| 083B06 | 2921279 | PAK |
| 083B07 | 1171633 | PAK |
| 083B08 | 4420132 | PAK |
| 083B09 | 31980 | PAK |
| 083B10 | 3907136 | PAK |
| 083B12 | 4685960 | PAK |
| 083C01 | 4012333 | PAK |
| 083C02 | 3022373 | PAK |
| 083C03 | 468523 | PAK |
| 083C04 | 4034151 | PAK |
| 083C05 | 396118 | PAK |
| 083C06 | 5293680 | PAK |
| 083C07 | 1293431 | PAK |
| 083C08 | 4401199 | PAK |
| 083C09 | 366867 | PAK |
| 083C10 | 6204818 | PAK |
| 083C11 | 5187279 | PAK |
| 083C12 | 3872392 | PAK |
| 083D01 | 2832251 | PAK |
| 083D02 | 1416748 | PAK |
| 083D03 | 4469598 | PAK |
| 083D04 | 5119182 | PAK |
| 083D05 | 1751320 | PAK |
| 083D06 | 5980257 | PAK |
| 083D07 | 4362468 | PAK |
| 083D08 | 3993541 | PAK |
| 083D09 | 3770841 | PAK |
| 083D10 | 6237754 | PAK |
| 083D11 | 1034469 | PAK |
| 083D12 | 6234059 | PAK |
| 083E01 | 4411673 | PAK |
| 083E02 | 3423518 | PAK |
| 083E03 | 1332604 | PAK |
| 083E04 | 5804638 | PAK |
| 083E05 | 1787707 | PAK |
| 083E06 | 5635763 | PAK |

TABLE 3-continued

| Mutant Name | Insertion Point | host strain |
| --- | --- | --- |
| 083E07 | 178198 | PAK |
| 083E08 | 5789601 | PAK |
| 083E09 | 3818650 | PAK |
| 083E10 | 3870905 | PAK |
| 083E12 | 4890746 | PAK |
| 083F01 | 4203293 | PAK |
| 083F02 | 5667462 | PAK |
| 083F03 | 1386132 | PAK |
| 083F04 | 5925983 | PAK |
| 083F05 | 4895470 | PAK |
| 083F06 | 4707301 | PAK |
| 083F07 | 5763918 | PAK |
| 083F08 | 3640824 | PAK |
| 083F09 | 2731781 | PAK |
| 083F10 | 4647353 | PAK |
| 083F11 | 5643969 | PAK |
| 083G01 | 5547683 | PAK |
| 083G03 | 799610 | PAK |
| 083G04 | 5587827 | PAK |
| 083G05 | 2714398 | PAK |
| 083G06 | 1544844 | PAK |
| 083G07 | 4573074 | PAK |
| 083G08 | 5427542 | PAK |
| 083G10 | 5975093 | PAK |
| 083G11 | 4607366 | PAK |
| 083G12 | 99263 | PAK |
| 083H02 | 3007368 | PAK |
| 083H04 | 2991762 | PAK |
| 083H05 | 674579 | PAK |
| 083H06 | 2256581 | PAK |
| 083H07 | 5384447 | PAK |
| 083H08 | 637531 | PAK |
| 083H09 | 5768052 | PAK |
| 083H10 | 2879985 | PAK |
| 083H11 | 395319 | PAK |
| 084A01 | 4553752 | PAK |
| 084A02 | 479428 | PAK |
| 084A03 | 5270850 | PAK |
| 084A04 | 6202406 | PAK |
| 084A05 | 1679652 | PAK |
| 084A06 | 6084097 | PAK |
| 084A07 | 4323707 | PAK |
| 084A08 | 1110870 | PAK |
| 084A09 | 239961 | PAK |
| 084A10 | 1674912 | PAK |
| 084A11 | 5172603 | PAK |
| 084A12 | 5355408 | PAK |
| 084B01 | 2079699 | PAK |
| 084B02 | 5174413 | PAK |
| 084B03 | 3669990 | PAK |
| 084B04 | 1498898 | PAK |
| 084B05 | 2211625 | PAK |
| 084B06 | 1476875 | PAK |
| 084B07 | 3377877 | PAK |
| 084B08 | 36557 | PAK |
| 084B09 | 3862767 | PAK |
| 084B10 | 947938 | PAK |
| 084B11 | 4924648 | PAK |
| 084B12 | 3508200 | PAK |
| 084C03 | 1525921 | PAK |
| 084C04 | 5356341 | PAK |
| 084C05 | 2249277 | PAK |
| 084C07 | 5977522 | PAK |
| 084C08 | 1928099 | PAK |
| 084C11 | 1034469 | PAK |
| 084C12 | 1811918 | PAK |
| 084D01 | 2162290 | PAK |
| 084D02 | 5211146 | PAK |
| 084D03 | 1599066 | PAK |
| 084D04 | 3293179 | PAK |
| 084D05 | 704498 | PAK |
| 084D06 | 34375 | PAK |
| 084D07 | 5524752 | PAK |
| 084D08 | 2111922 | PAK |
| 084D09 | 5815942 | PAK |
| 084D10 | 1566192 | PAK |
| 084D11 | 494940 | PAK |
| 084D12 | 1026770 | PAK |
| 084E01 | 2353428 | PAK |
| 084E02 | 4724795 | PAK |
| 084E03 | 1470035 | PAK |
| 084E04 | 4455604 | PAK |
| 084E05 | 1971606 | PAK |
| 084E06 | 2375068 | PAK |
| 084E07 | 511254 | PAK |
| 084E08 | 4044804 | PAK |
| 084E09 | 4135134 | PAK |
| 084E10 | 5294753 | PAK |
| 084E12 | 6145481 | PAK |
| 084F01 | 2564578 | PAK |
| 084F02 | 2603677 | PAK |
| 084F03 | 6120612 | PAK |
| 084F04 | 1800780 | PAK |
| 084F05 | 1903894 | PAK |
| 084F06 | 5093257 | PAK |
| 084F07 | 6216637 | PAK |
| 084F08 | 3174550 | PAK |
| 084F09 | 2889826 | PAK |
| 084F10 | 2250597 | PAK |
| 084F11 | 4809751 | PAK |
| 084F12 | 177910 | PAK |
| 084G01 | 2929158 | PAK |
| 084G02 | 3741054 | PAK |
| 084G03 | 848917 | PAK |
| 084G04 | 3648576 | PAK |
| 084G05 | 3179811 | PAK |
| 084G06 | 1741398 | PAK |
| 084G07 | 5903652 | PAK |
| 084G08 | 5854198 | PAK |
| 084G09 | 219333 | PAK |
| 084G10 | 4575568 | PAK |
| 084H01 | 5735299 | PAK |
| 084H02 | 5444353 | PAK |
| 084H03 | 3891666 | PAK |
| 084H04 | 4055599 | PAK |
| 084H05 | 4399348 | PAK |
| 084H06 | 4398214 | PAK |
| 084H07 | 2155088 | PAK |
| 084H08 | 4337823 | PAK |
| 084H09 | 4637449 | PAK |
| 084H10 | 2591324 | PAK |
| 084H11 | 395317 | PAK |
| 085A01 | 3579960 | PAK |
| 085A02 | 5204218 | PAK |
| 085A03 | 4611603 | PAK |
| 085A04 | 5583129 | PAK |
| 085A05 | 396969 | PAK |
| 085A06 | 2361082 | PAK |
| 085A07 | 1164653 | PAK |
| 085A08 | 790647 | PAK |
| 085A09 | 2202520 | PAK |
| 0S5A10 | 687458 | PAK |
| 085A11 | 6217614 | PAK |
| 085B02 | 5533229 | PAK |
| 085B03 | 1013896 | PAK |
| 085B06 | 5220580 | PAK |
| 085B07 | 5279763 | PAK |
| 085B09 | 6210806 | PAK |
| 085B11 | 3823842 | PAK |
| 085B12 | 3745512 | PAK |
| 085C01 | 1141579 | PAK |
| 085C02 | 5788046 | PAK |
| 085C04 | 4443353 | PAK |
| 085C08 | 2941406 | PAK |
| 085C10 | 110460 | PAK |
| 085D03 | 5914051 | PAK |
| 085D05 | 4929673 | PAK |
| 085D06 | 5485464 | PAK |
| 085D07 | 4929673 | PAK |
| 085D10 | 364281 | PAK |
| 085D12 | 860399 | PAK |
| 085E02 | 1787707 | PAK |
| 085E04 | 2428233 | PAK |
| 085E05 | 849987 | PAK |

TABLE 3-continued

| Mutant Name | Insertion Point | host strain |
|---|---|---|
| 085E10 | 3602283 | PAK |
| 085F02 | 6145100 | PAK |
| 085F03 | 1819420 | PAK |
| 085F05 | 6073415 | PAK |
| 085F08 | 1742949 | PAK |
| 085F09 | 1423375 | PAK |
| 085F10 | 6082315 | PAK |
| 085F11 | 956872 | PAK |
| 085F12 | 5067443 | PAK |
| 085G03 | 2711775 | PAK |
| 085G09 | 3301507 | PAK |
| 085G10 | 5505971 | PAK |
| 085G11 | 6126368 | PAK |
| 085G12 | 2842641 | PAK |
| 086A01 | 198345 | PAK |
| 086A02 | 6204898 | PAK |
| 086A04 | 5420771 | PAK |
| 086A05 | 3255956 | PAK |
| 086A07 | 5612200 | PAK |
| 086A08 | 3047319 | PAK |
| 086A09 | 2879208 | PAK |
| 086A12 | 451833 | PAK |
| 086B01 | 5130454 | PAK |
| 086B03 | 4427961 | PAK |
| 086B04 | 3377876 | PAK |
| 086B06 | 1987963 | PAK |
| 086B07 | 3865649 | PAK |
| 086B08 | 4915077 | PAK |
| 086B09 | 5458814 | PAK |
| 086B10 | 4349835 | PAK |
| 086B11 | 2845521 | PAK |
| 086B12 | 4975737 | PAK |
| 086C01 | 388966 | PAK |
| 086C02 | 2254621 | PAK |
| 086C03 | 6202406 | PAK |
| 086C04 | 4466132 | PAK |
| 086C06 | 5743703 | PAK |
| 086C07 | 1315075 | PAK |
| 086C08 | 666027 | PAK |
| 086C09 | 8840 | PAK |
| 086C10 | 5369448 | PAK |
| 086C11 | 1742406 | PAK |
| 086C12 | 6142832 | PAK |
| 086D02 | 6206337 | PAK |
| 086D03 | 2867673 | PAK |
| 086D04 | 1455447 | PAK |
| 086D05 | 23217 | PAK |
| 086D06 | 3755500 | PAK |
| 086D07 | 3629020 | PAK |
| 086D08 | 1401774 | PAK |
| 086D09 | 2920622 | PAK |
| 086D10 | 6109633 | PAK |
| 086D11 | 278171 | PAK |
| 086D12 | 864263 | PAK |
| 086E01 | 3914725 | PAK |
| 086E02 | 2293743 | PAK |
| 086E03 | 6203541 | PAK |
| 086E04 | 30801 | PAK |
| 086E06 | 856388 | PAK |
| 086E09 | 3864556 | PAK |
| 086E10 | 4635000 | PAK |
| 086E11 | 3704858 | PAK |
| 086E12 | 2509916 | PAK |
| 086F01 | 825986 | PAK |
| 086F02 | 3706020 | PAK |
| 086F04 | 6076093 | PAK |
| 086F05 | 582633 | PAK |
| 086F06 | 1873797 | PAK |
| 086F07 | 5156367 | PAK |
| 086F09 | 2501692 | PAK |
| 086F10 | 4602918 | PAK |
| 086F11 | 4845490 | PAK |
| 086G01 | 1423729 | PAK |
| 086G02 | 1034469 | PAK |
| 086G03 | 4593063 | PAK |
| 086G05 | 2024120 | PAK |
| 086G06 | 1152487 | PAK |

TABLE 3-continued

| Mutant Name | Insertion Point | host strain |
|---|---|---|
| 086G08 | 1292321 | PAK |
| 086G09 | 6122857 | PAK |
| 086G12 | 5372758 | PAK |
| 086H02 | 303960 | PAK |
| 086H04 | 465078 | PAK |
| 086H06 | 2979248 | PAK |
| 086H07 | 552998 | PAK |
| 086H08 | 5187084 | PAK |
| 086H09 | 6154678 | PAK |
| 086H10 | 4922402 | PAK |
| 087A03 | 1813824 | PAK |
| 087C01 | 2411124 | PAK |
| 087C02 | 619136 | PAK |
| 087C04 | 3498567 | PAK |
| 087C05 | 1034469 | PAK |
| 087C06 | 5454141 | PAK |
| 087C07 | 5994576 | PAK |
| 087C08 | 4937051 | PAK |
| 087C09 | 5028748 | PAK |
| 087C10 | 6038840 | PAK |
| 087C11 | 2467419 | PAK |
| 087C12 | 5026473 | PAK |
| 087D01 | 6161421 | PAK |
| 087D02 | 5923952 | PAK |
| 087D03 | 5947596 | PAK |
| 087D04 | 1558663 | PAK |
| 087D07 | 1171374 | PAK |
| 087D08 | 2941159 | PAK |
| 087D09 | 1444871 | PAK |
| 087D12 | 180042 | PAK |
| 087E01 | 5251463 | PAK |
| 087E02 | 4449587 | PAK |
| 087E04 | 4813877 | PAK |
| 087E05 | 1549931 | PAK |
| 087E06 | 3596975 | PAK |
| 087E07 | 307732 | PAK |
| 087E08 | 3003011 | PAK |
| 087E09 | 415538 | PAK |
| 087E10 | 405862 | PAK |
| 087E12 | 2222581 | PAK |
| 087F04 | 1566192 | PAK |
| 087F05 | 4584772 | PAK |
| 087F06 | 5846587 | PAK |
| 087F07 | 5766050 | PAK |
| 087F08 | 4911293 | PAK |
| 087F09 | 4284168 | PAK |
| 087F10 | 3831871 | PAK |
| 087F11 | 531596 | PAK |
| 087F12 | 2454528 | PAK |
| 087G01 | 2713224 | PAK |
| 087G02 | 6145528 | PAK |
| 087G03 | 4192609 | PAK |
| 087G04 | 5897517 | PAK |
| 087G05 | 3483981 | PAK |
| 087G06 | 2940174 | PAK |
| 087G07 | 558968 | PAK |
| 087G08 | 5698885 | PAK |
| 087G10 | 5714605 | PAK |
| 087G11 | 2335065 | PAK |
| 087H02 | 4911292 | PAK |
| 087H07 | 1775502 | PAK |
| 087H08 | 2419133 | PAK |
| 088A01 | 1924390 | PAK |
| 088A02 | 2974197 | PAK |
| 088A03 | 2503673 | PAK |
| 088A05 | 1532047 | PAK |
| 088A06 | 1764006 | PAK |
| 088A07 | 3877260 | PAK |
| 088A08 | 711492 | PAK |
| 088A10 | 611033 | PAK |
| 088A11 | 5306830 | PAK |
| 088A12 | 5864830 | PAK |
| 088B01 | 3827704 | PAK |
| 088B03 | 3072802 | PAK |
| 088B04 | 3799166 | PAK |
| 088B05 | 2962457 | PAK |
| 088B06 | 2938549 | PAK |

TABLE 3-continued

| Mutant Name | Insertion Point | host strain |
|---|---|---|
| 088B08 | 1576571 | PAK |
| 088B10 | 1577666 | PAK |
| 088B11 | 3789249 | PAK |
| 088B12 | 4669131 | PAK |
| 088C01 | 5311216 | PAK |
| 088C02 | 1786254 | PAK |
| 088C03 | 449605 | PAK |
| 088C04 | 5939041 | PAK |
| 088C05 | 2812481 | PAK |
| 088C07 | 4252575 | PAK |
| 088C10 | 2892202 | PAK |
| 088C11 | 1431320 | PAK |
| 088C12 | 2745851 | PAK |
| 088D03 | 6152972 | PAK |
| 088D04 | 5191990 | PAK |
| 088D06 | 1538858 | PAK |
| 088D07 | 1905584 | PAK |
| 088D08 | 2789609 | PAK |
| 088D09 | 3267954 | PAK |
| 088D10 | 2569116 | PAK |
| 088D11 | 4691711 | PAK |
| 088D12 | 1235153 | PAK |
| 088E01 | 57562 | PAK |
| 088E02 | 4207404 | PAK |
| 088E03 | 1078883 | PAK |
| 088E04 | 2820374 | PAK |
| 088E05 | 2916493 | PAK |
| 088E06 | 3521505 | PAK |
| 088E07 | 2752299 | PAK |
| 088E08 | 5772985 | PAK |
| 088E09 | 3701621 | PAK |
| 088E10 | 111417 | PAK |
| 088E11 | 5559719 | PAK |
| 088E12 | 279463 | PAK |
| 088F01 | 1330905 | PAK |
| 088F02 | 3218437 | PAK |
| 088F03 | 1388350 | PAK |
| 088F04 | 101672 | PAK |
| 088F05 | 6231676 | PAK |
| 088F06 | 5841435 | PAK |
| 088F07 | 125754 | PAK |
| 088F08 | 4079727 | PAK |
| 088F09 | 2475063 | PAK |
| 088F10 | 2900701 | PAK |
| 088F11 | 6189178 | PAK |
| 088F12 | 5981325 | PAK |
| 088G01 | 3770594 | PAK |
| 088G02 | 3439168 | PAK |
| 088G05 | 4383492 | PAK |
| 088G07 | 496788 | PAK |
| 088G08 | 960638 | PAK |
| 088G09 | 496787 | PAK |
| 088G11 | 6229282 | PAK |
| 088G12 | 716896 | PAK |
| 088H01 | 3528213 | PAK |
| 088H02 | 5592500 | PAK |
| 088H03 | 4007295 | PAK |
| 088H04 | 648881 | PAK |
| 088H05 | 3870709 | PAK |
| 088H08 | 5929961 | PAK |
| 088H09 | 1495443 | PAK |
| 088H10 | 5848854 | PAK |
| 089A01 | 1438646 | PAK |
| 089A02 | 4720534 | PAK |
| 089A03 | 5503345 | PAK |
| 089A05 | 3783404 | PAK |
| 089A06 | 34613 | PAK |
| 089A07 | 3234408 | PAK |
| 089A10 | 1124910 | PAK |
| 089A11 | 4049768 | PAK |
| 089A12 | 5938920 | PAK |
| 089B01 | 295383 | PAK |
| 089B02 | 4730507 | PAK |
| 089B03 | 5458154 | PAK |
| 089B04 | 1286525 | PAK |
| 089B06 | 2429475 | PAK |
| 089B09 | 5586107 | PAK |
| 089C01 | 4290698 | PAK |
| 089C02 | 4724369 | PAK |
| 089C03 | 4818750 | PAK |
| 089C04 | 2056630 | PAK |
| 089C05 | 5129791 | PAK |
| 089C06 | 5034522 | PAK |
| 089C07 | 5892491 | PAK |
| 089C09 | 490442 | PAK |
| 089C10 | 4922878 | PAK |
| 089C11 | 2275507 | PAK |
| 089C12 | 3873804 | PAK |
| 089D02 | 5405971 | PAK |
| 089D04 | 582633 | PAK |
| 089D05 | 5315770 | PAK |
| 089D06 | 612978 | PAK |
| 089D07 | 6129697 | PAK |
| 089D08 | 1034355 | PAK |
| 089E02 | 2940015 | PAK |
| 089E03 | 103643 | PAK |
| 089E04 | 3490340 | PAK |
| 089E05 | 3881601 | PAK |
| 089E07 | 4850786 | PAK |
| 089E08 | 766813 | PAK |
| 089E09 | 4449629 | PAK |
| 089E10 | 4957966 | PAK |
| 089E11 | 1460248 | PAK |
| 089E12 | 1447089 | PAK |
| 089F01 | 5457538 | PAK |
| 089F02 | 6030099 | PAK |
| 089F03 | 1367268 | PAK |
| 089F05 | 1853266 | PAK |
| 089F06 | 6141275 | PAK |
| 089F07 | 6030030 | PAK |
| 089F08 | 1322069 | PAK |
| 089F09 | 595688 | PAK |
| 089F10 | 259390 | PAK |
| 089F11 | 373535 | PAK |
| 089F12 | 882433 | PAK |
| 089G01 | 4921726 | PAK |
| 089G02 | 3855140 | PAK |
| 089G03 | 986611 | PAK |
| 089G04 | 5180778 | PAK |
| 089G05 | 5172858 | PAK |
| 089G06 | 1626572 | PAK |
| 089G07 | 5179433 | PAK |
| 089G08 | 281319 | PAK |
| 089G09 | 3612080 | PAK |
| 089H03 | 4242850 | PAK |
| 089H04 | 3351349 | PAK |
| 089H05 | 4242918 | PAK |
| 089H06 | 5414047 | PAK |
| 089H07 | 3191920 | PAK |
| 089H08 | 1787657 | PAK |
| 089H09 | 554383 | PAK |
| 089H11 | 395319 | PAK |
| 090A02 | 1992615 | PAK |
| 090A04 | 6214172 | PAK |
| 090A05 | 675129 | PAK |
| 090A06 | 3305445 | PAK |
| 090A07 | 4600856 | PAK |
| 090A08 | 1992614 | PAK |
| 090A09 | 4627666 | PAK |
| 090A10 | 4742860 | PAK |
| 090A12 | 4895279 | PAK |
| 090B01 | 1222672 | PAK |
| 090B02 | 6138740 | PAK |
| 090B03 | 2333499 | PAK |
| 090B04 | 5241431 | PAK |
| 090B05 | 464675 | PAK |
| 090B07 | 533661 | PAK |
| 090B08 | 3573599 | PAK |
| 090B09 | 5215401 | PAK |
| 090B10 | 4472551 | PAK |
| 090B12 | 3553127 | PAK |
| 090C01 | 4080510 | PAK |
| 090C02 | 6098680 | PAK |
| 090C03 | 6054907 | PAK |

TABLE 3-continued

| Mutant Name | Insertion Point | host strain |
|---|---|---|
| 090C04 | 3081109 | PAK |
| 090C05 | 272090 | PAK |
| 090C06 | 113883 | PAK |
| 090C07 | 3876757 | PAK |
| 090C08 | 1023420 | PAK |
| 090C09 | 1549165 | PAK |
| 090C10 | 5094045 | PAK |
| 090C11 | 3602160 | PAK |
| 090C12 | 2968429 | PAK |
| 090D01 | 5401696 | PAK |
| 090D03 | 4345746 | PAK |
| 090D04 | 4139828 | PAK |
| 090D05 | 4706334 | PAK |
| 090D06 | 3835472 | PAK |
| 090D10 | 3009084 | PAK |
| 090D011 | 5001279 | PAK |
| 090D12 | 2146982 | PAK |
| 090E01 | 3191920 | PAK |
| 090E02 | 4451417 | PAK |
| 090E03 | 3620183 | PAK |
| 090E04 | 873748 | PAK |
| 090E06 | 6094111 | PAK |
| 090E07 | 5032417 | PAK |
| 090E08 | 1838906 | PAK |
| 090E09 | 5798170 | PAK |
| 090E10 | 2384781 | PAK |
| 090E11 | 3909573 | PAK |
| 090E12 | 5160877 | PAK |
| 090F01 | 2537829 | PAK |
| 090F02 | 2922924 | PAK |
| 090F03 | 1781582 | PAK |
| 090F04 | 2414792 | PAK |
| 090F05 | 3826484 | PAK |
| 090F06 | 303454 | PAK |
| 090F07 | 3479263 | PAK |
| 090F08 | 1781584 | PAK |
| 090F09 | 6122087 | PAK |
| 090F10 | 4700118 | PAK |
| 090F11 | 3826543 | PAK |
| 090F12 | 809956 | PAK |
| 090G01 | 5403635 | PAK |
| 090G02 | 6078850 | PAK |
| 090G03 | 1452652 | PAK |
| 090G04 | 1345427 | PAK |
| 090G05 | 1034370 | PAK |
| 090G06 | 4190476 | PAK |
| 090G07 | 2831054 | PAK |
| 090G08 | 4298292 | PAK |
| 090G09 | 5786012 | PAK |
| 090G10 | 2991535 | PAK |
| 090G11 | 2251412 | PAK |
| 090G12 | 4190475 | PAK |
| 090H01 | 765565 | PAK |
| 090H02 | 1991122 | PAK |
| 090H04 | 5583010 | PAK |
| 090H05 | 1589283 | PAK |
| 090H06 | 395318 | PAK |
| 090H07 | 6057929 | PAK |
| 090H08 | 6108287 | PAK |
| 090H10 | 1107766 | PAK |
| 090H11 | 395262 | PAK |
| 091A03 | 3395714 | PAK |
| 091A04 | 765565 | PAK |
| 091A07 | 765565 | PAK |
| 091A06 | 1397699 | PAK |
| 091A09 | 4529801 | PAK |
| 091A11 | 765565 | PAK |
| 091A12 | 3944818 | PAK |
| 091B01 | 6147237 | PAK |
| 091B02 | 5217569 | PAK |
| 091B03 | 6203084 | PAK |
| 091B04 | 765565 | PAK |
| 091B06 | 3499443 | PAK |
| 091B08 | 6239255 | PAK |
| 091B09 | 6203084 | PAK |
| 091B10 | 426660 | PAK |
| 091B11 | 3431890 | PAK |
| 091B12 | 789594 | PAK |
| 091C01 | 6203084 | PAK |
| 091C03 | 2796194 | PAK |
| 091C04 | 6219417 | PAK |
| 091C06 | 765565 | PAK |
| 091C07 | 3611416 | PAK |
| 091C08 | 2796195 | PAK |
| 091C10 | 6219417 | PAK |
| 091C11 | 5728164 | PAK |
| 091C12 | 1718503 | PAK |
| 091D02 | 5138906 | PAK |
| 091D03 | 4381152 | PAK |
| 091D04 | 4036811 | PAK |
| 091D07 | 1532827 | PAK |
| 091D08 | 3181651 | PAK |
| 091D10 | 701270 | PAK |
| 091D12 | 4548215 | PAK |
| 091E01 | 4158798 | PAK |
| 091E05 | 492392 | PAK |
| 091E06 | 6094162 | PAK |
| 091E07 | 4158798 | PAK |
| 091E0B | 4024826 | PAK |
| 091E09 | 582633 | PAK |
| 091E10 | 1971583 | PAK |
| 091E11 | 5898406 | PAK |
| 091E12 | 424758 | PAK |
| 091F01 | 5185520 | PAK |
| 091F03 | 6122087 | PAK |
| 091F07 | 211737 | PAK |
| 091F08 | 759235 | PAK |
| 091F09 | 389523 | PAK |
| 091F10 | 1561328 | PAK |
| 091F11 | 1034419 | PAK |
| 091F12 | 5841748 | PAK |
| 091G01 | 1633402 | PAK |
| 091G04 | 1875814 | PAK |
| 091G05 | 3844960 | PAK |
| 091G06 | 765566 | PAK |
| 091G07 | 2802263 | PAK |
| 091G08 | 5655022 | PAK |
| 091G09 | 765565 | PAK |
| 091G10 | 4475739 | PAK |
| 091G11 | 5238576 | PAK |
| 091G12 | 5293459 | PAK |
| 091H01 | 3176678 | PAK |
| 091H03 | 3707444 | PAK |
| 091H06 | 346680 | PAK |
| 091H07 | 30512 | PAK |
| 091H08 | 762969 | PAK |
| 091H11 | 346680 | PAK |
| 092A01 | 1530164 | PAK |
| 092A04 | 5371146 | PAK |
| 092A07 | 1530164 | PAK |
| 092A08 | 3440009 | PAK |
| 092A10 | 1633344 | PAK |
| 092B02 | 6109594 | PAK |
| 092B06 | 4501135 | PAK |
| 092B08 | 1106685 | PAK |
| 092B09 | 5699595 | PAK |
| 092B11 | 845976 | PAK |
| 092B12 | 6073209 | PAK |
| 092C01 | 179397 | PAK |
| 092C06 | 3511416 | PAK |
| 092C10 | 2613913 | PAK |
| 092C12 | 346680 | PAK |
| 092D01 | 1866137 | PAK |
| 092D05 | 2355668 | PAK |
| 092D06 | 1102424 | PAK |
| 092D08 | 1138714 | PAK |
| 092D09 | 1895733 | PAK |
| 092D10 | 1761178 | PAK |
| 092D11 | 3627718 | PAK |
| 092D12 | 4158888 | PAK |
| 092E01 | 465774 | PAK |
| 092E03 | 2379175 | PAK |
| 092E04 | 4158885 | PAK |
| 092E06 | 645041 | PAK |

TABLE 3-continued

| Mutant Name | Insertion Point | host strain |
|---|---|---|
| 092E07 | 5499578 | PAK |
| 092E08 | 1084294 | PAK |
| 092E09 | 3488035 | PAK |
| 092E10 | 1901430 | PAK |
| 092E12 | 645041 | PAK |
| 092F01 | 6109967 | PAK |
| 092F02 | 1548870 | PAK |
| 092F03 | 3392116 | PAK |
| 092F04 | 2978707 | PAK |
| 092F06 | 3720645 | PAK |
| 092F07 | 6109967 | PAK |
| 092F08 | 5851968 | PAK |
| 092F09 | 3949483 | PAK |
| 092F11 | 1526152 | PAK |
| 092G01 | 3949482 | PAK |
| 092G02 | 376353 | PAK |
| 092G03 | 2922092 | PAK |
| 092G04 | 3899547 | PAK |
| 092G06 | 2503087 | PAK |
| 092G08 | 2922084 | PAK |
| 092H01 | 1654209 | PAK |
| 092H04 | 2531522 | PAK |
| 092H05 | 6192708 | PAK |
| 092H07 | 485973 | PAK |
| 092H09 | 5371147 | PAK |
| 092H10 | 1372356 | PAK |
| 093A01 | 5554286 | PAK |
| 093A05 | 5866519 | PAK |
| 093A08 | 6091283 | PAK |
| 093A09 | 3577646 | PAK |
| 093A10 | 969610 | PAK |
| 093A11 | 5866519 | PAK |
| 093A12 | 4896654 | PAK |
| 093B02 | 6082860 | PAK |
| 093B04 | 1683592 | PAK |
| 093B05 | 5007967 | PAK |
| 093B07 | 3825317 | PAK |
| 093B08 | 2333166 | PAK |
| 093B12 | 5279267 | PAK |
| 093C02 | 5680917 | PAK |
| 093C04 | 5189665 | PAK |
| 093C05 | 4027323 | PAK |
| 093C06 | 3659821 | PAK |
| 093C09 | 1909358 | PAK |
| 093C11 | 4027323 | PAK |
| 093D01 | 1659865 | PAK |
| 093D02 | 864790 | PAK |
| 093D03 | 2830872 | PAK |
| 093D04 | 5166142 | PAK |
| 093D06 | 4396748 | PAK |
| 093D07 | 5375474 | PAK |
| 093D09 | 1874931 | PAK |
| 093D10 | 6203645 | PAK |
| 093D11 | 13290t0 | PAK |
| 093E02 | 4810959 | PAK |
| 093E05 | 528927 | PAK |
| 093E07 | 411617 | PAK |
| 093E08 | 4211245 | PAK |
| 093E09 | 779446 | PAK |
| 093E11 | 5289271 | PAK |
| 093F03 | 2595222 | PAK |
| 093F04 | 5887575 | PAK |
| 093F05 | 5425500 | PAK |
| 093F07 | 3749963 | PAK |
| 093F08 | 513805 | PAK |
| 093F09 | 2595222 | PAK |
| 093F10 | 5887576 | PAK |
| 093F11 | 2531724 | PAK |
| 093G02 | 3226870 | PAK |
| 093G03 | 3488032 | PAK |
| 093G04 | 5292830 | PAK |
| 093G06 | 6203645 | PAK |
| 093G07 | 3225870 | PAK |
| 093G11 | 6203645 | PAK |
| 093G12 | 3410232 | PAK |
| 093H02 | 3226870 | PAK |
| 093H03 | 3589486 | PAK |
| 093H04 | 5836582 | PAK |
| 093H05 | 831017 | PAK |
| 093H06 | 402954 | PAK |
| 093H07 | 103662 | PAK |
| 093H08 | 648754 | PAK |
| 093H09 | 5635652 | PAK |
| 093H10 | 1895733 | PAK |
| 093H11 | 831017 | PAK |
| 094A01 | 5903514 | PAK |
| 094A03 | 3986218 | PAK |
| 094A04 | 2545386 | PAK |
| 094A06 | 4419800 | PAK |
| 094A09 | 3986218 | PAK |
| 094A11 | 1101735 | PAK |
| 094A12 | 4419800 | PAK |
| 094B01 | 5228063 | PAK |
| 094B02 | 4739899 | PAK |
| 094B04 | 3825260 | PAK |
| 094B05 | 3622968 | PAK |
| 094B06 | 2726912 | PAK |
| 094B08 | 426314 | PAK |
| 094B09 | 3061193 | PAK |
| 094B11 | 6065895 | PAK |
| 094C01 | 3403301 | PAK |
| 094C02 | 571133 | PAK |
| 094C03 | 5381585 | PAK |
| 094C04 | 5229133 | PAK |
| 094C05 | 2157836 | PAK |
| 094C06 | 2271124 | PAK |
| 094C07 | 2216040 | PAK |
| 094C08 | 2285867 | PAK |
| 094C09 | 5381585 | PAK |
| 094C10 | 5229133 | PAK |
| 094C12 | 3253777 | PAK |
| 094D02 | 3107601 | PAK |
| 094D03 | 2729064 | PAK |
| 094D04 | 3114256 | PAK |
| 094D05 | 255453 | PAK |
| 094D06 | 2403324 | PAK |
| 094D07 | 5141676 | PAK |
| 094D08 | 4431820 | PAK |
| 094D09 | 661246 | PAK |
| 094D11 | 255453 | PAK |
| 094D12 | 2403324 | PAK |
| 094E01 | 2925440 | PAK |
| 094E02 | 2403324 | PAK |
| 094E03 | 3479353 | PAK |
| 094E04 | 1003206 | PAK |
| 094E05 | 6010999 | PAK |
| 094E06 | 4398217 | PAK |
| 094E07 | 1844309 | PAK |
| 094E08 | 580853 | PAK |
| 094E09 | 2661331 | PAK |
| 094E10 | 3908456 | PAK |
| 094E11 | 956511 | PAK |
| 094E12 | 1764262 | PAK |
| 094F01 | 1403687 | PAK |
| 094F02 | 5787723 | PAK |
| 094F03 | 4601560 | PAK |
| 094F04 | 330763 | PAK |
| 094F05 | 6203591 | PAK |
| 094F06 | 4639566 | PAK |
| 094F07 | 4398164 | PAK |
| 094F08 | 5787723 | PAK |
| 094F09 | 4749329 | PAK |
| 094F12 | 362257 | PAK |
| 094G01 | 2459837 | PAK |
| 094G03 | 1716441 | PAK |
| 094G04 | 6179905 | PAK |
| 094G06 | 754721 | PAK |
| 094G07 | 780917 | PAK |
| 094G08 | 4600754 | PAK |
| 094G09 | 1715441 | PAK |
| 094G10 | 1321087 | PAK |
| 094G11 | 4377878 | PAK |
| 094G12 | 5619103 | PAK |
| 094H01 | 1025325 | PAK |

TABLE 3-continued

| Mutant Name | Insertion Point | host strain |
|---|---|---|
| 094H03 | 5299440 | PAK |
| 094H04 | 5995139 | PAK |
| 094H06 | 3018705 | PAK |
| 094H07 | 5947959 | PAK |
| 094H08 | 5732970 | PAK |
| 094H09 | 1471272 | PAK |
| 094H11 | 3018705 | PAK |
| 095A01 | 4558168 | PAK |
| 095A02 | 6104055 | PAK |
| 095A03 | 182047 | PAK |
| 095A05 | 5398247 | PAK |
| 095A06 | 5932951 | PAK |
| 095A08 | 182047 | PAK |
| 095A09 | 182052 | PAK |
| 095B01 | 5436767 | PAK |
| 095B02 | 5768971 | PAK |
| 095B03 | 486920 | PAK |
| 095B06 | 42639121 | PAK |
| 095B07 | 5436767 | PAK |
| 095B08 | 3438217 | PAK |
| 095B10 | 1286952 | PAK |
| 095B12 | 307311 | PAK |
| 095C01 | 2393315 | PAK |
| 095C04 | 526166 | PAK |
| 095C06 | 5938968 | PAK |
| 095C08 | 4460260 | PAK |
| 095C09 | 487643 | PAK |
| 095C10 | 4029458 | PAK |
| 095C11 | 3050694 | PAK |
| 095D01 | 5401444 | PAK |
| 095D03 | 2936842 | PAK |
| 095C06 | 1232844 | PAK |
| 095C11 | 1232846 | PAK |
| 095E02 | 5482215 | PAK |
| 095E03 | 3915316 | PAK |
| 095E04 | 6117736 | PAK |
| 095E05 | 5897802 | PAK |
| 095E06 | 4404169 | PAK |
| 095E09 | 3915316 | PAK |
| 095E10 | 5160431 | PAK |
| 095E11 | 4128331 | PAK |
| 095E12 | 2922937 | PAK |
| 095F01 | 5124369 | PAK |
| 095F02 | 452065 | PAK |
| 095F03 | 5725186 | PAK |
| 095F05 | 5421427 | PAK |
| 095F06 | 2720844 | PAK |
| 095F07 | 6122018 | PAK |
| 095F08 | 2724808 | PAK |
| 095F09 | 5929690 | PAK |
| 095F11 | 3166 | PAK |
| 095F12 | 2720845 | PAK |
| 095G01 | 4119115 | PAK |
| 095G02 | 3919729 | PAK |
| 095G03 | 2272158 | PAK |
| 095G05 | 1242650 | PAK |
| 095G07 | 3635245 | PAK |
| 095G09 | 3431893 | PAK |
| 095G10 | 2895537 | PAK |
| 095G11 | 1003203 | PAK |
| 095H03 | 159928 | PAK |
| 095H04 | 4113337 | PAK |
| 095H11 | 6109189 | PAK |
| 096A01 | 530428 | PAK |
| 096A03 | 4389578 | PAK |
| 096A04 | 3040962 | PAK |
| 096A06 | 531720 | PAK |
| 096A07 | 5492589 | PAK |
| 096A08 | 1434589 | PAK |
| 096A09 | 1381795 | PAK |
| 096A10 | 1382253 | PAK |
| 096A11 | 5493498 | PAK |
| 096A12 | 530707 | PAK |
| 096B01 | 1433889 | PAK |
| 096B02 | 4153460 | PAK |
| 096B03 | 531792 | PAK |
| 096B04 | 297231 | PAK |

TABLE 3-continued

| Mutant Name | Insertion Point | host strain |
|---|---|---|
| 096B05 | 2722413 | PAK |
| 096B06 | 217396 | PAK |
| 096B07 | 1807000 | PAK |
| 096B09 | 5732334 | PAK |
| 096B10 | 3305794 | PAK |
| 096B11 | 4160781 | PAK |
| 096B12 | 478140 | PAK |
| 096C01 | 2124731 | PAK |
| 096C02 | 6157287 | PAK |
| 096C03 | 432404 | PAK |
| 096C04 | 3375066 | PAK |
| 096C05 | 3582397 | PAK |
| 096C06 | 1556031 | PAK |
| 096C09 | 1236494 | PAK |
| 096C10 | 1082081 | PAK |
| 096C12 | 2921847 | PAK |
| 096D01 | 5278037 | PAK |
| 096D02 | 4691929 | PAK |
| 096D03 | 1312761 | PAK |
| 096D05 | 3766331 | PAK |
| 096D06 | 3618831 | PAK |
| 096D08 | 3288101 | PAK |
| 096D09 | 3393370 | PAK |
| 096D10 | 5451697 | PAK |
| 096D11 | 2545588 | PAK |
| 096D12 | 435401 | PAK |
| 096E01 | 5559527 | PAK |
| 096E02 | 6136512 | PAK |
| 096E03 | 6085113 | PAK |
| 096E04 | 3552384 | PAK |
| 096E05 | 71489 | PAK |
| 096E07 | 3364637 | PAK |
| 096E08 | 1031827 | PAK |
| 096E09 | 4439932 | PAK |
| 096E10 | 5974070 | PAK |
| 096E12 | 5897198 | PAK |
| 096F01 | 6090356 | PAK |
| 096F02 | 4623990 | PAK |
| 096F04 | 3001077 | PAK |
| 096F05 | 582026 | PAK |
| 096F06 | 2113721 | PAK |
| 096F07 | 6177153 | PAK |
| 096F08 | 522311 | PAK |
| 096F09 | 2480453 | PAK |
| 096F10 | 3967630 | PAK |
| 096F11 | 5463589 | PAK |
| 096F12 | 1384430 | PAK |
| 096G02 | 5934531 | PAK |
| 096G03 | 831797 | PAK |
| 096G04 | 1834383 | PAK |
| 096G05 | 341113 | PAK |
| 096G07 | 5069732 | PAK |
| 096G08 | 5673352 | PAK |
| 096G09 | 5603275 | PAK |
| 096G10 | 3748246 | PAK |
| 096G11 | 2498661 | PAK |
| 096G12 | 4378950 | PAK |
| 096H01 | 198769 | PAK |
| 096H05 | 1139969 | PAK |
| 096H06 | 2638223 | PAK |
| 096H08 | 3696870 | PAK |
| 096H11 | 395319 | PAK |
| 097A03 | 2474711 | PAK |
| 097A04 | 1555200 | PAK |
| 097A05 | 1807650 | PAK |
| 097A08 | 1832131 | PAK |
| 097B01 | 762446 | PAK |
| 097B03 | 5817828 | PAK |
| 097B04 | 5920564 | PAK |
| 097B05 | 4811110 | PAK |
| 097B06 | 1511755 | PAK |
| 097B07 | 4837348 | PAK |
| 097B09 | 5981470 | PAK |
| 097B10 | 1870245 | PAK |
| 097B12 | 761330 | PAK |
| 097C01 | 3318058 | PAK |
| 097C02 | 142689 | PAK |

TABLE 3-continued

| Mutant Name | Insertion Point | host strain |
|---|---|---|
| 097C03 | 2498661 | PAK |
| 097C04 | 4646707 | PAK |
| 097C05 | 4697711 | PAK |
| 097C08 | 2551153 | PAK |
| 097C10 | 2921847 | PAK |
| 097C11 | 3323555 | PAK |
| 097C12 | 2086538 | PAK |
| 097D01 | 5218314 | PAK |
| 097D02 | 2791096 | PAK |
| 097D03 | 317080 | PAK |
| 097D05 | 5859040 | PAK |
| 097D06 | 6126766 | PAK |
| 097D07 | 305994 | PAK |
| 097D08 | 2316080 | PAK |
| 097D10 | 845147 | PAK |
| 097E01 | 1939224 | PAK |
| 097E02 | 5947030 | PAK |
| 097E03 | 1455180 | PAK |
| 097E04 | 535406 | PAK |
| 097E06 | 92131 | PAK |
| 097E07 | 2661753 | PAK |
| 097E08 | 1534379 | PAK |
| 097E09 | 1923013 | PAK |
| 097E11 | 946716 | PAK |
| 097E12 | 1760054 | PAK |
| 097F01 | 1216981 | PAK |
| 097F02 | 5936250 | PAK |
| 097F04 | 4646060 | PAK |
| 097F05 | 3722558 | PAK |
| 097F06 | 416322 | PAK |
| 097F07 | 807168 | PAK |
| 097F08 | 3958066 | PAK |
| 097F09 | 6070674 | PAK |
| 097F10 | 1015065 | PAK |
| 097F11 | 2079313 | PAK |
| 097F12 | 2944727 | PAK |
| 097G01 | 3306943 | PAK |
| 097G02 | 4600978 | PAK |
| 097G03 | 201256 | PAK |
| 097G04 | 141180 | PAK |
| 097G05 | 668598 | PAK |
| 097G06 | 930508 | PAK |
| 097G07 | 4683964 | PAK |
| 097G08 | 804537 | PAK |
| 097G09 | 1169531 | PAK |
| 097G12 | 5864840 | PAK |
| 097H01 | 6144871 | PAK |
| 097H04 | 4128263 | PAK |
| 097H06 | 5715245 | PAK |
| 098A08 | 5186256 | PAK |
| 098B02 | 6098698 | PAK |
| 098C08 | 803486 | PAK |
| 098D03 | 5566011 | PAK |
| 098D10 | 1749654 | PAK |
| 098E06 | 4379310 | PAK |
| 098E07 | 5548222 | PAK |
| 100A10 | 5633329 | PAK |
| 100A12 | 2010887 | PAK |
| 100B01 | 4425203 | PAK |
| 100B05 | 38886 | PAK |
| 100B08 | 57542 | PAK |
| 100B09 | 4735712 | PAK |
| 100C02 | 2937464 | PAK |
| 100C04 | 2991465 | PAK |
| 100C05 | 2104886 | PAK |
| 100C07 | 3155126 | PAK |
| 100C10 | 4887907 | PAK |
| 100C11 | 4466283 | PAK |
| 100D02 | 1886005 | PAK |
| 100D07 | 1150859 | PAK |
| 100D08 | 6129850 | PAK |
| 100D10 | 3998375 | PAK |
| 100E02 | 5982874 | PAK |
| 100E04 | 3565977 | PAK |
| 100E07 | 5926607 | PAK |
| 100E09 | 5292694 | PAK |
| 100F02 | 1377709 | PAK |
| 100F03 | 1709857 | PAK |
| 100F04 | 3216674 | PAK |
| 100F06 | 1630473 | PAK |
| 100F07 | 5694215 | PAK |
| 100F11 | 2980997 | PAK |
| 100F12 | 5258731 | PAK |
| 100G02 | 3269100 | PAK |
| 100G03 | 3683024 | PAK |
| 100G04 | 1883147 | PAK |
| 100G06 | 5555224 | PAK |
| 100G08 | 72076 | PAK |
| 100G09 | 5681235 | PAK |
| 100G11 | 1005293 | PAK |
| 100G12 | 183767 | PAK |
| 100H02 | 978120 | PAK |
| 100H04 | 5281391 | PAK |
| 100H05 | 4556077 | PAK |
| 102A01 | 3452314 | PAK |
| 102A02 | 391703 | PAK |
| 102A03 | 3018408 | PAK |
| 102A06 | 4731956 | PAK |
| 102A07 | 2497716 | PAK |
| 102A08 | 174831 | PAK |
| 102A09 | 1854691 | PAK |
| 102A10 | 5517588 | PAK |
| 102A12 | 5498289 | PAK |
| 102B02 | 3210226 | PAK |
| 102B03 | 5995515 | PAK |
| 102B04 | 4274315 | PAK |
| 102B05 | 6088276 | PAK |
| 102B07 | 4549073 | PAK |
| 102B08 | 1513191 | PAK |
| 102B09 | 1157104 | PAK |
| 102B10 | 4299980 | PAK |
| 102C01 | 2893491 | PAK |
| 102C02 | 4707477 | PAK |
| 102C03 | 3579409 | PAK |
| 102C04 | 1993472 | PAK |
| 102C05 | 2191812 | PAK |
| 102012 | 2619663 | PAK |
| 105A02 | 3146111 | PAK |
| 105A03 | 2907711 | PAK |
| 105A04 | 5823917 | PAK |
| 105A05 | 674373 | PAK |
| 105A06 | 5447669 | PAK |
| 105A07 | 157380 | PAK |
| 105A08 | 4153081 | PAK |
| 105A09 | 167596 | PAK |
| 105A11 | 3786585 | PAK |
| 105A12 | 6218519 | PAK |
| 105B01 | 5228108 | PAK |
| 105B03 | 2920601 | PAK |
| 105B05 | 5475565 | PAK |
| 105B07 | 1260544 | PAK |
| 105B09 | 2027715 | PAK |
| 105B10 | 3727987 | PAK |
| 105B12 | 5035853 | PAK |
| 105C01 | 4006611 | PAK |
| 105C03 | 5393852 | PAK |
| 105C04 | 743777 | PAK |
| 105C05 | 3213906 | PAK |
| 105C07 | 3211243 | PAK |
| 105C08 | 1206226 | PAK |
| 105C09 | 2364618 | PAK |
| 105C10 | 4337751 | PAK |
| 105C12 | 6106838 | PAK |
| 105D01 | 2860132 | PAK |
| 105D02 | 3471740 | PAK |
| 105D03 | 4347642 | PAK |
| 105D04 | 3199505 | PAK |
| 105D05 | 5121607 | PAK |
| 105D07 | 3131652 | PAK |
| 105D08 | 6112599 | PAK |
| 105D09 | 3565902 | PAK |
| 105D10 | 3786778 | PAK |
| 105E01 | 3452071 | PAK |
| 105E02 | 5478080 | PAK |

TABLE 3-continued

| Mutant Name | Insertion Point | host strain |
|---|---|---|
| 105E03 | 1997012 | PAK |
| 105E04 | 5789330 | PAK |
| 105E05 | 5321880 | PAK |
| 105E06 | 5439593 | PAK |
| 105E07 | 5539005 | PAK |
| 105E09 | 1206904 | PAK |
| 105E10 | 3782392 | PAK |
| 105E11 | 3009917 | PAK |
| 105E12 | 1407481 | PAK |
| 105F01 | 5097680 | PAK |
| 105F02 | 4204370 | PAK |
| 105F03 | 662194 | PAK |
| 105F04 | 5023097 | PAK |
| 105F07 | 4416494 | PAK |
| 105F08 | 2423594 | PAK |
| 105F09 | 6215642 | PAK |
| 105F10 | 3950671 | PAK |
| 105F11 | 4619077 | PAK |
| 105F12 | 5901833 | PAK |
| 105G01 | 1027128 | PAK |
| 105G02 | 1306879 | PAK |
| 105G03 | 1430019 | PAK |
| 105G04 | 910676 | PAK |
| 105G05 | 4819647 | PAK |
| 105G07 | 4111311 | PAK |
| 105G10 | 5471094 | PAK |
| 105G11 | 4671383 | PAK |
| 105G12 | 586791 | PAK |
| 105H01 | 3738509 | PAK |
| 105H02 | 5408525 | PAK |
| 105H03 | 543473 | PAK |
| 105H04 | 4274328 | PAK |
| 105H05 | 5310625 | PAK |
| 105H07 | 418998 | PAK |
| 105H08 | 4221177 | PAK |
| 105H09 | 5395031 | PAK |
| 105H10 | 202993 | PAK |
| 106A02 | 1406242 | PAK |
| 106A05 | 4041900 | PAK |
| 106A12 | 1694196 | PAK |
| 106B01 | 3329053 | PAK |
| 106B03 | 5479369 | PAK |
| 106B04 | 4058977 | PAK |
| 106B05 | 5773245 | PAK |
| 106B06 | 4364910 | PAK |
| 106B07 | 3982497 | PAK |
| 106B08 | 5571575 | PAK |
| 106C02 | 4617184 | PAK |
| 106C06 | 3422994 | PAK |
| 106C07 | 3690841 | PAK |
| 106C08 | 3946546 | PAK |
| 106C09 | 4628841 | PAK |
| 106C10 | 1638040 | PAK |
| 106C11 | 5887396 | PAK |
| 106D02 | 4908894 | PAK |
| 106D05 | 1294065 | PAK |
| 106D06 | 4911795 | PAK |
| 106D07 | 3929164 | PAK |
| 106D09 | 1969450 | PAK |
| 106D12 | 5385089 | PAK |
| 106E03 | 2876519 | PAK |
| 106E04 | 3882516 | PAK |
| 106E07 | 5787794 | PAK |
| 106E10 | 736975 | PAK |
| 106F03 | 3304927 | PAK |
| 106F04 | 5157575 | PAK |
| 106F07 | 2795460 | PAK |
| 106F10 | 374804 | PAK |
| 106F11 | 5405974 | PAK |
| 106G01 | 4134527 | PAK |
| 106G04 | 1030460 | PAK |
| 106G06 | 1007081 | PAK |
| 106G07 | 326921 | PAK |
| 106G08 | 6047689 | PAK |
| 106G09 | 4853252 | PAK |
| 106H01 | 5974342 | PAK |
| 106H02 | 4475257 | PAK |
| 106H03 | 2824275 | PAK |
| 106H04 | 489476 | PAK |
| 106H05 | 2438922 | PAK |
| 106H07 | 489641 | PAK |
| 106H10 | 4420124 | PAK |
| 107A01 | 2870293 | PAK |
| 107A02 | 3993035 | PAK |
| 107A04 | 6195229 | PAK |
| 107A05 | 5148190 | PAK |
| 107A06 | 1660062 | PAK |
| 107A09 | 5700254 | PAK |
| 107A10 | 1617888 | PAK |
| 107A11 | 4365702 | PAK |
| 107A12 | 4572873 | PAK |
| 107B01 | 603009 | PAK |
| 107B02 | 6109633 | PAK |
| 107B04 | 4365857 | PAK |
| 107B05 | 524124 | PAK |
| 107B06 | 5673352 | PAK |
| 107B07 | 5771521 | PAK |
| 107B08 | 5219074 | PAK |
| 107B10 | 5216364 | PAK |
| 107B11 | 2142674 | PAK |
| 107B12 | 2879083 | PAK |
| 107C01 | 799610 | PAK |
| 107C02 | 3527748 | PAK |
| 107C04 | 5832135 | PAK |
| 107C05 | 6203764 | PAK |
| 107C06 | 4126143 | PAK |
| 107C07 | 4340714 | PAK |
| 107C09 | 2819728 | PAK |
| 107C11 | 3161156 | PAK |
| 107D01 | 2536757 | PAK |
| 107D03 | 1034469 | PAK |
| 107D04 | 5384777 | PAK |
| 107D08 | 1847078 | PAK |
| 107D09 | 5122549 | PAK |
| 107E01 | 1291924 | PAK |
| 107E02 | 2899720 | PAK |
| 107E03 | 1654413 | PAK |
| 107E04 | 5478844 | PAK |
| 107E05 | 2173316 | PAK |
| 107E06 | 3237320 | PAK |
| 107E07 | 1075076 | PAK |
| 107E08 | 32999212 | PAK |
| 107E09 | 3227200 | PAK |
| 107E10 | 4827607 | PAK |
| 107E11 | 3987706 | PAK |
| 107E12 | 1867945 | PAK |
| 107F01 | 4795437 | PAK |
| 107F03 | 2922973 | PAK |
| 107F04 | 460916 | PAK |
| 107F05 | 4974335 | PAK |
| 107F06 | 3222230 | PAK |
| 107F07 | 2948029 | PAK |
| 107F09 | 3579778 | PAK |
| 107F10 | 1442186 | PAK |
| 107F11 | 2699147 | PAK |
| 107F12 | 2728727 | PAK |
| 107G01 | 2880186 | PAK |
| 107G03 | 1325920 | PAK |
| 107G04 | 76728 | PAK |
| 107G05 | 3765920 | PAK |
| 107G06 | 22245 | PAK |
| 107G08 | 626945 | PAK |
| 107G10 | 3953527 | PAK |
| 107G12 | 4007303 | PAK |
| 107H02 | 6ll4720 | PAK |
| 107H03 | 6234109 | PAK |
| 107H05 | 5772985 | PAK |
| 107H06 | 4122563 | PAK |
| 107H07 | 4230542 | PAK |
| 107H10 | 2071810 | PAK |
| 108A01 | 877575 | PAK |
| 108A02 | 1263274 | PAK |
| 108A03 | 689978 | PAK |
| 108A04 | 2626148 | PAK |

TABLE 3-continued

| Mutant Name | Insertion Point | host strain |
| --- | --- | --- |
| 108A05 | 2383145 | PAK |
| 108A06 | 239961 | PAK |
| 108A07 | 2058525 | PAK |
| 108A08 | 5189496 | PAK |
| 108A09 | 4480696 | PAK |
| 108A10 | 3765893 | PAK |
| 108B02 | 2320898 | PAK |
| 108B04 | 5984775 | PAK |
| 108B06 | 5588598 | PAK |
| 108B07 | 5737004 | PAK |
| 108B08 | 1913207 | PAK |
| 108B09 | 5632702 | PAK |
| 108B10 | 681527 | PAK |
| 108C03 | 4451825 | PAK |
| 108C04 | 6084560 | PAK |
| 108C05 | 3498688 | PAK |
| 108C06 | 3318091 | PAK |
| 108C07 | 1818501 | PAK |
| 108C08 | 2590671 | PAK |
| 108C09 | 2825852 | PAK |
| 108C10 | 5094238 | PAK |
| 108C11 | 5087265 | PAK |
| 108C12 | 206549 | PAK |
| 108D02 | 2977831 | PAK |
| 108D03 | 6101833 | PAK |
| 108D04 | 2110665 | PAK |
| 108D05 | 3638719 | PAK |
| 108D06 | 1509801 | PAK |
| 108D07 | 397420 | PAK |
| 108D08 | 2296087 | PAK |
| 108D09 | 3819312 | PAK |
| 108D10 | 3819312 | PAK |
| 108D11 | 1034469 | PAK |
| 108E02 | 5251812 | PAK |
| 108E03 | 4405948 | PAK |
| 108E05 | 4158182 | PAK |
| 108E07 | 4647900 | PAK |
| 108E08 | 5263109 | PAK |
| 108E10 | 122843 | PAK |
| 108E11 | 919489 | PAK |
| 108F01 | 4388164 | PAK |
| 108F03 | 1445976 | PAK |
| 108F04 | 5272678 | PAK |
| 108F05 | 892822 | PAK |
| 108F06 | 399656 | PAK |
| 108F07 | 319164 | PAK |
| 108F08 | 5815675 | PA K |
| 108F10 | 1832539 | PAK |
| 108F11 | 6032332 | PAK |
| 108F12 | 2972451 | PAK |
| 108G01 | 3455405 | PAK |
| 108G02 | 6149336 | PAK |
| 108G03 | 1431971 | PAK |
| 108G04 | 2310244 | PAK |
| 108G09 | 4707429 | PAK |
| 108G10 | 4516494 | PAK |
| 108G11 | 4111230 | PAK |
| 108G12 | 5919111 | PAK |
| 108H01 | 5079442 | PAK |
| 108H02 | 4029385 | PAK |
| 108H03 | 4132821 | PAK |
| 108H04 | 4459263 | PAK |
| 108H05 | 2113085 | PAK |
| 108H06 | 6166433 | PAK |
| 108H07 | 5954426 | PAK |
| 108H08 | 4315226 | PAK |
| 108H09 | 3412809 | PAK |
| 108H10 | 1348174 | PAK |
| 109A01 | 1163504 | PAK |
| 109A02 | 464685 | PAK |
| 109A03 | 2314352 | PAK |
| 109A04 | 5076765 | PAK |
| 109A06 | 3634921 | PAK |
| 109A08 | 3011480 | PAK |
| 109A09 | 2649129 | PAK |
| 109A12 | 572961 | PAK |
| 109B01 | 2994565 | PAK |
| 109B02 | 4134518 | PAK |
| 109B03 | 1168009 | PAK |
| 109B04 | 4403019 | PAK |
| 109B05 | 5148025 | PAK |
| 109B06 | 1360365 | PAK |
| 109B11 | 4834239 | PAK |
| 109C03 | 5082885 | PAK |
| 109C04 | 5125455 | PAK |
| 109C05 | 963281 | PAK |
| 109C07 | 4098351 | PAK |
| 109C08 | 1906772 | PAK |
| 109C10 | 554592 | PAK |
| 109C11 | 1712727 | PAK |
| 109D01 | 2978766 | PAK |
| 109D02 | 5739740 | PAK |
| 109D03 | 4111348 | PAK |
| 109D04 | 3348537 | PAK |
| 109D05 | 1653528 | PAK |
| 109D06 | 2586676 | PAK |
| 109D08 | 2495337 | PAK |
| 109D09 | 1244933 | PAK |
| 109D10 | 3440332 | PAK |
| 109D11 | 5081696 | PAK |
| 109D12 | 1414688 | PAK |
| 109E06 | 2869404 | PAK |
| 109E07 | 6119366 | PAK |
| 109E08 | 4438182 | PAK |
| 109E10 | 3462237 | PAK |
| 109E11 | 5978911 | PAK |
| 109F03 | 5164542 | PAK |
| 109F06 | 2612728 | PAK |
| 109F07 | 1431698 | PAK |
| 109F09 | 5966111 | PAK |
| 109F10 | 3979443 | PAK |
| 109F11 | 1895148 | PAK |
| 109F12 | 2502205 | PAK |
| 109G02 | 3405537 | PAK |
| 109G03 | 5302319 | PAK |
| 109G04 | 3421514 | PAK |
| 109G05 | 2241880 | PAK |
| 109G06 | 300721 | PAK |
| 109G08 | 974134 | PAK |
| 109G11 | 3672688 | PAK |
| 109G12 | 5447669 | PAK |
| 109H07 | 751625 | PAK |
| 109H08 | 3790156 | PAK |
| 109H09 | 3017497 | PAK |
| 109H10 | 3221700 | PAK |
| 109H11 | 395319 | PAK |
| 110A05 | 4507307 | PAK |
| 110A06 | 3634921 | PAK |
| 110A07 | 4867606 | PAK |
| 110A09 | 2649129 | PAK |
| 110B02 | 4134518 | PAK |
| 110B03 | 1168009 | PAK |
| 110B04 | 4403019 | PAK |
| 110B05 | 5148025 | PAK |
| 110B07 | 1925210 | PAK |
| 110B08 | 548578 | PAK |
| 110B09 | 283937 | PAK |
| 110B11 | 1281003 | PAK |
| 110C03 | 4564149 | PAK |
| 110C04 | 1995686 | PAK |
| 110C05 | 6030412 | PAK |
| 110C06 | 5702292 | PAK |
| 110C07 | 5929333 | PAK |
| 110C08 | 1906772 | PAK |
| 110C09 | 4379214 | PAK |
| 110C10 | 156178 | PAK |
| 110C11 | 5905997 | PAK |
| 110D02 | 5739738 | PAK |
| 110D03 | 4111347 | PAK |
| 110D07 | 2602778 | PAK |
| 110D08 | 2495337 | PAK |
| 110D09 | 1244933 | PAK |
| 110D11 | 137127 | PAK |
| 110E03 | 2758060 | PAK |

TABLE 3-continued

| Mutant Name | Insertion Point | host strain |
|---|---|---|
| 110E05 | 3791661 | PAK |
| 110E06 | 5648127 | PAK |
| 110E08 | 2552595 | PAK |
| 110E10 | 3462237 | PAK |
| 110E11 | 5978911 | PAK |
| 110F03 | 5164542 | PAK |
| 110F04 | 965825 | PAK |
| 110F06 | 2612728 | PAK |
| 110F08 | 2457016 | PAK |
| 110F10 | 3979443 | PAK |
| 110F12 | 2502205 | PAK |
| 110G01 | 4067217 | PAK |
| 110G03 | 5302319 | PAK |
| 110G05 | 2241880 | PAK |
| 110G06 | 300720 | PAK |
| 110G07 | 1060985 | PAK |
| 110G09 | 1562812 | PAK |
| 110G10 | 2368017 | PAK |
| 110G11 | 3672587 | PAK |
| 110H03 | 3788343 | PAK |
| 110H06 | 2131688 | PAK |
| 110H07 | 3251479 | PAK |
| 110H08 | 3694984 | PAK |
| 110H11 | 395319 | PAK |
| 111A01 | 1996840 | PAK |
| 111A02 | 5747812 | PAK |
| 111A06 | 5633087 | PAK |
| 111A07 | 1384430 | PAK |
| 111A08 | 3051085 | PAK |
| 111B02 | 5406824 | PAK |
| 111B05 | 5768191 | PAK |
| 111B09 | 5980113 | PAK |
| 111B10 | 1232258 | PAK |
| 111B11 | 5529641 | PAK |
| 111D01 | 1668774 | PAK |
| 111D02 | 3011480 | PAK |
| 111D04 | 3363275 | PAK |
| 111D06 | 5051027 | PAK |
| 111D08 | 3270578 | PAK |
| 111D09 | 3264267 | PAK |
| 111D11 | 4110080 | PAK |
| 111E01 | 5032839 | PAK |
| 111E04 | 4169325 | PAK |
| 111E05 | 4227321 | PAK |
| 111E06 | 1015135 | PAK |
| 111E07 | 3582879 | PAK |
| 111E08 | 2613746 | PAK |
| 111E10 | 435933 | PAK |
| 111E11 | 5580139 | PAK |
| 111E12 | 1364583 | PAK |
| 111F02 | 5871907 | PAK |
| 111F03 | 2831315 | PAK |
| 111F04 | 1555200 | PAK |
| 111F05 | 5130353 | PAK |
| 111F07 | 3064370 | PAK |
| 111F08 | 2082204 | PAK |
| 111F10 | 620059 | PAK |
| 111F11 | 4108350 | PAK |
| 111F12 | 5145266 | PAK |
| 111G01 | 5437249 | PAK |
| 111G03 | 5319061 | PAK |
| 111G04 | 3900522 | PAK |
| 111G05 | 2698040 | PAK |
| 111G06 | 5290709 | PAK |
| 111G10 | 4721220 | PAK |
| 111G11 | 1932663 | PAK |
| 111H03 | 3508386 | PAK |
| 111H04 | 803486 | PAK |
| 111H09 | 1494852 | PAK |
| 111H10 | 2014466 | PAK |
| 112A01 | 3779652 | PAK |
| 112A02 | 1561153 | PAK |
| 112A03 | 5426548 | PAK |
| 112A04 | 1532975 | PAK |
| 112A06 | 2466447 | PAK |
| 112A07 | 3624757 | PAK |
| 112A09 | 4174882 | PAK |
| 112A10 | 1353512 | PAK |
| 112A11 | 4859430 | PAK |
| 112B02 | 1089019 | PAK |
| 112B04 | 2239498 | PAK |
| 112B07 | 4404806 | PAK |
| 112B08 | 5548347 | PAK |
| 112B09 | 5602049 | PAK |
| 112B11 | 2803663 | PAK |
| 112B12 | 467201 | PAK |
| 112C01 | 2183658 | PAK |
| 112C04 | 3845716 | PAK |
| 112C06 | 3589068 | PAK |
| 112C07 | 4593704 | PAK |
| 112C09 | 4978969 | PAK |
| 112C12 | 1760054 | PAK |
| 112D02 | 2812641 | PAK |
| 112D03 | 256968 | PAK |
| 112D04 | 5385935 | PAK |
| 112D05 | 6230328 | PAK |
| 112D06 | 2355497 | PAK |
| 112D07 | 3788320 | PAK |
| 112D08 | 2951558 | PAK |
| 112D10 | 544371 | PAK |
| 112D11 | 5086244 | PAK |
| 112E02 | 4436804 | PAK |
| 112E05 | 4435404 | PAK |
| 112E07 | 5128726 | PAK |
| 112E09 | 192388 | PAK |
| 112E10 | 3887007 | PAK |
| 112E12 | 305807 | PAK |
| 112F01 | 2642411 | PAK |
| 112F03 | 4847111 | PAK |
| 112F05 | 3272923 | PAK |
| 112F06 | 6230327 | PAK |
| 112G01 | 4966562 | PAK |
| 112G03 | 1630609 | PAK |
| 112G05 | 1701238 | PAK |
| 112G07 | 1082725 | PAK |
| 112G08 | 2633733 | PAK |
| 112G11 | 3049617 | PAK |
| 112G12 | 5746379 | PAK |
| 112H01 | 5064126 | PAK |
| 112H02 | 2561135 | PAK |
| 112H03 | 2125457 | PAK |
| 112H04 | 1501154 | PAK |
| 112H05 | 6030636 | PAK |
| 112H06 | 2697499 | PAK |
| 112H07 | 2789497 | PAK |
| 112H09 | 1433338 | PAK |
| 112H11 | 395318 | PAK |
| 113A01 | 4267361 | PAK |
| 113A02 | 5712045 | PAK |
| 113A04 | 4727927 | PAK |
| 113A06 | 5372033 | PAK |
| 113A08 | 2354515 | PAK |
| 113A11 | 803486 | PAK |
| 113B02 | 4967527 | PAK |
| 113B03 | 1030389 | PAK |
| 113B05 | 683084 | PAK |
| 113B06 | 5634258 | PAK |
| 113B09 | 5094981 | PAK |
| 113B10 | 307524 | PAK |
| 113B11 | 3400907 | PAK |
| 113B12 | 5031005 | PAK |
| 113C01 | 189915 | PAK |
| 113C02 | 6187058 | PAK |
| 113C03 | 5954488 | PAK |
| 113C05 | 190350 | PAK |
| 113C06 | 3753549 | PAK |
| 113C08 | 5423318 | PAK |
| 113C09 | 6046780 | PAK |
| 113C10 | 5499271 | PAK |
| 113D01 | 3752919 | PAK |
| 113D02 | 3644386 | PAK |
| 113D03 | 3838670 | PA K |
| 113D05 | 5580549 | PAK |
| 113D06 | 4898887 | PAK |

TABLE 3-continued

| Mutant Name | Insertion Point | host strain |
|---|---|---|
| 113D07 | 4622957 | PAK |
| 113D08 | 5787514 | PAK |
| 113D09 | 4921747 | PAK |
| 113D10 | 515289 | PAK |
| 113D12 | 4891587 | PAK |
| 113E03 | 5240724 | PAK |
| 113E04 | 5398114 | PAK |
| 113E08 | 3319655 | PAK |
| 113E09 | 57232 | PAK |
| 113E10 | 1412997 | PAK |
| 113E11 | 5391998 | PAK |
| 113E12 | 4434747 | PAK |
| 113F01 | 1527902 | PAK |
| 113F02 | 5393730 | PAK |
| 113F03 | 3317982 | PAK |
| 113F04 | 536148 | PAK |
| 113F05 | 5556188 | PAK |
| 113F06 | 4898887 | PAK |
| 113F07 | 3120188 | PAK |
| 113F09 | 4595430 | PAK |
| 113F10 | 1296429 | PAK |
| 113F11 | 1583542 | PAK |
| 113F12 | 1053521 | PAK |
| 113G02 | 817821 | PAK |
| 113G03 | 3835225 | PAK |
| 113G04 | 3414144 | PAK |
| 113G05 | 4743664 | PAK |
| 113G07 | 2897186 | PAK |
| 113G10 | 2168773 | PAK |
| 113G11 | 4335633 | PAK |
| 113H01 | 2018084 | PAK |
| 113H02 | 2743332 | PAK |
| 113H03 | 2526344 | PAK |
| 113H04 | 2367240 | PAK |
| 113H05 | 3707698 | PAK |
| 113H06 | 3844818 | PAK |
| 113H07 | 646545 | PAK |
| 113H09 | 72074 | PAK |
| 113H10 | 4655974 | PAK |
| 114A02 | 1814139 | PAK |
| 114A03 | 1524872 | PAK |
| 114A04 | 1524872 | PAK |
| 114A05 | 5097936 | PAK |
| 114A06 | 2379222 | PAK |
| 114A07 | 2916569 | PAK |
| 114A08 | 265275 | PAK |
| 114A09 | 3490617 | PAK |
| 114A11 | 5947901 | PAK |
| 114B01 | 4154345 | PAK |
| 114B02 | 3380555 | PAK |
| 114B03 | 3380556 | PAK |
| 114B04 | 4229635 | PAK |
| 114B05 | 4590326 | PAK |
| 114B06 | 4140179 | PAK |
| 114B07 | 206485 | PAK |
| 114B08 | 317243 | PAK |
| 114B10 | 4308507 | PAK |
| 114B11 | 4700060 | PAK |
| 114C01 | 4802308 | PAK |
| 114C02 | 1823063 | PAK |
| 114C03 | 4472975 | PAK |
| 114C04 | 5585743 | PAK |
| 114C05 | 4808708 | PAK |
| 114C06 | 5667685 | PAK |
| 114C07 | 3213476 | PAK |
| 114C08 | 1275444 | PAK |
| 114C09 | 4706883 | PAK |
| 114C10 | 4906313 | PAK |
| 114C12 | 993040 | PAK |
| 114D02 | 1812942 | PAK |
| 114D03 | 5642070 | PAK |
| 114D05 | 2498661 | PAK |
| 114D06 | 1277286 | PAK |
| 114D07 | 2893252 | PAK |
| 114D08 | 918090 | PAK |
| 114D10 | 1855738 | PAK |
| 114D11 | 5877908 | PAK |
| 114D12 | 4248408 | PAK |
| 114E01 | 2504284 | PAK |
| 114E02 | 1341154 | PAK |
| 114E04 | 4018663 | PAK |
| 114E05 | 6023743 | PAK |
| 114E06 | 1051049 | PAK |
| 114E08 | 2805183 | PAK |
| 114E09 | 5750561 | PAK |
| 114E10 | 2934676 | PAK |
| 114F01 | 3152978 | PAK |
| 114F03 | 2688374 | PAK |
| 114F04 | 4713147 | PAK |
| 114F05 | 2893168 | PAK |
| 114F07 | 2719832 | PAK |
| 114F08 | 4207165 | PAK |
| 114F11 | 4817596 | PAK |
| 114F12 | 3200787 | PAK |
| 114G03 | 3259309 | PAK |
| 114G05 | 734182 | PAK |
| 114G07 | 3939674 | PAK |
| 114G08 | 4387778 | PAK |
| 114G09 | 3375065 | PAK |
| 114G11 | 2878943 | PAK |
| 114H01 | 2620965 | PAK |
| 114H02 | 4394125 | PAK |
| 114H04 | 2757732 | PAK |
| 114H05 | 2089418 | PAK |
| 114H09 | 4424387 | PAK |
| 115A01 | 2876780 | PAK |
| 115A03 | 5194834 | PAK |
| 115A04 | 2013098 | PAK |
| 115A06 | 1801859 | PAK |
| 115A07 | 1801859 | PAK |
| 115A08 | 5225763 | PAK |
| 115A10 | 332199 | PAK |
| 115A12 | 4905491 | PAK |
| 115B01 | 5290425 | PAK |
| 115202 | 2903653 | PAK |
| 115B04 | 3653186 | PAK |
| 115B05 | 2639950 | PAK |
| 115B06 | 752714 | PAK |
| 115B10 | 5217873 | PAK |
| 115C04 | 190649 | PAK |
| 115C05 | 1916409 | PAK |
| 115C06 | 2320058 | PAK |
| 115C10 | 581698 | PAK |
| 115C12 | 4222292 | PAK |
| 115D01 | 2837570 | PAK |
| 115D02 | 2429248 | PAK |
| 115D04 | 5361223 | PAK |
| 115D05 | 2653649 | PAK |
| 115D06 | 1547530 | PAK |
| 115D11 | 2650300 | PAK |
| 115E01 | 1165115 | PAK |
| 115E03 | 2359332 | PAK |
| 115E05 | 4661340 | PAK |
| 115F04 | 284446 | PAK |
| 115F07 | 3861626 | PAK |
| 115F09 | 1575285 | PAK |
| 115F10 | 5939866 | PAK |
| 115F12 | 4344833 | PAK |
| 115G01 | 3642619 | PAK |
| 115G02 | 5365853 | PAK |
| 115G03 | 5928956 | PAK |
| 115G04 | 2745897 | PAK |
| 115G05 | 2521910 | PAK |
| 115G06 | 3019131 | PAK |
| 115G08 | 1034367 | PAK |
| 115G10 | 306435 | PAK |
| 115G11 | 4501025 | PAK |
| 115H04 | 541918 | PAK |
| 115H05 | 4451693 | PAK |
| 115H06 | 5953333 | PAK |
| 115H07 | 3210226 | PAK |
| 116A02 | 380079 | PAK |
| 116A04 | 4032652 | PAK |
| 116A05 | 3981474 | PAK |

TABLE 3-continued

| Mutant Name | Insertion Point | host strain |
|---|---|---|
| 116A07 | 4059459 | PAK |
| 116A08 | 4059459 | PAK |
| 116B01 | 6108826 | PAK |
| 116B02 | 4455104 | PAK |
| 116B03 | 3636514 | PAK |
| 116B04 | 5855701 | PAK |
| 116B05 | 5657416 | PAK |
| 116B06 | 2039724 | PAK |
| 116C01 | 2161954 | PAK |
| 116C03 | 5081696 | PAK |
| 116C05 | 4067261 | PAK |
| 116C06 | 855456 | PAK |
| 116C07 | 3429703 | PAK |
| 116C12 | 1010010 | PAK |
| 116D02 | 1952652 | PAK |
| 116D05 | 3429562 | PAK |
| 116D07 | 3735414 | PAK |
| 116D08 | 4495481 | PAK |
| 116D10 | 1801859 | PAK |
| 116D11 | 1801859 | PAK |
| 116E02 | 4042381 | PAK |
| 116E05 | 5435373 | PAK |
| 116E07 | 3445426 | PAK |
| 116E09 | 3209959 | PAK |
| 116E10 | 3209959 | PAK |
| 116F01 | 958346 | PAK |
| 116F02 | 4411714 | PAK |
| 116F03 | 4573238 | PAK |
| 116F05 | 5410627 | PAK |
| 116F06 | 5410627 | PAK |
| 116G02 | 1173665 | PAK |
| 116G03 | 2830303 | PAK |
| 116G04 | 1617471 | PAK |
| 115G05 | 2074358 | PAK |
| 116H01 | 3212064 | PAK |
| 116H02 | 5527227 | PAK |
| 116H03 | 1998133 | PAK |
| 116H04 | 4576086 | PAK |
| 116H05 | 24887 | PAK |
| 116H07 | 3827451 | PAK |
| 117A02 | 4493309 | PAK |
| 117A03 | 6046552 | PAK |
| 117A05 | 2307517 | PAK |
| 117A06 | 1046276 | PAK |
| 117A07 | 895050 | PAK |
| 117B01 | 3123527 | PAK |
| 117B03 | 1030389 | PAK |
| 117B04 | 2670082 | PAK |
| 117B05 | 916143 | PAK |
| 117B10 | 760224 | PAK |
| 117001 | 4405894 | PAK |
| 117004 | 2937824 | PAK |
| 117C05 | 6156485 | PAK |
| 117009 | 5863398 | PAK |
| 117D01 | 3137411 | PAK |
| 117D07 | 4038275 | PAK |
| 117E01 | 6217425 | PAK |
| 117E03 | 4690152 | PAK |
| 117E04 | 3079163 | PAK |
| 117E05 | 5916316 | PAK |
| 117E06 | 2097750 | PAK |
| 117E11 | 4304783 | PAK |
| 117F03 | 4697711 | PAK |
| 117F05 | 3003279 | PAK |
| 117F08 | 2058004 | PAK |
| 117G01 | 4050608 | PAK |
| 117G02 | 3001253 | PAK |
| 117G03 | 877131 | PAK |
| 117G04 | 2965246 | PAK |
| 117G07 | 648563 | PAK |
| 117H02 | 5732667 | PAK |
| 117H04 | 998397 | PAK |
| 117H06 | 4423608 | PAK |
| 117H10 | 685112 | PAK |
| 118A01 | 5967821 | PAK |
| 118A04 | 3146865 | PAK |
| 118A06 | 145513 | PAK |
| 118A11 | 3623215 | PAK |
| 118A12 | 6104538 | PAK |
| 118B03 | 4676635 | PAK |
| 118B05 | 3731380 | PAK |
| 118B06 | 1279661 | PAK |
| 118B07 | 3167549 | PAK |
| 118B08 | 1783525 | PAK |
| 118B09 | 72576 | PAK |
| 118B11 | 1540747 | PAK |
| 118B12 | 3153888 | PAK |
| 118C02 | 2236695 | PAK |
| 118C03 | 4063618 | PAK |
| 118C04 | 5082624 | PAK |
| 118C05 | 1129246 | PAK |
| 118C06 | 2077571 | PAK |
| 118C07 | 540936 | PAK |
| 118C08 | 696768 | PAK |
| 118C09 | 4885553 | PAK |
| 118C11 | 2878184 | PAK |
| 118D02 | 4898768 | PAK |
| 118D03 | 5939219 | PAK |
| 118D04 | 892199 | PAK |
| 118D05 | 4768448 | PAK |
| 118D06 | 2790097 | PAK |
| 118D07 | 5911639 | PAK |
| 118D08 | 5139379 | PAK |
| 118D11 | 1160555 | PAK |
| 118E01 | 3564930 | PAK |
| 118E02 | 5454857 | PAK |
| 118E03 | 2729224 | PAK |
| 118E04 | 1772986 | PAK |
| 118E05 | 2786380 | PAK |
| 118E06 | 3692855 | PAK |
| 118E07 | 768532 | PAK |
| 118E08 | 4001648 | PAK |
| 118E09 | 4671960 | PAK |
| 118E11 | 3370020 | PAK |
| 118E12 | 4846556 | PAK |
| 118F01 | 1500537 | PAK |
| 118F02 | 847151 | PAK |
| 118F03 | 3709028 | PAK |
| 118F04 | 416330 | PAK |
| 118F06 | 1410985 | PAK |
| 118F07 | 3113621 | PAK |
| 118F09 | 5131941 | PAK |
| 118F10 | 2491556 | PAK |
| 118F11 | 1013462 | PAK |
| 118F12 | 1839922 | PAK |
| 118G01 | 1703305 | PAK |
| 118G03 | 6206293 | PAK |
| 118G05 | 1419492 | PAK |
| 118G06 | 2455631 | PAK |
| 118G08 | 91337 | PAK |
| 118G09 | 3915937 | PAK |
| 118G10 | 5464552 | PAK |
| 118H01 | 6073528 | PAK |
| 118H02 | 5140599 | PAK |
| 118H03 | 254010 | PAK |
| 118H05 | 3792730 | PAK |
| 118H08 | 3691198 | PAK |
| 118H09 | 521014 | PAK |
| 118H10 | 4625741 | PAK |
| 118H11 | 3792729 | PAK |
| 119A01 | 4041962 | PAK |
| 119A03 | 2006172 | PAK |
| 119A05 | 6011519 | PAK |
| 119A07 | 1395198 | PAK |
| 119A08 | 2006172 | PAK |
| 119A09 | 451433 | PAK |
| 119A10 | 5017614 | PAK |
| 119A11 | 2911716 | PAK |
| 119A12 | 6028132 | PAK |
| 119B02 | 1593697 | PAK |
| 119B03 | 1204601 | PAK |
| 119B04 | 2222204 | PAK |
| 119B06 | 4930396 | PAK |
| 119B07 | 3961991 | PAK |

TABLE 3-continued

| Mutant Name | Insertion Point | host strain |
|---|---|---|
| 119B08 | 2998659 | PAK |
| 119B09 | 1563340 | PAK |
| 119B11 | 5482330 | PAK |
| 119B12 | 2668897 | PAK |
| 119C01 | 1932412 | PAK |
| 119C03 | 5410564 | PAK |
| 119C04 | 846093 | PAK |
| 119C05 | 4838127 | PAK |
| 119C06 | 5958896 | PAK |
| 119C07 | 1297009 | PAK |
| 119C08 | 1352727 | PAK |
| 119C09 | 1384381 | PAK |
| 119C10 | 1570707 | PAK |
| 119C12 | 5633960 | PAK |
| 119D01 | 2503623 | PAK |
| 119D02 | 1146608 | PAK |
| 119D03 | 104935 | PAK |
| 119D04 | 694997 | PAK |
| 119D05 | 2414214 | PAK |
| 119D06 | 2072014 | PAK |
| 119D07 | 4200754 | PAK |
| 119D08 | 5398179 | PAK |
| 119D09 | 3210176 | PAK |
| 119D10 | 2414276 | PAK |
| 119D11 | 368416 | PAK |
| 119E01 | 1827891 | PAK |
| 119E02 | 2643520 | PAK |
| 119E03 | 2677476 | PAK |
| 119E04 | 1084416 | PAK |
| 119E06 | 341141 | PAK |
| 119E08 | 5203237 | PAK |
| 119E12 | 380238 | PAK |
| 119F02 | 830704 | PAK |
| 119F03 | 2477778 | PAK |
| 119F05 | 375185 | PAK |
| 119F07 | 3264217 | PAK |
| 119F08 | 185711 | PAK |
| 119F09 | 3348743 | PAK |
| 119F10 | 3560771 | PAK |
| 119F11 | 3022151 | PAK |
| 119F12 | 2795858 | PAK |
| 119G01 | 1376552 | PAK |
| 119G02 | 2917399 | PAK |
| 119G03 | 3178048 | PAK |
| 119G04 | 164603 | PAK |
| 119G06 | 3959145 | PAK |
| 119G07 | 2236285 | PAK |
| 119G08 | 5135211 | PAK |
| 119G09 | 243060 | PAK |
| 119Gb | 935600 | PAK |
| 119G12 | 5244149 | PAK |
| 119H01 | 1131422 | PAK |
| 119H02 | 5712135 | PAK |
| 119H04 | 5244149 | PAK |
| 119H06 | 2666767 | PAK |
| 119H07 | 4011918 | PAK |
| 119H08 | 6190473 | PAK |
| 119H09 | 4189007 | PAK |
| 119H10 | 2370621 | PAK |
| 119H11 | 395318 | PAK |
| 120A01 | 4309453 | PAK |
| 120A02 | 4214324 | PAK |
| 120A04 | 1279710 | PAK |
| 120A05 | 4320673 | PAK |
| 120A07 | 3677797 | PAK |
| 120A08 | 75194 | PAK |
| 120A09 | 5751705 | PAK |
| 120A10 | 4379999 | PAK |
| 120A11 | 1947587 | PAK |
| 120B01 | 4180722 | PAK |
| 120B02 | 2845110 | PAK |
| 120B03 | 817185 | PAK |
| 120B04 | 2194119 | PAK |
| 120B05 | 1920105 | PAK |
| 120B07 | 2262228 | PAK |
| 120B08 | 1422047 | PAK |
| 120B09 | 527433 | PAK |
| 120B11 | 1920048 | PAK |
| 120B12 | 1694215 | PAK |
| 120C01 | 772175 | PAK |
| 120C05 | 204930 | PAK |
| 120C07 | 1626162 | PAK |
| 120C08 | 1934198 | PAK |
| 120C09 | 5229098 | PAK |
| 120C10 | 5693816 | PAK |
| 120C11 | 5099194 | PAK |
| 120C12 | 1883262 | PAK |
| 120D03 | 980104 | PAK |
| 120D04 | 511523 | PAK |
| 120D07 | 5136618 | PAK |
| 120D08 | 980105 | PAK |
| 120D09 | 324436 | PAK |
| 120D10 | 3714775 | PAK |
| 120D11 | 1134850 | PAK |
| 120E02 | 3580943 | PAK |
| 120E03 | 6055457 | PAK |
| 120E04 | 6142881 | PAK |
| 120E05 | 2702406 | PAK |
| 120E06 | 279250 | PAK |
| 120E08 | 1167157 | PAK |
| 120E09 | 2375315 | PAK |
| 120E11 | 279250 | PAK |
| 120F01 | 946534 | PAK |
| 120F02 | 2802047 | PAK |
| 120F03 | 5861742 | PAK |
| 120F04 | 1166666 | PAK |
| 120F05 | 1310691 | PAK |
| 120F08 | 983009 | PAK |
| 120F09 | 1824165 | PAK |
| 120F10 | 3702486 | PAK |
| 120F12 | 5911669 | PAK |
| 120G03 | 5368416 | PAK |
| 120G04 | 4078845 | PAK |
| 120G05 | 1024299 | PAK |
| 120G06 | 751030 | PAK |
| 120G07 | 1760889 | PAK |
| 120G09 | 4867399 | PAK |
| 120G10 | 1024240 | PAK |
| 120G11 | 3287597 | PAK |
| 120G12 | 3689760 | PAK |
| 120H01 | 1828480 | PAK |
| 120H03 | 3946394 | PAK |
| 120H05 | 481060 | PAK |
| 120H08 | 3494218 | PAK |
| 120H09 | 3084423 | PAK |
| 120H11 | 481060 | PAK |
| 127A01 | 1811021 | PAK |
| 127A02 | 882614 | PAK |
| 127A03 | 2320809 | PAK |
| 127A04 | 3066514 | PAK |
| 127A06 | 1971116 | PAK |
| 127A07 | 3844243 | PAK |
| 127A08 | 5358968 | PAK |
| 127A09 | 3124423 | PAK |
| 127A10 | 2591334 | PAK |
| 127A11 | 5002353 | PAK |
| 127A12 | 1716383 | PAK |
| 127B01 | 5048892 | PAK |
| 127B02 | 6121566 | PAK |
| 127B03 | 3510655 | PAK |
| 127B04 | 2846515 | PAK |
| 127B05 | 3662765 | PAK |
| 127B06 | 920955 | PAK |
| 127B08 | 2108051 | PAK |
| 127B09 | 383221 | PAK |
| 127B11 | 3379074 | PAK |
| 127B12 | 3724462 | PAK |
| 127C01 | 4578437 | PAK |
| 127C03 | 1475122 | PAK |
| 127C05 | 967946 | PAK |
| 127C06 | 4903818 | PAK |
| 127C07 | 1281326 | PAK |
| 127C08 | 499484 | PAK |
| 127C09 | 2239498 | PAK |

TABLE 3-continued

| Mutant Name | Insertion Point | host strain |
|---|---|---|
| 127C10 | 1437352 | PAK |
| 127C11 | 5406124 | PAK |
| 127C12 | 640654 | PAK |
| 127D01 | 678637 | PAK |
| 127D02 | 4685854 | PAK |
| 127D03 | 2388838 | PAK |
| 127D04 | 5651280 | PAK |
| 127D05 | 3062288 | PAK |
| 127D06 | 4822945 | PAK |
| 127D08 | 4515092 | PAK |
| 127D09 | 5304143 | PAK |
| 127D10 | 3453147 | PAK |
| 127D11 | 4118014 | PAK |
| 127D12 | 5657415 | PAK |
| 127E01 | 2610841 | PAK |
| 127E02 | 6176754 | PAK |
| 127E04 | 3578490 | PAK |
| 127E05 | 5439348 | PAK |
| 127E07 | 1814147 | PAK |
| 127E08 | 2263412 | PAK |
| 127E09 | 1509151 | PAK |
| 127E10 | 5200345 | PAK |
| 127E12 | 2058491 | PAK |
| 127F01 | 909979 | PAK |
| 127F02 | 106186 | PAK |
| 127F03 | 1650446 | PAK |
| 127F04 | 5975581 | PAK |
| 127F05 | 5760379 | PAK |
| 127F06 | 2619599 | PAK |
| 127F07 | 4502367 | PAK |
| 127F08 | 3280101 | PAK |
| 127F09 | 3879360 | PAK |
| 127F10 | 246350 | PAK |
| 127F11 | 555094 | PAK |
| 127F12 | 4163540 | PAK |
| 127G01 | 2830608 | PAK |
| 127G02 | 4636291 | PAK |
| 127G03 | 2000932 | PAK |
| 127G04 | 4364604 | PAK |
| 127G05 | 5640892 | PAK |
| 127G06 | 2576880 | PAK |
| 127G07 | 3420773 | PAK |
| 127G08 | 3829597 | PAK |
| 127G09 | 2263881 | PAK |
| 127G10 | 1431799 | PAK |
| 127G11 | 2455357 | PAK |
| 127G12 | 1645123 | PAK |
| 127H01 | 2936396 | PAK |
| 127H02 | 1474974 | PAK |
| 127H03 | 6708826 | PAK |
| 127H04 | 783067 | PAK |
| 127H05 | 2438429 | PAK |
| 127H06 | 5713811 | PAK |
| 127H07 | 5910084 | PAK |
| 127H08 | 3199304 | PAK |
| 127H09 | 4459189 | PAK |
| 127H10 | 5074520 | PAK |
| 128A01 | 3376875 | PAK |
| 128A02 | 1558017 | PAK |
| 128A03 | 3610065 | PAK |
| 128A04 | 327934 | PAK |
| 128A05 | 693580 | PAK |
| 128A06 | 4336159 | PAK |
| 128A07 | 2045727 | PAK |
| 128A08 | 3584390 | PAK |
| 128A09 | 6231294 | PAK |
| 128A10 | 5263318 | PAK |
| 128A11 | 1828589 | PAK |
| 128A12 | 4117859 | PAK |
| 128B01 | 5028959 | PAK |
| 128B02 | 5834361 | PAK |
| 128B03 | 1309097 | PAK |
| 128B04 | 5927460 | PAK |
| 128B05 | 2823175 | PAK |
| 128B06 | 1013361 | PAK |
| 128B07 | 5392906 | PAK |
| 128B08 | 471140 | PAK |

TABLE 3-continued

| Mutant Name | Insertion Point | host strain |
|---|---|---|
| 128B09 | 1158244 | PAK |
| 128B10 | 3690827 | PAK |
| 128B11 | 319164 | PAK |
| 128B12 | 1274286 | PAK |
| 128C01 | 2903863 | PAK |
| 128C03 | 1583556 | PAK |
| 128C04 | 4239950 | PAK |
| 128C05 | 352630 | PAK |
| 128C06 | 2238203 | PAK |
| 128C07 | 191460 | PAK |
| 128C08 | 2555440 | PAK |
| 128C09 | 4502551 | PAK |
| 128C10 | 5787794 | PAK |
| 128C11 | 5966404 | PAK |
| 128C12 | 1518050 | PAK |
| 128D01 | 5794578 | PAK |
| 128D02 | 3991703 | PAK |
| 128D03 | 16196 | PAK |
| 128D05 | 3984128 | PAK |
| 128D07 | 3794299 | PAK |
| 128D08 | 5995517 | PAK |
| 128D09 | 2660954 | PAK |
| 128D10 | 1569337 | PAK |
| 128D11 | 2921335 | PAK |
| 128D12 | 2425044 | PAK |
| 128E01 | 5966111 | PAK |
| 128E02 | 3306943 | PAK |
| 128E03 | 2741690 | PAK |
| 128E04 | 4391349 | PAK |
| 128E05 | 5871610 | PAK |
| 128E06 | 6172919 | PAK |
| 128E07 | 5467036 | PAK |
| 128E08 | 4964485 | PAK |
| 128E09 | 2743836 | PAK |
| 128E10 | 2089868 | PAK |
| 128E11 | 129593 | PAK |
| 128E12 | 1157196 | PAK |
| 128F01 | 1188885 | PAK |
| 128F02 | 2964269 | PAK |
| 128F03 | 5147397 | PAK |
| 128F04 | 1788764 | PAK |
| 128F05 | 2711533 | PAK |
| 128F06 | 1998957 | PAK |
| 128F07 | 3128663 | PAK |
| 128F08 | 4160731 | PAK |
| 128F09 | 6047221 | PAK |
| 128F10 | 4183202 | PAK |
| 128F11 | 5040209 | PAK |
| 128F12 | 1119633 | PAK |
| 128G01 | 577858 | PAK |
| 128G02 | 5467600 | PAK |
| 128G03 | 2011826 | PAK |
| 128G04 | 4809021 | PAK |
| 128G06 | 842835 | PAK |
| 128G07 | 3416704 | PAK |
| 128G08 | 2799545 | PAK |
| 128G09 | 3286224 | PAK |
| 128G10 | 4204052 | PAK |
| 128G11 | 1998460 | PAK |
| 128G12 | 3417081 | PAK |
| 128H01 | 4315005 | PAK |
| 128H02 | 5871468 | PAK |
| 128H04 | 2055604 | PAK |
| 128H05 | 5262156 | PAK |
| 128H06 | 5642070 | PAK |
| 128H07 | 519591 | PAK |
| 128H08 | 2143545 | PAK |
| 128H09 | 739991 | PAK |
| 128H10 | 3121771 | PAK |
| 129A01 | 286633 | PAK |
| 129A02 | 5822685 | PAK |
| 129A03 | 6110545 | PAK |
| 129A04 | 112487 | PAK |
| 129A05 | 5436525 | PAK |
| 129A06 | 940724 | PAK |
| 129A07 | 5831499 | PAK |
| 129A08 | 1748856 | PAK |

TABLE 3-continued

| Mutant Name | Insertion Point | host strain |
|---|---|---|
| 129A09 | 2008660 | PAK |
| 129A11 | 577069 | PAK |
| 129B01 | 4613082 | PAK |
| 129B02 | 2393422 | PAK |
| 129B04 | 1068552 | PAK |
| 129B05 | 3669772 | PAK |
| 129B07 | 2653945 | PAK |
| 129B09 | 5803423 | PAK |
| 129B11 | 2627706 | PAK |
| 129B12 | 5019357 | PAK |
| 129C01 | 49439 | PAK |
| 129C02 | 886575 | PAK |
| 129C03 | 6152725 | PAK |
| 129C04 | 1420504 | PAK |
| 129C05 | 6223113 | PAK |
| 129C06 | 6195107 | PAK |
| 129C08 | 17854981 | PAK |
| 129C10 | 2096736 | PAK |
| 129C11 | 3426881 | PAK |
| 129C12 | 4034076 | PAK |
| 129D02 | 5962076 | PAK |
| 129D03 | 5073520 | PAK |
| 129D04 | 6017548 | PAK |
| 129D05 | 4363806 | PAK |
| 129D06 | 5080093 | PAK |
| 129D07 | 3900463 | PAK |
| 129D08 | 914248 | PAK |
| 129D09 | 3667024 | PAK |
| 129D10 | 5716492 | PAK |
| 129D11 | 3804233 | PAK |
| 129D12 | 5286074 | PAK |
| 129E01 | 3648191 | PAK |
| 129E02 | 4291291 | PAK |
| 129E03 | 1533061 | PAK |
| 129E04 | 1192376 | PAK |
| 129E05 | 2946232 | PAK |
| 129E06 | 5289773 | PAK |
| 129E07 | 1715583 | PAK |
| 129E10 | 1528293 | PAK |
| 129E11 | 3472894 | PAK |
| 129E12 | 57734 | PAK |
| 129F02 | 4510298 | PAK |
| 129F03 | 2476570 | PAK |
| 129F04 | 5875425 | PAK |
| 129F05 | 5866423 | PAK |
| 129F06 | 1147530 | PAK |
| 129F07 | 6130299 | PAK |
| 129F08 | 4883792 | PAK |
| 129F09 | 1617780 | PAK |
| 129F10 | 3944667 | PAK |
| 129F11 | 1423536 | PAK |
| 129G01 | 1609882 | PAK |
| 129G02 | 3189360 | PAK |
| 129G03 | 441653 | PAK |
| 129G04 | 534444 | PAK |
| 129G05 | 3224468 | PAK |
| 129G06 | 5838157 | PAK |
| 129G07 | 431713 | PAK |
| 129G08 | 3784160 | PAK |
| 129G09 | 2706647 | PAK |
| 129G10 | 4041242 | PAK |
| 129G12 | 4005226 | PAK |
| 129H03 | 1312197 | PAK |
| 129H04 | 1188103 | PAK |
| 129H05 | 4264036 | PAK |
| 129H06 | 254705 | PAK |
| 129H07 | 1987812 | PAK |
| 129H08 | 4620051 | PAK |
| 129H10 | 4490870 | PAK |
| 130A01 | 5677731 | PAK |
| 130A03 | 2048965 | PAK |
| 130A05 | 2633009 | PAK |
| 130A06 | 705721 | PAK |
| 130A07 | 3784593 | PAK |
| 130B02 | 4355931 | PAK |
| 130B03 | 4901120 | PAK |
| 130B04 | 4795721 | PAK |
| 130B05 | 5715245 | PAK |
| 130B06 | 3403471 | PAK |
| 130B07 | 1777346 | PAK |
| 130B08 | 846143 | PAK |
| 130B11 | 4409759 | PAK |
| 130B12 | 5424286 | PAK |
| 130C02 | 4596176 | PAK |
| 130C05 | 3274923 | PAK |
| 130C07 | 1715152 | PAK |
| 130C08 | 303470 | PAK |
| 130C09 | 4575247 | PAK |
| 130C10 | 2484159 | PAK |
| 130C11 | 4901120 | PAK |
| 130C12 | 60660 | PAK |
| 130D01 | 2380588 | PAK |
| 130D02 | 2813674 | PAK |
| 130D03 | 2498665 | PAK |
| 130D04 | 1511042 | PAK |
| 130D07 | 1851283 | PAK |
| 130D08 | 1120861 | PAK |
| 130D11 | 4637417 | PAK |
| 130D12 | 2845867 | PAK |
| 130E01 | 5578202 | PAK |
| 130E03 | 2631742 | PAK |
| 130E04 | 2498664 | PAK |
| 130E06 | 4921237 | PAK |
| 130E07 | 5916690 | PAK |
| 130E08 | 2912318 | PAK |
| 130E11 | 4180766 | PAK |
| 130E12 | 1757975 | PAK |
| 130F01 | 1589032 | PAK |
| 130F02 | 5138168 | PAK |
| 130F04 | 511658 | PAK |
| 130F06 | 1683308 | PAK |
| 130F07 | 4412984 | PAK |
| 130F08 | 3416448 | PAK |
| 130F09 | 5750325 | PAK |
| 130G01 | 24332893 | PAK |
| 130G02 | 46356623 | PAK |
| 130G03 | 5747917 | PAK |
| 130G04 | 5023683 | PAK |
| 130G06 | 1866164 | PAK |
| 130G07 | 347966 | PAK |
| 130G08 | 1121942 | PAK |
| 130G09 | 137978 | PAK |
| 130G10 | 334870 | PAK |
| 130G11 | 160550 | PAK |
| 130G12 | 2928625 | PAK |
| 130H01 | 5355408 | PAK |
| 130H03 | 5127696 | PAK |
| 130H07 | 134180 | PAK |
| 130H08 | 5952873 | PAK |
| 130H10 | 131936 | PAK |
| 132A02 | 2388185 | PAK |
| 132A03 | 5611705 | PAK |
| 132A04 | 3123426 | PAK |
| 132A05 | 2461358 | PAK |
| 132A06 | 2972310 | PAK |
| 132A08 | 2316080 | PAK |
| 132A09 | 591118 | PAK |
| 132A10 | 3635099 | PAK |
| 132A12 | 5992210 | PAK |
| 132B04 | 196003 | PAK |
| 132B05 | 3263455 | PAK |
| 132B06 | 1473630 | PAK |
| 132B07 | 523921 | PAK |
| 132B08 | 512067 | PAK |
| 132B09 | 4811609 | PAK |
| 132B10 | 1769346 | PAK |
| 132B11 | 1162098 | PAK |
| 132C01 | 4385881 | PAK |
| 132C02 | 1430231 | PAK |
| 132C04 | 3997502 | PAK |
| 132C05 | 3370062 | PAK |
| 132C06 | 4310844 | PAK |
| 132C07 | 3001843 | PAK |
| 132C08 | 362735 | PAK |

TABLE 3-continued

| Mutant Name | Insertion Point | host strain |
|---|---|---|
| 132C09 | 1336587 | PAK |
| 132C10 | 6010516 | PAK |
| 132C11 | 2737797 | PAK |
| 132C12 | 4288568 | PAK |
| 132D01 | 5160219 | PAK |
| 132D03 | 94432 | PAK |
| 132D04 | 110176 | PAK |
| 132D05 | 3517147 | PAK |
| 132D06 | 1574174 | PAK |
| 132D08 | 3823602 | PAK |
| 132D09 | 4246220 | PAK |
| 132D11 | 4157483 | PAK |
| 132D12 | 3894010 | PAK |
| 132E02 | 594378 | PAK |
| 132E03 | 615724 | PAK |
| 132E04 | 5258312 | PAK |
| 132E05 | 2830303 | PAK |
| 132E06 | 3500842 | PAK |
| 132E08 | 4242780 | PAK |
| 132E09 | 5056423 | PAK |
| 132E10 | 5554287 | PAK |
| 132E12 | 2871862 | PAK |
| 132F01 | 4165625 | PAK |
| 132F02 | 1839911 | PAK |
| 132F03 | 40421 | PAK |
| 132F04 | 779641 | PAK |
| 132F06 | 1091339 | PAK |
| 132F07 | 4824482 | PAK |
| 132F08 | 454130 | PAK |
| 132F09 | 6259212 | PAK |
| 132F10 | 646945 | PAK |
| 132F11 | 967493 | PAK |
| 132G03 | 3107807 | PAK |
| 132G05 | 2920616 | PAK |
| 132G06 | 6237949 | PAK |
| 132G07 | 1166781 | PAK |
| 132G08 | 3044930 | PAK |
| 132G09 | 6185300 | PAK |
| 132G12 | 5603070 | PAK |
| 132H01 | 2656025 | PAK |
| 132H03 | 4214521 | PAK |
| 132H04 | 6091795 | PAK |
| 132H06 | 211372 | PAK |
| 132H08 | 5123071 | PAK |
| 133A01 | 134217 | PAK |
| 133A04 | 2519425 | PAK |
| 133A05 | 6220607 | PAK |
| 133A06 | 5359765 | PAK |
| 133A07 | 4721220 | PAK |
| 133A09 | 2505755 | PAK |
| 133A11 | 3224463 | PAK |
| 133A12 | 4746483 | PAK |
| 133B01 | 998262 | PAK |
| 133B03 | 2473175 | PAK |
| 133B04 | 1872765 | PAK |
| 133B05 | 3369314 | PAK |
| 133B06 | 3975064 | PAK |
| 133B07 | 4150485 | PAK |
| 133B08 | 1562167 | PAK |
| 133B09 | 2063113 | PAK |
| 133B11 | 5180841 | PAK |
| 133C04 | 646956 | PAK |
| 133C06 | 5066204 | PAK |
| 133C07 | 2199980 | PAK |
| 133C11 | 2830716 | PAK |
| 133C12 | 3808897 | PAK |
| 133D03 | 5684456 | PAK |
| 133D04 | 2861464 | PAK |
| 133D06 | 5867534 | PAK |
| 133D07 | 3704046 | PAK |
| 133D08 | 1647665 | PAK |
| 133D09 | 3788320 | PAK |
| 133D11 | 2972460 | PAK |
| 133E01 | 3512813 | PAK |
| 133E02 | 2340727 | PAK |
| 133E03 | 5367110 | PAK |
| 133E04 | 5088644 | PAK |
| 133E06 | 888027 | PAK |
| 133E09 | 5860338 | PAK |
| 133E11 | 543407 | PAK |
| 133F01 | 1169996 | PAK |
| 133F02 | 3284846 | PAK |
| 133F03 | 3791674 | PAK |
| 133F04 | 3001638 | PAK |
| 133F05 | 1974955 | PAK |
| 133F06 | 5693044 | PAK |
| 133F08 | 347275 | PAK |
| 133F11 | 4173414 | PAK |
| 133F12 | 2830716 | PAK |
| 133G01 | 4417306 | PAK |
| 133G02 | 5469588 | PAK |
| 133G03 | 2311301 | PAK |
| 133G05 | 2090369 | PAK |
| 133G06 | 3986117 | PAK |
| 133G07 | 3788320 | PAK |
| 133G08 | 1562167 | PAK |
| 133G09 | 1514982 | PAK |
| 133G11 | 4173414 | PAK |
| 133G12 | 543407 | PAK |
| 133H01 | 4746483 | PAK |
| 133H03 | 1402490 | PAK |
| 133H04 | 1402491 | PAK |
| 133H05 | 1588214 | PAK |
| 133H06 | 2222680 | PAK |
| 133H07 | 2222680 | PAK |
| 133H08 | 1384431 | PAK |
| 133H09 | 5994419 | PAK |
| 134A02 | 2576753 | PAK |
| 134A04 | 5494077 | PAK |
| 134A06 | 2688453 | PAK |
| 134A07 | 716818 | PAK |
| 134A09 | 3173887 | PAK |
| 134A10 | 597468 | PAK |
| 134A11 | 689062 | PAK |
| 134A12 | 589475 | PAK |
| 134B01 | 2964017 | PAK |
| 134B03 | 1004613 | PAK |
| 134B04 | 1076888 | PAK |
| 134B05 | 4434207 | PAK |
| 134B06 | 3369630 | PAK |
| 134B08 | 3565805 | PAK |
| 134B09 | 1079265 | PAK |
| 134B10 | 5081696 | PAK |
| 134B11 | 1711170 | PAK |
| 134C01 | 2985756 | PAK |
| 134C03 | 2685404 | PAK |
| 134C04 | 3933050 | PAK |
| 134C05 | 4056662 | PAK |
| 134C08 | 5657415 | PAK |
| 134C10 | 6015057 | PAK |
| 134C12 | 5976740 | PAK |
| 134D01 | 1528915 | PAK |
| 134D03 | 2052537 | PAK |
| 134D04 | 2213259 | PAK |
| 134D06 | 4634700 | PAK |
| 134D09 | 5316951 | PAK |
| 134D10 | 760164 | PAK |
| 134D11 | 4423288 | PAK |
| 134D12 | 5736987 | PAK |
| 134E01 | 2500195 | PAK |
| 134E02 | 2500193 | PAK |
| 134E03 | 1474058 | PAK |
| 134E05 | 3176728 | PAK |
| 134E08 | 3081818 | PAK |
| 134E10 | 4475036 | PAK |
| 134E11 | 5651569 | PAK |
| 134F03 | 1764842 | PAK |
| 134F04 | 3898881 | PAK |
| 134F05 | 1576837 | PAK |
| 134F08 | 1760938 | PAK |
| 134F09 | 1362626 | PAK |
| 134F10 | 2038176 | PAK |
| 134F12 | 3923558 | PAK |
| 134G01 | 1913587 | PAK |

TABLE 3-continued

| Mutant Name | Insertion Point | host strain |
|---|---|---|
| 134G04 | 4974035 | PAK |
| 134G10 | 5412162 | PAK |
| 134G11 | 6048785 | PAK |
| 134H03 | 1409584 | PAK |
| 134H04 | 2553883 | PAK |
| 134H05 | 351470 | PAK |
| 134H06 | 2322164 | PAK |
| 134H08 | 2316080 | PAK |
| 134H10 | 4697711 | PAK |
| 135A01 | 5761946 | PAK |
| 135A03 | 6140275 | PAK |
| 135A04 | 5966111 | PAK |
| 135A05 | 3607877 | PAK |
| 135A09 | 1707330 | PAK |
| 135A11 | 6150757 | PAK |
| 135B03 | 1608735 | PAK |
| 135B04 | 2930973 | PAK |
| 135B05 | 2917720 | PAK |
| 135B09 | 387593 | PAK |
| 135B10 | 6143502 | PAK |
| 135B12 | 5925381 | PAK |
| 135C03 | 2820191 | PAK |
| 135C05 | 1879863 | PAK |
| 135C08 | 683870 | PAK |
| 135D01 | 5910711 | PAK |
| 135D03 | 1676417 | PAK |
| 135D04 | 1384431 | PAK |
| 135D08 | 4108215 | PAK |
| 135D09 | 6192292 | PAK |
| 135D10 | 2488160 | PAK |
| 135D11 | 5849598 | PAK |
| 135D12 | 4106784 | PAK |
| 135E01 | 2809080 | PAK |
| 135E03 | 5981323 | PAK |
| 135E05 | 647382 | PAK |
| 135E08 | 2243817 | PAK |
| 135E10 | 1575039 | PAK |
| 135F01 | 4732060 | PAK |
| 135F03 | 1903275 | PAK |
| 135F04 | 2239138 | PAK |
| 135F05 | 2334365 | PAK |
| 135F09 | 5353636 | PAK |
| 135F12 | 817239 | PAK |
| 135G01 | 5719352 | PAK |
| 135G03 | 1882537 | PAK |
| 135G04 | 1315517 | PAK |
| 135G05 | 1273594 | PAK |
| 135G08 | 1342941 | PAK |
| 135G09 | 1952650 | PAK |
| 135G10 | 864723 | PAK |
| 135G11 | 4636291 | PAK |
| 135H03 | 5784728 | PAK |
| 135H08 | 3782326 | PAK |
| 135H09 | 5184760 | PAK |
| 135H10 | 5952152 | PAK |
| 136A01 | 1718165 | PAK |
| 136A02 | 2393400 | PAK |
| 136A03 | 524575 | PAK |
| 136A05 | 5384089 | PAK |
| 136A06 | 4976538 | PAK |
| 136A07 | 2057442 | PAK |
| 136A09 | 4387245 | PAK |
| 136A11 | 5648833 | PAK |
| 136A12 | 503825 | PAK |
| 136B04 | 505555 | PAK |
| 136B06 | 92131 | PAK |
| 136B07 | 376806 | PAK |
| 136B08 | 1890229 | PAK |
| 136B09 | 3064388 | PAK |
| 136B11 | 4927081 | PAK |
| 136B12 | 4500512 | PAK |
| 136C01 | 766735 | PAK |
| 136C02 | 1120523 | PAK |
| 136C03 | 493715 | PAK |
| 136C04 | 1757430 | PAK |
| 136C05 | 226108 | PAK |
| 136C07 | 6108826 | PAK |
| 136C08 | 4839045 | PAK |
| 136C09 | 3174664 | PAK |
| 136C10 | 1384430 | PAK |
| 136D01 | 311047 | PAK |
| 136D03 | 2362509 | PAK |
| 136D04 | 4450952 | PAK |
| 136D07 | 1828522 | PAK |
| 136D08 | 204929 | PAK |
| 136D09 | 5686350 | PAK |
| 136D10 | 5148392 | PAK |
| 136D11 | 2788026 | PAK |
| 136D12 | 3518139 | PAK |
| 136E02 | 2341044 | PAK |
| 136E04 | 2052537 | PAK |
| 136E05 | 2266499 | PAK |
| 136E06 | 252573 | PAK |
| 136E07 | 481060 | PAK |
| 136E09 | 802563 | PAK |
| 136E10 | 1192902 | PAK |
| 136E11 | 1168239 | PAK |
| 136E12 | 6148002 | PAK |
| 136F01 | 5985574 | PAK |
| 136F02 | 2500955 | PAK |
| 136F03 | 3155936 | PAK |
| 136F04 | 434199 | PAK |
| 136F07 | 1516167 | PAK |
| 136F08 | 3873389 | PAK |
| 136F11 | 1079265 | PAK |
| 136G01 | 2610451 | PAK |
| 136G03 | 5455694 | PAK |
| 136G04 | 4333629 | PAK |
| 136G05 | 1534346 | PAK |
| 136G06 | 3437629 | PAK |
| 136G07 | 5710982 | PAK |
| 136G08 | 2570304 | PAK |
| 136G09 | 3052625 | PAK |
| 136G10 | 5914201 | PAK |
| 136G12 | 2660880 | PAK |
| 136H01 | 3885014 | PAK |
| 136H02 | 2815750 | PAK |
| 136H03 | 1287875 | PAK |
| 136H04 | 3615427 | PAK |
| 136H05 | 1534379 | PAK |
| 136H06 | 2647365 | PAK |
| 136H10 | 142776 | PAK |
| 137A03 | 718749 | PAK |
| 137A04 | 4709718 | PAK |
| 137A05 | 2114742 | PAK |
| 137A06 | 4887907 | PAK |
| 137A07 | 925287 | PAK |
| 137A09 | 1298874 | PAK |
| 137A10 | 5560950 | PAK |
| 137A11 | 1775025 | PAK |
| 137A12 | 3648233 | PAK |
| 137B02 | 1159179 | PAK |
| 137B03 | 4101984 | PAK |
| 137B04 | 4101984 | PAK |
| 137B05 | 3107680 | PAK |
| 137B06 | 1569296 | PAK |
| 137B07 | 1419150 | PAK |
| 137B08 | 2458915 | PAK |
| 137B09 | 1833616 | PAK |
| 137B10 | 2141916 | PAK |
| 138F02 | 1839893 | PAK |
| 138F03 | 6117227 | PAK |
| 138F05 | 3628426 | PAK |
| 138F06 | 6101733 | PAK |
| 138F07 | 2721235 | PAK |
| 138F08 | 5247124 | PAK |
| 138F10 | 841069 | PAK |
| 138F11 | 4912909 | PAK |
| 138F12 | 4202904 | PAK |
| 138G02 | 6035564 | PAK |
| 138G03 | 2062404 | PAK |
| 138G04 | 2914978 | PAK |
| 138G06 | 5371569 | PAK |
| 138G07 | 4898889 | PAK |

TABLE 3-continued

| Mutant Name | Insertion Point | host strain |
|---|---|---|
| 138G08 | 2032484 | PAK |
| 138G09 | 1555200 | PAK |
| 138G11 | 4246599 | PAK |
| 138H03 | 3472994 | PAK |
| 138H04 | 848629 | PAK |
| 138H06 | 4144805 | PAK |
| 138H07 | 6209136 | PAK |
| 138H09 | 551781 | PAK |
| 139A01 | 4565522 | PAK |
| 139A02 | 1059423 | PAK |
| 139A05 | 6145447 | PAK |
| 139A06 | 3168170 | PAK |
| 139A07 | 595354 | PAK |
| 139A08 | 3177097 | PAK |
| 139A09 | 566924 | PAK |
| 139A11 | 2236609 | PAK |
| 139A12 | 1427957 | PAK |
| 139B03 | 2491006 | PAK |
| 139B04 | 3362546 | PAK |
| 139B05 | 5855139 | PAK |
| 139B06 | 4113348 | PAK |
| 139B08 | 5278608 | PAK |
| 139B09 | 5772790 | PAK |
| 139B10 | 523252 | PAK |
| 139B12 | 57808 | PAK |
| 139C01 | 5357965 | PAK |
| 139C02 | 4444716 | PAK |
| 139C04 | 4246599 | PAK |
| 139C06 | 2025210 | PAK |
| 139C07 | 5187805 | PAK |
| 139C08 | 5350177 | PAK |
| 139C09 | 5519304 | PAK |
| 139C10 | 1244793 | PAK |
| 139C11 | 5159293 | PAK |
| 139D01 | 818243 | PAK |
| 139D02 | 5270676 | PAK |
| 139D04 | 2951345 | PAK |
| 139D06 | 5141848 | PAK |
| 139D07 | 1280009 | PAK |
| 139D08 | 953023 | PAK |
| 139D10 | 733829 | PAK |
| 139D11 | 6224157 | PAK |
| 139D12 | 5994308 | PAK |
| 139E02 | 5077239 | PAK |
| 139E03 | 6123477 | PAK |
| 139E04 | 5657823 | PAK |
| 139E05 | 300315 | PAK |
| 139E06 | 2800578 | PAK |
| 139E07 | 4926167 | PAK |
| 139E09 | 2800848 | PAK |
| 139E10 | 3688837 | PAK |
| 139F01 | 1240595 | PAK |
| 139F02 | 258947 | PAK |
| 139F03 | 2999079 | PAK |
| 139F05 | 3603321 | PAK |
| 139F06 | 2009424 | PAK |
| 139F07 | 6168388 | PAK |
| 139F08 | 3663212 | PAK |
| 139F09 | 3653261 | PAK |
| 139F11 | 554252 | PAK |
| 139F12 | 11919267 | PAK |
| 140A05 | 13955042 | PAK |
| 140A06 | 956379 | PAK |
| 140A07 | 1168719 | PAK |
| 140A08 | 1016483 | PAK |
| 140A09 | 5270661 | PAK |
| 140A10 | 4623477 | PAK |
| 140A12 | 2633129 | PAK |
| 140B01 | 4298474 | PAK |
| 140B02 | 5157575 | PAK |
| 140B03 | 1532222 | PAK |
| 140B04 | 5871180 | PAK |
| 140B05 | 5977608 | PAK |
| 140B06 | 829418 | PAK |
| 140B08 | 3832516 | PAK |
| 140B09 | 3480355 | PAK |
| 140B10 | 4038577 | PAK |
| 140B11 | 4038569 | PAK |
| 140B12 | 5949521 | PAK |
| 140C01 | 1923620 | PAK |
| 140C04 | 1600315 | PAK |
| 140C05 | 382830 | PAK |
| 140C06 | 1902876 | PAK |
| 140C07 | 2981848 | PAK |
| 140C08 | 2461473 | PAK |
| 140C09 | 2013794 | PAK |
| 140C11 | 5585891 | PAK |
| 140D02 | 5651912 | PAK |
| 140D03 | 2148402 | PAK |
| 140D04 | 3574562 | PAK |
| 140D06 | 3383538 | PAK |
| 140D07 | 1961834 | PAK |
| 140D08 | 1564249 | PAK |
| 140D09 | 3770926 | PAK |
| 140D10 | 3131806 | PAK |
| 140D11 | 6051112 | PAK |
| 140D12 | 4808966 | PAK |
| 140E02 | 398527 | PAK |
| 140E04 | 4841791 | PAK |
| 140E05 | 4827197 | PAK |
| 140E06 | 6212401 | PAK |
| 140E07 | 4057572 | PAK |
| 140E09 | 5361429 | PAK |
| 140E10 | 2898138 | PAK |
| 140E11 | 2127692 | PAK |
| 140E12 | 1683120 | PAK |
| 140F01 | 3519919 | PAK |
| 140F02 | 3419732 | PAK |
| 140F03 | 1587836 | PAK |
| 140F04 | 2353285 | PAK |
| 140F05 | 2370762 | PAK |
| 140F06 | 3023871 | PAK |
| 140F08 | 5918849 | PAK |
| 140F09 | 5153893 | PAK |
| 140F10 | 1578205 | PAK |
| 140F11 | 4891756 | PAK |
| 140F12 | 189664 | PAK |
| 140G01 | 1837588 | PAK |
| 140G04 | 442493 | PAK |
| 140G05 | 995744 | PAK |
| 140G06 | 2981848 | PAK |
| 140G07 | 6232799 | PAK |
| 140G08 | 3149367 | PAK |
| 140G10 | 5166800 | PAK |
| 140G12 | 555273 | PAK |
| 140H01 | 2720636 | PAK |
| 140H02 | 1932615 | PAK |
| 140H05 | 6029781 | PAK |
| 140H06 | 628380 | PAK |
| 140H07 | 5959538 | PAK |
| 140H08 | 3281562 | PAK |
| 140H09 | 2747356 | PAK |
| 140H10 | 2952752 | PAK |
| 141A01 | 3175713 | PAK |
| 141A02 | 853263 | PAK |
| 141A03 | 4425519 | PAK |
| 141A04 | 5437535 | PAK |
| 141A05 | 21810 | PAK |
| 141A06 | 1309993 | PAK |
| 141A07 | 5645688 | PAK |
| 141A08 | 1182618 | PAK |
| 141A09 | 3210065 | PAK |
| 141A10 | 1989911 | PAK |
| 141A11 | 3129901 | PAK |
| 141A12 | 3110621 | PAK |
| 141B01 | 1574713 | PAK |
| 141B02 | 2096074 | PAK |
| 141B03 | 4520836 | PAK |
| 141B04 | 1895472 | PAK |
| 141B05 | 2601062 | PAK |
| 141B06 | 5291174 | PAK |
| 141B07 | 5794998 | PAK |
| 141B10 | 229130 | PAK |
| 141B11 | 3211432 | PAK |

TABLE 3-continued

| Mutant Name | Insertion Point | host strain |
|---|---|---|
| 141C01 | 5806420 | PAK |
| 141C03 | 3571637 | PAK |
| 141C04 | 4111230 | PAK |
| 141C05 | 4176435 | PAK |
| 141C06 | 5571127 | PAK |
| 141C07 | 4430306 | PAK |
| 141C08 | 5934160 | PAK |
| 141C09 | 5031712 | PAK |
| 141D01 | 3651396 | PAK |
| 141D02 | 3424904 | PAK |
| 141D03 | 2414678 | PAK |
| 141D05 | 5367831 | PAK |
| 141D06 | 3828180 | PAK |
| 141D07 | 15418 | PAK |
| 141D08 | 5110846 | PAK |
| 141D09 | 2831288 | PAK |
| 141D11 | 5353583 | PAK |
| 141D12 | 4404149 | PAK |
| 141E01 | 1764790 | PAK |
| 141E02 | 385918 | PAK |
| 141E04 | 1196908 | PAK |
| 141E05 | 1581069 | PAK |
| 141E06 | 3824649 | PAK |
| 141E07 | 4619833 | PAK |
| 141E09 | 197608 | PAK |
| 141E10 | 2288920 | PAK |
| 141E11 | 2398410 | PAK |
| 141E12 | 572856 | PAK |
| 141F01 | 572855 | PAK |
| 141F02 | 2511098 | PAK |
| 141F03 | 5786688 | PAK |
| 141F05 | 4481788 | PAK |
| 141F06 | 400977 | PAK |
| 141F07 | 395946 | PAK |
| 141F10 | 2688532 | PAK |
| 141F11 | 4140889 | PAK |
| 141G02 | 3767627 | PAK |
| 141G03 | 5151108 | PAK |
| 141G05 | 4048078 | PAK |
| 141G06 | 3627693 | PAK |
| 141G07 | 4522019 | PAK |
| 141G09 | 6201791 | PAK |
| 141G10 | 368828 | PAK |
| 141G11 | 5756759 | PAK |
| 141H02 | 5272668 | PAK |
| 141H04 | 3235122 | PAK |
| 141H05 | 6035564 | PAK |
| 141H06 | 6035564 | PAK |
| 141H08 | 5033156 | PAK |
| 142A01 | 3131653 | PAK |
| 142A05 | 58020 | PAK |
| 142A06 | 5860855 | PAK |
| 142A07 | 58020 | PAK |
| 142A09 | 3400008 | PAK |
| 142A10 | 2893561 | PAK |
| 142A11 | 5582412 | PAK |
| 142B01 | 3383351 | PAK |
| 142B03 | 856389 | PAK |
| 142B04 | 4835144 | PAK |
| 142B05 | 1248145 | PAK |
| 142B06 | 2272288 | PAK |
| 142B07 | 1354644 | PAK |
| 142B08 | 5140846 | PAK |
| 142B09 | 696203 | PAK |
| 142B12 | 740871 | PAK |
| 142C01 | 740871 | PAK |
| 142C02 | 2485163 | PAK |
| 142C05 | 1034469 | PAK |
| 142C09 | 4255622 | PAK |
| 142C11 | 2032316 | PAK |
| 142D02 | 4497209 | PAK |
| 142D03 | 3485054 | PAK |
| 142D05 | 3433005 | PAK |
| 142D06 | 3116955 | PAK |
| 142D09 | 3509590 | PAK |
| 142D10 | 5437249 | PAK |
| 142D12 | 1644597 | PAK |
| 142E01 | 5890073 | PAK |
| 142E02 | 5890073 | PAK |
| 142E03 | 6102318 | PAK |
| 142E06 | 380679 | PAK |
| 142E07 | 400655 | PAK |
| 142E10 | 1034469 | PAK |
| 142E11 | 3014982 | PAK |
| 142E12 | 789444 | PAK |
| 142F03 | 1905184 | PAK |
| 142F04 | 4873021 | PAK |
| 142F05 | 3084524 | PAK |
| 142F06 | 2930906 | PAK |
| 142F08 | 489002 | PAK |
| 142F09 | 3974710 | PAK |
| 142F10 | 5154909 | PAK |
| 142F12 | 4162335 | PAK |
| 142G03 | 967784 | PAK |
| 142G04 | 5717407 | PAK |
| 142G05 | 896150 | PAK |
| 142G06 | 5099048 | PAK |
| 142G07 | 6147193 | PAK |
| 142G09 | 710756 | PAK |
| 142G10 | 807831 | PAK |
| 142G11 | 5292638 | PAK |
| 142G12 | 4379409 | PAK |
| 142H01 | 2808940 | PAK |
| 142H02 | 3627334 | PAK |
| 142H06 | 3606426 | PAK |
| 142H07 | 1865983 | PAK |
| 142H08 | 3996492 | PAK |
| 142H09 | 3505737 | PAK |
| 142H10 | 1103395 | PAK |
| 143A02 | 24909 | PAK |
| 143A05 | 36720 | PAK |
| 143A06 | 3924250 | PAK |
| 143A07 | 1739662 | PAK |
| 143B01 | 4859651 | PAK |
| 143B05 | 5516048 | PAK |
| 143B06 | 1582135 | PAK |
| 143B07 | 5590983 | PAK |
| 143B08 | 6189775 | PAK |
| 143B09 | 1537840 | PAK |
| 143B10 | 3188262 | PAK |
| 143B11 | 3188262 | PAK |
| 143C02 | 6024397 | PAK |
| 143C05 | 3656246 | PAK |
| 143C08 | 6020044 | PAK |
| 143C10 | 459263 | PAK |
| 143C11 | 4564195 | PAK |
| 143C12 | 1323321 | PAK |
| 143D02 | 221817 | PAK |
| 143D03 | 515250 | PAK |
| 143D04 | 515251 | PAK |
| 143D06 | 1474934 | PAK |
| 143D08 | 1508502 | PAK |
| 143D09 | 2060200 | PAK |
| 143D10 | 5052016 | PAK |
| 143D11 | 3780756 | PAK |
| 143E01 | 905329 | PAK |
| 143E02 | 3857839 | PAK |
| 143E03 | 250716 | PAK |
| 143E05 | 6244985 | PAK |
| 143E06 | 4999766 | PAK |
| 143E07 | 4641998 | PAK |
| 143E08 | 5186965 | PAK |
| 143E09 | 6201228 | PAK |
| 143E10 | 5712802 | PAK |
| 143E12 | 1416290 | PAK |
| 143F02 | 3235122 | PAK |
| 143F04 | 5618608 | PAK |
| 143F05 | 574080 | PAK |
| 143F06 | 2500014 | PAK |
| 143F07 | 5075495 | PAK |
| 143F08 | 1116364 | PAK |
| 143F09 | 3260439 | PAK |
| 143F12 | 6065303 | PAK |
| 143G01 | 1025545 | PAK |

TABLE 3-continued

| Mutant Name | Insertion Point | host strain |
|---|---|---|
| 143G02 | 598013 | PAK |
| 143G04 | 5399574 | PAK |
| 143G05 | 3309414 | PAK |
| 143G06 | 5437908 | PAK |
| 143G07 | 3031647 | PAK |
| 143G08 | 4345476 | PAK |
| 143G10 | 5438288 | PAK |
| 143G12 | 2584849 | PAK |
| 143H02 | 6223363 | PAK |
| 143H04 | 3574634 | PAK |
| 143H05 | 2545454 | PAK |
| 143H06 | 5080184 | PAK |
| 143H07 | 2577489 | PAK |
| 143H08 | 1711787 | PAK |
| 143H09 | 5112371 | PAK |
| 143H10 | 1400592 | PAK |
| 144A06 | 4111916 | PAK |
| 144A08 | 6194060 | PAK |
| 144A11 | 5500080 | PAK |
| 144A12 | 1260783 | PAK |
| 144B01 | 589232 | PAK |
| 144B03 | 1989716 | PAK |
| 144B07 | 5966271 | PAK |
| 144B08 | 4404555 | PAK |
| 144B09 | 678164 | PAK |
| 144B10 | 4107242 | PAK |
| 144B11 | 423912 | PAK |
| 144B12 | 3572867 | PAK |
| 144C01 | 2259359 | PAK |
| 144C03 | 752819 | PAK |
| 144C04 | 731318 | PAK |
| 144C05 | 2291382 | PAK |
| 144C07 | 344331 | PAK |
| 144C08 | 2925236 | PAK |
| 144C09 | 5221428 | PAK |
| 144C10 | 5866311 | PAK |
| 144C12 | 5395375 | PAK |
| 144D03 | 5572038 | PAK |
| 144D05 | 4493922 | PAK |
| 144D06 | 3110659 | PAK |
| 144D08 | 2526366 | PAK |
| 144D09 | 6213204 | PAK |
| 144D10 | 5799082 | PAK |
| 144E02 | 5191997 | PAK |
| 144E03 | 2193252 | PAK |
| 144E04 | 1908362 | PAK |
| 144E05 | 137297 | PAK |
| 144E06 | 1403737 | PAK |
| 144E07 | 5538436 | PAK |
| 144E10 | 3503226 | PAK |
| 144E12 | 1361870 | PAK |
| 144F02 | 5727752 | PAK |
| 144F03 | 61454 | PAK |
| 144F04 | 381962 | PAK |
| 144F05 | 5668640 | PAK |
| 144F06 | 998275 | PAK |
| 144F08 | 5937166 | PAK |
| 144F09 | 1326016 | PAK |
| 144F11 | 3055208 | PAK |
| 144G02 | 4582955 | PAK |
| 144G03 | 209539 | PAK |
| 144G04 | 5951246 | PAK |
| 144G05 | 1745997 | PAK |
| 144G06 | 1746006 | PAK |
| 144G08 | 5178303 | PAK |
| 144G09 | 5569024 | PAK |
| 144G10 | 4814592 | PAK |
| 144G11 | 3658944 | PAK |
| 144H01 | 3933215 | PAK |
| 144H02 | 34Z9885 | PAK |
| 144H03 | 824899 | PAK |
| 144H05 | 3582889 | PAK |
| 144H06 | 976845 | PAK |
| 144H10 | 1149911 | PAK |
| 145A01 | 2310384 | PAK |
| 145A03 | 32134 | PAK |
| 145A04 | 4282708 | PAK |

TABLE 3-continued

| Mutant Name | Insertion Point | host strain |
|---|---|---|
| 145A07 | 2720151 | PAK |
| 145A08 | 1092513 | PAK |
| 145A11 | 2465040 | PAK |
| 145B01 | 26647 | PAK |
| 145B02 | 5635467 | PAK |
| 145B04 | 4443197 | PAK |
| 145B05 | 5667263 | PAK |
| 145B06 | 5153158 | PAK |
| 145B08 | 1117276 | PAK |
| 145B09 | 3331124 | PAK |
| 145B10 | 2600863 | PAK |
| 145B11 | 459283 | PAK |
| 145B12 | 882282 | PAK |
| 145C01 | 2695088 | PAK |
| 145C02 | 2311106 | PAK |
| 145C03 | 2624779 | PAK |
| 145C04 | 5149124 | PAK |
| 145C05 | 4898888 | PAK |
| 145C06 | 3500842 | PAK |
| 145C07 | 3857015 | PAK |
| 145C08 | 1082277 | PAK |
| 145C09 | 2452515 | PAK |
| 145C11 | 3596975 | PAK |
| 145D01 | 5530798 | PAK |
| 145D03 | 5533221 | PAK |
| 145D05 | 2927667 | PAK |
| 145D08 | 6020131 | PAK |
| 145D11 | 715367 | PAK |
| 145D12 | 3127776 | PAK |
| 145E01 | 1869192 | PAK |
| 145E02 | 5712193 | PAK |
| 145E03 | 1079672 | PAK |
| 145E04 | 1454770 | PAK |
| 145E05 | 1122220 | PAK |
| 145E06 | 5903062 | PAK |
| 145E07 | 5656621 | PAK |
| 145E09 | 2177979 | PAK |
| 145E10 | 1437351 | PAK |
| 145E11 | 452549 | PAK |
| 145E12 | 3455820 | PAK |
| 145F02 | 2934740 | PAK |
| 145F03 | 2214627 | PAK |
| 145F04 | 5589978 | PAK |
| 145F05 | 390903 | PAK |
| 145F06 | 1818090 | PAK |
| 145F07 | 3107363 | PAK |
| 145F08 | 86193 | PAK |
| 145F09 | 5401965 | PAK |
| 145F10 | 5074926 | PAK |
| 145F12 | 4957248 | PAK |
| 145G02 | 5455694 | PAK |
| 145G03 | 4623703 | PAK |
| 145G04 | 1579179 | PAK |
| 145G05 | 3944659 | PAK |
| 145G06 | 5860932 | PAK |
| 145G07 | 5017788 | PAK |
| 145G08 | 4656499 | PAK |
| 145G09 | 3872065 | PAK |
| 145G10 | 174679 | PAK |
| 145G12 | 581560 | PAK |
| 145H01 | 5077359 | PAK |
| 145H04 | 1270409 | PAK |
| 145H05 | 546759 | PAK |
| 145H07 | 2752701 | PAK |
| 145H08 | 2185296 | PAK |
| 145H09 | 2534012 | PAK |
| 145H10 | 397477 | PAK |
| 146A01 | 4601205 | PAK |
| 146A02 | 5372123 | PAK |
| 146A04 | 3667034 | PAK |
| 146A05 | 3129120 | PAK |
| 146A06 | 3689610 | PAK |
| 146A07 | 719491 | PAK |
| 146A08 | 3390278 | PAK |
| 146A09 | 5822926 | PAK |
| 146B01 | 5210123 | PAK |
| 146B02 | 279719 | PAK |

TABLE 3-continued

| Mutant Name | Insertion Point | host strain |
|---|---|---|
| 146B03 | 1707230 | PAK |
| 146B05 | 394249 | PAK |
| 146B07 | 3010618 | PAK |
| 146B08 | 1561820 | PAK |
| 146B09 | 259527 | PAK |
| 146B10 | 1201858 | PAK |
| 146B11 | 5119490 | PAK |
| 146B12 | 5048691 | PAK |
| 146C01 | 5048892 | PAK |
| 146C04 | 6239357 | PAK |
| 146C05 | 1384431 | PAK |
| 146C06 | 2786430 | PAK |
| 146C07 | 4240377 | PAK |
| 146C08 | 1705239 | PAK |
| 146C09 | 572961 | PAK |
| 146C10 | 994911 | PAK |
| 146C11 | 2601387 | PAK |
| 146C12 | 2459337 | PAK |
| 146D02 | 4559343 | PAK |
| 146D04 | 5944261 | PAK |
| 146D06 | 4887907 | PAK |
| 146D07 | 5904579 | PAK |
| 146D08 | 1445263 | PAK |
| 146D09 | 1310580 | PAK |
| 146E02 | 3247070 | PAK |
| 146E04 | 817690 | PAK |
| 146E05 | 4542919 | PAK |
| 146E06 | 3797655 | PAK |
| 146E08 | 3040574 | PAK |
| 146E09 | 5860559 | PAK |
| 146E10 | 4122865 | PAK |
| 146E12 | 1382456 | PAK |
| 146F01 | 3022174 | PAK |
| 146F03 | 2854123 | PAK |
| 146F05 | 4521892 | PAK |
| 146F07 | 1900928 | PAK |
| 146F08 | 622178 | PAK |
| 146F09 | 79673 | PAK |
| 146F10 | 841043 | PAK |
| 146F11 | 1002796 | PAK |
| 146G01 | 3210226 | PAK |
| 146G03 | 5751097 | PAK |
| 146G06 | 3763199 | PAK |
| 146G07 | 2870456 | PAK |
| 146G08 | 3770700 | PAK |
| 146G10 | 5421632 | PAK |
| 146H01 | 4586115 | PAK |
| 146H04 | 4716342 | PAK |
| 146H06 | 994092 | PAK |
| 146H07 | 2757922 | PAK |
| 146H09 | 4721933 | PAK |
| 147A01 | 2453983 | PAK |
| 147A02 | 5661537 | PAK |
| 147A03 | 3114040 | PAK |
| 147A04 | 5898272 | PAK |
| 147A05 | 2344149 | PAK |
| 147A06 | 1395082 | PAK |
| 147A08 | 1167907 | PAK |
| 147A09 | 3638868 | PAK |
| 147A11 | 3042034 | PAK |
| 147A12 | 803486 | PAK |
| 147B01 | 2697879 | PAK |
| 147B02 | 4648799 | PAK |
| 147B03 | 329704 | PAK |
| 147B04 | 2176505 | PAK |
| 147B05 | 4982074 | PAK |
| 147B06 | 35014 | PAK |
| 147B09 | 1449555 | PAK |
| 147B10 | 3659659 | PAK |
| 147B11 | 3958094 | PAK |
| 147B12 | 5702608 | PAK |
| 147C02 | 2505127 | PAK |
| 147C04 | 4672010 | PAK |
| 147C05 | 1860906 | PAK |
| 147C06 | 5384768 | PAK |
| 147C07 | 3406911 | PAK |
| 147C08 | 851773 | PAK |
| 147C09 | 3029578 | PAK |
| 147C10 | 2477009 | PAK |
| 147C12 | 5981818 | PAK |
| 147D02 | 2032572 | PAK |
| 147D03 | 6083524 | PAK |
| 147D04 | 569045 | PAK |
| 147D05 | 5659476 | PAK |
| 147D06 | 4363781 | PAK |
| 147D07 | 1631833 | PAK |
| 147D08 | 1940369 | PAK |
| 147D09 | 1342088 | PAK |
| 147D10 | 1581147 | PAK |
| 147D11 | 5397430 | PAK |
| 147D12 | 1150858 | PAK |
| 147E03 | 3002610 | PAK |
| 147E04 | 4154804 | PAK |
| 147E05 | 3400991 | PAK |
| 147E06 | 933215 | PAK |
| 147E07 | 1684274 | PAK |
| 147E09 | 2981848 | PAK |
| 147E12 | 3225838 | PAK |
| 147F01 | 792524 | PAK |
| 147F02 | 548210 | PAK |
| 147F03 | 3634920 | PAK |
| 147F04 | 3837435 | PAK |
| 147F05 | 1596282 | PAK |
| 147F06 | 676417 | PAK |
| 147F08 | 2235989 | PAK |
| 147F09 | 5679156 | PAK |
| 147F10 | 2154856 | PAK |
| 147F11 | 3444352 | PAK |
| 147G01 | 5600549 | PAK |
| 147G03 | 5654992 | PAK |
| 147G04 | 67011 | PAK |
| 147G05 | 3472902 | PAK |
| 147G07 | 2663140 | PAK |
| 147G08 | 862656 | PAK |
| 147G09 | 1378207 | PAK |
| 147G10 | 5459807 | PAK |
| 147G11 | 3494899 | PAK |
| 147G12 | 3225838 | PAK |
| 147H04 | 5686691 | PAK |
| 147H05 | 927593 | PAK |
| 147H07 | 5058546 | PAK |
| 147H08 | 2516026 | PAK |
| 147H09 | 256971 | PAK |
| 148A01 | 1517114 | PAK |
| 148A02 | 3774332 | PAK |
| 148A03 | 5738810 | PAK |
| 148A04 | 5399725 | PAK |
| 148A05 | 3938899 | PAK |
| 148A06 | 2795402 | PAK |
| 148A07 | 1856834 | PAK |
| 148A10 | 4661339 | PAK |
| 148A11 | 619175 | PAK |
| 148A12 | 2892684 | PAK |
| 148B01 | 227554 | PAK |
| 148B02 | 4976058 | PAK |
| 148B03 | 3781351 | PAK |
| 148B04 | 2235908 | PAK |
| 148B05 | 94206 | PAK |
| 148B07 | 4505173 | PAK |
| 148B08 | 2473610 | PAK |
| 148B11 | 716901 | PAK |
| 148C02 | 938135 | PAK |
| 148C03 | 5504728 | PAK |
| 148C04 | 3581560 | PAK |
| 148C05 | 5742954 | PAK |
| 148C06 | 5633976 | PAK |
| 148C07 | 43209 | PAK |
| 148C08 | 1598622 | PAK |
| 148C09 | 4889471 | PAK |
| 148C11 | 1655142 | PAK |
| 148D02 | 5254615 | PAK |
| 148D03 | 204929 | PAK |
| 148D04 | 1454637 | PAK |
| 148D05 | 609041 | PAK |

TABLE 3-continued

| Mutant Name | Insertion Point | host strain |
|---|---|---|
| 148D06 | 886405 | PAK |
| 148D07 | 2968759 | PAK |
| 148D08 | 918914 | PAK |
| 148D09 | 6204695 | PAK |
| 148D10 | 5582412 | PAK |
| 148D11 | 2700822 | PAK |
| 148E01 | 1341154 | PAK |
| 148E04 | 4906766 | PAK |
| 148E05 | 4097476 | PAK |
| 148E07 | 3331171 | PAK |
| 148E08 | 5186946 | PAK |
| 148E10 | 36952 | PAK |
| 148E11 | 1894331 | PAK |
| 148F01 | 3781629 | PAK |
| 148F02 | 338786 | PAK |
| 148F03 | 2287009 | PAK |
| 148F04 | 5938188 | PAK |
| 148F05 | 546759 | PAK |
| 148F06 | 2609402 | PAK |
| 148F07 | 4308508 | PAK |
| 148F08 | 5466730 | PAK |
| 148F09 | 1984189 | PAK |
| 148F10 | 634058 | PAK |
| 148F11 | 338715 | PAK |
| 148G02 | 4431849 | PAK |
| 148G03 | 537178 | PAK |
| 148G04 | 4317259 | PAK |
| 148G06 | 1899467 | PAK |
| 148G08 | 6106851 | PAK |
| 148G09 | 3576563 | PAK |
| 148G10 | 1980773 | PAK |
| 148G11 | 5494285 | PAK |
| 148G12 | 4476018 | PAK |
| 148H01 | 1560740 | PAK |
| 148H02 | 1980773 | PAK |
| 148H03 | 1457074 | PAK |
| 148H04 | 374560 | PAK |
| 148H05 | 5775133 | PAK |
| 148H06 | 1220901 | PAK |
| 148H08 | 206740 | PAK |
| 148H09 | 4149662 | PAK |
| 148H10 | 5877561 | PAK |
| 149A01 | 2719832 | PAK |
| 149A02 | 2680174 | PAK |
| 149A03 | 2664188 | PAK |
| 149A04 | 345984 | PAK |
| 149A05 | 2682401 | PAK |
| 149A07 | 2715493 | PAK |
| 149A08 | 1165057 | PAK |
| 149A12 | 2671137 | PAK |
| 149B01 | 2661753 | PAK |
| 149B03 | 959779 | PAK |
| 149B04 | 6143862 | PAK |
| 149B05 | 333405 | PAK |
| 149B07 | 1262344 | PAK |
| 149B08 | 3490576 | PAK |
| 149B11 | 1419164 | PAK |
| 149B12 | 3018334 | PAK |
| 149C01 | 1388385 | PAK |
| 149C02 | 1110268 | PAK |
| 149C03 | 3401418 | PAK |
| 149C04 | 5151657 | PAK |
| 149C05 | 973853 | PAK |
| 149C06 | 2497369 | PAK |
| 149C07 | 3805173 | PAK |
| 149C09 | 3116617 | PAK |
| 149C11 | 3041586 | PAK |
| 149D03 | 2379612 | PAK |
| 149D04 | 4449369 | PAK |
| 149D05 | 3586854 | PAK |
| 149D06 | 5203940 | PAK |
| 149D08 | 6148049 | PAK |
| 149D11 | 2708931 | PAK |
| 149D12 | 1392368 | PAK |
| 149E02 | 5913940 | PAK |
| 149E03 | 5033821 | PAK |
| 149E04 | 5249113 | PAK |
| 149E05 | 944760 | PAK |
| 149E06 | 3029737 | PAK |
| 149E07 | 42161 | PAK |
| 149E08 | 2270211 | PAK |
| 149E09 | 5661762 | PAK |
| 149E11 | 5715245 | PAK |
| 149F02 | 2185216 | PAK |
| 149F03 | 1068488 | PAK |
| 149F04 | 5657415 | PAK |
| 149F05 | 5885039 | PAK |
| 149F06 | 3405166 | PAK |
| 149F07 | 888188 | PAK |
| 149F08 | 531458 | PAK |
| 149F09 | 3677847 | PAK |
| 149F10 | 804821 | PAK |
| 149F12 | 4455163 | PAK |
| 149G02 | 3804648 | PAK |
| 149G03 | 5200253 | PAK |
| 149G06 | 3900538 | PAK |
| 149G07 | 5293179 | PAK |
| 149G08 | 317709 | PAK |
| 149G10 | 5134620 | PAK |
| 149G11 | 3348153 | PAK |
| 149H01 | 4108103 | PAK |
| 149H02 | 2874924 | PAK |
| 149H03 | 4421910 | PAK |
| 149H04 | 1768379 | PAK |
| 149H05 | 780328 | PAK |
| 149H06 | 2021476 | PAK |
| 149H07 | 4206245 | PAK |
| 149H08 | 4370471 | PAK |
| 149H10 | 5178807 | PAK |
| 150A01 | 5482026 | PAK |
| 150A02 | 1451373 | PAK |
| 150A05 | 3751262 | PAK |
| 150A06 | 354189 | PAK |
| 150A07 | 2930587 | PAK |
| 150A08 | 692780 | PAK |
| 150A09 | 254894 | PAK |
| 150A10 | 5075363 | PAK |
| 150A12 | 1209014 | PAK |
| 150B01 | 4353831 | PAK |
| 150B02 | 6083524 | PAK |
| 150B03 | 5642143 | PAK |
| 150B05 | 1827578 | PAK |
| 150B06 | 602828 | PAK |
| 150B08 | 703522 | PAK |
| 150B09 | 2969682 | PAK |
| 150B11 | 4047635 | PAK |
| 150B12 | 1169920 | PAK |
| 150C02 | 67774 | PAK |
| 150C03 | 1187780 | PAK |
| 150C04 | 2804482 | PAK |
| 150C05 | 985330 | PAK |
| 150C06 | 4373139 | PAK |
| 150C07 | 690165 | PAK |
| 150C08 | 1769816 | PAK |
| 150C10 | 5830882 | PAK |
| 150C11 | 5936353 | PAK |
| 150C12 | 1991158 | PAK |
| 150D01 | 2023091 | PAK |
| 150D03 | 3202134 | PAK |
| 150D07 | 6195267 | PAK |
| 150D08 | 3722252 | PAK |
| 150D10 | 186653 | PAK |
| 150D11 | 1429947 | PAK |
| 150D12 | 3963109 | PAK |
| 150E06 | 6097051 | PAK |
| 150E07 | 615432 | PAK |
| 150E08 | 1127784 | PAK |
| 150E09 | 5892285 | PAK |
| 150E10 | 2933101 | PAK |
| 150E11 | 3642270 | PAK |
| 150E12 | 2052537 | PAK |
| 150F01 | 6219367 | PAK |
| 150F03 | 3034698 | PAK |
| 150F04 | 5897198 | PAK |

TABLE 3-continued

| Mutant Name | Insertion Point | host strain |
|---|---|---|
| 150F06 | 1804330 | PAK |
| 150F08 | 2904066 | PAK |
| 150F09 | 2735385 | PAK |
| 150F10 | 319649 | PAK |
| 150F11 | 934669 | PAK |
| 150F12 | 4516118 | PAK |
| 150G01 | 4560628 | PAK |
| 150G03 | 4879694 | PAK |
| 150G04 | 1282395 | PAK |
| 150G06 | 346213 | PAK |
| 150G07 | 5747739 | PAK |
| 150G10 | 2925246 | PAK |
| 150G11 | 5554112 | PAK |
| 150G12 | 1259007 | PAK |
| 150H02 | 2337293 | PAK |
| 150H04 | 1310689 | PAK |
| 150H06 | 2823453 | PAK |
| 151A01 | 2024252 | PA01 |
| 151A04 | 5290020 | PA01 |
| 151A08 | 2593196 | PA01 |
| 151A12 | 1887414 | PA01 |
| 151B01 | 3956855 | PA01 |
| 151B02 | 2769540 | PA01 |
| 151B03 | 449667 | PA01 |
| 151B04 | 3314648 | PA01 |
| 151B05 | 3266169 | PA01 |
| 151B10 | 4326921 | PA01 |
| 151D01 | 3881730 | PA01 |
| 151D02 | 4884235 | PA01 |
| 151D03 | 5367474 | PA01 |
| 151D0S | 5734735 | PA01 |
| 151D07 | 3507034 | PA01 |
| 151E02 | 451455 | PA01 |
| 151E03 | 5648190 | PA01 |
| 151E05 | 3435494 | PA01 |
| 151E09 | 2299548 | PA01 |
| 151E10 | 2529950 | PA01 |
| 151F01 | 3368456 | PA01 |
| 151F05 | 5416526 | PA01 |
| 151G02 | 1077526 | PA01 |
| 151G03 | 625714 | PA01 |
| 151G05 | 1053513 | PA01 |
| 151G07 | 3098268 | PA01 |
| 151G09 | 1195792 | PA01 |
| 151G10 | 2502271 | PA01 |
| 151G11 | 5721127 | PA01 |
| 151H07 | 2803218 | PA01 |
| 151H09 | 5814204 | PA01 |
| 152A02 | 4122428 | PA01 |
| 152A04 | 270701 | PA01 |
| 152A05 | 1052246 | PA01 |
| 152A06 | 4101605 | PA01 |
| 152A07 | 1872122 | PA01 |
| 152A10 | 1582135 | PA01 |
| 152B01 | 290650 | PA01 |
| 152B03 | 3649040 | PA01 |
| 152B11 | 3376691 | PA01 |
| 152B12 | 603069 | PA01 |
| 152C01 | 5197602 | PA01 |
| 152C03 | 4890017 | PA01 |
| 152C05 | 2008645 | PA01 |
| 152C06 | 1601881 | PA01 |
| 152C11 | 2774001 | PA01 |
| 152C02 | 3356924 | PA01 |
| 152C08 | 5863981 | PA01 |
| 152D10 | 5429316 | PA01 |
| 152E01 | 4067073 | PA01 |
| 152E03 | 4114598 | PA01 |
| 152E05 | 2261801 | PA01 |
| 152E07 | 5294995 | PA01 |
| 152F01 | 3716487 | PA01 |
| 152F03 | 1618948 | PA01 |
| 152F09 | 1098937 | PA01 |
| 152F11 | 3507034 | PA01 |
| 152G01 | 1581482 | PA01 |
| 152G04 | 5367474 | PA01 |
| 152G06 | 1116442 | PA01 |
| 152G07 | 5878443 | PA01 |
| 152G09 | 5775034 | PA01 |
| 152G11 | 1298017 | PA01 |
| 152G12 | 1400451 | PA01 |
| 152H01 | 5727451 | PA01 |
| 152H02 | 1964590 | PA01 |
| 152H05 | 1798156 | PA01 |
| 152H06 | 3861943 | PA01 |
| 152H08 | 258362 | PA01 |
| 152H09 | 6125519 | PA01 |
| 152H10 | 2007157 | PA01 |
| 153A01 | 1642376 | PA01 |
| 153A02 | 3285673 | PA01 |
| 153A05 | 5822685 | PA01 |
| 153A07 | 2035293 | PA01 |
| 153A09 | 1582135 | PA01 |
| 153A10 | 6075617 | PA01 |
| 153A12 | 5583931 | PA01 |
| 153B01 | 1048428 | PA01 |
| 153B04 | 869436 | PA01 |
| 153B09 | 5850910 | PA01 |
| 153B10 | 4515804 | PA01 |
| 153B11 | 1528294 | PA01 |
| 153C02 | 1953265 | PA01 |
| 153C03 | 1001886 | PA01 |
| 153C04 | 1930152 | PA01 |
| 153C05 | 1262099 | PA01 |
| 153C10 | 4155540 | PA01 |
| 153C12 | 5087413 | PA01 |
| 153D03 | 4276002 | PA01 |
| 153D04 | 5770792 | PA01 |
| 153D05 | 3020242 | PA01 |
| 153D07 | 67563 | PA01 |
| 153D08 | 102538 | PA01 |
| 153D10 | 3177675 | PA01 |
| 153D11 | 1001886 | PA01 |
| 153E01 | 2978088 | PA01 |
| 153E02 | 5151949 | PA01 |
| 153E03 | 279820 | PA01 |
| 153E04 | 3290328 | PA01 |
| 153E05 | 3813760 | PA01 |
| 153E06 | 1562159 | PA01 |
| 153E10 | 3808959 | PA01 |
| 153F03 | 1648474 | PA01 |
| 153F04 | 6057244 | PA01 |
| 153F05 | 4921807 | PA01 |
| 153F06 | 5045793 | PA01 |
| 153F07 | 4007300 | PA01 |
| 153F08 | 1562159 | PA01 |
| 153F11 | 5805203 | PA01 |
| 153G02 | 4926330 | PA01 |
| 153G04 | 284033 | PA01 |
| 153G05 | 2238788 | PA01 |
| 153H02 | 5866630 | PA01 |
| 153H03 | 809331 | PA01 |
| 153H08 | 6231871 | PA01 |
| 153H09 | 6204815 | PA01 |
| 153H10 | 2461359 | PA01 |
| 153H11 | 5092983 | PA01 |
| 157A02 | 4884700 | PA01 |
| 157A03 | 5975186 | PA01 |
| 157A04 | 1908237 | PA01 |
| 157A05 | 5958618 | PA01 |
| 157A06 | 824403 | PA01 |
| 157A07 | 1581388 | PA01 |
| 157A08 | 3818917 | PA01 |
| 157A09 | 4793686 | PA01 |
| 157A10 | 4551123 | PA01 |
| 157A11 | 273807 | PA01 |
| 157A12 | 1859426 | PA01 |
| 157B02 | 5850794 | PA01 |
| 157B03 | 2288861 | PA01 |
| 157B04 | 3116632 | PA01 |
| 157B07 | 3767294 | PA01 |
| 157B08 | 4124112 | PA01 |
| 157B09 | 42573 | PA01 |
| 157B11 | 2680259 | PA01 |

TABLE 3-continued

| Mutant Name | Insertion Point | host strain |
|---|---|---|
| 157C01 | 147623 | PA01 |
| 157C03 | 2980754 | PA01 |
| 157C05 | 5723459 | PA01 |
| 157C06 | 551899 | PA01 |
| 157C07 | 5007313 | PA01 |
| 157C11 | 4048011 | PA01 |
| 157C12 | 5397714 | PA01 |
| 157D01 | 572597 | PA01 |
| 157D02 | 6157015 | PA01 |
| 157D03 | 1448947 | PA01 |
| 157D05 | 3250645 | PA01 |
| 157D07 | 4891764 | PA01 |
| 157D08 | 4662342 | PA01 |
| 157D09 | 4247751 | PA01 |
| 157D12 | 1713828 | PA01 |
| 157E02 | 5259920 | PA01 |
| 157E03 | 1351043 | PA01 |
| 157E04 | 5823535 | PA01 |
| 157E05 | 4980162 | PA01 |
| 157E06 | 41870 | PA01 |
| 157E07 | 3504641 | PA01 |
| 157E09 | 1036208 | PA01 |
| 157E10 | 1223356 | PA01 |
| 157F01 | 3179077 | PA01 |
| 157F03 | 6205197 | PA01 |
| 157F07 | 6108163 | PA01 |
| 157F08 | 4046311 | PA01 |
| 157F09 | 298662 | PA01 |
| 157F11 | 5821324 | PA01 |
| 157G02 | 5609452 | PA01 |
| 157G03 | 5971194 | PA01 |
| 157G04 | 3256112 | PA01 |
| 157G06 | 3660559 | PA01 |
| 157G07 | 226728 | PA01 |
| 157G09 | 1246547 | PA01 |
| 157G11 | 5887357 | PA01 |
| 157G12 | 3418092 | PA01 |
| 157H02 | 3304923 | PA01 |
| 157H03 | 1126952 | PA01 |
| 157H04 | 3461804 | PA01 |
| 157H05 | 4153082 | PA01 |
| 157H06 | 5695631 | PA01 |
| 157H07 | 162319 | PA01 |
| 157H10 | 3474932 | PA01 |
| 157H11 | 2024252 | PA01 |
| 158A01 | 6080414 | PA01 |
| 158A08 | 5193409 | PA01 |
| 158A09 | 3678189 | PA01 |
| 158A10 | 2526109 | PA01 |
| 158A11 | 3380281 | PA01 |
| 158A12 | 2190466 | PA01 |
| 158B01 | 5321702 | PA01 |
| 158B07 | 5368567 | PA01 |
| 158B08 | 381452 | PA01 |
| 158B09 | 2631729 | PA01 |
| 158B10 | 1292665 | PA01 |
| 153B11 | 5712347 | PA01 |
| 158C02 | 3268192 | PA01 |
| 158C05 | 4998604 | PA01 |
| 158C06 | 4514580 | PA01 |
| 158C07 | 348317 | PA01 |
| 158C08 | 6241384 | PA01 |
| 158C09 | 5063251 | PA01 |
| 158C12 | 597514 | PA01 |
| 158D01 | 657988 | PA01 |
| 158D02 | 5032955 | PA01 |
| 158D03 | 4573441 | PA01 |
| 158D04 | 4037942 | PA01 |
| 158D05 | 3066722 | PA01 |
| 158D07 | 813072 | PA01 |
| 158D09 | 961771 | PA01 |
| 158D10 | 46038 | PA01 |
| 158D11 | 367607 | PA01 |
| 158E01 | 5368567 | PA01 |
| 158E02 | 5218504 | PA01 |
| 158E03 | 5397714 | PA01 |
| 158E04 | 348317 | PA01 |
| 158E05 | 1290452 | PA01 |
| 158E06 | 3332267 | PA01 |
| 158E07 | 4057053 | PA01 |
| 158E08 | 2903436 | PA01 |
| 158E09 | 3090784 | PA01 |
| 158E10 | 2022774 | PA01 |
| 158F01 | 5020600 | PA01 |
| 158F02 | 3140135 | PA01 |
| 158F03 | 1137141 | PA01 |
| 158F05 | 1984077 | PA01 |
| 158F06 | 5841792 | PA01 |
| 158F08 | 6054284 | PA01 |
| 158F09 | 2319393 | PA01 |
| 158F10 | 5623913 | PA01 |
| 158F12 | 365538 | PA01 |
| 158G03 | 2926319 | PA01 |
| 158G05 | 1580547 | PA01 |
| 158G06 | 1965759 | PA01 |
| 158G09 | 4424187 | PA01 |
| 158G10 | 5949402 | PA01 |
| 158G11 | 328727 | PA01 |
| 158G12 | 1758902 | PA01 |
| 158H01 | 2850997 | PA01 |
| 158H02 | 4609156 | PA01 |
| 158H03 | 3405846 | PA01 |
| 158H05 | 228287 | PA01 |
| 158H06 | 2850997 | PA01 |
| 158H07 | 5968219 | PA01 |
| 158H08 | 3169045 | PA01 |
| 158H09 | 3225429 | PA01 |
| 158H10 | 2842829 | PA01 |
| 158H11 | 2024252 | PA01 |
| 159A02 | 2670329 | PA01 |
| 159A03 | 2960033 | PA01 |
| 159A04 | 3148519 | PA01 |
| 159A06 | 4057053 | PA01 |
| 159A08 | 2148180 | PA01 |
| 159A09 | 357524 | PA01 |
| 159A11 | 3357471 | PA01 |
| 159A12 | 108054 | PA01 |
| 159B04 | 2059801 | PA01 |
| 159B05 | 1542567 | PA01 |
| 159B06 | 1430926 | PA01 |
| 159B08 | 4250418 | PA01 |
| 159B10 | 4257734 | PA01 |
| 159B11 | 2385339 | PA01 |
| 159B12 | 1517113 | PA01 |
| 159C01 | 573910 | PA01 |
| 159C03 | 464333 | PA01 |
| 159C04 | 2507094 | PA01 |
| 159C05 | 3960045 | PA01 |
| 159C07 | 6083525 | PA01 |
| 159C08 | 408554 | PA01 |
| 159C09 | 5768487 | PA01 |
| 159C10 | 968173 | PA01 |
| 159C11 | 4099011 | PA01 |
| 159C12 | 889493 | PA01 |
| 159D02 | 3742040 | PA01 |
| 159D04 | 5156500 | PA01 |
| 159D07 | 5958709 | PA01 |
| 159D11 | 2420856 | PA01 |
| 159D12 | 1481549 | PA01 |
| 159E03 | 71951 | PA01 |
| 159E06 | 1060979 | PA01 |
| 159E07 | 1838870 | PA01 |
| 159E10 | 6169036 | PA01 |
| 159E11 | 3380281 | PA01 |
| 159E12 | 4321995 | PA01 |
| 159F01 | 5259920 | PA01 |
| 159F02 | 3650993 | PA01 |
| 159F04 | 4276151 | PA01 |
| 159F05 | 4425275 | PA01 |
| 159F06 | 1355033 | PA01 |
| 159F07 | 1694788 | PA01 |
| 159F08 | 297452 | PA01 |
| 159F09 | 3342162 | PA01 |
| 159G01 | 1951933 | PA01 |

TABLE 3-continued

| Mutant Name | Insertion Point | host strain |
|---|---|---|
| 159G04 | 4985650 | PA01 |
| 159G05 | 2598751 | PA01 |
| 159G06 | 1636680 | PA01 |
| 159G07 | 1024001 | PA01 |
| 159G09 | 2600863 | PA01 |
| 159G10 | 1019885 | PA01 |
| 159G11 | 1758902 | PA01 |
| 159G12 | 6178053 | PA01 |
| 159H01 | 824898 | PA01 |
| 159H04 | 2024291 | PA01 |
| 159H05 | 2670329 | PA01 |
| 159H07 | 909223 | PA01 |
| 159H08 | 6168577 | PA01 |
| 159H09 | 2337293 | PA01 |
| 159H10 | 3474932 | PA01 |
| 159H11 | 2024252 | PA01 |
| 160A01 | 940076 | PA01 |
| 160A02 | 2887551 | PA01 |
| 160A04 | 108053 | PA01 |
| 160A06 | 255065 | PA01 |
| 160A09 | 1403079 | PA01 |
| 160A10 | 2080596 | PA01 |
| 160A12 | 2479953 | PA01 |
| 160B02 | 886880 | PA01 |
| 160B03 | 6140782 | PA01 |
| 160B04 | 1582134 | PA01 |
| 160B07 | 3378413 | PA01 |
| 160B08 | 1405005 | PA01 |
| 160B09 | 3773433 | PA01 |
| 160B10 | 771730 | PA01 |
| 160B12 | 1192100 | PA01 |
| 160C02 | 957984 | PA01 |
| 160C04 | 1150833 | PA01 |
| 160C10 | 1951934 | PA01 |
| 160C11 | 5883869 | PA01 |
| 160D03 | 3986008 | PA01 |
| 160D07 | 1582134 | PA01 |
| 160D09 | 1789005 | PA01 |
| 160D11 | 1704186 | PA01 |
| 160O12 | 1783427 | PA01 |
| 160E02 | 6260275 | PA01 |
| 160E03 | 3022373 | PA01 |
| 160E04 | 5891106 | PA01 |
| 160E07 | 2988351 | PA01 |
| 160E09 | 1610535 | PA01 |
| 160E10 | 112498 | PA01 |
| 160E11 | 5981231 | PA01 |
| 160F01 | 428867 | PA01 |
| 160F02 | 1942528 | PA01 |
| 160F03 | 964609 | PA01 |
| 160F04 | 5980854 | PA01 |
| 160F05 | 439014 | PA01 |
| 160F06 | 1963010 | PA01 |
| 160F07 | 5177092 | PA01 |
| 160F08 | 330279 | PA01 |
| 160F09 | 5561460 | PA01 |
| 160F10 | 1504725 | PA01 |
| 160F11 | 2863176 | PA01 |
| 160F12 | 1405793 | PA01 |
| 160G04 | 5892448 | PA01 |
| 160G05 | 1019886 | PA01 |
| 160G06 | 2702962 | PA01 |
| 160G07 | 3706540 | PA01 |
| 160G09 | 3235122 | PA01 |
| 160G10 | 2337293 | PA01 |
| 160G12 | 4884700 | PA01 |
| 160H01 | 3767291 | PA01 |
| 160H02 | 439437 | PA01 |
| 160H06 | 539660 | PA01 |
| 160H09 | 5006039 | PA01 |
| 160H10 | 4398438 | PA01 |
| 160H11 | 2024252 | PA01 |
| 161A01 | 2789375 | PA01 |
| 161A03 | 2658999 | PA01 |
| 161A04 | 4001994 | PA01 |
| 161A05 | 5424453 | PA01 |
| 161A07 | 2095679 | PA01 |
| 161A09 | 58284 | PA01 |
| 161A10 | 39Z5556 | PA01 |
| 161A11 | 1517114 | PA01 |
| 161A12 | 1704186 | PA01 |
| 161B01 | 6215279 | PA01 |
| 161B03 | 1420692 | PA01 |
| 161B04 | 4518554 | PA01 |
| 161B05 | 162321 | PA01 |
| 161B07 | 2835740 | PA01 |
| 161B08 | 5367830 | PA01 |
| 161B10 | 5006037 | PA01 |
| 161B11 | 5529376 | PA01 |
| 161B12 | 3815173 | PA01 |
| 161C01 | 818572 | PA01 |
| 161C02 | 3053943 | PA01 |
| 161C03 | 5368567 | PA01 |
| 161C04 | 853216 | PA01 |
| 161C05 | 5395878 | PA01 |
| 161C06 | 5407090 | PA01 |
| 161C08 | 399746 | PA01 |
| 161C09 | 550020 | PA01 |
| 161C10 | 1219522 | PA01 |
| 161C11 | 3678583 | PA01 |
| 161C12 | 3592235 | PA01 |
| 161D02 | 1857142 | PA01 |
| 161D03 | 5529375 | PA01 |
| 161D04 | 1314830 | PA01 |
| 161D07 | 6155451 | PA01 |
| 161D08 | 4121641 | PA01 |
| 161D10 | 738857 | PA01 |
| 161D11 | 1337553 | PA01 |
| 161E01 | 369507 | PA01 |
| 161E02 | 4720986 | PA01 |
| 161E03 | 1046904 | PA01 |
| 161E04 | 6157015 | PA01 |
| 161E07 | 1740616 | PA01 |
| 161E08 | 4134183 | PA01 |
| 161E10 | 3505657 | PA01 |
| 161E11 | 657988 | PA01 |
| 161E12 | 4492441 | PA01 |
| 161F01 | 5057450 | PA01 |
| 161F03 | 458426 | PA01 |
| 161F05 | 5623913 | PA01 |
| 161F06 | 4492441 | PA01 |
| 161F07 | 3266073 | PA01 |
| 161F08 | 386935 | PA01 |
| 161F09 | 5020603 | PA01 |
| 161F11 | 5651280 | PA01 |
| 161G01 | 5540538 | PA01 |
| 161G03 | 62734 | PA01 |
| 161G04 | 891681 | PA01 |
| 161O05 | 5053679 | PA01 |
| 161G06 | 4367273 | PA01 |
| 161G07 | 3915718 | PA01 |
| 161G08 | 4130509 | PA01 |
| 161G10 | 891681 | PA01 |
| 161G11 | 23349 | PA01 |
| 161H02 | 2758037 | PA01 |
| 161H04 | 1686760 | PA01 |
| 161H05 | 1813416 | PA01 |
| 161H07 | 5718751 | PA01 |
| 161H08 | 3647317 | PA01 |
| 161H09 | 2960217 | PA01 |
| 161H11 | 2024252 | PA01 |
| 162B01 | 2681513 | PA01 |
| 162B02 | 4199275 | PA01 |
| 162B09 | 41870 | PA01 |
| 162B10 | 4324206 | PA01 |
| 162B12 | 4329197 | PA01 |
| 162C04 | 331446 | PA01 |
| 162C10 | 4200393 | PA01 |
| 162C11 | 5058150 | PA01 |
| 162C12 | 928837 | PA01 |
| 162D04 | 4866383 | PA01 |
| 162D05 | 2900660 | PA01 |
| 162D06 | 4321996 | PA01 |
| 162D07 | 2072432 | PA01 |

TABLE 3-continued

| Mutant Name | Insertion Point | host strain |
|---|---|---|
| 162D08 | 4745704 | PA01 |
| 162D09 | 366266 | PA01 |
| 162D11 | 2043785 | PA01 |
| 162D12 | 3019863 | PA01 |
| 162E02 | 6191681 | PA01 |
| 162E06 | 4513267 | PA01 |
| 162E08 | 3634669 | PA01 |
| 162E10 | 1740405 | PA01 |
| 162F01 | 6178080 | PA01 |
| 162F03 | 5456567 | PA01 |
| 162F04 | 86151 | PA01 |
| 162F09 | 614801 | PA01 |
| 162F10 | 1320232 | PA01 |
| 162G01 | 2013897 | PA01 |
| 162G02 | 2549629 | PA01 |
| 162G03 | 5288830 | PA01 |
| 162G04 | 3304923 | PA01 |
| 162G06 | 4133455 | PA01 |
| 162G11 | 1077252 | PA01 |
| 162H01 | 3815173 | PA01 |
| 162H02 | 5673778 | PA01 |
| 162H04 | 1906807 | PA01 |
| 162H05 | 1223356 | PA01 |
| 162H07 | 1898995 | PA01 |
| 162H08 | 3053943 | PA01 |
| 162H09 | 554266 | PA01 |
| 162H10 | 5254935 | PA01 |
| 162H11 | 2024252 | PA01 |
| 163A01 | 1389074 | PA01 |
| 163A02 | 1450136 | PA01 |
| 163A05 | 3461365 | PA01 |
| 163A08 | 1885657 | PA01 |
| 163B01 | 774049 | PA01 |
| 163B06 | 6193301 | PA01 |
| 163B08 | 427385 | PA01 |
| 163B10 | 6049867 | PA01 |
| 163C05 | 2938842 | PA01 |
| 163C06 | 5251985 | PA01 |
| 163C07 | 3367564 | PA01 |
| 163C08 | 1959908 | PA01 |
| 163C10 | 767555 | PA01 |
| 163C12 | 4371658 | PA01 |
| 163D01 | 6061403 | PA01 |
| 163D05 | 1021887 | PA01 |
| 163D06 | 3460638 | PA01 |
| 163D09 | 6178946 | PA01 |
| 163D10 | 300674 | PA01 |
| 163D11 | 1185026 | PA01 |
| 163D12 | 4371658 | PA01 |
| 163E02 | 3341290 | PA01 |
| 163E04 | 2693034 | PA01 |
| 163E07 | 894630 | PA01 |
| 163E09 | 3658392 | PA01 |
| 163E11 | 1862468 | PA01 |
| 163E12 | 675520 | PA01 |
| 163F01 | 5006037 | PA01 |
| 163F05 | 4615607 | PA01 |
| 163F06 | 4154730 | PA01 |
| 163F07 | 6022307 | PA01 |
| 163F08 | 303673 | PA01 |
| 163F10 | 5909814 | PA01 |
| 163F11 | 1320232 | PA01 |
| 163G01 | 5605559 | PA01 |
| 163G04 | 4042731 | PA01 |
| 163G05 | 4220190 | PA01 |
| 163G06 | 6240253 | PA01 |
| 163G08 | 714975 | PA01 |
| 163G09 | 1557400 | PA01 |
| 163G10 | 3592227 | PA01 |
| 163G11 | 4437335 | PA01 |
| 163G12 | 341023 | PA01 |
| 163H02 | 4517354 | PA01 |
| 163H03 | 5942350 | PA01 |
| 163H04 | 5043623 | PA01 |
| 163H08 | 419887 | PA01 |
| 163H09 | 4112926 | PA01 |
| 164A01 | 142332 | PA01 |
| 164A02 | 2058994 | PA01 |
| 164A03 | 5844539 | PA01 |
| 164A04 | 2412680 | PA01 |
| 164A07 | 5220414 | PA01 |
| 164A08 | 2152205 | PA01 |
| 164A10 | 920155 | PA01 |
| 164A11 | 920150 | PA01 |
| 164B01 | 65315 | PA01 |
| 164B03 | 252365 | PA01 |
| 164B05 | 1022558 | PA01 |
| 164B08 | 1655424 | PA01 |
| 164B09 | 1137119 | PA01 |
| 164B10 | 1296762 | PA01 |
| 164B11 | 1599165 | PA01 |
| 164B12 | 3218774 | PA01 |
| 164C01 | 5271365 | PA01 |
| 164C02 | 6133958 | PA01 |
| 164C03 | 5556276 | PA01 |
| 164C04 | 4691547 | PA01 |
| 164C05 | 5456928 | PA01 |
| 164C06 | 1290741 | PA01 |
| 164C07 | 5481297 | PA01 |
| 164C08 | 2684131 | PA01 |
| 164C09 | 4521214 | PA01 |
| 164C11 | 5768035 | PA01 |
| 164D01 | 5721924 | PA01 |
| 164D03 | 1582132 | PA01 |
| 164D04 | 5040637 | PA01 |
| 164D06 | 1429084 | PA01 |
| 164D07 | 2678766 | PA01 |
| 164D08 | 2626339 | PA01 |
| 164D09 | 39799 | PA01 |
| 164D10 | 4932888 | PA01 |
| 164E01 | 130348 | PA01 |
| 164E02 | 5903062 | PA01 |
| 164E03 | 8780142 | PA01 |
| 164E06 | 940747 | PA01 |
| 164E07 | 599615 | PA01 |
| 164E08 | 5263348 | PA01 |
| 164E09 | 894630 | PA01 |
| 164E10 | 1906892 | PA01 |
| 164E11 | 1601881 | PA01 |
| 164E12 | 2781791 | PA01 |
| 164F01 | 5994594 | PA01 |
| 164F03 | 320752 | PA01 |
| 164F05 | 4472097 | PA01 |
| 164F06 | 5142000 | PA01 |
| 164F09 | 946484 | PA01 |
| 164F10 | 5083277 | PA01 |
| 164F11 | 5854455 | PA01 |
| 164G02 | 4551247 | PA01 |
| 164G03 | 3751362 | PA01 |
| 164G04 | 5434902 | PA01 |
| 164G05 | 1203434 | PA01 |
| 164G06 | 1297547 | PA01 |
| 164G07 | 1152093 | PA01 |
| 164G08 | 5567276 | PA01 |
| 164G09 | 1757420 | PA01 |
| 164G10 | 2300649 | PA01 |
| 164G11 | 4810847 | PA01 |
| 164G12 | 4440367 | PA01 |
| 164H02 | 481393 | PA01 |
| 164H03 | 4284005 | PA01 |
| 164H11 | 2024252 | PA01 |
| 165A06 | 4618389 | PA01 |
| 165A07 | 5694210 | PA01 |
| 165A11 | 761876 | PA01 |
| 165B01 | 3231737 | PA01 |
| 165B04 | 4047635 | PA01 |
| 165B07 | 3706869 | PA01 |
| 165B08 | 1139296 | PA01 |
| 165B09 | 3643355 | PA01 |
| 165B12 | 5653582 | PA01 |
| 165C02 | 5694210 | PA01 |
| 165C03 | 2399019 | PA01 |
| 165C05 | 4673714 | PA01 |
| 165C07 | 544808 | PA01 |

TABLE 3-continued

| Mutant Name | Insertion Point | host strain |
|---|---|---|
| 165C08 | 1711301 | PA01 |
| 165C10 | 946484 | PA01 |
| 165C12 | 4440367 | PA01 |
| 165D01 | 2000354 | PA01 |
| 165E03 | 1530709 | PA01 |
| 165E04 | 2515739 | PA01 |
| 165E06 | 2024290 | PA01 |
| 165E08 | 931505 | PA01 |
| 165E09 | 660566 | PA01 |
| 165E10 | 1999203 | PA01 |
| 165F01 | 3979079 | PA01 |
| 165F05 | 2837728 | PA01 |
| 165F10 | 518730 | PA01 |
| 165F11 | 1351298 | PA01 |
| 165F12 | 14705272 | PA01 |
| 165G02 | 761876 | PA01 |
| 165G03 | 50333782 | PA01 |
| 165G04 | 2282835 | PA01 |
| 165G08 | 807180 | PA01 |
| 165G09 | 954087 | PA01 |
| 165G10 | 4870890 | PA01 |
| 165H01 | 661998 | PA01 |
| 165H02 | 2375963 | PA01 |
| 165H04 | 17467752 | PA01 |
| 165H06 | 4749361 | PA01 |
| 165H08 | 3644301 | PA01 |
| 165H09 | 1078894 | PA01 |
| 165H11 | 2024252 | PA01 |
| 166A02 | 3505585 | PA01 |
| 166A03 | 6219617 | PA01 |
| 166A04 | 1170196 | PA01 |
| 166A05 | 2147215 | PA01 |
| 166A08 | 5501093 | PA01 |
| 166A10 | 4522687 | PA01 |
| 166A12 | 1835685 | PA01 |
| 166B01 | 1286580 | PA01 |
| 166B03 | 1079350 | PA01 |
| 166B05 | 640385 | PA01 |
| 166B06 | 6227025 | PA01 |
| 166B08 | 2906882 | PA01 |
| 166B09 | 1974767 | PA01 |
| 166B11 | 5123935 | PA01 |
| 166C01 | 2668026 | PA01 |
| 166C03 | 2570611 | PA01 |
| 166C04 | 1655999 | PA01 |
| 166C06 | 1115069 | PA01 |
| 166C07 | 2024704 | PA01 |
| 166C08 | 5456821 | PA01 |
| 166C10 | 5564061 | PA01 |
| 166C11 | 670686 | PA01 |
| 166C12 | 323308 | PA01 |
| 166D01 | 5559912 | PA01 |
| 166D06 | 5050984 | PA01 |
| 166D08 | 517605 | PA01 |
| 166D09 | 3023054 | PA01 |
| 166D10 | 4589642 | PA01 |
| 166D11 | 4483454 | PA01 |
| 166D12 | 4212283 | PA01 |
| 166E01 | 1183788 | PA01 |
| 166E03 | 5449046 | PA01 |
| 166E04 | 6227025 | PA01 |
| 166E06 | 4066924 | PA01 |
| 166E08 | 3306499 | PA01 |
| 166E09 | 2173490 | PA01 |
| 166E10 | 505588 | PA01 |
| 166F01 | 4585465 | PA01 |
| 166F02 | 4365789 | PA01 |
| 166F03 | 6228869 | PA01 |
| 166F07 | 5770155 | PA01 |
| 166F08 | 1927015 | PA01 |
| 166F09 | 4414026 | PA01 |
| 166F11 | 622095 | PA01 |
| 166F12 | 961274 | PA01 |
| 166G01 | 5564061 | PA01 |
| 166G03 | 1302068 | PA01 |
| 166G06 | 5698552 | PA01 |
| 166G09 | 5977582 | PA01 |

TABLE 3-continued

| Mutant Name | Insertion Point | host strain |
|---|---|---|
| 166G11 | 6035646 | PA01 |
| 166H01 | 1972286 | PA01 |
| 166H02 | 912492 | PA01 |
| 166H03 | 2726657 | PA01 |
| 166H04 | 3214292 | PA01 |
| 166H06 | 5254049 | PA01 |
| 166H07 | 2019843 | PA01 |
| 166H08 | 4494227 | PA01 |
| 166H09 | 3986398 | PA01 |
| 166H10 | 2557656 | PA01 |
| 166H11 | 2024252 | PA01 |
| 167A01 | 177923 | PA01 |
| 167A02 | 3804716 | PA01 |
| 167A04 | 5118187 | PA01 |
| 167A05 | 659142 | PA01 |
| 167A06 | 715509 | PA01 |
| 167A07 | 5684985 | PA01 |
| 167A08 | 2058994 | PA01 |
| 167A09 | 3955647 | PA01 |
| 167A10 | 4118673 | PA01 |
| 157A11 | 1746364 | PA01 |
| 167A12 | 1830069 | PA01 |
| 167B04 | 4975465 | PA01 |
| 167B05 | 5461641 | PA01 |
| 167B06 | 3420969 | PA01 |
| 167B07 | 5736341 | PA01 |
| 167B08 | 4538762 | PA01 |
| 167B09 | 3658392 | PA01 |
| 167B10 | 2075793 | PA01 |
| 167B11 | 4392105 | PA01 |
| 167B12 | 6220007 | PA01 |
| 167C02 | 377871 | PA01 |
| 167C03 | 3213694 | PA01 |
| 167C04 | 801157 | PA01 |
| 167C05 | 228078 | PA01 |
| 167C07 | 4367574 | PA01 |
| 167C08 | 2229343 | PA01 |
| 167C10 | 1383796 | PA01 |
| 167C12 | 814430 | PA01 |
| 167D01 | 5357665 | PA01 |
| 167D02 | 5026326 | PA01 |
| 167D03 | 1220413 | PA01 |
| 167D04 | 352288 | PA01 |
| 167D06 | 912492 | PA01 |
| 167D07 | 5032357 | PA01 |
| 167D08 | 632607 | PA01 |
| 167D10 | 4299389 | PA01 |
| 167D11 | 5539080 | PA01 |
| 167D12 | 1657083 | PA01 |
| 167E03 | 678072 | PA01 |
| 167E04 | 940619 | PA01 |
| 167E05 | 5375361 | PA01 |
| 167E07 | 3627888 | PA01 |
| 167E08 | 1962430 | PA01 |
| 167E09 | 687550 | PA01 |
| 167E10 | 5056159 | PA01 |
| 167E11 | 5280103 | PA01 |
| 167E12 | 170396 | PA01 |
| 167F01 | 228616 | PA01 |
| 167F02 | 3590 | PA01 |
| 167F03 | 944736 | PA01 |
| 167F05 | 793590 | PA01 |
| 167F06 | 1709171 | PA01 |
| 167F08 | 480370 | PA01 |
| 167F09 | 5587391 | PA01 |
| 167F10 | 5648183 | PA01 |
| 167F11 | 3847279 | PA01 |
| 167G01 | 4650013 | PA01 |
| 167G02 | 5594460 | PA01 |
| 167G03 | 944736 | PA01 |
| 167G04 | 1050218 | PA01 |
| 167G05 | 1227816 | PA01 |
| 167G06 | 3464395 | PA01 |
| 167G07 | 5271401 | PA01 |
| 167G08 | 3213694 | PA01 |
| 167G09 | 4883121 | PA01 |
| 167G10 | 3839348 | PA01 |

TABLE 3-continued

| Mutant Name | Insertion Point | host strain |
|---|---|---|
| 167G11 | 1574191 | PA01 |
| 167G12 | 3237341 | PA01 |
| 167H01 | 1625271 | PA01 |
| 167H02 | 5189476 | PA01 |
| 167H03 | 5002563 | PA01 |
| 167H04 | 376399 | PA01 |
| 167H05 | 2668026 | PA01 |
| 167H06 | 4410630 | PA01 |
| 167H07 | 4212283 | PA01 |
| 167H09 | 5936162 | PA01 |
| 167H10 | 95407 | PA01 |
| 168A01 | 5430219 | PA01 |
| 168A03 | 4739834 | PA01 |
| 168A04 | 2946436 | PA01 |
| 168A05 | 2236896 | PA01 |
| 168A08 | 3123552 | PA01 |
| 168A11 | 355836 | PA01 |
| 168B01 | 979433 | PA01 |
| 168B02 | 1900110 | PA01 |
| 168B03 | 2894526 | PA01 |
| 168B06 | 3374258 | PA01 |
| 168B08 | 1566406 | PA01 |
| 168B09 | 3809683 | PA01 |
| 168B10 | 1274045 | PA01 |
| 168C01 | 5547896 | PA01 |
| 168C02 | 261377 | PA01 |
| 168C03 | 1151573 | PA01 |
| 168C04 | 3403335 | PA01 |
| 168C05 | 229062 | PA01 |
| 168C06 | 1127986 | PA01 |
| 168C07 | 3036987 | PA01 |
| 168C09 | 5183525 | PA01 |
| 168C10 | 1343505 | PA01 |
| 168C11 | 2686627 | PA01 |
| 168C12 | 5278577 | PA01 |
| 168D01 | 4501410 | PA01 |
| 168D02 | 1986105 | PA01 |
| 168D03 | 1429084 | PA01 |
| 168D05 | 4810359 | PA01 |
| 168D06 | 1018388 | PA01 |
| 168D09 | 3659268 | PA01 |
| 168D10 | 6198870 | PA01 |
| 168D11 | 300674 | PA01 |
| 168D12 | 3072972 | PA01 |
| 168E01 | 5176497 | PA01 |
| 168E02 | 5479579 | PA01 |
| 168E03 | 1011138 | PA01 |
| 168E04 | 1772965 | PA01 |
| 168E06 | 4300130 | PA01 |
| 168E08 | 2677709 | PA01 |
| 168E09 | 5649789 | PA01 |
| 168F01 | 1006391 | PA01 |
| 168F02 | 5000428 | PA01 |
| 168F04 | 3659896 | PA01 |
| 168F05 | 3698084 | PA01 |
| 168F06 | 3979081 | PA01 |
| 168F07 | 5919682 | PA01 |
| 168F09 | 5433630 | PA01 |
| 168F11 | 426001 | PA01 |
| 168F12 | 1716600 | PA01 |
| 168G01 | 5583826 | PA01 |
| 168G02 | 5807299 | PA01 |
| 168G04 | 6215271 | PA01 |
| 168G05 | 4680833 | PA01 |
| 168G06 | 695431 | PA01 |
| 168G07 | 2037979 | PA01 |
| 168G09 | 4529101 | PA01 |
| 168G11 | 4138587 | PA01 |
| 168G12 | 1572717 | PA01 |
| 168H02 | 3926327 | PA01 |
| 168H04 | 223060 | PA01 |
| 168H05 | 1988302 | PA01 |
| 168H06 | 4320040 | PA01 |
| 168H07 | 3616674 | PA01 |
| 168H09 | 5366890 | PA01 |
| 168H10 | 3474415 | PA01 |
| 168H11 | 671637 | PA01 |
| 169A04 | 4401580 | PA01 |
| 169A08 | 4591448 | PA01 |
| 169A09 | 5254049 | PA01 |
| 169A11 | 657616 | PA01 |
| 169A12 | 4810359 | PA01 |
| 169B01 | 5118186 | PA01 |
| 169B03 | 3383809 | PA01 |
| 169B04 | 1963821 | PA01 |
| 169B07 | 3704053 | PA01 |
| 169B08 | 4585465 | PA01 |
| 169B09 | 4118672 | PA01 |
| 169B11 | 5159339 | PA01 |
| 169B12 | 4596076 | PA01 |
| 169F01 | 5282875 | PA01 |
| 169F07 | 3988922 | PA01 |
| 169F08 | 5310271 | PA01 |
| 169F11 | 4365789 | PA01 |
| 169F12 | 3306499 | PA01 |
| 169G02 | 4587769 | PA01 |
| 169G07 | 2116304 | PA01 |
| 169G08 | 711492 | PA01 |
| 169G09 | 5407752 | PA01 |
| 169G10 | 547097 | PA01 |
| 169G11 | 365142 | PA01 |
| 169H01 | 1429084 | PA01 |
| 169H02 | 5149396 | PA01 |
| 169H03 | 1625271 | PA01 |
| 169H07 | 5965717 | PA01 |
| 169H10 | 1604979 | PA01 |
| 169H11 | 671637 | PA01 |
| 170A01 | 3882319 | PA01 |
| 170A02 | 427331 | PA01 |
| 170A03 | 1894542 | PA01 |
| 170A05 | 4814077 | PA01 |
| 170A06 | 965782 | PA01 |
| 170A07 | 4796125 | PA01 |
| 170A08 | 2147214 | PA01 |
| 170A09 | 268244 | PA01 |
| 170A10 | 1898833 | PA01 |
| 170A11 | 5256933 | PA01 |
| 170A12 | 1021792 | PA01 |
| 170B01 | 2392201 | PA01 |
| 170B02 | 315272 | PA01 |
| 170B03 | 3327835 | PA01 |
| 170B05 | 5006976 | PA01 |
| 170B06 | 1641307 | PA01 |
| 170B07 | 1818388 | PA01 |
| 170B08 | 3264426 | PA01 |
| 170B09 | 1567960 | PA01 |
| 170B11 | 1327867 | PA01 |
| 170B12 | 1064475 | PA01 |
| 170C01 | 4627156 | PA01 |
| 170C02 | 5773359 | PA01 |
| 170C03 | 316557 | PA01 |
| 170C04 | 93744 | PA01 |
| 170C06 | 5820044 | PA01 |
| 170C07 | 3295709 | PA01 |
| 170C10 | 1482922 | PA01 |
| 170C11 | 2122537 | PA01 |
| 170C12 | 1028922 | PA01 |
| 170D01 | 632299 | PA01 |
| 170D02 | 603202 | PA01 |
| 170D03 | 316557 | PA01 |
| 170D04 | 141279 | PA01 |
| 170D06 | 5210498 | PA01 |
| 170D08 | 126367 | PA01 |
| 170D10 | 5098394 | PA01 |
| 170E01 | 5646839 | PA01 |
| 170E02 | 417042 | PA01 |
| 170E03 | 5005306 | PA01 |
| 170E05 | 5263318 | PA01 |
| 170E06 | 3565815 | PA01 |
| 170E07 | 5254049 | PA01 |
| 170E08 | 452551 | PA01 |
| 170E10 | 323308 | PA01 |
| 170E11 | 5032357 | PA01 |
| 170F02 | 4489897 | PA01 |

TABLE 3-continued

| Mutant Name | Insertion Point | host strain |
|---|---|---|
| 170F03 | 1830069 | PA01 |
| 170F06 | 4559762 | PA01 |
| 170F07 | 4589642 | PA01 |
| 170F09 | 2025751 | PA01 |
| 170F10 | 5186394 | PA01 |
| 170F12 | 4256570 | PA01 |
| 170G01 | 4990665 | PA01 |
| 170G02 | 5441822 | PA01 |
| 170G05 | 4736296 | PA01 |
| 170G06 | 3974627 | PA01 |
| 170G07 | 9667351 | PA01 |
| 170G08 | 3046825 | PA01 |
| 170G09 | 861892 | PA01 |
| 170G10 | 266177 | PA01 |
| 170G11 | 3047204 | PA01 |
| 170G12 | 918545 | PA01 |
| 170H03 | 2976291 | PA01 |
| 170H04 | 478669 | PA01 |
| 170H07 | 6152321 | PA01 |
| 170H08 | 34043 | PA01 |
| 170H09 | 5930686 | PA01 |
| 170H10 | 4786074 | PA01 |
| 171A01 | 5515089 | PA01 |
| 171A07 | 203394 | PA01 |
| 171A09 | 2729734 | PA01 |
| 171A11 | 5184209 | PA01 |
| 171B01 | 3505585 | PA01 |
| 171B02 | 660566 | PA01 |
| 171B03 | 3203982 | PA01 |
| 171B04 | 3258876 | PA01 |
| 171B05 | 362761 | PA01 |
| 171B07 | 6104962 | PA01 |
| 171B09 | 3739434 | PA01 |
| 171B11 | 1104788 | PA01 |
| 171C01 | 397111 | PA01 |
| 171C03 | 4657805 | PA01 |
| 171C04 | 5415103 | PA01 |
| 171C05 | 4917936 | PA01 |
| 171C06 | 3091659 | PA01 |
| 171C07 | 3572626 | PA01 |
| 171C09 | 2931077 | PA01 |
| 171C10 | 6123879 | PA01 |
| 171C11 | 1129976 | PA01 |
| 171D07 | 6050836 | PA01 |
| 171D10 | 5165457 | PA01 |
| 171D11 | 1444725 | PA01 |
| 171D12 | 3293888 | PA01 |
| 171E01 | 55302373 | PA01 |
| 171E04 | 747510 | PA01 |
| 171E12 | 5201685 | PA01 |
| 171F06 | 1660413 | PA01 |
| 171F08 | 1007058 | PA01 |
| 171F09 | 709828 | PA01 |
| 171F11 | 5913087 | PA01 |
| 171G01 | 5485475 | PA01 |
| 171G04 | 4853308 | PA01 |
| 171G05 | 5956461 | PA01 |
| 171G06 | 1562289 | PA01 |
| 171G07 | 5685021 | PA01 |
| 171G08 | 6219617 | PA01 |
| 171G09 | 363669 | PA01 |
| 171G10 | 5632974 | PA01 |
| 171G11 | 1375885 | PA01 |
| 171H01 | 5291470 | PA01 |
| 171H02 | 2631446 | PA01 |
| 171H03 | 4650014 | PA01 |
| 171H04 | 5906182 | PA01 |
| 171H06 | 1452418 | PA01 |
| 171H07 | 833297 | PA01 |
| 171H08 | 760800 | PA01 |
| 171H09 | 415390 | PA01 |
| 171H10 | 5456821 | PA01 |
| 171H11 | 671638 | PA01 |
| 172A01 | 4015252 | PA01 |
| 172A02 | 5433569 | PA01 |
| 172A04 | 4673714 | PA01 |
| 172A09 | 272981 | PA01 |
| 172A10 | 1183787 | PA01 |
| 172A12 | 6242238 | PA01 |
| 172B04 | 2288870 | PA01 |
| 172B09 | 6072616 | PA01 |
| 172B11 | 2333501 | PA01 |
| 172B12 | 304311 | PA01 |
| 172C01 | 2898525 | PA01 |
| 172C04 | 940619 | PA01 |
| 172C05 | 3979079 | PA01 |
| 172C07 | 3979079 | PA01 |
| 172C09 | 5407752 | PA01 |
| 172C10 | 3954605 | PA01 |
| 172C12 | 142332 | PA01 |
| 172D01 | 5431716 | PA01 |
| 172D02 | 5254106 | PA01 |
| 172D04 | 767461 | PA01 |
| 172D05 | 3805104 | PA01 |
| 172D09 | 2345056 | PA01 |
| 172D10 | 307672 | PA01 |
| 172D11 | 253824 | PA01 |
| 172D12 | 253824 | PA01 |
| 172E01 | 5803364 | PA01 |
| 172E07 | 1269623 | PA01 |
| 172E08 | 5300630 | PA01 |
| 172E09 | 4501878 | PA01 |
| 172E12 | 5456928 | PA01 |
| 172F01 | 3608762 | PA01 |
| 172F03 | 2853117 | PA01 |
| 172F08 | 6193201 | PA01 |
| 172F09 | 5594460 | PA01 |
| 172F10 | 1274507 | PA01 |
| 172F11 | 5705812 | PA01 |
| 172G01 | 938940 | PA01 |
| 172G02 | 3835227 | PA01 |
| 172G07 | 411726 | PA01 |
| 172G08 | 3515481 | PA01 |
| 172G09 | 5373814 | PA01 |
| 172G10 | 332444 | PA01 |
| 172G11 | 4257085 | PA01 |
| 172G12 | 974001 | PA01 |
| 172H03 | 4485523 | PA01 |
| 172H06 | 2380377 | PA01 |
| 172H08 | 1383796 | PA01 |
| 172H10 | 2025751 | PA01 |
| 172H11 | 671637 | PA01 |
| 173A01 | 4607711 | PA01 |
| 173A02 | 1104569 | PA01 |
| 173A03 | 1835685 | PA01 |
| 173A04 | 891689 | PA01 |
| 173A05 | 4741858 | PA01 |
| 173A06 | 5764636 | PA01 |
| 173A08 | 931505 | PA01 |
| 173B05 | 5358757 | PA01 |
| 173B06 | 1987056 | PA01 |
| 173B08 | 5768034 | PA01 |
| 173B09 | 3696870 | PA01 |
| 173B11 | 6118108 | PA01 |
| 173B12 | 3875131 | PA01 |
| 173C01 | 6226412 | PA01 |
| 173C03 | 1382220 | PA01 |
| 173C04 | 5163874 | PA01 |
| 173C05 | 4284077 | PA01 |
| 173C06 | 5721924 | PA01 |
| 173C07 | 149820 | PA01 |
| 173C08 | 918947 | PA01 |
| 173C09 | 2686824 | PA01 |
| 173C10 | 4366772 | PA01 |
| 173C11 | 2558353 | PA01 |
| 173D03 | 1894540 | PA01 |
| 173D04 | 1278473 | PA01 |
| 173D05 | 1830069 | PA01 |
| 173D07 | 1963822 | PA01 |
| 173D08 | 6200971 | PA01 |
| 173D12 | 1439067 | PA01 |
| 173E02 | 1103071 | PA01 |
| 173E04 | 4210333 | PA01 |
| 173E05 | 4898212 | PA01 |

TABLE 3-continued

| Mutant Name | Insertion Point | host strain |
|---|---|---|
| 173E06 | 4834919 | PA01 |
| 173E07 | 416132 | PA01 |
| 173E08 | 4222582 | PA01 |
| 173E09 | 3474415 | PA01 |
| 173E12 | 4664571 | PA01 |
| 173F01 | 3263727 | PA01 |
| 173F02 | 5449046 | PA01 |
| 173F03 | 2726108 | PA01 |
| 173F04 | 5672532 | PA01 |
| 173F05 | 953252 | PA01 |
| 173F06 | 5584391 | PA01 |
| 173F07 | 223060 | PA01 |
| 173F08 | 4047002 | PA01 |
| 173F09 | 2122724 | PA01 |
| 773F10 | 1971286 | PA01 |
| 173F11 | 3521422 | PA01 |
| 173F12 | 120795 | PA01 |
| 173G01 | 1434130 | PA01 |
| 173G04 | 6050838 | PA01 |
| 173G07 | 1291331 | PA01 |
| 173G09 | 5556278 | PA01 |
| 173G10 | 5987063 | PA01 |
| 173H02 | 1416748 | PA01 |
| 173H04 | 3597983 | PA01 |
| 173H05 | 4080135 | PA01 |
| 173H06 | 2797587 | PA01 |
| 173H07 | 3625168 | PA01 |
| 173H08 | 5273292 | PA01 |
| 174A05 | 4834919 | PA01 |
| 174A06 | 3393156 | PA01 |
| 174A07 | 1002390 | PA01 |
| 174A08 | 5530237 | PA01 |
| 174A10 | 6219617 | PA01 |
| 174A11 | 1781790 | PA01 |
| 174A12 | 4392105 | PA01 |
| 174B01 | 6193301 | PA01 |
| 174B02 | 338950 | PA01 |
| 174B03 | 547097 | PA01 |
| 174B04 | 3578842 | PA01 |
| 174B05 | 3613401 | PA01 |
| 174B06 | 1370522 | PA01 |
| 174B08 | 4392178 | PA01 |
| 174B09 | 2380377 | PA01 |
| 174B11 | 5101927 | PA01 |
| 174B12 | 2136510 | PA01 |
| 174C05 | 3062996 | PA01 |
| 174C06 | 4810359 | PA01 |
| 174C07 | 3462288 | PA01 |
| 174C08 | 5214226 | PA01 |
| 174C09 | 6193301 | PA01 |
| 174C11 | 1513243 | PA01 |
| 174D01 | 6194108 | PA01 |
| 174D04 | 3804716 | PA01 |
| 174D06 | 34043 | PA01 |
| 174D07 | 1566405 | PA01 |
| 174D08 | 489696 | PA01 |
| 174D09 | 2152205 | PA01 |
| 174D10 | 2136510 | PA01 |
| 174E02 | 60106 | PA01 |
| 174E06 | 1878481 | PA01 |
| 174E08 | 6196584 | PA01 |
| 174E09 | 663176 | PA01 |
| 174E11 | 1296762 | PA01 |
| 174E12 | 3053978 | PA01 |
| 174F02 | 5502181 | PA01 |
| 174F03 | 1044464 | PA01 |
| 174F04 | 4420322 | PA01 |
| 174F05 | 5183351 | PA01 |
| 174F06 | 5447669 | PA01 |
| 174F07 | 3757343 | PA01 |
| 174F08 | 719830 | PA01 |
| 174F09 | 5968489 | PA01 |
| 174F10 | 554927 | PA01 |
| 174G01 | 3115342 | PA01 |
| 174G02 | 1991177 | PA01 |
| 174G04 | 5472978 | PA01 |
| 174G05 | 894630 | PA01 |
| 174G08 | 5382429 | PA01 |
| 174G10 | 6108965 | PA01 |
| 174G11 | 3201319 | PA01 |
| 174G12 | 2136510 | PA01 |
| 174H03 | 5062705 | PA01 |
| 174H08 | 1452418 | PA01 |
| 174H09 | 5256933 | PA01 |
| 175A01 | 375528 | PA01 |
| 175A02 | 1170196 | PA01 |
| 175A03 | 5002041 | PA01 |
| 175A05 | 5472979 | PA01 |
| 175A07 | 3323326 | PA01 |
| 175A09 | 3615180 | PA01 |
| 175A10 | 5509978 | PA01 |
| 175A11 | 4591448 | PA01 |
| 175B01 | 2693035 | PA01 |
| 175B04 | 1044754 | PA01 |
| 175B05 | 6242239 | PA01 |
| 175B08 | 5697208 | PA01 |
| 175B11 | 290549 | PA01 |
| 175B12 | 598334 | PA01 |
| 175C02 | 5964853 | PA01 |
| 175C03 | 533560 | PA01 |
| 175C04 | 1715494 | PA01 |
| 175C05 | 1082558 | PA01 |
| 175C06 | 961274 | PA01 |
| 175C07 | 5728050 | PA01 |
| 175C08 | 3690651 | PA01 |
| 175C10 | 4138587 | PA01 |
| 175C11 | 4691547 | PA01 |
| 175D01 | 3218918 | PA01 |
| 175D03 | 5515089 | PA01 |
| 175D04 | 1530709 | PA01 |
| 175D05 | 4998867 | PA01 |
| 175D06 | 5692569 | PA01 |
| 175D07 | 3400008 | PA01 |
| 175D08 | 670970 | PA01 |
| 175D10 | 204224 | PA01 |
| 175D11 | 204224 | PA01 |
| 175D12 | 5026326 | PA01 |
| 175E03 | 1852718 | PA01 |
| 175E04 | 1045997 | PA01 |
| 175E05 | 4673714 | PA01 |
| 175E07 | 5597371 | PA01 |
| 175E10 | 2122725 | PA01 |
| 175E12 | 2000354 | PA01 |
| 175F01 | 2089460 | PA01 |
| 175F04 | 5187683 | PA01 |
| 175F05 | 4846618 | PA01 |
| 175F07 | 3494092 | PA01 |
| 175F08 | 5764636 | PA01 |
| 175F09 | 3560813 | PA01 |
| 175G01 | 544809 | PA01 |
| 175G02 | 4100725 | PA01 |
| 175G03 | 709828 | PA01 |
| 175G04 | 4726909 | PA01 |
| 175G06 | 2471654 | PA01 |
| 175G09 | 4657805 | PA01 |
| 175G10 | 411276 | PA01 |
| 175G11 | 3560822 | PA01 |
| 175G12 | 261377 | PA01 |
| 175H01 | 1873266 | PA01 |
| 175H03 | 3889588 | PA01 |
| 175H05 | 3385681 | PA01 |
| 175H08 | 1278969 | PA01 |
| 176A01 | 5476139 | PA01 |
| 176A02 | 2300649 | PA01 |
| 176A03 | 5946328 | PA01 |
| 176A04 | 980186 | PA01 |
| 176A06 | 5702294 | PA01 |
| 176A10 | 1288870 | PA01 |
| 176A11 | 3166359 | PA01 |
| 176A12 | 3026526 | PA01 |
| 176B03 | 974003 | PA01 |
| 176B04 | 3434144 | PA01 |
| 176B06 | 189496 | PA01 |
| 176B07 | 2658326 | PA01 |

TABLE 3-continued

| Mutant Name | Insertion Point | host strain |
|---|---|---|
| 176B09 | 1672877 | PA01 |
| 176B10 | 4156563 | PA01 |
| 176C01 | 3624552 | PA01 |
| 176C02 | 4623729 | PA01 |
| 176C05 | 3997039 | PA01 |
| 176C06 | 1312397 | PA01 |
| 176C07 | 2420191 | PA01 |
| 176C08 | 4600725 | PA01 |
| 176C09 | 5361094 | PA01 |
| 176C10 | 5746383 | PA01 |
| 176C11 | 6021128 | PA01 |
| 176C12 | 948082 | PA01 |
| 176D03 | 891689 | PA01 |
| 176D04 | 4434397 | PA01 |
| 176D05 | 3981911 | PA01 |
| 176D07 | 5029046 | PA01 |
| 176D08 | 2410595 | PA01 |
| 176D09 | 5728050 | PA01 |
| 176D12 | 2684131 | PA01 |
| 176E03 | 4251143 | PA01 |
| 176E04 | 23120231 | PA01 |
| 176E05 | 5201820 | PA01 |
| 176E06 | 2383527 | PA01 |
| 176E11 | 2516386 | PA01 |
| 176E12 | 551781 | PA01 |
| 176F01 | 4748413 | PA01 |
| 176F03 | 5565126 | PA01 |
| 176F04 | 5867397 | PA01 |
| 176F05 | 6168905 | PA01 |
| 176F06 | 4531158 | PA01 |
| 176F08 | 2007205 | PA01 |
| 176F09 | 1851568 | PA01 |
| 176F10 | 5501548 | PA01 |
| 176F11 | 6208257 | PA01 |
| 176F12 | 6208256 | PA01 |
| 176G01 | 2705050 | PA01 |
| 176G02 | 2282835 | PA01 |
| 176G06 | 824096 | PA01 |
| 176G07 | 4810359 | PA01 |
| 176G10 | 5375334 | PA01 |
| 176H01 | 4234156 | PA01 |
| 176H02 | 6178521 | PA01 |
| 176H04 | 2408884 | PA01 |
| 176H06 | 2258932 | PA01 |
| 176H10 | 4841030 | PA01 |
| 176H11 | 1548917 | PA01 |
| 177A05 | 2322366 | PA01 |
| 177A07 | 5931558 | PA01 |
| 177B06 | 1963063 | PA01 |
| 177B07 | 3123552 | PA01 |
| 177B08 | 1029251 | PA01 |
| 177B09 | 1574191 | PA01 |
| 177B10 | 1802886 | PA01 |
| 177B11 | 5321517 | PA01 |
| 177F08 | 6232610 | PA01 |
| 177F11 | 4866960 | PA01 |
| 177G07 | 3814644 | PA01 |
| 177G11 | 5086573 | PA01 |
| 177G12 | 6242240 | PA01 |
| 177H05 | 1991177 | PA01 |
| 177H08 | 1306839 | PA01 |
| 177H10 | 4350073 | PA01 |
| 177H11 | 6122841 | PA01 |
| 178A01 | 266177 | PA01 |
| 178A03 | 1963822 | PA01 |
| 178A04 | 676267 | PA01 |
| 178A05 | 1963819 | PA01 |
| 178A06 | 5559890 | PA01 |
| 178A07 | 1491198 | PA01 |
| 178A09 | 5981344 | PA01 |
| 178A10 | 5319523 | PA01 |
| 178A11 | 2322698 | PA01 |
| 178A12 | 6133959 | PA01 |
| 178B03 | 784277 | PA01 |
| 178B04 | 3116173 | PA01 |
| 178B06 | 3610421 | PA01 |
| 178B07 | 793590 | PA01 |
| 178B08 | 1064932 | PA01 |
| 178B10 | 3922167 | PA01 |
| 178B11 | 5174040 | PA01 |
| 178C01 | 3876264 | PA01 |
| 178C02 | 4348968 | PA01 |
| 178C09 | 5913087 | PA01 |
| 178C12 | 4794311 | PA01 |
| 178D03 | 4488316 | PA01 |
| 178D06 | 1151572 | PA01 |
| 178D08 | 4134534 | PA01 |
| 178D10 | 1289165 | PA01 |
| 178D11 | 2215589 | PA01 |
| 178D12 | 4002033 | PA01 |
| 178E01 | 5667218 | PA01 |
| 178E10 | 1382221 | PA01 |
| 178E11 | 2734809 | PA01 |
| 178F01 | 908797 | PA01 |
| 178F02 | 1715059 | PA01 |
| 178F03 | 5294736 | PA01 |
| 178F04 | 1770709 | PA01 |
| 178F05 | 553937 | PA01 |
| 178F07 | 5729721 | PA01 |
| 178F08 | 6130445 | PA01 |
| 178F10 | 4864670 | PA01 |
| 178F11 | 1535897 | PA01 |
| 178F12 | 5155366 | PA01 |
| 178G02 | 6058864 | PA01 |
| 178G04 | 3688998 | PA01 |
| 178G05 | 5488437 | PA01 |
| 178G07 | 5126696 | PA01 |
| 178G08 | 5247546 | PA01 |
| 178G09 | 5449913 | PA01 |
| 178G10 | 3208354 | PA01 |
| 178H02 | 5294020 | PA01 |
| 178H03 | 1261827 | PA01 |
| 178H04 | 4870724 | PA01 |
| 178H05 | 105482 | PA01 |
| 178H07 | 2780078 | PA01 |
| 178H08 | 4213280 | PA01 |
| 178H09 | 3612678 | PA01 |
| 178H10 | 5970802 | PA01 |
| 178H11 | 553937 | PA01 |
| 182A01 | 1428840 | PA01 |
| 182A02 | 2652983 | PA01 |
| 182A03 | 729799 | PA01 |
| 182A04 | 954087 | PA01 |
| 182A05 | 2356388 | PA01 |
| 182A06 | 5422237 | PA01 |
| 182A07 | 5930881 | PA01 |
| 182A08 | 1627843 | PA01 |
| 182A09 | 1073573 | PA01 |
| 182A10 | 4627156 | PA01 |
| 182A11 | 4455075 | PA01 |
| 182A12 | 3066338 | PA01 |
| 182B01 | 1070676 | PA01 |
| 182B02 | 1005515 | PA01 |
| 182B03 | 4490119 | PA01 |
| 182B04 | 2408226 | PA01 |
| 182B05 | 5476139 | PA01 |
| 182B06 | 5188479 | PA01 |
| 182B07 | 3577840 | PA01 |
| 182B08 | 3115342 | PA01 |
| 182B09 | 2420143 | PA01 |
| 182B10 | 3201337 | PA01 |
| 182B11 | 660566 | PA01 |
| 182B12 | 272611 | PA01 |
| 182C01 | 2504200 | PA01 |
| 182C02 | 4080366 | PA01 |
| 182C03 | 3804716 | PA01 |
| 182C04 | 4627156 | PA01 |
| 182C05 | 5730055 | PA01 |
| 182C06 | 583125 | PA01 |
| 182C07 | 3153882 | PA01 |
| 182C08 | 4257084 | PA01 |
| 182C09 | 1912838 | PA01 |
| 182C10 | 3231739 | PA01 |
| 182C12 | 2963758 | PA01 |

TABLE 3-continued

| Mutant Name | Insertion Point | host strain |
|---|---|---|
| 182D01 | 5441160 | PA01 |
| 182D02 | 5707062 | PA01 |
| 182D03 | 1674800 | PA01 |
| 182D04 | 1604979 | PA01 |
| 182D05 | 3653147 | PA01 |
| 182D06 | 5005306 | PA01 |
| 182D07 | 3258876 | PA01 |
| 182D08 | 6189446 | PA01 |
| 182D10 | 4008708 | PA01 |
| 182D11 | 2658326 | PA01 |
| 182D12 | 4161229 | PA01 |
| 182E01 | 5086573 | PA01 |
| 182E03 | 288832 | PA01 |
| 182E04 | 4233110 | PA01 |
| 182E05 | 1753681 | PA01 |
| 182E06 | 6155745 | PA01 |
| 182E07 | 593155 | PA01 |
| 182E08 | 3197084 | PA01 |
| 182E09 | 311534 | PA01 |
| 182E10 | 1882265 | PA01 |
| 182E11 | 2971537 | PA01 |
| 182E12 | 5508537 | PA01 |
| 182F01 | 5901481 | PA01 |
| 182F02 | 3250915 | PA01 |
| 182F03 | 5913087 | PA01 |
| 182F04 | 995424 | PA01 |
| 182F05 | 2915395 | PA01 |
| 182F06 | 3804716 | PA01 |
| 182F07 | 5806839 | PA01 |
| 182F08 | 5295342 | PA01 |
| 182F09 | 2479696 | PA01 |
| 182F12 | 6208260 | PA01 |
| 182G01 | 1345184 | PA01 |
| 182G02 | 2668026 | PA01 |
| 182G04 | 2844615 | PA01 |
| 182G05 | 3090579 | PA01 |
| 182G06 | 1814561 | PA01 |
| 182G08 | 1566549 | PA01 |
| 182G09 | 1526024 | PA01 |
| 182G10 | 1882265 | PA01 |
| 182G11 | 3383809 | PA01 |
| 182G12 | 3566494 | PA01 |
| 182H02 | 5289018 | PA01 |
| 182H03 | 5633947 | PA01 |
| 182H04 | 1293986 | PA01 |
| 182H06 | 3479637 | PA01 |
| 182H08 | 199249 | PA01 |
| 182H09 | 1548077 | PA01 |
| 182H10 | 1011868 | PA01 |
| 183A01 | 940611 | PA01 |
| 183A02 | 4585465 | PA01 |
| 183A03 | 1462511 | PA01 |
| 183A04 | 5509978 | PA01 |
| 183A05 | 4594314 | PA01 |
| 183A06 | 4157011 | PA01 |
| 183A07 | 3578834 | PA01 |
| 183A08 | 2996087 | PA01 |
| 183A09 | 5736496 | PA01 |
| 183A10 | 4597353 | PA01 |
| 183A11 | 4417872 | PA01 |
| 183B01 | 3904412 | PA01 |
| 183B02 | 6037542 | PA01 |
| 183B03 | 2300649 | PA01 |
| 183B04 | 1137119 | PA01 |
| 183B05 | 4080135 | PA01 |
| 183B06 | 4177707 | PA01 |
| 183B07 | 4134535 | PA01 |
| 183B08 | 940611 | PA01 |
| 183B09 | 1627843 | PA01 |
| 183B10 | 3317862 | PA01 |
| 183B11 | 2317876 | PA01 |
| 184A02 | 2051514 | PA01 |
| 184A03 | 109116 | PA01 |
| 184A04 | 588504 | PA01 |
| 184A05 | 712594 | PA01 |
| 184A06 | 1843818 | PA01 |
| 184A07 | 3221194 | PA01 |
| 184A09 | 450677 | PA01 |
| 184A11 | 4382673 | PA01 |
| 184A12 | 1429515 | PA01 |
| 184B02 | 1075520 | PA01 |
| 184B05 | 4832027 | PA01 |
| 184B06 | 3175439 | PA01 |
| 184B08 | 5031738 | PA01 |
| 184B10 | 5820044 | PA01 |
| 184B11 | 54537 | PA01 |
| 184B12 | 5032227 | PA01 |
| 184C01 | 1064475 | PA01 |
| 184C04 | 442247 | PA01 |
| 184C05 | 4138587 | PA01 |
| 184C06 | 575242 | PA01 |
| 184C07 | 3494091 | PA01 |
| 184C09 | 1256610 | PA01 |
| 184C10 | 2215589 | PA01 |
| 184C11 | 5807299 | PA01 |
| 184C12 | 5774878 | PA01 |
| 184D01 | 2641137 | PA01 |
| 184D02 | 397420 | PA01 |
| 184D04 | 1865221 | PA01 |
| 184D05 | 5082225 | PA01 |
| 184D06 | 5008341 | PA01 |
| 184D09 | 2858100 | PA01 |
| 184D10 | 4990665 | PA01 |
| 184D11 | 1638651 | PA01 |
| 184D12 | 818865 | PA01 |
| 184E01 | 5939634 | PA01 |
| 184E02 | 2477596 | PA01 |
| 184E03 | 4704214 | PA01 |
| 184E04 | 4432254 | PA01 |
| 184E05 | 1675650 | PA01 |
| 184E06 | 1070676 | PA01 |
| 184E07 | 1138633 | PA01 |
| 184E08 | 2981764 | PA01 |
| 184E10 | 5123392 | PA01 |
| 184E11 | 112440 | PA01 |
| 184E12 | 5759817 | PA01 |
| 184F01 | 5165608 | PA01 |
| 184F02 | 5211233 | PA01 |
| 186C02 | 3292647 | PA01 |
| 186C03 | 3237390 | PA01 |
| 186C04 | 1184851 | PA01 |
| 186C05 | 3565815 | PA01 |
| 186C06 | 897572 | PA01 |
| 186C07 | 1104569 | PA01 |
| 186C08 | 94180 | PA01 |
| 186C11 | 415374 | PA01 |
| 186D01 | 2409164 | PA01 |
| 186D03 | 1665013 | PA01 |
| 186D04 | 2712102 | PA01 |
| 186D05 | 3809683 | PA01 |
| 186D06 | 5151949 | PA01 |
| 186D08 | 514031 | PA01 |
| 186D10 | 5366890 | PA01 |
| 186D12 | 5919321 | PA01 |
| 186E02 | 1635441 | PA01 |
| 186E04 | 394454 | PA01 |
| 186E05 | 2356388 | PA01 |
| 186E06 | 998878 | PA01 |
| 186E07 | 3997039 | PA01 |
| 186E08 | 4201186 | PAQ1 |
| 186E09 | 1568877 | PAQ1 |
| 186E10 | 5319920 | PA01 |
| 186E11 | 4283770 | PA01 |
| 186F01 | 2504863 | PA01 |
| 186F02 | 4194427 | PA01 |
| 186F06 | 5526603 | PA01 |
| 186F08 | 5915708 | PA01 |
| 186F09 | 2837048 | PA01 |
| 186F10 | 547097 | PA01 |
| 186F11 | 3329714 | PA01 |
| 186G01 | 1133808 | PA01 |
| 186G03 | 944073 | PA01 |
| 186G04 | 5000428 | PA01 |
| 186G05 | 3218919 | PA01 |

TABLE 3-continued

| Mutant Name | Insertion Point | host strain |
|---|---|---|
| 186G06 | 1022509 | PA01 |
| 186G07 | 4501878 | PA01 |
| 186G09 | 4910846 | PA01 |
| 186G11 | 2026225 | PA01 |
| 186H01 | 3269233 | PA01 |
| 186H03 | 4335652 | PA01 |
| 186H05 | 4627085 | PA01 |
| 186H06 | 489696 | PA01 |
| 186H07 | 3288834 | PA01 |
| 186H08 | 514030 | PA01 |
| 186H09 | 1262980 | PA01 |
| 186H11 | 4456344 | PA01 |
| 187A01 | 5358754 | PA01 |
| 187A03 | 3527708 | PA01 |
| 187A06 | 2798212 | PA01 |
| 187A07 | 3643734 | PA01 |
| 187A08 | 3169709 | PA01 |
| 187B02 | 1248204 | PA01 |
| 187B03 | 620033 | PA01 |
| 187B05 | 1672871 | PA01 |
| 187B06 | 1436296 | PA01 |
| 187B08 | 3574398 | PA01 |
| 187B09 | 2070289 | PA01 |
| 187B11 | 6122838 | PA01 |
| 187B12 | 1425075 | PA01 |
| 187C04 | 2893369 | PA01 |
| 187C05 | 4194335 | PA01 |
| 187C08 | 558371 | PA01 |
| 187C09 | 1630609 | PA01 |
| 187C11 | 6725265 | PA01 |
| 187D04 | 2080505 | PA01 |
| 187D08 | 4704465 | PA01 |
| 187D10 | 171220 | PA01 |
| 187D11 | 359303 | PA01 |
| 187D12 | 565772 | PA01 |
| 187E01 | 3036987 | PA01 |
| 187E04 | 4875866 | PA01 |
| 187E06 | 2116304 | PA01 |
| 187E09 | 171220 | PA01 |
| 187E10 | 4826613 | PA01 |
| 187E12 | 1641218 | PA01 |
| 187F06 | 4846617 | PA01 |
| 187F08 | 4280266 | PA01 |
| 187F09 | 306705 | PA01 |
| 187F11 | 5282097 | PA01 |
| 187G01 | 5754589 | PA01 |
| 187G02 | 5983927 | PA01 |
| 187G03 | 2686946 | PA01 |
| 187G04 | 1893427 | PA01 |
| 187G07 | 4047635 | PA01 |
| 187G08 | 6112599 | PA01 |
| 187G09 | 5054289 | PA01 |
| 187G11 | 2333501 | PA01 |
| 187H01 | 11663017 | PA01 |
| 187H03 | 1462511 | PA01 |
| 187H04 | 804767 | PA01 |
| 187H05 | 4210666 | PA01 |
| 187H07 | 4047636 | PA01 |
| 188A05 | 397380 | PA01 |
| 188A06 | 1660313 | PA01 |
| 188A09 | 1296762 | PA01 |
| 188A10 | 4307961 | PA01 |
| 188A11 | 1974767 | PA01 |
| 188A12 | 2916631 | PA01 |
| 188B01 | 4998865 | PA01 |
| 188B02 | 1842339 | PA01 |
| 188B04 | 3508767 | PA01 |
| 188B05 | 6240735 | PA01 |
| 188B06 | 4856918 | PA01 |
| 188B07 | 1837677 | PA01 |
| 188B08 | 564851 | PA01 |
| 188B10 | 5358757 | PA01 |
| 188B11 | 1832265 | PA01 |
| 188B12 | 1858598 | PA01 |
| 188C01 | 4055589 | PA01 |
| 188C02 | 3918104 | PA01 |
| 188C03 | 370932 | PA01 |
| 188C04 | 517029 | PA01 |
| 188C05 | 1078894 | PA01 |
| 188C06 | 2375365 | PA01 |
| 188C07 | 6155862 | PA01 |
| 188C08 | 1772965 | PA01 |
| 188C09 | 5742183 | PA01 |
| 188C10 | 3213549 | PA01 |
| 188C11 | 3893453 | PA01 |
| 188C12 | 1381577 | PA01 |
| 188D01 | 325965 | PA01 |
| 188D02 | 4902110 | PA01 |
| 188D03 | 2412680 | PA01 |
| 188D04 | 5508400 | PA01 |
| 188D05 | 789435 | PA01 |
| 188D06 | 1429084 | PA01 |
| 188D07 | 5764162 | PA01 |
| 188D08 | 5062994 | PA01 |
| 188D09 | 63823 | PA01 |
| 188D10 | 3217315 | PA01 |
| 188D11 | 3975557 | PA01 |
| 188D12 | 5358757 | PA01 |
| 188E01 | 3479637 | PA01 |
| 188E02 | 4744539 | PA01 |
| 188E03 | 1601421 | PA01 |
| 188E04 | 1674800 | PA01 |
| 188E05 | 4821722 | PA01 |
| 188E06 | 5126695 | PA01 |
| 188E07 | 5729357 | PA01 |
| 188E08 | 2437187 | PA01 |
| 188E09 | 5597084 | PA01 |
| 188E11 | 4080366 | PA01 |
| 188F01 | 4581056 | PA01 |
| 188F02 | 6139211 | PA01 |
| 188F03 | 1452081 | PA01 |
| 188F04 | 4435277 | PA01 |
| 188F05 | 1006391 | PA01 |
| 188F06 | 5424187 | PA01 |
| 188F07 | 623372 | PA01 |
| 188F08 | 591968 | PA01 |
| 188F09 | 2472466 | PA01 |
| 188F11 | 120468 | PA01 |
| 188F12 | 933281 | PA01 |
| 188G03 | 2097505 | PA01 |
| 188G04 | 3914200 | PA01 |
| 188G05 | 4845087 | PA01 |
| 188G06 | 5699954 | PA01 |
| 188G07 | 1919371 | PA01 |
| 188G08 | 3659268 | PA01 |
| 188G09 | 4901449 | PA01 |
| 188G10 | 1022558 | PA01 |
| 188G11 | 2125613 | PA01 |
| 188G12 | 4898212 | PA01 |
| 188H01 | 4417263 | PA01 |
| 188H02 | 1365594 | PA01 |
| 188H03 | 1924832 | PA01 |
| 188H04 | 5776167 | PA01 |
| 188H06 | 3810199 | PA01 |
| 188H07 | 576495 | PA01 |
| 188H08 | 995837 | PA01 |
| 188H09 | 420238 | PA01 |
| 188H10 | 5749808 | PA01 |
| 188H11 | 4835152 | PA01 |
| 189A02 | 2683697 | PA01 |
| 189A03 | 2204091 | PA01 |
| 189A04 | 6135875 | PA01 |
| 189A05 | 2686275 | PA01 |
| 189A07 | 5824535 | PA01 |
| 189A11 | 413341 | PA01 |
| 189A12 | 658522 | PA01 |
| 189B01 | 3209115 | PA01 |
| 189B02 | 4210333 | PA01 |
| 189B03 | 5038933 | PA01 |
| 189B04 | 3760820 | PA01 |
| 189B06 | 377871 | PA01 |
| 189B07 | 4673714 | PA01 |
| 189B08 | 4066923 | PA01 |
| 189B09 | 5554732 | PA01 |

TABLE 3-continued

| Mutant Name | Insertion Point | host strain |
|---|---|---|
| 189B10 | 4566265 | PA01 |
| 189B11 | 5247554 | PA01 |
| 189B12 | 4627156 | PA01 |
| 189C01 | 399648 | PA01 |
| 189C02 | 5033377 | PA01 |
| 189C03 | 2367412 | PA01 |
| 189C04 | 1878482 | PA01 |
| 189C05 | 5282594 | PA01 |
| 189C07 | 6108965 | PA01 |
| 189C08 | 323309 | PA01 |
| 189C10 | 5184209 | PA01 |
| 189C11 | 365296 | PA01 |
| 189D01 | 3329714 | PA01 |
| 189D02 | 3203981 | PA01 |
| 189D03 | 5530237 | PA01 |
| 189D05 | 5930686 | PA01 |
| 189D06 | 2730607 | PA01 |
| 189D08 | 511272 | PA01 |
| 189D09 | 5254058 | PA01 |
| 189D10 | 436876 | PA01 |
| 189D11 | 4064352 | PA01 |
| 189E01 | 5667621 | PA01 |
| 189E03 | 1948242 | PA01 |
| 189E06 | 982332 | PA01 |
| 189E07 | 5006975 | PA01 |
| 189E09 | 1562289 | PA01 |
| 189E10 | 2440201 | PA01 |
| 189E11 | 4819723 | PA01 |
| 189F02 | 4800094 | PA01 |
| 189F04 | 5994593 | PA01 |
| 189F08 | 189670 | PA01 |
| 189F11 | 5087607 | PA01 |
| 189G01 | 5042230 | PA01 |
| 189G02 | 4834919 | PA01 |
| 189G03 | 1075520 | PA01 |
| 189G04 | 3327837 | PA01 |
| 189G05 | 1569993 | PA01 |
| 189G06 | 168446 | PA01 |
| 189G07 | 4488091 | PA01 |
| 189G08 | 3814644 | PA01 |
| 189G09 | 4834919 | PA01 |
| 189G11 | 5913088 | PA01 |
| 189G12 | 1300919 | PA01 |
| 189H01 | 3489902 | PA01 |
| 189H02 | 2975145 | PA01 |
| 189H03 | 1394658 | PA01 |
| 189H04 | 4130479 | PA01 |
| 189H06 | 1502133 | PA01 |
| 189H07 | 6034355 | PA01 |
| 189H10 | 6076867 | PA01 |
| 189H11 | 2666444 | PA01 |
| 190A02 | 1332750 | PA01 |
| 190A03 | 4587717 | PA01 |
| 190A04 | 2984129 | PA01 |
| 190A06 | 3616674 | PA01 |
| 190A07 | 2938842 | PA01 |
| 190A10 | 1155875 | PA01 |
| 190A11 | 4508569 | PA01 |
| 190A12 | 1885660 | PA01 |
| 190B01 | 1985278 | PA01 |
| 190B02 | 5749808 | PA01 |
| 190B04 | 168083 | PA01 |
| 190B06 | 523322 | PA01 |
| 190B07 | 517604 | PA01 |
| 190B09 | 4796125 | PA01 |
| 190B12 | 1849783 | PA01 |
| 190C01 | 126366 | PA01 |
| 190C02 | 5554117 | PA01 |
| 190C03 | 3958293 | PA01 |
| 190C04 | 2848392 | PA01 |
| 190C05 | 5641136 | PA01 |
| 190C07 | 3306499 | PA01 |
| 190C08 | 4233110 | PA01 |
| 190C09 | 442247 | PA01 |
| 190C10 | 3122931 | PA01 |
| 190C11 | 3590984 | PA01 |
| 190C12 | 1560670 | PA01 |
| 190D02 | 3741172 | PA01 |
| 190D03 | 1394657 | PA01 |
| 190D04 | 3255250 | PA01 |
| 190D05 | 5321517 | PA01 |
| 190D06 | 2333501 | PA01 |
| 190D07 | 4156562 | PA01 |
| 190D08 | 5280699 | PA01 |
| 190D09 | 6089159 | PA01 |
| 190D10 | 605572 | PA01 |
| 190D11 | 3997039 | PA01 |
| 190D12 | 4892448 | PA01 |
| 190E01 | 4026261 | PA01 |
| 190E02 | 5633947 | PA01 |
| 190E03 | 4901449 | PA01 |
| 190E04 | 4344260 | PA01 |
| 190E05 | 4044314 | PA01 |
| 190E06 | 4024884 | PA01 |
| 190E07 | 2687188 | PA01 |
| 190E08 | 3920652 | PA01 |
| 190E09 | 449835 | PA01 |
| 190E10 | 2333501 | PA01 |
| 190E11 | 899204 | PA01 |
| 190E12 | 5560519 | PA01 |
| 190F01 | 5187753 | PA01 |
| 190F02 | 5187753 | PA01 |
| 190F03 | 204224 | PA01 |
| 190F04 | 5568853 | PA01 |
| 190F05 | 1402129 | PA01 |
| 190F06 | 6143311 | PA01 |
| 190F07 | 3509985 | PA01 |
| 190F08 | 6174656 | PA01 |
| 190F10 | 2023760 | PA01 |
| 190F11 | 2631446 | PA01 |
| 190F12 | 808490 | PA01 |
| 190G01 | 5823734 | PA01 |
| 190G02 | 554383 | PA01 |
| 190G04 | 5370879 | PA01 |
| 190G06 | 575242 | PA01 |
| 190G07 | 3442739 | PA01 |
| 190G10 | 4492082 | PA01 |
| 190G11 | 1383796 | PA01 |
| 190G12 | 628495 | PA01 |
| 190H01 | 5535774 | PA01 |
| 190H02 | 1183789 | PA01 |
| 190H04 | 229062 | PA01 |
| 190H06 | 4244764 | PA01 |
| 190H07 | 3672132 | PA01 |
| 190H08 | 3115342 | PA01 |
| 190H09 | 1413753 | PA01 |
| 191A01 | 5583826 | PA01 |
| 191A02 | 3479637 | PA01 |
| 191A03 | 6050836 | PA01 |
| 191A04 | 1963822 | PA01 |
| 191A05 | 5648287 | PA01 |
| 191A06 | 893023 | PA01 |
| 191A07 | 6231871 | PA01 |
| 191A08 | 2356388 | PA01 |
| 191A09 | 6075274 | PA01 |
| 191A10 | 3335342 | PA01 |
| 191A11 | 5420760 | PA01 |
| 191A12 | 5187700 | PA01 |
| 191B01 | 2129299 | PA01 |
| 191B02 | 3005393 | PA01 |
| 191B03 | 2047361 | PA01 |
| 191B04 | 3688925 | PA01 |
| 191B05 | 831276 | PA01 |
| 191B06 | 3640412 | PA01 |
| 191B07 | 1997316 | PA01 |
| 191B08 | 2368341 | PA01 |
| 191B09 | 3348319 | PA01 |
| 191B11 | 2586194 | PA01 |
| 191C01 | 3916435 | PA01 |
| 191C02 | 3442739 | PA01 |
| 191C04 | 3421963 | PA01 |
| 191C05 | 6070234 | PA01 |
| 191C07 | 517451 | PA01 |
| 191C08 | 3988921 | PA01 |

TABLE 3-continued

| Mutant Name | Insertion Point | host strain |
|---|---|---|
| 191C09 | 1586100 | PA01 |
| 191C10 | 5044606 | PA01 |
| 191C11 | 1356201 | PA01 |
| 191C12 | 5202152 | PA01 |
| 191D02 | 4331437 | PA01 |
| 191D03 | 1701383 | PA01 |
| 191D04 | 3421963 | PA01 |
| 191D05 | 1384927 | PA01 |
| 191D06 | 1681776 | PA01 |
| 191D07 | 3175439 | PA01 |
| 191D08 | 1011868 | PA01 |
| 191D10 | 1241897 | PA01 |
| 191D12 | 4543991 | PA01 |
| 191E01 | 5718784 | PA01 |
| 191E02 | 1234613 | PA01 |
| 191E03 | 2652983 | PA01 |
| 191E04 | 3812386 | PA01 |
| 191E05 | 52809 | PA01 |
| 191E06 | 3878268 | PA01 |
| 191E07 | 1959996 | PA01 |
| 191E08 | 3216381 | PA01 |
| 191E09 | 1079350 | PA01 |
| 191E10 | 1306423 | PA01 |
| 191E11 | 1871262 | PA01 |
| 191F01 | 2558158 | PA01 |
| 191F03 | 1278969 | PA01 |
| 191F05 | 3707860 | PA01 |
| 191F06 | 5257401 | PA01 |
| 191F07 | 4599683 | PA01 |
| 191F08 | 2532400 | PA01 |
| 191F09 | 2383527 | PA01 |
| 191F10 | 2455711 | PA01 |
| 191F11 | 1293986 | PA01 |
| 191F12 | 5944631 | PA01 |
| 191G01 | 4328508 | PA01 |
| 191G02 | 437155 | PA01 |
| 191G03 | 5956462 | PA01 |
| 191G04 | 5805792 | PA01 |
| 191G05 | 632969 | PA01 |
| 191G06 | 789489 | PA01 |
| 191G07 | 4531158 | PA01 |
| 191G08 | 1906139 | PA01 |
| 191G11 | 3712733 | PA01 |
| 191G12 | 466234 | PA01 |
| 191H01 | 5806839 | PA01 |
| 191H02 | 1772965 | PA01 |
| 191H03 | 3591242 | PA01 |
| 191H04 | 1985278 | PA01 |
| 191H05 | 5365451 | PA01 |
| 191H08 | 31125 | PA01 |
| 191H09 | 926841 | PA01 |
| 191H10 | 2673692 | PA01 |
| 191H11 | 3578834 | PA01 |
| 192A01 | 4704214 | PA01 |
| 192A02 | 962506 | PA01 |
| 192A04 | 2686275 | PA01 |
| 192A05 | 182376 | PA01 |
| 192A06 | 1620769 | PA01 |
| 192A08 | 1079350 | PA01 |
| 192A09 | 4845087 | PA01 |
| 192A10 | 2726343 | PA01 |
| 192A12 | 5888034 | PA01 |
| 192B01 | 3658392 | PA01 |
| 192B03 | 201779 | PA01 |
| 192B05 | 3264426 | PA01 |
| 192B06 | 1288868 | PA01 |
| 192B07 | 3627888 | PA01 |
| 192B08 | 4824482 | PA01 |
| 192B09 | 4589642 | PA01 |
| 192C01 | 2191509 | PA01 |
| 192C02 | 4589642 | PA01 |
| 192C03 | 4138075 | PA01 |
| 192C04 | 4233858 | PA01 |
| 192C05 | 2749174 | PA01 |
| 192C06 | 3117862 | PA01 |
| 192C07 | 3434368 | PA01 |
| 192C09 | 5441159 | PA01 |

TABLE 3-continued

| Mutant Name | Insertion Point | host strain |
|---|---|---|
| 192C11 | 4982425 | PA01 |
| 192C12 | 147329 | PA01 |
| 192D03 | 6053399 | PA01 |
| 192D04 | 3150430 | PA01 |
| 192D05 | 1732584 | PA01 |
| 192D06 | 4570312 | PA01 |
| 192D07 | 3209115 | PA01 |
| 192D10 | 2300649 | PA01 |
| 192D11 | 2041177 | PA01 |
| 192D12 | 585793 | PA01 |
| 192E01 | 3760820 | PA01 |
| 192E02 | 2216564 | PA01 |
| 192E03 | 4845087 | PA01 |
| 192E05 | 46840 | PA01 |
| 192E06 | 3954605 | PA01 |
| 192E09 | 3250915 | PA01 |
| 192F01 | 2641298 | PA01 |
| 192F02 | 894630 | PA01 |
| 192F03 | 5022834 | PA01 |
| 192F04 | 2423759 | PA01 |
| 192F05 | 314459 | PA01 |
| 192F06 | 601226 | PA01 |
| 192F07 | 5393185 | PA01 |
| 192F08 | 5073539 | PA01 |
| 192F09 | 5842394 | PA01 |
| 192F11 | 916942 | PA01 |
| 192F12 | 60549 | PA01 |
| 192G01 | 1526024 | PA01 |
| 192G02 | 2783180 | PA01 |
| 192G03 | 5142000 | PA01 |
| 192G05 | 2849806 | PA01 |
| 192G06 | 200416 | PA01 |
| 192G07 | 118239 | PA01 |
| 192G08 | 5157544 | PA01 |
| 192G09 | 5143606 | PA01 |
| 192G10 | 670970 | PA01 |
| 192G11 | 5950802 | PA01 |
| 192H01 | 2719500 | PA01 |
| 192H02 | 5998040 | PA01 |
| 192H04 | 1530709 | PA01 |
| 192H05 | 1006391 | PA01 |
| 192H06 | 615372 | PA01 |
| 192H08 | 1289165 | PA01 |
| 192H09 | 4481438 | PA01 |
| 192H10 | 833296 | PA01 |
| 192H11 | 2047361 | PA01 |
| 193A01 | 3393219 | PA01 |
| 193A04 | 5436533 | PA01 |
| 193A05 | 5781635 | PA01 |
| 193A06 | 5946328 | PA01 |
| 193A07 | 1732584 | PA01 |
| 193A08 | 1018388 | PA01 |
| 193A10 | 4325244 | PA01 |
| 193A11 | 1788050 | PA01 |
| 193A12 | 5838773 | PA01 |
| 193B02 | 306705 | PA01 |
| 193B03 | 85317 | PA01 |
| 193B04 | 5219090 | PA01 |
| 193B05 | 3474415 | PA01 |
| 193B07 | 2420143 | PA01 |
| 193B08 | 3561054 | PA01 |
| 193B09 | 4334349 | PA01 |
| 193B10 | 3057774 | PA01 |
| 193B12 | 1599173 | PA01 |
| 193C01 | 1429515 | PA01 |
| 193C02 | 1469855 | PA01 |
| 193C03 | 399648 | PA01 |
| 193C04 | 2012772 | PA01 |
| 193C05 | 1388277 | PA01 |
| 193C06 | 4901449 | PA01 |
| 193C07 | 5151949 | PA01 |
| 193C08 | 6139211 | PA01 |
| 193C09 | 1018388 | PA01 |
| 193C10 | 1968943 | PA01 |
| 193C11 | 5786206 | PA01 |
| 193C12 | 4238213 | PA01 |
| 193D01 | 5228308 | PA01 |

TABLE 3-continued

| Mutant Name | Insertion Point | host strain |
|---|---|---|
| 193D02 | 3261610 | PA01 |
| 193D04 | 4594312 | PA01 |
| 193D06 | 5764636 | PA01 |
| 193D07 | 4433947 | PA01 |
| 193D09 | 1947677 | PA01 |
| 193D10 | 3423853 | PA01 |
| 193D11 | 2516384 | PA01 |
| 193D12 | 1814028 | PA01 |
| 193E01 | 5291470 | PA01 |
| 193E02 | 3974627 | PA01 |
| 193E03 | 1524451 | PA01 |
| 193E04 | 1876783 | PA01 |
| 193E05 | 1336119 | PA01 |
| 193E06 | 1513243 | PA01 |
| 193E07 | 1362370 | PA01 |
| 193E08 | 4334349 | PA01 |
| 193E09 | 5791602 | PA01 |
| 193E10 | 177669 | PA01 |
| 193E11 | 2300649 | PA01 |
| 193E12 | 834659 | PA01 |
| 193F01 | 663862 | PA01 |
| 193F02 | 4044312 | PA01 |
| 193F03 | 2057629 | PA01 |
| 193F04 | 6239369 | PA01 |
| 193F05 | 4013215 | PA01 |
| 193F06 | 2963758 | PA01 |
| 193F09 | 189670 | PA01 |
| 193F10 | 3306499 | PA01 |
| 193F11 | 517029 | PA01 |
| 193F12 | 4433737 | PA01 |
| 193G01 | 3875131 | PA01 |
| 193G06 | 3844818 | PA01 |
| 193G09 | 5738774 | PA01 |
| 193G11 | 2753846 | PA01 |
| 193G12 | 858251 | PA01 |
| 193H03 | 171422 | PA01 |
| 193H04 | 4892448 | PA01 |
| 193H06 | 2998207 | PA01 |
| 193H07 | 641937 | PA01 |
| 193H08 | 1008182 | PA01 |
| 193H09 | 6186514 | PA01 |
| 193H10 | 5959116 | PA01 |
| 193H11 | 3235377 | PA01 |
| 194A01 | 6075274 | PA01 |
| 194A02 | 1657083 | PA01 |
| 194A03 | 5056159 | PA01 |
| 194A04 | 6019919 | PA01 |
| 194A05 | 5634042 | PA01 |
| 194A06 | 2812906 | PA01 |
| 194A08 | 2367415 | PA01 |
| 194A09 | 6198756 | PA01 |
| 194A10 | 2926783 | PA01 |
| 194A11 | 2095138 | PA01 |
| 194B02 | 399332 | PA01 |
| 194B04 | 1289165 | PA01 |
| 194B06 | 5695090 | PA01 |
| 194B07 | 5913087 | PA01 |
| 194B11 | 472803 | PA01 |
| 194B12 | 3748607 | PA01 |
| 194C01 | 2685290 | PA01 |
| 194C02 | 196608 | PA01 |
| 194C03 | 2978019 | PA01 |
| 194C04 | 1403728 | PA01 |
| 194C05 | 5284466 | PA01 |
| 194C06 | 4864670 | PA01 |
| 194C07 | 6100785 | PA01 |
| 194C08 | 1274854 | PA01 |
| 194C10 | 924756 | PA01 |
| 194C11 | 3056553 | PA01 |
| 194C12 | 1299118 | PA01 |
| 194D01 | 2652983 | PA01 |
| 194D02 | 1907299 | PA01 |
| 194D03 | 6231871 | PA01 |
| 194D04 | 3888481 | PA01 |
| 194D07 | 519951 | PA01 |
| 194D08 | 5060661 | PA01 |
| 194D11 | 5794761 | PA01 |
| 194D12 | 3231291 | PA01 |
| 194E01 | 3294959 | PA01 |
| 194E02 | 6239304 | PA01 |
| 194E05 | 4589642 | PA01 |
| 194E06 | 5251985 | PA01 |
| 194E07 | 4697847 | PA01 |
| 194E08 | 3109205 | PA01 |
| 194E09 | 5837080 | PA01 |
| 194E10 | 1588305 | PA01 |
| 194E12 | 5444779 | PA01 |
| 194F01 | 5159016 | PA01 |
| 194F02 | 5862707 | PA01 |
| 194F03 | 5736841 | PA01 |
| 194F04 | 3553451 | PA01 |
| 194F05 | 3980804 | PA01 |
| 194F07 | 4488318 | PA01 |
| 194F08 | 1429515 | PA01 |
| 194F11 | 2114038 | PA01 |
| 194O01 | 2477595 | PA01 |
| 194O02 | 1230430 | PA01 |
| 194G05 | 2729736 | PA01 |
| 194G06 | 2614405 | PA01 |
| 194G07 | 420644 | PA01 |
| 194G08 | 53299 | PA01 |
| 194G09 | 2933151 | PA01 |
| 194G11 | 2471654 | PA01 |
| 194H02 | 13604 | PA01 |
| 194H03 | 1913470 | PA01 |
| 194H06 | 6019919 | PA01 |
| 194H07 | 1064475 | PA01 |
| 194H09 | 663176 | PA01 |
| 194H10 | 2423759 | PA01 |
| 195A03 | 1883259 | PA01 |
| 195A05 | 2888474 | PA01 |
| 195A06 | 5834406 | PA01 |
| 195A08 | 323308 | PA01 |
| 195A09 | 2399019 | PA01 |
| 195A10 | 5938440 | PA01 |
| 195A11 | 4490119 | PA01 |
| 195B01 | 1868512 | PA01 |
| 195B06 | 1781790 | PA01 |
| 195B07 | 2906880 | PA01 |
| 195B08 | 1382220 | PA01 |
| 195B09 | 934913 | PA01 |
| 195B10 | 5358754 | PA01 |
| 195B11 | 5930686 | PA01 |
| 195B12 | 269732 | PA01 |
| 195C01 | 4834919 | PA01 |
| 195C02 | 807597 | PA01 |
| 195C03 | 4975465 | PA01 |
| 195C05 | 297920 | PA01 |
| 195C07 | 1972278 | PA01 |
| 195C08 | 3199850 | PA01 |
| 195C10 | 3489902 | PA01 |
| 195C12 | 1579968 | PA01 |
| 195D05 | 1599173 | PA01 |
| 195D06 | 1155875 | PA01 |
| 195D07 | 2894526 | PA01 |
| 195D10 | 1579968 | PA01 |
| 195D11 | 4673714 | PA01 |
| 195D12 | 3250915 | PA01 |
| 195E02 | 3194927 | PA01 |
| 195E03 | 1746364 | PA01 |
| 195E04 | 3408830 | PA01 |
| 195E05 | 547097 | PA01 |
| 195E06 | 1064475 | PA01 |
| 195E07 | 2312023 | PA01 |
| 195E08 | 349406 | PA01 |
| 195E09 | 2538241 | PA01 |
| 195E11 | 3118896 | PA01 |
| 195E12 | 3158748 | PA01 |
| 195F01 | 5086573 | PA01 |
| 195F02 | 894627 | PA01 |
| 195F05 | 2705053 | PA01 |
| 195F09 | 6190659 | PA01 |
| 195F10 | 2312027 | PA01 |
| 195F12 | 5948087 | PA01 |

TABLE 3-continued

| Mutant Name | Insertion Point | host strain |
|---|---|---|
| 195G01 | 1082558 | PA01 |
| 195G02 | 2437188 | PA01 |
| 195G03 | 559478 | PA01 |
| 195G04 | 2516386 | PA01 |
| 195G05 | 2247698 | PA01 |
| 195G06 | 1709171 | PA01 |
| 195G07 | 550997 | PA01 |
| 195G08 | 6231371 | PA01 |
| 195G09 | 5358757 | PA01 |
| 195G10 | 6226922 | PA01 |
| 195G11 | 4061276 | PA01 |
| 195H02 | 5042124 | PA01 |
| 195H04 | 4307961 | PA01 |
| 195H05 | 1367221 | PA01 |
| 195H06 | 3239118 | PA01 |
| 195H07 | 917913 | PA01 |
| 195H08 | 3400008 | PA01 |
| 195H09 | 3400008 | PA01 |
| 195H10 | 1010631 | PA01 |
| 195H11 | 3653147 | PA01 |
| 196A02 | 1300919 | PA01 |
| 196A03 | 4666239 | PA01 |
| 196A04 | 3362994 | PA01 |
| 196A05 | 4631871 | PA01 |
| 196A06 | 2170171 | PA01 |
| 196A07 | 5257400 | PA01 |
| 196A08 | 5034303 | PA01 |
| 196A09 | 1877843 | PA01 |
| 196A10 | 4308064 | PA01 |
| 196A11 | 177832 | PA01 |
| 196A12 | 188566 | PA01 |
| 196B01 | 4551248 | PA01 |
| 196B02 | 2720143 | PA01 |
| 196B03 | 1500753 | PA01 |
| 196B04 | 2683697 | PA01 |
| 196B05 | 1788050 | PA01 |
| 196B06 | 5685997 | PA01 |
| 196B07 | 4065488 | PA01 |
| 196B08 | 1530709 | PA01 |
| 196B09 | 1111876 | PA01 |
| 196B10 | 2236896 | PA01 |
| 196B11 | 1627845 | PA01 |
| 196B12 | 3795763 | PA01 |
| 196C01 | 3329714 | PA01 |
| 196C03 | 3592736 | PA01 |
| 196C04 | 2285378 | PA01 |
| 196C07 | 6162849 | PA01 |
| 196C08 | 3160169 | PA01 |
| 196C09 | 4062330 | PA01 |
| 196C10 | 5332032 | PA01 |
| 196C11 | 660973 | PA01 |
| 196C12 | 5251750 | PA01 |
| 196D01 | 479737 | PA01 |
| 196D02 | 632607 | PA01 |
| 196D03 | 5961995 | PA01 |
| 196D04 | 5890834 | PA01 |
| 196D06 | 1087675 | PA01 |
| 196D07 | 6012267 | PA01 |
| 196D08 | 6178520 | PA01 |
| 196D09 | 4594391 | PA01 |
| 196D11 | 3712792 | PA01 |
| 196D12 | 1548917 | PA01 |
| 196E02 | 3941477 | PA01 |
| 196E03 | 466234 | PA01 |
| 196E04 | 2719500 | PA01 |
| 196E05 | 383221 | PA01 |
| 196E06 | 2888987 | PA01 |
| 196E07 | 362761 | PA01 |
| 196E08 | 1297546 | PA01 |
| 196E09 | 2027466 | PA01 |
| 196E10 | 620889 | PA01 |
| 196E11 | 306705 | PA01 |
| 196E12 | 1525219 | PA01 |
| 196F01 | 4100725 | PA01 |
| 196F02 | 2192172 | PA01 |
| 196F03 | 1152092 | PA01 |
| 196F04 | 5743512 | PA01 |
| 196F05 | 6165886 | PA01 |
| 196F07 | 31157 | PA01 |
| 196F08 | 3598508 | PA01 |
| 196F09 | 2547870 | PA01 |
| 196F10 | 6075227 | PA01 |
| 196F11 | 1550024 | PA01 |
| 196F12 | 5188479 | PA01 |
| 196G01 | 789435 | PA01 |
| 196G02 | 1715057 | PA01 |
| 196G04 | 5321565 | PA01 |
| 196G05 | 4538762 | PA01 |
| 196G06 | 3935665 | PA01 |
| 196G07 | 1985981 | PA01 |
| 196G08 | 4367574 | PA01 |
| 196G10 | 362761 | PA01 |
| 196G11 | 2399019 | PA01 |
| 196G12 | 5706023 | PA01 |
| 196H01 | 3418100 | PA01 |
| 196H02 | 1304734 | PA01 |
| 196H03 | 632607 | PA01 |
| 196H04 | 1830069 | PA01 |
| 196H05 | 974001 | PA01 |
| 196H06 | 582086 | PA01 |
| 196H07 | 1894541 | PA01 |
| 196H08 | 5737710 | PA01 |
| 196H09 | 5821316 | PA01 |
| 196H10 | 916942 | PA01 |
| 196H11 | 5094618 | PA01 |
| 197A01 | 2477596 | PA01 |
| 197A02 | 5284518 | PA01 |
| 197A03 | 6259458 | PA01 |
| 197A04 | 1759442 | PA01 |
| 197A05 | 547097 | PA01 |
| 197A06 | 1046252 | PA01 |
| 197A07 | 5158778 | PA01 |
| 197A08 | 3087708 | PA01 |
| 197A09 | 338950 | PA01 |
| 197A10 | 3329549 | PA01 |
| 197A11 | 5497562 | PA01 |
| 197A12 | 1572853 | PA01 |
| 197B01 | 621214 | PA01 |
| 197B02 | 5120966 | PA01 |
| 197B03 | 5906859 | PA01 |
| 197B06 | 5611217 | PA01 |
| 197B07 | 368323 | PA01 |
| 197B08 | 2729735 | PA01 |
| 197B09 | 465477 | PA01 |
| 197B10 | 3250915 | PA01 |
| 197B11 | 1082558 | PA01 |
| 197B12 | 1494950 | PA01 |
| 197C01 | 621214 | PA01 |
| 197C02 | 4970251 | PA01 |
| 197C03 | 4049954 | PA01 |
| 197C04 | 1330058 | PA01 |
| 197C05 | 3407713 | PA01 |
| 197C06 | 3350770 | PA01 |
| 197C07 | 1576228 | PA01 |
| 197C09 | 423257 | PA01 |
| 197C11 | 5007738 | PA01 |
| 197C12 | 1043818 | PA01 |
| 197D01 | 2767307 | PA01 |
| 197D02 | 1436299 | PA01 |
| 197D04 | 3955647 | PA01 |
| 197D06 | 5890835 | PA01 |
| 197D07 | 2215589 | PA01 |
| 197D09 | 2129299 | PA01 |
| 197D10 | 5032334 | PA01 |
| 197D11 | 5254049 | PA01 |
| 197D12 | 920155 | PA01 |
| 197E01 | 5476826 | PA01 |
| 197E02 | 1087677 | PA01 |
| 197E03 | 397255 | PA01 |
| 197E04 | 5306956 | PA01 |
| 197E05 | 1998167 | PA01 |
| 197E06 | 3922684 | PA01 |
| 197E07 | 4842503 | PA01 |
| 197E08 | 4633066 | PA01 |

TABLE 3-continued

| Mutant Name | Insertion Point | host strain |
|---|---|---|
| 197E09 | 2367415 | PA01 |
| 197E10 | 2386729 | PA01 |
| 197E11 | 5278577 | PA01 |
| 197E12 | 397111 | PA01 |
| 197F01 | 1018338 | PA01 |
| 197F02 | 5702292 | PA01 |
| 197F03 | 3659896 | PA01 |
| 197F05 | 3689001 | PA01 |
| 197F06 | 413341 | PA01 |
| 197F07 | 874599 | PA01 |
| 197F08 | 1261736 | PA01 |
| 197F09 | 3958042 | PA01 |
| 197F10 | 521754 | PA01 |
| 197F11 | 177923 | PA01 |
| 197F12 | 1797894 | PA01 |
| 197G01 | 21773 | PA01 |
| 197G02 | 1885660 | PA01 |
| 197G03 | 2282835 | PA01 |
| 197G04 | 4696229 | PA01 |
| 197G05 | 57542 | PA01 |
| 197G06 | 1635441 | PA01 |
| 197G07 | 518755 | PA01 |
| 197G08 | 4328537 | PA01 |
| 197G09 | 339984 | PA01 |
| 197G10 | 1307376 | PA01 |
| 197G11 | 1625272 | PA01 |
| 197G12 | 532802 | PA01 |
| 197H01 | 2024704 | PA01 |
| 197H03 | 1349379 | PA01 |
| 197H05 | 5273199 | PA01 |
| 197H06 | 1394657 | PA01 |
| 197H07 | 5476139 | PA01 |
| 197H08 | 2790051 | PA01 |
| 197H09 | 4844962 | PA01 |
| 197H10 | 5240807 | PA01 |
| 197H11 | 4611050 | PA01 |
| 198A02 | 670788 | PA01 |
| 198A03 | 4831383 | PA01 |
| 198A04 | 2302736 | PA01 |
| 198A05 | 3578842 | PA01 |
| 198A06 | 5083277 | PA01 |
| 198A07 | 369075 | PA01 |
| 198A08 | 4233408 | PA01 |
| 198A09 | 4623736 | 2A01 |
| 198A10 | 2345225 | PA01 |
| 198A12 | 2626060 | PA01 |
| 198B05 | 2842463 | PA01 |
| 198B06 | 6183482 | PA01 |
| 198B07 | 1175244 | PA01 |
| 198B08 | 1353913 | PA01 |
| 198B09 | 1576228 | PA01 |
| 198B10 | 1892190 | PA01 |
| 198B12 | 63933 | PA01 |
| 198C01 | 5069695 | PA01 |
| 198C02 | 4970251 | PA01 |
| 198C03 | 4664571 | PA01 |
| 198C04 | 407700 | PA01 |
| 198C05 | 1262981 | PA01 |
| 198C06 | 4576457 | PA01 |
| 198C07 | 821358 | PA01 |
| 198C08 | 2626060 | PA01 |
| 198C09 | 953007 | PA01 |
| 198C10 | 1184851 | PA01 |
| 198C11 | 3397775 | PA01 |
| 198C12 | 1985981 | PA01 |
| 198D01 | 1380721 | PA01 |
| 198D02 | 1300396 | PA01 |
| 198D03 | 5187363 | PA01 |
| 198D04 | 3462462 | PA01 |
| 198D06 | 1756203 | PA01 |
| 198D07 | 5408320 | PA01 |
| 198D08 | 328549 | PA01 |
| 198D09 | 931235 | PA01 |
| 198D10 | 5254049 | PA01 |
| 198D11 | 975370 | PA01 |
| 198D12 | 5388536 | PA01 |
| 198E01 | 1075520 | PA01 |
| 198E02 | 1281021 | PA01 |
| 198E03 | 5983858 | PA01 |
| 198E04 | 4210693 | PA01 |
| 198E05 | 3069310 | PA01 |
| 198E06 | 1705568 | PA01 |
| 198E07 | 5003203 | PA01 |
| 198E08 | 2343238 | PA01 |
| 198E09 | 3809683 | PA01 |
| 198E10 | 1417026 | PA01 |
| 198E11 | 881939 | PA01 |
| 198E12 | 2519304 | PA01 |
| 198F02 | 5795092 | PA01 |
| 198F03 | 303111 | PA01 |
| 198F04 | 1940601 | PA01 |
| 196F05 | 1744773 | PA01 |
| 198F06 | 5930687 | PA01 |
| 198F07 | 5502181 | PA01 |
| 198F08 | 4529101 | PA01 |
| 198F09 | 63934 | PA01 |
| 198F11 | 63933 | PA01 |
| 198G01 | 2868773 | PA01 |
| 198G02 | 5906182 | PA01 |
| 198G03 | 1474344 | PA01 |
| 198G04 | 2380377 | PA01 |
| 198G05 | 321061 | PA01 |
| 198G07 | 3574398 | PA01 |
| 198G08 | 5756509 | PA01 |
| 198G10 | 2774085 | PA01 |
| 198G11 | 63933 | PA01 |
| 198G12 | 4134535 | PA01 |
| 198H01 | 4864670 | PA01 |
| 198H02 | 4864660 | PA01 |
| 198H03 | 807597 | PA01 |
| 198H04 | 4307644 | PA01 |
| 198H06 | 2024860 | PA01 |
| 198H07 | 1429218 | PA01 |
| 198H08 | 4650014 | PA01 |
| 198H09 | 5556278 | PA01 |
| 198H10 | 1206000 | PA01 |
| 198H11 | 1006404 | PA01 |
| 199A02 | 5149050 | PA01 |
| 199A03 | 1151673 | PA01 |
| 199A04 | 1005820 | PA01 |
| 199A05 | 5775644 | PA01 |
| 199A06 | 801158 | PA01 |
| 199A07 | 4344260 | PA01 |
| 199A09 | 3566494 | PA01 |
| 199A11 | 4153214 | PA01 |
| 199B01 | 5547725 | PA01 |
| 199B02 | 1756716 | PA01 |
| 199B03 | 4392105 | PA01 |
| 199B04 | 588504 | PA01 |
| 199B06 | 5436443 | PA01 |
| 199B07 | 5278577 | PA01 |
| 199B08 | 4831383 | PA01 |
| 199B10 | 4559762 | PA01 |
| 199B12 | 4594394 | PA01 |
| 199C01 | 3099144 | PA01 |
| 199C02 | 5073539 | PA01 |
| 199C03 | 179241 | PA01 |
| 199C04 | 3744782 | PA01 |
| 199C05 | 444036 | PA01 |
| 199C06 | 4354058 | PA01 |
| 199C08 | 4054030 | PA01 |
| 199C09 | 1402129 | PA01 |
| 199C10 | 4531158 | PA01 |
| 199C12 | 1439067 | PA01 |
| 199D02 | 471331 | PA01 |
| 199D03 | 1037317 | PA01 |
| 199D04 | 2345056 | PA01 |
| 199D05 | 4866960 | PA01 |
| 199D06 | 5559905 | PA01 |
| 199D08 | 4872115 | PA01 |
| 199D09 | 858252 | PA01 |
| 199D10 | 4559159 | PA01 |
| 199D11 | 582086 | PA01 |
| 199D12 | 831276 | PA01 |

TABLE 3-continued

| Mutant Name | Insertion Point | host strain |
|---|---|---|
| 199E01 | 6199101 | PA01 |
| 199E02 | 5587391 | PA01 |
| 199E03 | 2780129 | PA01 |
| 199E04 | 2183884 | PA01 |
| 199E05 | 1370589 | PA01 |
| 199E06 | 1356200 | PA01 |
| 199E07 | 6238669 | PA01 |
| 199E08 | 3570463 | PA01 |
| 199E10 | 4814077 | PA01 |
| 199E11 | 5444780 | PA01 |
| 199E12 | 960376 | PA01 |
| 199F01 | 4054030 | PA01 |
| 199F03 | 5127425 | PA01 |
| 199F04 | 5083277 | PA01 |
| 199F05 | 1087675 | PA01 |
| 199F06 | 158083 | PA01 |
| 199F07 | 24664 | PA01 |
| 199F08 | 6118109 | PA01 |
| 199F09 | 1048056 | PA01 |
| 199F10 | 3479048 | PA01 |
| 199G01 | 4704106 | PA01 |
| 199G02 | 3505585 | PA01 |
| 199G03 | 3810859 | PA01 |
| 199G04 | 4125268 | PA01 |
| 199G05 | 5083277 | PA01 |
| 199G07 | 5641477 | PA01 |
| 199G09 | 5632007 | PA01 |
| 199G10 | 356993 | PA01 |
| 199G11 | 632969 | PA01 |
| 199G12 | 3733759 | PA01 |
| 199H01 | 1431620 | PA01 |
| 199H02 | 804767 | PA01 |
| 199H03 | 5697208 | PA01 |
| 199H05 | 1240147 | PA01 |
| 199H06 | 6093484 | PA01 |
| 199H07 | 5187700 | PA01 |
| 199H08 | 1434130 | PA01 |
| 199H09 | 5271365 | PA01 |
| 199H10 | 5890834 | PA01 |
| 199H11 | 6141394 | PA01 |
| 200A01 | 4998867 | PA01 |
| 200A02 | 2479696 | PA01 |
| 200A04 | 5198857 | PA01 |
| 200A05 | 5151949 | PA01 |
| 200A06 | 1018388 | PA01 |
| 200A07 | 4025432 | PA01 |
| 200A08 | 1611467 | PA01 |
| 200A09 | 1570079 | PA01 |
| 200A10 | 664438 | PA01 |
| 200A11 | 1234613 | PA01 |
| 200A12 | 2522176 | PA01 |
| 200B01 | 306020 | PA01 |
| 200B02 | 3416856 | PA01 |
| 200B03 | 489696 | PA01 |
| 200B04 | 1642436 | PA01 |
| 200B05 | 3659268 | PA01 |
| 200B06 | 3961517 | PA01 |
| 200B08 | 4153214 | PA01 |
| 200B09 | 4153214 | PA01 |
| 200B10 | 6067436 | PA01 |
| 200B11 | 3652820 | PA01 |
| 200B12 | 2349849 | PA01 |
| 200C01 | 2538241 | PA01 |
| 200C03 | 1588305 | PA01 |
| 200C04 | 6196985 | PA01 |
| 200C05 | 5768034 | PA01 |
| 200C06 | 2116304 | PA01 |
| 200C08 | 1698386 | PA01 |
| 200C09 | 5183525 | PA01 |
| 200C11 | 3122931 | PA01 |
| 200C12 | 3250914 | PA01 |
| 200D01 | 5436533 | PA01 |
| 200D02 | 6176104 | PA01 |
| 200D03 | 109116 | PA01 |
| 200D04 | 3816551 | PA01 |
| 200D05 | 2602286 | PA01 |
| 200D07 | 5173989 | PA01 |
| 200D08 | 5853812 | PA01 |
| 200D11 | 114208 | PA01 |
| 200D12 | 5118761 | PA01 |
| 200E02 | 1781790 | PA01 |
| 200E03 | 3904412 | PA01 |
| 200E04 | 1292952 | PA01 |
| 200E05 | 3988590 | PA01 |
| 200E06 | 2345056 | PA01 |
| 200E07 | 3685973 | 2A01 |
| 200E08 | 4523815 | PA01 |
| 200E10 | 3293888 | PA01 |
| 200E11 | 1635441 | PA01 |
| 200E12 | 1293986 | PA01 |
| 200F02 | 1601681 | PA01 |
| 200F03 | 2080740 | PA01 |
| 200F04 | 2437187 | PA01 |
| 200F05 | 3979079 | PA01 |
| 200F06 | 3393156 | PA01 |
| 200F07 | 1996444 | PA01 |
| 200F08 | 3134852 | PA01 |
| 200F09 | 132107 | PA01 |
| 200F10 | 1823277 | PA01 |
| 200F11 | 1010779 | PA01 |
| 200G01 | 3069310 | PA01 |
| 200G02 | 1119528 | PA01 |
| 200G03 | 4414026 | PA01 |
| 200G06 | 6122316 | PA01 |
| 200G07 | 2080740 | PA01 |
| 200G08 | 471331 | PA01 |
| 200G09 | 1429515 | PA01 |
| 200G11 | 2855635 | PA01 |
| 200G12 | 4138075 | PA01 |
| 200H01 | 2423550 | PA01 |
| 200H02 | 1417209 | PA01 |
| 200H04 | 2480765 | PA01 |
| 200H05 | 4048173 | PA01 |
| 200H07 | 1504373 | PA01 |
| 200H09 | 4514834 | PA01 |
| 200H10 | 887586 | PA01 |
| 201A04 | 2183884 | PA01 |
| 201A06 | 5282876 | PA01 |
| 201A07 | 1991177 | PA01 |
| 201A08 | 1278212 | PA01 |
| 201A09 | 2095138 | PA01 |
| 201A12 | 1991177 | PA01 |
| 201B02 | 6239304 | PA01 |
| 201B07 | 1802886 | PA01 |
| 201B08 | 20951667 | PA01 |
| 201B12 | 481393 | PA01 |
| 201C03 | 3400008 | PA01 |
| 201C08 | 4118672 | PA01 |
| 201C11 | 5768034 | PA01 |
| 201C12 | 6257292 | PA01 |
| 201D05 | 359564 | PA01 |
| 201D07 | 5263348 | PA01 |
| 201D08 | 3847056 | PA01 |
| 201D09 | 279736 | PA01 |
| 201D10 | 5937406 | PA01 |
| 201D12 | 5937406 | PA01 |
| 201E03 | 4501878 | PA01 |
| 201E08 | 6050836 | PA01 |
| 201E09 | 5800121 | PA01 |
| 201E11 | 5120965 | PA01 |
| 201F01 | 3294959 | PA01 |
| 201F06 | 3847278 | PA01 |
| 201F09 | 6012267 | PA01 |
| 201G07 | 2655369 | PA01 |
| 201G11 | 5169536 | PA01 |
| 201H05 | 4650014 | PA01 |
| 201H07 | 767461 | PA01 |
| 201H08 | 4481437 | PA01 |
| 201H09 | 1064475 | PA01 |
| 202A01 | 4589642 | PA01 |
| 202A02 | 458964 | PA01 |
| 202A04 | 2129299 | PA01 |
| 202A05 | 2298479 | PA01 |
| 202A06 | 588504 | PA01 |

TABLE 3-continued

| Mutant Name | Insertion Point | host strain |
|---|---|---|
| 202A07 | 359564 | PA01 |
| 202A08 | 3596417 | PA01 |
| 202A09 | 5433632 | PA01 |
| 202A10 | 982652 | PA01 |
| 202A11 | 5994593 | PA01 |
| 202B01 | 2814599 | PA01 |
| 202B03 | 2930684 | PA01 |
| 202B04 | 5005306 | PA01 |
| 202B05 | 3612678 | PA01 |
| 202B06 | 5469203 | PA01 |
| 202B07 | 384728 | PA01 |
| 202B08 | 5151949 | PA01 |
| 202B10 | 3760820 | PA01 |
| 202B11 | 3385758 | PA01 |
| 202C01 | 5768034 | PA01 |
| 202C02 | 4284077 | PA01 |
| 202C03 | 1512997 | PA01 |
| 202C04 | 2129411 | PA01 |
| 202C06 | 1530709 | PA01 |
| 202C07 | 5373812 | PA01 |
| 202C08 | 3223253 | PA01 |
| 202C10 | 3288834 | PA01 |
| 202C12 | 1082558 | PA01 |
| 202D01 | 4212283 | PA01 |
| 202D02 | 222110 | PA01 |
| 202D03 | 94180 | PA01 |
| 202D04 | 3046825 | PA01 |
| 202D06 | 680915 | PA01 |
| 202D07 | 4345761 | PA01 |
| 202D08 | 3826382 | PA01 |
| 202D09 | 4308064 | |
| 202D10 | 3505585 | PA01 |
| 202D11 | 1335367 | PA01 |
| 202D12 | 4794311 | PA01 |
| 202E01 | 1782659 | PA01 |
| 202E02 | 427594 | PA01 |
| 202E03 | 1898833 | PA01 |
| 202E04 | 5776318 | PA01 |
| 202E05 | 710987 | PA01 |
| 202E06 | 3236850 | PA01 |
| 202E07 | 5247546 | PA01 |
| 202E08 | 4035071 | PA01 |
| 202E09 | 204518 | PA01 |
| 202E10 | 1560670 | PA01 |
| 202E11 | 5200932 | PA01 |
| 202F02 | 5060661 | PA01 |
| 202F03 | 1124960 | PA01 |
| 202F04 | 3658392 | PA01 |
| 202F05 | 941859 | PA01 |
| 202F06 | 2658277 | PA01 |
| 202F07 | 1853284 | PA01 |
| 202F08 | 3076721 | PA01 |
| 202F09 | 1777702 | PA01 |
| 202F10 | 6198756 | PA01 |
| 202F11 | 435027 | PA01 |
| 202F12 | 2477889 | PA01 |
| 202G01 | 3442739 | PA01 |
| 202G02 | 4494227 | PA01 |
| 202G03 | 104799 | PA01 |
| 202G04 | 4350073 | PA01 |
| 202G05 | 4694750 | PA01 |
| 202G06 | 5583826 | PA01 |
| 202G07 | 5584391 | PA01 |
| 202G08 | 4847864 | PA01 |
| 202G09 | 2162450 | PA01 |
| 202G10 | 2001513 | PA01 |
| 202G12 | 1018388 | PA01 |
| 202H01 | 4308064 | PA01 |
| 202H02 | 3129165 | PA01 |
| 202H04 | 4257084 | PA01 |
| 202H05 | 4450702 | PA01 |
| 202H06 | 5086573 | PA01 |
| 202H07 | 4860947 | PA01 |
| 202H10 | 6090707 | PA01 |
| 202H11 | 4138588 | PA01 |
| 203A01 | 5077360 | PA01 |
| 203A07 | 899039 | PA01 |
| 203A08 | 2000354 | PA01 |
| 203A09 | 973442 | PA01 |
| 203B01 | 5077360 | PA01 |
| 203B03 | 2310593 | PA01 |
| 203B04 | 2310591 | PA01 |
| 203B05 | 1388277 | PA01 |
| 203B08 | 5987063 | PA01 |
| 203B09 | 3759317 | PA01 |
| 203B10 | 3433540 | PA01 |
| 203C05 | 2367415 | PA01 |
| 203C09 | 5393185 | PA01 |
| 203C10 | 2399019 | PA01 |
| 203C11 | 4523815 | PA01 |
| 203C12 | 5157086 | PA01 |
| 203D02 | 3608762 | PA01 |
| 203D08 | 4707421 | PA01 |
| 203D09 | 4130479 | PA01 |
| 203D11 | 4170091 | PA01 |
| 203E05 | 4492081 | PA01 |
| 203E06 | 4194333 | PA01 |
| 203E07 | 4632089 | PA01 |
| 203F03 | 30371 | PA01 |
| 203F09 | 1375885 | PA01 |
| 203F11 | 944736 | PA01 |
| 203F12 | 24665 | PA01 |
| 203G02 | 3329714 | PA01 |
| 203G05 | 5475672 | PA01 |
| 203G06 | 1510511 | PA01 |
| 203G09 | 5318004 | PA01 |
| 203G12 | 2117618 | PA01 |
| 203H02 | 441133 | PA01 |
| 203H07 | 1164559 | PA01 |
| 203H08 | 545189 | PA01 |
| 203H10 | 6092467 | PA01 |
| 204A01 | 1064475 | PA01 |
| 204A03 | 4145224 | PA01 |
| 204A05 | 3706462 | PA01 |
| 204A06 | 3175439 | PA01 |
| 204A07 | 2506126 | PA01 |
| 204A08 | 3288834 | PA01 |
| 204A09 | 1972791 | PA01 |
| 204A10 | 138297 | PA01 |
| 204A11 | 1126432 | PA01 |
| 204A12 | 2976291 | PA01 |
| 204B01 | 2504863 | PA01 |
| 204B02 | 5571358 | PA01 |
| 204B03 | 3577840 | PA01 |
| 204B05 | 486675 | PA01 |
| 204B06 | 52810 | PA01 |
| 204B07 | 670970 | PA01 |
| 204B08 | 4585465 | PA01 |
| 204B09 | 4350073 | PA01 |
| 204B11 | 5201685 | PA01 |
| 204B12 | 2915395 | PA01 |
| 204C01 | 5648517 | PA01 |
| 204C03 | 5444780 | PA01 |
| 204C04 | 5401050 | PA01 |
| 204C05 | 1078894 | PA01 |
| 204C06 | 2024704 | PA01 |
| 204C07 | 3023023 | PA01 |
| 204C08 | 4547868 | PA01 |
| 204C09 | 1582645 | PA01 |
| 204C10 | 2837048 | PA01 |
| 204C11 | 4657805 | PA01 |
| 204C12 | 4657805 | PA01 |
| 204D01 | 1185192 | PA01 |
| 204D04 | 2496516 | PA01 |
| 204D06 | 3188786 | PA01 |
| 204D09 | 1283125 | PA01 |
| 204D10 | 4871941 | PA01 |
| 204D11 | 1641078 | PA01 |
| 204D12 | 8183483 | PA01 |
| 204E02 | 1166059 | PA01 |
| 204E03 | 5183525 | PA01 |
| 204E04 | 5946328 | PA01 |
| 204E05 | 4558862 | PA01 |
| 204E06 | 5407317 | PA01 |

TABLE 3-continued

| Mutant Name | Insertion Point | host strain |
|---|---|---|
| 204E08 | 3417511 | PA01 |
| 204E09 | 5158635 | PA01 |
| 204E11 | 894630 | PA01 |
| 204E12 | 946484 | PA01 |
| 204F01 | 144732 | PA01 |
| 204F02 | 5452705 | PA01 |
| 204F06 | 3997039 | PA01 |
| 204F07 | 2453351 | PA01 |
| 204F08 | 632969 | PA01 |
| 204F09 | 5157544 | PA01 |
| 204F10 | 1546129 | PA01 |
| 204F11 | 4392178 | PA01 |
| 204F12 | 3418100 | PA01 |
| 204G01 | 1681776 | PA01 |
| 204G02 | 5286965 | PA01 |
| 204G03 | 4813041 | PA01 |
| 204G04 | 3986398 | PA01 |
| 204G05 | 2302736 | PA01 |
| 204G06 | 1086488 | PA01 |
| 204G07 | 5476139 | PA01 |
| 204G09 | 552176 | PA01 |
| 204G10 | 5934657 | PA01 |
| 204G11 | 2051514 | PA01 |
| 204G12 | 5149544 | PA01 |
| 204H01 | 1002390 | PA01 |
| 204H02 | 5431716 | PA01 |
| 204H03 | 5508970 | PA01 |
| 204H04 | 5508970 | PA01 |
| 204H06 | 32883 | PA01 |
| 204H08 | 2951328 | PA01 |
| 204H09 | 3751210 | PA01 |
| 204H10 | 1397828 | PA01 |
| 205A04 | 800304 | 2A01 |
| 205A06 | 3653256 | PA01 |
| 205A08 | 5309318 | PA01 |
| 205A11 | 2022762 | PA01 |
| 205B05 | 2686825 | PA01 |
| 205B08 | 3418100 | PA01 |
| 205B09 | 5040742 | PA01 |
| 205B11 | 3258710 | PA01 |
| 205C03 | 4515013 | PA01 |
| 205C04 | 5500123 | PA01 |
| 205C08 | 1038724 | PA01 |
| 205C09 | 1021791 | PA01 |
| 205C11 | 5398475 | PA01 |
| 205C12 | 1436904 | PA01 |
| 205D07 | 1296887 | PA01 |
| 205E05 | 1866247 | PA01 |
| 205E06 | 4325244 | PA01 |
| 205E07 | 2256103 | PA01 |
| 205E09 | 1567960 | PA01 |
| 205E11 | 899039 | PA01 |
| 205E12 | 4655453 | PA01 |
| 205F01 | 6196585 | PA01 |
| 205F03 | 5000428 | PA01 |
| 205F05 | 5187700 | PA01 |
| 205F09 | 598392 | PA01 |
| 205G05 | 5398475 | PA01 |
| 205G06 | 5398475 | PA01 |
| 205G09 | 2440205 | PA01 |
| 205H02 | 1173804 | PA01 |
| 205H05 | 530714 | PA01 |
| 205H07 | 3202112 | PA01 |
| 205H09 | 885011 | PA01 |
| 206A02 | 1260924 | PA01 |
| 206A03 | 1906891 | PA01 |
| 206A06 | 2162449 | PA01 |
| 206A08 | 3408993 | PA01 |
| 206A09 | 4570312 | PA01 |
| 206A12 | 1382220 | PA01 |
| 206B02 | 269731 | PA01 |
| 206B05 | 339459 | PA01 |
| 206B12 | 590618 | PA01 |
| 206C01 | 5764162 | PA01 |
| 206C03 | 4531368 | PA01 |
| 206C04 | 3839120 | PA01 |
| 206C05 | 1018388 | PA01 |
| 206C06 | 2023760 | PA01 |
| 206C09 | 3433540 | PA01 |
| 206C10 | 3069356 | PA01 |
| 206C12 | 2705053 | PA01 |
| 206D01 | 5034303 | PA01 |
| 206D02 | 1460737 | PA01 |
| 206D03 | 5884879 | PA01 |
| 206D06 | 135129 | PA01 |
| 206D07 | 2133873 | PA01 |
| 206D08 | 4194331 | PA01 |
| 206D10 | 1513243 | PA01 |
| 206D12 | 1885660 | PA01 |
| 206E01 | 843356 | PA01 |
| 206E03 | 5513935 | PA01 |
| 206E04 | 4280266 | PA01 |
| 206E06 | 1427492 | PA01 |
| 206E08 | 716260 | PA01 |
| 206E10 | 2559947 | PA01 |
| 206E12 | 1018388 | PA01 |
| 206F01 | 5918900 | PA01 |
| 206F07 | 3434587 | PA01 |
| 206F03 | 1353959 | PA01 |
| 206F10 | 1007058 | PA01 |
| 206F11 | 1007058 | PA01 |
| 206F12 | 4896949 | PA01 |
| 206G01 | 715509 | PA01 |
| 206G02 | 1070676 | PA01 |
| 206G03 | 4446673 | PA01 |
| 206G06 | 93913 | PA01 |
| 206G09 | 2794950 | PA01 |
| 206G10 | 3108154 | PA01 |
| 206G11 | 946926 | PA01 |
| 206G12 | 4452477 | PA01 |
| 206H01 | 1548077 | PA01 |
| 206H02 | 271574 | PA01 |
| 206H03 | 1329770 | PA01 |
| 206H04 | 1402129 | PA01 |
| 206H06 | 5953052 | PA01 |
| 206H07 | 767363 | PA01 |
| 206H08 | 1572851 | PA01 |
| 206H11 | 3608762 | PA01 |
| 207A02 | 6193301 | PA01 |
| 207A03 | 5930214 | PA01 |
| 207A04 | 3374216 | PA01 |
| 207A05 | 375528 | PA01 |
| 207A06 | 2506126 | PA01 |
| 207A07 | 1010520 | PA01 |
| 207A08 | 1164559 | PA01 |
| 207A10 | 1833025 | PA01 |
| 207A11 | 5420760 | PA01 |
| 207A12 | 774051 | PA01 |
| 207B01 | 3054726 | PA01 |
| 207B02 | 916942 | PA01 |
| 207B04 | 5094530 | PA01 |
| 207B05 | 813366 | PA01 |
| 207B06 | 5539080 | PA01 |
| 207B07 | 1963822 | PA01 |
| 207B06 | 6022758 | PA01 |
| 207B09 | 2506126 | PA01 |
| 207B10 | 758473 | PA01 |
| 207B11 | 6118085 | PA01 |
| 207B12 | 1137119 | PA01 |
| 207C01 | 2480764 | PA01 |
| 207C02 | 5768034 | PA01 |
| 207C04 | 2399017 | PA01 |
| 207C05 | 4847345 | PA01 |
| 207C06 | 4833047 | PA01 |
| 207C07 | 3888481 | PA01 |
| 207C08 | 1830069 | PA01 |
| 207C09 | 1079350 | PA01 |
| 207C10 | 1394657 | PA01 |
| 207C11 | 3974627 | PA01 |
| 207C12 | 1203434 | PA01 |
| 207D01 | 5795988 | PA01 |
| 207D02 | 3652820 | PA01 |
| 207D03 | 5315658 | PA01 |
| 207D04 | 504074 | PA01 |

TABLE 3-continued

| Mutant Name | Insertion Point | host strain |
|---|---|---|
| 207D06 | 93744 | PA01 |
| 207D07 | 1351298 | PA01 |
| 207D08 | 620889 | PA01 |
| 207D09 | 5981336 | PA01 |
| 207D10 | 5679371 | PA01 |
| 207D11 | 4507686 | PA01 |
| 207E03 | 179242 | PA01 |
| 207E04 | 5256962 | PA01 |
| 207E07 | 4199800 | PA01 |
| 207E08 | 802522 | PA01 |
| 207E10 | 5273292 | PA01 |
| 207E12 | 767363 | PA01 |
| 207F04 | 5854080 | PA01 |
| 207F07 | 4134535 | PA01 |
| 207F10 | 2848392 | PA01 |
| 207F11 | 5214226 | PA01 |
| 207G01 | 3250915 | PA01 |
| 207G03 | 4845292 | PA01 |
| 207G06 | 4865696 | PA01 |
| 207G07 | 2990245 | PA01 |
| 207G10 | 711492 | PA01 |
| 207G12 | 1874570 | PA01 |
| 207H02 | 2116427 | PA01 |
| 207H03 | 5282876 | PA01 |
| 207H04 | 427386 | PA01 |
| 207H05 | 94180 | PA01 |
| 207H06 | 1006391 | PA01 |
| 207H07 | 3000611 | PA01 |
| 207H08 | 3479636 | PA01 |
| 207H09 | 38079 | PA01 |
| 207H10 | 6161381 | PA01 |
| 207H11 | 3374216 | PA01 |
| 208A01 | 5169700 | PA01 |
| 208A02 | 6207447 | PA01 |
| 208A04 | 4307644 | PA01 |
| 208A05 | 1818388 | PA01 |
| 208A06 | 3644300 | PA01 |
| 208A07 | 1184851 | PA01 |
| 208A08 | 899039 | PA01 |
| 208A09 | 1579968 | PA01 |
| 208A10 | 3748677 | PA01 |
| 208A11 | 175368 | PA01 |
| 208A12 | 3955708 | PA01 |
| 208B01 | 2147215 | PA01 |
| 208B02 | 1051075 | PA01 |
| 208B03 | 5751317 | PA01 |
| 208B04 | 2706223 | PA01 |
| 208B05 | 2963758 | PA01 |
| 208B07 | 5452798 | PA01 |
| 208B09 | 551772 | PA01 |
| 208B10 | 2696925 | PA01 |
| 208B11 | 1868512 | PA01 |
| 208B12 | 789906 | PA01 |
| 208C01 | 2144553 | PA01 |
| 208C02 | 1884350 | PA01 |
| 208C03 | 1884350 | PA01 |
| 208C04 | 2595198 | PA01 |
| 208C05 | 468401 | PA01 |
| 208C06 | 2516386 | PA01 |
| 208C07 | 323308 | PA01 |
| 208C08 | 1906892 | PA01 |
| 208C09 | 6226412 | PA01 |
| 208C10 | 3397774 | PA01 |
| 208C11 | 369550 | PA01 |
| 208C12 | 1295166 | PA01 |
| 208D01 | 24664 | PA01 |
| 208D02 | 1426102 | PA01 |
| 208D03 | 5000428 | PA01 |
| 208D05 | 5041900 | PA01 |
| 208D06 | 5191572 | PA01 |
| 208D07 | 2453351 | PA01 |
| 208D09 | 807493 | PA01 |
| 208D10 | 2364618 | PA01 |
| 208D11 | 2495714 | PA01 |
| 208E01 | 2282835 | PA01 |
| 208E02 | 1274370 | PA01 |
| 208E03 | 5714574 | PA01 |
| 208E05 | 3237193 | PA01 |
| 208E06 | 5729356 | PA01 |
| 208E07 | 1300920 | PA01 |
| 208E08 | 2614404 | PA01 |
| 208E09 | 5726385 | PA01 |
| 208E11 | 4707308 | PA01 |
| 208E12 | 5405477 | PA01 |
| 208F01 | 5668952 | PA01 |
| 208F05 | 60548 | PA01 |
| 208F08 | 4366772 | PA01 |
| 208F09 | 2558615 | PA01 |
| 208F10 | 23683417 | PA01 |
| 208F12 | 54400687 | PA01 |
| 208G01 | 1203434 | PA01 |
| 208G02 | 4164444 | PA01 |
| 208G04 | 3250914 | PA01 |
| 208G05 | 1452418 | PA01 |
| 208G05 | 1566549 | PA01 |
| 208G07 | 57513177 | PA01 |
| 208G08 | 906184 | PA01 |
| 208G09 | 3653148 | PA01 |
| 208G10 | 4030117 | PA01 |
| 208G11 | 428804 | PA01 |
| 208G12 | 11030827 | PA01 |
| 208H01 | 1203434 | PA01 |
| 208H02 | 1798810 | PA01 |
| 208H03 | 6207447 | PA01 |
| 208H04 | 1656566 | PA01 |
| 208H06 | 1047003 | PA01 |
| 208H07 | 37127937 | PA01 |
| 208H09 | 6045616 | PA01 |
| 208H10 | 1972791 | PA01 |
| 208H11 | 769385 | PA01 |
| 209A01 | 37957637 | PA01 |
| 209A02 | 15080947 | PA01 |
| 209A03 | 34369497 | PA01 |
| 209A05 | 3464395 | PA01 |
| 209A06 | 4351076 | PA01 |
| 209A08 | 142790 | PA01 |
| 209A09 | 12479597 | PA01 |
| 209A10 | 54616417 | PA01 |
| 209A11 | 4724385 | PA01 |
| 209A12 | 4167152 | PA01 |
| 209B02 | 29388427 | PA01 |
| 209B03 | 59814057 | PA01 |
| 209B04 | 3059063 | PA01 |
| 209B05 | 5306956 | PA01 |
| 209B07 | 30602027 | PA01 |
| 209B06 | 5060863 | PA01 |
| 209B09 | 31754397 | PA01 |
| 209B11 | 2016265 | PA01 |
| 209B12 | 62313717 | PA01 |
| 209C01 | S619966 | PA01 |
| 209C03 | 1002390 | PA01 |
| 209C04 | 25670997 | PA01 |
| 209C05 | 1121627 | PA01 |
| 209C07 | 5649595 | PA01 |
| 209C10 | 32013197 | PA01 |
| 209C11 | 4161229 | PA01 |
| 209C12 | 5139876 | PA01 |
| 209D01 | 5939635 | PA01 |
| 209002 | 5302623 | PA01 |
| 209003 | 5539080 | PA01 |
| 209004 | 4130479 | PA01 |
| 209D05 | 5550334 | PA01 |
| 209006 | 2097505 | PA01 |
| 209007 | 2491449 | PA01 |
| 209008 | 1877848 | PA01 |
| 209010 | 2007205 | PA01 |
| 209011 | 1434130 | PA01 |
| 209D12 | 365141 | PA01 |
| 209E01 | 1078894 | PA01 |
| 209E02 | 5006975 | PA01 |
| 209E03 | 2375364 | PA01 |
| 209E04 | 6122838 | PA01 |
| 209E08 | 6055701 | PA01 |
| 209E09 | 5564061 | PA01 |

TABLE 3-continued

| Mutant Name | Insertion Point | host strain |
|---|---|---|
| 209E11 | 1849784 | PA01 |
| 209E12 | 5163272 | PA01 |
| 209F01 | 2129412 | PA01 |
| 209F06 | 1756203 | PA01 |
| 209F07 | 3131148 | PA01 |
| 209F08 | 4976159 | PA01 |
| 209F10 | 4998866 | PA01 |
| 209G04 | 1215123 | PA01 |
| 209G09 | 4152866 | PA01 |
| 209G11 | 2658277 | PA01 |
| 209G12 | 1681776 | PA01 |
| 209H01 | 2607884 | PA01 |
| 209H03 | 3914200 | PA01 |
| 209H04 | 295826 | PA01 |
| 209H06 | 4100728 | PA01 |
| 209H07 | 3418100 | PA01 |
| 209H08 | 2780079 | PA01 |
| 209H09 | 6153237 | PA01 |
| 209H10 | 5768034 | PA01 |
| 209H11 | 2070291 | PA01 |
| 210A01 | 1566548 | PA01 |
| 210A02 | 1566549 | PA01 |
| 210A03 | 2978019 | PA01 |
| 210A04 | 342605 | PA01 |
| 210A05 | 204224 | PA01 |
| 210A06 | 3932330 | PA01 |
| 210A07 | 1018475 | PA01 |
| 210A09 | 1231310 | PA01 |
| 210A10 | 2229888 | PA01 |
| 210A11 | 3220503 | PA01 |
| 210B01 | 2979372 | PA01 |
| 210B02 | 1300919 | PA01 |
| 210B03 | 3914199 | PA01 |
| 210B04 | 5746383 | PA01 |
| 210B05 | 3591242 | PA01 |
| 210B07 | 1082558 | PA01 |
| 210B08 | 1161513 | PA01 |
| 210B09 | 397732 | PA01 |
| 210B11 | 2978019 | PA01 |
| 210C01 | 2124983 | PA01 |
| 210C03 | 2930684 | PA01 |
| 210C04 | 2082490 | PA01 |
| 210C05 | 2082490 | PA01 |
| 210C07 | 2046881 | PA01 |
| 210C08 | 5768034 | PA01 |
| 210C09 | 1016630 | PA01 |
| 210C10 | 1080473 | PA01 |
| 210C11 | 915803 | PA01 |
| 210C12 | 3442739 | PA01 |
| 210D01 | 3744782 | PA01 |
| 210D02 | 1383796 | PA01 |
| 210D04 | 1938348 | PA01 |
| 210D05 | 3496050 | PA01 |
| 210D07 | 566400 | PA01 |
| 210D08 | 1199969 | PA01 |
| 210D09 | 2847431 | PA01 |
| 210D11 | 3627888 | PA01 |
| 210D12 | 4839272 | PA01 |
| 210E01 | 4531158 | PA01 |
| 210E02 | 3839120 | PA01 |
| 210E03 | 5225978 | PA01 |
| 210E04 | 6054624 | PA01 |
| 210E05 | 5791803 | PA01 |
| 210E06 | 3262459 | PA01 |
| 210E07 | 1028922 | PA01 |
| 210E08 | 5736496 | PA01 |
| 210E09 | 1290741 | PA01 |
| 210E10 | 819958 | PA01 |
| 210E11 | 264113 | PA01 |
| 210E12 | 3005783 | PA01 |
| 210F01 | 9481261 | PA01 |
| 210F02 | 5174041 | PA01 |
| 210F03 | 2729756 | PA01 |
| 210F04 | 2437164 | PA01 |
| 210F05 | 120468 | PA01 |
| 210F06 | 4492082 | PA01 |
| 210F07 | 1225209 | PA01 |
| 210F08 | 3995547 | PA01 |
| 210F11 | 2089460 | PA01 |
| 210F12 | 2090489 | PA01 |
| 210G01 | 1109319 | PA01 |
| 210G02 | 1222906 | PA01 |
| 210G03 | 5667217 | PA01 |
| 210G04 | 5456821 | PA01 |
| 210G05 | 4156562 | PA01 |
| 210G06 | 5118668 | PA01 |
| 210G08 | 4237859 | PA01 |
| 210G09 | 1185192 | PA01 |
| 210G11 | 4675165 | PA01 |
| 210G12 | 5648597 | PA01 |
| 210H01 | 2262738 | PA01 |
| 210H02 | 498406 | PA01 |
| 210H03 | 330753 | PA01 |
| 210H04 | 3456266 | PA01 |
| 210H05 | 2705053 | PA01 |
| 210H06 | 5247545 | PA01 |
| 210H07 | 3685973 | PA01 |
| 210H08 | 184761 | PA01 |
| 210H10 | 1513243 | PA01 |
| 210H11 | 2345225 | PA01 |
| 211A01 | 1041171 | PA01 |
| 211A02 | 5530237 | PA01 |
| 211A03 | 1746364 | PA01 |
| 211A04 | 5493271 | PA01 |
| 211A05 | 3199850 | PA01 |
| 211A06 | 4251879 | PA01 |
| 211A07 | 1008183 | PA01 |
| 211A09 | 3233217 | PA01 |
| 211A10 | 47133 | PA01 |
| 211A11 | 2122725 | PA01 |
| 211A12 | 6183483 | PA01 |
| 211B01 | 4047636 | PA01 |
| 211B02 | 1551713 | PA01 |
| 211B03 | 4911296 | PA01 |
| 211B04 | 5806839 | PA01 |
| 211B06 | 2560986 | PA01 |
| 211B07 | 4351074 | PA01 |
| 211B08 | 3288834 | PA01 |
| 211B09 | 4666239 | PA01 |
| 211B10 | 2349849 | PA01 |
| 211B11 | 1838025 | PA01 |
| 211B12 | 5890628 | PA01 |
| 211C01 | 6133959 | PA01 |
| 211C04 | 5890628 | PA01 |
| 211C05 | 517029 | PA01 |
| 211C06 | 428407 | PA01 |
| 211C07 | 4414026 | PA01 |
| 211C08 | 1103071 | PA01 |
| 211C10 | 6054624 | PA01 |
| 211C11 | 6055515 | PA01 |
| 211C12 | 3479637 | PA01 |
| 211D01 | 5611963 | PA01 |
| 211D03 | 5404050 | PA01 |
| 211D04 | 1717810 | PA01 |
| 211D06 | 5736945 | PA01 |
| 211D07 | 5915883 | PA01 |
| 211D08 | 1439067 | PA01 |
| 211D10 | 709828 | PA01 |
| 211D11 | 3574398 | PA01 |
| 211D12 | 5058053 | PA01 |
| 211E01 | 5310269 | PA01 |
| 211E02 | 4923520 | PA01 |
| 211E03 | 5530236 | PA01 |
| 211E04 | 6177590 | PA01 |
| 211E05 | 5536732 | PA01 |
| 211E07 | 621214 | PA01 |
| 211E08 | 779630 | PA01 |
| 211E09 | 858252 | PA01 |
| 211E11 | 983106 | PA01 |
| 211E12 | 5881570 | PA01 |
| 211F03 | 1793474 | PA01 |
| 211F04 | 2919009 | PA01 |
| 211F05 | 5038237 | PA01 |
| 211F06 | 1298975 | PA01 |

TABLE 3-continued

| Mutant Name | Insertion Point | host strain |
|---|---|---|
| 211F07 | 3988591 | PA01 |
| 211F08 | 2705052 | PA01 |
| 211F10 | 431629 | PA01 |
| 211F11 | 4618389 | PA01 |
| 211F12 | 6178519 | PA01 |
| 211G01 | 1417026 | PA01 |
| 211G02 | 310573 | PA01 |
| 211G03 | 1635441 | PA01 |
| 211G04 | 1576228 | PAd |
| 211G06 | i383796 | PA01 |
| 211G07 | 4673714 | PA01 |
| 211G08 | 376398 | PA01 |
| 211G09 | 4273050 | PA01 |
| 211G10 | 171220 | PA01 |
| 211G11 | 486674 | PA01 |
| 211G12 | 4481760 | PA01 |
| 211H01 | 556544 | PA01 |
| 211H02 | 1456777 | PA01 |
| 211H03 | 4531368 | PA01 |
| 211H04 | 4185121 | PA01 |
| 211H05 | 1635441 | PA01 |
| 211H06 | 287970 | PA01 |
| 211H07 | 2507838 | PA01 |
| 211H08 | 982552 | PA01 |
| 211H09 | 2507837 | PA01 |
| 211H10 | 3965601 | PA01 |
| 211H11 | 644769 | PA01 |
| 212A01 | 3054726 | PA01 |
| 212A02 | 3518465 | PA01 |
| 212A03 | 1878482 | PA01 |
| 212A04 | 2139722 | PA01 |
| 212A05 | 1690213 | PA01 |
| 212A06 | 3303910 | PA01 |
| 212A07 | 1155636 | PA01 |
| 212A08 | 204225 | PA01 |
| 212A09 | 940611 | PA01 |
| 212A11 | 2559947 | PA01 |
| 212A12 | 4097853 | PA01 |
| 212B01 | 487194 | PA01 |
| 212B03 | 4237127 | PA01 |
| 212B04 | 1353369 | PA01 |
| 212B05 | 101648 | PA01 |
| 212B08 | 1079350 | PA01 |
| 212B09 | 1489268 | PA01 |
| 212B10 | 4543990 | PA01 |
| 212B11 | 2437187 | PA01 |
| 212B12 | 956281 | PA01 |
| 212C01 | 5320192 | PA01 |
| 212C02 | 2634700 | PA01 |
| 212C03 | 2418322 | PA01 |
| 212C05 | 3217315 | PA01 |
| 212C06 | 2783180 | PA01 |
| 212C07 | 6077307 | PA01 |
| 212C09 | 4868953 | PA01 |
| 212C11 | 2253177 | PA01 |
| 212C12 | 3383809 | PA01 |
| 212D01 | 44426 | PA01 |
| 212D02 | 5869999 | PA01 |
| 212D04 | 268244 | PA01 |
| 212D05 | 5169708 | PA01 |
| 212D06 | 4548485 | PA01 |
| 212D07 | 2924072 | PA01 |
| 212D08 | 1884350 | PA01 |
| 212D09 | 1047003 | PA01 |
| 212D10 | 3225955 | PA01 |
| 212D11 | 1627843 | PA01 |
| 212D12 | 1536899 | PA01 |
| 212E01 | 3577840 | PA01 |
| 212E03 | 1006405 | PA01 |
| 212E05 | 4515966 | PA01 |
| 212E06 | 3323357 | PA01 |
| 212E07 | 3329714 | PA01 |
| 212E08 | 5493271 | PA01 |
| 212E10 | 4222583 | PA01 |
| 212F01 | 4097853 | PA01 |
| 212F03 | 6026292 | PA01 |
| 212F04 | 2513187 | PA01 |
| 212F05 | 3005392 | PA01 |
| 212F07 | 442247 | PA001 |
| 212F08 | 2173490 | PA01 |
| 212F09 | 93881 | PA01 |
| 212F10 | 1920197 | PA01 |
| 212F11 | 3574398 | PA01 |
| 212F12 | 3149561 | PA01 |
| 212G02 | 899039 | PA01 |
| 212G03 | 1868512 | PA01 |
| 212G04 | 5401097 | PA01 |
| 212G05 | 249452 | PA01 |
| 212G07 | 4433790 | PA01 |
| 212G08 | 5256962 | PA01 |
| 212G09 | 494948 | PA01 |
| 212G11 | 2116304 | PA01 |
| 212G12 | 1523526 | PA01 |
| 212H03 | 2538241 | PA01 |
| 212H04 | 204225 | PA01 |
| 212H05 | 196608 | PA01 |
| 212H06 | 575242 | PA01 |
| 212H07 | 531755 | PA01 |
| 212H10 | 5173878 | PA01 |
| 212H11 | 1799610 | PA01 |
| 213A01 | 1802886 | PA01 |
| 213A03 | 1185192 | PA01 |
| 213A04 | 4481799 | PA01 |
| 213A05 | 4339105 | PA01 |
| 213A06 | 1985981 | PA01 |
| 213A07 | 5302623 | PA01 |
| 213A08 | 1776862 | PA01 |
| 213A09 | 2092352 | PA01 |
| 213A10 | 397462 | PA01 |
| 213A11 | 5085439 | PA01 |
| 213A12 | 547097 | PA01 |
| 213B01 | 1540029 | PA01 |
| 213802 | 3383809 | PA01 |
| 213804 | 3897607 | PA01 |
| 213B05 | 6050836 | PA01 |
| 213B07 | 5740849 | PA01 |
| 213B09 | 6050300 | PA01 |
| 213B10 | 2380377 | PA01 |
| 213B11 | 3761189 | PA01 |
| 213B12 | 6099646 | PA01 |
| 213C01 | 1635020 | PA01 |
| 213C02 | 5398475 | PA01 |
| 213C03 | 1114089 | PA01 |
| 213C05 | 5062994 | PA01 |
| 213C06 | 415993 | PA01 |
| 213C07 | 325029 | PA01 |
| 213C08 | 5497562 | PA01 |
| 213C10 | 4836928 | PA01 |
| 213C11 | 6014682 | PA01 |
| 213C12 | 4176072 | PA01 |
| 213D01 | 1078989 | PA01 |
| 213D02 | 3235377 | PA01 |
| 213D04 | 362761 | PA01 |
| 213D05 | 1963822 | PA01 |
| 213D06 | 359488 | PA01 |
| 213D07 | 1360470 | PA01 |
| 213D08 | 359488 | PA01 |
| 213D11 | 546268 | PA01 |
| 213D12 | 3876354 | PA01 |
| 213E01 | 1781790 | PA01 |
| 213E03 | 41191597 | PA01 |
| 213E05 | 2136510 | PA01 |
| 213E06 | 817116 | PA01 |
| 213E07 | 1304734 | PA01 |
| 213E08 | 3288834 | PA01 |
| 213E09 | 6129947 | PA01 |
| 213E10 | 5431715 | PA01 |
| 213E11 | 5781283 | PA01 |
| 213E12 | 5094530 | PA01 |
| 213F04 | 359564 | PA01 |
| 213F05 | 1814561 | PA01 |
| 213F07 | 409737 | PA01 |
| 213F08 | 65418 | PA01 |
| 213F09 | 2269034 | PA01 |

TABLE 3-continued

| Mutant Name | Insertion Point | host strain |
|---|---|---|
| 213F10 | 2907156 | PA01 |
| 213F11 | 621214 | PA01 |
| 213F12 | 4618778 | PA01 |
| 213G02 | 50610 | PA01 |
| 213G03 | 4013674 | PA01 |
| 213G05 | 1175244 | PA01 |
| 213G06 | 870533 | PA01 |
| 213G07 | 2848392 | PA01 |
| 213G08 | 1884350 | PA01 |
| 213G09 | 5318004 | PA01 |
| 213G11 | 5649851 | PA01 |
| 213H01 | 1948242 | PA01 |
| 213H02 | 13124634 | PA01 |
| 213H03 | 204224 | PA01 |
| 213H04 | 4485523 | PA01 |
| 213H05 | 359564 | PA01 |
| 213H06 | 5743036 | PA01 |
| 213H07 | 4721155 | PA01 |
| 213H09 | 492126 | PA01 |
| 213H10 | 288426 | PA01 |
| 214A01 | 3643355 | PA01 |
| 214A02 | 2023760 | PA01 |
| 214A03 | 6178520 | PA01 |
| 214A04 | 1911547 | PA01 |
| 214A05 | 1530709 | PA01 |
| 214A06 | 1832265 | PA01 |
| 214A07 | 2029012 | PA01 |
| 214A09 | 4531369 | PA01 |
| 214A10 | 431629 | PA01 |
| 214A12 | 306705 | PA01 |
| 214B01 | 55431 | PA01 |
| 214B02 | 4810359 | PA01 |
| 214B05 | 1354643 | PA01 |
| 214B07 | 4204238 | PA01 |
| 214B08 | 3510655 | PA01 |
| 214B09 | 5424122 | PA01 |
| 214811 | 1926174 | PA01 |
| 214B12 | 466457 | PA01 |
| 214C01 | 2208458 | PA01 |
| 214C02 | 2495716 | PA01 |
| 214C03 | 1079350 | PA01 |
| 214C05 | 1428841 | PA01 |
| 214C06 | 2705053 | PA01 |
| 214C12 | 2726106 | PA01 |
| 214D01 | 3442739 | PA01 |
| 214D04 | 2943719 | PA01 |
| 214D05 | 5854085 | PA01 |
| 214D06 | 1833458 | PA01 |
| 214D07 | 4199791 | PA01 |
| 214D08 | 4403888 | PA01 |
| 214D10 | 2343237 | PA01 |
| 214E01 | 931505 | PA01 |
| 214E03 | 3442739 | PA01 |
| 214E05 | 5979223 | PA01 |
| 214E06 | 5979223 | PA01 |
| 214E07 | 3704676 | PA01 |
| 214E08 | 4492082 | PA01 |
| 214E09 | 937742 | PA01 |
| 214E10 | 2215587 | PA01 |
| 214E11 | 398190 | PA01 |
| 214F01 | 2888987 | PA01 |
| 214F02 | 3374109 | PA01 |
| 214F03 | 5714574 | PA01 |
| 214F04 | 4553579 | PA01 |
| 214F05 | 223060 | PA01 |
| 214F06 | 2668026 | PA01 |
| 214F07 | 5358757 | PA01 |
| 214F09 | 2641137 | PA01 |
| 214F11 | 2719501 | PA01 |
| 214G05 | 2712102 | PA01 |
| 214G06 | 1924832 | PA01 |
| 214G07 | 326372 | PA01 |
| 214G08 | 2147214 | PA01 |
| 214G09 | 800299 | PA01 |
| 214G10 | 1874570 | PA01 |
| 214G11 | 2477596 | PA01 |
| 214G12 | 552448 | PA01 |

TABLE 3-continued

| Mutant Name | Insertion Point | host strain |
|---|---|---|
| 215A01 | 1669748 | PA01 |
| 215A03 | 1403774 | PA01 |
| 215A10 | 359584 | PA01 |
| 215B01 | 6152322 | PA01 |
| 215B04 | 4034019 | PA01 |
| 215B05 | 2389714 | PA01 |
| 215B06 | 4839271 | PA01 |
| 215B07 | 4155066 | PA01 |
| 215B08 | 4098085 | PA01 |
| 215B09 | 546269 | PA01 |
| 215D02 | 1551037 | PA01 |
| 215D11 | 1078823 | PA01 |
| 215E02 | 3204160 | PA01 |
| 215E03 | 3929603 | PA01 |
| 215E04 | 3397911 | PA01 |
| 215E12 | 4313378 | PA01 |
| 215F04 | 2345224 | PA01 |
| 215F11 | 3169709 | PA01 |
| 215G02 | 1657081 | PA01 |
| 215G03 | 1776864 | PA01 |
| 215G07 | 1428659 | PA01 |
| 215H02 | 4492082 | PA01 |
| 215H03 | 3712733 | PA01 |
| 215H04 | 2007205 | PA01 |
| 215H08 | 1995877 | PA01 |
| 216A08 | 1070675 | PA01 |
| 216A11 | 481393 | PA01 |
| 216B08 | 6198757 | PA01 |
| 216B11 | 3358655 | PA01 |
| 216B12 | 2990462 | PA01 |
| 216C03 | 5056159 | PA01 |
| 216C05 | 866792 | PA01 |
| 216C10 | 4420322 | PA01 |
| 216D05 | 6087728 | PA01 |
| 216D07 | 2116304 | PA01 |
| 216D09 | 3201319 | PA01 |
| 216G05 | 1117230 | PA01 |
| 216G06 | 3870651 | PA01 |
| 216H03 | 1045876 | PA01 |
| 216H07 | 1526024 | PA01 |
| 217A02 | 5270098 | PA01 |
| 217A03 | 481393 | PA01 |
| 217A09 | 661234 | PA01 |
| 217B05 | 5263318 | PA01 |
| 217B06 | 5968489 | PA01 |
| 217B08 | 5390024 | PA01 |
| 217B10 | 5697208 | PA01 |
| 217B12 | 2333500 | PA01 |
| 217C04 | 2012771 | PA01 |
| 217C05 | 4149020 | PA01 |
| 217C07 | 546268 | PA01 |
| 217C09 | 546268 | PA01 |
| 217C10 | 546270 | PA01 |
| 217C11 | 546268 | PA01 |
| 217D02 | 1286664 | PA01 |
| 217D06 | 546268 | PA01 |
| 217D07 | 1289165 | PA01 |
| 217D08 | 546268 | PA01 |
| 217E01 | 4251879 | PA01 |
| 217F01 | 5646692 | PA01 |
| 217F02 | 1687894 | PA01 |
| 217F05 | 546271 | PA01 |
| 217F07 | 338950 | PA01 |
| 217F09 | 2506126 | PA01 |
| 217F11 | 3390739 | PA01 |
| 217F12 | 3390740 | PA01 |
| 217G05 | 6012265 | PA01 |
| 217G06 | 885011 | PA01 |
| 217G07 | 546268 | PA01 |
| 217G09 | 1146734 | PA01 |
| 217G11 | 3515481 | PA01 |
| 217H02 | 546269 | PA01 |
| 217H04 | 4031786 | PA01 |
| 217H05 | 3891961 | PA01 |
| 217H06 | 5768037 | PA01 |
| 217H08 | 546268 | PA01 |
| 217H11 | 3553452 | PA01 |

TABLE 3-continued

| Mutant Name | Insertion Point | host strain |
|---|---|---|
| 218A01 | 954087 | PA01 |
| 218A02 | 628202 | PA01 |
| 218A03 | 3809683 | PA01 |
| 218A04 | 197279 | PA01 |
| 218A05 | 5568853 | PA01 |
| 218A06 | 4910637 | PA01 |
| 218A08 | 5217883 | PA01 |
| 218A09 | 4492177 | PA01 |
| 218A10 | 1830069 | PA01 |
| 218A11 | 4257084 | PA01 |
| 218A12 | 65418 | PA01 |
| 218B01 | 4144351 | PA01 |
| 218B03 | 767461 | PA01 |
| 218B05 | 436240 | PA01 |
| 218B06 | 436240 | PA01 |
| 218B07 | 2173490 | PA01 |
| 218B08 | 2173490 | PA01 |
| 218B10 | 5273292 | PA01 |
| 218B12 | 5147713 | PA01 |
| 218C02 | 307866 | PA01 |
| 218C03 | 492126 | PA01 |
| 218C05 | 2453351 | PA01 |
| 218C06 | 4704214 | PA01 |
| 218C07 | 371914 | PA01 |
| 218C08 | 2408226 | PA01 |
| 218C11 | 6228869 | PA01 |
| 218C12 | 1046253 | PA01 |
| 218D02 | 297517 | PA01 |
| 218D04 | 297519 | PA01 |
| 218D06 | 3725010 | PA01 |
| 218D07 | 1985278 | PA01 |
| 218D08 | 999927 | PA01 |
| 218D09 | 3192085 | PA01 |
| 218D10 | 4284004 | PA01 |
| 218D11 | 3707859 | PA01 |
| 218E01 | 3627888 | PA01 |
| 218E02 | 5980173 | PA01 |
| 218E03 | 2963758 | PA01 |
| 218E07 | 3578842 | PA01 |
| 218E08 | 946484 | PA01 |
| 218E10 | 1064932 | PA01 |
| 218E11 | 683870 | PA01 |
| 218E12 | 4748413 | PA01 |
| 218F02 | 3813551 | PA01 |
| 218F03 | 339460 | PA01 |
| 218F04 | 5982276 | PA01 |
| 218F05 | 5142000 | PA01 |
| 218F06 | 2023760 | PA01 |
| 218F07 | 4275578 | PA01 |
| 218F08 | 6122079 | PA01 |
| 218F09 | 565522 | PA01 |
| 218F10 | 4314876 | PA01 |
| 218F11 | 5147705 | PA01 |
| 218G01 | 1690213 | PA01 |
| 218G02 | 6227025 | PA01 |
| 218G03 | 4990664 | PA01 |
| 218G06 | 1809683 | PA01 |
| 218G07 | 1429084 | PA01 |
| 218G08 | 125185 | PA01 |
| 218G09 | 5944773 | PA01 |
| 218G10 | 142140 | PA01 |
| 218H01 | 374860 | PA01 |
| 218H03 | 4902111 | PA01 |
| 218H05 | 338950 | PA01 |
| 218H06 | 4835152 | PA01 |
| 218H07 | 4835152 | PA01 |
| 218H08 | 253551 | PA01 |
| 218H11 | 768212 | PA01 |
| 219A01 | 3954605 | PA01 |
| 219A02 | 2124983 | PA01 |
| 219A03 | 1018388 | PA01 |
| 219A04 | 894630 | PA01 |
| 219A09 | 6189403 | PA01 |
| 219A10 | 1427357 | PA01 |
| 219B02 | 4675165 | PA01 |
| 219B03 | 4612833 | PA01 |
| 219B04 | 2959606 | PA01 |
| 219B05 | 5500125 | PA01 |
| 219B06 | 5163272 | PA01 |
| 219B07 | 739442 | PA01 |
| 219B10 | 1186050 | PA01 |
| 219B11 | 1354643 | PA01 |
| 219C01 | 5807299 | PA01 |
| 219C04 | 5842394 | PA01 |
| 219C05 | 1428659 | PA01 |
| 219C07 | 147329 | PA01 |
| 219C09 | 3659896 | PA01 |
| 219C11 | 4299389 | PA01 |
| 219D02 | 1717810 | PA01 |
| 219D03 | 2375365 | PA01 |
| 219D04 | 363632 | PA01 |
| 219D05 | 5157544 | PA01 |
| 219D06 | 5256933 | PA01 |
| 219D09 | 912492 | PA01 |
| 219D10 | 3209115 | PA01 |
| 219D12 | 229062 | PA01 |
| 219E01 | 3643734 | PA01 |
| 219E04 | 807180 | PA01 |
| 219E05 | 5497561 | PA01 |
| 219E06 | 4623728 | PA01 |
| 219E08 | 5181233 | PA01 |
| 219E09 | 5280699 | PA01 |
| 219E10 | 1513243 | PA01 |
| 219E11 | 5694210 | PA01 |
| 219E12 | 874289 | PA01 |
| 219F03 | 6192289 | PA01 |
| 219F04 | 5373424 | PA01 |
| 219F05 | 2544966 | PA01 |
| 219F06 | 1669748 | PA01 |
| 219F08 | 2747845 | PA01 |
| 219F10 | 1535896 | PA01 |
| 219F11 | 1597361 | PA01 |
| 219F12 | 51924 | PA01 |
| 219G01 | 3341291 | PA01 |
| 219G02 | 5980173 | PA01 |
| 219G04 | 2780079 | PA01 |
| 219G06 | 1260624 | PA01 |
| 219G08 | 5807299 | PA01 |
| 219G11 | 621219 | PA01 |
| 219G12 | 2341527 | PA01 |
| 219H02 | 3748607 | PA01 |
| 219H05 | 5254106 | PA01 |
| 219H09 | 4864670 | PA01 |
| 219H10 | 4605059 | PA01 |
| 219H11 | 3578842 | PA01 |
| 221A03 | 5165608 | PA01 |
| 221A04 | 3616674 | PA01 |
| 221A05 | 3616674 | PA01 |
| 221A09 | 4194427 | PA01 |
| 221A10 | 5697208 | PA01 |
| 221A11 | 906144 | PA01 |
| 221B02 | 1128863 | PA01 |
| 221B04 | 5005306 | PA01 |
| 221B07 | 5807299 | PA01 |
| 221B08 | 389138 | PA01 |
| 221B09 | 1535898 | PA01 |
| 221B10 | 1524451 | PA01 |
| 221C01 | 1351298 | PA01 |
| 221C02 | 1428659 | PA01 |
| 221C07 | 2780079 | PA01 |
| 221C09 | 6147917 | PA01 |
| 221D02 | 1876783 | PA01 |
| 221D03 | 441618 | PA01 |
| 221D04 | 114208 | PA01 |
| 221D05 | 1927015 | PA01 |
| 221D06 | 1927015 | PA01 |
| 221D07 | 389138 | PA01 |
| 221D08 | 4284004 | PA01 |
| 221D09 | 2129299 | PA01 |
| 221D10 | 2816137 | PA01 |
| 221D11 | 6017696 | PA01 |
| 221D12 | 1954769 | PA01 |
| 221E01 | 3149421 | PA01 |
| 221E02 | 1954769 | PA01 |

TABLE 3-continued

| Mutant Name | Insertion Point | host strain |
|---|---|---|
| 221E03 | 397111 | PA01 |
| 221E04 | 295826 | PA01 |
| 221E05 | 1756716 | PA01 |
| 221E06 | 2345225 | PA01 |
| 221E07 | 1028922 | PA01 |
| 221E08 | 4665321 | PA01 |
| 221E09 | 1258980 | PA01 |
| 221E10 | 4911294 | PA01 |
| 221F02 | 5807299 | PA01 |
| 221F03 | 1412674 | PA01 |
| 221F04 | 5222012 | PA01 |
| 221F05 | 5793067 | PA01 |
| 221F06 | 1948242 | PA01 |
| 221F08 | 2253537 | PA01 |
| 221G02 | 54536 | PA01 |
| 221G03 | 2282835 | PA01 |
| 221G04 | 5659898 | PA01 |
| 221G0S | 3522383 | PA01 |
| 221G06 | 5868602 | PA01 |
| 221G08 | 3659896 | PA01 |
| 221G11 | 3659896 | PA01 |
| 221H01 | 4558862 | PA01 |
| 221H02 | 6215271 | PA01 |
| 221H04 | 1037317 | PA01 |
| 221H05 | 6075274 | PA01 |
| 221H07 | 3146923 | PA01 |
| 221H08 | 5551711 | PA01 |
| 221H09 | 1383796 | PA01 |
| 221H10 | 2849807 | PA01 |
| 221H11 | 1164569 | PA01 |
| 222A05 | 5254049 | PA01 |
| 222A11 | 1064475 | PA01 |
| 222B01 | 3578842 | PA01 |
| 222B08 | 6160886 | PA01 |
| 222C01 | 4866959 | PA01 |
| 222C06 | 2849701 | PA01 |
| 222C08 | 2165361 | PA01 |
| 222E12 | 4790295 | PA01 |
| 222F05 | 5272676 | PA01 |
| 222F11 | 5676227 | PA01 |
| 222G07 | 1426101 | PA01 |
| 222H09 | 3456266 | PA01 |
| 223A02 | 5905666 | PA01 |
| 223A03 | 1044464 | PA01 |
| 223A08 | 5242954 | PA01 |
| 223A09 | 800304 | PA01 |
| 223A11 | 4194332 | PA01 |
| 223A12 | 973842 | PA01 |
| 223B01 | 2022761 | PA01 |
| 223B03 | 1832265 | PA01 |
| 223B05 | 3876264 | PA01 |
| 223B07 | 5069695 | PA01 |
| 223B11 | 4194332 | PA01 |
| 223C03 | 3239117 | PA01 |
| 223C04 | 5263348 | PA01 |
| 223C05 | 3848409 | PA01 |
| 223C08 | 556544 | PA01 |
| 223C11 | 6055515 | PA01 |
| 223C12 | 6168358 | PA01 |
| 223D03 | 3916604 | PA01 |
| 223D06 | 503879 | PA01 |
| 223D07 | 4280522 | PA01 |
| 223D08 | 5123935 | PA01 |
| 223D09 | 3219768 | PA01 |
| 223D10 | 3293888 | PA01 |
| 223D12 | 899039 | PA01 |
| 223E01 | 3926495 | PA01 |
| 223E02 | 4144783 | PA01 |
| 223E03 | 340386 | PA01 |
| 223E05 | 1354641 | PA01 |
| 223E06 | 4501879 | PA01 |
| 223E07 | 1906891 | PA01 |
| 223E08 | 2471654 | PA01 |
| 223E09 | 4845087 | PA01 |
| 223E10 | 5155159 | PA01 |
| 223E11 | 5155159 | PA01 |
| 223E12 | 4585465 | PA01 |
| 223F01 | 2428896 | PA01 |
| 223F02 | 1289165 | PA01 |
| 223F03 | 2375364 | PA01 |
| 223F04 | 5913087 | PA01 |
| 223F05 | 5173878 | PA01 |
| 223F06 | 5967018 | PA01 |
| 223F07 | 5967026 | PA01 |
| 223F09 | 3472893 | PA01 |
| 223F10 | 6122079 | PA01 |
| 223F11 | 2692097 | PA01 |
| 223F12 | 1103071 | PA01 |
| 223G01 | 4627085 | PA01 |
| 223G04 | 1195802 | PA01 |
| 223G05 | 5171632 | PA01 |
| 223G07 | 5632974 | PA01 |
| 223G08 | 3627888 | PA01 |
| 223G09 | 4494640 | PA01 |
| 223G10 | 1906139 | PA01 |
| 223G12 | 552448 | PA01 |
| 223H03 | 876432 | PA01 |
| 223H05 | 2930684 | PA01 |
| 223H06 | 5930686 | PA01 |
| 223H08 | 4016150 | PA01 |
| 223H10 | 170395 | PA01 |
| 225A02 | 1652817 | PA01 |
| 225A03 | 247511 | PA01 |
| 225A05 | 3809627 | PA01 |
| 225A10 | 1364483 | PA01 |
| A1 | 3398642 | PAK |
| A2 | 3379723 | PAK |
| A3 | 2791021 | PAK |
| A4 | 2715492 | PAK |
| A5 | 2733396 | PAK |
| B4 | 659794 | PAK |
| B6 | 3509503 | PAK |
| BEMA01 | 5822687 | PA01 |
| BEMA02 | 1876791 | PA01 |
| BEMA03 | 4708706 | PA01 |
| BEMA04 | 1970426 | PA01 |
| BEMA05 | 1017919 | PA01 |
| BEMA06 | 5804328 | PA01 |
| BEMA07 | 1901425 | PA01 |
| BEMA09 | 1897874 | PA01 |
| BEMA11 | 5316153 | PA01 |
| BEMA12 | 1970426 | PA01 |
| BEMB04 | 3510219 | PA01 |
| BEMB05 | 518952 | PA01 |
| BEMB06 | 1522099 | PA01 |
| BEMB09 | 884859 | PA01 |
| BEMB10 | 1023901 | PA01 |
| BEMC01 | 2798272 | PA01 |
| BEMC09 | 5957696 | PA01 |
| BEMC10 | 5685243 | PA01 |
| BEMC11 | 1586817 | PA01 |
| C1 | 4583326 | PAK |
| C4 | 3144781 | PAK |
| D6 | 3509503 | PAK |
| D1 | 4583326 | PAK |
| D2 | 3509503 | PAK |
| D4 | 4638260 | PAK |
| D6 | 3144781 | PAK |
| yq-tray-434 | 5707222 | PAK |
| yq-tray-436 | 6154439 | PAK |
| yq-tray-438 | 1725057 | PAK |
| yq-tray-440 | 336321 | PAK |
| yq-tray-441 | 3761498 | PAK |
| yq-tray-445 | 5299919 | PAK |
| yq-tray-509 | 3659364 | PAK |
| yq-tray-510 | 5252933 | PAK |
| yq-tray-512 | 1921018 | PAK |
| yq-tray-514 | 157070 | PAK |
| yq-tray-515 | 4788598 | PAK |
| yq-tray-517 | 1051875 | PAK |
| yq-tray-518 | 1051875 | PAK |
| yq-tray-519 | 5617558 | PAK |
| yq-tray-520 | 3593363 | PAK |
| yq-tray-522 | 339721 | PAK |

TABLE 3-continued

| Mutant Name | Insertion Point | host strain |
|---|---|---|
| yq-tray-523 | 456995 | PAK |
| yq-tray-526 | 3947588 | PAK |
| yq-tray-L2 | 772748 | PAK |
| yq-tray-L4 | 974632 | PAK |
| yq-tray-L6 | 4711864 | PAK |
| yq-tube-423 | 6154439 | PAK |
| yq-tube-425 | 6154439 | PAK |
| yq-tube-426 | 1922890 | PAK |
| yq-tube-427 | 455162 | PAK |
| yq-tube-432 | 5429711 | PAK |
| yq-tube-433 | 3551095 | PAK |
| yq-tube-436 | 6154439 | PAK |
| yq-tube-438 | 1725056 | PAK |
| yq-tube-440 | 336321 | PAK |
| yq-tube-441 | 3761498 | PAK |
| yq-tube-443 | 2905443 | PAK |
| yq-tube-445 | 5299920 | PAK |
| yq-tube-509 | 3659364 | PAK |
| yq-tube-510 | 5252933 | PAK |
| yq-tube-511 | 5863244 | PAK |
| yq-tube-512 | 1921018 | PAK |
| yq-tube-514 | 157070 | PAK |
| yq-tube-515 | 4788598 | PAK |
| yq-tube-518 | 1051874 | PAK |
| yq-tube-520 | 3593364 | PAK |
| yq-tube-521 | 4088804 | PAK |
| yq-tube-522 | 339721 | PAK |
| yq-tube-523 | 456995 | PAK |
| yq-tube-525 | 420142 | PAK |
| yq-tube-526 | 3947590 | PAK |
| yq-tube-L2 | 772748 | PAK |
| yq-tube-L4 | 974632 | PAK |
| yq-tube-L5 | 842580 | PAK |
| yq-tube-L6 | 4711864 | PAK |
| yq001 | 346171 | PAK |
| yq002 | 5638088 | PAK |
| yq003 | 5010879 | PAK |
| yq004 | 4815201 | PAK |
| yq005 | 3440810 | PAK |
| yq006 | 4060566 | PAK |
| yq007 | 5621597 | PAK |
| yq008 | 5450213 | PAK |
| yq009 | 5852319 | PAK |
| yq010 | 5336484 | PAK |
| yq011 | 420422 | PAK |
| yq012 | 718708 | PAK |
| yq013 | 1051362 | PAK |
| yq014 | 1433889 | PAK |
| yq015 | 5304562 | PAK |
| yq016 | 346171 | PAK |
| yq017 | 563809 | PAK |
| yq018 | 5010879 | PAK |
| yq019 | 4815202 | PAK |
| yq020 | 3440810 | PAK |
| yq021 | 4060566 | PAK |
| yq022 | 562159 | PAK |
| yq023 | 5450214 | PAK |
| yq024 | 5852319 | PAK |
| yq025 | 5336483 | PAK |
| yq026 | 42042 | PAK |
| yq027 | 718708 | PAK |
| yq028 | 1051363 | PAK |
| yq029 | 1433889 | PAK |
| yq030 | 5304562 | PAK |
| yq044 | 4910942 | PAK |
| yq045 | 3158388 | PAK |
| yq046 | 5781323 | PAK |
| yq047 | 3462938 | PAK |
| yq048 | 4806787 | PAK |
| yq049 | 5254917 | PAK |
| yq050 | 879367 | PAK |
| yq051 | 3666061 | PAK |
| yq052 | 5682932 | PAK |
| yq054 | 4437930 | PAK |
| yq056 | 2355967 | PAK |
| yq057 | 1036633 | PAK |
| yq058 | 2310864 | PAK |
| yq060 | 3968 | PAK |
| yq062 | 5326359 | PAK |
| yq063 | 4787579 | PAK |
| yq064 | 3006981 | PAK |
| yq065 | 24632 | PAK |
| yq066 | 5197201 | PAK |
| yq067 | 17465 | PAK |
| yq068 | 1855301 | PAK |
| yq069 | 5376060 | PAK |
| yq070 | 5781323 | PAK |
| yq071 | 1868969 | PAK |
| yq072 | 2341355 | PAK |
| yq074 | 7607 | PAK |
| yq075 | 2668034 | PAK |
| yq076 | 6002335 | PAK |
| yq078 | 5045325 | PAK |
| yq079 | 136420 | PAK |
| yq080 | 450182 | PAK |
| yq081 | 5342602 | PAK |
| yq082 | 4960596 | PAK |
| yq084 | 6184207 | PAK |
| yq085 | 4540967 | PAK |
| yq086 | 6069286 | PAK |
| yq087 | 4863021 | PAK |
| yq088 | 5943943 | PAK |
| yq089 | 6105445 | PAK |
| yq090 | 4922981 | PAK |
| yq091 | 5640098 | PAK |
| yq092 | 3573502 | PAK |
| yq093 | 3947134 | PAK |
| yq094 | 6014140 | PAK |
| yq095 | 4060078 | PAK |
| yq096 | 2738432 | PAK |
| yq097 | 3142555 | PAK |
| yq098 | 1349094 | PAK |
| yq099 | 5255164 | PAK |
| yq100 | 4939275 | PAK |
| yq101 | 1958774 | PAK |
| yq102 | 6256002 | PAK |
| yq103 | 5449654 | PAK |
| yq104 | 5303638 | PAK |
| yq105 | 5855552 | PAK |
| yq106 | 1355230 | PAK |
| yq107 | 6014340 | PAK |
| yq109 | 7211 | PAK |
| yq111 | 1725699 | PAK |
| yq112 | 4792140 | PAK |
| yq113 | 3525719 | PAK |
| yq114 | 3562829 | PAK |
| yq115 | 483336 | PAK |
| yq116 | 3948019 | PAK |
| yq118 | 3551530 | PAK |
| yq120 | 5674845 | PAK |
| yq121 | 6132273 | PAK |
| yq122 | 4218739 | PAK |
| yq123 | 5993718 | PAK |
| yq124 | 4904227 | PAK |
| yq125 | 5827382 | PAK |
| yq127 | 5232107 | PAK |
| yq128 | 4191195 | PAK |
| yq129 | 4281645 | PAK |
| yq131 | 4079776 | PAK |
| yq132 | 499212 | PAK |
| yq133 | 1445149 | PAK |
| yq134 | 1848577 | PAK |
| yq135 | 5617827 | PAK |
| yq136 | 3769518 | PAK |
| yq137 | 3324609 | PAK |
| yq138 | 4787523 | PAK |
| yq139 | 4314367 | PAK |
| yq140 | 274655 | PAK |
| yq141 | 4013122 | PAK |
| yq142 | 1091008 | PAK |
| yq144 | 5273651 | PAK |
| yq145 | 527365 | PAK |
| yq146 | 1050594 | PAK |
| yq147 | 5844719 | PAK |

TABLE 3-continued

| Mutant Name | Insertion Point | host strain |
|---|---|---|
| yq148 | 4790607 | PAK |
| yq149 | 2955955 | PAK |
| yq150 | 2605446 | PAK |
| yq151 | 6132505 | PAK |
| yq152 | 5764392 | PAK |
| yq153 | 467804 | PAK |
| yq154 | 5224478 | PAK |
| yq155 | 5943918 | PAK |
| yq156 | 4523197 | PAK |
| yq157 | 3418100 | PAK |
| yq158 | 3445426 | PAK |
| yq159 | 5209130 | PAK |
| yq150 | 365889 | PAK |
| yq161 | 5968499 | PAK |
| yq162 | 3879399 | PAK |
| yq163 | 5923053 | PAK |
| yq165 | 4998512 | PAK |
| yq167 | 4508569 | PAK |
| yq170 | 5781283 | PAK |
| yq171 | 756481 | PAK |
| yq172 | 6032525 | PAK |
| yq173 | 5301398 | PAK |
| yq174 | 6013215 | PAK |
| yq176 | 488500 | PAK |
| yq177 | 3474448 | PAK |
| yq179 | 3593527 | PAK |
| yq180 | 4831330 | PAK |
| yq181 | 6106545 | PAK |
| yq182 | 1600391 | PAK |
| yq184 | 3070088 | PAK |
| yq185 | 5638129 | PAK |
| yq186 | 450406 | PAK |
| yq189 | 4525467 | PAK |
| yq190 | 2913281 | PAK |
| yq191 | 1244951 | PAK |
| yq192 | 1748207 | PAK |
| yq193 | 4303927 | PAK |
| yq194 | 456035 | PAK |
| yq195 | 5342235 | PAK |
| yq196 | 3552017 | PAK |
| yq198 | 1081709 | PAK |
| yq199 | 4860003 | PAK |
| yq201 | 608110 | PAK |
| yq202 | 5853213 | PAK |
| yq203 | 6138043 | PAK |
| yq204 | 6138043 | PAK |
| yq206 | 3190834 | PAK |
| yq207 | 1227518 | PAK |
| yq208 | 6077287 | PAK |
| yq209 | 396394 | PAK |
| yq210 | 1858593 | PAK |
| yq212 | 1920624 | PAK |
| yq213 | 5341642 | PAK |
| yq214 | 4057373 | PAK |
| yq216 | 5707528 | PAK |
| yq217 | 4792484 | PAK |
| yq218 | 3630984 | PAK |
| yq219 | 3323901 | PAK |
| yq220 | 5346101 | PAK |
| yq221 | 4335938 | PAK |
| yq223 | 395319 | PAK |
| yq224 | 4790530 | PAK |
| yq227 | 4799812 | PAK |
| yq228 | 4525490 | PAK |
| yq229 | 4158658 | PAK |
| yq230 | 355575 | PAK |
| yq231 | 1664781 | PAK |
| yq232 | 5618190 | PAK |
| yq233 | 4481541 | PAK |
| yq236 | 4783201 | PAK |
| yq237 | 3631841 | PAK |
| yq238 | 5279426 | PAK |
| yq239 | 80263 | PAK |
| yq240 | 4060540 | PAK |
| yq241 | 5750274 | PAK |
| yq242 | 6136055 | PAK |
| yq243 | 457532 | PAK |
| yq244 | 5054238 | PAK |
| yq245 | 5340298 | PAK |
| yq246 | 5442141 | PAK |
| yq247 | 1752445 | PAK |
| yq248 | 26811 | PAK |
| yq249 | 472171 | PAK |
| yq250 | 5310020 | PAK |
| yq251 | 6258564 | PAK |
| yq252 | 3631270 | PAK |
| yq253 | 3986330 | PAK |
| yq254 | 1909905 | PAK |
| yq256 | 4961011 | PAK |
| yq257 | 5344886 | PAK |
| yq258 | 1794056 | PAK |
| yq259 | 5622663 | PAK |
| yq260 | 1920818 | PAK |
| yq261 | 448226 | PAK |
| yq262 | 5622870 | PAK |
| yq263 | 1848341 | PAK |
| yq264 | 1724204 | PAK |
| yq265 | 4985498 | PAK |
| yq266 | 1727594 | PAK |
| yq267 | 3173887 | PAK |
| yq269 | 20580 | PAK |
| yq270 | 4752054 | PAK |
| yq271 | 2059133 | PAK |
| yq272 | 6006278 | PAK |
| yq274 | 3122299 | PAK |
| yq275 | 4190985 | PAK |
| yq276 | 6260937 | PAK |
| yq277 | 6006151 | PAK |
| yq279 | 5677964 | PAK |
| yq280 | 4260408 | PAK |
| yq281 | 1824685 | PAK |
| yq282 | 1911391 | PAK |
| yq283 | 6185077 | PAK |
| yq285 | 5944595 | PAK |
| yq286 | 4522691 | PAK |
| yq288 | 4191034 | PAK |
| yq289 | 1662859 | PAK |
| yq290 | 5787228 | PAK |
| yq291 | 3509945 | PAK |
| yq292 | 5457826 | PAK |
| yq293 | 4161674 | PAK |
| yq294 | 6218220 | PAK |
| yq295 | 4909720 | PAK |
| yq296 | 3242506 | PAK |
| yq299 | 4785423 | PAK |
| yq300 | 1053171 | PAK |
| yq301 | 3481634 | PAK |
| yq302 | 3604968 | PAK |
| yq303 | 1848611 | PAK |
| yq304 | 5556783 | PAK |
| yq305 | 2994123 | PAK |
| yq306 | 532805 | PAK |
| yq307 | 4909720 | PAK |
| yq308 | 4652185 | PAK |
| yq309 | 2183791 | PAK |
| yq312 | 514649 | PAK |
| yq313 | 514649 | PAK |
| yq321 | 2922983 | PAK |
| yq322 | 3938305 | PAK |
| yq323 | 3008585 | PAK |
| yq324 | 5706853 | PAK |
| yq325 | 1955778 | PAK |
| yq326 | 2060699 | PAK |
| yq327 | 4476464 | PAK |
| yq329 | 1683461 | PAK |
| yq330 | 453170 | PAK |
| yq331 | 328420 | PAK |
| yq332 | 4816371 | PAK |
| yq333 | 5551527 | PAK |
| yq337 | 5408952 | PAK |
| yq338 | 3656220 | PAK |
| yq339 | 6246268 | PAK |
| yq340 | 5689845 | PAK |
| yq343 | 3129643 | PAK |

TABLE 3-continued

| Mutant Name | Insertion Point | host strain |
|---|---|---|
| yq344 | 4942834 | PAK |
| yq345 | 4962990 | PAK |
| yq346 | 3593373 | PAK |
| yq347 | 4862188 | PAK |
| yq350 | 4475236 | PAK |
| yq352 | 5687238 | PAK |
| yq353 | 4815115 | PAK |
| yq354 | 420070 | PAK |
| yq355 | 5254986 | PAK |
| yq359 | 404488 | PAK |
| yq360 | 4579247 | PAK |
| yq362 | 3364174 | PAK |
| yq363 | 420046 | PAK |
| yq365 | 1554758 | PAK |
| yq366 | 2178380 | PAK |
| yq368 | 5642385 | PAK |
| yq369 | 1051695 | PAK |
| yq370 | 483080 | PAK |
| yq372 | 1954705 | PAK |
| yq373 | 1725290 | PAK |
| yq374 | 398646 | PAK |
| yq375 | 241422 | PAK |
| yq376 | 3415649 | PAK |
| yq377 | 2169080 | PAK |
| yq378 | 4248879 | PAK |
| yq380 | 4016636 | PAK |
| yq381 | 804155 | PAK |
| yq382 | 3230 | PAK |
| yq383 | 482768 | PAK |
| yq386 | 5707528 | PAK |
| yq387 | 5327307 | PAK |
| yq388 | 2046 | PAK |
| yq389 | 5637883 | PAK |
| yq390 | 2227022 | PAK |
| yq391 | 1831923 | PAK |
| yq392 | 5208464 | PAK |
| yq393 | 5918375 | PAK |
| yq394 | 4248933 | PAK |
| yq396 | 1751917 | PAK |
| yq397 | 510423 | PAK |
| yq398 | 514693 | PAK |
| yq399 | 5827390 | PAK |
| yq400 | 2934612 | PAK |
| yq401 | 2672028 | PAK |
| yq403 | 5254098 | PAK |
| yq405 | 3593339 | PAK |
| yq407 | 3593640 | PAK |
| yq408 | 636054 | PAK |
| yq409 | 456578 | PAK |
| yq410 | 3947139 | PAK |
| yq411 | 4792319 | PAK |
| yq412 | 6033032 | PAK |
| yq414 | 4535117 | PAK |
| yq415 | 473367 | PAK |
| yq416 | 6007245 | PAK |
| yq417 | 3324453 | PAK |
| yq418 | 4801907 | PAK |
| yq419 | 6013292 | PAK |
| yq420 | 600770 | PAK |
| yq423 | 4478003 | PAK |
| yq425 | 6154439 | PAK |
| yq432 | 5429711 | PAK |
| yq440 | 336321 | PAK |
| yq441 | 3761499 | PAK |
| yq449 | 457460 | PAK |
| yq451 | 1954013 | PAK |
| yq453 | 6200072 | PAK |
| yq454 | 5694746 | PAK |
| yq456 | 1501881 | PAK |
| yq462 | 1380923 | PAK |
| yq465 | 833533 | PAK |
| yq466 | 3415145 | PAK |
| yq467 | 3415145 | PAK |
| yq468 | 6033567 | PAK |
| yq469 | 1834663 | PAK |
| yq470 | 482451 | PAK |
| yq471 | 615716 | PAK |
| yq472 | 5623696 | PAK |
| yq473 | 4466909 | PAK |
| yq475 | 615716 | PAK |
| yq476 | 5617195 | PAK |
| yq478 | 6184599 | PAK |
| yq486 | 5694899 | PAK |
| yq490 | 5616691 | PAK |
| yq492 | 5855086 | PAK |
| yq493 | 3949423 | PAK |
| yq494 | 474372 | PAK |
| yq495 | 718241 | PAK |
| yq496 | 1349427 | PAK |
| yq497 | 273258 | PAK |
| yq498 | 5859288 | PAK |
| yq499 | 4274525 | PAK |
| yq501 | 6181080 | PAK |
| yq502 | 5415806 | PAK |
| yq503 | 5707622 | PAK |
| yq506 | 4273277 | PAK |
| yq508 | 4862384 | PAK |
| yq527 | 5530108 | PAK |
| yq528 | 6083751 | PAK |
| yq535 | 455290 | PAK |
| yq536 | 3606825 | PAK |
| yq537 | 1981576 | PAK |
| yq540 | 839186 | PAK |
| yq541 | 4861418 | PAK |
| yq542 | 6007715 | PAK |
| yq545 | 3281356 | PAK |
| yq546 | 5694889 | PAK |
| yq547 | 3554932 | PAK |
| yq548 | 4819920 | PAK |
| yq549 | 4791519 | PAK |
| yq551 | 5260804 | PAK |
| yq556 | 4801971 | PAK |
| yq557 | 642573 | PAK |
| yq558 | 4317166 | PAK |
| yq559 | 3324609 | PAK |
| yq560 | 4800242 | PAK |
| yq561 | 5197173 | PAK |
| yq562 | 5253316 | PAK |
| yq563 | 555662 | PAK |
| yq564 | 5922452 | PAK |
| yq568 | 4804815 | PAK |
| yq569 | 4807928 | PAK |
| yq570 | 4261077 | PAK |
| yq571 | 1719155 | PAK |
| yq572 | 4988719 | PAK |
| yq574 | 3324900 | PAK |
| yq575 | 4536660 | PAK |
| yq576 | 419363 | PAK |
| yq579 | 5849545 | PAK |
| yq580 | 456046 | PAK |
| yq581 | 855748 | PAK |
| yq582 | 1690865 | PAK |
| yq583 | 5991336 | PAK |
| yq584 | 5853904 | PAK |
| yq585 | 5694892 | PAK |
| yq586 | 5484510 | PAK |
| yq587 | 454274 | PAK |
| yq588 | 5788824 | PAK |
| yq589 | 5857361 | PAK |
| yq590 | 5707319 | PAK |
| yq592 | 5916385 | PAK |
| yq593 | 42750780 | PAK |
| yq594 | 3936955 | PAK |
| yq596 | 3551821 | PAK |
| yq597 | 5208616 | PAK |
| yq599 | 6132782 | PAK |
| yq602 | 4549080 | PAK |
| yq603 | 4383148 | PAK |
| yq604 | 1424381 | PAK |
| yq605 | 480240 | PAK |

We claim:

1. A method of screening for an antibacterial agent, comprising:
   a step of contacting a test compound with an isolated *Pseudomonas aeruginosa* protein LpxC;
   a further step of determining whether the test compound binds to the protein; and
   a further step of determining whether the test compound has either bactericidal or bacteriostatic activity against *Pseudomonas aeruginosa*.

2. The method of claim 1 further comprising determining whether the test compound is active against the protein.

3. The method of claim 2 wherein determining whether the test compound is active comprises determining whether the test compound inhibits a biochemical pathway that involves the protein.

4. The method of claim 1 wherein determining whether the test compound has either bactericidal or bacteriostatic activity comprises determining whether the test compound suppresses the growth of a *Pseudomonas aeruginosa* bacterium comprising the protein.

* * * * *